(12) United States Patent
Haynes et al.

(10) Patent No.: US 10,450,368 B2
(45) Date of Patent: Oct. 22, 2019

(54) HIV-1 NEUTRALIZING ANTIBODIES AND USES THEREOF (CD4BS ANTIBODIES)

(71) Applicant: DUKE UNIVERSITY, Durham, NC (US)

(72) Inventors: Barton F. Haynes, Durham, NC (US); Hua-Xin Liao, Durham, NC (US); Mattia Bonsignori, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 15/559,171

(22) PCT Filed: Mar. 21, 2016

(86) PCT No.: PCT/US2016/023355
§ 371 (c)(1),
(2) Date: Sep. 18, 2017

(87) PCT Pub. No.: WO2016/149695
PCT Pub. Date: Sep. 22, 2016

(65) Prior Publication Data
US 2018/0079801 A1   Mar. 22, 2018

Related U.S. Application Data

(60) Provisional application No. 62/135,309, filed on Mar. 19, 2015, provisional application No. 62/191,095, filed on Jul. 10, 2015, provisional application No. 62/222,115, filed on Sep. 22, 2015, provisional application No. 62/260,100, filed on Nov. 25, 2015, provisional application No. 62/301,993, filed on Mar. 1, 2016.

(51) Int. Cl.
*C07K 16/10* (2006.01)
*A61K 39/00* (2006.01)

(52) U.S. Cl.
CPC ...... *C07K 16/1063* (2013.01); *C07K 16/1045* (2013.01); *A61K 2039/507* (2013.01); *C07K 2317/21* (2013.01); *C07K 2317/31* (2013.01); *C07K 2317/34* (2013.01); *C07K 2317/52* (2013.01); *C07K 2317/55* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,458,704 B2 | 12/2008 | Naoi |
| 8,637,035 B2 * | 1/2014 | Wu ........... C07K 16/1081 424/159.1 |
| 8,784,821 B1 | 7/2014 | Kufer et al. |
| 8,795,667 B2 | 8/2014 | Johnson et al. |
| 2004/0162298 A1 | 8/2004 | Ho et al. |
| 2005/0037000 A1 | 2/2005 | Stavenhagen et al. |
| 2005/0064514 A1 | 3/2005 | Stavenhagen et al. |
| 2009/0060910 A1 | 3/2009 | Johnson et al. |
| 2010/0093979 A1 | 4/2010 | Lazar |
| 2010/0174053 A1 | 7/2010 | Johnson et al. |
| 2011/0081347 A1 | 4/2011 | Gorlatov |
| 2013/0295121 A1 | 11/2013 | Johnson et al. |
| 2014/0088295 A1 | 3/2014 | Smith et al. |
| 2014/0099318 A1 | 4/2014 | Huang et al. |
| 2014/0170149 A1 | 6/2014 | Neijssen et al. |
| 2014/0205607 A1 | 7/2014 | Mascola et al. |
| 2014/0206846 A1 | 7/2014 | Beckmann |
| 2014/0248295 A1 | 9/2014 | Song et al. |
| 2014/0328836 A1 | 11/2014 | Johnson et al. |
| 2015/0152183 A1 | 6/2015 | Chamberlain et al. |

FOREIGN PATENT DOCUMENTS

| | | |
|---|---|---|
| EP | 2158221 A2 | 3/2010 |
| EP | 2376109 A1 | 10/2011 |
| EP | 2601216 A1 | 6/2013 |
| EP | 2714079 A2 | 4/2014 |
| WO | WO-2001/043779 A2 | 6/2001 |
| WO | WO-2004/063351 A2 | 7/2004 |
| WO | WO-2010/080538 A1 | 7/2010 |
| WO | WO-2011/038290 A2 | 3/2011 |
| WO | WO-2012/018687 A1 | 2/2012 |
| WO | WO-2012/162068 A2 | 11/2012 |
| WO | WO-2014/159940 A1 | 10/2014 |

(Continued)

OTHER PUBLICATIONS

Watkins et al. (PLoS, 2011, p. 1-7).*

(Continued)

*Primary Examiner* — Agnieszka Boesen
(74) *Attorney, Agent, or Firm* — Wilmer Cutler Pickering Hale and Dorr LLP

(57) ABSTRACT

The invention relates to the identification of monoclonal HIV-1 neutralizing antibodies, such as, but not limited to, antibodies that bind to the CD4 binding site (CD4bs) of HIV-1 gp120, their recombinant expression and purification and uses. In certain aspects, the invention provides a pharmaceutical composition comprising anyone of the antibodies of the invention or fragments thereof or any combination thereof. In certain aspects the invention provides methods to treat or prevent HIV-1 infection in a subject comprising administering to the subject a pharmaceutical composition comprising any one of the inventive antibodies or fragments thereof.

39 Claims, 158 Drawing Sheets
Specification includes a Sequence Listing.

(56) References Cited

FOREIGN PATENT DOCUMENTS

| WO | WO 2014/172366 | * | 10/2014 | ............ C07K 19/00 |
|---|---|---|---|---|
| WO | WO-2015/021089 A1 | | 2/2015 | |
| WO | WO-2015/026892 A1 | | 2/2015 | |
| WO | WO-2015/026894 A2 | | 2/2015 | |
| WO | WO-2016/149695 A1 | | 9/2016 | |
| WO | WO-2016/196975 A1 | | 12/2016 | |

OTHER PUBLICATIONS

Scheid, J. F., et al., "Broad diversity of neutralizing antibodies isolated from memory B cells in HIV-infected individuals," Nature—Letters, vol. 458, pp. 636-640 (Apr. 2, 2009).
Sui, Z., et al., "Cross-protection against influenza virus infection by intranasal administration of M2-based vaccine with chitosan as an adjuvant," Arch. Virol., vol. 155, pp. 535-544 (2010).
van Dongen, J., et al., "Design and standardization of PCR primers and protocols for detection of clonal immunoglobulin and T-cell receptor gene recombinations in suspect lymphoproliferations: Report of the BIOMED-2 Concerted Action BMH4-CT98-3936," Leukemia, vol. 17, pp. 2257-2317 (2003).
Alam, S. M., et al., "Role of HIV Membrane in Neutralization by Two Broadly Neutralizing Antibodies," Proceedings of the National Academy of Sciences of the United States of America, vol. 106, pp. 20234-20239 (Dec. 1, 2009).
Alam, S. M., et al., "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes," Journal of Immunology, vol. 178, pp. 4424-4435 (2007).
Altschul, S. F., et al., "Basic Local Alignment Search Tool," Journal of Molecular Biology, vol. 215, pp. 403-410 (May 15, 1990).
Altschul, S. F., et al., "Issues in Searching Molecular Sequence Databases," Nature Genetics, vol. 6, pp. 119-129 (Feb. 6, 1994).
Atwell, S., et al., "Stable Heterodimers From Remodeling the Domain Interface of a Homodimer Using a Phage Display Library," Journal of Molecular Biology, vol. 270, pp. 26-35 (Apr. 25, 1997).
Bai, S., et al., "A Guide to Rational Dosing of Monoclonal Antibodies," Clinical Pharmacokinetics, vol. 51, No. 2, pp. 119-135 (Feb. 2012).
Barouch, D. H., et al., "Therapeutic Efficacy of Potent Neutralizing HIV-1 Specific Monoclonal Antibodies in SHIV-Infected Rhesus Monkeys," Nature, vol. 503, pp. 224-228, Author Manuscript—24 total pages (Nov. 14, 2013).
Bird, R. E., et al., "Single-Chain Antigen-Binding Proteins," Science, vol. 242, pp. 423-426 (Aug. 9, 1988).
Bonsignori, M., et al., "An Autoreactive Antibody from an SLE/HIV-1 Individual Broadly Neutralizes HIV-1," Journal of Clinical Investigation, vol. 124, pp. 1835-1843 (Jan. 9, 2014).
Bonsignori, M., et al., "Analysis of a Clonal Lineage of HIV-1 Envelope V2/V3 Conformational Epitope-Specific Broadly Neutralizing Antibodies and Their Inferred Unmutated Common Ancestors," Journal of Virology, vol. 85, pp. 9998-10009 (Jul. 18, 2011).
Bonsignori, M., et al., "HIV-1 Antibodies from Infection and Vaccination: Insights for Guiding Vaccine Design," Trends Microbiology, vol. 20, No. 11, pp. 532-539, Author Manuscript—15 total pages (Nov. 1, 2012).
Bonsignori, M., et al., "Maturation Pathway from Germline to Broad HIV-1 Neutralizer of a CD-4 Mimic Antibody," Cell, vol. 165, pp. 449-463 (Apr. 7, 2016).
Boyd, S. D., et al., "Measurement and Clinical Monitoring of Human Lymphocyte Clonality by Massively Parallel V-D-J Pyrosequencing," Science Translation Medicine, vol. 1, No. 12, pp. 1-8, with Editor's Summary—10 total pages (Dec. 23, 2009).
Byrne, H., et al., "A Tale of Two Specificities: Bispecific Antibodies for Therapeutic and Diagnostic Applications," Trends in Biotechnology, vol. 31, No. 11, pp. 621-632 (2013).
Chen, K. S. and Mitchell, D. A., "Monoclonal Antibody Therapy for Malignant Glioma," 39 total pages including cover pages, table of contents and Chapter 10—pp. 121-141, Advances in Experimental Medicine and Biology, vol. 746, Yamanaka R. (eds) Glioma, Springer, New York, NY (2012).
Chen, Y., et al., "Development of polyether urethane intravaginal rings for the sustained delivery of hydroxychloroquine," Drug Des. Devel. Ther., vol. 8, pp. 1801-1815 (2014).
Chuang, G., et al., "Eliminating Antibody Polyreactivity Through Addition of N-Linked Glycosylation," Protein Science, vol. 24, pp. 1019-1030 (Mar. 2, 2015).
Collaborative Computational Project, "The CCP4 Suite: Programs for Protein Crystallography," Acta Crystallographica, Section D, Biological Crystallography, vol. 50, pp. 760-763 (Sep. 1, 1994).
Corpet, F., "Multiple Sequence Alignment with Hierarchical Clustering," Nucleic Acids Research, vol. 16, No. 22, pp. 10881-10890 (Nov. 25, 1988).
Costa, A. R., et al., "Guidelines to Cell Engineering for Monoclonal Antibody Production," European Journal of Pharmaceutics and Biopharmaceutics, vol. 74, No. 2, pp. 127-138 (Feb. 2010).
Doria-Rose, N. A., "HIV Neutralizing Antibodies: Clinical Correlates and Implications for Vaccines" The Journal of Infectious Diseases, vol. 201, No. 7, pp. 981-983 (Apr. 1, 2010).
Dosenovic, P., et al., "Immunization for HIV-1 Broadly Neutralizing Antibodies in Human Ig Knockin Mice," Cell vol. 161, pp. 1505-1515 (Jun. 18, 2015).
Edgar, R. C., "MUSCLE: Multiple Sequence Alignment with High Accuracy and High Throughput," Nucleic Acids Research, vol. 32, No. 5, pp. 1792-1797 (Mar. 19, 2004).
Fahrner, R. L., et al., "Industrial Purification of Pharmaceutical Antibodies: Development, Pperation, and Validation of Chromatography Processes," Biotechnology & Genetic Engineering Reviews, vol. 18, pp. 301-327 (2001).
Fera, D., et al., "Affinity Maturation in an HIV Broadly Neutralizing B-Cell Lineage Through Reorientation of Variable Domains," Proceedings of the National Academy of Sciences of the United States of America, vol. 111, pp. 10275-10280 (Jun. 30, 2014).
Foote, J. and Milstein, C., "Kinetic maturation of an immune response," Nature, vol. 352, 530-532 (Aug. 8, 1991).
Gao, F., et al., "Cooperation of B Cell Lineages in Induction of HIV-1-Broadly Neutralizing Antibodies," Cell, vol. 158, No. 3, pp. 481-491, Author Manuscript—15 total pages (Jul. 31, 2014).
Garber, K., "Bispecific Antibodies Rise Again," Nature Reviews Drug Discovery, vol. 13, pp. 799-801 (2014).
GenBank Accession Nos. KU570032 through KU570053, last downloaded from https://www.ncbi.nlm.nih.gov/ on Jul. 24, 2018 (3 total pages).
Georgiev, I. S., et al., "Delineating Antibody Recognition in Polyclonal Sera from Patterns of HIV-1 Isolate Neutralization," Science, vol. 340, pp. 751-756 (May 10, 2013).
Giorgi, E. E., et al., "Estimating Time Since Infection in Early Homogeneous HIV-1 Samples Using a Poisson Model," BMC Bioinformatics, vol. 11, 7 total pages (2010).
Gray, E. S., et al., "Isolation of a Monoclonal Antibody that Targets the Alpha-2 Helix of gp120 and Represents the Initial Autologous Neutralizing-Antibody Response in an HIV-1 Subtype C-Infected Individual," Journal of Virology, vol. 85, pp. 7719-7729 (May 12, 2011).
Haynes, B. F., et al., "B-Cell-Lineage Immunogen Design in Vaccine Development with HIV-1 as a Case Study," National Biotechnology, vol. 30, pp. 423-433 (2012).
Haynes, B. F., et al., "Cardiolipin Polyspecific Autoreactivity in Two Broadly Neutralizing HIV-1 Antibodies," Science, vol. 308, pp. 1906-1908 (Jun. 24, 2005).
Haynes, B. F., et al., "Host Controls of HIV Neutralizing Antibodies," Science, vol. 344, pp. 588-589, Author Manuscript—5 total pages (May 9, 2014).
Haynes, B. F. and Bradley, T., "Broadly Neutralizing Antibodies and the Development of Vaccines," JAMA, vol. 313, No. 24, pp. 2419-2420 (Jun. 23/30, 2015).
Haynes, B. F., "New Approaches to HIV Vaccine Development," Current Opinion Immunology, vol. 35, pp. 39-47, Author Manuscript—16 total pages (2015).
Hladik, F., et al., "Mucosal effects of tenofovir 1% gel," eLife, vol. 4, e04525, pp. 1-21 (Feb. 3, 2015).

(56) References Cited

OTHER PUBLICATIONS

Holliger, P., et al., "Specific Killing of Lymphoma Cells by Cytotoxic T-Cells Mediated by a Bispecific Diabody," Protein Engineering, vol. 9, pp. 299-305 (1996).
Hraber, P., et al., "Longitudinal Antigenic Sequences and Sites from Intra-Host Evolution (LASSIE) Identifies Immune-Selected HIV Variants," Viruses, vol. 7, No. 10, pp. 5443-5475 (Oct. 21, 2015).
Hraber, P., et al., "Prevalence of Broadly Neutralizing Antibody Responses During Chronic HIV-1 Infection," AIDS, vol. 28, No. 2, pp. 163-169, Author Manuscript—13 total pages (Jan. 14, 2014).
Huston, J. S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the United States of America, vol. 85, pp. 5879-5883 (Aug. 1988).
International Search Report and Written Opinion issued by United States Patent and Trademark Office for PCT/US2016/023355 dated Jul. 29, 2016 (9 pages).
Jardine, J. G, et al., "Rational HIV Immunogen Design to Target Specific Germline B Cell Receptors," Science, vol. 340, No. 6133, pp. 711-716, Author Manuscript—13 total pages (May 10, 2013).
Jardine, J. G., et al., "Priming a Broadly Neutralizing Antibody Response to HIV-1 Using a Germline-Targeting Immunogen," Science, vol. 349, No. 6244, pp. 156-161, Author Manuscript—20 total pages (Jul. 10, 2015).
Keele, B. F., et al., "Identification and Characterization of Transmitted and Early Founder Virus Envelopes in Primary HIV-1 Infection," Proceedings of the National Academy of Sciences of the United States of America, vol. 105, o. 21, pp. 7552-7557 (May 27, 2008).
Kepler, T. B., "Reconstructing a B-Cell Clonal Lineage. I. Statistical Inference of Unobserved Ancestors," F1000Research, vol. 2, No. 103, pp. 1-12 (Apr. 3, 2013).
Kepler, T. B., et al., "Reconstructing a B-Cell Clonal Lineage. II. Mutation, Selection, and Affinity Maturation," Frontiers in Immunology, vol. 5, No. 170, pp. 1-10 (Apr. 22, 2014).
Kim, J. Y., et al., "CHO Cells in Biotechnology for Production of Recombinant Proteins: Current State and Further Potential," Applied Microbiology and Biotechnology, vol. 93, No. 3, pp. 917-930 (Feb. 2012).
Kipriyanov, S. M., et al., "Bispecific Tandem Diabody for Tumor Therapy with Improved Antigen Binding and Pharmacokinectics," J. Mol. Biol., vol., vol. 293, pp. 41-56 (1999).
Klein, F., et al., "Somatic Mutations of the Immunoglobulin Framework are Generally Required for Broad and Potent HIV-1 Neutralization," Cell, vol. 153, No. 1, pp. 126-138 (Mar. 28, 2013).
Ko, S.-Y., et al., "Enhanced Neonatal Fc Receptor Function Improves Protection Against Primate SHIV Infection," Nature, vol. 514, No. 7524, pp. 642-645, Author Manuscript—22 total pages (Oct. 30, 2014).
Kostelny, S. A., et al., "Formation of a Bispecific Antibody by the Use of Leucine Zippers," J. Immunol., vol. 148, No. 5, pp. 1547-1553, 8 total pages (Mar. 1, 1992).
Kuo, T., et al., "Neonatal Fc Receptor and IgG-based Therapeutics," mAbs, vol. 3, No. 5, pp. 422-430 (2011).
Li, M., et al., "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).
Liao, H.-X., et al., "Co-Evolution of a Broadly Neutralizing HIV-1 Antibody and Founder Virus," Nature, vol. 496, No. 7446, pp. 469-476, Author Manuscript—25 total pages (Apr. 25, 2013).
Liao, H.-X., et al., "High-Throughput Isolation of Immunoglobulin Genes from Single Human B Cells and Expression as Monoclonal Antibodies," Journal of Virological Methods, vol. 158, Nos. 1-2, pp. 171-179, Author Manuscript—22 total pages (Jun. 2009).
Liao, J. H., et al., "A Multivalent Marine Lectin from Crenomytilus grayanus Possesses Anti-cancer Activity through Recognizing Globotriose Gb3," J. Am. Chem. Soc., vol. 138, pp. 4787-4795 (Mar. 24, 2016).

Liu, M., et al., "Polyreactivity and Autoreactivity Among HIV-1 Antibodies," Journal of Virology, vol. 89, No. 1, pp. 784-798 (Jan. 2015).
Mascola, J. R, and Haynes, B. F., "HIV-1 neutralizing antibodies: understanding nature's pathways," Immunol. Rev., vol. 254, No. 1, pp. 225-244, Author Manuscript—29 total pages (Jul. 2013).
McCafferty, J., et al., "Phage Antibodies: filamentous phase displaying antibody variable domains," Nature, vol. 348, pp. 552-554 (Dec. 6, 1990).
McDonald, I. K. and Thornton, J. M., "Satisfying Hydrogen Bonding Potential in Proteins," J. Mol. Biol., vol. 238, pp. 777-793 (Feb. 22, 1994).
McGuire, A. T., et al., "Engineering HIV Envelope Protein to Activate Germline B Cell Receptors of Broadly Neutralizing Anti-CD4 Binding Site antibodies," Journal of Experimental Medicine, vol. 210, No. 4, 9 total pages (Mar. 25, 2013).
Moldt, B., et al., "A Nonfucosylated Variant of the Anti-HIV-1 Monoclonal Antibody b12 Has Enhanced FcγRIIIa-Mediated Antiviral Activity in Vitro but Does Not Improve Protection Against Mucosal SHIV Challenge in Macaques," Journal of Virology, vol. 86, No. 11, pp. 6189-6196, (Jun. 2012).
Montefiori, D. C., "Measuring HIV Neutralization in a Luciferase Reporter Gene Assay," HIV Protocols: Methods in Molecular Biology, vol. 485, pp. 395-405 (2009).
Moore, P., et al., "Application of Dual Affinity Retargeting Molecules to Achieve Optimal Redirected T-cell Killing of B-cell Lymphoma," Blood Journal, vol. 117, No. 17, pp. 4542-4551 (2011).
Nagorsen, D. and Baeuerle, P. A., "Immunomodulatory therapy of cancer with T cell-engaging BiTE antibody blinatumomab," Exp. Cell Res., vol. 317, pp. 1255-1260 (Mar. 16, 2011).
Needleman, S. B., et al., "A General Method Applicable to the Search for Similarities in the Amino Acid Sequence of Two Proteins," Journal of Molecular Biology, vol. 48, No. 3, pp. 443-453 (Mar. 28, 1970).
Otwinowski, Z., and Minor, W., "Processing of X-ray Diffraction Data Collected in Oscillation Mode," Methods Enzymol., vol. 276, pp. 307-326 (1997).
Pearson, W. R., et al., "Improved Tools for Biological Sequence Comparison," Proceedings of the National Academy of Sciences U.S.A., vol. 85, No. 8, pp. 2444-2448 (Apr. 1988).
Pettersen, E. F., et al., "UCSF Chimera—A Visualization System for Exploratory Research and Analysis," Journal of Computational Chemistry, vol. 25, No. 13, pp. 1605-1612 (Oct. 25, 2004).
Protein Data Bank Accession Nos. 5F90_A and 5F90_B, last downloaded from https://www.ncbi.nlm.nih.gov/ on Jul. 24, 2018 (2 total pages).
Protein Data Bank Accession Nos. 5F96_G, 5F96_H and 5F96_L, last downloaded from https://www.ncbi.nlm.nih.gov/ on Jul. 24, 2018 (3 total pages).
Protein Data Bank Accession Nos. 5F9W_A, 5F9W_B, 5F9W_C, 5F9W_G, 5F9W_H and 5F9W_L, last downloaded from https://www.ncbi.nlm.nih.gov/ on Jul. 24, 2018 (6 total pages).
Pugach, P., et al. "A Native-Like SOSIP.664 Trimer Based on an HIV-1 Subtype B env Gene," Journal of Virology, vol. 89, No. 6, pp. 3380-3395 (Mar. 2015).
Ridgway, J. B. B., et al., "'Knobs-Into-Holes' Engineering of Antibody CH3 Domains for Heavy Chain Heterodimerization," Protein Engineering, vol. 9, No. 7, pp. 617-621 (1996).
Robbie, G. J., et al., "A Novel Investigational Fc-Modified Humanized Monoclonal Antibody, Motavizumab-YTE, Has an Extended Half-Life in Healthy Adults," Antimicrobial Agents and Chemotherapy, vol. 57, No. 12, pp. 6147-6153 (Dec. 2013).
Romain, G., et al., "Antibody Fc Engineering Improves Frequency and Promotes Kinetic Boosting of Serial Killing Mediated by NK Cells," Blood Journal, vol. 124, No. 22, pp. 3241-3249, (Nov. 20, 2014).
Rouet, R., et al., "Bispecific Antibodies with Native Chain Structure," Nature Biotechnology, vol. 32, No. 2, 136-137 (Feb. 2014).
Rudicell, R. S., et al., "Enhanced Potency of a Broadly Neutralizing HIV-I Antibody in Vitro Improves Protection against Lentiviral Infection in Vivo," Journal of Virology, vol. 88, No. 21, pp. 12669-12682 (Nov. 2014).

(56) References Cited

OTHER PUBLICATIONS

Sanders, R. W., et al., "A Next-Generation Cleaved, Soluble HIV-1 Env Trimer, BGSOS SOSIP.664 gp140, Expresses Multiple Epitopes for Broadly Neutralizing but Not Non-Neutraliging Antibodies," Public Library of Science Pathogens, vol. 9, No. 9, pp. 1-20 (Sep. 19, 2013).
Sarzotti-Kelsoe, M., et al., "Optimization and Validation of the TZM-bl Assay for Standardized Assessments of Neutralizing Antibodies Against HIV-1," Journal of Immunoligical Methods, vol. 409, pp. 131-146, Author Manuscript—37 total pages (Jul. 2014).
Scheid, J. F., et al., "Broad Diversity of Neutralizing Antibodies Isolated from Memory B Cells in HIV-infected Individuals," Nature, vol. 458, No. 7238, pp. 636-640, Abstract Only—2 total pages (Apr. 2, 2009).
Scheid, J. F., et al., "Sequence and Structural Convergence of Broad and Potent HIV Antibodies that Mimic CD4 Binding," Science, vol. 333, No. 6049, pp. 1633-1637, Author Manuscript—11 pages (Sep. 16, 2011).
Scheres, S. H., "A Bayesian View on Cryo-EM Structure Determination," Journal of Molecular Biology, vol. 415, Nos. 2-4, 20 total pages (Jan. 13, 2012).
Seaman, M. S., et al., "Tiered Categorization of a Diverse Panel of HIV-1 Env Pseudoviruses for Assessment of Neutralizing Antibodies," Journal of Virology, vol. 84, No. 3, pp. 1439-1452 (Feb. 2010).
Seimetz, D., et al., "Development and approval of the trifunctional antibody catumaxomab (anti-EpCAM × anti-CD3) as a targeted cancer immunotherapy," Cancer Treatment Reviews, vol. 36, No. 6, pp. 458-467 (Oct. 2010).
Shields, R. L., et al., "High Resolution Mapping of the Binding Site on Human IgG1 for $Fc_\gamma RI$, $Fc_\gamma RII$, $Fc_\gamma RIII$, and FcRn and Design of IgG1 Variants with Improved Binding to the $Fc_\gamma R$," Journal of Biological Chemistry, vol. 276, No. 9, pp. 6591-6604 (Mar. 2, 2001).
Shingai, M., et al., "Antibody Mediated Immunotherapy of Macaques Chronically Infected with SHIV Suppresses Viremia," Nature, vol. 503, No. 7475, pp. 277-280, Author Manuscript—21 total pages (Nov. 14, 2013).
Smith, T. F. and Waterman, M. S., "Comparison of Biosequences," Adv. Appl. Math., vol. 2, pp. 482-489 (1981).
Songsivilai, S., "Bispecific Antibody: A Tool for Diagnosis and Treatment of Disease," Clinical and Experimental Immunology, vol. 79, No. 3, pp. 315-321 (Mar. 1990).
Stone, A., "Multipurpose prevention technologies for reproductive and sexual health," Reprod. Health Matters, vol. 22, No. 44, pp. 213-217 (2014).
Sui, Z. W., et al, "Cross-Protection Against Influenza Virus Infection by Intranasal Administration of M2-Based Vaccine with Chitosan as an Adjuvant," Archives of Virology, vol. 155, No. 4, pp. 535-544, Abstract Only—2 total pages (Apr. 2010).
Suloway, C., et al., "Automated Molecular Microscopy: the New Leginon System," Journal of Structural Biology, vol. 151, No. 1, pp. 41-60, Abstract Only—2 total pages (Jul. 2005).
Tang, G., et al., "EMAN2: An Extensible Image Processing Suite for Electron Microscopy," Journal of Structural Biology, vol. 157, No. 1, 9 total pages (Jan. 2007).
Tomaras, G. D., et al., "Initial B-Cell Responses to Transmitted Human Immunodeficiency Virus Type 1: Virion-Binding Immunoglobulin M (IgM) and IgG Antibodies Followed by Plasma Anti-gp41 Antibodies with Ineffective Control of Initial Viremia," Journal of Virology, vol. 82, No. 24, pp. 12449-12463 (Dec. 2008).
U.S. Appl. No. 61/972,531 entitled "Compositions Comprising CH505 Sensitive Envelopes" filed Mar. 31, 2014 (105 total pages).
U.S. Appl. No. 62/027,427 entitled "Compositions Comprising CH505 Sensitive Envelopes" filed Jul. 22, 2014 (175 total pages).
U.S. Appl. No. 62/170,558 entitled "Neutralizing Antibodies to HIV-1 ENV and Their Use" filed Jun. 3, 2015 (135 total pages).
van Dongen, J. J., et al., "Design and Standardization of PCR Primers and Protocols for Detection of Clonal Immunoglobulin and T-Cell Receptor Gene Recombinations in Suspect Lymphoproliferations: Report of the BIOMED-2 Concerted Action BMH4-CT98-3936," Leukemia, vol. 17, No. 12, pp. 2257-2317, Abstract Only—2 total pages (Dec. 12, 2003).
Venturi, V., et al., "A Mechanism for TCR Sharing Between T Cell Subsets and Individuals Revealed by Pyrosequencing," Journal of Immunology, vol. 186, pp. 4285-4294 (Mar. 7, 2011).
Verkoczy, L., et al., "Autoreactivity in an HIV-1 Broadly Reactive Neutralizing Antibody Variable Region Heavy Chain Induces Immunologic Tolerance," Proceedings of the National Academy of Sciences of the United States of America, vol. 107, No. 1, pp. 181-186 (Jan. 5, 2010).
Verkoczy, L., et al., "Induction of HIV-1 Broad Neutralizing Antibodies in 2F5 Knock-in Mice: Selection against Membrane Proximal External Region—Associated Autoreactivity Limits T-Dependent Responses," Journal of Immunology, vol. 191, No. 5, pp. 2538-2550, Author Manuscript—24 total pages (Sep. 1, 2013).
Verkoczy, L., et al., "Role of Immune Mechanisms in Induction of HIV-1 Broadly Neutralizing Antibodies," Current Opinions in Immunology, vol. 23, No. 3, pp. 383-390, Author Manuscript—12 total pages (Jun. 2011).
Wu, C., et al., "Generation and Characterization of a Dual Variable Domain Immunoglobulin (DVD-Ig™) Molecule," Antibody Engineering, vol. 2, Springer Berlin Heidelberg, 23 total pages (2010).
Wu, X., et al., "Focused Evolution of HIV-1 Neutralizing Antibodies Revealed by Structures and Deep Sequencing," Science, vol. 333, No. 6049, pp. 1593-1602, Author Manuscript—17 total pages (Sep. 16, 2011).
Wu, X., et al., "Maturation and Diversity of the VRC01-Antibody Lineage over 15 Years of Chronic HIV-I Infection," Cell, vol. 161, No. 3, pp. 470-485, Author Manuscript—31 total pages (Apr. 23, 2015).
Wu, X., et al., "Rational Design of Envelope Identifies Broadly Neutralizing Human Monoclonal Antibodies to HIV-1," Science, vol. 329, No. 5993, pp. 856-861, Author Manuscript—12 total pages (Aug. 13, 2010).
Xie, Z., et al., "A New Format of Bispecific Antibody: Highly Efficient Heterodimerization, Expression and Tumor Cell Lysis," Journal of Immunological Methods, vol. 296, Nos. 1-2 pp. 95-101 (Nov. 19, 2014).
Yang, G., et al., "Identification of Autoantigens Recognized by the 2F5 and 4E10 Broadly Neutralizing HIV-1 Antibodies," The Journal of Experimental Medicine, vol. 210, No. 2, pp. 241-256 (2013).
Yang, L., et al., "Passive Immunization against HIV/AIDS by Antibody Gene Transfer," Viruses, vol. 6, pp. 428-447 (2014).
Zalevsky, et al., "Enhanced Antibody Half-Life Improves in vivo Activity," Nature Biotechnology, vol. 28, No. 2, pp. 157-159, Author Manuscript—6 total pages (Feb. 2010).
Zhou, T., et al., "Structural Basis for Broad and Potent Neutralization of HIV-1 by Antibody VRC01," Science, vol. 329, No. 5339, pp. 811-817, Author Manuscript—19 total pages (Aug. 13, 2010).
Zhou, T., et al., "Structural Definition of a Conserved Neutralization Epitope on HIV-I gp120," Nature, vol. 445, No. 7129, pp. 732-737, Author Manuscript—15 total pages (Feb. 15, 2007).
Zhou, T., et al., "Structural Repertoire of HIV-I-Neutralizing Antibodies Targeting the CD4 Supersite in 14 Donors," Cell, vol. 161, No. 6, pp. 1280-1292, Author Manuscript—26 total pages (Jun. 4, 2015).

\* cited by examiner

>DH542_nt_HC (SEQ ID NO: 1)

CAGGTGCAGCTGGTGCAGTCTGGGGCTCAAATGAAGAACCCTGGGGCCT
CAGTGAAGGTCTCCTGCGCGCCTTCTGGATATACCTTCACCGACTTTTACA
TACATTGGTTGCGCCAGGCCCCTGGCCAGGGGCTTCAGTGGATGGGATG
GATGAACCCTCAGACTGGTCGCACAAACACTGCACGAAACTTTCAGGGG
AGGGTCACCATGACCAGGGACACGTCCATCGGCACAGCCTACATGGAGT
TGAGAAGCCTGACATCTGACGACACGGCCATATATTACTGTACGACAGG
GGGATGGATCAGTCTTTACTATGATAGTAGTTATTACCCCAACTTTGACC
ACTGGGGTCAGGGAACCCTGCTCACCGTCTCCTCAG

>DH542_nt_LC (SEQ ID NO: 2)

ACCAGTCTGCTGACTCAGCCTGCCTCCGTGTCTGGGTCTCCTGGACAGTC
GATCACCATCTCCTGCACTGGAACCAAGTATGATGTTGGGAGTCATGACC
TTGTCTCCTGGTACCAACAGTACCCAGGCAAAGTCCCCAAATACATGATTT
ATGAAGTCAATAAACGGCCCTCAGGAGTTTCTAATCGCTTCTCTGGCTCC
AAATCTGGCAACACGGCCTCCCTGACAATCTCTGGGCTCCGGGCTGAGGA
CGAGGCTGACTATTATTGCTGTTCATTTGGAGGGAGTGCCACCGTGGTCT
GCGGCGGCGGGACCAAGGTGACCGTCCTAG

>DH542_aa_HC (SEQ ID NO: 3)

QVQLVQSGAQMKNPGASVKVSCAPSGYTFTDFYIHWLRQAPGQGLQWM
GWMNPQTGRTNTARNFQGRVTMTRDTSIGTAYMELRSLTSDDTAIYYCTT
GGWISLYYDSSYYPNFDHWGQGTLLTVSS

>DH542_aa_LC (SEQ ID NO: 4)

TSLLTQPASVSGSPGQSITISCTGTKYDVGSHDLVSWYQQYPGKVPKYMIYE
VNKRPSGVSNRFSGSKSGNTASLTISGLRAEDEADYYCCSFGGSATVVCGGG
TKVTVL

FIG. 1

DH270 lineage - Heavy chain nucleotide sequences

```
                             ....|....| ....|....| ....|....| ....|....| ....|....|
                                     10         20         30         40         50
UCA(SEQ ID NO:5)             CAGGTGCAGC TGGTGCAGTC TGGGGCTGAG GTGAAGAAGC CTGGGGCCTC
I5(SEQ ID NO:6)              CAGGTGCAGC TGGTGCAGTC TGGGGCTGAG RTGAAGAAGC CTGGGGCCTC
I1(SEQ ID NO:7)              CAGGTGCAGC TGGTGCAGTC TGGGGCTGAG DTGAAGAAGC CTGGGGCCTC
DH473H(SEQ ID NO:8)          GAGGTTCAGC TGGTGGAGTC TGGGGCTGAG TTGAAGGAGC CTGGGGCCTC
DH391H(SEQ ID NO:9)          CAGGTGCAGC TGGTGCAGTC TGGGGCTGAA CTGAAGAAGC CTGGGGCCTC
I4(SEQ ID NO:10)             CAGGTGCAGC TGGTGCAGTC TGGGGCTGAG ATGAAGAAGC CTGGGGCCTC
I3(SEQ ID NO:11)             CAGGTGCAGC TGGTGCAGTC TGGGGCTGAA ATGAAGAACC CTGGGGCCTC
DH542H(SEQ ID NO:12)         CAGGTGCAGC TGGTGCAGTC TGGGGCTCAA ATGAAGAACC CTGGGGCCTC
I2(SEQ ID NO:13)             CAGGTGCAGC TGGTGCAGTC TGGGGCTGAA ATGAAGAACC CTGGGGCCTC
DH471H(SEQ ID NO:14)         CAGGTGCAGC TGGTGCAGTC TGGGGCTGAA GTGAAGAACC CTGGGGCCTC
DH429H(SEQ ID NO:15)         GAGGTGCAGC TGGTGCAGTC TGGGGCTGAA ATGAAGAACC CTGGGGCCTC
DH270H(SEQ ID NO:16)         CAGGTGCAGC TGGTGCAGTC TGGGGCTGAG ATGAAGAAGC CTGGGGCCTC

....|....| ....|....| ....|....| ....|....| ....|....|
                                     60         70         80         90        100
UCA                          AGTGAAGGTC TCCTGCAAGG CTTCT                         A
I5                           AGTGAAGGTC TCCTGCAAGG CTTCT                         A
I1                           AGTGAAGGTC TCCTGCAAGG CTTCT                         A
DH473H                       AGTGAAAGTC TCCTGCAAGG CTTCT                         A
DH391H                       AGTGAAGGTC TCCTGCAAGG CTTCT                         G
I4                           AGTGAAGGTC TCCTGCAAGG CTTCT                         A
I3                           AGTGAAGGTC TCCTGCGCGS CTTCT                         A
DH542H                       AGTGAAGGTC TCCTGCGCGC CTTCT                         A
I2                           AGTGAAAGTC TCCTGCGCGS CTTCT                         A
DH471H                       AGTGAAAGTC TCCTGCGCGC CTTCT                         A
DH429H                       AGTGAAAGTC TCCTGCGCGG CTTCT                         A
DH270H                       AGTGAGGGTC TCCTGCAAGG CTTCT                         A

....|....| ....|....| ....|....| ....|....| ....|....|
                                    110        120        130        140        150
UCA                          TGCACTGGGT GCGACAGGCC CCTGGACAAG GGCTTGAGTG GATGGGATGG
I5                           TACACTGGGT GCGACAGGCC CCTGGACAAG GGCTTGAGTG GATGGGATGG
I1                           TACACTGGGT GCGACAGGCC CCTGGACAAG GGCTTGAGTG GATGGCATGG
DH473H                       TACACTGGGT GCGACAGGCC CCTGGACAAG GTCTTGAGTG GATGGCATGG
DH391H                       TACACTGGCT GCGACAGGCC CCTGGACAGG GGCTTGAGTG GGTGGCTTGG
I4                           TACACTGGGT GCGACAGGCC CCTGGACAAG GGCTTGAGTG GATGGGATGG
I3                           TACACTGGGT GCGACAGGCC CCTGGACAAG GGCTTSAGTG GATGGGATGG
DH542H                       TACATTGGTT GCGCCAGGCC CCTGGCCAGG GGCTTCAGTG GATGGGATGG
I2                           TACACTGGGT GCGACTGGCC CCTGGACAAG GGCTTSAGTG GATGGGATGG
DH471H                       TACACTGGGT GCGACTGGCC CCTGGACAAG GGCTTGAGTG GCTGGGGTGG
DH429H                       TACACTGGGT GCGACTGGCC CCTGGACACG GGCTCCAGTG GATGGGATGG
DH270H                       TACACTGGGT GCGACAGGCC CCTGGACAAG GGCCTGAGTG GATGGGATGG

....|....| ....|....| ....|....| ....|....| ....|....|
                                    160        170        180        190        200
UCA                                                         ACTAT GCACAGAAGT TCAGGGCAG
I5                                                          AACTMT GCACAGAAGT TCAGGGCAG
I1                                                          ARCTMT GCACGGAAGT TCAGGGCAG
DH473H                                                      AGCTTT GCCCGGGGGT TCAGGGCAG
```

FIG. 2

|        |                                              |
|--------|----------------------------------------------|
| DH391H | ░░░░░░░░░░ ░░░░░░░░░░ ░░░ATCTCT CCACGGAAGT TTCAGGGCAG |
| I4     | ░░░░░░░░░░ ░░░░░░░░░░ ░░░AACTMT GCACAGAAGT TTCAGGGCAG |
| I3     | ░░░░░░░░░░ ░░░░░░░░░░ ░░░AACAMT GCACAAAACT TTCAGGGCAG |
| DH542H | ░░░░░░░░░░ ░░░░░░░░░░ ░░░AACACT GCACGAAACT TTCAGGGGAG |
| I2     | ░░░░░░░░░░ ░░░░░░░░░░ ░░░AATAAT GCACAAAACT TTCAGGGCAG |
| DH471H | ░░░░░░░░░░ ░░░░░░░░░░ ░░░AATCAA GGACAAAACT TTCAGGGCAG |
| DH429H | ░░░░░░░░░░ ░░░░░░░░░░ ░░░AATAAT GCACAAGATT TTCAGGGCAG |
| DH270H | ░░░░░░░░░░ ░░░░░░░░░░ ░░░AACTCT CCACAGAAGT TTCAGGGCAG |

```
            ....|....| ....|....| ....|....| ....|....| ....|....|
                210        220        230        240        250
UCA         GGTCACCATG ACCAGGGACA CGTCCATCAG CACAGCCTAC ATGGAGCTGA
I5          GGTCACCATG ACCAGGGACA CGTCCATCAG CACAGCCTAC ATGGAGCTGA
I1          GGTCACCATG ACCAGGGACA CGTCCATCAG CACRGCCTAC ATGGAACTGA
DH473H      GGTCACCATG ACCAGGGAAA CGTCCGTCAG CACGGCCTAT ATGGAACTGA
DH391H      GGTCACGATG ACTACGGACA CGTCCATGAA TGTTGCCTAC ATGGAACTGA
I4          GGTCACCATG ACCAGGGACA CGTCCATCAG CACAGCCTAC ATGGAGCTGA
I3          GGTCACCATG ACCAGGGACA CGTCCATCGG CACAGCCTAC ATGGAGYTGA
DH542H      GGTCACCATG ACCAGGGACA CGTCCATCGG CACAGCCTAC ATGGAGTTGA
I2          GGTCACCATG ACCAGGGACA CGTCCATCGG CACAGCCTAC ATGGAGYTGA
DH471H      GGTCACCATG ACCAGGGACA CGTCCATCGG CACAGCCTAC ATGGAGTTGA
DH429H      GGTCACCCTG ACCAGGGACA CGTCCATCGG CACAGCCTAC ATGGAGCTGA
DH270H      GGTCACCATG ACCAGGGACA CGTCCATCAG CACAGCCTAC ATGGACCTGA
```

|        |                                              |
|--------|----------------------------------------------|
|        | CDR3                                         |
|        | ....\|....\| ....\|....\| ....\|....\| ....\|....\| ....\|....\| |
|        | 260        270        280        290        300 |
| UCA    | GCAGGCTGAG ATCTGACGAC ACGGCCGTGT ATTACTGTGC GAGAGGGGGR |
| I5     | GCAGVCTGAG ATCTGACGAC ACGGCCGTGT ATTACTGTGC GAGAGGGGGR |
| I1     | GAAGMCTGAG ATCTGACGAC ACGGCCGTCT ATTACTGTGC GAGAGGGGGA |
| DH473H | GAAGACTGAG ATCTGACGAC ACGGCCGTGT ATTACTGTGC GAAAGCGGGA |
| DH391H | GAGGCTTGAG ATCTGACGAC ACGGCCGTCT ATTTCTGTGC GAGAGGGGGA |
| I4     | GCAGVCTGAC ATCTGACGAC ACGGCCGTGT ATTACTGTGC GACAGGGGGR |
| I3     | GVAGCCTGAC ATCTGACGAC ACGGCCGTVT ATTACTGTGC GACAGGGGGR |
| DH542H | GAAGCCTGAC ATCTGACGAC ACGGCCATAT ATTACTGTAC GACAGGGGGA |
| I2     | GGAGCCTGAC ATCTGACGAC ACGGCCGTCT ATTACTGTGT GACAGGGGGR |
| DH471H | GGAGCCTCAC ATCTGACGAC ACGGCCGTCT ATTACTGTGT GACAGGGGCC |
| DH429H | GGAGGCTGAC ATCTGACGAC ACGGCCGTCT ATTACTGTGT GACAGGGGGG |
| DH270H | ACAGACTGAC GTCTGACGAC ACGGCCATGT ATTACTGTAC GACCGGGGGG |

|        |                                              |
|--------|----------------------------------------------|
|        | ....\|....\| ....\|....\| ....\|....\| ....\|....\| ....\|....\| |
|        | 310        320        330        340        350 |
| UCA    | TGGATCRGTC TTTACTATGA TAGTAGTGGT TACCCTAACT TTGACTACTG |
| I5     | TGGATCRGTC TTTACTATGA TAGTAGTGGT TACCCTAACT TTGACTACTG |
| I1     | TGGATCRGTC TTTACGTTGA TTATAGTGGT TACCCTAACT TTGACTCCTG |
| DH473H | TACATCGCCC TTTACGTTGA CTATAGTGGT TACCCTAACT TTAATTCCTG |
| DH391H | TGGATCAGTC TCTACGTTGA TTACAGTTAT TACCCTAACT TTGACTCGTG |
| I4     | TGGATCRGTC TTTACTATGA TAGTAGTGGT TACCCTAACT TTGACTACTG |
| I3     | TGGATCAGTC TTTACTATGA TAGTAGTTAT TACCCTAACT TTGACCACTG |
| DH542H | TGGATCAGTC TTTACTATGA TAGTAGTTAT TACCCCAACT TTGACCACTG |
| I2     | TGGATCAGTC HTTATTATGA TAGTAGTTAT TACCCTAACT TTGACCACTG |
| DH471H | TGGATCAGTC ATTATTATGA TAGTAGTTAT TATCCTAACT TTGACCACTG |

FIG. 2 cont.

```
DH429H    TGGATCAGTC CTTATTATGA TAGTAGTTAT TACCCTAATT TTGACTACTG
DH270H    TGGATCGGTC TTTACTCTGA TAGTAGTCGT TACCCTAACT TTGACTACTG
```

```
                    ....|....| ....|....| ....|....| ..
                       360        370        380
        UCA     GGGCCAGGGA ACCCTGGTCA CCGTCTCCTC AG
        I5      GGGCCAGGGA ACCCTGGTCA CCGTCTCCTC AG
        I1      GGGCCAGGGA ACCCTGGTCA CCGTCTCCTC AG
        DH473H  GGGCCAGGGA ACCCTGGTCA CCGTCTCCTC AG
        DH391H  GGGCCAGGGA ACCCTGGTCT CCGTCTCTTC AG
        I4      GGGCCAGGGA ACCCTGGTCA CCGTCTCCTC AG
        I3      GGGTCAGGGA ACCCTGGTCA CCGTCTCCTC AG
        DH542H  GGGTCAGGGA ACCCTGCTCA CCGTCTCCTC AG
        I2      GGGTCAGGGA ACCCTGGTCA CCGTCTCCTC AG
        DH471H  GGGTCAGGGA ACCCTGGTCA CCGTCTCCTC AG
        DH429H  GGGTCAGGGA ACCCTGATCA CCGTCTCCTC AG
        DH270H  GGGCCAGGGA ACCCTGGTCA CCGTCTCCTC AG
```

FIG. 2 cont.

DH270 lineage - Heavy chain amino acid sequences

```
                         ....|....| ....|....| ....|....| ....|....| ....|....|
                              10         20         30         40         50
UCA(SEQ ID NO:17)        QVQLVQSGAE VKKPGASVKV SCKAS      MHWVRQA PGQGLEWMGW
I5(SEQ ID NO:18)         QVQLVQSGAE XKKPGASVKV SCKAS      IHWVRQA PGQGLEWMGW
I1(SEQ ID NO:19)         QVQLVQSGAE XKKPGASVKV SCKAS      IHWVRQA PGQGLEWMAW
DH473H(SEQ ID NO:20)     EVQLVESGPE LKEPGASVKV SCKAS      IHWVRQA PGQGLEWMAW
DH391H(SEQ ID NO:21)     QVQLVQSGAE LKKPGASVKV SCKAS      VHWLRQA PGQGLEWVAW
I4(SEQ ID NO:22)         QVQLVQSGAE MKKPGASVKV SCKAS      IHWVRQA PGQGLEWMGW
I3(SEQ ID NO:23)         QVQLVQSGAE MKNPGASVKV SCKXS      IHWVRQA PGQGLXWMGW
DH542H(SEQ ID NO:24)     QVQLVQSGAQ MKNPGASVKV SCAPS      IHWLRQA PGQGLQWMGW
I2(SEQ ID NO:25)         QVQLVQSGAE MKNPGASVKV SCAXS      IHWVRLA PGQGLXWMGW
DH471H(SEQ ID NO:26)     QVQLVQSGAE VKNPGASVKV SCAPS      IHWVRLA PGQGLEWLGW
DH429H(SEQ ID NO:27)     EVQLVQSGAE MKNPGASVKV SCAAS      IHWVRLA PGHGLQWMGW
DH270H(SEQ ID NO:28)     QVQLVQSGAE MKKPGASVRV SCKAS      IHWVRQA PGQGPEWMGW

CDR3
                         ....|....| ....|....| ....|....| ....|....| ....|....|
                              60         70         80         90        100
UCA                             NY AQKFQGRVTM TRDTSISTAY MELSRLRSDD TAVYYCARGX
I5                              NX AQKFQGRVTM TRDTSISTAY MELSXLRSDD TAVYYCARGX
I1                              XX ARKFQGRVTM TRDTSISXAY MELRXLRSDD TAVYYCARGG
DH473H                          SF ARGFQGRVTM TRETSVSTAY MELRRLRSDD TAVYYCAKAG
DH391H                          IS PRKFQGRVTM TTDTSMNVAY MELRGLRSDD TAVYFCARGG
I4                              NX AQKFQGRVTM TRDTSISTAY MELSXLTSDD TAVYYCATGX
I3                              NX AQNFQGRVTM TRDTSIGTAY MEXXSLTSDD TAXYYCATGX
DH542H                          NT ARNFQGRVTM TRDTSIGTAY MELRSLTSDD TAIYYCTTGG
I2                              NN AQNFQGRVTM TRDTSIGTAY MEXRSLTSDD TAVYYCVTGX
DH471H                          NQ GQNFQGRVTM TRDTSIGTAY MELRSLTSDD TAVYYCVTGA
DH429H                          NN AQDFQGRVTL TRDTSIGTAY MELRRLTSDD TAVYYCVTGG
DH270H                          NS PQKFQGRVTM TRDTSISTAY MDLNRLTSDD TAMYYCTTGG

....|....| ....|....| ....|..
                              110        120
UCA                      WIXLYYDSSG YPNFDYWGQG TLVTVSS
I5                       WIXLYYDSSG YPNFDYWGQG TLVTVSS
I1                       WIXLYVDYSG YPNFDSWGQG TLVTVSS
DH473H                   YIALYVDYSG YPNFNSWGQG TLVTVSS
DH391H                   WISLYVDYSY YPNFDSWGQG TLVSVSS
I4                       WIXLYYDSSG YPNFDYWGQG TLVTVSS
I3                       WISLYYDSSY YPNFDHWGQG TLVTVSS
DH542H                   WISLYYDSSY YPNFDHWGQG TLLTVSS
I2                       WISKYYDSSY YPNFDHWGQG TLVTVSS
DH471H                   WISDYYDSSY YPNFDHWGQG TLVTVSS
DH429H                   WISPYYDSSY YPNFDHWGQG TLITVSS
DH270H                   WIGLYSDTSG YPNFDYWGQG TLVTVSS
```

FIG. 2 cont.

DH270 lineage - Light chain nucleotide sequences

```
                        ....|....| ....|....| ....|....| ....|....| ....|....|
                            10         20         30         40         50
UCA(SEQ ID NO:29)       CAGTCTGCCC TGACTCAGCC TGCCTCCGTG TCTGGGTCTC CTGGACAGTC
I5(SEQ ID NO:30)        CAGTCTGCCC TGACTCAGCC TGCCTCCGTG TCTGGGTCTC CTGGACAGTC
I1(SEQ ID NO:31)        CAGTCTGCCC TGACTCAGCC TGCCTCCGTG TCTGGGTCTC CTGGACAGTC
DH473H(SEQ ID NO:32)    CAGTCTGCCC TGACTCAGCC TGCCTCCGTG TCTGGGTCTC CTGGCCAGTC
DH391H(SEQ ID NO:33)    CAGCCTGTGC TGACTCAGCC TGCCTCCGTG TCTGGGTCTC CTGGACAGTC
I4(SEQ ID NO:34)        CAGTCTGCCC TGACTCAGCC TGCCTCCGTG TCTGGGTCTC CTGGACAGTC
I3 (SEQ ID NO:35)       CAGTCTGYSC TGACTCAGCC TGCCTCCGTG TCTGGGTCTC CTGGACAGTC
DH542H(SEQ ID NO:36)    ACCAGTCTGC TGACTCAGCC TGCCTCCGTG TCTGGGTCTC CTGGACAGTC
I2(SEQ ID NO:37)        CAGTCTGYSC TGACTCAGCC TGCCTCCGTG TCTGGGTCTC CTGGACAGTC
DH471H(SEQ ID NO:38)    CTGCCTGTGC TGACTCAGCC TGCCTCCGTG TCTGGGTCTC CTGGGCAGTC
DH429H(SEQ ID NO:39)    CAGTCTGCCC TGACTCAGCC TGCCTCCGTG TCTGGGTCTC CTGGACAGTC
DH270H(SEQ ID NO:40)    CAGTCTGCCC TGACTCAGCC TGCCTCCGTG TCTGGGTCTC CTGGACAGTC

....|....| ....|....| ....|....| ....|....| ....|....|
                            60         70         80         90        100
UCA                     GATCACCATC TCCTGCACTG GAACC
I5                      GATCACCATC TCCTGCACTG GAACC
I1                      GATCACCATC TCCTGCACTG GAACC
DH473H                  GATCACCATC TCCTGCACTG GAACC
DH391H                  GATCACCATC TCCTGCACTG GAAGC
I4                      GATCACCATC TCCTGCACTG GAACC
I3                      GATCACCATC TCCTGCACTG GAACC
DH542H                  GATCACCATC TCCTGCACTG GAACC
I2                      GATCACCATC TCCTGCACTG GAACC
DH471H                  GATCACCATC TCCTGCACTG GGACC
DH429H                  GATCACCATC TCCTGCACTG GAACC
DH270H                  GATCACCATC TCCTGCACTG GAACC

....|....| ....|....| ....|....| ....|....| ....|....|
                           110        120        130        140        150
UCA                          GTCTCCTG GTACCAACAG CACCCAGGCA AAGCCCCCAA ACTCATGATT
I5                           GTCTCCTG GTACCAACAG CACCCAGGCA AAGCCCCCAA ACTCATGATT
I1                           GTCTCCTG GTACCAACAG CACCCAGGCA AAGCCCCCAA ACTCATGATT
DH473H                       GTCTCCTG GTACCAACAG CACCCAGGCA AAGCCCCCAA ACTCATTATT
DH391H                       GTGTCCTG GTACCAGCAG CACCCAGGCA AAGCCCCCAA ACTGATGATT
I4                           GTCTCCTG GTACCAACAG CACCCAGGCA AAGCCCCCAA ATACATGATT
I3                           GTCTCCTG GTACCAACAG CACCCAGGCA AAGCCCCCAA ATACATGATT
DH542H                       GTCTCCTG GTACCAACAG TACCCAGGCA AAGTCCCCAA ATACATGATT
I2                           GTCTCCTG GTACCAACAG CACCCAGGCA AAGCCCCCAA ATACATGATT
DH471H                       GTCTCCTG GTACCAGCAC CACCCAGGCA AAGCCCCCAA ATATTTGATT
DH429H                       GTCTCCTG GTTCCAACAG CACCCAGGCA AAGCCCCCAA ATACATGATT
DH270H                       GTCTCCTG GTATCAACAG CACCCAGGCA AAGTCCCCAA ATACATAATT

....|....| ....|....| ....|....| ....|....| ....|....|
                           160        170        180        190        200
UCA                     TAT                AAGCGGCC CTCAGGGGTT TCTAATCGCT TCTCTGGCTC
I5                      TAT                AAGCGGCC CTCAGGGGTT TCTAATCGCT TCTCTGGCTC
I1                      TAT                AAGTGGCC CTCAGGGGTT TCTAATCGCT TCTCTGGCTC
```

FIG. 2 cont.

```
DH473H     TAT░░░░░ ░░CAGTGGCC CTCAGGGGTT TCTAAGCGCT TCTCTGGCTC
DH391H     TAT░░░░░ ░░AAGTGGGC CTCAGGGGTT TCTGATCGCT TCGCTGGCTC
I4         TAT░░░░░ ░░AAGCGGCC CTCAGGGGTT TCTAATCGCT TCTCTGGCTC
I3         TAT░░░░░ ░░AAGCGGCC CTCAGGAGTT TCTAATCGCT TCTCTGGCTC
DH542H     TAT░░░░░ ░░AAACGGCC CTCAGGAGTT TCTAATCGCT TCTCTGGCTC
I2         TAT░░░░░ ░░AAGTGGCC CTCAGGAGTT TCTCATCGCT TCTCTGGCTC
DH471H     TAT░░░░░ ░░AAGTGGCC CTCAGGAGTT TCTCATCGCT TCTCTGGCTC
DH429H     TAT░░░░░ ░░AAGTGGCC CTCAGGAGTT TCTCATCGCT TCTCTGGTTC
DH270H     TAT░░░░░ ░░AAGCGGCC CTCAGGGGTT TCTAATCGCT TCTCTGGCTC
```

```
           ....|....| ....|....| ....|....| ....|....| ....|....|
               210        220        230        240        250
UCA        CAAGTCTGGC AACACGGCCT CCCTGACAAT CTCTGGGCTC CAGGCTGAGG
I5         CAAGTCTGGC AACACGGCCT CCCTGACAAT CTCTGGGCTC CAGGCTGAGG
I1         CAAGTCTGGC AACACGGCCT CCCTGACAAT CTCTGGGCTC CAGGCTGAGG
DH473H     CAAGTCTGGC AACACGGCCT CCCTGACAAT CTCTGGGCTC CAGGCTGAGG
DH391H     CAAGTCTGGC AACACGGCCT CCCTGACAAT CTCTAGACTC CAGGCTGAGG
I4         CAAGTCTGGC AACACGGCCT CCCTGACAAT CTCTGGGCTC CAGGCTGAGG
I3         CAAATCTGGC AACACGGCCT CCCTGACAAT CTCTGGGCTC CAGGCTGAGG
DH542H     CAAATCTGGC AACACGGCCT CCCTGACAAT CTCTGGGCTC CGGGCTGAGG
I2         CAAATCTGGC AACACGGCCT CCCTGACAAT CTCTGGGCTC CAGGCTGAGG
DH471H     CAAATCTGGC AACACGGCCT CCCTGACAAT CTCTGGGCTC CAGGTTGAGG
DH429H     CAAATCTGGC AACACGGCCT CCCTGACAAT CTCTGGGCTC CAGGCTGAGG
DH270H     CAAGTCTGGC AACACGGCCT CCCTGACAAT CTCTGGGCTC CAGGCTGAGG
```

```
                                         CDR3
           ....|....| ....|....| ....|....| ....|....| ....|....|
               260        270        280        290        300
UCA        ACGAGGCTGA TTATTACTGC TGCTCATATG CAGGTAGTAG CACTGTAWTA
I5         ACGAGGCTGA TTATTACTGY TGCTCATATG CAGGTAGTAG CACTGTAWTA
I1         ACGAGGCTVA TTATTACTGT TGCTCATATG CAGGTAGTAG CACTGTAATA
DH473H     ACGAGGCTCA TTATTACTGT TGCTCATATG CAGGCAGTAG CACTGTAATA
DH391H     ACGAGGCTAA TTACTTTTGT TCCTCATCTA CAAATAGTGC CACTGTCATA
I4         ACGAGGCTGA TTATTACTGY TGCTCATATG CAGGTAGTAG CACTGTADTW
I3         ACGAGGCTGA CTATTATTGC TGCTCATTTG GAGGTAGTGC CACTGTRGTC
DH542H     ACGAGGCTGA CTATTATTGC TGTTCATTTG GAGGGAGTGC CACCGTGGTC
I2         ACGAGGCTGA CTATTATTGC TGCTCATTCG GAGGTAGTGC CACTGTRGTC
DH471H     ACGAGGCTGA CTATTATTGC TGCTCATTCG GAGGTAGTGC CGCTGTGGTC
DH429H     ACGAGGCTGA CTATTATTGC TGCTCATTCG GAGGTAGTGC CACTGTAGTC
DH270H     ACGAGGCCAC TTATTACTGT TGTTCATATG CAGGTAGTAG CATTATATTT
```

```
                       ....|....| ....|....| ....|....| .
                           310        320        330
           UCA        TTCGGCGGAG GGACCAAGCT GACCGTCCTA G
           I5         TTCGGCGGAG GGACCAAGCT GACCGTCCTA G
           I1         TTCGGCGGAG GGACCAAGCT GACCGTCCTA G
           DH473H     TTCGGCGGAG GGACCTCGCT GACCGTCCTA G
           DH391H     TTCGGCGGAG GGACCAAGCT GACCGTCCTA G
           I4         TTCGGCGGAG GGACCAAGCT GACCGTCCTA G
           I3         TGCGGCGGAG GGACCAAGGT GACCGTCCTA G
           DH542H     TGCGGCGGCG GGACCAAGGT GACCGTCCTA G
           I2         TGCGGCGGAG GGACCAAGGT GACCGTCCTA G
           DH471H     TGCGGCGGAG GGACCAAGGT GACCGTCCTA G
```

FIG. 2 cont.

```
DH429H     TGCGGCGGAG GGACCAAGGT GACCGTCCTA G
DH270H     TTCGGCGGTG GGACCAAGCT GACCGTCATA G
```

DH270 lineage - Light chain amino acid sequences

```
                        ....|....| ....|....| ....|....| ....|....| ....|....|
                            10         20         30         40         50
UCA(SEQ ID NO:41)       QSALTQPASV SGSPGQSITI SCTGT          VSWYQQ HPGKAPKLMI
I5(SEQ ID NO:42)        QSALTQPASV SGSPGQSITI SCTGT          VSWYQQ HPGKAPKLMI
I1(SEQ ID NO:43)        QSALTQPASV SGSPGQSITI SCTGT          VSWYQQ HPGKAPKLMI
DH473H(SEQ ID NO:44)    QSALTQPASV SGSPGQSITI SCTGT          VSWYQQ HPGKAPKLII
DH391H(SEQ ID NO:45)    QPVLTQPASV SGSPGQSITI SCTGS          VSWYQQ HPGKAPKLMI
I4(SEQ ID NO:46)        QSALTQPASV SGSPGQSITI SCTGT          VSWYQQ HPGKAPKYMI
I3(SEQ ID NO:47)        QSXLTQPASV SGSPGQSITI SCTGT          VSWYQQ HPGKAPKYMI
DH542H(SEQ ID NO:48)    TSLLTQPASV SGSPGQSITI SCTGT          VSWYQQ YPGKVPKYMI
I2(SEQ ID NO:49)        QSXLTQPASV SGSPGQSITI SCTGT          VSWYQQ HPGKAPKYMI
DH471H(SEQ ID NO:50)    LPVLTQPASV SGSPGQSITI SCTGT          VSWYQH HPGKAPKYLI
DH429H(SEQ ID NO:51)    QSALTQPASV SGSPGQSITI SCTGT          VSWFQQ HPGKAPKYMI
DH270H(SEQ ID NO:52)    QSALTQPASV SGSPGQSITI SCTGT          VSWYQQ HPGKVPKYII

CDR3
                        ....|....| ....|....| ....|....| ....|....| ....|....|
                            60         70         80         90        100
UCA                     Y   KRPSGV SNRFSGSKSG NTASLTISGL QAEDEADYYC CSYAGSSTVX
I5                      Y   KRPSGV SNRFSGSKSG NTASLTISGL QAEDEADYYX CSYAGSSTVX
I1                      Y   KWPSGV SNRFSGSKSG NTASLTISGL QAEDEAXYYC CSYAGSSTVI
DH473H                  Y   QWPSGV SKRFSGSKSG NTASLTISGL QAEDEAHYYC CSYAGSSTVI
DH391H                  Y   KWASGV SDRFAGSKSG NTASLTISRL QAEDEANYFC SSSTNSATVI
I4                      Y   KRPSGV SNRFSGSKSG NTASLTISGL QAEDEADYYX CSYAGSSTVX
I3                      Y   KRPSGV SNRFSGSKSG NTASLTISGL QAEDEADYYC CSFGGSATXV
DH542H                  Y   KRPSGV SNRFSGSKSG NTASLTISGL RAEDEADYYC CSFGGSATVV
I2                      Y   KWPSGV SHRFSGSKSG NTASLTISGL QAEDEADYYC CSFGGSATXV
DH471H                  Y   KWPSGV SHRFSGSKSG NTASLTISGL QVEDEADYYC CSFGGSAAVV
DH429H                  Y   KWPSGV SHRFSGSKSG NTASLTISGL QAEDEADYYC CSFGGSATVV
DH270H                  Y   KRPSGV SNRFSGSKSG NTASLTISGL QAEDEATYYC CSYAGSSIIF
```

FIG. 2 cont.

| Antibody | IC50 | IC80 | IC50 <50ug/ml | IC80 <5ug/ml | Antibody Specificity |
|---|---|---|---|---|---|
| PGT121 | 0.06 | 0.27 | 63% | 48% | V3-glycan |
| PGT128 | 0.07 | NA | 63% | NA | V3-glycan |
| DH270A1 | 0.07 | 0.22 | 63% | 61% | V3-glycan |
| DH429 | 0.06 | 0.22 | 63% | 60% | V3-glycan |
| VRC01 | 0.27 | 0.73 | 87% | 81% | VH1-2 CD4bs |
| CH31 | 0.10 | 0.42 | 83% | 80% | VH1-2 CD4bs (VRC01-like) |
| CH01 | 3.79 | NA | 46% | NA | V1V2-glycan |
| CH01+ CH31 | 3.73 | NA | 83% | NA | V1V2-glycan + VH1-2 CD4bs |
| CH103 | 4.54 | NA | 55% | NA | HCDR3 binder CD4bs |
| CH98 | 4.20 | NA | 63% | NA | HCDR3 binder CD4bs |
| DH493 | 5.00 | NA | 83% | NA | VH1-46 CD4bs (ANC131-like) |
| DH540 | 0.10 | NA | 90% | NA | N276-dependent CD4bs Ab (HJ16-like) |

FIG. 3

| Antibody | IC50 | IC80 | IC50 <50ug/ml | IC80 <5ug/ml | Antibody Specificity |
|---|---|---|---|---|---|
| DH429 | 0.06 | 0.22 | 63% | 60% | V3-glycan |
| DH512 | 0.65 | 5.12 | 100% | 50% | MPER (10E8-like) |
| CH31 | 0.10 | 0.42 | 83% | 80% | VH1-2 CD4bs (VRC01-like) |
| CH01 | 3.79 | NA | 46% | NA | V1V2-glycan |
| CH01+ CH31 | 3.73 | NA | 93% | NA | V1V2-glycan + VH1-2 CD4bs |
| DH493 | 5.98 | NA | 83% | NA | VH1-46 CD4bs (ANC131-like) |
| DH540 | 0.10 | NA | 90% | NA | N276-dependent CD4bs Ab (HJ16-like) |

FIG. 4

| BnAb | Specificity | Breadth | Median IC50 (ug/ml) |
|---|---|---|---|
| DH512 | gp41 | 100% | 1.09 |
| 10E8 | gp41 | 98% | 0.39 |
| CH557 | CD4bs | 100% | 0.62 |
| VRC01 | CD4bs | 90% | 0.38 |
| VRC07 | CD4bs | 93% | 0.15 |
| DH542 | V3-glycan | 71% | 0.06 |
| PGT121 | V3-glycan | 70% | 0.03 |
| PGT128 | V3-glycan | 72% | 0.02 |

FIG. 5

>DH511VH (SEQ ID NO: 53)

GAGGTTCAGCTGGTGGAGTCTGGGGGAGGCTTGGTGAAGCCGGGGGGGTCTCT
TAGACTCCCCGGTGCAGCCTCTGGTTTCACTTTCACCAACACGTGGATGAGTT
GGGTCCGTCAGGCGCCAGGGAAGGGACTGGAGTGGGTCGGTCGGATTAGCCGG
AACAAAGATGGCGCGAAAACAGAGTACGCCGCACCCGTGAGAGGCAGATTCAC
CATCTCAAGAGATGACTCCAGAGACACATTGTATCTGCAGATGACCAGCCTGA
AAATAGAGGATTCAGGCCGGTATTTTGCACCGCAGATCTTGGGGAGCCCGTG
GTGTCACGATCCATTTTTGAGTGGGGGTCTTATTATTATATGGACCTCTG
GGGCAAGGGGACCACGGTCACCGTCTCTTCA

>DH511VK (SEQ ID NO: 54)

GACATCCAGTTGACCCAGTCTCCATCTCCCCTGTCTGCGTCTGTGGGAGACAC
AGTCACTATCACTTGTCGGGCCAGCCAGAAGATTAGCGACTATTTGAACTGGT
ACCAACAGAAGCCGGGGAGAGCCCCCAAAATACTCATTTACGCTGCGTCCAAG
TTGGGGAGTGGCGTCCCATCAAGGTTCAGTGGCAGTGGATATGGCAGAGATTT
CACTCTCACCATCACCGGTCTGCAGCCTGAAGATTTTGCAACCTATTATTGTC
AGGAGGCTTACAGTTCTACTCCACGTTAACTTTTGGCCAGGGGACCAGGCTG
GATCTCAAAC

>DH512VH (SEQ ID NO: 55)

CAGGTGCAGCTGGTACAGTCTGGGGGAGGTCTGGTGAAGCCGGGGGGGTCCCT
CACACTCTCCTGTTCAGCCTCTGGATTCTTTTTCGATAATTCATGGATGGGGT
GGGTCCGTCAGGCGCCAGGGAAGGGACTGGAGTGGGTTGGCCGCATTAGAAGG
CTCAAAGACGGTGCGACAGGAGAATATGGTGCAGCCGTGAAGGACAGATTCAC
CATTTCAAGAGATGACAGTAGAAATATGCTGTACCTGCACATGAGGACCCTGA
AAACCGAGGACTCAGGCACTTATTATTGTACCATGGATGAGGGGACCCCAGTA
ACACGCTTCTTAGAATGGGGCTACTTCTATTATTATATGGCCGTTTGGGGCAG
AGGGACCACGGTCATCGTCTCTTCA

FIG. 6

>DH512VK (SEQ ID NO: 56)

GACATCGTGATGACCCAGTCTCCGTCCTCCGTGTCTGCATCTGTGGGAGACAG
AGTCACCATCACTTGCCGGGCAAGTCAGAATATTAGAGACTATTTAAATTGGT
ATCAACATAAACCCGGGGGATCCCCTAGACTCCTAATTTATGCTGCGTCAACT
TTGCAAACTGGGGTCCCGTCCAGATTCAGCGGCAGTGGATCTGGGAACCTTTT
CACTCTCACCATTACCAATCTGCAACCTGAAGATTTTGCAACTTATTATTGTC
AAGAGAATTATAATACTATCCCCTCGCTCAGCTTTGGTCAGGGGACCAAGGTG
GACATCAGGC

>DH513VH (SEQ ID NO: 57)

GAGGTTCAGCTGGTGGAGTCTGGGGGAGGCTTGGTGAAGCCGGGGGGGTCTCT
TAGACTCTCCTGTGTAGCCTCTGGCTTCACTTTCAGCAACACGTGGATGAGTT
GGGTCCGTCAGGCGCCAGGGAAGGGACTGGAGTGGGTCGGTCGGATTAGCCGG
AACAAAGATGGCGCGAAAACAGAGTACGCCGCACCCGTGAGAGGCAGATTCAC
CATCTCAAGAGATGACTCCAGAGACACATTGTATCTGCAGATGAGCAGCCTGA
AAATAGAGGATTCAGGCCGGTATTTTTGCACCGCAGATCTTGGGGAGGCCGTT
GTGTCACGATTTTTTGAGTGGGGGTCCTATTATTACTACATGGACTTCTGGGG
CAAGGGGACCACGGTCACCGTCTCTTCA

>DH513VK (SEQ ID NO: 58)

GACATTCAGATGACCCAATCTCCATCTCCCCTGTCTGCGTCTGTGGGAGACAC
AGTCACTATCACTTGCCGGGCCAGCCAGAAGATTAGCGACTATTTGAACTGGT
ACCAACAGAGGCCGGGGAGAGCCCCCAAGATCCTCATTTACGCTGCGTCCAAG
TTGGCAAGCGACGTCCCATCAAGATTTAGTGGCAGTGGATATGGCAGAGATTT
CACTCTCACCATAACCGGTCTGCAGCCTGAAGATTTTGCAACCTATTATTGTC
AGGAGGCTTACAGTTCTACCCCCACGTTAACTTTTGGCCAGGGGACCAGGCTG
GATCTCAAAC

>DH514VH (SEQ ID NO: 59)

GAGGTGCAGCTGGTGGAGTCTGGGGGCGGCTTGATAAAGCCGGGACAGTCACT
CACACTATTCTGTGTGGGCTTTGGATTCAACTTCGCTAACGACTGGATGGGCT
GGGTCCGCCAGGCTCCAGGGAAGGGACTGGAATGGGTTGGGCGTATAAGGAGA
CTGAAAGATGGTGCGAAAGCTGAATATGGATCTTCCGTGAAGGGTAGATTCAC
CATCTCAAGGGATGATTCCAAAAACACCCTATACTTGCACATGAGCAGCCTCA
AGGTCGAAGACACAGCCGTCTACTATTGCACCCGAGACGAGGGGGCCCCAGTT
ACCCGGTTTCTGGAGTGGGGCTCCTATTACTACTACATGGCCGTCTGGGGCAA
AGGGACCACGGTCACCGTCTCTTCA

FIG. 6 cont.

>DH514VK (SEQ ID NO: 60)

GACATCCAGTTGACCCAGTCTCCAGCCTCTCTGTCTGCATCTGTAGGAGACAC
AGTGACTATCACTTGCCGGGCAAGTCAGAGTATAAAAGATTACATAAATTGGT
ATCAACACAAATCCGGGAGCGCCCCTAGACTCCTGATTTATGCTGCGTCAACC
TTACAAAGTGGAATCTCGTCAAGGTTCACTGGCAGTGGGTCTGGGACACAGTT
CACTCTCACCATTAACAGTCTGCAACCTGAAGATTTTGCGACTTATTATTGTC
AAGAGGCTTATAACACCAACCCCACACTCTCCTTTGGTCAGGGGACCAGGGTG
GACAAGAAGC

>DH515VH (SEQ ID NO: 61)

GAGGTTCAGCTGGTGGAGTCTGGGGGCGGCTTGGTGAAGCCGGGACAGTCACT
CACACTTTCCTGTGTGGGCTTTGGATTCAATTTCGCTAACGACTGGATGGGCT
GGGTCCGCCAGGCTCCAGGGAAGGGACTGGAATGGGTTGGTCGAATAAGGAGA
CTAAAAGACGGTGCGACAACAGAATATTCTTCATCCGTGAAGGGGAGATTCAG
TGTCTCAAGAGATGATTCAAGGAACACAGTATACTTACACATGAGTAGCCTCA
AAGTCCAGGACATTGGCGTCTATTATTGTACTCGAGACGAGGGGGCCCCGGTT
ACTCGATTTCTGGAGTGGGGCTCCTATTACTACTATATGGCCGTCTGGGGCAG
AGGGACCACGGTCACCGTCTCTTCA

>DH515VK (SEQ ID NO: 62)

GACATCCAGATGACCCAGTCTCCAACCTCTCTGTCTGCATCTGTAGGAGACAC
AGTTGCTATCACTTGCCGGGCAAGTCAGAGTGTTAAAGATTATGTGAATTGGT
ATCAACACAAATCCGGGAGCGCCCCTCGACTCCTGATTTATGCTGCCTCAGTC
TTACATACTGGAGTCTCGTCAAGGTTCACTGGCAGTGGGTCTGGGACACAGTT
CACTCTCACCATTAGCAGTCTACAACCTGAAGATTTTGCTACTTATTATTGTC
AAGAGGCTTATAACACCTATCCACACTCTCCTTTGGTCAGGGGACCAGGGTG
GACAGGAAAC

FIG. 6 cont.

>DH516VH (SEQ ID NO: 63)

GAGGTTCAGCTGGTGGAGTCTGGGGGAGGCTTGGTGAAGCCGGGGGGGTCTCT
TAGACTCTCCTGTGTAGCCTCTGGCTTCACTTTCAGCAACACGTGGATGAGTT
GGGTCCGTCAGGCGCCAGGGAAGGGACTGGAGTGGGTCGGTCGGATTAGCCGG
AACAAAGATGGCGCGAAAACAGACTACGCCGCACCCGTGAGAGGCAGATTCAC
CATCTCCAGAGATGACTCCAGAGACACATTGTATCTGCAGATGAGCAGCCTGA
AAATAGAGGATTCAGGCCGGTATTTTTGCACCGCAGATCTTGGGGAGGCCGTG
GTGTCACGATTTTTTGAGTGGGGGTCCTATTATTACTACATGGACTTCTGGGG
CAAGGGGACCACGGTCACCGTCTCTTCA

>DH516VK (SEQ ID NO: 64)

GATATTGTGATGACCCAGTCTCCACCTCCCCTGTCTGCGTCTGTGGGAGACAC
AGTCACTATCACTTGCCGGGCCAGCCAGAAGATTAGCGACTATTTGAACTGGT
ACCAACAGAGGCCGGGGAGAGCCCCCAAAATACTCATTTACGCTGCGTCCAAG
TTGGGAAGCGACGTCCCATCAAGGTTCAGTGGCAGTGGATATGGCAGAGATTT
CACTCTCACCATCACCGGTCTGCAGCCTGAAGATTTTGCAACCTATTATTGTC
AGGAGGCTTACAGTTCTACTCCACGTTAAGTTTTGGCCAGGGGACCAGGCTG
GATCTCAAAC

>DH517VH (SEQ ID NO: 65)

GAAAGGCAGGTGGTGGAATATGGGGGAGGCTTGGTGAAGCCGGGGGGGTCTCT
TAGACTCTCTGTTTACCGTTTGCCTTTGGGTTCAGGGCCCCTGGAGGAGTT
CTGTCCGTCACGCGCCTGGGGCGGAGCGGAGTGGGTCGGTCGGATTAGCCGG
AACAAAGATGGCGCGAAAACAGAGTACGCCGCACCCGTGAGAGGCAGATTCAC
CATCTCAAGAGATGACTCCAGAGACACATTGTATCTGCAGATGACCAGCCTGA
AAATAGAGGATTCAGGCCGGTATTTTTGCACCGCAGATCTTGGGGAGCCCGTG
GTGTCACGATTTTTTGAGTGGGGGTCTTATTATTATATGGACCTCTGGGG
CAAGGGGACCACGGTCACCGTCTCTTCA

>DH517VL (SEQ ID NO: 66)

TCTTCTGAGCTGACTCAGGACCCCACTGTGTCTGTGGCCTTGGGCCAGACAGT
CAAGATCAGATGCCAAGGAGCCAGCCTCAGAGACTGTTATGCGACCTGGTACC
GGCAGAAGCCAGGACAGGCCCCAACACTTCTCATTTATGATATAAATAAGAGG
CCCTCAGGTATCCCAGACCGATTCTCTGCCTCCTACTCAGGGAGCACTTCTTC
CTTGACCATTATTGGGGCTCAGCCGGAAGATGAGGCTGACTATTTTGTGCTT
CGCGGGACAGGAGTGGTGACCGTCTTGGCGTCTTCGGCGGTGGGACCAAACTG
ACCGTCCTG

FIG. 6 cont.

>DH518VH (SEQ ID NO: 67)

CAGCTGCAGGAGTCGGGTCCCAGACTGGTGAGGCCTTCGGAGACCCTGTCCCT
CACCTGCACTGTATCTGGCTCTGGTGTCTCCGTCAGTCGTGGGAGTTATTATT
GGGGCTGGATACGCCAGTCCCCAGAAAGGGACTCGAATGGATTGGAAGTGTC
TATTCCACTACTAGTGGAAAAACCTACTACAACCGTCCCTCAAGAGTCGAGT
CACCTTTTCGAAGGACACGTCCCAGAACGCCTTCTCCCTGACTCTGACGTCTA
TTACCGCCGCGGACACGGCCGTCTATTACTGTGCAAGACAATTTGGCTTCATG
GGGGGCTTTTGGAGTGGTATCCGCACTATTTTGACTTCTGGGGCCCGGGAAT
CCAGGTCGTCGTGTCTTCT

>DH518VK (SEQ ID NO: 68)

GACATTGTGATGACCCAGTCTCCATCCTACCTGTCTACATCTGTCGGTGACAG
CATCACCATCACTTGCCGGGCAAGTCAGAGTATTAAACATATGTAAATTGGT
ATCAACAAAGACCAGGGAGAGCCCCTAAACTCCTCATCTATTCTTCATCCACT
TTGCAACCTGGGGTCCCGTCAAGATTCAGCGCCAGTGGATCTGGGACAGATTT
CGTTCTCTCCATCACCAATTTGCAGTCTGAAGATTTTGCAACTTACTACTGTC
AACAGACCTACTACACCCCTCTACTTTTGGCCAGGGGACCACACTGGACATC
AAG

>DH536VH (SEQ ID NO: 69)

CAGGTGCAGCTGGTACAGTCTGGGGCTGAGGTGAAGAAGCCTGGGTCCTCGGT
CAAGGTCTCCTGCAAGGCCTCTGGAGGCTCCTTCTACACCTATACTATCAACT
GGGTGCGACAGGCCCCTGGACAAGGGCTTGAGTGGATGGGCAGGGTCACCACT
ATGTTTGGTGTAACACTTTACGCACAGAAATTCCAGGGCAGAGTCACACTTAC
CGCGGACAAATCCACGAGCACAGCCTACATGGAACTGAGCAGTCTAAGATCTG
AGGACACGGCCGTCTATTATTGTGCGACAGATGGGCCTGACAATTTTTGGAGT
GGCTTGTCTCATGCTTTCGATCTCTGGGGCCAGGGGACAATGGTCACCGTCTC
TTCA

>DH536VL (SEQ ID NO: 70)

CAGTCTGCCCTGACTCAGCCTGCCTCCGTGGCTGGGTCTCCTGGACAGTCGAT
CACCATCTCCTGCACTGGAACCAGCAGTGACATTGGTGATTCTAAGTATGTCT
CCTGGTACCAACAGTTCCCAGGCAAAGCCCCCAAAGTCATGATTTATGAGGTC
AGTTATCGGCCCTCAGGAGTCTCTAGCCGCTTCTCTGGCTCCAAGTCTGGCAA
CACGGCCTCCCTGACCATCTCTGGACTCCAGACTGAGGACGAGGCTGATTATT
ATTGCATGGCATATACAGGCACCTTCACTGCTATTTTCGGCGGAGGGACCAAG
CTGACCGTCCTG

FIG. 6 cont.

>DH537VH (SEQ ID NO: 71)

CAGGTGCAGCTGGTGCAGTCTGGGGCTGAGGTGAGGAAGGCTGGGTCGTCGGT
GAAGGTCTCCTGCAAGGCTTCTGGAGGCACCTTCACCAGCTATGGCTTCAGCT
GGATACGGCAGGCCCCTGGCCAAGGGCTTGAGTGGATGGGAAACGTCATCCCT
GTCTTTGGTTCAACAAACTACGCACAGAAATTTCAGGGCAGAGTCAGTATTAC
CGCGGACGAAGCCACGGGCACAGTCCACATGGACCTCACCAGCCTGACATCTG
ACGACACGGCCGTTTATTACTGTGTGAGGTCGAGTAGAGAACTGCCAACGTCA
ATGGAACGGTGGTTCGACCCCTGGGGCCAGGGAACCCAGGTCATTGTCTCCTC
G

>DH537VK (SEQ ID NO: 72)

GACATCCAGATGACCCAGTCTCCATCCTCCCTGTCTGCATCTGTGGGAGACAG
CGTCACCATTACTTGCCGGGCAAGTCAGAGCATTAACACCTATTTAAATTGGT
ATCAGCAGAAACCAGGGAAGGCCCCTAAACTCCTGATCTATTCTGCATCCAAT
TTACACAATGGGGTCCCATCGAGGTTCAGTGGCAGTGGATCTGGGACATCTTT
CACTCTCACCATCAACAATCTACAACCTGAAGATTTTGCAACTTACTACTGTC
AACAGAGTTACAGTGCCCCTTACACTTTTGGCCAGGGGACCAAGTCAGACACC
AAA

FIG. 6 cont.

>DH511VH (SEQ ID NO: 73)

EVQLVESGGGLVKPGGSLRLPGAASGFTFTNTWMSWVRQAPGKGLEWVGRISR
NKDGAKTEYAAPVRGRFTISRDDSRDTLYLQMTSLKIEDSGRYFCTADLGEPV
VSRSIFEWGSYYYMDLWGKGTTVTVSS

>DH511VK (SEQ ID NO: 74)

DIQLTQSPSPLSASVGDTVTITCRASQKISDYLNWYQQKPGRAPKILIYAASK
LGSGVPSRFSGSGYGRDFTLTITGLQPEDFATYYCQEAYSSTPTLTFGQGTRL
DLK

>DH512VH (SEQ ID NO: 75)

QVQLVQSGGGLVKPGGSLTLSCSASGFFFDNSWMGWVRQAPGKGLEWVGRIRR
LKDGATGEYGAAVKDRFTISRDDSRNMLYLHMRTLKTEDSGTYYCTMDEGTPV
TRFLEWGYFYYYMAVWGRGTTVIVSS

>DH512VK (SEQ ID NO: 76)

DIVMTQSPSSVSASVGDRVTITCRASQNIRDYLNWYQHKPGGSPRLLIYAAST
LQTGVPSRFSGSGSGNLFTLTITNLQPEDFATYYCQENYNTIPSLSFGQGTKV
DIR

>DH513VH (SEQ ID NO: 77)

EVQLVESGGGLVKPGGSLRLSCVASGFTFSNTWMSWVRQAPGKGLEWVGRISR
NKDGAKTEYAAPVRGRFTISRDDSRDTLYLQMSSLKIEDSGRYFCTADLGEAV
VSRFFEWGSYYYMDFWGKGTTVTVSS

>DH513 (SEQ ID NO: 78)

VKDIQMTQSPSPLSASVGDTVTITCRASQKISDYLNWYQQRPGRAPKILIYAA
SKLASDVPSRFSGSGYGRDFTLTITGLQPEDFATYYCQEAYSSTPTLTFGQGT
RLDLK

>DH514VH (SEQ ID NO: 79)

EVQLVESGGGLIKPGQSLTLFCVGFGFNFANDWMGWVRQAPGKGLEWVGRIRR
LKDGAKAEYGSSVKGRFTISRDDSKNTLYLHMSSLKVEDTAVYYCTRDEGAPV
TRFLEWGSYYYMAVWGKGTTVTVSS

FIG. 7

>DH514VK (SEQ ID NO: 80)

DIQLTQSPASLSASVGDTVTITCRASQSIKDYINWYQHKSGSAPRLLIYAAST
LQSGISSRFTGSGSGTQFTLTINSLQPEDFATYYCQEAYNTNPTLSFGQGTRV
DKK

>DH515VH (SEQ ID NO: 81)

EVQLVESGGGLVKPGQSLTLSCVGFGNFANDWMGWVRQAPGKGLEWVGRIRR
LKDGATTEYSSSVKGRFSVSRDDSRNTVYLHMSSLKVQDIGVYYCTRDEGAPV
TRFLEWGSYYYMAVWGRGTTVTVSS

>DH515VK (SEQ ID NO: 82)

DIQMTQSPTSLSASVGDTVAITCRASQSVKDYVNWYQHKSGSAPRLLIYAASV
LHTGVSSRFTGSGSGTQFTLTISSLQPEDFATYYCQEAYNTYPTLSFGQGTRV
DRK

>DH516VH (SEQ ID NO: 83)

EVQLVESGGGLVKPGGSLRLSCVASGFTFSNTWMSWVRQAPGKGLEWVGRISR
NKDGAKTDYAAPVRGRFTISRDDSRDTLYLQMSSLKIEDSGRYFCTADLGEAV
VSRFFEWGSYYYYMDFWGKGTTVTVSS

>DH516VK (SEQ ID NO: 84)

DIVMTQSPPPLSASVGDTVTITCRASQKISDYLNWYQQRPGRAPKILIYAASK
LGSDVPSRFSGSGYGRDFTLTITGLQPEDFATYYCQEAYSSTPTLSFGQGTRL
DLK

>DH517VH (SEQ ID NO: 85)

ERQVVEYGGGLVKPGGSLRLSCLPFAFGFRAPWRSSVRHAPGGGAEWVGRISR
NKDGAKTEYAAPVRGRFTISRDDSRDTLYLQMTSLKIEDSGRYFCTADLGEPV
VSRFFEWGSYYYMDLWGKGTTVTVSS

>DH517VL (SEQ ID NO: 86)

SSELTQDPTVSVALGQTVKIRCQGASLRDCYATWYRQKPGQAPTLLIYDINKR
PSGIPDRFSASYSGSTSSLTIIGAQPEDEADYFCASRDSGDRLGVFGGGTKL
TVL

FIG. 7 cont.

>DH518VH (SEQ ID NO: 87)

QLQESGPRLVRPSETLSLTCTVSGSGVSVSRGSYYWGWIRQSPEKGLEWIGSV
YSTTSGKTYYNPSLKSRVTFSKDTSQNAFSLTLTSITAADTAVYYCARQFGFM
GGFLEWYPHYFDFWGPGIQVVVSS

>DH536VH (SEQ ID NO: 88)

QVQLVQSGAEVKKPGSSVKVSCKASGGSFYTYTINWVRQAPGQGLEWMGRVTT
MFGVTLYAQKFQGRVTLTADKSTSTAYMELSSLRSEDTAVYYCATDGPDNFWS
GLSHAFDLWGQGTMVTVSS

>DH518VK (SEQ ID NO: 89)

DIVMTQSPSYLSTSVGDSITITCRASQSIKTYVNWYQQRPGRAPKLLIYSSST
LQPGVPSRFSASGSGTDFVLSITNLQSEDFATYYCQQTYYTPSTFGQGTTLDI
K

>DH536VH (SEQ ID NO: 90)

QVQLVQSGAEVKKPGSSVKVSCKASGGSFYTYTINWVRQAPGQGLEWMGRVTT
MFGVTLYAQKFQGRVTLTADKSTSTAYMELSSLRSEDTAVYYCATDGPDNFWS
GLSHAFDLWGQGTMVTVSS

>DH536VL (SEQ ID NO: 91)

QSALTQPASVAGSPGQSITISCTGTSSDIGDSKYVSWYQQFPGKAPKVMIYEV
SYRPSGVSSRFSGSKSGNTASLTISGLQTEDEADYYCMAYTGTFTAIFGGGTK
LTVL

>DH537VH (SEQ ID NO: 92)

QVQLVQSGAEVRKAGSSVKVSCKASGGTFTSYGFSWIRQAPGQGLEWMGNVIP
VFGSTNYAQKFQGRVSITADEATGTVHMDLTSLTSDDTAVYYCVRSSRELPTS
MERWFDPWGQGTQVIVSS

>DH537VK (SEQ ID NO: 93)

DIQMTQSPSSLSASVGDSVTITCRASQSINTYLNWYQQKPGKAPKLLIYSASN
LHNGVPSRFSGSGSGTSFTLTINNLQPEDFATYYCQQSYSAPYTFGQGTKSDT
K

FIG. 7 cont.

```
DH511VH (SEQ ID NO:94)  EVQLVESGGG LVKPGGSLRL PGAASGFTFT NTWMSWVRQA
DH512VH (SEQ ID NO:95)  Q----Q---- ---------- SCS-----F-D -S--G-----
DH513VH (SEQ ID NO:96)  ---------- ---------- SCV-------- ----------
DH514VH (SEQ ID NO:97)  ---------- --I---Q--T- FCVGF---N-A -D--G-----
DH515VH (SEQ ID NO:98)  ---------- ------Q--T- SCVGF---N-A -D--G-----
DH516VH (SEQ ID NO:99)  ---------- ---------- SCV-------- ----------
                                                                    40

PGKGLEWVGR ISRNKDGAKT EYAAPVRGRF
DH511VH                 ---------- -R-L----TG --G-A-KD--
DH512VH                 ---------- ---------- ----------
DH513VH                 ---------- ---------- ----------
DH514VH                 ---------- -R-L-----A --GSS-K---
DH515VH                 ---------- -R-L----T- --SSS-K---
DH516VH                 ---------- ---------- D---------
                                                        70

TISRDDSRDT LYLQMTSLKI EDSGRYFCTA
DH511VH                 ---NM----- --H-RT--T- ----T-Y--M
DH512VH                 ---------- -------S-- ----------
DH513VH                 ---------- ---------- ----------
DH514VH                 ---KN----- --H-S----V --TAV-Y--R
DH515VH                 SV--N----- V--H-S----V Q-I-V-Y--R
DH516VH                 ---------- -------S-- ----------
                                                        100

DLGEPVVSRS IFEWGSYYYY MDLWGKGTTV TVSS
DH511VH                 -E-T--.T-- --FL---YF- -AV--R---- -I--
DH512VH                 ------.--- --F------- --F------- ----
DH513VH                 --A---.--- --FL------ -AV------- ----
DH514VH                 -E-A--.T-- --FL------ --F------- ----
DH515VH                 -E-A--.T-- --FL------ -AV--R---- ----
DH516VH                 ---A--.--- --F------- ----F----- ----
                                                             134
```

FIG 8A

```
                                                                              40
DH511VK (SEQ ID NO:100) DIQLTQSPSP LSASVGDTVT ITCRASQKIS DYLNWYQQKP
DH512VK (SEQ ID NO:101) --VM------ -V-R------ -------N-R --------H-
DH513VK (SEQ ID NO:102) ---M------ ---------- ---------- --------R-
DH514VK (SEQ ID NO:103) -----AS--- ---------- ------S-K- ---I---H-S
DH515VK (SEQ ID NO:104) ---M---TS- -------A-- ------SVK- --V----H-S
DH516VK (SEQ ID NO:105) --VM----P- ---------- ---------- --------R-

70
DH511VK  GRAPKILIYA ASKLGSGVPS RFSGSGYGRD
DH512VK  -GS-RL---- --T-QT---- ----S-NL--
DH513VK  ---------- ---A-D---- ----------
DH514VK  -S--RL---- --T-Q--IS- --T---S-TQ
DH515VK  -S--RL---- --V-HT--S- --T---S-TQ
DH516VK  ---------- -------D-- ----------

109
DH511VK  FTLTITGLQP EDFATYYCQE AYSSTPTLTF GQGTRLDLK
DH512VK  ----N----- ---------- N-NTI-S--- ---KV-IR-
DH513VK  ---------- ---------- ---------- ---------
DH514VK  ---NS----- ---------- --NTN-S--- ----V-K--
DH515VK  ---SS----- ---------- --NTY-S--- ----V-R--
DH516VK  ---------- ---------- -------S-- ---------
```

FIG. 8B

| | | | | | | | | 70 |
|---|---|---|---|---|---|---|---|---|
| DH511VH | (SEQ ID NO:106) | EVQLVESGGG | LVKPGGSLRL | PGAASGFTFT | WT..WMSWVR | QAPGKGLEWV | GRISRNKDGA | KTEYAAPVRG |
| DH512VH | (SEQ ID NO:107) | Q------Q--- | ------T--- | SCS-----F-D | -S..--G--- | ---------- | ----R--L-- | TG---G-A--KD |
| DH513VH | (SEQ ID NO:108) | ----------- | ----------- | SCV------S | ------G--- | ---------- | ---------- | ---------- |
| DH514VH | (SEQ ID NO:109) | ----------- | ---I---Q--T- | FCVGF---N-A | -D...-G--- | ---------- | ----R--L-- | --A---GSS-K- |
| DH515VH | (SEQ ID NO:110) | ----------- | -------Q--T- | SCVGF---N-A | -D......G--- | ---------- | ----R--L-- | --T---SSS-K- |
| DH516VH | (SEQ ID NO:111) | ----------- | --------S-- | SCV-------S | -........... | ---------- | ---------- | ------D---- |
| 10E8VH | (SEQ ID NO:112) | ----------- | ----------- | SCS-----D-D | -A..--T--- | ---P------ | ---TGPGE-W | SVD------E- |
| 4E10VH | (SEQ ID NO:113) | Q------Q--AE | VKR---S-VTV | SCK---GS-S | TY..AL---- | ------R---M | -GVIPLL..T | I--N--PRFQ- |
| 2F5VH | (SEQ ID NO:114) | RIT-K----PP | -----TQT-T- | TCSF-----SLS | DFGVGVG-I- | -P---A----L | AI-YSDD... | DKR-SPSLNT |

| | | | | | | | 139 |
|---|---|---|---|---|---|---|---|
| DH511VH | RFTISRDDSR | DTLYLQMTSL | KIEDSGRYFC | TADLGEPVVS | ESIFEWGSY. | .YYYMDLWG | KGTTVTVSS |
| DH512VH | ----------- | NM----H-RT- | --T-----T-Y- | -M-E-T---T | ..FL---YF- | -------AV-- | ----R---I- |
| DH513VH | ----------- | ---------S-- | ---------- | ------A--- | ..F------- | ---------F- | ---------- |
| DH514VH | ----------- | ----N---H-S- | --V--TAV-Y- | -R-E-A---T | ..FL------ | -------AV-- | ---------- |
| DH515VH | ---SV------ | ----N-V--H-S- | -VQ-I-V-Y- | -R-E-A---T | ..FL------ | -------AV-- | ------R--- |
| DH516VH | ----------- | ---------S-- | ---------- | ------A--- | ..F------- | ---------F- | ---------- |
| 10E8VH | ----------- | ----LN--I--NF- | --E-NN--- | RM-----L-- | ARTGKY.... | ..YDF-SG-P | PGEE-FQD-- | R--L----- |
| 4E10VH | -I--TA-R-T | S--A---ELN- | -RP--TAV-Y- | AREGTT.... | ....G---WLG | KPIGAFAH-- | Q--L----- |
| 2F5VH | --L---TK-T-K | NQVV-V---RV | SPV--TAT--- | AHRR--PTT.. | ..L-GVPIAR | GPVNA--V-- | Q--I----I- |

FIG. 9A

```
                DIQLTQSPSP LSASVGDTVT ITCRASQKIS .DYLNWYQQK PGRAPKLLIY AASKLGSSVP
DH511VK  (SEQ ID NO:115)   --VM------S V-------R-- ---------- ---------N-R .--------H- ---GS--RL-- ----T--QT--
DH512VK  (SEQ ID NO:116)   ---M------- ---------- ---------- ---------N-R .--------R- ---------- ----A--D---
DH513VK  (SEQ ID NO:117)   ----------- ------AS--- ---------- --------S-K .---I-----H- S--S----RI- ----T--Q--IS
DH514VK  (SEQ ID NO:118)   ----------- ----------A ---------- -------SVK .---V-----H- S--S----RL- ----V--HT--S
DH515VK  (SEQ ID NO:119)   ---M------TS ---------- ---------- -------SVK .---V-----H- S--S----RL- ----V--HT--S
DH516VK  (SEQ ID NO:120)   ---VM-----P- ---------- ---------- ----------. ---------R- ---------- -----D-----
4E10VK   (SEQ ID NO:121)   E-V------GT Q--L--P-ERA- LS------SVG NNK-A-----R ---Q---RL-- G---SRP----A
2F5VK    (SEQ ID NO:122)   AL-------S ---------RI- ---------GVT .SA-A---R-- ---SP--QL-- D---S--E---
10E8VL   (SEQ ID NO:123)   SYE----.ETG V--VAL-R---- ----GDSL.R SH-AS----K- ---Q--IL-F- GKNNRP-----
                                                                                                        60

SRFSGSGYGR DFTLTITGLQ PEDFATYYCQ RAYSST.FTL TFGQGTRLDL K
DH511VK         ---------- ------S--N L-------N-- ---------- -N-NTI--S-- S-------KV--I R
DH512VK         ---------- ---------- ---------- ---------- ---------- -
DH513VK         ---T-----S--T Q------NS-- ---------- ---NTN----- S-------V--K  -
DH514VK         ---T-----S--T Q------SS-- ---------- ---NTY...-- S-------V--R  -
DH515VK         ---------- ---------- ---------- ---------- ----------S  -
DH516VK         ---------- ---------- ---------- ---------- ----------   -
4E10VK          D--------S--T ------SR-E ------V---- QYGQ..-SLS --------KVEV  -
2F5VK           ---------S--T E------ST-R ---------- QLHF..-YPH ---G---V--V R
10E8VL          D------AS-N RAS---S-A- A---D-E---S SRDK-GSRLS V--G--K-TV L  111
```

FIG. 9B

| | | IC50 (ug/ml) in TZM-bl Cells[2] | | |
|---|---|---|---|---|
| | | CH555_4A/293i | CH556_4A/293i | CH557_4A/293i |
| | | CH0505 | CH0505 | CH0505 |
| | | Lot#68RKK | Lot#69RKK | Lot#70RKK |
| Virus Name | Virus Lot | Rec'd&Aliq 11/MAY/15 | Rec'd&Aliq 11/MAY/15 | Rec'd&Aliq 11/MAY/15 |
| SVA-MLV | 5545 | >50 | >50 | >50 |
| Q23.17 | 2435 | >50 | >50 | 0.09 |
| DJ263.8 | 2220 | >50 | >50 | 0.18 |
| C1080.c03 | 3757 | >50 | >50 | 1.6 |
| 6540.v4.c1 | 2746 | >50 | >50 | 39 |
| Q168.a2 | 1715 | >50 | >50 | 0.08 |
| 6101.10 | 737 | >50 | >50 | 0.77 |
| BG1168.1 | 530 | >50 | >50 | 2.0 |
| DU172.17 | 4168 | >50 | >50 | 0.25 |
| DU156.12 | 4166 | 0.42 | >50 | 0.30 |
| DU422.1 | 3803 | >50 | >50 | 0.89 |
| 57128.vrc15 | 1940 | >50 | >50 | 4.9 |
| X1632-S2-B10 | 2900 | >50 | >50 | 0.20 |
| Q769.d22 | 4405 | >50 | >50 | 0.08 |
| ZM106F.PB9 | 824 | >50 | >50 | 0.5 |
| CNE58 | 6509 | >50 | >50 | 1.7 |
| 92RW020.2 | 1573 | 1.3 | >50 | 0.28 |
| CAAN5342.A2 | 995 | >50 | >50 | 1.7 |
| JR-FL | 730 | >50 | >50 | 0.13 |
| PVO.4 | 3801 | >50 | >50 | 1.5 |
| THRO4156.18 | 967 | >50 | >50 | 30 |
| TRJO4551.58 | 4159 | >50 | >50 | 0.58 |
| TRO.11 | 772 | >50 | >50 | 0.66 |
| YU2 | 4098 | >50 | >50 | 0.08 |
| ZM55F.PB28a | 819 | >50 | >50 | 1.0 |

FIG. 10

| Virus Name | Virus Lot | IC50 (ug/ml) in TZM-bl Cells[2] | | | |
|---|---|---|---|---|---|
| | | CH558_4A/293I CH0505 Lot#71RKK Rec'd&Aliq 11/MAY/15 | CH560_4A CH0505 Lot#218SMI Rec'd&Aliq 11/MAY/15 | CH561_4A CH0505 Lot#219SMI Rec'd&Aliq 11/MAY/15 | CH562_4A CH0505 Lot#220SMI Rec'd&Aliq 11/MAY/15 |
| SVA-MLV | 5545 | >50 | >50 | >50 | >50 |
| Q23.17 | 2435 | 0.52 | >50 | >50 | >50 |
| DJ263.8 | 2220 | 33 | 2.6 | 3.8 | 2.6 |
| C1080.c03 | 3757 | 25 | >50 | >50 | >50 |
| 6540.v4.c1 | 2746 | >50 | 1.2 | 0.51 | 0.62 |
| Q168.a2 | 1715 | 0.68 | 5.1 | 42 | 37 |
| 6101.10 | 737 | 8.2 | 6.6 | 10.0 | 10.5 |
| BG1168.1 | 530 | >50 | 7.3 | 17 | 17 |
| DU172.17 | 4168 | 1.1 | 14 | >50 | >50 |
| DU156.12 | 4166 | 1.8 | >50 | >50 | >50 |
| DU422.1 | 3803 | 6.0 | >50 | >50 | >50 |
| 57128.vrc15 | 1940 | >50 | >50 | >50 | >50 |
| X1632-S2-B10 | 2900 | 0.93 | 2.0 | 2.1 | 1.8 |
| Q769.d22 | 4405 | 1.2 | 3.2 | 3.7 | 1.5 |
| ZM106F.PB9 | 824 | 2.7 | 26 | 35 | 26 |
| CNE58 | 6509 | >50 | 8.0 | 30 | 18 |
| 92RW020.2 | 1573 | 1.2 | 26 | 50 | 29 |
| CAAN5342.A2 | 995 | 25 | 49 | >50 | 49 |
| JR-FL | 730 | 25 | 0.19 | 0.27 | 0.26 |
| PVO.4 | 3801 | 7.4 | >50 | >50 | >50 |
| THRO4156.18 | 967 | >50 | 4.9 | 5.8 | 5.8 |
| TRJO4551.58 | 4159 | >50 | >50 | >50 | >50 |
| TRO.11 | 772 | 9.4 | >50 | >50 | >50 |
| YU2 | 4098 | 0.21 | 2.2 | 3.7 | 2.9 |
| ZM55F.PB28a | 819 | 6.4 | 10.5 | 14 | 9.2 |

FIG. 10 cont.

| | | IC50 (ug/ml) in TZM-bl Cells[1] | | |
|---|---|---|---|---|
| | | DH210_4A/293i | DH211_4A/293i | CH01-31 |
| | | CH0505 | CH0505 | |
| | | Lot#155HC | Lot#217SMI | |
| Virus Name | Virus Lot | Rec'd&Aliq 11/MAY/15 | Rec'd&Aliq 11/MAY/15 | prep. 26/MAR/15 |
| SVA-MLV | 5545 | >50 | >50 | >25 |
| Q23.17 | 2435 | >50 | >50 | <0.011 |
| DJ263.8 | 2220 | >50 | >50 | 0.84 |
| C1080.c03 | 3757 | >50 | >50 | 0.05 |
| 6540.v4.c1 | 2746 | >50 | >50 | 0.58 |
| Q168.a2 | 1715 | >50 | >50 | 0.08 |
| 6101.10 | 737 | >50 | >50 | 0.57 |
| BG1168.1 | 530 | >50 | >50 | 2.1 |
| DU172.17 | 4168 | >50 | >50 | 0.73 |
| DU156.12 | 4166 | >50 | >50 | 0.30 |
| DU422.1 | 3803 | >50 | >50 | >25 |
| 57128.vrc15 | 1940 | >50 | >50 | >25 |
| X1632-S2-B10 | 2900 | >50 | >50 | 0.07 |
| Q769.d22 | 4405 | >50 | >50 | 0.07 |
| ZM106F.PB9 | 824 | >50 | >50 | 9.2 |
| CNE58 | 6509 | >50 | >50 | 0.11 |
| 92RW020.2 | 1573 | >50 | >50 | 0.05 |
| CAAN5342.A2 | 995 | >50 | >50 | >25 |
| JR-FL | 730 | >50 | >50 | 0.03 |
| PVO.4 | 3801 | >50 | >50 | 0.86 |
| THRO4156.18 | 967 | >50 | >50 | 3.1 |
| TRJO4551.58 | 4159 | >50 | >50 | 0.42 |
| TRO.11 | 772 | >50 | >50 | 0.25 |
| YU2 | 4098 | >50 | >50 | 0.10 |
| ZM55F.PB28a | 819 | >50 | >50 | 3.1 |

FIG. 10 cont.

| mAb | VH | D | JH | Mut. Frq. | HCDR3 length (AA) | HCDR3 | VL | JL | Mut. Frq. | LCDR3 length (AA) |
|---|---|---|---|---|---|---|---|---|---|---|
| DH557 | 1-46 | 2-21 | 4 | 25.7 | 15 | CVRNVGTAGSLLHYDHW | K3-15 | 1 | 14.3 | 8 |

FIG. 11

>CH557_aa_HC (SEQ ID NO: 124)
QVRLAQYGGGVKRLGATMTLSCVASGYTFNDYYIHWVRQAPGQGFEL
LGYIDPANGRPDYAGALRERLSFYRDKSMETLYMDLRSLRYDDTAMY
YCVRNVGTAGSLLHYDHWGSGSPVIVSS

>CH557_aa_LC (SEQ ID NO: 125)
EIVLTQSPATLSASPGERVTLTCRASRSVRNNVAWYQHKGGQSPRLL
IYDASTRAAGVPARFSGSASGTEFTLAISNLESEDFTVYFCLQYNNW
WTFGQGTRVDIK

>CH557_nt_HC (SEQ ID NO: 126)
CAGGTCCGACTAGCCCAATATGGTGGTGGGGTGAAGAGGCTAGGGGC
CACAATGACCCTTTCCTGCGTGGCATCTGGATACACCTTCAACGACT
ACTACATACATTGGGTGCGGCAGGCCCTGGACAAGGCTTTGAGTTG
TTGGGATACATCGACCCGCTAATGGTCGCCCAGACTACGCAGGGGC
GTTGAGGGAGAGACTCTCCTTCTACAGGGACAAGTCCATGGAGACGC
TGTACATGGACCTGAGGAGCCTAAGATATGACGACACGGCCATGTAT
TATTGTGTTAGAAATGTGGGGACCGCTGGCAGCTTGCTGCATTATGA
CCACTGGGGCTCGGGAAGCCCGGTCATCGTCTCCTCC

>CH557_nt_LC (SEQ ID NO: 127)
GAAATTGTGTTGACGCAGTCTCCAGCCACCCTGTCCGCGTCTCCAGG
GGAAGAGTCACCCTAACTTGCAGGGCCAGTCGGAGTGTCCGAAACA
ACGTGGCCTGGTATCAGCACAAGGGTGGCCAGAGTCCCAGGCTCCTC
ATTTATGATGCGTCCACGAGGGCCGCTGGTGTCCCAGCCAGGTTCAG
CGGCAGTGCATCTGGGACAGAGTTCACTCTCGCCATCAGCAACTTGG
AGTCTGAAGATTTTACAGTCTACTTCTGTCTGCAGTATAATAACTGG
TGGACCTTCGGCCAAGGGACCAGGGTGGACATCAAA

FIG. 12

IMGT
Heavy

| | | | | |
|---|---|---|---|---|
| (SEQ ID NO:216) 40.01 | QVQLIQSGPQFKTPGASVTVSCKAS | GYIFTDYL | IHWVRLVPGKGLEWLGR | INTNAGLM |
| (SEQ ID NO:217) 40.02 | QVRLMQSGPQLKTPGASVTVSCKAS | GYIFTDYL | IHWVRLVPGKGLEWLGR | INTNGGLM |
| (SEQ ID NO:218) 40.03 | QVQLIQSGPQLKTPGASVTVSCKAS | GYVFADYL | IHWVRLVPGKGLEWLGR | INTNAGLM |
| (SEQ ID NO:219) 40.04 | QVRLMQSGTEFKTPGASVKVSCKTS | GYIFSDYL | IHWVRLVPGKGLEWLGR | INTNAGLM |
| | ----FR1---- | ----CDR1---- | ----FR2---- | ----CDR2---- | continued:

| | | |
|---|---|---|
| YLSHKFEGRLILRRVVDKRTPSLGTVNMELRNVRSDDSAIYFC | GRVVDGFNAAGPLEF | WGQGSPVIVSS |
| YLSYKFEGRLILRRDVDKRTPSLGTVIMELRNLRSDDSAIYFC | GRVVDGFNAAGPLEF | WGQGSPVIVSS |
| YLSHKFEGRLILRRDRDWRTPSLGTLVMELRNLKSDDSAIYFC | GRVVDGFNAAGPLEF | WGQGSPVIVSS |
| YLSPRFEGRVILRRESSFRTPSLGTVNMELRNLKFDDSAVYFC | GRVVDGFNAAGPLEF | WGQGSLVIVSS |
| ----FR3---- | ----CDR3---- | ----FR4---- |

Figure 13

IMGT

Light:

| | | FR1 | CDR1 | FR2 |
|---|---|---|---|---|
| (SEQ ID NO:220) | 40.01 | QVVMTQSPATLSLSPGETAAVSCRAS | QYVDRS | ISWYQLKTGRAPRLLVYY |
| (SEQ ID NO:221) | 40.02 | QVVMTQSPVTLSVSPGETAAVSCRAS | QYVDRS | ISWYQLKTGRAPRLLVYY |
| (SEQ ID NO:222) | 40.03 | QVLMTQSPATLSVSPGETAAVSCRAS | QYVDRS | ISWYQVKSGRAPRLLVYY |
| (SEQ ID NO:223) | 40.04 | EVVMTQSPATLSVSPGEPAALSCGAS | DIIDRS | VSWYQLKPGRAPRLLVYY |
| | | ---FR1--- | ---CDR1--- | ---FR2--- | continued:

| | FR3 | CDR3 | FR4 |
|---|---|---|---|
| AAS | SRSIGVPDRFSGSGSGRDFTLTIRGVQSDDFAVYYC | QQDYWMPVTF | GQGTRLDMK |
| AAS | SRSIGVPDRFSGSGSGRDFTLTIRGVQSDDFAVYYC | QQDYWMPVTF | GQGTRLDMK |
| AAS | SRSIGYPDRFSGSGSGTDFTLTIRGVQSDDFAVYYC | QQDYGWPVTF | GQGTRLDMK |
| AAS | SRSIGIPDRFSGSGSGTAFTLTIRGVQSDDFALYYC | QQDKYWPVTF | GQGTRLDMK |
| CDR2 | ---FR3--- | ---CDR3--- | ---FR4--- |

Figure 13 cont.

```
KABAT
Heavy
                        1                   2                   3                        4                   5                   6
               1234567890123456789012345678901234567890  12345  67890123456789  0123456789012345
(SEQ ID NO:216) 40.01  QVQLLQSGPGQKTPGASVTVSCKASGYIFT       DYLIH  WVRLVPGKGLEWLG  RINTNAGLMYLSHKFEG
(SEQ ID NO:217) 40.02  QVRLMQSGPQLKTPGASVTVSCKASGYIFT       DYLIH  WVRLVPGKGLEWLG  RINTNGGLMYLSIKFEG
(SEQ ID NO:218) 40.03  QVQLLQSGPQLKTFGASVTVSCKASGYYFA       DYLIH  WVRLVPGKGLEWLG  RINTNAGLMYLSHKFEG
(SEQ ID NO:219) 40.04  QVRLMQSGTFRTPGASVRYSCKTSGYIFS       DYLIH  WVRLVPGKGLEWLG  RINTNAGLMYLSRKFEG
                       -----------FR1-------------------   -CDR1- ----FR2-------  -----CDR2------- continued:
                        7              8                   9                   0ABCDE12  34567890123
               67890123A------BC34567890123456789012345678901234  567890ABCDE12  34567890123
               RLILRRDVDMRTPSLGTVNMELRNVRSDDSAIYFCGR              VVDGFNAAGPLEF  WGQGSPVTVSS
               RLILRRDVDMRTPSLGTVNMELRNVRSDDSAIYFCGR              VVDGFNAAGPLEF  WGQGSPVTVSS
               RLILRRDRDMRTPSLGTLVMELRNLKSDDSAIYFCGR              VVDGFNAAGPLEF  WGQGSPVTVSS
               RVILRRESSFRTPSLGTVVNELRNLKFDDSAVYFCGR              VVDGFNAAGPLEF  WGQGSLVTVSS
               ---------------------FR3---------------------     -----CDR3----  -----FR4----

Figure 13 cont.
```

KABAT

Light

```
                    1                   2                   3                   4                   5
           1234567890123456789012345678901234567890123456789012345678901234
(SEQ ID NO:220) 40.01  QVVMTQSPATLSLSPGETAAVSC RASQYVDRSIS WYQLKTGRAPRLLVY AASSRSI
(SEQ ID NO:221) 40.02  QVVMTQSPVTLSVSPGETAAVSC RASQYVDRSIS WYQLKTGRAPRLLVY AASSRSI
(SEQ ID NO:222) 40.03  QVLMTQSPATLSVSPGETAAVSC RASQYVDRSIS WYQVKSGRAPRLLVY AASSRSI
(SEQ ID NO:223) 40.04  EVVMTQSPATLSVSPGEEAALSC GASDIDRSVS WYQLKPGRAPRLLVY AASSRSI
                      -----------FR1---------  ---CDR1---  -----FR2------  ---CDR2
``` continued:

```
              6                   7                   8                   9                   0
       7890123456789012345678901234567890123456789012345678901234567 901234567 8901234567890
       GVPDRFSGSGSGSGRDFTLTIRGVQSDDFALYYC QQDYYMPVT FGQGTRLDMK
       GVPDRFSGSGSGSGRDFTLTIRGVQSDDFALYYC QQDYYMPVT FGQGTRLDMK
       GVPDRFSGSGSGSGTDFTLTIRGVQSDDFAVYYC QQDYGMPVT FGQGTRLDMK
       GIPDRFSGSGSGTAFFLTIRGVQSDDFALYYC   QQDYYMPVT FGQGTRLDMK
       -----------------FR3-------------- ---CDR3-- ---FR4---
```

Figure 13 cont.

| Antibody ID | VH | D | JH | Mutation frequency | CDRH3 length | VK | JK | Mutation frequency | CDRL3 length | Week of isolation |
|---|---|---|---|---|---|---|---|---|---|---|
| UCA | 1-46*01 | 3-10*01 | 4*02 | 0.0% | 15 | 3-15*01 | 1*01 | 0.0% | 8 | - |
| CH235 | 1-46*01 | 3-10*01 | 4*02 | 7.9% | 15 | 3-15*01 | 1*01 | 3.5% | 8 | 41 |
| CH236 | 1-46*01 | 3-10*01 | 4*02 | 8.2% | 15 | 3-15*01 | 1*01 | 2.2% | 8 | 41 |
| CH239 | 1-46*01 | 3-10*01 | 4*02 | 7.9% | 15 | 3-15*01 | 1*01 | 4.7% | 8 | 41 |
| CH240 | 1-46*01 | 3-10*01 | 4*02 | 7.1% | 15 | 3-15*01 | 1*01 | 3.1% | 8 | 41 |
| CH241 | 1-46*01 | 3-10*01 | 4*02 | 11.4% | 15 | 3-15*01 | 1*01 | 3.1% | 8 | 41 |
| CH491 | 1-46*01 | 3-10*01 | 4*02 | 14.7% | 15 | 3-15*01 | 1*01 | 2.2% | 8 | 100* |
| CH493 | 1-46*01 | 3-10*01 | 4*02 | 19.3% | 15 | 3-15*01 | 1*01 | 2.2% | 8 | 152* |
| CH555 | 1-46*01 | 3-10*01 | 4*02 | 21.5% | 15 | 3-15*01 | 1*01 | 16.0% | 8 | 264 |
| CH556 | 1-46*01 | 3-10*01 | 4*02 | 25.1% | 15 | 3-15*01 | 1*01 | 17.0% | 8 | 323 |
| CH557 | 1-46*01 | 3-10*01 | 4*02 | 25.6% | 15 | 3-15*01 | 1*01 | 12.3% | 8 | 323 |
| CH558 | 1-46*01 | 3-10*01 | 4*02 | 23.4% | 15 | 3-15*01 | 1*01 | 11.0% | 8 | 323 |

* Paired with CH236 V-light chain

FIG. 14

Amino acid alignment of CH235 lineage antibody heavy chains

```
                         10        20        30        40
                ....|....|....|....|....|....|....|....|
(SEQ ID NO:128) UCA_HC   QVQLVQSGAEVKKPGASVKVSCKASGYTFTSYYMHWVRQA
(SEQ ID NO:129) CH240_HC ---------------T---R----TI------NNF-V---
(SEQ ID NO:130) CH235_HC ---------------T---R----TI------NNF-V---
(SEQ ID NO:131) CH239_HC ---------------T---Q----N--V------------
(SEQ ID NO:132) CH236_HC ------------R--T---R----TI------NNF-V---
(SEQ ID NO:133) CH241_HC ------------A--R---R----TI---R---T---I--
(SEQ ID NO:134) CH491_HC ------------A--R---R----TI------SHI-----
(SEQ ID NO:135) CH493_HC --R-L-Y-GG--R--MTI-V---N-ND--I----------
(SEQ ID NO:136) CH555_HC -----------T--R---TL--RT---N-ID-FI---R--
(SEQ ID NO:137) CH558_HC ------GG--R--STTTI-V---S-ND--I----------
(SEQ ID NO:138) CH556_HC ------GT--S--T--TL--T--N-ID--I---R------
(SEQ ID NO:139) CH557_HC --R-A-Y-GG--RL--TMTL-V---ND--I----------
```

Figure 15A

```
                    30              40              50              60              70              80
                    |...|....|....|....|....|....|....|....|....|....|....|....|....|
UCA_HC     FGQGLEWMGIINPSGGSTSYAQKFQGRVTMTRDTSTSTVYMELSSLRSED
CH240_HC   ----------------C--W-D-V-RI--G----------R--G------
CH235_HC   ---------QL-W-D-M-R-N--N---I------------MR--------
CH239_HC   ----------C--W-D-V-RIN--------------R--G----------
CH236_HC   ------R--L-M-D--R-R-D---------------S---L---R--PD-
CH241_HC   ------P--M-D--V-RPTT-G----------RY--A-D----------I-
CH491_HC   -------L-W--R--R-D-SYR-ED--S-Y---M-I--D-RN-K-A----
CH493_HC   -------L-W-D-R--R-D-GA-GD--S-Y--K-MN-L--D-R---G---
CH555_HC   ----R--V-Y-D-R-RPD-PN-RD-SLY--M-I--LD-RD-TPD------
CH558_HC   ----VL-F-D--N-R-N--GA-GD-FS-Y--K-ME-L--D-RN--D----
CH556_HC   --RP-L--D-H-RPD-EG--RD-ISLY---V--DVRG-LD----------
CH557_HC   ---F-LL-Y-D-AN-RPD--GALRE-LSFY--K-ME-L--D-R---YD--
```

Figure 15A cont.

Amino acid alignment of CH235 lineage antibody light chains

```
                              10         20         30         40
                     ....|....|....|....|....|....|....|....|....|....|
(SEQ ID NO:140) UCA  LC   EIVLTQSPATLSVSPGERATLSCRASQSVSSNLAWYQQKPGQAPRLLIY
(SEQ ID NO:141) CH236 LC  ................................RN........R..R..
(SEQ ID NO:142) CH240 LC  ..........V..................T..R...........R...
(SEQ ID NO:143) CH241 LC  ................................R..I............H
(SEQ ID NO:144) CH235 LC  ................................R........R......
(SEQ ID NO:145) CH239 LC  ............................T..R..V..............
(SEQ ID NO:146) CH558 LC  ........A.....V..T..............RG.RN.V...HNV..S.
(SEQ ID NO:147) CH557 LC  ........A.....V..T..............R..RN.V...H.G..S.
(SEQ ID NO:148) CH555 LC  ...D....A.....V..................GTKV...RHVR..P..
(SEQ ID NO:149) CH556 LC  .TT.D...A........................A..G.QV..FRHIR..P....S
```

Figure 15B

|  | 50 | 60 | 70 | 80 | 90 |
|---|---|---|---|---|---|
| UCA LC | GAST | RATGIPARFSGS | GSGTEFTLTISS | LQSEDFAVYCQQ | |
| CH236 LC | ..S. | ............ | ............ | .M.......... | ... |
| CH240 LC | ..S. | ............ | ............ | .V.......... | .L. |
| CH241 LC | .... | .....G...... | .......P.A.V | ............ | ... |
| CH235 LC | .T.. | ......V..... | .........R.. | .A..M....... | .L.L |
| CH239 LC | ..S. | ............ | ............ | ...A.M...... | .L. |
| CH558 LC | .D.. | ......P..... | .........A.. | .A...I..TL.. | .H. |
| CH557 LC | .D.. | ......A.V... | .........A.. | .A...N.E..T. | .F.L |
| CH555 LC | .... | ......A..... | .........G.. | .N...NNF.... | .E.L |
| CH556 LC | .... | ......A.V... | .........D.. | ...GM......E | .F. |

Figure 15B cont.

| | | 100 | |
|---|---|---|---|
| UCA LC | | YNNWWTFGQGTKVEIK | |
| CH236 LC | | ................ | |
| CH240 LC | | ................ | |
| CH241 LC | | ..D............. | |
| CH235 LC | | ................ | |
| CH239 LC | | .DD............. | |
| CH558 LC | | ...........R.D.N | |
| CH557 LC | | ...........R.D.. | |
| CH555 LC | | .KS..........DN. | |
| CH556 LC | | .HM........R.DKN | |

FIG. 15B cont.

Alignment of CH557 heavy chain amino acid sequence compared to CH235 lineage antibodies with increasing levels of somatic mutations and neutralization breadth. Contact sites with gp120 identified from CH235/gp120 co-crystal structure are indicated with asterisks. Amino acid mutations within the contact sites are bolded and underlined.

```
                            |-----------FR1-----------|--CDR1--|-------FR2-------|--CDR2--|--
                                       * *                     *******
UCA_HC    (SEQ ID NO:150) QVQLVQSGAE VKKPGASVKV SCKASGYTFT SYYMHWVRQA PGQGLEWMGI INPSGGSTSY
CH236_HC  (SEQ ID NO:151) QVQLVQSGAA VKRPGASVTI SCRASGYTFT TYYIHWVRQA PGQRLELMGM IDPSRGRTDY
CH235_HC  (SEQ ID NO:152) QVQLVQSGAE VKKPGASVTV SCQASGYTFT NYYVHWVRQA PGQGLQLMGW IDPSWGRTNY
CH493_HC  (SEQ ID NO:153) QVRLLQYGGG VKRPGASMTI SCVASGYNFN DYYIHWVRQA PGQGLELMGW IDPSGGRTDY
CH557_HC  (SEQ ID NO:154) QVRLAQYGGG VKRLGATMTL SCVASGYTFN DYYIHWVRQA PGQGFELLGY IDPANGRPDY

-------------FR3---------------------|------CDR3------|---FR4----|
                            **  *       *                                **
UCA_HC                    AQKFQGRVTM TRDTSTSTVY MELSSLRSED TAVYYCARDV GTEGSLLHFD YWGQGTLVTVSS
CH236_HC                  AQKFQGRVTM SRDTSTSTLY MELRSLRPDD TALYYCVRNV GTEGSLLHYD YWGQGTLVTVSS
CH235_HC                  AQNFQGRITM TRDTSTSTVY MEMRSLRSED TAVYYCARNV ATEGSLLHYD YWGQGTLVTVSA
CH493_HC                  AGAFGDRVSM YRDKSMNTLY MDLRSLRSGD TAMYYCVRNV GTAGSLLHYD HWGLGVMVTVSS
CH557_HC                  AGALRERLSF YRDKSMETLY MDLRSLRYDD TAMYYCVRNV GTAGSLLHYD HWGSGSPVIVSS
```

FIG. 16

Alignment of CH557 light chain amino acid sequence compared to CH235 lineage antibodies with increasing levels of somatic mutations and neutralization breadth.

```
        |------------FR1-----------|--CDR1--|-------FR2-------|CDR2|
UCA_LC   EIVLTQSPAT LSVSPGERAT SNLAWYQQKP GQAPRLLIYG ASTRATGIPA
CH236_LC EIVLTQSPAT LSVSPGERVT LSCRASQSVR NNLAWYRQKR GQAPRLLIYG ASTRATGIPA
CH235_LC EIVLTQSPAT LSVSPGERAT LSCRASQSVR SNLAWYQQRP GQAPRLLIYG TSTRATGVPA
CH557_LC EIVLTQSPAT LSASPGERVT LTCRASRSVR NNVAWYQHKG GQSPRLLIYD ASTRAAGVPA

|-------FR3--------|        |--CDR3--|  |---FR4----|
UCA_LC   RFSGSGSGTE FTLTISSLQS EDFAVYYCQQ YNNWWTFGQG TKVEIK
CH236_LC RFSGSGSGTE FTLTISSMQS EDFAVYYCQQ YNNWWTFGQG TKVEIK
CH235_LC RFSGRGSGTE FTLAISSMQS EDFAVYLCLQ YNNWWTFGQG TKVEIK
CH557_LC RFSGSASGTE FTLAISNLES EDFTVYFCLQ YNNWWTFGQG TRVDIK
```

FIG. 17

In yellow/highlighted CDR1, 2 and 3

>CH235_129w66 (SEQ ID NO: 159)

QVQLVQSGAAVKKPGASVRVSCKASGYTFTSSHIHWVRQAPGQALEWLGMIDP
RFGRPTRPQKFQGRVTLTRDTYTTTVYMSLSSLTPEDTAVYYCARSVETSESY
LHFDYWGQGTLVTVSS

>CH235_68w100 (SEQ ID NO: 160)

QVQLVQSGAAVKRPGASVTISCRASGYTFTTYYIHWVRQAPGQGLELMGWINP
RGGRTDYSYRFEDRVSMYRDTSMSIVYMDLRNLKSADTAVYYCVRNVGTSGSL
LHYDFWGQGSLVTVSS

>CH235_115w100 (SEQ ID NO: 161)

QVQLVQSGAAVKKPGASVRVSCKASGYTFTSSHIHWVRQAPGQGPEWMGMVDP
RFGRPTYAQKFQGRVAMTRDIYTSTVYMDLRSLKSEDTAIYFCVRNAETEGSL
LHIEYWGQGTRVTVSS

>CH235_75w152 (SEQ ID NO: 162)

QVRLLQYGGGVKRPGASMTISCVASGYNFNDYYIHWVRQAPGQGLELMGWIDP
SGGRTDYAGAFGDRVSMYRDKSMNTLYMDLRSLRSGDTAMYYCVRNVGTAGSL
LHYDHWGLGVMVTVSS

>CH236_VK_aa (SEQ ID NO: 163)

EIVLTQSPATLSVSPGERVTLSCRASQSVRNNLAWYRQKRGQAPRLLIYGAST
RATGIPARFSGSGSGTEFTLTISSMQSEDFAVYYCQQYNNWWTFGQGTKVEIK

>CH241_VK_aa (SEQ ID NO: 164)

EIVLTQSPATLSVSPGERATLSCRASQSVRSNIAWYQQKPGQAPRLLIHGAST
RATGIPGRFSGSGSGPEFTLAISSVQSEDFAVYYCQQYNDWWTFGQGTKVEIK

FIG. 18

Clean Sequences for Plasmid Production

| PtID | Ab ID | CH # | TX | VH | VL | Specificity |
|---|---|---|---|---|---|---|
| 703-01-050-5 | HES65W202GPOPB 129w66.1.1 | 490 | n/a | CH235_129 w66 | pCK001826 | In CH235 lineage from 454. Paired with CH241 LC. |
| 703-01-050-5 | HES65W202GU3T7 68w100.1.2 | 491 | n/a | CH235_68w 100 | pCK001690 | In CH235 lineage from 454. Paired with CH236 LC. |
| 703-01-050-5 | HES65W201B95MO 115w100.1.1 | 492 | n/a | CH235_115 w100 | pCK001826 | In CH235 lineage from 454. Paired with CH241 LC. |
| 703-01-050-5 | HES65W201DXWBB 75w152.4.3 | 493 | n/a | CH235_75w 152 | pCK001690 | In CH235 lineage from 454. Paired with CH236 LC. |

NOTE: VLs have already been produced (are those of CH241 and CH236).

Heavy chains

\>CH235_129w66 (SEQ ID NO: 165)
CAGGTGCAGCTGGTGCAGTCTGGGGCTGCGGTGAAGAAGCCTGGGGCCTCAGTGAGGGTTTC
CTGCAAGGCATCTGGATACACCTTCACCAGTTCTCATATCCACTGGGTGCGACAGGCCCCTG
GACAAGCACTTGAGTGGTTGGGAATGATCGACCCTCGTTTTGGTAGGCCAACCCGCCCTCAG
AAGTTCCAGGGCAGAGTCACCCTGACCAGAGACACGTACACGACTACAGTGTACATGTCACT
GAGCAGCCTGACACCTGAAGACACGGCCGTTTACTACTGTGCGAGAAGCGTGGAAACGAGTG
AGAGCTATCTCCACTTTGACTACTGGGGCCAGGGAACCCTGGTCACCGTCTCCTCAG

\>CH235_68w100 (SEQ ID NO: 166)
CAGGTGCAGCTGGTGCAGTCTGGGGCTGCGGTGAAGAGGCCTGGGGCCTCAGTGACGATTTC
CTGCAGGGCATCTGGATACACCTTCACCACCTACTATATACACTGGGTGCGACAGGCCCCTG
GACAAGGACTTGAGTTGATGGGATGGATCAACCCTCGTGGCGGTCGCACAGACTACTCTTAC
AGATTTGAGGACAGAGTCAGTATGTACAGGGACACGTCCATGAGTATAGTCTACATGGACTT
GAGGAACCTGAAATCTGCGGACACGGCCGTCTACTATTGTGTGAGAAATGTGGGAACCAGTG
GGAGCTTGCTCCACTATGACTTCTGGGGCCAGGGAAGCCTGGTCACCGTCTCCTCAG

\>CH235_115w100 (SEQ ID NO: 167)
CAGGTGCAGCTGGTGCAGTCTGGGGCTGCGGTGAAGAAGCCTGGGGCCTCAGTGAGGGTTTC
CTGCAAGGCATCTGGATACACCTTCACCAGTTCTCATATCCACTGGGTGCGACAGGCCCCTG
GACAAGGCCCTGAGTGGATGGGCATGGTCGACCCCGTTTTGGTCGCCCAACCTACGCACAG
AAGTTTCAGGGCAGGGTCGCCATGACCAGGGACATTTACACGAGCACAGTCTACATGGACTT
GAGGAGCCTAAAATCTGAGGACACGGCCATCTATTTCTGTGTGAGAAATGCGGAAACGGAGG
GCAGCTTACTCCACATTGAGTACTGGGGCCAGGGAACCCGGGTCACCGTCTCCTCAG

FIG. 19

>CH235_75w152 (SEQ ID NO: 168)
CAGGTGCGACTACTACAATATGGGGGTGGAGTGAAGAGGCCTGGGGCCTCAAT
GACGATTTCCTGCGTGGCGTCTGGATACAACTTCAACGACTACTATATACACT
GGGTGCGACAGGCCCCTGGACAAGGCCTCGAATTGATGGGATGGATCGACCCT
AGTGGTGGTCGCACAGATTACGCAGGGGCGTTTGGGGACAGAGTGTCCATGTA
CAGGGACAAGTCCATGAACACACTCTACATGGACCTGAGGAGCCTGAGATCTG
GCGACACGGCCATGTATTATTGTGTTAGAAATGTGGGAACGGCTGGCAGCTTG
CTCCACTATGACCACTGGGGCCTGGGAGTTATGGTCACCGTCTCCTCAG

>CH236_VK_nt (SEQ ID NO: 169)
GAAATTGTGTTGACGCAGTCTCCAGCCACCCTGTCTGTATCTCCAGGGGAAAG
AGTCACCCTCTCCTGCAGGGCCAGTCAGAGTGTTAGAAACAACTTAGCCTGGT
ACCGGCAGAAACGTGGCCAGGCTCCCAGACTCCTCATCTATGGTGCATCCACC
AGGGCCACTGGTATCCCAGCCAGGTTCAGTGGCAGTGGGTCTGGGACAGAGTT
CACTCTTACCATCAGCAGCATGCAGTCTGAAGATTTTGCAGTTTATTACTGTC
AGCAGTATAATAACTGGTGGACGTTCGGCCAAGGGACCAAGGTGGAAATCAAA
C

>CH241_VK_nt (SEQ ID NO: 170)
GAAATTGTGTTGACGCAGTCTCCAGCCACCCTGTCTGTGTCTCCAGGGGAAAG
AGCCACCCTCTCCTGCAGGGCCAGTCAGAGTGTTAGAAGCAACATAGCCTGGT
ACCAACAAAAACCTGGCCAGGCTCCCAGGCTCCTCATCCATGGTGCATCCACC
AGGGCCACAGGTATCCCAGGCAGGTTCAGTGGCAGTGGGTCTGGGCCAGAGTT
CACTCTCGCCATCAGCAGCGTGCAGTCTGAAGATTTTGCAGTTTATTACTGTC
AGCAGTATAATGACTGGTGGACGTTCGGCCAAGGGACCAAGGTGGAAATCAAA
C

FIG. 19 cont.

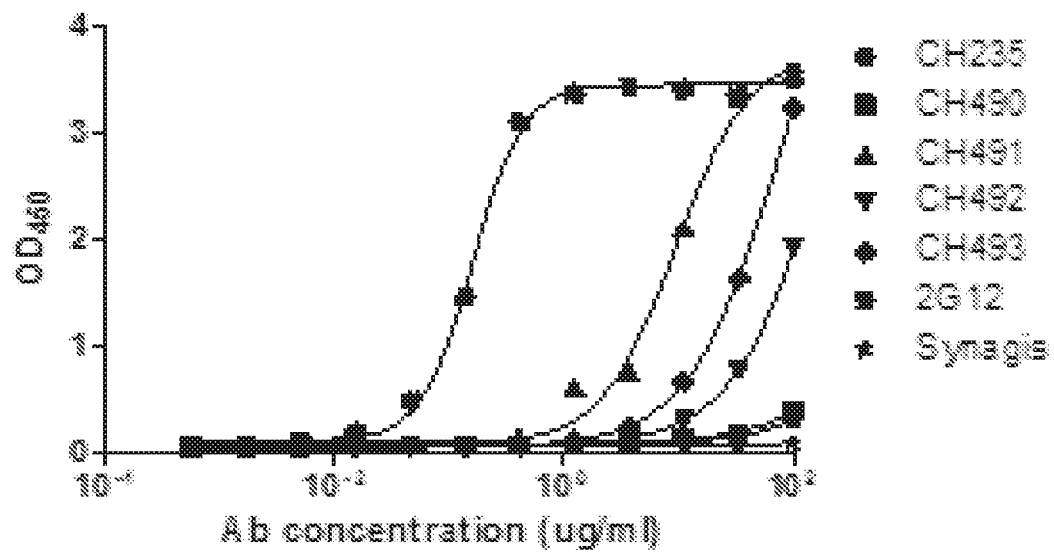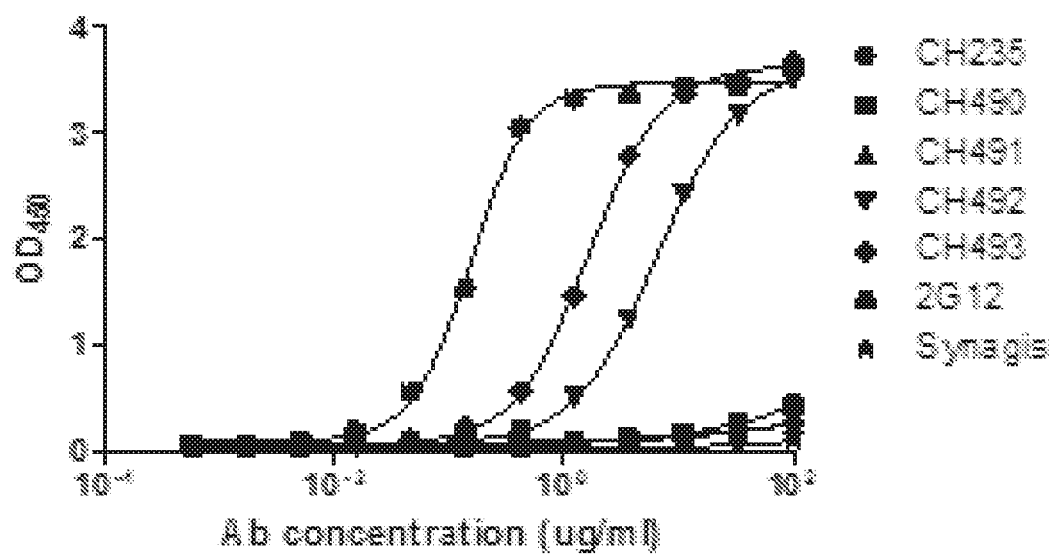
FIG. 21 cont.

| Virus Name | Clade | Virus Lot | CH235UCA_LL 217SJA | DH235UCArk_V2_4A/293i 5RKK | DH235VH_J1_V2_4A/293i 218SJA | DH235VH_J2_V2_4A/293i 256JAH | DH235VH_J3_v2_4A/293i 257JAH | DH235_J4_V2_4A/293i 4RKK |
|---|---|---|---|---|---|---|---|---|
| Q23.17 | A | 2435 | >50 | >50 | | >50 | >50 | >50 |
| DJ263.8 | AG | 2220 | >50 | >50 | >50 | >50 | >50 | >50 |
| C1080.c03 | AE | 3756 | >50 | >50 | >50 | >50 | >50 | >50 |
| 6540.v4.c1 | AC | 2746 | >50 | >50 | >50 | >50 | >50 | >50 |
| Q168.a2 | AD | 1715 | >50 | >50 | >50 | >50 | >50 | >50 |
| 6101.1 | B | 737 | >50 | >50 | >50 | >50 | >50 | >50 |
| BG1168.1 | B | 530 | >50 | >50 | >50 | >50 | >50 | >50 |
| DU172.17 | C | 4168 | >50 | >50 | >50 | >50 | >50 | >50 |
| DU156.12 | C | 4166 | >50 | >50 | >50 | >50 | >50 | >50 |
| DU422.1 | C | 3803 | >50 | >50 | >50 | >50 | >50 | >50 |
| 57128.vrc15 | D | 1940 | >50 | >50 | >50 | >50 | >50 | >50 |
| X1632-S2-B10 | G | 2900 | >50 | >50 | >50 | >50 | >50 | >50 |
| Q679.d22 | A | 3278 | >50 | >50 | >50 | >50 | >50 | >50 |
| ZM106F.PB9 | C | 824 | >50 | >50 | >50 | >50 | >50 | >50 |
| CNE58 | C | 6509 | >50 | >50 | >50 | >50 | >50 | >50 |
| 92RW020.2 | A | 1573 | >50 | >50 | | >50 | >50 | >50 |
| CAAN5342.A2 | B | 995 | >50 | >50 | >50 | >50 | >50 | >50 |
| JR-FL | B | 730 | >50 | >50 | >50 | >50 | >50 | >50 |
| PVO.4 | B | 3801 | >50 | >50 | >50 | >50 | >50 | >50 |
| THRO4156.18 | B | 967 | >50 | >50 | >50 | >50 | >50 | >50 |
| TRJO4551.58 | B | 4159 | >50 | >50 | >50 | >50 | >50 | >50 |
| TRO.11 | B | 772 | >50 | >50 | >50 | >50 | >50 | >50 |
| YU2 | B | 4098 | >50 | >50 | >50 | >50 | >50 | >50 |
| ZM55F.PB28a | C | 819 | >50 | >50 | >50 | >50 | >50 | >50 |
| percent positive | | | 0 | 0 | 8 | 0 | 0 | 0 |

[1]Values are the antibody concentration (μg/ml) at which relative luminescence units (RLUs) were reduced 50% compared to virus control wells (no test sample).
Note: Values in bold are considered positive for neutralizing antibody activity
nt = not tested

FIG. 22

| | | | IC50 (ug/ml) in TZM-bl Cells[1] | | | |
|---|---|---|---|---|---|---|
| | | | DH235_4A | CH236_4A/293i | CH239_4A/293i | CH240_4A/293i |
| Virus Name | Clade | Virus Lot | 223SJA | 215SJA | 216SJA | 254JAH |
| Q23.17 | A | 2435 | 1.7 | 3.8 | 6.7 | >50 |
| DJ263.8 | AG | 2220 | >50 | >50 | >50 | >50 |
| C1080.c03 | AE | 3756 | >50 | >50 | >50 | >50 |
| 6540.v4.c1 | AC | 2746 | >50 | >50 | >50 | >50 |
| Q168.a2 | AD | 1715 | >50 | >50 | >50 | >50 |
| 6101.1 | B | 737 | >50 | >50 | >50 | >50 |
| BG1168.1 | B | 530 | >50 | >50 | >50 | >50 |
| DU172.17 | C | 4168 | 1.8 | 5.6 | 11 | >50 |
| DU156.12 | C | 4166 | 13 | >50 | >50 | >50 |
| DU422.1 | C | 3803 | >50 | >50 | >50 | >50 |
| 57128.vrc15 | D | 1940 | >50 | >50 | >50 | >50 |
| X1632-S2-B10 | G | 2900 | >50 | >50 | >50 | >50 |
| Q679.d22 | A | 3278 | >50 | >50 | >50 | >50 |
| ZM106F.PB9 | C | 824 | >50 | >50 | >50 | >50 |
| CNE58 | C | 6509 | >50 | >50 | >50 | >50 |
| 92RW020.2 | A | 1573 | 1.5 | 26 | 6.3 | >50 |
| CAAN5342.A2 | B | 995 | >50 | >50 | >50 | >50 |
| JR-FL | B | 730 | 1.6 | >50 | 2.8 | >50 |
| PVO.4 | B | 3801 | >50 | >50 | >50 | >50 |
| THRO4156.18 | B | 967 | >50 | >50 | >50 | >50 |
| TRJO4551.58 | B | 4159 | >50 | >50 | >50 | >50 |
| TRO.11 | B | 772 | 13 | >50 | 30 | >50 |
| YU2 | B | 4098 | >50 | >50 | 16 | >50 |
| ZM55F.PB28a | C | 819 | >50 | >50 | >50 | >50 |
| percent positive | | | 25 | 13 | 25 | 0 |

FIG. 22 cont.

| Virus Name | Clade | Virus Lot | CH241_4A 296HC | CH490_4A 311HC | CH491_4A 226SJA | CH492_4A/293i 22RKK | CH493_4A 29RKK | CH01-31 |
|---|---|---|---|---|---|---|---|---|
| Q23.17 | A | 2435 | 19 | >50 | 1.1 | >50 | 0.95 | 0.02 |
| DJ263.8 | AG | 2220 | >50 | >50 | >50 | >50 | 1.5 | 0.25 |
| C1080.c03 | AE | 3756 | >50 | >50 | >50 | >50 | 50 | 0.14 |
| 6540.v4.c1 | AC | 2746 | >50 | >50 | >50 | >50 | >50 | 0.46 |
| Q168.a2 | AD | 1715 | >50 | >50 | >50 | >50 | 1.2 | 0.10 |
| 6101.1 | B | 737 | 11 | >50 | >50 | >50 | 8.1 | 0.57 |
| BG1168.1 | B | 530 | >50 | >50 | >50 | >50 | 8.4 | 1.7 |
| DU172.17 | C | 4168 | 3.2 | >50 | 1.1 | >50 | 1.5 | 0.59 |
| DU156.12 | C | 4166 | >50 | >50 | 4.5 | >50 | 1.6 | 0.36 |
| DU422.1 | C | 3803 | >50 | >50 | 8.1 | >50 | 5.9 | >25 |
| 57128.vrc15 | D | 1940 | >50 | >50 | >50 | >50 | >50 | >25 |
| X1632-S2-B10 | G | 2900 | >50 | >50 | 0.52 | >50 | 1.1 | 0.09 |
| Q679.d22 | A | 3278 | >50 | >50 | >50 | >50 | 1.1 | 0.08 |
| ZM106F.PB9 | C | 824 | 48 | >50 | 5.0 | >50 | 2.6 | 1.2 |
| CNE58 | C | 6509 | >50 | >50 | >50 | >50 | >50 | 0.09 |
| 92RW020.2 | A | 1573 | 3.3 | >50 | 1.7 | >50 | 0.74 | 0.09 |
| CAAN5342.A2 | B | 995 | >50 | >50 | >50 | >50 | 9.8 | >25 |
| JR-FL | B | 730 | 2.9 | >50 | 12 | >50 | 5.4 | 0.03 |
| PVO.4 | B | 3801 | 23 | >50 | 8.4 | nt | 8.1 | 0.92 |
| THRO4156.18 | B | 967 | >50 | >50 | >50 | nt | >50 | 2.6 |
| TRJO4551.58 | B | 4159 | >50 | >50 | >50 | nt | 2.1 | 0.31 |
| TRO.11 | B | 772 | >50 | >50 | >50 | nt | 4.5 | 0.26 |
| YU2 | B | 4098 | 1.0 | >50 | 0.20 | nt | 0.32 | 0.07 |
| ZM55F.PB28a | C | 819 | 28 | >50 | 15 | nt | 5.0 | 2.9 |
| percent positive | | | 38 | 0 | 46 | 0 | 83 | 88 |

FIG. 22 cont.

| Ab | M5 | M6 | M10 | M19 | M11 | M7 | M8 | M9 | M20 | M21 |
|---|---|---|---|---|---|---|---|---|---|---|
| CH235 | 0.30 | 0.81 | 0.71 | 2.16 | 2.67 | >50 | >50 | >50 | >50 | >50 |
| CH490 | 0.12 | >50 | >50 | >50 | >50 | >50 | >50 | >50 | >50 | >50 |
| CH491 | 0.16 | 0.34 | 0.18 | 0.40 | 0.50 | >50* | >50 | >50 | >50 | >50 |
| CH493 | 0.19 | 0.40 | 0.24 | 0.53 | 0.39 | 0.77 | 0.66 | 0.55 | 0.94 | 0.74 |

FIG. 23

CH0505 Loop D Mutants

| S.No. | ID | CH01-31 | CH235 | CH490 | CH491 | CH493 |
|---|---|---|---|---|---|---|
| | Lot | Catalent | 223SJA | 311HC | 226SJA | 29RKK |
| | Sample ID | IC50 (ug/ml) in TZM-bl cells | | | | |
| 1 | CH0505.TF.M5 | 3.97 | 0.30 | 0.12 | 0.16 | 0.19 |
| 2 | CH0505.TF.M6 | 0.04 | 0.81 | >50 | 0.34 | 0.40 |
| 3 | CH0505.TF.M7 | 0.05 | >50 | >50 | >50* | 0.77 |
| 4 | CH0505.TF.M8 | 0.07 | >50 | >50 | >50 | 0.66 |
| 5 | CH0505.TF.M9 | 0.71 | >50 | >50 | >50 | 0.55 |
| 6 | CH0505.TF.M10 | 0.23 | 0.71 | >50 | 0.18 | 0.14 |
| 7 | CH0505.TF.M11 | 0.73 | 26.68 | >50 | 0.50 | 0.39 |
| 8 | CH0505.TF.M19 | 2.95 | 2.16 | >50 | 0.40 | 0.53 |
| 9 | CH0505.TF.M20 | 0.56 | >50 | >50 | >50 | 0.94 |
| 10 | CH0505.TF.M21 | 0.06 | >50 | >50 | >50 | 0.74 |

*48% neutralization at 50 ug/ml

FIG. 24

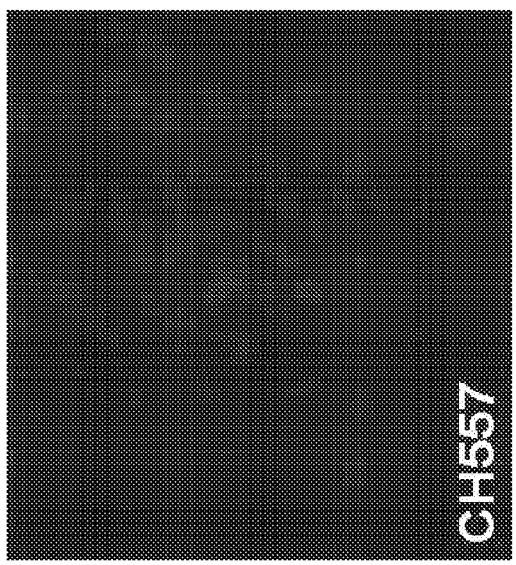
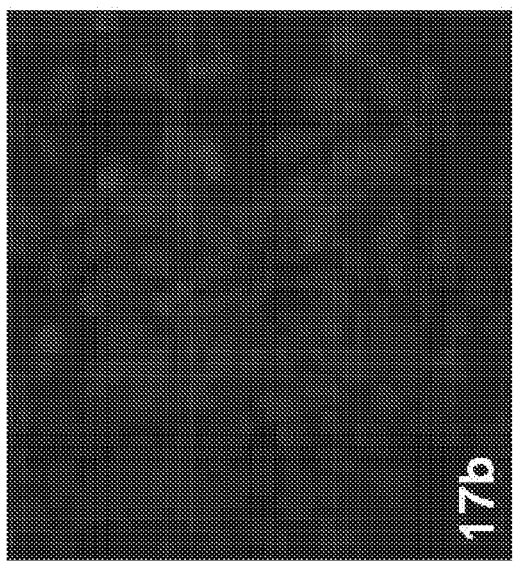
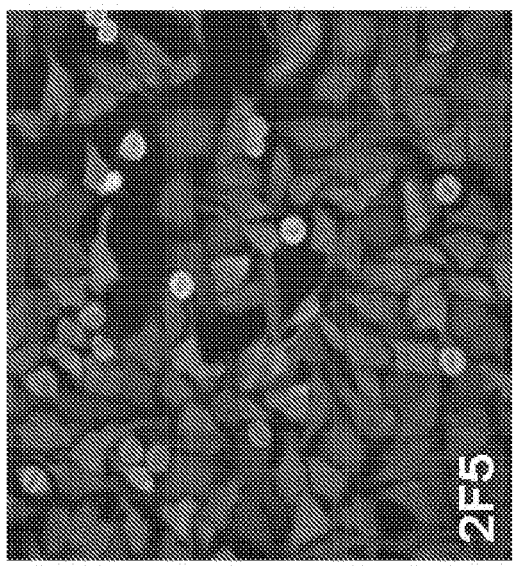
FIG. 25

High Throughput Antibody Screen - Panel P

Assay - Luc/TZM-bl
values represent IC50 in ug/ml

<0.100
0.100-1.00
1.00-10.0
>10.0

| Virus ID | Clade | Panel P CH557 | Panel P CH235 | Panel P VRC01 | Panel H VRC07-523-LS | Panel P N6 | Panel D 3BNC117 | Panel D 8ANC131 | Panel F CH103 | Panel A F105 | Panel P CH522 |
|---|---|---|---|---|---|---|---|---|---|---|---|
| 0260.v5.c36 | A | 1.02 | >50 | 0.468 | 0.175 | 0.148 | 0.200 | 1.18 | >50 | >50 | >50 |
| 0330.v4.C3 | A | 0.313 | >50 | 0.047 | 0.007 | 0.103 | 0.013 | 0.084 | 7.84 | >50 | >50 |
| 0439.v5.c1 | A | 0.374 | >50 | 0.129 | 0.045 | 0.074 | 0.215 | 0.262 | 8.37 | >50 | >50 |
| 3365.v2.c20 | A | 0.068 | >50 | 0.030 | 0.008 | 0.010 | 0.111 | 4.30 | 4.00 | >50 | >50 |
| 3415.v1.c1 | A | 0.450 | >50 | 0.084 | 0.013 | 0.019 | 0.094 | 0.430 | 2.46 | >50 | >50 |
| 3718.v3.c11 | A | 0.360 | 0.074 | 0.165 | 0.009 | 0.111 | >50 | 1.31 | 39.6 | >50 | >50 |
| 398-F1.F6_20 | A | 1.76 | >50 | 0.181 | 0.025 | 0.119 | 0.071 | 2.73 | >50 | >50 | >50 |
| BB201.B42 | A | 0.573 | >50 | 0.316 | 0.111 | 0.106 | 3.35 | 7.32 | 9.19 | >50 | |
| BB539.2B13 | A | 0.111 | >50 | 0.053 | 0.004 | | 0.033 | 0.195 | 27.2 | >50 | >50 |
| BG505.W6M.C2 | A | 0.290 | >50 | 0.224 | 0.046 | 0.022 | 0.124 | 0.298 | >50 | >50 | >50 |
| B1369.9A | A | 0.290 | >50 | 0.224 | 0.046 | 0.062 | 0.030 | 0.798 | >50 | >50 | >50 |
| BS208.B1 | A | 0.263 | >50 | 0.022 | 0.0010 | 0.064 | 0.002 | 0.078 | >50 | >50 | >50 |
| KER2008.12 | A | >50 | >50 | 0.591 | 0.192 | 0.296 | 0.248 | >50 | >50 | >50 | >50 |
| KER2018.11 | A | 2.52 | >50 | 0.555 | 0.174 | 0.064 | 0.417 | 3.28 | 40.1 | >50 | >50 |
| KNH1209.18 | A | 0.251 | >50 | 0.099 | 0.034 | 0.079 | 0.040 | 1.99 | >50 | >50 | >50 |
| MB201.A1 | A | 0.333 | >50 | 0.212 | 0.033 | 0.045 | 0.464 | 27.8 | 27.7 | >50 | |
| MB539.2B7 | A | 1.71 | >50 | 0.500 | 0.102 | 0.067 | 0.187 | 3.10 | 3.70 | >50 | >50 |
| M1369.A5 | A | 0.416 | >50 | 0.269 | 0.110 | 0.070 | 0.053 | 0.850 | >50 | >50 | >50 |
| MS208.A1 | A | 0.463 | >50 | 0.178 | 0.029 | 0.099 | 0.019 | 0.931 | >50 | >50 | >50 |
| Q23.17 | A | 0.132 | 1.35 | 0.052 | 0.022 | 0.018 | 0.017 | 0.274 | 40.4 | >50 | >50 |
| Q259.17 | A | 0.106 | >50 | 0.075 | 0.006 | 0.129 | 0.037 | 0.756 | 38.5 | >50 | >50 |

FIG. 27A

| ID | Group | | | | | | | | | | |
|---|---|---|---|---|---|---|---|---|---|---|---|
| Q769.d22 | A | 0.110 | >50 | 0.016 | 0.013 | 0.007 | 0.015 | 0.998 | >50 | >50 |
| Q769.h5 | A | 0.139 | >50 | 0.062 | 0.012 | 0.025 | 0.028 | | >50 | >50 |
| Q842.d12 | A | 0.091 | 8.15 | 0.038 | 0.007 | 0.007 | 0.013 | 1.46 | >50 | >50 |
| QH209.14M.A2 | A | 0.374 | >50 | 0.068 | 0.006 | 0.008 | 0.013 | 1.16 | >50 | >50 |
| RW020.2 | A | 0.301 | 1.20 | 0.203 | 0.064 | 0.031 | 0.020 | 2.29 | >50 | >50 |
| UG037.8 | A | 0.188 | >50 | 0.088 | 0.013 | 0.014 | 0.020 | 0.378 | >50 | >50 |
| 246-F3.C10.2 | AC | | | | | | | 0.187 | >50 | |
| 3301.V1.C24 | AC | 0.473 | 0.32 | 0.097 | 0.007 | 0.017 | 0.046 | 5.54 | >50 | >50 |
| 3589.V1.C4 | AC | 0.309 | >50 | 0.047 | 0.012 | 0.019 | 0.061 | 0.06 | >50 | >50 |
| 6540.v4.c1 | AC | >50 | >50 | >50 | >50 | 0.077 | >50 | 1.77 | >50 | >50 |
| 6545.V4.C1 | AC | >50 | >50 | >50 | >50 | 0.020 | >50 | >50 | >50 | >50 |
| 0815.V3.C3 | ACD | 0.012 | >50 | 0.013 | 0.0010 | 0.003 | 0.213 | 0.06 | >50 | 0.2 |
| 6095.V1.C10 | ACD | 1.33 | >50 | 0.506 | 0.210 | 0.132 | 0.046 | >50 | 4.69 | >50 |
| 3468.V1.C12 | AD | 0.070 | 2.47 | 0.050 | 0.006 | 0.010 | 0.073 | 6.79 | >50 | >50 |
| Q168.a2 | AD | 0.261 | >50 | 0.098 | 0.030 | 0.077 | 0.050 | 0.299 | >50 | >50 |
| Q461.e2 | AD | 0.818 | >50 | 0.497 | 0.031 | 0.098 | 0.069 | 1.26 | >50 | >50 |
| 620345.c1 | AE | 1.94 | >50 | >50 | >50 | 1.26 | >50 | >50 | >50 | >50 |
| BJOX009000.02.4 | AE | 5.50 | >50 | 1.54 | 0.311 | 0.187 | | | >50 | >50 |
| BJOX010000.06.2 | AE | 0.08 | >50 | 6.79 | 1.26 | 0.518 | | | >50 | >50 |
| BJOX025000.01.1 | AE | 0.271 | 0.05 | 8.46 | 0.128 | 0.011 | 0.096 | >50 | >50 | >50 |
| BJOX028000.10.3 | AE | 0.168 | >50 | 0.256 | 0.0040 | 0.005 | 0.064 | >50 | >50 | >50 |
| C1080.c3 | AE | 2.69 | >50 | 2.10 | 0.148 | 0.178 | | | >50 | >50 |
| C2101.c1 | AE | 0.261 | 0.23 | 0.179 | 0.032 | 0.044 | 0.029 | 0.2 | >50 | >50 |
| C3347.c11 | AE | 0.117 | >50 | 0.025 | 0.024 | 0.010 | 0.019 | 5.30 | >50 | >50 |
| C4118.09 | AE | 0.084 | 3.30 | 0.248 | 0.013 | 0.017 | | 9.97 | >50 | >50 |
| CM244.ec1 | AE | 0.160 | 1.19 | 0.089 | 0.003 | 0.005 | | | >50 | >50 |
| CNE3 | AE | 2.45 | >50 | 1.63 | 0.122 | 0.017 | 0.125 | 2.75 | >50 | >50 |
| CNE5 | AE | 1.03 | 0.2 | 0.323 | 0.053 | 0.074 | 0.386 | >50 | >50 | >50 |

FIG. 27A cont.

| | | | | | | | | | | | |
|---|---|---|---|---|---|---|---|---|---|---|---|
| CNE55 | AE | 0.400 | >50 | 0.359 | 0.046 | | | | >50 | >50 | >50 |
| CNE56 | AE | 1.10 | | 0.343 | 0.066 | 0.074 | | | >50 | >50 | >50 |
| CNE59 | AE | 0.943 | | 0.623 | 0.057 | 0.106 | 0.343 | | >50 | >50 | >50 |
| CNE8 | AE | 1.10 | >50 | 0.510 | 0.118 | 0.096 | | | >50 | >50 | >50 |
| M02138 | AE | | | | | | 0.154 | | | >50 | |
| R1166.c1 | AE | 0.758 | >50 | 3.00 | 0.231 | 0.453 | 0.230 | >50 | >50 | >50 | >50 |
| R2184.c4 | AE | 0.563 | 5.82 | 0.133 | 0.434 | 2.029 | | 9.00 | >50 | >50 | >50 |
| R3265.c6 | AE | 0.172 | >50 | 0.710 | 0.111 | 0.029 | | >50 | >50 | >50 | >50 |
| TH023.6 | AE | | | | 0.005 | | | | | | |
| TH966.8 | AE | 0.304 | 0.732 | 0.284 | 0.043 | 0.034 | | | >50 | >50 | >50 |
| TH976.17 | AE | 0.286 | 0.975 | 0.332 | 0.046 | 0.053 | | | >50 | >50 | >50 |
| 235-47 | AG | 0.293 | >50 | 0.062 | 0.003 | 0.009 | 0.012 | 4.54 | 0.628 | >50 | >50 |
| 242-14 | AG | 2.83 | >50 | >50 | 0.136 | 0.212 | >50 | >50 | >50 | >50 | >50 |
| 263-8 | AG | 0.447 | >50 | 0.168 | 0.023 | 0.013 | 0.447 | 0.209 | >50 | >50 | >50 |
| 269-12 | AG | >50 | >50 | 0.293 | 0.046 | 0.025 | 0.151 | 2.92 | 0.1 | >50 | >50 |
| 271-11 | AG | 0.080 | >50 | 0.054 | 0.007 | 0.011 | 0.067 | 2.18 | 8.52 | >50 | >50 |
| 928-28 | AG | 0.542 | >50 | 0.476 | 0.086 | 0.067 | 0.155 | 2.26 | >50 | >50 | >50 |
| DJ263.8 | AG | 0.276 | >50 | 0.066 | 0.003 | 0.059 | 0.015 | 0.022 | 0.784 | >50 | 7.18 |
| T250-4 | AG | >50 | >50 | >50 | >50 | 0.007 | >50 | >50 | >50 | >50 | >50 |
| T251-18 | AG | 4.02 | >50 | 4.42 | 0.215 | 0.383 | 0.203 | 1.79 | | >50 | >50 |
| T253-11 | AG | 1.65 | >50 | 0.501 | 0.064 | 0.109 | 0.116 | 10.4 | | >50 | >50 |
| T255-34 | AG | 0.608 | >50 | 0.725 | 0.032 | 0.056 | 0.051 | 9.76 | | >50 | >50 |
| T257-31 | AG | 2.66 | >50 | 2.47 | 0.266 | 0.173 | 0.181 | 31.1 | | >50 | >50 |
| T266-60 | AG | | >50 | 2.37 | 0.317 | 0.193 | 0.017 | 1.35 | | >50 | >50 |
| T278-50 | AG | >50 | >50 | >50 | >50 | >50 | >50 | >50 | >50 | >50 | >50 |
| T280-5 | AG | 0.109 | >50 | 0.052 | 0.003 | 0.021 | 0.014 | 0.002 | 0.986 | >50 | >50 |
| T33-7 | AG | 0.018 | >50 | 0.018 | 0.0010 | 0.007 | 0.017 | 0.959 | 8.44 | >50 | >50 |
| 3988.25 | B | 0.917 | >50 | 0.369 | 0.059 | 0.084 | >50 | >50 | 9.84 | >50 | >50 |

FIG. 27A cont.

| | | | | | | | | | | |
|---|---|---|---|---|---|---|---|---|---|---|
| 5768.04 | B | 0.715 | >50 | 0.354 | 0.065 | 0.053 | 0.201 | | 7.08 | >50 | >50 |
| 6101.10 | B | 0.467 | >50 | 0.023 | 0.005 | 0.003 | | | 1.80 | >50 | >50 |
| 6535.3 | B | 4.85 | >50 | 2.10 | 0.114 | 0.063 | 0.262 | 0.362 | 4.67 | 3.08 | |
| 7165.18 | B | >50 | >50 | | 1.43 | 0.912 | 6.54 | >50 | >50 | >50 | >50 |
| 45_01dG5 | B | | >50 | 0.011 | 0.0006 | | | | 0.796 | >50 | >50 |
| 89.6.DG | B | 2.23 | >50 | 1.30 | 0.092 | 0.195 | 0.109 | 0.810 | 1.40 | >50 | >50 |
| AC10.29 | B | 2.13 | >50 | 1.41 | 0.624 | 0.238 | 6.05 | >50 | >50 | >50 | >50 |
| ADA.DG | B | 0.907 | >50 | 0.563 | 0.114 | 0.120 | 0.006 | 0.393 | 1.49 | 2.02 | 1.69 |
| BaL.01 | B | 0.237 | >50 | 0.124 | 0.004 | 0.023 | 0.012 | 0.132 | 0.676 | >50 | >50 |
| BaL.26 | B | 0.214 | >50 | 0.060 | 0.0010 | 0.015 | 0.006 | 0.061 | 0.001 | | |
| BG1168.01 | B | 1.42 | >50 | 0.738 | 0.060 | 0.077 | 0.179 | 0.562 | | | |
| BL01.DG | B | >50 | >50 | >50 | >50 | >50 | >50 | >50 | >50 | >50 | >50 |
| BR07.DG | B | 1.51 | >50 | 1.81 | 0.191 | 0.335 | 0.135 | 1.77 | 9.67 | >50 | >50 |
| BX08.16 | B | 2.35 | >50 | 0.389 | 0.040 | 0.047 | 0.102 | 2.26 | 1.15 | 9.73 | 6.44 |
| CAAN.A2 | B | 2.23 | >50 | 0.963 | 0.140 | 0.136 | 0.673 | 1.72 | >50 | >50 | >50 |
| CNE10 | B | 5.26 | >50 | 0.689 | 0.042 | 0.104 | 0.057 | 0.941 | | | >50 |
| CNE12 | B | 2.56 | >50 | 0.695 | 0.129 | 0.200 | 0.005 | 1.42 | | | >50 |
| CNE14 | B | 0.594 | >50 | 0.199 | 0.019 | 0.023 | 0.014 | 5.19 | 0.522 | | |
| CNE4 | B | 1.16 | >50 | 0.639 | 0.129 | 0.137 | 0.113 | | | | |
| CNE57 | B | 1.25 | >50 | 0.496 | 0.172 | 0.076 | 0.166 | | | | |
| HO86.8 | B | 0.174 | >50 | >50 | >50 | 2.00 | >50 | >50 | >50 | >50 | >50 |
| HT593.1 | B | 0.984 | >50 | 0.606 | 0.080 | 0.156 | 0.229 | 0.817 | 0.124 | 0.167 | 0.241 |
| HXB2.DG | B | 0.173 | | 0.063 | 0.009 | 0.008 | | | | | |
| JRCSF.JB | B | 0.596 | >50 | 0.436 | 0.037 | 0.135 | 0.002 | 0.245 | 0.906 | >50 | >50 |
| JRFL.JB | B | 0.127 | 1.82 | 0.051 | 0.0005 | 0.003 | | | | | |
| MN.3 | B | 0.142 | >50 | 0.011 | 0.0009 | 0.002 | | | 0.187 | >50 | 1.81 |
| PVO.04 | B | 1.47 | >50 | 0.552 | 0.078 | 0.013 | 0.071 | 0.477 | 0.693 | >50 | >50 |
| QH0515.01 | B | 1.40 | | 1.43 | 0.494 | 0.377 | 0.175 | >50 | | >50 | >50 |

FIG. 27A cont.

| | | | | | | | | | |
|---|---|---|---|---|---|---|---|---|---|
| QH0692.42 | B | 2.25 | >50 | 1.37 | 0.302 | 0.484 | 0.275 | 2.63 | | >50 | >50 |
| REJO.67 | B | 1.09 | >50 | 0.113 | 0.003 | 0.022 | 0.039 | 0.052 | 2.15 | >50 | >50 |
| RHPA.7 | B | | | | 0.666 | 0.017 | 0.013 | 5.10 | 8.53 | >50 | >50 |
| SC422.8 | B | 0.798 | >50 | 0.127 | 0.023 | 0.038 | 0.049 | 0.158 | 2.44 | >50 | >50 |
| SF162.LS | B | 0.534 | >50 | 0.228 | 0.119 | | 0.053 | 0.103 | 0.843 | 2.92 | 2.83 |
| SS1196.01 | B | 0.827 | >50 | 0.246 | 0.047 | 0.069 | 0.038 | 0.271 | 1.34 | 6.24 | |
| THRO.18 | B | >50 | >50 | 4.63 | 0.965 | 0.890 | 2.80 | | >50 | >50 | >50 |
| TRJO.58 | B | 0.524 | >50 | 0.116 | 0.198 | | 0.052 | | | | >50 |
| TRO.11 | B | 0.714 | | 0.502 | 0.095 | 0.053 | 0.033 | 9.97 | 5.34 | >50 | >50 |
| WITO.33 | B | 0.418 | >50 | 0.140 | 0.047 | 0.056 | 0.030 | | 7.35 | >50 | >50 |
| X2278.C2.B6 | B | 0.425 | >50 | 0.133 | | | | | | >50 | >50 |
| YU2.DG | B | 0.235 | >50 | 0.113 | 0.030 | 0.030 | 0.029 | 0.221 | 1.80 | >50 | >50 |
| BJOX02000.03.2 | BC | 0.739 | >50 | >50 | | | | | | >50 | >50 |
| CH038.12 | BC | | | 0.519 | 0.052 | 0.094 | >50 | >50 | 3.54 | >50 | >50 |
| CH070.1 | BC | 2.39 | >50 | 9.99 | 0.088 | 0.119 | 7.89 | 3.81 | >50 | >50 | >50 |
| CH117.4 | BC | 0.340 | >50 | | 0.007 | 0.027 | 0.663 | >50 | 4.09 | >50 | >50 |
| CH119.10 | BC | 1.24 | >50 | 0.577 | 0.045 | | | | | | |
| CH181.12 | BC | 0.612 | >50 | 0.481 | 0.063 | 0.065 | 0.124 | 9.50 | 5.00 | >50 | >50 |
| CNE15 | BC | 0.249 | | | 0.067 | 0.015 | >50 | | | | |
| CNE19 | BC | 0.134 | >50 | 0.169 | 0.005 | 0.015 | | | | | |
| CNE20 | BC | 0.254 | >50 | 9.25 | 0.005 | 0.009 | | | 1.80 | >50 | >50 |
| CNE21 | BC | 0.527 | >50 | 0.357 | 0.041 | 0.037 | | | >50 | >50 | >50 |
| CNE40 | BC | 0.207 | >50 | 0.370 | 0.034 | 0.018 | 0.116 | | 0.505 | 0.242 | 0.221 |
| CNE7 | BC | 1.36 | >50 | 0.286 | 0.039 | 0.024 | >50 | | | | |
| 286.36 | C | 0.699 | >50 | 0.322 | 0.070 | 0.047 | 0.057 | 0.713 | 8.36 | >50 | >50 |
| 288.38 | C | 1.62 | >50 | 1.49 | 0.263 | 0.169 | 0.063 | 0.683 | 8.45 | >50 | >50 |
| 0013095-2.11 | C | | >50 | | 0.009 | 0.038 | 0.208 | | 5.71 | >50 | >50 |
| 001428-2.42 | C | | >50 | | | | | | 1.51 | >50 | >50 |

FIG. 27A cont.

| Name | | | | | | | | | | | |
|---|---|---|---|---|---|---|---|---|---|---|---|
| 0077_V1.C16 | C | 6.84 | >50 | 1.28 | 0.046 | >50 | >50 | >50 | >50 | >50 | |
| 00836-2.5 | C | 1.09 | >50 | 0.119 | 0.007 | >50 | >50 | | >50 | >50 | |
| 0921.V2.C14 | C | 0.344 | | 0.182 | 0.014 | 0.243 | | >50 | >50 | >50 | |
| 16055-2.3 | C | 0.159 | >50 | 0.053 | 0.003 | 3.24 | 0.386 | >50 | >50 | >50 | |
| 16845-2.22 | C | 7.47 | >50 | 3.60 | 0.257 | | >50 | >50 | >50 | >50 | |
| 16936-2.21 | C | 0.500 | >50 | 0.110 | 0.012 | | | 5.57 | >50 | >50 | |
| 25710-2.43 | C | 0.382 | >50 | 0.594 | 0.090 | | 3.67 | >50 | >50 | >50 | |
| 25711-2.4 | C | 0.974 | >50 | 0.555 | | >50 | >50 | >50 | >50 | >50 | |
| 25925-2.22 | C | 0.641 | >50 | 0.474 | 0.062 | 0.136 | | | >50 | >50 | |
| 26191-2.48 | C | 0.583 | >50 | 0.166 | 0.046 | | | >50 | >50 | >50 | |
| 3168.V4.C10 | C | 0.372 | >50 | 0.255 | 0.030 | 0.110 | 9.47 | | >50 | >50 | |
| 3637.V5.C3 | C | | >50 | 1.45 | 0.255 | >50 | | | >50 | >50 | |
| 3873.V1.C24 | C | >50 | >50 | 0.791 | 0.181 | 6.97 | 0.460 | >50 | >50 | >50 | |
| 426c | C | | | | 0.105 | | | | | | |
| 6322.V4.C1 | C | 0.944 | >50 | >50 | | >50 | >50 | >50 | >50 | >50 | |
| 6471.V1.C16 | C | >50 | >50 | >50 | >50 | >50 | >50 | >50 | >50 | >50 | |
| 6631.V3.C10 | C | 5.83 | >50 | >50 | 0.148 | >50 | >50 | >50 | >50 | >50 | |
| 6644.V2.C33 | C | >50 | >50 | 0.243 | 0.028 | | | >50 | 2.30 | 4.49 | |
| 6785.V5.C14 | C | >50 | >50 | 0.286 | 0.065 | 0.195 | | 0.377 | >50 | >50 | |
| 6838.V1.C35 | C | 1.08 | >50 | 0.210 | 0.102 | 0.281 | | 8.95 | >50 | >50 | |
| 96ZM651.02 | C | 1.18 | >50 | 0.570 | 0.025 | 0.443 | 0.462 | | >50 | >50 | |
| BR025.9 | C | >50 | >50 | 0.593 | 0.037 | >50 | >50 | 8.99 | >50 | >50 | |
| CAP210.E8 | C | >50 | >50 | >50 | | 8.16 | | >50 | >50 | >50 | |
| CAP244.D3 | C | 1.52 | >50 | 1.33 | 0.058 | | 0.330 | >50 | >50 | >50 | |
| CAP256.206.C9 | C | 1.32 | | 0.971 | 0.081 | 0.494 | >50 | >50 | >50 | >50 | |
| CAP45.G3 | C | 0.568 | >50 | 7.00 | 0.034 | 0.589 | | >50 | >50 | >50 | |
| Ce1176.A3 | C | 1.24 | >50 | 2.60 | 0.252 | | | | | | |
| CE703010217.B6 | C | 0.319 | >50 | 0.366 | 0.023 | | | >50 | >50 | >50 | |
| CNE30 | C | 1.21 | >50 | 0.525 | 0.169 | 0.291 | 1.22 | >50 | >50 | >50 | |

FIG. 27A cont.

|  |  |  |  |  |  |  |  |  |  |
|---|---|---|---|---|---|---|---|---|---|
| CNE31 | C | 2.78 | >50 | 0.786 | 0.131 | 0.330 |  | >50 | >50 | >50 |
| CNE53 | C | 0.274 | 1.77 | 0.087 | 0.010 | 0.041 | 2.08 | 6.92 | >50 | >50 |
| CNE58 | C | 1.95 | >50 | 0.225 | 0.026 | 0.014 | 1.20 | 0.543 | >50 | >50 |
| DU123.06 | C | 4.25 | >50 | 7.92 | 0.133 | 0.183 | >50 | >50 | >50 | >50 |
| DU151.02 | C | 0.287 | 3.94 | 0.048 | 0.016 | 0.041 | >50 | >50 | >50 | >50 |
| DU156.12 | C | 0.285 | 9.48 | 0.046 | 0.007 | 0.009 | 2.4 | >50 | >50 | >50 |
| DU172.17 | C | 0.361 | 1.92 | 0.047 | 0.057 | 0.041 | >50 | >50 | >50 | >50 |
| DU422.01 | C | 0.944 | >50 | >50 | 2.36 | 0.034 | >50 | >50 | >50 | >50 |
| MW965.26 | C | 0.573 | 6.10 | 0.023 | 0.003 | 0.003 | 4.93 | 0.014 | >50 | 1.23 |
| SO18.18 | C | 0.110 | >50 | 0.058 | 0.004 | 0.008 | 1.50 | 1.88 | >50 | >50 |
| TV1.29 | C | 4.63 | >50 | >50 | 1.79 | >50 | >50 | >50 | >50 | >50 |
| TZA125.17 | C | >50 | >50 | >50 | 1.41 | 0.746 | 4.14 | >50 | >50 | >50 |
| TZBD.02 | C | 0.219 | >50 | 0.078 | 0.015 | 0.013 | >50 | 5.55 | >50 | >50 |
| ZA012.29 | C | 0.971 | 1.2 | 0.384 | 0.046 | 0.033 | 26.7 | 26.4 | >50 | >50 |
| ZM106.9 | C | 0.620 | >50 | 0.311 | 0.031 | 0.075 | 0.087 | 4.82 | >50 | >50 |
| ZM109.4 | C | 0.416 | >50 | 0.177 | 0.034 | 0.059 | 6.22 | 22.2 | >50 | >50 |
| ZM135.10a | C | >50 | >50 | 2.25 | 0.107 | 0.139 | 22.2 | >50 | >50 | >50 |
| ZM176.66 | C | 0.183 | >50 | 0.063 | 0.0015 | 0.006 | >50 | 0.227 | >50 | >50 |
| ZM197.7 | C | 1.40 | >50 | 0.428 | 0.191 | 0.019 | >50 | 35.4 | >50 | >50 |
| ZM214.15 | C | 2.22 | >50 | 0.893 | 0.277 | 0.088 | 1.63 | 4.17 | >50 | >50 |
| ZM215.8 | C | 0.315 | 6.19 | 0.215 | 0.043 | 0.048 | 7.96 | 2.57 | >50 | >50 |
| ZM233.6 | C | 1.25 | 5.71 | 1.02 | 0.064 | 0.067 | >50 | 7.35 | >50 | >50 |
| ZM249.1 | C | 0.273 | 9.99 | 0.057 | 0.017 | 0.015 | 10.0 | 7.23 | >50 | >50 |
| ZM53.12 | C | 0.558 | >50 | 0.625 | 0.149 | 0.149 | 7.8 | 4.59 | >50 | >50 |
| ZM55.28a | C | 0.665 | >50 | 0.285 | 0.023 | 0.023 | 0.565 | >50 | >50 |  >50 |
| 3326.V4.C3 | CD | 0.114 | >50 | 0.068 | 0.0008 | 48.1 | 1.44 | 0.693 | >50 | >50 |
| 3337.V2.C6 | CD | 0.429 | >50 | 0.040 | 0.011 | 0.005 | 0.017 | >50 | >50 | >50 |
| 3817.v2.c59 | CD | 3.63 | >50 | >50 | 0.137 | 0.382 | 0.216 | >50 | >50 | >50 |

FIG. 27A cont.

| Virus | Clade | C1 | C2 | C3 | C4 | C5 | C6 | C7 | C8 |
|---|---|---|---|---|---|---|---|---|---|
| 191821.E6.1 | D | | | | | | | | |
| 231965.c1 | D | 1.23 | >50 | 0.353 | 0.030 | 0.025 | | 2.1 | >50 |
| 247-23 | D | 0.691 | >50 | 1.84 | 0.014 | 0.017 | 1.07 | 4.0 | >50 |
| 3016.v5.c45 | D | >50 | >50 | 0.155 | 0.875 | 0.012 | >50 | 4.15 | >50 |
| 57128.vrc15 | D | 6.59 | >50 | >50 | 0.015 | 0.648 | >50 | >50 | 0.940 |
| 6405.v4.c34 | D | >50 | >50 | 1.55 | 0.666 | 0.382 | 30.3 | >50 | >50 |
| A03349M1.vrc4a | D | 4.08 | >50 | 4.10 | 0.212 | 0.066 | 43.1 | >50 | >50 |
| A07412M1.vrc12 | D | 0.351 | >50 | 0.082 | 0.940 | 0.655 | 5.09 | >50 | >50 |
| NKU3006.ec1 | D | 0.466 | 4.61 | 0.596 | 0.020 | 0.027 | | 1.4 | >50 |
| UG021.16 | D | | | | 0.169 | 0.147 | 0.510 | >50 | 0.382 |
| UG024.2 | D | | | | 0.019 | | >50 | >50 | 0.053 |
| P0402.c2.11 | G | 2.19 | >50 | 0.330 | 0.016 | 0.082 | | 2.1 | >50 |
| P1981.C5.3 | G | 0.972 | >50 | 0.154 | 0.029 | 0.061 | | >50 | >50 |
| X1193.c1 | G | 1.98 | >50 | 0.053 | 0.029 | 0.035 | | 3.0 | >50 |
| X1254.c3 | G | 0.484 | >50 | 0.130 | 0.003 | 0.055 | | >50 | >50 |
| X1632.S2.B10 | G | >50 | >50 | >50 | 0.30.8 | 0.050 | 0.630 | 1.48 | >50 |
| X2088.c9 | G | 2.58 | >50 | 0.537 | 0.102 | | | >50 | >50 |
| X2131.C1.B5 | G | >50 | >50 | >50 | >50 | >50 | >50 | >50 | >50 |
| SIVmac251.30.SG3 | NA | >50 | >50 | >50 | >50 | >50 | >50 | >50 | >50 |
| SVA.MLV | NA | >50 | >50 | >50 | >50 | >50 | >50 | >50 | >50 |

FIG. 27A cont.

| | CH557 | CH235 | VRC01 | VRC07-523-LS | N6 | 3BNC117 | 8ANC131 | CH103 | F105 | CH522 |
|---|---|---|---|---|---|---|---|---|---|---|
| # Viruses | 199 | 199 | 199 | 195 | 199 | 181 | 181 | 196 | 206 | 199 |
| Total VS Neutralized | | | | | | | | | | |
| IC50 <50ug/ml | 179 | 35 | 179 | 187 | 195 | 153 | 140 | 104 | 14 | 14 |
| IC50 <10ug/ml | 173 | 19 | 177 | 186 | 193 | 150 | 102 | 69 | 12 | 10 |
| IC50 <1.0ug/ml | 115 | 2 | 146 | 180 | 191 | 141 | 55 | 19 | 5 | 2 |
| IC50 <0.1ug/ml | 10 | 0 | 47 | 130 | 146 | 89 | 17 | 3 | 1 | 0 |
| IC50 <0.01ug/ml | 0 | 0 | 1 | 45 | 22 | 11 | 0 | 0 | 0 | 0 |
| % VS Neutralized | | | | | | | | | | |
| IC50 <50ug/ml | 90 | 18 | 90 | 96 | 98 | 85 | 77 | 53 | 7 | 7 |
| IC50 <10ug/ml | 87 | 10 | 89 | 95 | 97 | 83 | 56 | 35 | 6 | 5 |
| IC50 <1.0ug/ml | 58 | 1 | 73 | 92 | 96 | 78 | 30 | 10 | 2 | 1 |
| IC50 <0.1ug/ml | 5 | 0 | 24 | 67 | 73 | 49 | 9 | 2 | 0 | 0 |
| IC50 <0.01ug/ml | 0 | 0 | 1 | 23 | 11 | 6 | 0 | 0 | 0 | 0 |
| Median IC50 | 0.583 | 9.48 | 0.293 | 0.045 | 0.047 | 0.073 | 1.89 | 6.84 | 2.61 | 4.61 |
| Geometric Mean | 0.658 | 6.84 | 0.300 | 0.037 | 0.045 | 0.092 | 1.77 | 4.54 | 1.65 | 3.87 |

FIG. 27B

High Throughput Antibody Screen - Panel P
Assay - Luc/TZM-bl
values represent IC80 in ug/ml    IC80: <0.100 / 0.100-1.00 / 1.00-10.0 / >10.0

| Virus ID | Clade | Panel P CH557 | Panel P CH235 | Panel P VRC01 | Panel H VRC07-523-LS | Panel P N6 | Panel D 3BNC117 | Panel D 8ANC131 | Panel F CH103 | Panel A F105 | Panel P CH522 |
|---|---|---|---|---|---|---|---|---|---|---|---|
| 0260.v5.c36 | A | 2.65 | >50 | 1.54 | 0.568 | 0.148 | 0.733 | 4.66 | >50 | >50 | >50 |
| 0330.v4.c3 | A | 0.759 | >50 | 0.167 | 0.060 | 0.034 | 0.070 | 0.453 | 20.3 | >50 | >50 |
| 0439.v5.c1 | A | 1.29 | >50 | 0.436 | 0.352 | 0.088 | 0.776 | 0.940 | >50 | >50 | >50 |
| 3365.v2.c20 | A | 0.227 | >50 | 0.116 | 0.021 | 0.029 | 0.044 | 1.57 | 40.0 | >50 | >50 |
| 3415.v1.c1 | A | 1.28 | >50 | 0.243 | 0.109 | 0.064 | 0.276 | 1.74 | 4.73 | >50 | >50 |
| 3718.v3.c11 | A | 0.948 | >50 | 2.58 | 0.066 | 0.036 | >50 | 11.1 | >50 | >50 | >50 |
| 398-F1_F6_20 | A | 4.42 | >50 | 0.612 | 0.181 | 0.083 | 0.297 | >50 | >50 | >50 | >50 |
| BB201.B42 | A | 1.67 | >50 | 0.733 | 0.464 | 0.292 | 2.3 | >50 | >50 | >50 | >50 |
| BB539.2B13 | A |  |  | 0.135 | 0.035 |  | 0.197 | 0.915 |  |  |  |
| BG505.W6M.C2 | A | 0.314 | >50 | 0.615 | 0.274 | 0.068 | 0.078 | 1.79 | >50 | >50 | >50 |
| BJ369.9A | A | 0.811 | >50 | 0.068 | 0.012 | 0.217 | 0.142 | 5.39 | >50 | >50 | >50 |
| BS208.B1 | A | 0.598 | >50 | 1.48 | 0.737 | 0.030 | 0.010 | 0.745 | >50 | >50 | >50 |
| KER2008.12 | A | >50 | >50 | 1.49 | 0.936 | 0.729 | 1.36 | >50 | >50 | >50 | >50 |
| KER2018.11 | A | 5.84 | >50 | 0.305 | 0.179 | 0.310 | 1.51 | 14.0 | >50 | >50 | >50 |
| KNH1209.18 | A | 0.656 | >50 | 0.532 | 0.311 | 0.117 | 0.159 | 10.1 | >50 | >50 | >50 |
| MB201.A1 | A | 0.883 | >50 | 1.08 | 0.301 | 0.157 | 4.97 | >50 | >50 | >50 | >50 |
| MB539.2B7 | A | 3.62 | >50 | 0.826 | 0.352 | 0.219 | 0.382 | 27.3 | 14.7 | >50 | >50 |
| MI369.A5 | A | 1.15 | >50 | 0.663 | 0.235 | 0.136 | 0.210 | 7.25 | >50 | >50 | >50 |
| MS208.A1 | A | 1.31 | >50 | 0.663 | 0.235 | 0.136 | 0.118 | 27.1 | >50 | >50 | >50 |

FIG. 28A

| | | | | | | | | | |
|---|---|---|---|---|---|---|---|---|---|
| Q23.17 | A | 0.318 | 5.28 | 0.156 | 0.109 | 0.063 | 0.062 | 0.896 | >50 | >50 |
| Q259.17 | A | 0.308 | >50 | 0.234 | 0.044 | 1.56 | 0.067 | 3.72 | 12.9 | >50 |
| Q769.d22 | A | 0.293 | >50 | 0.087 | 0.055 | 0.044 | 0.045 | 0.213 | 33.9 | >50 |
| Q769.h5 | A | 0.426 | >50 | 0.158 | 0.073 | 0.064 | 0.039 | 0.249 | 2.67 | >50 |
| Q842.d12 | A | 0.239 | 18.3 | 0.111 | 0.038 | 0.028 | 0.012 | 0.085 | 5.10 | >50 |
| QH209.14M.A2 | A | 1.09 | >50 | 0.148 | 0.051 | 0.024 | 0.043 | 22.6 | 5.75 | >50 |
| RW020.2 | A | 0.774 | 4.59 | 0.715 | 0.321 | 0.110 | 0.106 | 1.60 | 47.1 | >50 |
| UG037.8 | A | 0.601 | >50 | 0.227 | 0.084 | 0.071 | 0.108 | 0.935 | 11.9 | >50 |
| 246-F3.C10.2 | AC | | | | | | | | | >50 |
| 3301.V1.C24 | AC | 1.33 | >50 | 0.269 | 0.026 | 0.021 | 0.109 | 0.245 | 12.2 | >50 |
| 3589.V1.C4 | AC | 2.01 | >50 | 0.181 | 0.072 | 0.036 | 0.182 | 15.7 | >50 | >50 |
| 6540.v4.c1 | AC | >50 | >50 | >50 | >50 | 1.19 | >50 | >50 | 7.74 | >50 |
| 6545.V4.C1 | AC | >50 | >50 | >50 | >50 | >50 | >50 | >50 | >50 | >50 |
| 0815.V3.C3 | ACD | 0.133 | >50 | 0.067 | 0.005 | 0.016 | 0.058 | 0.654 | >50 | >50 |
| 6095.V1.C10 | ACD | 4.09 | >50 | 1.76 | 0.937 | 0.592 | 0.808 | 7.94 | >50 | >50 |
| 3468.V1.C12 | AD | 0.200 | 14.4 | 0.159 | 0.044 | 0.027 | 0.705 | 41.1 | 26.4 | >50 |
| Q168.a2 | AD | 0.619 | >50 | 0.240 | 0.112 | 0.082 | 0.172 | 1.20 | >50 | >50 |
| Q461.e2 | AD | 2.54 | >50 | 0.968 | 0.361 | 0.200 | 0.330 | 7.46 | >50 | >50 |
| 620345.c1 | AE | 8.44 | >50 | >50 | >50 | >50 | >50 | >50 | >50 | >50 |
| BJOX009000.02.4 | AE | 2.18 | >50 | 5.02 | 1.41 | 0.764 | | | | >50 |
| BJOX010000.06.2 | AE | >50 | >50 | 19.1 | 3.40 | 1.50 | | | | >50 |
| BJOX025000.01.1 | AE | 0.885 | >50 | >50 | 0.427 | 0.070 | | | | >50 |
| BJOX028000.10.3 | AE | 0.507 | >50 | 1.06 | 0.012 | 0.013 | 0.665 | >50 | >50 | >50 |
| C1080.c3 | AE | 7.74 | >50 | 9.07 | 0.794 | 0.792 | 0.222 | >50 | >50 | >50 |
| C2101.c1 | AE | 0.792 | >50 | 0.562 | 0.269 | 0.151 | | | | >50 |
| C3347.c11 | AE | 0.332 | >50 | 0.289 | 0.110 | 0.028 | 0.106 | 26.3 | >50 | >50 |

FIG. 28A cont.

| ID | Clade | | | | | | | | | | |
|---|---|---|---|---|---|---|---|---|---|---|---|
| C4118.09 | AE | 0.234 | | | 0.452 | 0.097 | 0.161 | 0.106 | >50 | >50 | >50 |
| CM244.ec1 | AE | 0.503 | 6.31 | 0.325 | 0.045 | 0.035 | | | >50 | >50 |
| CNE3 | AE | 2.52 | >50 | 8.35 | 0.626 | 0.067 | 0.430 | 28.7 | >50 | >50 |
| CNE5 | AE | 2.78 | >50 | 1.01 | 0.267 | 0.281 | 1.34 | >50 | >50 | >50 |
| CNE55 | AE | 1.25 | >50 | 0.973 | 0.218 | 0.225 | 0.530 | >50 | >50 | >50 |
| CNE56 | AE | 3.25 | >50 | 1.10 | 0.381 | 0.326 | 0.355 | 28.1 | >50 | >50 |
| CNE59 | AE | 3.03 | >50 | 2.32 | 0.353 | 0.422 | | >50 | >50 | >50 |
| CNE8 | AE | 2.64 | >50 | 1.38 | 0.411 | 0.233 | 0.573 | | | |
| MO2138 | AE | | | | 0.752 | | 0.568 | >50 | >50 | >50 |
| R1166.c1 | AE | 3.52 | >50 | 7.96 | 1.96 | 1.24 | 0.805 | >50 | >50 | >50 |
| R2184.c4 | AE | 1.63 | 16.1 | 0.353 | 0.106 | 0.080 | 0.178 | 45.0 | >50 | >50 |
| R3265.c6 | AE | 0.631 | >50 | 1.86 | 0.384 | 0.183 | 0.500 | >50 | >50 | >50 |
| TH023.6 | AE | | | | 0.071 | | | | | |
| TH966.8 | AE | 0.889 | 2.43 | 0.814 | 0.208 | 0.108 | 0.363 | >50 | >50 | >50 |
| TH976.17 | AE | 0.752 | 2.83 | 0.913 | 0.177 | 0.168 | 0.197 | 12.7 | >50 | >50 |
| 235-47 | AG | 0.762 | >50 | 0.202 | 0.020 | 0.029 | 0.124 | 13.6 | 10.1 | >50 |
| 242-14 | AG | 10.3 | >50 | >50 | | 1.38 | >50 | >50 | >50 | >50 |
| 263-8 | AG | 1.65 | >50 | 0.485 | 0.112 | 0.090 | 0.188 | 1.03 | >50 | >50 |
| 269-12 | AG | >50 | >50 | 0.864 | 0.212 | 0.085 | 0.446 | 7.73 | >50 | >50 |
| 271-11 | AG | 0.201 | >50 | 0.244 | 0.044 | 0.033 | 0.026 | 13.4 | 10.1 | >50 |
| 928-28 | AG | 1.78 | >50 | 1.20 | 0.282 | 0.200 | 0.619 | 9.42 | 36.0 | >50 |
| DJ263.8 | AG | 0.962 | >50 | 0.510 | 0.027 | 1.29 | 0.133 | 13.4 | 2.83 | >50 |
| T250-4 | AG | >50 | >50 | >50 | >50 | 0.026 | >50 | 0.183 | >50 | >50 |
| T251-18 | AG | 13.1 | >50 | 9.86 | 0.898 | 1.14 | 0.858 | 7.32 | >50 | >50 |
| T253-11 | AG | 5.25 | >50 | 1.09 | 0.227 | 0.308 | 0.328 | 10.1 | >50 | >50 |

FIG. 20A cont.

| | | | | | | | | | | |
|---|---|---|---|---|---|---|---|---|---|---|
| T255-34 | AG | 2.04 | >50 | 2.49 | 0.242 | 0.223 | 0.296 | >50 | >50 | >50 |
| T257-31 | AG | 8.40 | >50 | 6.61 | 1.32 | 0.527 | 0.694 | >50 | >50 | >50 |
| T266-60 | AG | 16.2 | >50 | 6.76 | 1.48 | 0.490 | 0.119 | 7.12 | >50 | >50 |
| T278-50 | AG | >50 | >50 | >50 | >50 | >50 | >50 | >50 | >50 | >50 |
| T280-5 | AG | 0.263 | >50 | 0.190 | 0.023 | 0.010 | 0.060 | 0.143 | 11.6 | >50 |
| T33-7 | AG | 0.107 | >50 | 0.060 | 0.008 | 0.020 | 0.021 | 3.07 | >50 | >50 |
| 3988.25 | B | 1.90 | >50 | 1.04 | 0.284 | 0.285 | >50 | >50 | 46.1 | >50 |
| 5768.04 | B | 1.89 | >50 | 0.895 | 0.284 | 0.145 | 1.38 | >50 | 24.9 | >50 |
| 6101.10 | B | 1.40 | >50 | 0.073 | 0.023 | 0.011 | 0.104 | 0.290 | 6.08 | >50 |
| 6535.3 | B | 16.5 | >50 | 5.81 | 0.390 | 0.234 | 1.72 | 2.00 | 12.2 | >50 |
| 7165.18 | B | >50 | >50 | >50 | 5.14 | 3.25 | 16.7 | >50 | >50 | 1.0 |
| 45_01dG5 | B | 0.154 | >50 | 0.072 | 0.002 | 0.003 | >50 | 2.63 | >50 | >50 |
| 89.6.DG | B | 8.35 | >50 | 2.12 | 0.420 | 0.516 | 0.501 | 4.03 | >50 | >50 |
| AC10.29 | B | 6.27 | >50 | 3.34 | 1.63 | 0.731 | >50 | >50 | >50 | >50 |
| ADA.DG | B | 3.71 | >50 | 1.55 | 0.405 | 0.299 | 0.341 | 1.96 | >50 | >50 |
| Bal.01 | B | 0.534 | >50 | 0.434 | 0.077 | 0.048 | 0.051 | 0.692 | >50 | >50 |
| BaL.26 | B | 0.454 | >50 | 0.200 | 0.004 | 0.021 | 0.023 | 0.308 | >50 | >50 |
| BG1168.01 | B | 3.37 | >50 | 3.50 | 0.246 | 0.192 | 0.676 | 1.98 | >50 | >50 |
| BL01.DG | B | >50 | >50 | >50 | >50 | >50 | >50 | >50 | 12.7 | >50 |
| BR07.DG | B | 4.47 | >50 | 4.82 | 0.927 | 0.879 | 0.688 | 2.4 | >50 | >50 |
| BX08.16 | B | >50 | >50 | 0.990 | 0.229 | 0.125 | 0.281 | 2.56 | 2.7 | >50 |
| CAAN.A2 | B | 6.21 | >50 | 2.85 | 0.519 | 0.369 | 2.57 | 6.96 | >50 | >50 |
| CNE10 | B | 16.2 | >50 | 2.15 | 0.294 | 0.251 | 0.232 | 3.23 | >50 | >50 |
| CNE12 | B | 7.71 | >50 | 1.83 | 0.473 | 0.480 | 0.253 | 5.41 | >50 | >50 |
| CNE14 | B | 1.86 | >50 | 0.736 | 0.077 | 0.075 | 0.396 | 12.4 | 1.30 | >50 |
| CNE4 | B | 3.80 | >50 | 1.93 | 0.586 | 0.392 | 0.481 | >50 | >50 | >50 |
| CNE57 | B | 3.76 | >50 | 1.30 | 0.406 | 0.223 | 0.202 | 4.0 | >50 | >50 |

FIG. 28A cont.

| | | | | | | | | | | | | |
|---|---|---|---|---|---|---|---|---|---|---|---|---|
| HO86.8 | B | 0.599 | >50 | >50 | >50 | 37.6 | >50 | >50 | >50 | >50 | >50 | |
| HT593.1 | B | 2.94 | >50 | 1.87 | 0.365 | 0.427 | 0.922 | 3.22 | >50 | >50 | >50 | |
| HXB2.DG | B | 0.438 | >50 | 0.164 | 0.038 | 0.023 | 0.197 | 0.155 | 0.393 | 0.624 | 0.880 | |
| JRCSF.JB | B | 1.77 | >50 | 1.02 | 0.194 | 0.346 | 0.119 | 1.34 | 12.5 | >50 | >50 | |
| JRFL.JB | B | 0.402 | 17.8 | 0.126 | 0.004 | 0.011 | 0.013 | 0.174 | 0.067 | >50 | >50 | |
| MN.3 | B | 0.437 | >50 | 0.041 | 0.002 | 0.005 | >50 | >50 | 1.11 | >50 | 12.3 | |
| PVO.04 | B | 3.41 | >50 | 1.22 | 0.306 | 0.197 | 0.294 | 2.40 | >50 | >50 | >50 | |
| QH0515.01 | B | 4.25 | >50 | 3.45 | 1.98 | 0.847 | 1.14 | >50 | 3.23 | >50 | >50 | |
| QH0692.42 | B | 5.69 | >50 | 2.92 | 2.22 | 1.15 | 1.47 | 12.3 | >50 | >50 | >50 | |
| REJO.67 | B | 2.71 | >50 | 0.228 | 0.032 | 0.047 | 0.132 | 0.201 | >50 | >50 | >50 | |
| RHPA.7 | B | 0.224 | >50 | 0.134 | 0.054 | 0.046 | 0.071 | 14.1 | 3.24 | >50 | >50 | |
| SC422.8 | B | 2.27 | >50 | 0.386 | 0.180 | 0.157 | 0.192 | 0.830 | 9.15 | >50 | >50 | |
| SF162.LS | B | 2.57 | >50 | 0.656 | 0.127 | 0.118 | 0.034 | 0.453 | 2.92 | 20.4 | 13.7 | |
| SS1196.01 | B | 3.05 | >50 | 0.622 | 0.228 | 0.189 | 0.144 | 1.21 | 2.58 | >50 | >50 | |
| THRO.18 | B | >50 | >50 | 16.7 | 5.36 | 4.03 | 12.3 | >50 | >50 | >50 | >50 | |
| TRJO.58 | B | 1.55 | >50 | 0.292 | 0.143 | 0.216 | 0.216 | 44.7 | 17.2 | >50 | >50 | |
| TRO.11 | B | 1.98 | >50 | 1.27 | 0.316 | 0.255 | 0.125 | 23.1 | 31.5 | >50 | >50 | |
| WITO.33 | B | 1.12 | >50 | 0.356 | 0.220 | 0.144 | 0.161 | 33.8 | | | | |
| X2278.C2.B6 | B | 1.16 | >50 | 0.409 | | 0.077 | | | 5.44 | | | |
| YU2.DG | B | 0.548 | >50 | 0.292 | 0.070 | 0.079 | 0.099 | 0.792 | | | | |
| BJOX002000.03.2 | BC | 2.68 | >50 | >50 | 0.165 | 0.140 | >50 | >50 | | | | |
| CH038.12 | BC | >50 | >50 | 1.18 | | 0.208 | >50 | >50 | 7.73 | >50 | >50 | |
| CH070.1 | BC | 7.54 | >50 | >50 | 0.350 | 0.441 | >50 | 12.7 | >50 | >50 | >50 | |
| CH117.4 | BC | 0.898 | >50 | 0.256 | 0.044 | 0.074 | 15.8 | | 14.2 | | | |
| CH119.10 | BC | 3.01 | >50 | 1.97 | | 0.127 | | | | | | |
| CH181.12 | BC | 1.80 | >50 | 1.25 | 0.265 | 0.171 | 0.414 | >50 | 32.1 | >50 | >50 | |
| CNE15 | BC | 0.687 | >50 | 0.292 | 0.051 | 0.072 | >50 | >50 | >50 | >50 | >50 | |

FIG. 28A cont.

| | | | | | | | | | |
|---|---|---|---|---|---|---|---|---|---|
| CNE19 | BC | 0.356 | >50 | 0.641 | | | | >50 | >50 |
| CNE20 | BC | 0.670 | >50 | >50 | | | | >50 | >50 |
| CNE21 | BC | 1.47 | >50 | 1.24 | 0.158 | | >50 | >50 | >50 |
| CNE40 | BC | 0.723 | >50 | 3.61 | 0.180 | 0.495 | 3.14 | 1.78 | 0.991 |
| CNE7 | BC | 8.67 | >50 | 1.01 | 0.202 | >50 | >50 | >50 | >50 |
| 286.36 | C | 1.90 | >50 | 0.756 | 0.191 | 0.401 | 3.39 | >50 | >50 |
| 288.38 | C | 5.81 | >50 | 5.36 | 0.822 | 0.346 | 4.06 | >50 | >50 |
| 0013095.2.11 | C | >50 | >50 | 0.318 | | 2.23 | >50 | >50 | >50 |
| 001428.2.42 | C | 0.213 | >50 | | | 0.060 | 0.191 | >50 | >50 |
| 0077_V1.C16 | C | | >50 | 4.12 | 0.300 | >50 | >50 | >50 | >50 |
| 00836-2.5 | C | >50 | >50 | 0.708 | | | >50 | >50 | >50 |
| 0921.V2.C14 | C | 1.08 | >50 | 0.673 | 0.168 | 0.669 | >50 | >50 | >50 |
| 16055-2.3 | C | 0.471 | >50 | 0.176 | | | 1.66 | >50 | >50 |
| 16845-2.22 | C | | >50 | | 2.73 | 1.03 | >50 | >50 | >50 |
| 16936-2.21 | C | 1.36 | >50 | 0.373 | | 0.402 | 0.480 | >50 | >50 |
| 25710-2.43 | C | 1.07 | >50 | 1.87 | 0.581 | 0.213 | | | >50 |
| 25711-2.4 | C | 3.43 | >50 | 1.69 | 0.279 | 0.185 | >50 | >50 | >50 |
| 25925-2.22 | C | 2.16 | >50 | 1.27 | 0.277 | 0.264 | 0.549 | >50 | >50 |
| 26191-2.48 | C | 1.57 | >50 | 0.558 | 0.236 | 0.116 | 0.183 | >50 | >50 |
| 3168.V4.C10 | C | 1.23 | >50 | 0.362 | 0.145 | 0.161 | 0.267 | >50 | >50 |
| 3637.V5.C3 | C | | >50 | 5.93 | 1.06 | 0.395 | | >50 | >50 |
| 3873.V1.C24 | C | >50 | >50 | 2.82 | 0.672 | 0.335 | 4.46 | >50 | >50 |
| 426c | C | | | >50 | | | | | |
| 6322.V4.C1 | C | 5.15 | >50 | >50 | 0.136 | 0.112 | >50 | >50 | >50 |
| 6471.V1.C16 | C | >50 | >50 | >50 | >50 | >50 | >50 | >50 | >50 |
| 6631.V3.C10 | C | | >50 | 0.614 | 0.614 | 0.222 | >50 | >50 | >50 |
| 6644.V2.C33 | C | >50 | >50 | 0.455 | 0.160 | 0.190 | 0.229 | 1.51 | >50 |

FIG. 28A cont.

| | | | | | | | | | | |
|---|---|---|---|---|---|---|---|---|---|---|
| 6785.V5.C14 | C | >50 | | 0.734 | 0.229 | 0.247 | 0.679 | | >50 | >50 |
| 6838.V1.C35 | C | 3.41 | >50 | 0.588 | 0.144 | 0.075 | 0.746 | 1.94 | >50 | >50 |
| 96ZM651.02 | C | 4.18 | >50 | 2.29 | 0.366 | 0.165 | 1.77 | >50 | >50 | >50 |
| BR025.9 | C | >50 | >50 | 3.08 | 0.060 | 0.068 | >50 | 0.262 | >50 | >50 |
| CAP210.E8 | C | >50 | >50 | >50 | 6.05 | >50 | >50 | >50 | >50 | >50 |
| CAP244.D3 | C | 4.13 | >50 | 2.78 | 0.714 | 0.317 | 0.309 | 2.28 | >50 | >50 |
| CAP256.206.C9 | C | 3.36 | >50 | 2.52 | | 0.287 | 1.86 | >50 | >50 | >50 |
| CAP45.G3 | C | 1.77 | >50 | | 0.162 | 0.101 | | >50 | >50 | >50 |
| Ce1176.A3 | C | 3.55 | >50 | 6.78 | | 0.662 | | | >50 | >50 |
| CE703010217.B6 | C | 0.948 | >50 | 0.935 | | 0.097 | | | >50 | >50 |
| CNE30 | C | 3.64 | >50 | 2.18 | 0.476 | 0.574 | 1.05 | 6.52 | >50 | >50 |
| CNE31 | C | >50 | >50 | 2.11 | 0.373 | 0.827 | >50 | >50 | >50 | >50 |
| CNE53 | C | 0.725 | 6.06 | 0.268 | 0.064 | 0.145 | 0.327 | | >50 | >50 |
| CNE58 | C | 4.17 | >50 | 0.586 | 0.086 | 0.041 | 1.41 | | >50 | 1.46 |
| DU123.06 | C | | | >50 | 0.565 | 0.152 | 1.77 | >50 | >50 | >50 |
| DU151.02 | C | 0.827 | >50 | >50 | 0.344 | 0.125 | >50 | >50 | >50 | >50 |
| DU156.12 | C | 0.829 | 6.87 | 0.230 | 0.043 | 0.027 | 0.121 | | >50 | >50 |
| DU172.17 | C | 1.12 | >50 | >50 | 0.454 | 0.231 | 2.46 | >50 | >50 | >50 |
| DU422.01 | C | 2.76 | >50 | >50 | | 0.096 | >50 | >50 | >50 | >50 |
| MW965.26 | C | 1.56 | >50 | 0.381 | 0.026 | 0.008 | 0.023 | | 0.091 | |
| SO18.18 | C | 0.250 | >50 | 0.187 | 0.041 | 0.022 | 0.176 | 7.71 | 7.48 | >50 |
| TV1.29 | C | >50 | >50 | >50 | | >50 | >50 | >50 | >50 | >50 |
| TZA125.17 | C | >50 | >50 | >50 | | 2.58 | >50 | >50 | >50 | >50 |
| TZBD.02 | C | 0.938 | >50 | 0.217 | 0.015 | 0.034 | >50 | | >50 | |
| ZA012.29 | C | 2.99 | >50 | 0.823 | 0.166 | 0.067 | 0.319 | | >50 | >50 |
| ZM106.9 | C | 1.43 | >50 | 0.641 | 0.122 | 0.065 | 0.325 | 8.11 | >50 | >50 |
| ZM109.4 | C | 1.21 | >50 | 0.508 | 0.202 | 0.160 | 0.242 | >50 | >50 | >50 |

*FIG. 28A cont.*

| | | | | | | | | | | | |
|---|---|---|---|---|---|---|---|---|---|---|---|
| ZM135.10a | C | >50 | | 8.58 | 0.458 | 0.460 | 0.280 | >50 | >50 | >50 | >50 |
| ZM176.66 | C | 0.590 | >50 | 0.407 | 0.007 | 0.014 | >50 | >50 | >50 | >50 | |
| ZM197.7 | C | 4.79 | >50 | 1.81 | 0.722 | 0.190 | 1.29 | >50 | >50 | >50 | >50 |
| ZM214.15 | C | 6.50 | >50 | 2.50 | 0.971 | 0.321 | 0.744 | 17.4 | >50 | >50 | >50 |
| ZM215.8 | C | 0.764 | >50 | 0.748 | 0.245 | 0.167 | 0.070 | 2.14 | >50 | >50 | >50 |
| ZM233.6 | C | 3.58 | 16.5 | 4.44 | 0.302 | 0.229 | 0.912 | >50 | >50 | >50 | >50 |
| ZM249.1 | C | 0.678 | 43.1 | 0.181 | 0.126 | 0.052 | 0.207 | >50 | 17.1 | >50 | >50 |
| ZM53.12 | C | 1.85 | >50 | 2.40 | 0.626 | 0.449 | 1.06 | >50 | >50 | >50 | >50 |
| ZM55.28a | C | 2.35 | >50 | 0.519 | 0.089 | 0.059 | 0.179 | 13.3 | 14.2 | >50 | >50 |
| 3326.V4.C3 | CD | 0.307 | >50 | 1.89 | 0.003 | 0.006 | >50 | >50 | >50 | >50 | >50 |
| 3337.V2.C6 | CD | 1.57 | >50 | 0.225 | 0.037 | 0.033 | 0.040 | 0.170 | 3.76 | >50 | >50 |
| 3817.v2.c59 | CD | 9.90 | >50 | >50 | 1.06 | 1.39 | 0.752 | >50 | >50 | >50 | >50 |
| 191821.E6.1 | D | | | 0.266 | | | | | | | |
| 231965.c1 | D | >50 | >50 | 1.25 | 0.111 | 0.073 | 0.172 | 4.69 | >50 | >50 | >50 |
| 247-23 | D | 2.03 | >50 | 10.3 | 7.86 | 0.439 | 0.124 | 44.1 | 14.3 | >50 | >50 |
| 3016.v5.c45 | D | >50 | >50 | 0.344 | 0.106 | 0.032 | 3.35 | >50 | >50 | >50 | >50 |
| 57128.vrc15 | D | >50 | >50 | >50 | 3.12 | 1.70 | 1.84 | >50 | >50 | >50 | >50 |
| 6405.v4.c34 | D | >50 | >50 | 3.83 | 0.676 | 0.185 | 0.578 | >50 | >50 | >50 | >50 |
| A03349M1.vrc4a | D | 10.8 | >50 | 9.98 | 3.29 | 2.09 | 2.34 | 17.7 | 14.1 | >50 | >50 |
| A07412M1.vrc12 | D | 0.945 | >50 | 0.303 | 0.118 | 0.109 | | | | | |
| NKU3006.ec1 | D | 1.33 | 17.7 | 1.42 | 0.903 | 0.574 | 0.323 | 2.40 | >50 | >50 | >50 |
| UG021.16 | D | | | | | | 5.09 | >50 | >50 | 2.53 | |
| UG024.2 | D | | | 0.105 | | | 0.194 | >50 | >50 | 0.569 | |

FIG. 28A cont.

| | | | | | | | | |
|---|---|---|---|---|---|---|---|---|
| P0402.c2.11 | G | 6.07 | >50 | 0.807 | 0.216 | 0.176 | | >50 | >50 | >50 |
| P1981.C5.3 | G | 2.48 | >50 | 0.415 | 0.148 | 0.166 | | >50 | >50 | >50 |
| X1193.c1 | G | 8.25 | >50 | 0.173 | 0.121 | 0.086 | | >50 | >50 | >50 |
| X1254.c3 | G | 1.59 | >50 | 0.732 | 0.036 | 0.141 | | 6.01 | >50 | >50 |
| X1632.S2.B10 | G | >50 | >50 | >50 | >50 | 0.152 | >50 | >50 | >50 | >50 |
| X2088.c9 | G | 10.7 | >50 | 1.75 | >50 | 0.422 | 1.93 | >50 | >50 | >50 |
| X2131.C1.B5 | G | >50 | >50 | >50 | >50 | >50 | >50 | >50 | >50 | >50 |
| SIVmac251.30.SG3 | NA | >50 | >50 | >50 | >50 | >50 | >50 | >50 | >50 | >50 |
| SVA.MLV | NA | >50 | >50 | >50 | >50 | >50 | >50 | >50 | >50 | >50 |

FIG. 26A cont.

| | CH557 | CH235 | VRC01 | VRC07-523-LS | N6 | 3BNC117 | 8ANC131 | CH103 | F105 | CH522 |
|---|---|---|---|---|---|---|---|---|---|---|
| # Viruses | 199 | 199 | 199 | 195 | 199 | 182 | 182 | 196 | 206 | 199 |
| Total VS Neutralized | | | | | | | | | | |
| IC80 <50ug/ml | 170 | 16 | 173 | 186 | 193 | 146 | 105 | 67 | 7 | 6 |
| IC80 <10ug/ml | 156 | 7 | 168 | 183 | 191 | 140 | 64 | 32 | 4 | 2 |
| IC80 <1.0ug/ml | 59 | 0 | 97 | 166 | 176 | 118 | 26 | 4 | 2 | 2 |
| IC80 <0.1ug/ml | 0 | 0 | 10 | 54 | 77 | 25 | 1 | 2 | 0 | 0 |
| IC80 <0.01ug/ml | 0 | 0 | 0 | 10 | 6 | 0 | 0 | 0 | 0 | 0 |
| % VS Neutralized | | | | | | | | | | |
| IC80 <50ug/ml | 85 | 8 | 87 | 95 | 97 | 80 | 58 | 34 | 3 | 3 |
| IC80 <10ug/ml | 78 | 4 | 84 | 94 | 96 | 77 | 35 | 16 | 2 | 1 |
| IC80 <1.0ug/ml | 30 | 0 | 49 | 85 | 88 | 65 | 14 | 2 | 1 | 1 |
| IC80 <0.1ug/ml | 0 | 0 | 5 | 28 | 39 | 14 | 1 | 1 | 0 | 0 |
| IC80 <0.01ug/ml | 0 | 0 | 0 | 5 | 3 | 0 | 0 | 0 | 0 | 0 |
| Median IC80 | 1.66 | 12.5 | 0.807 | 0.219 | 0.151 | 0.303 | 5.39 | 11.6 | 2.53 | 11.6 |
| Geometric Mean | 1.73 | 10.1 | 0.815 | 0.188 | 0.142 | 0.335 | 3.99 | 8.00 | 3.76 | 5.26 |

FIG. 29B

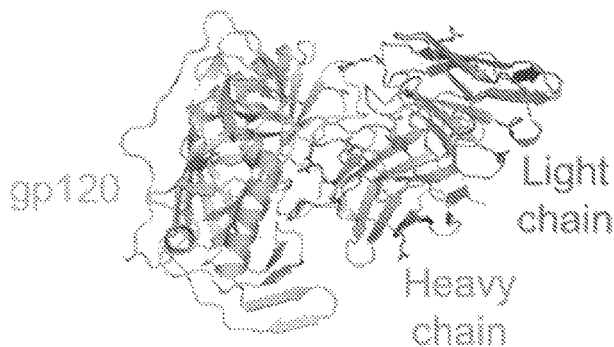
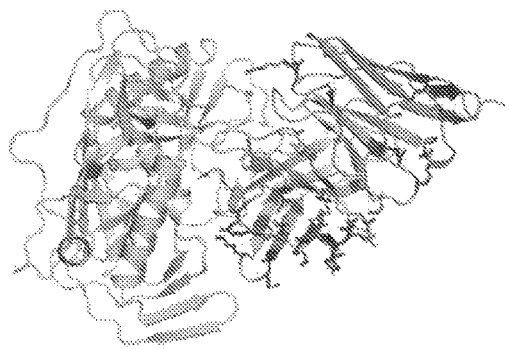
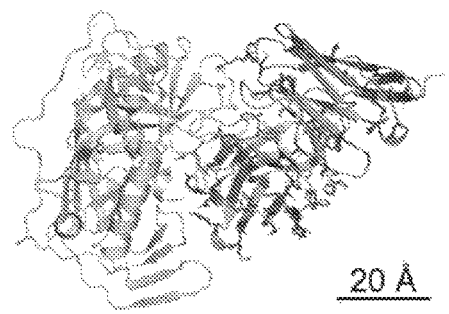
FIG. 30A

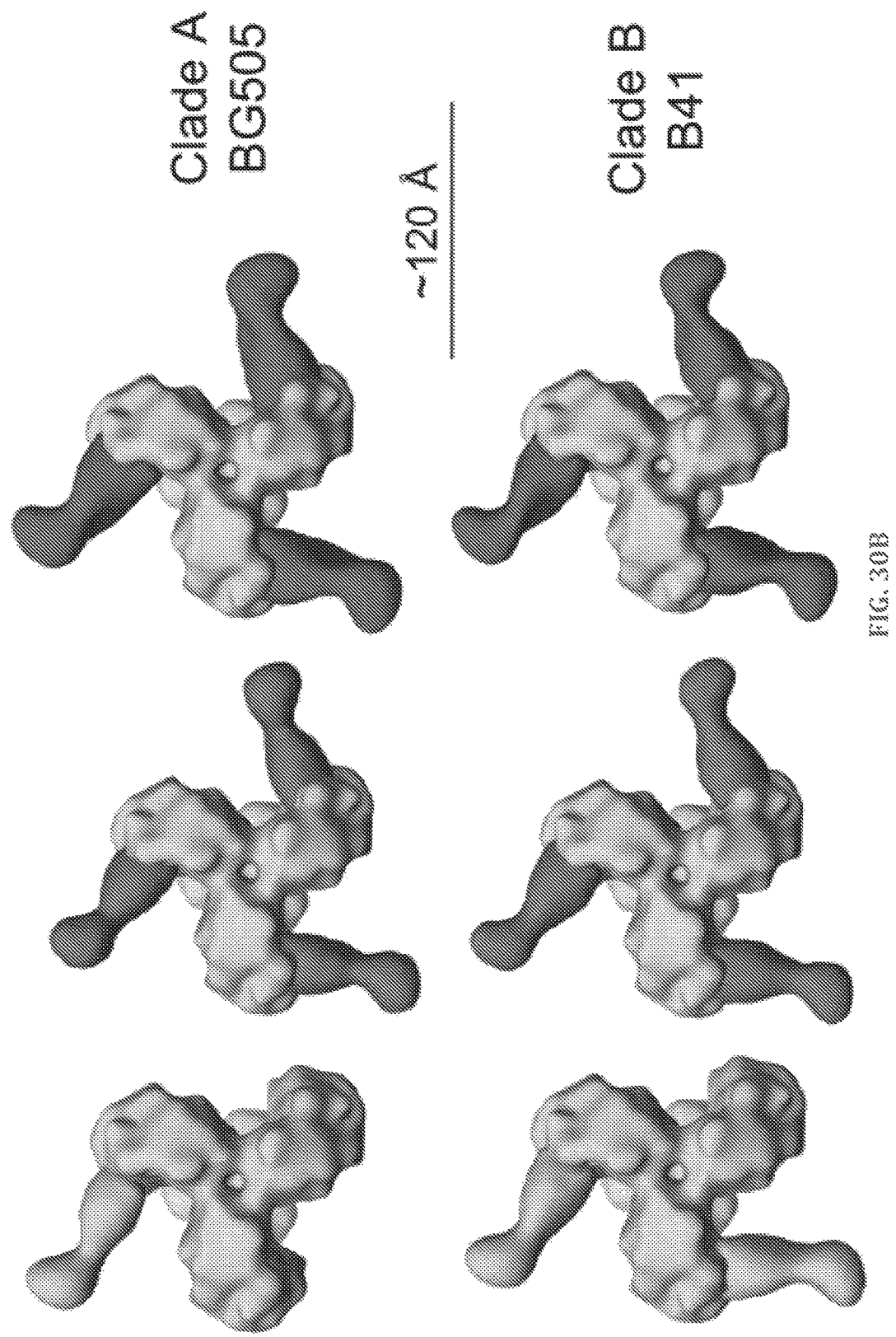

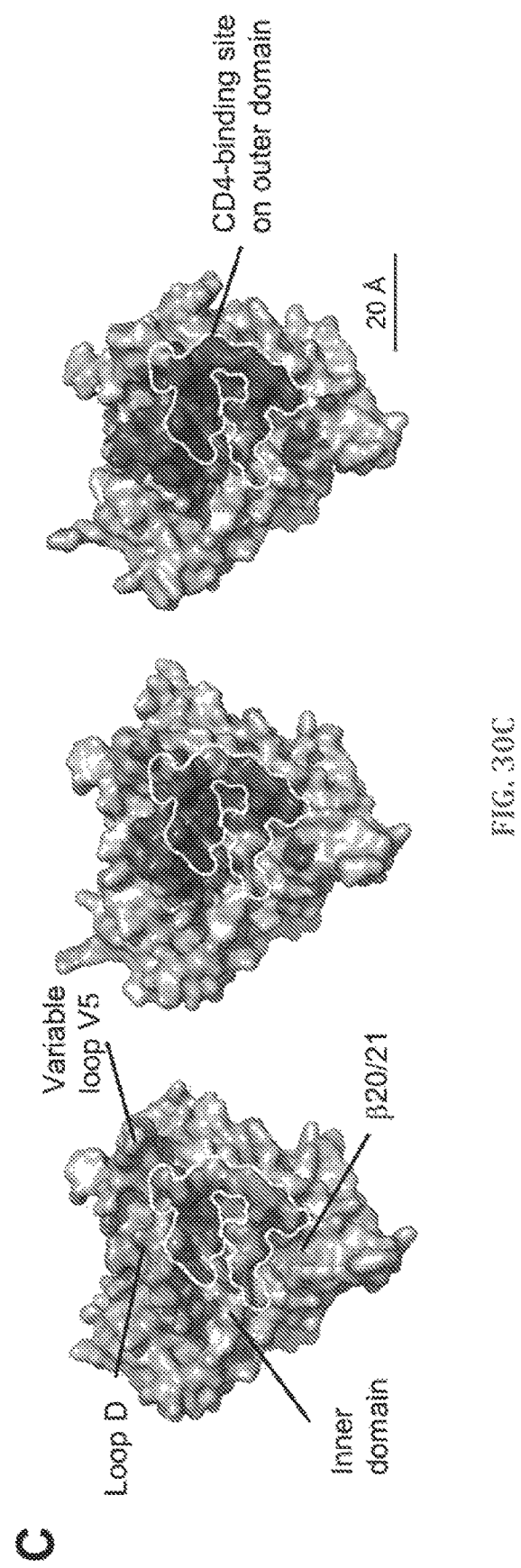

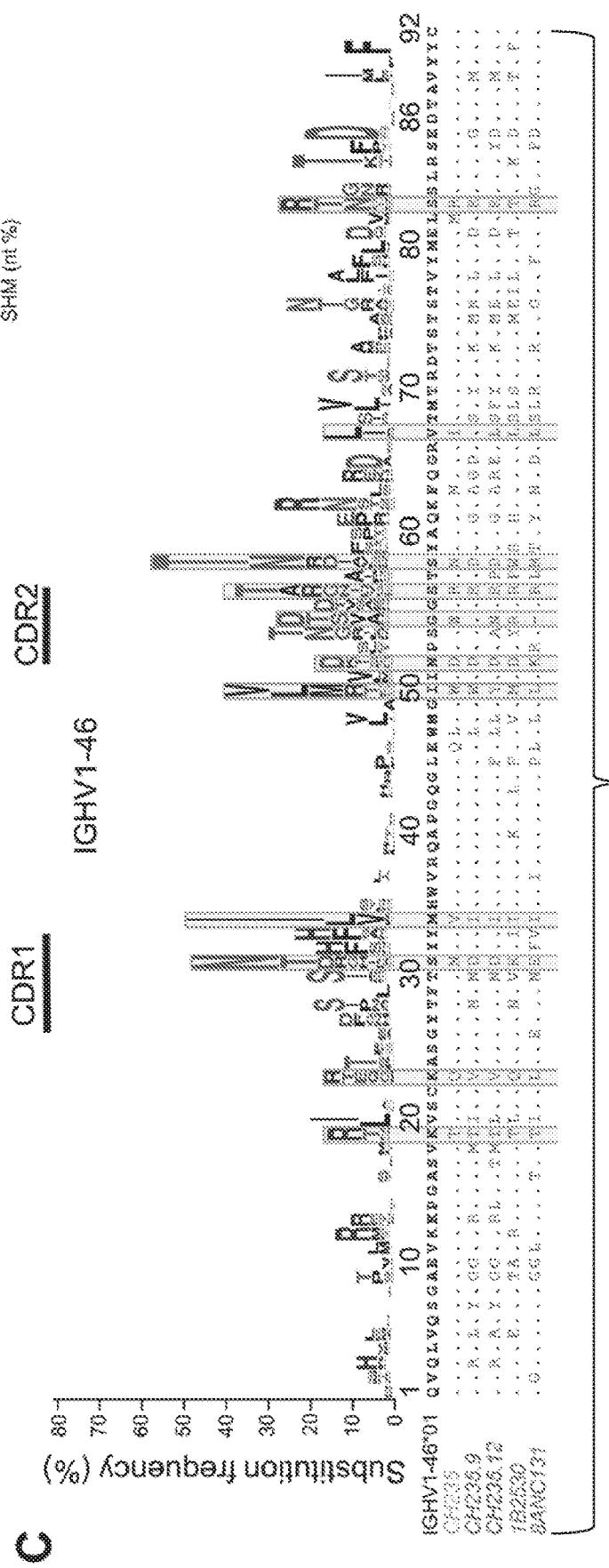
FIG. 31C
continued on next sheet

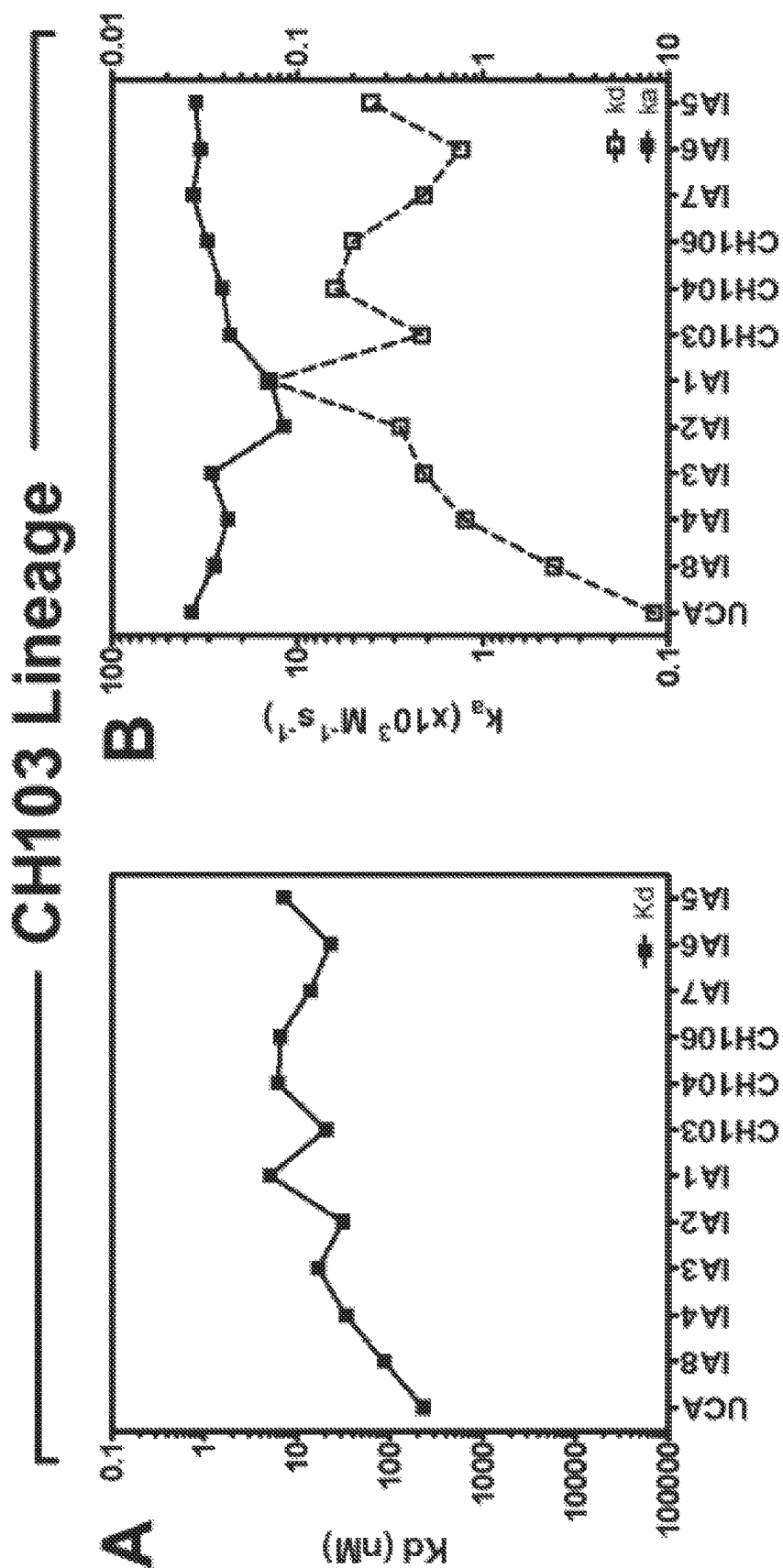
FIGS. 32A-B

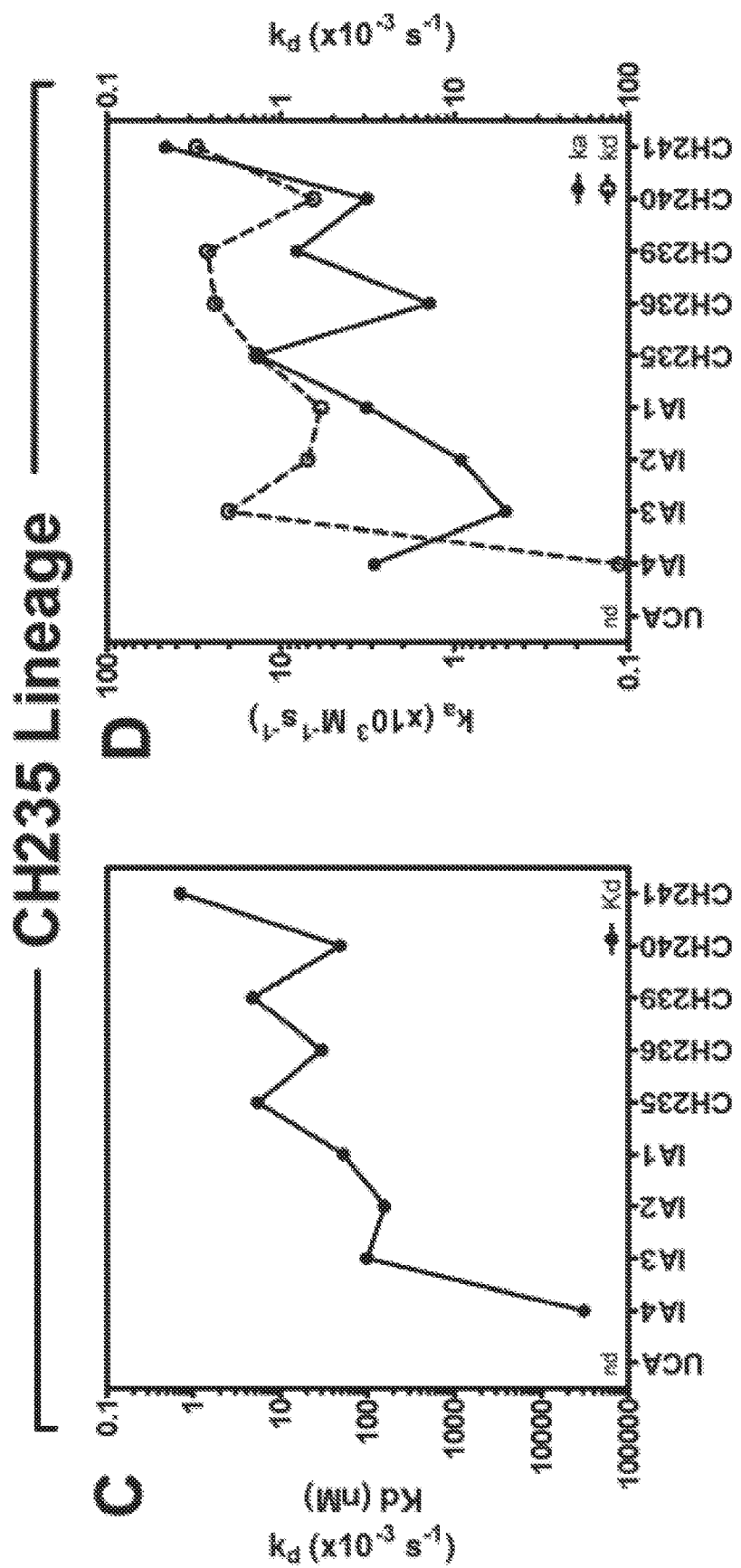
FIGS. 32C-D

FIGS. 33B-C

| | SSA | SSB | Sm | RNP | Scl70 | Jo1 | DNA | Cent. B | Histone |
|---|---|---|---|---|---|---|---|---|---|
| UCA | - | - | - | - | - | - | - | - | - |
| IA4 | - | - | - | - | - | - | - | - | - |
| IA1 | - | - | - | - | - | - | - | - | - |
| CH240 | - | - | - | - | - | - | - | - | - |
| CH239 | - | - | - | - | - | - | - | - | - |
| IA3 | - | - | - | - | - | - | + | - | - |
| IA2 | - | - | - | - | - | - | + | - | - |
| CH236 | - | - | - | - | - | - | + | - | - |
| CH235 | - | - | - | - | - | - | - | - | - |
| CH241 | - | - | - | - | - | - | + | - | - |
| CH235.7 | - | - | - | - | + | - | +++ | - | - |
| CH235.9 | - | - | - | - | - | - | + | - | - |
| CH235.10 | - | - | - | - | - | - | + | - | - |
| CH235.13 | - | - | - | - | - | - | - | - | - |
| CH235.11 | - | - | - | - | - | - | - | - | - |
| CH235.12 | - | - | - | - | - | - | - | - | - |

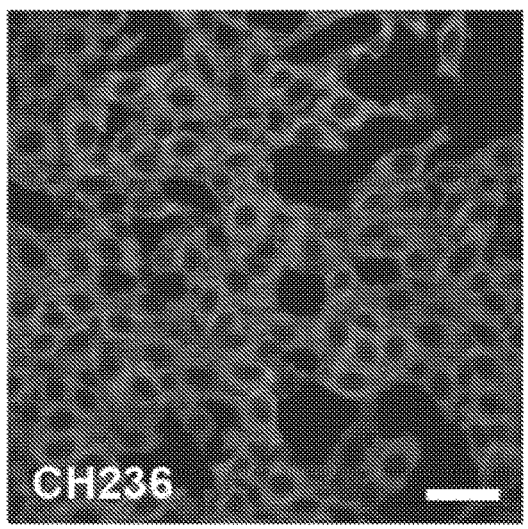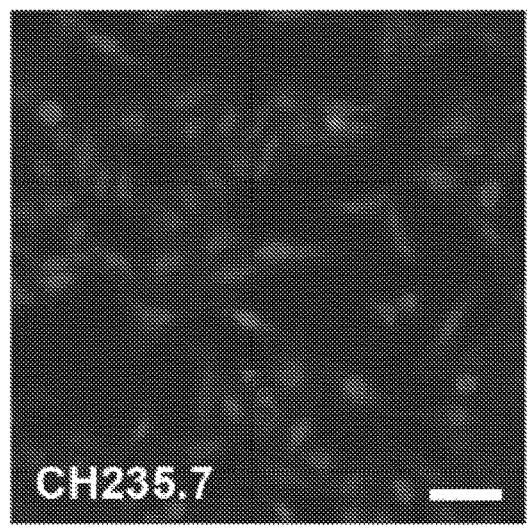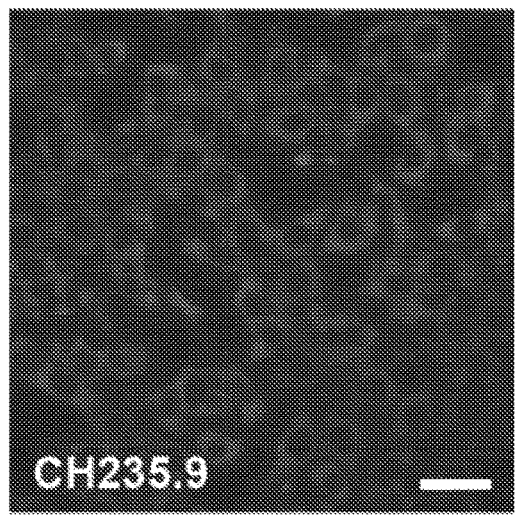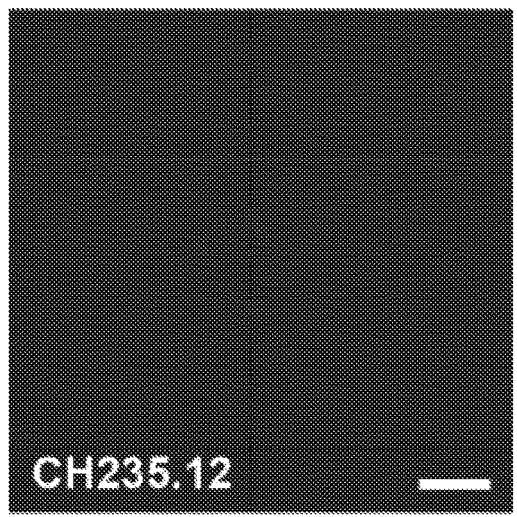
FIG. 35C

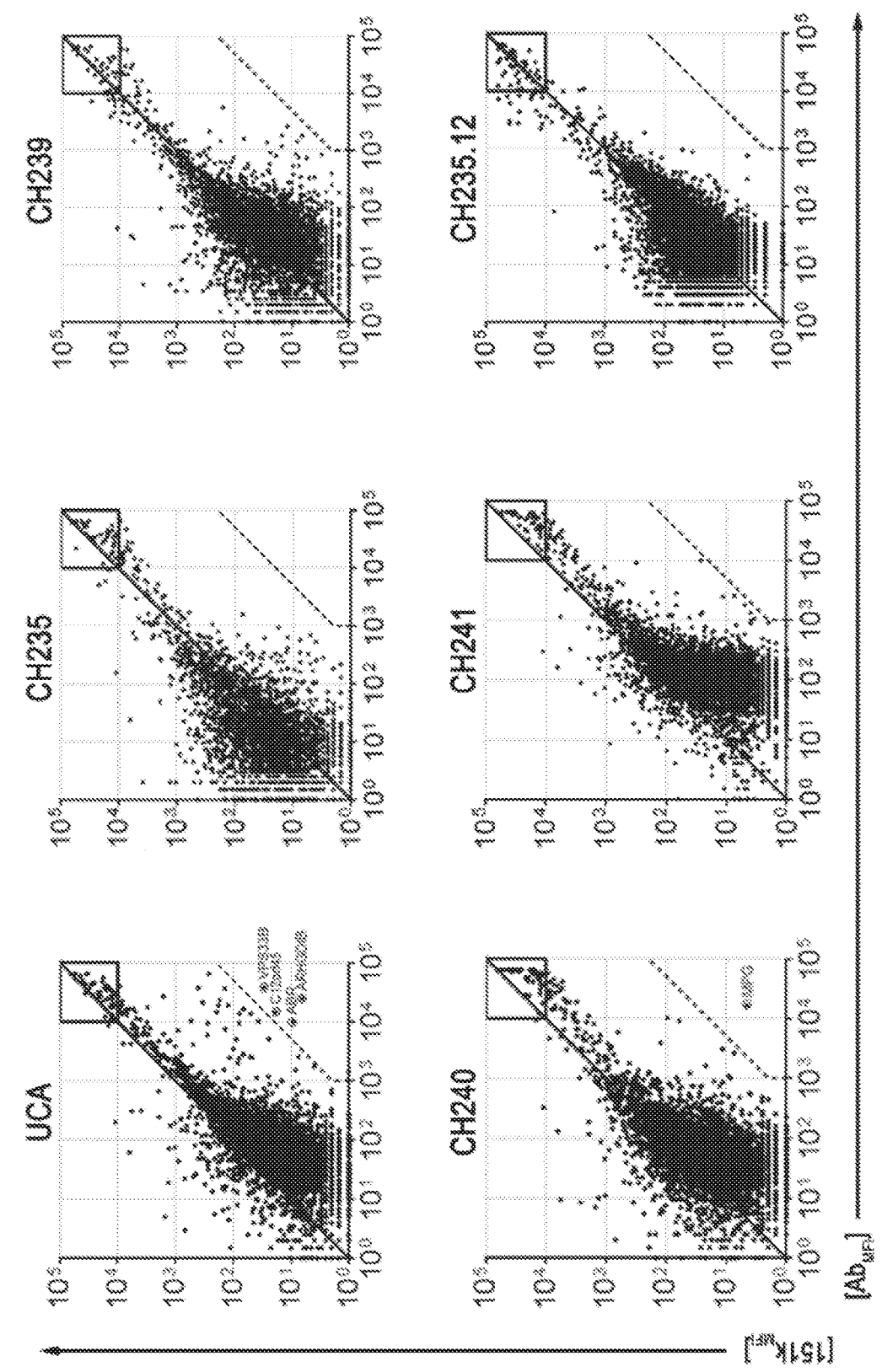
FIG. 35-D

FIG. 36A

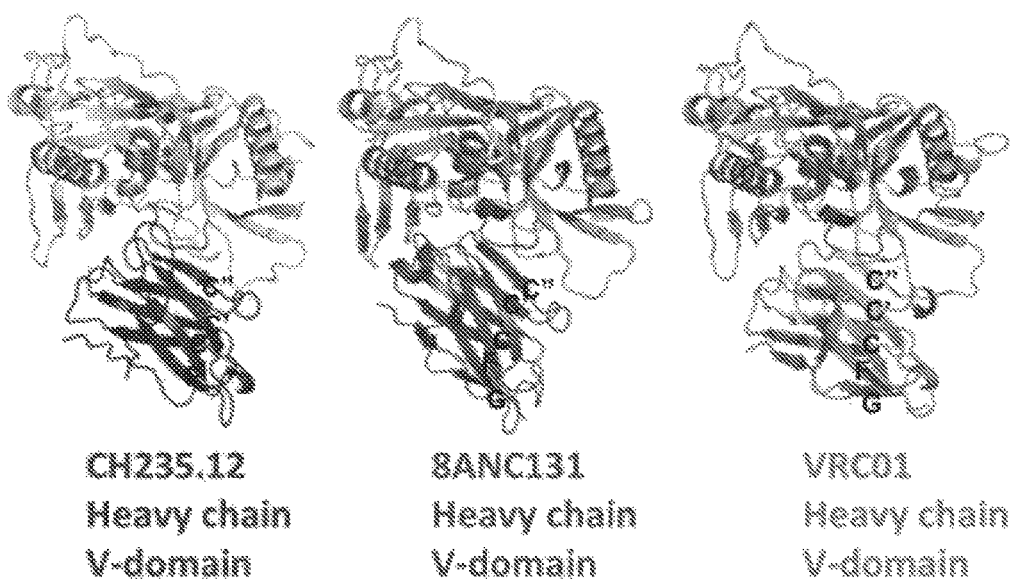
FIG. 37A

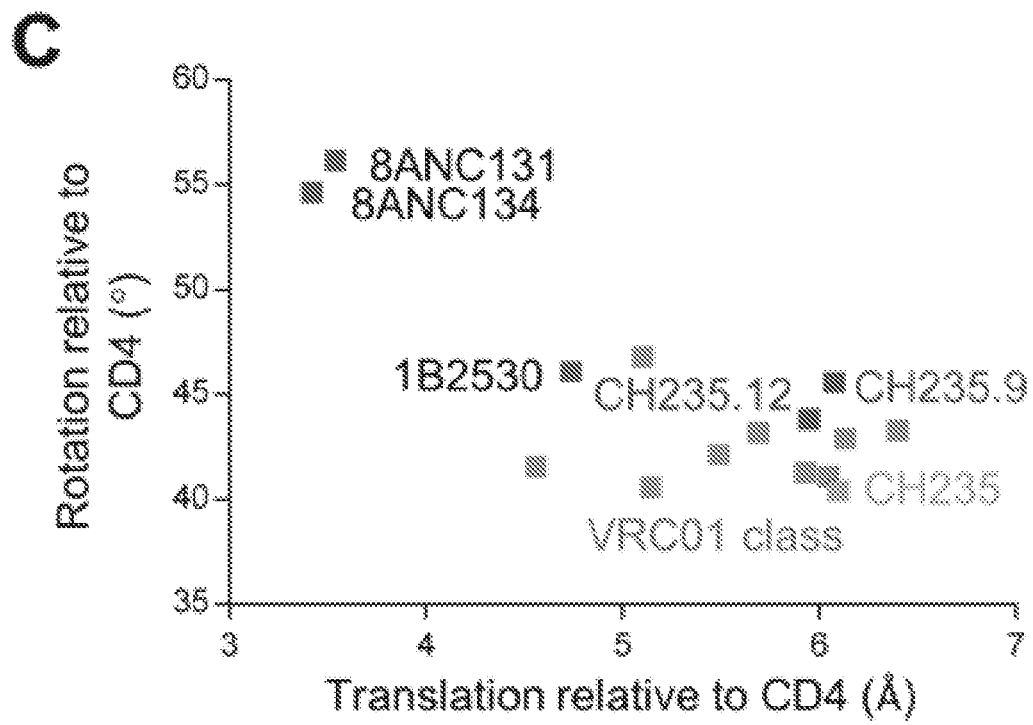
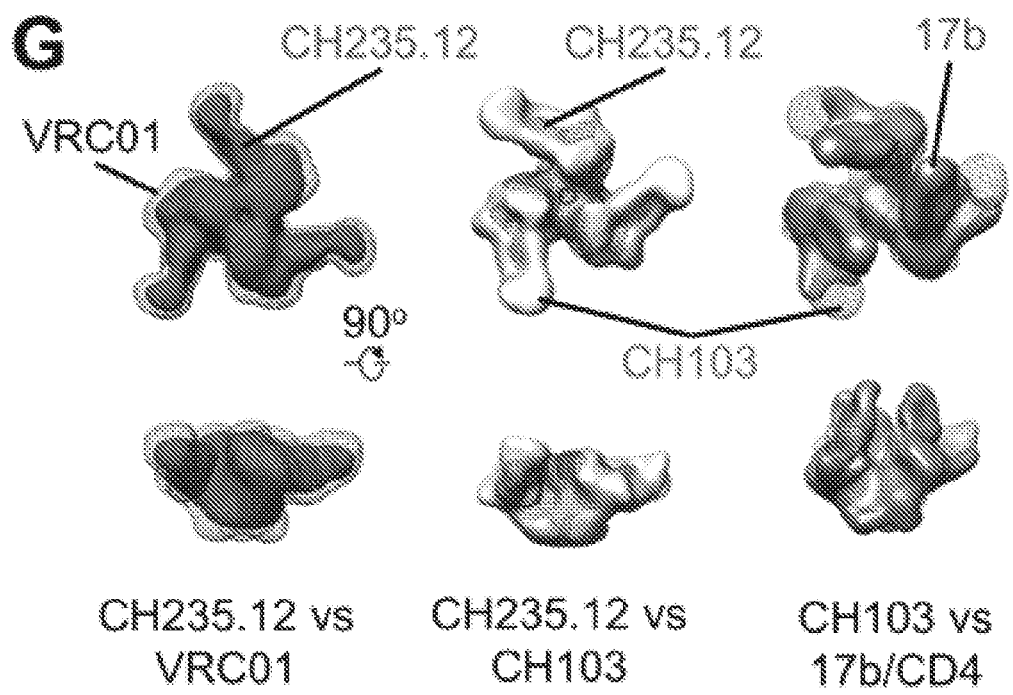
FIGS. 37C, G

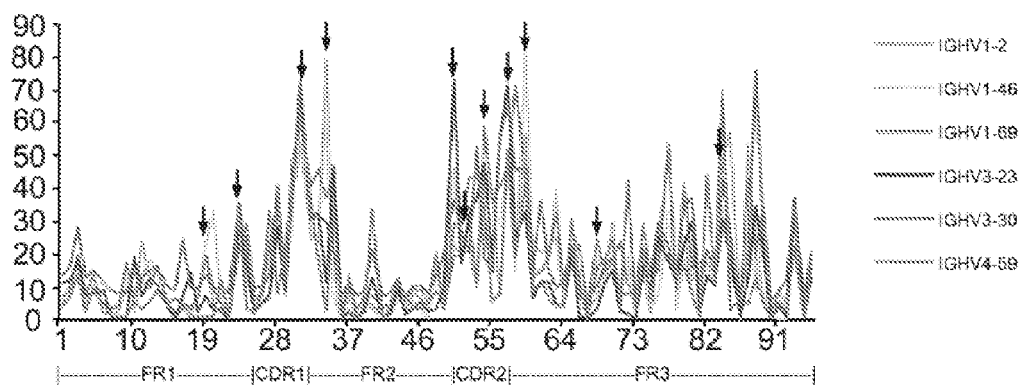
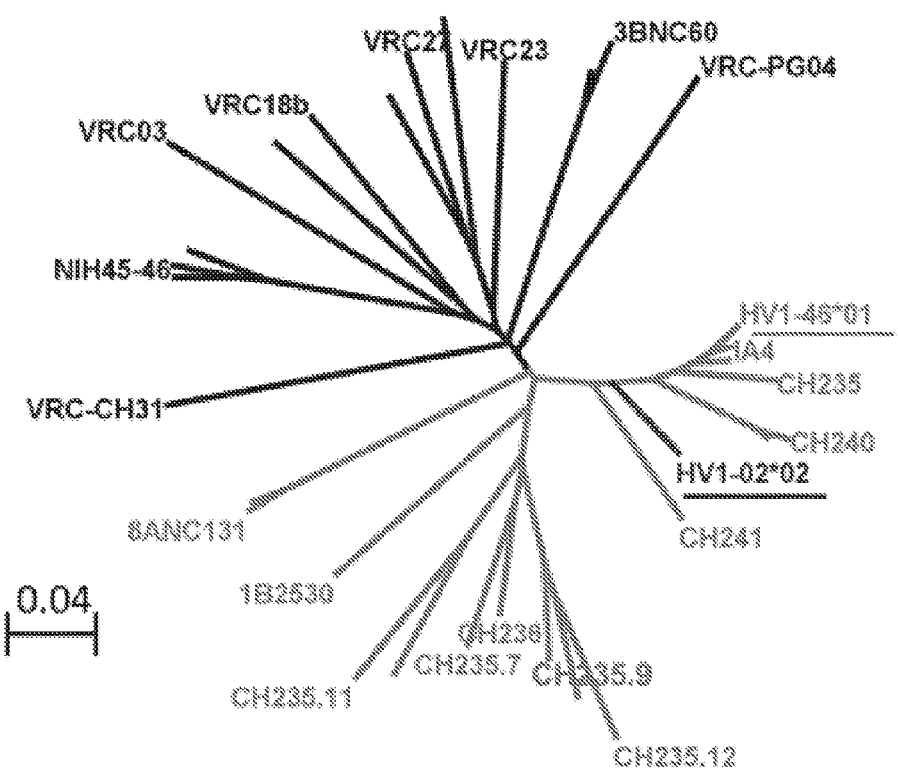
FIGS. 38D-E

```
                    |--------FR1--------|------CDR1------|--------FR2--------|--CDR2--|
                                                                                ********
                                              *                                 ********
                                              *                                 ********
(SEQ ID NO: 171) CH236_VH    QVQLVQSGAA VKRPGASVTI SCRASGYTFT TYYIHWVRQA PGQRLELMGM IDPSRGRTDY
(SEQ ID NO: 172) CH235.9_VH  QVRLLQYGGG VKRPGASMTI SCVASGYNFN DYYIHWVRQA PGQGLELMGW IDPSGGRTDY
(SEQ ID NO: 173) CH235.12_VH QVRLAQYGGG VKRLGATMTL SCVASGYTFN DYIHWVRQA  PGQGFELLGY IDPANGRPDY
(SEQ ID NO: 174) CH235.13_VH QVQLVQSGGG VKRPGSTTTI SCVASGYSFN DYYIHWVRQA PGQGIEVLGF IDPSNGRTNY
(SEQ ID NO: 175) CH235.10_VH QVQLVQSGAT VKKPRASVTL SCRTSGYNFI DYFTHWVRQA PGQRLEVMGY IDPSRGRPDY
(SEQ ID NO: 176) CH235.11_VH QVQLVQSGGT VKSPGTSVTL SCKTSGYNFI DYYIHWVRRA PGQRPELMGY IDPSHGRPDY
(SEQ ID NO: 177) CH235.7_VH  QVQLVQSGAA VKRPGASVTI SCRASGYTFT TYYIHWVRQA PGQGLELMGW INPRGGRTDY

|----FR3----|                      |----CDR3----|  |---FR4---|
                                                                ******
                      **                                        ******
CH236_VH     AQKFQGRVTM SRDTSTSTLY MELRSLRPDD TALYYCVRNV GTEGSLLHYD YWGQGTLVTVSS
CH235.9_VH   AGAFGDRVSM YRDKSMNTLY MDLRSLRSGD TAMYYCVRNV GTAGSLLHYD HWGLGVMVTVSS
CH235.12_VH  AGALRERLSF YRDKSMETLY MDLRSLRYDD TAMYYCVRNV GTAGSLLHYD HWGSGSPVIVSS
CH235.13_VH  AGAFGDRFSM YRDKSMETLY MDLRNLRSDD TAMYYCVRSE GTAGSLLHYD HWGTGSKIIVSS
CH235.10_VH  APNFRDRVSL YRDTSMSIVY LDLRDLTPDD TALYYCVRDD GTEGTVLHYD HWGPGTRVTVSP
CH235.11_VH  EGKFRDRISL YRDTSTSVVY MDVRGLRLDD TALYYCVRGG GVEVSSNHYD HWGPGTMVFVSP
CH235.7_VH   SYRFEDRVSM YRDTSMSIVY MDLRNLKSAD TAVYYCVRNV GTSGSLLHYD FWGQGSLVTVSS
```

FIG. 39B

| Antibody ID | VH | D | JH | Mutation frequency | CDRH3 length |
|---|---|---|---|---|---|
| UCA | 1-46*01 | 3-10*01 | 4*02 | 0.0% | 15 |
| CH235 | 1-46*01 | 3-10*01 | 4*02 | 7.9% | 15 |
| CH236 | 1-46*01 | 3-10*01 | 4*02 | 8.2% | 15 |
| CH239 | 1-46*01 | 3-10*01 | 4*02 | 7.9% | 15 |
| CH240 | 1-46*01 | 3-10*01 | 4*02 | 7.4% | 15 |
| CH241 | 1-46*01 | 3-10*01 | 4*02 | 11.5% | 15 |
| CH235.6 | 1-46*01 | 3-10*01 | 4*02 | 12.6% | 15 |
| CH235.7 | 1-46*01 | 3-10*01 | 4*02 | 14.8% | 15 |
| CH235.8 | 1-46*01 | 3-10*01 | 4*02 | 12.0% | 15 |
| CH235.9 | 1-46*01 | 3-10*01 | 4*02 | 19.6% | 15 |
| CH235.10 | 1-46*01 | 3-10*01 | 4*02 | 21.6% | 15 |
| CH235.11 | 1-46*01 | 3-10*01 | 4*02 | 25.1% | 15 |
| CH235.12 | 1-46*01 | 3-10*01 | 4*02 | 25.7% | 15 |
| CH235.13 | 1-46*01 | 3-10*01 | 4*02 | 23.5% | 15 |

FIG. 40C

| Antibody ID | VK | JK | Mutation frequency | CDRL3 length | Week of isolation |
|---|---|---|---|---|---|
| UCA | 3-15*01 | 1*01 | 0.0% | 8 | - |
| CH235 | 3-15*01 | 1*01 | 3.8% | 8 | 41 |
| CH236 | 3-15*01 | 1*01 | 2.8% | 8 | 41 |
| CH239 | 3-15*01 | 1*01 | 4.7% | 8 | 41 |
| CH240 | 3-15*01 | 1*01 | 3.1% | 8 | 41 |
| CH241 | 3-15*01 | 1*01 | 3.5% | 8 | 41 |
| CH235.6 | 3-15*01 | 1*01 | 3.5% | 8 | 66^ |
| CH235.7 | 3-15*01 | 1*01 | 2.8% | 8 | 100# |
| CH235.8 | 3-15*01 | 1*01 | 3.5% | 8 | 100^ |
| CH235.9 | 3-15*01 | 1*01 | 2.8% | 8 | 152# |
| CH235.10 | 3-15*01 | 1*01 | 16.7% | 8 | 264 |
| CH235.11 | 3-15*01 | 1*01 | 17.6% | 8 | 323 |
| CH235.12 | 3-15*01 | 1*01 | 12.9% | 8 | 323 |
| CH235.13 | 3-15*01 | 1*01 | 11.6% | 8 | 323 |

^ Paired with CH241 V-light chain and complemented with CH241 V-heavy.
Paired with CH236 V-light chain and complemented with CH236 V-heavy.
Mutation frequency is calculated on nucleotide sequences of the whole V(D)J rearrangement compared to UCA.
CDR H3 and CDR L3 lengths are expressed in amino acids.

FIG. 40C cont.

| Virus ID | Clade | CH235 | CH235.9 | CH235.12 | VRC01 |
|---|---|---|---|---|---|
| 0260.v5.c36 | A | >50 | 10.5 | 1.02 | 0.468 |
| 0330.v4.c3 | A | >50 | 1.88 | 0.313 | 0.047 |
| 0439.v5.c1 | A | >50 | 3.49 | 0.374 | 0.129 |
| 3365.v2.c20 | A | >50 | 1.29 | 0.068 | 0.030 |
| 3415.v1.c1 | A | >50 | 3.20 | 0.450 | 0.084 |
| 3718.v3.c11 | A | 12.3 | 1.80 | 0.360 | 0.165 |
| 398-F1_F6_20 | A | >50 | 5.48 | 1.76 | 0.181 |
| BB201.B42 | A | >50 | 7.20 | 0.573 | 0.316 |
| BG505.W6M.C2 | A | >50 | 0.823 | 0.111 | 0.053 |
| BI369.9A | A | >50 | 1.95 | 0.290 | 0.224 |
| BS208.B1 | A | >50 | 1.77 | 0.263 | 0.022 |
| KER2008.12 | A | >50 | >50 | >50 | 0.591 |
| KER2018.11 | A | >50 | 9.89 | 2.52 | 0.555 |
| KNH1209.18 | A | >50 | 1.21 | 0.251 | 0.099 |
| MB201.A1 | A | >50 | 12.9 | 0.333 | 0.212 |
| MB539.2B7 | A | >50 | 11.7 | 1.71 | 0.500 |
| MI369.A5 | A | >50 | 2.64 | 0.416 | 0.269 |
| MS208.A1 | A | >50 | 2.77 | 0.463 | 0.178 |
| Q23.17 | A | 1.35 | 0.405 | 0.132 | 0.052 |
| Q259.17 | A | >50 | 7.46 | 0.100 | 0.075 |
| Q769.d22 | A | >50 | 0.981 | 0.110 | 0.035 |
| Q769.h5 | A | >50 | 2.55 | 0.139 | 0.062 |
| Q842.d12 | A | 8.15 | 0.378 | 0.091 | 0.038 |
| QH209.14M.A2 | A | >50 | 5.76 | 0.374 | 0.060 |
| RW020.2 | A | 1.20 | 1.05 | 0.301 | 0.203 |
| UG037.8 | A | >50 | 1.10 | 0.188 | 0.089 |
| 246-F3.C10.2 | AC | | 1.33 | | |
| 3301.V1.C24 | AC | 20.9 | 1.91 | 0.473 | 0.097 |
| 3589.V1.C4 | AC | >50 | >50 | 0.309 | 0.047 |
| 6540.v4.c1 | AC | >50 | >50 | >50 | >50 |
| 6545.V4.C1 | AC | >50 | >50 | >50 | >50 |

FIG. 41

| | | | | | |
|---|---|---|---|---|---|
| 0815.V3.C3 | ACD | >50 | 0.549 | 0.056 | 0.015 |
| 6095.V1.C10 | ACD | >50 | 3.29 | 1.33 | 0.506 |
| 3468.V1.C12 | AD | 2.47 | 0.659 | 0.070 | 0.050 |
| Q168.a2 | AD | >50 | 1.10 | 0.261 | 0.098 |
| Q461.e2 | AD | >50 | 6.95 | 0.818 | 0.497 |
| 620345.c1 | AE | >50 | 8.61 | 1.94 | >50 |
| BJOX009000.02.4 | AE | >50 | >50 | 5.50 | 1.54 |
| BJOX010000.06.2 | AE | >50 | >50 | 10.6 | 6.79 |
| BJOX025000.01.1 | AE | 40.6 | 0.586 | 0.271 | 8.46 |
| BJOX028000.10.3 | AE | >50 | 0.886 | 0.168 | 0.256 |
| C1080.c3 | AE | >50 | 13.3 | 2.69 | 2.10 |
| C2101.c1 | AE | 12.6 | 3.37 | 0.261 | 0.179 |
| C3347.c11 | AE | >50 | 0.482 | 0.117 | 0.095 |
| C4118.09 | AE | 3.30 | 1.04 | 0.084 | 0.248 |
| CM244.ec1 | AE | 1.19 | | 0.160 | 0.089 |
| CNE3 | AE | >50 | >50 | 2.45 | 1.63 |
| CNE5 | AE | 17.6 | 2.94 | 1.03 | 0.323 |
| CNE55 | AE | >50 | 1.90 | 0.400 | 0.359 |
| CNE56 | AE | 42.9 | 2.96 | 1.10 | 0.343 |
| CNE59 | AE | 13.6 | 3.79 | 0.943 | 0.623 |
| CNE8 | AE | >50 | 3.22 | 1.10 | 0.510 |
| R1166.c1 | AE | >50 | 34.4 | 0.758 | 3.00 |
| R2184.c4 | AE | 5.82 | 6.83 | 0.563 | 0.133 |
| R3265.c6 | AE | >50 | 35.0 | 0.172 | 0.710 |
| TH966.8 | AE | 0.732 | 1.70 | 0.304 | 0.284 |
| TH976.17 | AE | 0.975 | 0.935 | 0.286 | 0.332 |
| 235-47 | AG | >50 | 2.25 | 0.293 | 0.061 |
| 242-14 | AG | >50 | >50 | 2.83 | >50 |
| 263-8 | AG | >50 | 2.93 | 0.447 | 0.168 |

FIG. 41 cont.

| Virus ID | Clade | CH235 | CH235.9 | CH235.12 | VRC01 |
|---|---|---|---|---|---|
| 269-12 | AG | >50 | >50 | >50 | 0.293 |
| 271-11 | AG | >50 | 0.652 | 0.090 | 0.054 |
| 928-28 | AG | >50 | 3.55 | 0.542 | 0.476 |
| DJ263.8 | AG | >50 | 2.90 | 0.276 | 0.066 |
| T250-4 | AG | >50 | >50 | >50 | >50 |
| T251-18 | AG | >50 | >50 | 4.02 | 4.42 |
| T253-11 | AG | >50 | >50 | 1.65 | 0.501 |
| T255-34 | AG | >50 | 7.83 | 0.608 | 0.725 |
| T257-31 | AG | >50 | 13.3 | 2.66 | 2.47 |
| T266-60 | AG | >50 | >50 | 10.3 | 2.37 |
| T278-50 | AG | >50 | >50 | >50 | >50 |
| T280-5 | AG | >50 | 0.308 | 0.109 | 0.059 |
| T33-7 | AG | >50 | 0.469 | 0.039 | 0.019 |
| 3988.25 | B | >50 | 3.49 | 0.917 | 0.369 |
| 5768.04 | B | >50 | 3.75 | 0.715 | 0.354 |
| 6101.10 | B | >50 | 3.14 | 0.467 | 0.023 |
| 6535.3 | B | >50 | >50 | 4.85 | 2.10 |
| 7165.18 | B | >50 | >50 | >50 | 45.0 |
| 45_01dG5 | B | >50 | 0.507 | 0.058 | 0.011 |
| 89.6.DG | B | >50 | 27.7 | 2.23 | 1.30 |
| AC10.29 | B | >50 | 9.55 | 2.13 | 1.41 |
| ADA.DG | B | >50 | 2.88 | 0.907 | 0.563 |
| Bal.01 | B | >50 | 0.326 | 0.237 | 0.124 |
| BaL.26 | B | >50 | 1.10 | 0.214 | 0.060 |
| BG1168.01 | B | >50 | 4.06 | 1.42 | 0.738 |
| BL01.DG | B | >50 | >50 | >50 | >50 |
| BR07.DG | B | >50 | 4.66 | 1.51 | 1.81 |
| BX08.16 | B | >50 | >50 | 2.35 | 0.389 |
| CAAN.A2 | B | >50 | 7.47 | 2.23 | 0.963 |

FIG. 41 cont.

| | | | | | |
|---|---|---|---|---|---|
| CNE10 | B | >50 | 23.2 | 5.26 | 0.689 |
| CNE12 | B | >50 | 8.19 | 2.56 | 0.695 |
| CNE14 | B | >50 | 12.5 | 0.594 | 0.199 |
| CNE4 | B | >50 | 5.97 | 1.16 | 0.639 |
| CNE57 | B | >50 | >50 | 1.25 | 0.496 |
| HO86.8 | B | >50 | 1.35 | 0.174 | >50 |
| HT593.1 | B | >50 | 2.23 | 0.984 | 0.606 |
| HXB2.DG | B | 18.1 | 0.243 | 0.173 | 0.063 |
| JRCSF.JB | B | >50 | 1.65 | 0.596 | 0.436 |
| JRFL.JB | B | 1.82 | 2.13 | 0.127 | 0.051 |
| MN.3 | B | >50 | 1.27 | 0.142 | 0.011 |
| PVO.04 | B | >50 | 3.53 | 1.47 | 0.552 |
| QH0515.01 | B | 26.4 | 7.95 | 1.40 | 1.43 |
| QH0692.42 | B | >50 | 10.8 | 2.25 | 1.37 |
| REJO.67 | B | >50 | >50 | 1.09 | 0.113 |
| RHPA.7 | B | 16.6 | 0.300 | 0.091 | 0.051 |
| SC422.8 | B | >50 | 3.73 | 0.798 | 0.127 |
| SF162.LS | B | >50 | 2.21 | 0.534 | 0.228 |
| SS1196.01 | B | >50 | >50 | 0.827 | 0.246 |
| THRO.18 | B | >50 | >50 | >50 | 4.63 |
| TRJO.58 | B | >50 | 1.76 | 0.524 | 0.116 |
| TRO.11 | B | 14.8 | 4.68 | 0.714 | 0.502 |
| WITO.33 | B | >50 | 3.65 | 0.418 | 0.140 |
| X2278.C2.B6 | B | >50 | 5.96 | 0.425 | 0.133 |
| YU2.DG | B | >50 | 0.761 | 0.235 | 0.113 |
| BJOX002000.03.2 | BC | >50 | 2.74 | 0.739 | >50 |
| CH038.12 | BC | >50 | >50 | 17.3 | 0.519 |
| CH070.1 | BC | >50 | >50 | 2.39 | 9.99 |
| CH117.4 | BC | >50 | 1.03 | 0.340 | 0.095 |
| CH119.10 | BC | >50 | 3.68 | 1.24 | 0.577 |
| CH181.12 | BC | >50 | 3.44 | 0.612 | 0.481 |

FIG. 41 cont.

| Virus ID | Clade | CH235 | CH235.9 | CH235.12 | VRC01 |
|---|---|---|---|---|---|
| CNE15 | BC | 15.2 | 1.16 | 0.249 | 0.100 |
| CNE19 | BC | 27.5 | 0.488 | 0.134 | 0.169 |
| CNE20 | BC | >50 | 1.09 | 0.254 | 9.25 |
| CNE21 | BC | >50 | 1.81 | 0.527 | 0.357 |
| CNE40 | BC | >50 | 0.477 | 0.207 | 0.370 |
| CNE7 | BC | >50 | >50 | 1.36 | 0.286 |
| 286.36 | C | >50 | 3.00 | 0.699 | 0.322 |
| 288.38 | C | >50 | 3.62 | 1.62 | 1.49 |
| 0013095-2.11 | C | >50 | >50 | 29.7 | 0.088 |
| 001428-2.42 | C | >50 | 0.417 | 0.087 | 0.006 |
| 0077_V1.C16 | C | >50 | 41.7 | 6.84 | 1.28 |
| 00836-2.5 | C | >50 | >50 | 1.09 | 0.119 |
| 0921.V2.C14 | C | 10.9 | 1.76 | 0.344 | 0.182 |
| 16055-2.3 | C | >50 | 0.768 | 0.159 | 0.063 |
| 16845-2.22 | C | >50 | 28.0 | 7.47 | 3.60 |
| 16936-2.21 | C | >50 | 1.85 | 0.500 | 0.110 |
| 25710-2.43 | C | >50 | 0.983 | 0.382 | 0.594 |
| 25711-2.4 | C | >50 | 4.57 | 0.974 | 0.555 |
| 25925-2.22 | C | >50 | 2.51 | 0.641 | 0.474 |
| 26191-2.48 | C | >50 | 1.65 | 0.583 | 0.166 |
| 3168.V4.C10 | C | >50 | 6.56 | 0.372 | 0.255 |
| 3637.V5.C3 | C | >50 | 10.5 | 12.2 | 1.45 |
| 3873.V1.C24 | C | >50 | >50 | >50 | 0.791 |
| 6322.V4.C1 | C | >50 | 4.74 | 0.944 | >50 |
| 6471.V1.C16 | C | >50 | >50 | >50 | >50 |
| 6631.V3.C10 | C | >50 | >50 | 5.83 | >50 |
| 6644.V2.C33 | C | >50 | >50 | >50 | 0.243 |
| 6785.V5.C14 | C | >50 | >50 | >50 | 0.286 |
| 6838.V1.C35 | C | >50 | 4.54 | 1.08 | 0.210 |
| 96ZM651.02 | C | >50 | 4.37 | 1.18 | 0.570 |

FIG. 41 cont.

| | | | | | |
|---|---|---|---|---|---|
| BR025.9 | C | >50 | >50 | >50 | 0.593 |
| CAP210.E8 | C | >50 | >50 | >50 | >50 |
| CAP244.D3 | C | >50 | 13.2 | 1.52 | 1.33 |
| CAP256.206.C9 | C | 14.6 | 3.73 | 1.32 | 0.971 |
| CAP45.G3 | C | >50 | 4.00 | 0.568 | 7.00 |
| Ce1176.A3 | C | >50 | 7.71 | 1.24 | 2.60 |
| CE703010217.B6 | C | >50 | 1.70 | 0.319 | 0.366 |
| CNE30 | C | >50 | 4.31 | 1.21 | 0.525 |
| CNE31 | C | >50 | >50 | 2.78 | 0.786 |
| CNE53 | C | 1.77 | 0.781 | 0.274 | 0.087 |
| CNE58 | C | >50 | >50 | 1.95 | 0.225 |
| DU123.06 | C | >50 | 17.5 | 4.25 | 7.92 |
| DU151.02 | C | 3.94 | 1.33 | 0.287 | 14.8 |
| DU156.12 | C | 9.48 | 1.65 | 0.285 | 0.086 |
| DU172.17 | C | 1.92 | 1.74 | 0.361 | >50 |
| DU422.01 | C | >50 | 2.85 | 0.944 | >50 |
| MW965.26 | C | 6.10 | 3.03 | 0.573 | 0.029 |
| SO18.18 | C | >50 | 1.24 | 0.110 | 0.058 |
| TV1.29 | C | >50 | 11.0 | 4.63 | >50 |
| TZA125.17 | C | >50 | >50 | >50 | >50 |
| TZBD.02 | C | >50 | 38.9 | 0.219 | 0.078 |
| ZA012.29 | C | 13.2 | 11.5 | 0.971 | 0.384 |
| ZM106.9 | C | >50 | 2.09 | 0.620 | 0.311 |
| ZM109.4 | C | >50 | 2.50 | 0.416 | 0.177 |
| ZM135.10a | C | >50 | >50 | >50 | 2.25 |
| ZM176.66 | C | >50 | 1.21 | 0.183 | 0.083 |
| ZM197.7 | C | >50 | 10.5 | 1.40 | 0.428 |
| ZM214.15 | C | >50 | 10.1 | 2.22 | 0.893 |
| ZM215.8 | C | 6.19 | 1.71 | 0.315 | 0.215 |
| ZM233.6 | C | 5.71 | 5.02 | 1.25 | 1.02 |

IC50 (μg/ml)
<0.100
0.100-1.00
1.00-10.0
>10.0
>50

| Virus ID | Clade | CH235 | CH235.9 | CH235.12 | VRC01 |
|---|---|---|---|---|---|
| ZM249.1 | C | 9.99 | 0.598 | 0.273 | 0.057 |
| ZM53.12 | C | >50 | 4.44 | 0.558 | 0.625 |
| ZM55.28a | C | >50 | 4.20 | 0.665 | 0.285 |
| 3326.V4.C3 | CD | >50 | 1.54 | 0.114 | 0.068 |
| 3337.V2.C6 | CD | >50 | 10.8 | 0.429 | 0.090 |
| 3817.v2.c59 | CD | >50 | 14.6 | 3.63 | >50 |
| 231965.c1 | D | >50 | >50 | 13.9 | 0.353 |
| 247-23 | D | >50 | 3.32 | 0.691 | 1.84 |
| 3016.v5.c45 | D | >50 | >50 | >50 | 0.155 |
| 57128.vrc15 | D | >50 | >50 | 6.59 | >50 |
| 6405.v4.c34 | D | >50 | >50 | >50 | 1.55 |
| A03349M1.vrc4a | D | >50 | 7.54 | 4.08 | 4.10 |
| A07412M1.vrc12 | D | >50 |  | 0.351 | 0.082 |
| NKU3006.ec1 | D | 4.61 | 1.29 | 0.466 | 0.596 |
| P0402.c2.11 | G |  | 3.65 |  |  |
| P1981.C5.3 | G | >50 | >50 | 2.19 | 0.330 |
| X1193.c1 | G | >50 | 4.08 | 0.972 | 0.154 |
| X1254.c3 | G | >50 | >50 | 1.98 | 0.059 |
| X1632.S2.B10 | G | >50 | 1.18 | 0.484 | 0.130 |
| X2088.c9 | G | >50 | >50 | >50 | >50 |
| X2131.C1.B5 | G | >50 | 10.3 | 2.58 | 0.537 |
| SIVmac251.30.SG3 | NA | >50 | >50 | >50 | >50 |
| SVA.MLV | NA | >50 | >50 | >50 | >50 |

|  | CH235 | CH235.9 | CH235.12 | VRC01 |
|---|---|---|---|---|
| # Viruses | 202 | 202 | 202 | 202 |
| Total VS Neutralized |  |  |  |  |
| IC50 <50 µg/ml | 35 | 153 | 179 | 179 |
| IC50 <10 µg/ml | 19 | 130 | 173 | 177 |
| IC50 <1.0 µg/ml | 2 | 25 | 115 | 146 |
| IC50 <0.1 µg/ml | 0 | 0 | 10 | 47 |
| IC50 <0.01 µg/ml | 0 | 0 | 0 | 1 |
| % VS Neutralized |  |  |  |  |
| IC50 <50 µg/ml | 17 | 76 | 89 | 89 |

FIG. 41 cont.

| Complex (antibody-gp120) | CH235-93TH057 | CH235.9-93TH057 | CH235.12-93TH057 |
|---|---|---|---|
| PDB ID | 5F9W | 5F9O | 5F96 |
| Data collection | | | |
| Space group | P3$_2$ | P2$_1$2$_1$2$_1$ | P2$_1$ |
| Cell dimensions | | | |
| $a, b, c$ (Å) | 123.4, 123.4, 127.3 | 63.5, 67.8, 225.6 | 53.7, 69.9, 127.3 |
| $\alpha, \beta, \gamma$ (°) | 90.0, 90.0, 120.0 | 90.0, 90.0, 90.0 | 90.0, 94.6, 90.0 |
| Resolution (Å) | 40.94-2.89 (2.99-2.89)* | 50.0-1.86 (2.00-1.93; 1.93-1.86) | 2.25 (2.29-2.25) |
| $R_{sym}$ or $R_{merge}$ | 0.22 (0.68) | 14.1 (41.8; 48.4) | 12.5 (41.4) |
| $I/\sigma I$ | 8.9 (1.9) | 7.06 (1.79; 1.25) | 15.5 (2.1) |
| Completeness (%) | 100 (100) | 89.7 (73.4; 46.8) | 97.6 (86.7) |
| Redundancy | 7.6 (6.7) | 3.4 (1.6; 1.2) | 3.0 (2.1) |
| Refinement | | | |
| Resolution (Å) | 40.9 – 2.89 | 35.8-1.86 | 34.5-2.25 |
| No. reflections | 48360 | 73935 | 43920 |
| $R_{work}/R_{free}$ | 17.5/22.9 | 20.4/22.0 | 18.3/23.0 |
| No. atoms | | | |
| Protein | 11932 | 6137 | 5976 |
| Ligand/ion | 393 | 53 | 213 |
| Water | 74 | 461 | 196 |
| B-factors (Å$^2$) | | | |
| Protein | 92.5 | 43.5 | 63.4 |
| Ligand/ion | 120.9 | 87.0 | 103.4 |
| Water | 77.5 | 47.2 | 59.3 |
| R.m.s deviations | | | |
| Bond lengths (Å) | 0.004 | 0.008 | 0.006 |
| Bond angles (°) | 0.78 | 1.27 | 0.92 |
| Ramachandran statistics | | | |
| Favored (%) | 96.0 | 97.1 | 97.0 |
| Outliers (%) | 0.1 | 0.0 | 0.1 |

*Values in parenthesis denote highest resolution shell.

FIG. 42

| Conforming antibody | # mutations ($x$) | Reference antibody | # sharing mutation positions ($c$) | Probability of seeing $c$ based on: | | $P_{VH1-46}/P_{uniform}$ |
|---|---|---|---|---|---|---|
| | | | | Uniform distribution ($P_{uniform}$) | VH1-46 mutation frequencies ($P_{VH1-46}$) | |
| CH235 | 15 | 1B2530 | 11 | 0.00432 | 0.17751 | 41.1 |
| CH235 | 15 | 8ANC131 | 13 | 0.00010 | 0.01744 | 174.4 |
| 1B2530 | 39 | 8ANC131 | 26 | 0.00001 | 0.04274 | 4274.0 |

FIG. 4.3A

| Conforming antibody | # mutations ($x$) | Reference antibody | # identical mutations ($i$) | Probability of seeing $i$ based on: | | $P_{VH1-46}/P_{uniform}$ |
|---|---|---|---|---|---|---|
| | | | | Uniform distribution ($P_{uniform}$) | VH1-46 mutation frequencies ($P_{VH1-46}$) | |
| CH235 | 15 | 1B2530 | 4 | 0.00022 | 0.10433 | 474.2 |
| CH235 | 15 | 8ANC131 | 4 | 0.00019 | 0.11546 | 607.7 |
| 1B2530 | 39 | 8ANC131 | 7 | 0.00001 | 0.14622 | 14622.0 |

FIG. 4.3B

| | IGHV1-2 | IGHV1-46 | IGHV1-69 | IGHV3-23 | IGHV3-30 |
|---|---|---|---|---|---|
| IGHV1-46 | 0.84 | | | | |
| IGHV1-69 | 0.74 | 0.74 | | | |
| IGHV3-23 | 0.54 | 0.63 | 0.68 | | |
| IGHV3-30 | 0.53 | 0.57 | 0.62 | 0.83 | |
| IGHV4-59 | 0.47 | 0.53 | 0.55 | 0.67 | 0.57 |

FIG. 4.3C

| | UCA | IA4 | IA3 | IA2 | IA1 | CH240 | CH236 | CH235 | CH239 | CH241 |
|---|---|---|---|---|---|---|---|---|---|---|
| sCD4 | nb | nb | nb | nb | >100 | nb | nb | 26.3 | 92.6 | 2.6 |
| CH106 | nb | nb | nb | nb | 82.4 | 68.9 | 82.2 | 16.5 | 45.4 | 1.5 |

*FIG. 44A*

| | CH235 | CH236 | CH239 | CH240 | CH241 | CH106 |
|---|---|---|---|---|---|---|
| CH106 | 4.3 | 6.8 | 4.6 | 2.3 | 14.3 | 2.5 |

*FIG. 44B*

| Virus ID | Week | Neutralization IC50, μg/ml | | | |
|---|---|---|---|---|---|
| | | UCA | IA4 | IA3 | CH235.11 |
| T/F | | >50 | >50 | 5.22 | 2.19 |
| CH505.w4.10 | 4 | >50 | 20.51 | 1.02 | 0.12 |
| CH505.w4.26 | 4 | >50 | >50 | 3.67 | 1.59 |
| CH505.w4.3 | 4 | >50 | >50 | 1.65 | 9.58 |
| CH505.w8.e12 | 14 | >50 | >50 | 34.99 | 0.06 |
| CH505.w8.e21 | 14 | >50 | >50 | >50 | 5.52 |
| CH505.w8.e29 | 14 | >50 | >50 | 5.34 | 6.19 |
| CH505.w8.e34 | 14 | >50 | >50 | 4.84 | 7.07 |
| CH505.w8.e6 | 14 | >50 | >50 | 5.73 | 17.42 |
| CH505.w8.e3 | 14 | >50 | >50 | 6.28 | 27.80 |
| CH505.w8.e4 | 14 | >50 | >50 | 3.60 | 35.26 |
| CH505.w12.e4 | 20 | >50 | >50 | >50 | 2.66 |
| CH505.w12.e19 | 20 | >50 | >50 | 8.99 | >50 |
| CH505.w12.e25 | 20 | >50 | >50 | 8.54 | >50 |
| CH505.w12.e27 | 20 | >50 | >50 | 10.28 | >50 |
| CH505.w24.e5 | 30 | >50 | >50 | >50 | 2.08 |
| CH505.w24.e34 | 30 | >50 | >50 | >50 | 2.18 |
| CH505.w24.e37 | 30 | >50 | >50 | >50 | 3.56 |
| CH505.w24.e24 | 30 | >50 | >50 | 29.77 | >50 |
| CH505.w24.e28 | 30 | >50 | >50 | >50 | >50 |
| CH505.w24.e13 | 30 | >50 | >50 | >50 | >50 |
| CH505.w48.e6 | 53 | >50 | >50 | >50 | >50 |
| CH505.w48.e22 | 53 | >50 | >50 | >50 | >50 |
| CH505.w48.e13 | 53 | >50 | >50 | >50 | >50 |
| CH505.w48.e28 | 53 | >50 | >50 | >50 | >50 |
| CH505.w48.e11 | 53 | >50 | >50 | >50 | >50 |
| CH505.w48.e31 | 53 | >50 | >50 | >50 | >50 |
| CH505.w96.A5 | 100 | >50 | >50 | >50 | >50 |
| CH505.w96.B8 | 100 | >50 | >50 | >50 | >50 |
| CH505.w96.B6 | 100 | >50 | >50 | >50 | >50 |
| CH505.w96.A10 | 100 | >50 | >50 | >50 | >50 |
| CH505.w96.A3 | 100 | >50 | >50 | >50 | >50 |
| CH505.w96.B4 | 100 | >50 | >50 | >50 | >50 |
| CH0505.C.w136.e.B23 | 136 | >50 | >50 | >50 | >50 |
| CH0505.C.w136.e.B18 | 136 | >50 | >50 | >50 | >50 |
| CH0505.C.w136.e.B24 | 136 | >50 | >50 | >50 | >50 |

FIG. 45

|  | Neutralization IC50, μg/ml | | | | |
|---|---|---|---|---|---|
| Virus ID | IA2 | IA1 | CH240 | CH236 | CH235 |
| T/F | 0.97 | 0.91 | 0.94 | 0.61 | 0.63 |
| CH505.w4.10 | 0.24 | 0.20 | 0.15 | 0.10 | 0.10 |
| CH505.w4.26 | 1.36 | 0.32 | 0.67 | 0.78 | 0.46 |
| CH505.w4.3 | 0.35 | 0.30 | 0.25 | 0.40 | 0.11 |
| CH505.w8.e12 | 2.22 | 0.85 | 0.93 | 0.53 | 0.42 |
| CH505.w8.e21 | 38.08 | 0.79 | 0.58 | 0.96 | 0.38 |
| CH505.w8.e29 | 1.02 | 0.86 | 0.88 | 1.05 | 0.75 |
| CH505.w8.e34 | 0.94 | 0.84 | 0.89 | 1.09 | 0.52 |
| CH505.w8.e6 | 1.64 | 0.92 | 0.73 | 0.63 | 0.31 |
| CH505.w8.e3 | 1.40 | 0.79 | 1.05 | 0.75 | 0.49 |
| CH505.w8.e4 | 1.00 | 0.72 | 0.60 | 0.88 | 0.27 |
| CH505.w12.e4 | 47.61 | 0.94 | 1.00 | 1.81 | 0.65 |
| CH505.w12.e19 | 2.12 | 1.99 | 1.63 | 1.24 | 1.16 |
| CH505.w12.e25 | 1.69 | 1.85 | 1.41 | 0.85 | 1.08 |
| CH505.w12.e27 | 2.06 | 0.98 | 1.13 | 0.46 | 0.39 |
| CH505.w24.e5 | 7.72 | 1.83 | 2.08 | 0.58 | 0.80 |
| CH505.w24.e34 | 4.98 | 5.18 | 5.61 | 2.27 | 3.23 |
| CH505.w24.e37 | 6.45 | 6.92 | 7.57 | 2.60 | 4.25 |
| CH505.w24.e24 | 27.95 | 4.62 | 4.12 | 3.69 | 2.06 |
| CH505.w24.e28 | >50 | 5.28 | 5.28 | 9.14 | 2.16 |
| CH505.w24.e13 | >50 | 4.73 | 5.11 | 4.39 | 1.15 |
| CH505.w48.e6 | >50 | >50 | >50 | >50 | >50 |
| CH505.w48.e22 | >50 | >50 | >50 | >50 | >50 |
| CH505.w48.e13 | >50 | >50 | >50 | >50 | >50 |
| CH505.w48.e28 | >50 | >50 | >50 | >50 | >50 |
| CH505.w48.e11 | >50 | >50 | >50 | >50 | >50 |
| CH505.w48.e31 | >50 | >50 | >50 | >50 | >50 |
| CH505.w96.A5 | >50 | >50 | >50 | >50 | >50 |
| CH505.w96.B8 | >50 | >50 | >50 | >50 | >50 |
| CH505.w96.B6 | >50 | >50 | >50 | >50 | >50 |
| CH505.w96.A10 | >50 | >50 | >50 | >50 | >50 |
| CH505.w96.A3 | >50 | >50 | >50 | >50 | >50 |
| CH505.w96.B4 | >50 | >50 | >50 | >50 | >50 |
| CH0505.C.w136.e.B23 | >50 | >50 | >50 | >50 | >50 |
| CH0505.C.w136.e.B18 | >50 | >50 | >50 | >50 | >50 |
| CH0505.C.w136.e.B24 | >50 | >50 | >50 | >50 | >50 |

FIG. 45 cont.

|  | Neutralization IC50, μg/ml | | | | |
| --- | --- | --- | --- | --- | --- |
| Virus ID | CH239 | CH241 | CH235.7 | CH235.13 | CH235.10 |
| T/F | 0.48 | 0.14 | 0.39 | 0.91 | 0.22 |
| CH505.w4.10 | <0.02 | <0.02 | 0.07 | 0.17 | 0.10 |
| CH505.w4.26 | 0.30 | 0.05 | 0.09 | 0.16 | 0.04 |
| CH505.w4.3 | 0.10 | <0.02 | 0.06 | 0.15 | 0.11 |
| CH505.w8.e12 | 0.41 | 0.09 | 0.07 | 0.18 | 0.02 |
| CH505.w8.e21 | 0.14 | 0.04 | 0.10 | 0.17 | 0.24 |
| CH505.w8.e29 | 0.61 | 0.17 | 0.17 | 0.35 | 0.15 |
| CH505.w8.e34 | 0.78 | 0.12 | 0.14 | 0.31 | 0.12 |
| CH505.w8.e6 | 0.43 | 0.17 | 0.21 | 0.34 | 0.21 |
| CH505.w8.e3 | 0.40 | 0.09 | 0.19 | 0.27 | 0.24 |
| CH505.w8.e4 | 0.40 | 0.08 | 0.20 | 0.34 | 0.13 |
| CH505.w12.e4 | 0.18 | 0.06 | 0.08 | 0.19 | 0.18 |
| CH505.w12.e19 | 1.11 | 0.27 | 0.29 | 0.47 | 0.24 |
| CH505.w12.e25 | 0.75 | 0.18 | 0.29 | 0.37 | 0.23 |
| CH505.w12.e27 | 0.27 | 0.10 | 0.16 | 0.30 | 0.12 |
| CH505.w24.e5 | 0.67 | 1.17 | 0.35 | 0.38 | 0.44 |
| CH505.w24.e34 | 3.02 | 3.68 | 0.74 | 0.60 | 0.38 |
| CH505.w24.e37 | 2.79 | 3.99 | 0.94 | 1.19 | 0.43 |
| CH505.w24.e24 | 1.54 | 0.49 | 0.64 | 0.72 | 0.43 |
| CH505.w24.e28 | 2.07 | 0.40 | 0.11 | 0.53 | 45.05 |
| CH505.w24.e13 | 1.49 | 2.96 | 0.16 | 0.39 | >50 |
| CH505.w48.e6 | 19.95 | >50 | 1.76 | 2.66 | 3.69 |
| CH505.w48.e22 | >50 | >50 | 12.55 | 5.43 | 3.06 |
| CH505.w48.e13 | 33.78 | >50 | 27.04 | 5.03 | 2.42 |
| CH505.w48.e28 | >50 | >50 | 25.29 | 5.08 | 2.58 |
| CH505.w48.e11 | >50 | >50 | 34.23 | 3.26 | 3.10 |
| CH505.w48.e31 | >50 | >50 | >50 | 25.92 | 1.53 |
| CH505.w96.A5 | >50 | >50 | >50 | >50 | >50 |
| CH505.w96.B8 | >50 | >50 | >50 | >50 | >50 |
| CH505.w96.B6 | >50 | >50 | >50 | >50 | >50 |
| CH505.w96.A10 | >50 | >50 | >50 | >50 | >50 |
| CH505.w96.A3 | >50 | 45.37 | >50 | >50 | >50 |
| CH505.w96.B4 | 48.62 | 41.17 | >50 | >50 | >50 |
| CH0505.C.w136.e.B23 | >50 | >50 | >50 | 29.73 | 11.41 |
| CH0505.C.w136.e.B18 | >50 | >50 | >50 | 32.27 | 27.81 |
| CH0505.C.w136.e.B24 | >50 | >50 | >50 | >50 | 43.03 |

FIG. 45 cont.

|  | Neutralization IC50, µg/ml | |
| --- | --- | --- |
| Virus ID | CH235.9 | CH235.12 |
| T/F | 0.51 | 0.22 |
| CH505.w4.10 | 0.08 | <0.02 |
| CH505.w4.26 | 0.16 | 0.03 |
| CH505.w4.3 | 0.11 | <0.02 |
| CH505.w8.e12 | 0.08 | <0.02 |
| CH505.w8.e21 | 0.14 | <0.02 |
| CH505.w8.e29 | 0.21 | 0.06 |
| CH505.w8.e34 | 0.16 | 0.05 |
| CH505.w8.e6 | 0.30 | 0.09 |
| CH505.w8.e3 | 0.25 | 0.11 |
| CH505.w8.e4 | 0.27 | 0.06 |
| CH505.w12.e4 | 0.08 | <0.02 |
| CH505.w12.e19 | 0.27 | 0.05 |
| CH505.w12.e25 | 0.38 | 0.07 |
| CH505.w12.e27 | 0.15 | 0.05 |
| CH505.w24.e5 | 0.26 | 0.07 |
| CH505.w24.e34 | 0.62 | 0.12 |
| CH505.w24.e37 | 0.70 | 0.19 |
| CH505.w24.e24 | 0.67 | 0.17 |
| CH505.w24.e28 | 0.37 | 0.17 |
| CH505.w24.e13 | 0.46 | 0.10 |
| CH505.w48.e6 | 1.25 | 0.46 |
| CH505.w48.e22 | 1.30 | 0.58 |
| CH505.w48.e13 | 1.39 | 0.48 |
| CH505.w48.e28 | 1.23 | 0.66 |
| CH505.w48.e11 | 2.48 | 0.75 |
| CH505.w48.e31 | 1.44 | 0.11 |
| CH505.w96.A5 | >50 | 3.68 |
| CH505.w96.B8 | >50 | 3.02 |
| CH505.w96.B6 | >50 | 8.35 |
| CH505.w96.A10 | >50 | 19.82 |
| CH505.w96.A3 | >50 | >50 |
| CH505.w96.B4 | >50 | >50 |
| CH0505.C.w136.e.B23 | 10.23 | 1.75 |
| CH0505.C.w136.e.B18 | 12.41 | 3.33 |
| CH0505.C.w136.e.B24 | 13.58 | 4.09 |

FIG. 45 cont.

|  |  | Neutralization IC50, µg/ml | | | |
|---|---|---|---|---|---|
| Virus ID | Week | UCA | IA4 | IA3 | CH235.11 |
| CH0505.C.w136.e.B33 | 136 | >50 | >50 | >50 | >50 |
| CH0505.C.w136.e.B38 | 136 | >50 | >50 | >50 | >50 |
| CH0505.C.w136.e.B2 | 136 | >50 | >50 | >50 | >50 |
| CH0505.C.w136.e.B3 | 136 | >50 | >50 | >50 | >50 |
| CH0505.C.w136.e.B4 | 136 | >50 | >50 | >50 | >50 |
| CH0505.C.w136.e.B5 | 136 | >50 | >50 | >50 | >50 |
| CH0505.C.w136.e.B12 | 136 | >50 | >50 | >50 | >50 |
| CH0505.C.w136.e.B27 | 136 | >50 | >50 | >50 | >50 |
| CH0505.C.w160.C2 | 160 | >50 | >50 | >50 | >50 |
| CH0505.C.w24.C9 | 160 | >50 | >50 | >50 | >50 |
| CH0505.C.w24.C10 | 160 | >50 | >50 | >50 | >50 |
| CH0505.C.w24.C11 | 160 | >50 | >50 | >50 | >50 |
| CH0505.C.w24.C12 | 160 | >50 | >50 | >50 | >50 |
| CH0505.C.w24.D2 | 160 | >50 | >50 | >50 | >50 |
| CH0505.C.w24.T3 | 160 | >50 | >50 | >50 | >50 |
| CH0505.w176.e11 | 176 | >50 | >50 | >50 | >50 |
| CH0505.w176.e12 | 176 | >50 | >50 | >50 | >50 |
| CH0505.w176.e13 | 176 | >50 | >50 | >50 | >50 |
| CH0505.w176.e1 | 176 | >50 | >50 | >50 | >50 |
| CH0505.w176.e2 | 176 | >50 | >50 | >50 | >50 |
| CH0505.w176.e10 | 176 | >50 | >50 | >50 | >50 |
| CH0505.w233.e1 | 233 | >50 | >50 | >50 | >50 |
| CH0505.w233.e3 | 233 | >50 | >50 | >50 | >50 |
| CH0505.w233.e4 | 233 | >50 | >50 | >50 | >50 |
| CH0505.w233.e7 | 233 | >50 | >50 | >50 | >50 |
| CH0505.w233.e17 | 233 | >50 | >50 | >50 | >50 |
| CH0505.w233.e18 | 233 | >50 | >50 | >50 | >50 |
| CH0505.w258.e4 | 258 | >50 | >50 | 34.10 | >50 |
| CH0505.w258.e1 | 258 | >50 | >50 | >50 | >50 |
| CH0505.w258.e7 | 258 | >50 | >50 | >50 | >50 |
| CH0505.w258.e6 | 258 | >50 | >50 | >50 | >50 |
| CH0505.w258.e5 | 258 | >50 | >50 | >50 | >50 |
| CH0505.w323.e1 | 323 | >50 | >50 | >50 | >50 |
| CH0505.w323.e11 | 323 | >50 | >50 | >50 | >50 |
| CH0505.w323.e13 | 323 | >50 | >50 | >50 | >50 |
| CH0505.w323.e14 | 323 | >50 | >50 | >50 | >50 |
| CH0505.w323.e15 | 323 | >50 | >50 | >50 | >50 |
| CH0505.w323.e16 | 323 | >50 | >50 | >50 | >50 |
| CH0505.w323.e17 | 323 | >50 | >50 | >50 | >50 |
| CH0505.w323.e18 | 323 | >50 | >50 | >50 | >50 |

FIG. 45 cont.

|  | Neutralization IC50, μg/ml | | | | |
| --- | --- | --- | --- | --- | --- |
|  | IA2 | IA1 | CH240 | CH236 | CH235 |
| CH0505.C.w136.e.B33 | >50 | >50 | >50 | >50 | >50 |
| CH0505.C.w136.e.B38 | >50 | >50 | >50 | >50 | >50 |
| CH0505.C.w136.e.B2 | >50 | >50 | >50 | >50 | >50 |
| CH0505.C.w136.e.B3 | >50 | >50 | >50 | >50 | >50 |
| CH0505.C.w136.e.B4 | >50 | >50 | >50 | >50 | >50 |
| CH0505.C.w136.e.B5 | >50 | >50 | >50 | >50 | >50 |
| CH0505.C.w136.e.B12 | >50 | >50 | >50 | >50 | >50 |
| CH0505.C.w136.e.B27 | >50 | >50 | >50 | >50 | >50 |
| CH0505.C.w160.C2 | >50 | >50 | >50 | >50 | >50 |
| CH0505.C.w24.C9 | >50 | >50 | >50 | >50 | >50 |
| CH0505.C.w24.C10 | >50 | >50 | >50 | >50 | >50 |
| CH0505.C.w24.C11 | >50 | >50 | >50 | >50 | >50 |
| CH0505.C.w24.C12 | >50 | >50 | >50 | >50 | >50 |
| CH0505.C.w24.D2 | >50 | >50 | >50 | >50 | >50 |
| CH0505.C.w24.T3 | >50 | >50 | >50 | >50 | >50 |
| CH0505.w176.e11 | >50 | >50 | >50 | >50 | >50 |
| CH0505.w176.e12 | >50 | >50 | >50 | >50 | >50 |
| CH0505.w176.e13 | >50 | >50 | >50 | >50 | >50 |
| CH0505.w176.e1 | >50 | >50 | >50 | >50 | >50 |
| CH0505.w176.e2 | >50 | >50 | >50 | >50 | >50 |
| CH0505.w176.e10 | >50 | >50 | >50 | >50 | >50 |
| CH0505.w233.e1 | >50 | >50 | >50 | >50 | >50 |
| CH0505.w233.e3 | >50 | >50 | >50 | >50 | >50 |
| CH0505.w233.e4 | >50 | >50 | >50 | >50 | >50 |
| CH0505.w233.e7 | >50 | >50 | >50 | >50 | >50 |
| CH0505.w233.e17 | >50 | >50 | >50 | >50 | >50 |
| CH0505.w233.e18 | >50 | >50 | >50 | >50 | >50 |
| CH0505.w258.e4 | >50 | >50 | >50 | >50 | >50 |
| CH0505.w258.e1 | >50 | >50 | >50 | >50 | >50 |
| CH0505.w258.e7 | >50 | >50 | >50 | >50 | >50 |
| CH0505.w258.e6 | >50 | >50 | >50 | >50 | >50 |
| CH0505.w258.e5 | >50 | >50 | >50 | >50 | >50 |
| CH0505.w323.e1 | >50 | >50 | >50 | >50 | >50 |
| CH0505.w323.e11 | >50 | >50 | >50 | >50 | >50 |
| CH0505.w323.e13 | >50 | >50 | >50 | >50 | >50 |
| CH0505.w323.e14 | >50 | >50 | >50 | >50 | >50 |
| CH0505.w323.e15 | >50 | >50 | >50 | >50 | >50 |
| CH0505.w323.e16 | >50 | >50 | >50 | >50 | >50 |
| CH0505.w323.e17 | >50 | >50 | >50 | >50 | >50 |
| CH0505.w323.e18 | >50 | >50 | >50 | >50 | >50 |

FIG. 45 cont.

|  | Neutralization IC50, µg/ml | | | | |
| --- | --- | --- | --- | --- | --- |
|  | CH239 | CH241 | CH235.7 | CH235.13 | CH235.10 |
| CH0505.C.w136.e.B33 | >50 | >50 | >50 | >50 | 32.79 |
| CH0505.C.w136.e.B38 | >50 | >50 | >50 | >50 | 32.68 |
| CH0505.C.w136.e.B2 | >50 | >50 | >50 | >50 | >50 |
| CH0505.C.w136.e.B3 | >50 | >50 | >50 | >50 | >50 |
| CH0505.C.w136.e.B4 | >50 | >50 | >50 | >50 | >50 |
| CH0505.C.w136.e.B5 | >50 | >50 | >50 | >50 | >50 |
| CH0505.C.w136.e.B12 | >50 | >50 | >50 | >50 | >50 |
| CH0505.C.w136.e.B27 | >50 | >50 | >50 | >50 | >50 |
| CH0505.C.w160.C2 | >50 | >50 | >50 | >50 | >50 |
| CH0505.C.w24.C9 | >50 | >50 | >50 | >50 | >50 |
| CH0505.C.w24.C10 | >50 | >50 | >50 | >50 | >50 |
| CH0505.C.w24.C11 | >50 | >50 | >50 | >50 | >50 |
| CH0505.C.w24.C12 | >50 | >50 | >50 | >50 | >50 |
| CH0505.C.w24.D2 | >50 | >50 | >50 | >50 | >50 |
| CH0505.C.w24.T3 | >50 | >50 | >50 | >50 | >50 |
| CH0505.w176.e11 | >50 | >50 | >50 | >50 | >50 |
| CH0505.w176.e12 | >50 | >50 | >50 | >50 | >50 |
| CH0505.w176.e13 | >50 | >50 | >50 | >50 | >50 |
| CH0505.w176.e1 | >50 | >50 | >50 | >50 | >50 |
| CH0505.w176.e2 | >50 | >50 | >50 | >50 | >50 |
| CH0505.w176.e10 | >50 | >50 | >50 | >50 | >50 |
| CH0505.w233.e1 | >50 | >50 | >50 | >50 | >50 |
| CH0505.w233.e3 | >50 | >50 | >50 | >50 | >50 |
| CH0505.w233.e4 | >50 | >50 | >50 | >50 | >50 |
| CH0505.w233.e7 | >50 | >50 | >50 | >50 | >50 |
| CH0505.w233.e17 | >50 | >50 | >50 | >50 | >50 |
| CH0505.w233.e18 | >50 | >50 | >50 | >50 | >50 |
| CH0505.w258.e4 | >50 | >50 | >50 | >50 | >50 |
| CH0505.w258.e1 | >50 | >50 | >50 | >50 | >50 |
| CH0505.w258.e7 | >50 | >50 | >50 | >50 | >50 |
| CH0505.w258.e6 | >50 | >50 | >50 | >50 | >50 |
| CH0505.w258.e5 | >50 | >50 | >50 | >50 | >50 |
| CH0505.w323.e1 | >50 | >50 | >50 | >50 | >50 |
| CH0505.w323.e11 | >50 | >50 | >50 | >50 | >50 |
| CH0505.w323.e13 | >50 | >50 | >50 | >50 | >50 |
| CH0505.w323.e14 | >50 | >50 | >50 | >50 | >50 |
| CH0505.w323.e15 | >50 | >50 | >50 | >50 | >50 |
| CH0505.w323.e16 | >50 | >50 | >50 | >50 | >50 |
| CH0505.w323.e17 | >50 | >50 | >50 | >50 | >50 |
| CH0505.w323.e18 | >50 | >50 | >50 | >50 | >50 |

FIG. 45 cont.

Neutralization IC50, µg/ml

| | CH235.9 | CH235.12 |
|---|---|---|
| CH0505.C.w136.e.B33 | 16.05 | 3.62 |
| CH0505.C.w136.e.B38 | 16.17 | 3.88 |
| CH0505.C.w136.e.B2 | 28.62 | 5.95 |
| CH0505.C.w136.e.B3 | >50 | >50 |
| CH0505.C.w136.e.B4 | >50 | >50 |
| CH0505.C.w136.e.B5 | >50 | >50 |
| CH0505.C.w136.e.B12 | >50 | >50 |
| CH0505.C.w136.e.B27 | >50 | >50 |
| CH0505.C.w160.C2 | >50 | >50 |
| CH0505.C.w24.C9 | >50 | >50 |
| CH0505.C.w24.C10 | >50 | >50 |
| CH0505.C.w24.C11 | >50 | >50 |
| CH0505.C.w24.C12 | >50 | >50 |
| CH0505.C.w24.D2 | >50 | >50 |
| CH0505.C.w24.T3 | >50 | >50 |
| CH0505.w176.e11 | >50 | 15.43 |
| CH0505.w176.e12 | >50 | 26.20 |
| CH0505.w176.e13 | >50 | 30.25 |
| CH0505.w176.e1 | >50 | 35.54 |
| CH0505.w176.e2 | >50 | 26.11 |
| CH0505.w176.e10 | >50 | >50 |
| CH0505.w233.e1 | >50 | >50 |
| CH0505.w233.e3 | >50 | >50 |
| CH0505.w233.e4 | >50 | >50 |
| CH0505.w233.e7 | >50 | >50 |
| CH0505.w233.e17 | >50 | >50 |
| CH0505.w233.e18 | >50 | >50 |
| CH0505.w258.e4 | >50 | >50 |
| CH0505.w258.e1 | >50 | >50 |
| CH0505.w258.e7 | >50 | >50 |
| CH0505.w258.e6 | >50 | >50 |
| CH0505.w258.e5 | >50 | >50 |
| CH0505.w323.e1 | >50 | >50 |
| CH0505.w323.e11 | >50 | >50 |
| CH0505.w323.e13 | >50 | >50 |
| CH0505.w323.e14 | >50 | >50 |
| CH0505.w323.e15 | >50 | >50 |
| CH0505.w323.e16 | >50 | >50 |
| CH0505.w323.e17 | >50 | >50 |
| CH0505.w323.e18 | >50 | >50 |

FIG. 45 cont.

| Virus ID | Virus Mutations | CH236 | CH235.7 | CH235.10 | CH235.11 | CH235.13 | CH235.12 |
|---|---|---|---|---|---|---|---|
| CH505.TF | - | 0.61 | 0.39 | 0.22 | 2.19 | 0.91 | 0.22 |
| CH505.TF.M5 | N279K | 0.26 | 0.16 | 0.17 | 0.31 | 0.18 | 0.02 |
| CH505.TF.M6 | V281A | 0.80 | 0.34 | 0.11 | 2.30 | 0.30 | 0.08 |
| CH505.TF.M10 | V281G | 1.75 | 0.18 | 0.19 | 1.52 | 0.14 | 0.02 |
| CH505.TF.M19 | V281D | 7.53 | 0.40 | >50 | >50 | 0.57 | 0.17 |
| CH505.TF.M11 | N279D+V281A | >50 | 0.50 | 0.21 | 15.35 | 0.25 | 0.08 |
| CH505.TF.M8 | N280S+V281A | >50 | >50 | >50 | 1.91 | 0.86 | 0.05 |
| CH505.TF.M21 | N280T+V281A | >50 | >50 | >50 | 10.16 | 16.72 | 0.13 |
| CH505.TF.M20 | N280S+V281G | >50 | >50 | >50 | 7.86 | 11.58 | 0.07 |
| CH505.TF.M7 | E275K+N279D+V281S | >50 | >50 | 0.61 | >50 | 2.12 | 0.13 |
| CH505.TF.M9 | E275K+N279D+V281G | >50 | >50 | 0.24 | 0.46 | 5.02 | 0.11 |

Neutralization IC50, µg/ml

FIG. 46

Neutralization IC50, µg/ml

| Virus ID | Virus Mutations | CH235.9 | CH235.9 N30T | CH235.9 D31T | CH235.9 G62Q | CH235.9 G65Q | G62Q+ G65Q | CH235.9 A103E |
|---|---|---|---|---|---|---|---|---|
| CH505.TF | - | 0.51 | 4.26 | 0.43 | 0.30 | 0.26 | 0.15 | 0.43 |
| CH505.TF.M5 | N279K | 0.19 | 0.90 | 0.11 | 0.12 | 0.14 | 0.12 | 0.03 |
| CH505.TF.M6 | V281A | 0.40 | 1.06 | 0.12 | 0.02 | 0.08 | 0.04 | 0.16 |
| CH505.TF.M10 | V281G | 0.24 | 0.83 | 0.07 | 0.02 | 0.09 | 0.08 | 0.07 |
| CH505.TF.M19 | V281D | 0.63 | 4.04 | 0.89 | 1.36 | 1.58 | 1.54 | 0.43 |
| CH505.TF.M11 | N279D+V281A | 0.39 | 1.25 | 0.12 | 0.02 | 0.14 | 0.13 | 0.24 |
| CH505.TF.M8 | N280S+V281A | 0.66 | 24.31 | 0.15 | 0.14 | 0.12 | 0.03 | 0.13 |
| CH505.TF.M21 | N280T+V281A | 0.74 | >50 | 0.23 | 0.15 | 0.25 | 0.27 | 0.19 |
| CH505.TF.M20 | N280S+V281G | 0.94 | 44.29 | 0.08 | 0.11 | 0.26 | 0.26 | 0.10 |
| CH505.TF.M7 | E275K+N279D+V281S | 0.77 | 44.21 | 0.38 | 0.37 | 0.49 | 0.38 | 0.19 |
| CH505.TF.M9 | E275K+N279D+V281G | 0.85 | 42.75 | 0.25 | 0.25 | 0.24 | 0.14 | 0.14 |

FIG. 46 cont.

| | Envelope ID | UCA | IA4 | IA3 | IA2 | CH240 | CH236 | CH239 | IA1 | CH235 Lineage | | | | | | | |
|---|---|---|---|---|---|---|---|---|---|---|---|---|---|---|---|---|---|
| | | | | | | | | | | CH235.7 | CH235.10 | CH235.11 | CH235.13 | CH235 | CH241 | CH235.9 | CH235.12 |
| | CH0505_CON D7gp120/293i | 0.00 | 0.00 | 5.09 | 4.77 | 5.26 | 6.89 | 8.74 | 6.89 | 9.64 | 7.23 | 0.26 | 6.23 | 9.73 | 13.27 | 8.67 | 8.39 |
| Week 4 | CH505w04.10D8gp120/293F | 0.26 | 0.00 | 6.55 | 6.25 | 6.47 | 8.10 | 12.11 | 8.53 | 10.31 | 2.64 | 1.17 | 7.63 | 10.88 | 14.01 | 8.78 | 9.10 |
| | CH505.w4.26D8gp120/293F | 0.00 | 0.35 | 4.65 | 4.41 | 4.66 | 6.71 | 8.39 | 6.77 | 9.78 | 6.40 | 0.24 | 5.67 | 9.85 | 13.34 | 8.09 | 7.69 |
| | 505.s.03.D8.gp120/293F | 0.00 | 0.00 | 5.13 | 5.03 | 5.33 | 6.90 | 8.82 | 7.39 | 10.68 | 7.20 | 0.36 | 6.32 | 10.26 | 13.88 | 8.44 | 8.23 |
| Week 14 | CH505w014.8D8gp120 | 0.00 | 0.16 | 3.13 | 2.68 | 3.19 | 5.93 | 6.98 | 5.49 | 8.17 | 4.48 | 0.00 | 4.62 | 9.07 | 12.73 | 5.08 | 6.31 |
| | CH505w014.2D8gp120/293F | 0.00 | 0.00 | 3.49 | 3.01 | 3.53 | 5.87 | 7.27 | 5.82 | 8.66 | 5.49 | 0.12 | 5.52 | 9.02 | 12.59 | 7.08 | 6.44 |
| | CH505w014.32D8gp120/293F | 0.00 | 0.00 | 4.72 | 4.51 | 4.58 | 6.47 | 8.39 | 6.63 | 9.68 | 6.33 | 0.26 | 5.57 | 10.62 | 13.47 | 7.86 | 7.63 |
| | CH505w014.3D8gp120 | 0.00 | 0.00 | 4.25 | 4.12 | 4.57 | 6.02 | 7.83 | 6.56 | 9.61 | 6.63 | 0.31 | 6.24 | 9.62 | 12.99 | 8.06 | 8.04 |
| | CH505.08.D11gp120/293F | 0.00 | 0.00 | 3.45 | 3.01 | 3.24 | 5.00 | 7.20 | 5.52 | 7.81 | 4.07 | 0.00 | 4.43 | 8.19 | 11.69 | 6.20 | 6.26 |
| | CH505w014.10D8gp120 | 0.00 | 0.00 | 0.00 | 0.00 | 1.92 | 4.24 | 9.83 | 5.57 | 8.95 | 0.85 | 0.26 | 5.89 | 9.43 | 13.26 | 8.74 | 8.00 |
| | CH505w014.21D8gp120/293F | 0.00 | 0.00 | 0.00 | 0.00 | 3.00 | 4.89 | 11.21 | 6.59 | 9.95 | 1.29 | 0.26 | 5.81 | 10.58 | 14.40 | 9.70 | 7.95 |
| Week 20 | CH505w020.15D8gp120 | 0.00 | 0.14 | 4.94 | 5.35 | 4.80 | 6.82 | 8.52 | 6.84 | 9.90 | 6.79 | 0.38 | 6.28 | 9.99 | 13.40 | 8.44 | 7.81 |
| | CH505w020.13D8gp120 | 0.08 | 0.00 | 3.87 | 3.56 | 3.49 | 5.68 | 7.15 | 5.85 | 8.93 | 6.30 | 0.30 | 5.54 | 8.63 | 12.19 | 7.29 | 7.31 |
| | CH505w020.22D8gp120/293F | 0.00 | 0.00 | 4.68 | 4.24 | 2.92 | 6.70 | 8.31 | 6.55 | 10.37 | 6.77 | 0.33 | 6.01 | 9.86 | 13.58 | 8.70 | 7.97 |
| | CH505w020.14D8gp120 | 0.00 | 0.00 | 2.72 | 1.22 | 3.83 | 6.72 | 9.01 | 6.52 | 9.35 | 5.63 | 0.11 | 6.14 | 9.91 | 13.08 | 8.15 | 8.33 |
| | CH505w020.8D8gp120/293F | 0.00 | 0.00 | 2.16 | 2.33 | 3.17 | 6.27 | 9.38 | 6.04 | 9.54 | 4.73 | 0.22 | 5.19 | 10.09 | 13.36 | 8.19 | 7.31 |
| | CH505w020.3D8gp120 | 0.00 | 0.00 | 2.00 | 0.76 | 2.32 | 5.80 | 8.18 | 5.32 | 8.34 | 3.80 | 0.10 | 4.93 | 9.61 | 12.83 | 6.91 | 6.61 |
| | CH505w020.30D8gp120 | 0.00 | 0.00 | 1.40 | 0.52 | 1.85 | 4.50 | 7.51 | 4.72 | 7.63 | 4.07 | 0.09 | 4.36 | 8.59 | 12.34 | 6.56 | 6.41 |
| | CH505w020.23D8gp120 | 0.00 | 0.00 | 2.57 | 1.09 | 2.85 | 4.95 | 8.93 | 5.89 | 8.65 | 4.12 | 0.09 | 5.03 | 9.84 | 13.45 | 8.07 | 6.73 |
| | CH505w020.11D8gp120 | 0.00 | 0.00 | 2.21 | 1.59 | 2.11 | 4.89 | 6.14 | 4.40 | 7.04 | 2.77 | 0.00 | 3.98 | 7.81 | 11.65 | 4.49 | 5.52 |
| | CH505w020.9D8gp120 | 0.00 | 0.00 | 1.67 | 0.52 | 2.20 | 5.60 | 7.81 | 5.02 | 7.88 | 2.86 | 0.07 | 3.99 | 8.95 | 12.06 | 6.33 | 6.28 |
| | CH505w020.4D8gp120/293F | 0.00 | 0.00 | 0.00 | 1.69 | 2.64 | 5.67 | 10.28 | 7.07 | 9.92 | 1.82 | 0.39 | 6.33 | 9.75 | 13.59 | 9.79 | 8.66 |
| | CH505w020.7D8gp120 | 0.00 | 0.00 | 0.00 | 0.00 | 3.06 | 5.38 | 10.27 | 6.45 | 9.47 | 1.36 | 0.27 | 6.63 | 9.63 | 13.32 | 9.59 | 8.85 |
| | CH505w020.26D8gp120 | 0.00 | 0.00 | 0.00 | 0.00 | 1.64 | 4.14 | 9.23 | 5.37 | 7.96 | 0.56 | 0.11 | 4.53 | 8.58 | 12.68 | 7.80 | 7.06 |

*FIG. 47*

| | | CH235 Lineage | | | | | | | | | | | | | | | |
|---|---|---|---|---|---|---|---|---|---|---|---|---|---|---|---|---|---|
| | Envelope ID | UCA | IA4 | IA3 | IA2 | CH240 | CH236 | CH239 | IA1 | CH235.7 | CH235.10 | CH235.11 | CH235.13 | CH235 | CH241 | CH235.9 | CH235.12 |
| Week 30 | CH505w030.6D8gp120/293F | 0.44 | 0.00 | 0.09 | 1.44 | 2.06 | 6.61 | 8.00 | 5.31 | 8.45 | 2.28 | 0.19 | 4.49 | 8.57 | 7.54 | 7.67 | 6.86 |
| | CH505w030.36D8gp120 | 0.56 | 0.00 | 1.03 | 0.55 | 1.21 | 4.82 | 5.51 | 3.43 | 7.60 | 3.34 | 0.28 | 4.53 | 7.01 | 5.74 | 7.02 | 7.21 |
| | CH505.w30.12D8gp140 | 0.32 | 0.00 | 0.00 | 0.10 | 0.00 | 0.54 | 2.04 | 1.02 | 2.26 | 0.08 | 0.14 | 0.97 | 5.05 | 7.32 | 2.11 | 1.80 |
| | CH505w030.20D8gp120/293F | 0.00 | 0.24 | 1.16 | 0.53 | 1.53 | 6.23 | 8.02 | 4.82 | 8.82 | 5.62 | 0.69 | 5.41 | 8.33 | 8.03 | 8.09 | 8.59 |
| | CH505w030.27D8gp120/293F | 0.08 | 0.00 | 0.46 | 4.14 | 3.68 | 6.94 | 7.84 | 6.28 | 9.09 | 5.63 | 1.33 | 5.99 | 8.85 | 7.94 | 8.02 | 8.48 |
| | CH505w030.10D8gp120 | 0.00 | 0.00 | 0.10 | 0.00 | 0.32 | 1.63 | 3.84 | 2.21 | 5.42 | 0.00 | 0.00 | 1.50 | 6.86 | 9.57 | 4.02 | 2.90 |
| | CH505w030.13D8gp120/293F | 0.00 | 0.00 | 0.11 | 0.00 | 0.34 | 1.78 | 4.03 | 2.67 | 6.05 | 0.00 | 0.00 | 1.82 | 7.18 | 10.04 | 4.63 | 3.28 |
| | CH505w030.25D8gp120 | 0.00 | 0.00 | 0.00 | 3.57 | 4.42 | 7.94 | 9.74 | 7.24 | 10.22 | 5.05 | 1.64 | 5.33 | 10.05 | 8.90 | 9.33 | 8.06 |
| | CH505w030.11D8gp120 | 0.00 | 0.00 | 0.00 | 3.40 | 3.32 | 4.98 | 5.83 | 5.86 | 9.15 | 5.91 | 0.10 | 4.61 | 9.11 | 6.52 | 8.63 | 7.00 |
| | CH505w030.18D8gp120 | 0.00 | 0.00 | 0.00 | 2.19 | 3.63 | 7.70 | 9.91 | 6.43 | 9.21 | 6.70 | 0.61 | 5.69 | 10.07 | 9.56 | 8.57 | 8.90 |
| | CH505w030.5D8gp120 | 0.00 | 0.00 | 0.00 | 1.57 | 5.73 | 8.82 | 11.24 | 8.48 | 11.14 | 3.50 | 1.90 | 6.73 | 10.54 | 9.42 | 10.19 | 9.56 |
| | CH505w030.23D8gp120 | 0.00 | 0.00 | 0.00 | 0.45 | 5.57 | 8.43 | 11.22 | 8.37 | 11.52 | 4.26 | 4.28 | 7.91 | 10.40 | 9.09 | 10.52 | 10.28 |
| | CH505w030.9D8gp120 | 0.00 | 0.00 | 0.00 | 0.97 | 1.37 | 5.55 | 6.37 | 3.86 | 8.73 | 3.77 | 0.59 | 4.34 | 7.79 | 6.56 | 7.78 | 7.33 |
| | CH505w030.15D8gp120 | 0.00 | 0.00 | 0.00 | 0.00 | 2.37 | 5.26 | 8.71 | 5.96 | 8.68 | 2.15 | 1.40 | 5.95 | 8.50 | 4.24 | 8.54 | 8.42 |
| | CH505w030.28D8gp120 | 0.00 | 0.00 | 0.00 | 0.00 | 0.31 | 1.51 | 3.57 | 2.38 | 5.01 | 0.00 | 0.00 | 1.84 | 6.72 | 9.62 | 4.16 | 3.18 |
| | CH505w030.17D8gp120 | 0.00 | 0.00 | 0.00 | 0.00 | 0.75 | 3.89 | 3.34 | 3.85 | 7.10 | 1.92 | 0.09 | 2.64 | 7.57 | 0.13 | 6.75 | 5.54 |
| | CH505.w30.12D8gp120 | 0.00 | 0.00 | 0.00 | 0.00 | 0.35 | 0.95 | 3.37 | 2.40 | 3.89 | 0.00 | 0.00 | 1.05 | 7.28 | 9.60 | 3.17 | 2.37 |
| | CH505w030.21D8gp120 | 0.00 | 0.00 | 0.00 | 0.00 | 0.00 | 0.00 | 0.00 | 0.00 | 0.00 | 0.00 | 0.12 | 0.00 | 0.00 | 3.27 | 0.00 | 1.01 |
| | CH505w030.19D8gp120/293F | 0.00 | 0.00 | 0.00 | 0.00 | 0.00 | 0.00 | 0.00 | 0.00 | 0.00 | 0.00 | 0.11 | 0.00 | 0.00 | 1.47 | 0.00 | 0.00 |
| Week 53 | CH505w053.16D8gp120 | 0.00 | 0.00 | 0.00 | 0.00 | 0.00 | 0.34 | 3.70 | 0.47 | 3.51 | 1.62 | 0.12 | 1.99 | 4.63 | 7.19 | 5.76 | 4.75 |
| | CH505w053.25D8gp120 | 0.00 | 0.00 | 0.00 | 0.00 | 0.00 | 0.00 | 0.36 | 0.25 | 3.33 | 1.44 | 0.00 | 0.74 | 3.81 | 0.00 | 6.23 | 4.67 |
| | CH505w053.3D8gp120 | 0.00 | 0.00 | 0.00 | 0.00 | 0.00 | 0.00 | 0.89 | 0.21 | 3.41 | 1.63 | 0.08 | 1.23 | 4.99 | 0.00 | 7.22 | 4.26 |
| | CH505w053.13D8gp120/293F | 0.00 | 0.00 | 0.00 | 0.00 | 0.00 | 0.00 | 0.15 | 0.09 | 2.14 | 2.07 | 0.11 | 2.30 | 2.18 | 0.00 | 6.53 | 5.79 |
| | CH505w053.31D8gp120/293F | 0.00 | 0.07 | 0.00 | 0.00 | 0.00 | 0.00 | 0.00 | 0.00 | 0.00 | 3.25 | 0.11 | 0.35 | 1.11 | 1.41 | 5.23 | 6.36 |
| | CH505.w53.19gp D8gp120 | 0.00 | 0.00 | 0.00 | 0.00 | 0.00 | 0.00 | 0.00 | 0.00 | 0.00 | 1.08 | 0.00 | 0.08 | 0.64 | 0.52 | 3.05 | 3.95 |
| | CH505w053.6D8gp120 | 0.00 | 0.00 | 0.00 | 0.00 | 0.00 | 0.00 | 0.00 | 0.00 | 0.00 | 0.54 | 0.00 | 0.09 | 0.13 | 0.00 | 4.89 | 4.76 |
| | CH505w053.29D8gp120 | 0.00 | 0.00 | 0.00 | 0.00 | 0.00 | 0.00 | 0.00 | 0.00 | 4.84 | 0.00 | 0.00 | 1.04 | 0.00 | 0.00 | 0.25 | 3.44 |

FIG. 47 cont.

CH235 Lineage

| Envelope ID | UCA | A4 | A3 | A2 | CH240 | CH236 | CH239 | A1 | CH235.7 | CH235.10 | CH235.11 | CH235.13 | CH235 | CH241 | CH235.9 | CH235.12 |
|---|---|---|---|---|---|---|---|---|---|---|---|---|---|---|---|---|
| Week 78 | | | | | | | | | | | | | | | | |
| CH0505.w78.env5.D11gp120/293F | 0.00 | 0.00 | 0.00 | 0.00 | 0.00 | 0.00 | 0.00 | 0.00 | 0.07 | 0.09 | 0.23 | 0.46 | 0.00 | 0.00 | 4.69 | 6.11 |
| CH505w078.33D8gp120/293F | 0.18 | 0.00 | 0.00 | 0.00 | 0.00 | 0.00 | 0.00 | 0.00 | 0.00 | 0.00 | 0.71 | 0.00 | 0.00 | 0.00 | 0.00 | 0.00 |
| CH505w078.1D8gp120/293F | 0.00 | 0.00 | 0.00 | 0.00 | 0.00 | 0.00 | 0.00 | 0.00 | 0.00 | 0.00 | 0.10 | 0.00 | 0.00 | 0.00 | 0.00 | 0.00 |
| CH505w078.9D8gp120 | 0.00 | 0.00 | 0.00 | 0.00 | 0.00 | 0.00 | 0.00 | 0.00 | 0.00 | 0.00 | 0.13 | 0.00 | 0.00 | 0.00 | 0.09 | 0.09 |
| CH505w078.6D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w078.38D8gp120 | 0.11 | 0.00 | 0.00 | 0.00 | 0.00 | 0.00 | 0.00 | 0.00 | 0.00 | 0.00 | 0.00 | 0.00 | 0.00 | 0.00 | 0.00 | 3.01 |
| CH505w078.15D8gp120/293F | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w078.10D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w078.17D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH0505.w78.7D8gp120/293F | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH0505.w78.env4.D11gp120/293i | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505.w78.25D8gp120 | 0.08 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| Week 100 | | | | | | | | | | | | | | | | |
| CH505w100.C7D8gp120/293F | 0.73 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w100.A13D8gp120 | 0.00 | 0.00 | 0.00 | 0.00 | 0.00 | 0.00 | 0.00 | 0.00 | 0.00 | 0.00 | 0.00 | 0.00 | 0.28 | 0.00 | 0.00 | 0.13 |
| CH505w100.B6D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.25 |
| CH505w100.B7D8gp120/293F | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.13 |
| CH505_w100V115b7.D7gp120/293F | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w100.A10D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 505_w100.A4.D8.gp120/293F | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505_w100V115A10.D7gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w100.A12D8gp120 | 0.08 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w100.A3D8gp120/293F | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w100.A6D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w100.B4D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505_w100V115A13.D7gp120/293F | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505_w100V115A6.D11gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505_w100V115B4.D11gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CH505w100.B2D8gp120/293F | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |

*FIG. 47 cont.*

| | Envelope ID | UCA | IA4 | IA3 | IA2 | CH240 | CH236 | CH239 | IA1 | CH235.7 | CH235.10 | CH235.11 | CH235.13 | CH235 | CH241 | CH235.9 | CH235.12 |
|---|---|---|---|---|---|---|---|---|---|---|---|---|---|---|---|---|---|
| Week 136 | CH505w136.B18D8gp120 | 0.00 | 0.00 | 0.00 | 0.00 | 0.25 | 3.51 | 0.74 | 2.36 | 3.53 | 5.54 | 0.11 | 1.76 | 7.53 | 0.89 | 5.76 | 8.31 |
| | CH505w136.B2D8gp120/293F | 0.00 | 0.00 | 0.00 | 0.00 | 0.00 | 0.00 | 0.00 | 0.00 | 0.07 | 0.64 | 0.00 | 0.00 | 0.74 | 0.00 | 2.38 | 2.58 |
| | CH505_w137V201B12.D11gp120 | 0.00 | 0.00 | 0.00 | 0.00 | 0.00 | 0.00 | 0.00 | 0.00 | 0.00 | 0.00 | 0.28 | 0.00 | 0.00 | 0.00 | 0.00 | 0.00 |
| | CH505w136.B3D8gp120/293F | 0.00 | 0.00 | 0.00 | 0.00 | 0.00 | 0.00 | 0.00 | 0.00 | 0.00 | 0.00 | 0.72 | 0.00 | 0.00 | 0.00 | 0.00 | 0.00 |
| | CH505w136.B5D8gp120 | 0.00 | 0.00 | 0.00 | 0.00 | 0.00 | 0.00 | 0.00 | 0.00 | 0.00 | 0.00 | 0.52 | 0.00 | 0.00 | 0.00 | 0.00 | 0.00 |
| | CH505w136.B8D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.34 | 0.11 |
| | CH505w136.B36D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.07 |
| | CH505w136.B20D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505_w137V209C12.D11gp120 | 0.08 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w136.B27D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w136.B29D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w136.B4D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w136.B12D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w136.B10D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| Week 160 | CH505w160.T4D8gp120/293F | 0.00 | 0.00 | 0.00 | 0.00 | 0.00 | 0.00 | 0.00 | 0.10 | 0.13 | 0.32 | 0.00 | 0.46 | 0.98 | 0.34 | 0.82 | 3.32 |
| | CH505w160.C2D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.31 |
| | CH505w160.C4D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.16 |
| | CH505w160.C12D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w160.C14D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.09 |
| | CH505w160.A1D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w160.C11D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w160.D1D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w160.D5D8gp120/293F | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| | CH505w160.T2D8gp120 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |

CH235 Lineage

*FIG. 47 cont.*

| | Envelope ID | UCA | IA4 | IA3 | IA2 | CH240 | CH236 | CH239 | IA1 | CH235.7 | CH235.10 | CH235.11 | CH235.13 | CH235 | CH241 | CH235.9 | CH235.12 |
|---|---|---|---|---|---|---|---|---|---|---|---|---|---|---|---|---|---|
| | | | | | | | | | | CH235 Lineage | | | | | | | |
| CH505 TF Mutants Loop D | CH505.M5D8gp120293F | 0.24 | 1.36 | 7.01 | 6.95 | 7.39 | 7.27 | 12.94 | 9.18 | 10.58 | 2.62 | 1.26 | 6.53 | 11.36 | 14.51 | 9.26 | 8.20 |
| | CH505.M10D8gp120 | 0.00 | 0.12 | 0.08 | 0.43 | 3.13 | 6.07 | 11.17 | 7.08 | 10.55 | 1.06 | 1.06 | 6.38 | 10.63 | 14.40 | 10.17 | 7.63 |
| | CH505.M6D8gp120/293F | 0.00 | 0.00 | 2.96 | 1.22 | 3.52 | 6.31 | 8.97 | 6.10 | 9.21 | 5.67 | 0.09 | 6.07 | 9.46 | 13.17 | 8.11 | 8.21 |
| | CH505.M11D8gp120/293F | 0.00 | 0.00 | 0.00 | 0.00 | 0.51 | 1.43 | 1.35 | 2.85 | 6.75 | 5.05 | 0.11 | 5.35 | 7.59 | 9.68 | 8.26 | 7.71 |
| | CH505.M19D8gp120 | 0.00 | 0.00 | 0.11 | 0.00 | 0.65 | 1.54 | 4.34 | 2.78 | 6.61 | 0.00 | 0.09 | 2.89 | 7.13 | 10.44 | 5.95 | 4.61 |
| | CH505.M8D8gp120 | 0.00 | 0.00 | 0.00 | 0.00 | 0.00 | 0.00 | 0.00 | 0.00 | 0.00 | 0.00 | 0.29 | 0.00 | 0.00 | 2.18 | 4.36 | 1.14 |
| | CH505.M20D8gp120/293F | 0.00 | 0.00 | 0.00 | 0.00 | 0.00 | 0.00 | 0.00 | 0.00 | 0.00 | 0.00 | 0.28 | 0.00 | 0.00 | 2.15 | 1.04 | 0.00 |
| | CH505.M21D8gp120/293F | 0.00 | 0.00 | 0.00 | 0.00 | 0.00 | 0.00 | 0.00 | 0.00 | 0.00 | 0.07 | 0.10 | 0.00 | 0.00 | 4.82 | 1.13 | 0.19 |
| | CH505.M9D8gp120/293F | 0.00 | 0.00 | 0.00 | 0.00 | 0.00 | 0.00 | 0.00 | 0.00 | 0.00 | 0.07 | 0.23 | 0.00 | 0.00 | 0.00 | 1.31 | 0.38 |
| | CH505.M7D8gp120/293F | 0.00 | 0.00 | 0.00 | 0.00 | 0.00 | 0.00 | 0.00 | 0.00 | 0.00 | 0.09 | 0.00 | 0.00 | 0.00 | 0.00 | 0.80 | 0.69 |

FIG. 47 cont.

| | Envelope ID | UCA | IA8 | IA7 | IA6 | IA4 | CH187 | CH188 | CH186 | CH200 | 1AH92U | IA3 | IA2 | IA1 | CH103 | CH104 |
|---|---|---|---|---|---|---|---|---|---|---|---|---|---|---|---|---|
| | CH0505_CON D7gp120/293i | 4.30 | 7.21 | 10.96 | 10.86 | 11.33 | 11.79 | 11.60 | 13.00 | 9.42 | 11.19 | 11.27 | 11.97 | 11.26 | 12.45 | 10.15 |
| Week 4 | CH505w004.10D8gp120/293F | 0.00 | 0.45 | 2.26 | 2.89 | 2.84 | 7.92 | 7.63 | 11.59 | 8.50 | 6.03 | 6.17 | 6.85 | 6.17 | 9.21 | 8.13 |
| | CH505.w4.26D8gp120 /293F | 3.20 | 5.48 | 9.05 | 9.04 | 9.53 | 11.86 | 11.88 | 13.47 | 9.51 | 10.20 | 10.05 | 10.63 | 10.28 | 12.35 | 11.08 |
| | 505.s.03.D8.gp120/293F | 3.53 | 5.45 | 9.21 | 9.07 | 10.14 | 12.58 | 12.35 | 14.05 | 10.14 | 9.42 | 9.97 | 10.83 | 10.38 | 12.63 | 10.41 |
| Week 14 | CH505w014.8D8gp120 | 0.00 | 0.95 | 0.62 | 2.43 | 2.62 | 8.89 | 9.28 | 12.29 | 2.46 | 7.26 | 1.73 | 3.60 | 3.38 | 11.22 | 3.86 |
| | CH505w014.2D8gp120/293F | 0.83 | 3.17 | 7.18 | 6.90 | 8.47 | 10.69 | 10.53 | 12.43 | 9.01 | 8.98 | 9.31 | 9.69 | 9.14 | 10.88 | 9.49 |
| | CH505w014.32D8gp120/293F | 1.61 | 4.25 | 7.88 | 7.82 | 8.46 | 11.99 | 11.89 | 13.50 | 10.00 | 9.14 | 9.58 | 10.21 | 9.53 | 11.93 | 10.91 |
| | CH505w014.3D8gp120 | 1.01 | 4.38 | 7.65 | 7.62 | 9.20 | 11.86 | 11.76 | 13.43 | 9.97 | 8.93 | 9.82 | 10.57 | 9.62 | 11.89 | 10.63 |
| | CH505.03.D11gp120/293F | 2.25 | 4.52 | 7.84 | 8.02 | 8.51 | 9.47 | 9.14 | 11.49 | 7.30 | 8.24 | 8.56 | 9.38 | 8.70 | 10.26 | 8.25 |
| | CH505w014.10D8gp120 | 0.31 | 2.22 | 5.14 | 6.33 | 7.07 | 12.04 | 12.09 | 13.78 | 9.44 | 9.44 | 9.32 | 9.92 | 9.38 | 11.92 | 10.74 |
| | CH505w014.21D8gp120/293F | 0.39 | 2.82 | 6.25 | 7.78 | 8.05 | 12.48 | 12.40 | 14.16 | 10.14 | 9.83 | 9.28 | 10.21 | 9.68 | 13.06 | 11.36 |
| Week 20 | CH505w020.15D8gp120 | 1.57 | 4.21 | 8.19 | 7.78 | 9.06 | 11.85 | 11.52 | 13.26 | 10.07 | 7.20 | 9.49 | 10.45 | 9.89 | 11.76 | 10.54 |
| | CH505w020.13D8gp120 | 0.83 | 2.41 | 6.37 | 6.05 | 7.28 | 9.25 | 8.96 | 11.14 | 8.27 | 8.22 | 8.45 | 9.02 | 8.64 | 10.34 | 8.31 |
| | CH505w020.22D8gp120/293F | 1.24 | 3.97 | 8.28 | 8.37 | 8.80 | 11.00 | 11.21 | 12.46 | 10.18 | 9.42 | 10.21 | 10.57 | 10.14 | 11.49 | 10.70 |
| | CH505w020.14D8gp120 | 0.33 | 3.40 | 7.23 | 7.94 | 8.64 | 11.17 | 10.85 | 12.83 | 8.68 | 10.41 | 10.50 | 10.98 | 10.27 | 12.55 | 10.39 |
| | CH505w020.8D8gp120/293F | 0.44 | 2.56 | 5.90 | 6.69 | 7.37 | 11.22 | 11.36 | 13.00 | 9.04 | 10.08 | 9.86 | 10.47 | 9.88 | 12.38 | 10.52 |
| | CH505w020.3D8gp120 | 0.77 | 2.57 | 5.88 | 5.98 | 7.05 | 11.21 | 11.44 | 13.36 | 7.12 | 10.18 | 8.37 | 9.28 | 8.86 | 12.43 | 9.80 |
| | CH505w020.30D8gp120 | 0.79 | 4.18 | 7.31 | 7.89 | 8.45 | 11.21 | 11.44 | 12.68 | 8.24 | 10.31 | 9.66 | 10.46 | 9.84 | 11.71 | 10.08 |
| | CH505w020.23D8gp120 | 0.94 | 3.57 | 7.17 | 7.89 | 8.58 | 12.39 | 12.43 | 14.02 | 9.59 | 9.89 | 10.14 | 10.65 | 9.85 | 12.83 | 11.56 |
| | CH505w020.11D8gp120 | 0.00 | 0.90 | 0.10 | 0.78 | 0.75 | 5.81 | 4.97 | 10.29 | 2.09 | 5.49 | 0.97 | 2.58 | 1.83 | 9.59 | 2.18 |
| | CH505w020.9D8gp120 | 0.38 | 2.84 | 4.89 | 6.79 | 7.41 | 11.01 | 10.90 | 12.66 | 6.89 | 9.74 | 8.68 | 9.65 | 8.99 | 11.85 | 8.86 |
| | CH505w020.4D8gp120/293F | 0.93 | 3.63 | 8.18 | 8.66 | 9.41 | 12.13 | 12.26 | 13.64 | 10.34 | 10.78 | 11.18 | 11.61 | 11.34 | 12.50 | 11.61 |
| | CH505w020.7D8gp120 | 0.57 | 2.74 | 7.63 | 8.09 | 8.75 | 11.51 | 11.60 | 12.94 | 9.76 | 10.56 | 10.83 | 11.27 | 10.85 | 12.46 | 11.11 |
| | CH505w020.26D8gp120 | 0.00 | 0.72 | 2.73 | 3.97 | 5.10 | 10.40 | 10.34 | 12.41 | 7.61 | 8.21 | 8.18 | 8.99 | 8.92 | 11.27 | 8.67 |

*FIG. 47 cont.*

| | Envelope ID | CH103 Lineage | | | | | | |
|---|---|---|---|---|---|---|---|---|
| | | CH105 | CH106 | CH243 | CH244 | CH245 | CH247 | CH248 |
| | CH0505_CON D7gp120/293i | 10.62 | 11.88 | 12.52 | 12.35 | 13.23 | 12.87 | 12.91 |
| Week 4 | CH505w004.10D8gp120/293F | 8.33 | 8.06 | 10.08 | 9.96 | 10.25 | 11.11 | 10.76 |
| | CH505.w4.26D8gp120 /293F | 10.45 | 11.05 | 13.00 | 12.79 | 13.38 | 12.82 | 13.05 |
| | 505.s.03.D8.gp120/293F | 11.18 | 11.28 | 13.40 | 12.96 | 13.86 | 13.08 | 13.34 |
| Week 14 | CH505w014.8D8gp120 | 6.01 | 7.94 | 10.86 | 10.07 | 10.64 | 12.59 | 11.68 |
| | CH505w014.2D8gp120/293F | 9.62 | 9.62 | 11.86 | 11.41 | 11.97 | 12.48 | 12.04 |
| | CH505w014.32D8gp120/293F | 10.70 | 10.54 | 12.94 | 12.92 | 13.42 | 12.65 | 13.05 |
| | CH505w014.3D8gp120 | 10.81 | 10.64 | 12.81 | 12.76 | 12.72 | 13.00 | 13.32 |
| | CH505.08.D11gp120/293F | 8.30 | 9.20 | 10.80 | 10.19 | 10.66 | 11.06 | 10.92 |
| | CH505w014.10D8gp120 | 10.81 | 10.37 | 13.24 | 12.98 | 12.86 | 13.12 | 12.85 |
| | CH505w014.21D8gp120/293F | 11.40 | 11.09 | 13.48 | 13.40 | 13.65 | 13.41 | 13.57 |
| Week 20 | CH505w020.15D8gp120 | 10.84 | 10.46 | 12.82 | 12.42 | 12.80 | 13.27 | 12.55 |
| | CH505w020.13D8gp120 | 8.22 | 9.44 | 10.36 | 9.82 | 9.71 | 10.68 | 10.78 |
| | CH505w020.22D8gp120/293F | 10.45 | 10.68 | 12.46 | 12.48 | 12.68 | 13.06 | 12.68 |
| | CH505w020.14D8gp120 | 10.42 | 11.23 | 12.61 | 12.32 | 12.11 | 12.08 | 12.48 |
| | CH505w020.8D8gp120/293F | 10.55 | 10.96 | 12.97 | 12.73 | 12.68 | 12.60 | 12.89 |
| | CH505w020.3D8gp120 | 10.11 | 10.25 | 12.73 | 12.76 | 12.68 | 12.69 | 12.27 |
| | CH505w020.30D8gp120 | 10.26 | 10.80 | 12.67 | 12.53 | 12.28 | 12.38 | 12.71 |
| | CH505w020.23D8gp120 | 11.20 | 11.30 | 13.53 | 13.17 | 12.97 | 13.24 | 13.24 |
| | CH505w020.11D8gp120 | 3.61 | 5.37 | 7.38 | 7.08 | 8.43 | 10.44 | 9.22 |
| | CH505w020.9D8gp120 | 9.31 | 10.02 | 12.22 | 11.92 | 11.43 | 12.54 | 12.30 |
| | CH505w020.4D8gp120/293F | 11.14 | 11.49 | 13.28 | 13.39 | 13.66 | 13.48 | 13.30 |
| | CH505w020.7D8gp120 | 10.62 | 11.29 | 12.76 | 12.41 | 12.40 | 12.35 | 12.88 |
| | CH505w020.26D8gp120 | 9.01 | 9.56 | 11.61 | 11.45 | 11.37 | 12.22 | 12.01 |

*FIG. 47cont.*

CH103 Lineage

| | Envelope ID | UCA | IA8 | IA7 | IA6 | IA4 | CH187 | CH188 | CH186 | CH200 | 1AH92U | IA3 | IA2 | IA1 | CH103 | CH104 |
|---|---|---|---|---|---|---|---|---|---|---|---|---|---|---|---|---|
| Week 30 | CH505w030.6D8gp120/293F | 0.00 | 0.00 | 0.00 | 0.00 | 0.00 | 1.71 | 1.85 | 10.03 | 6.28 | 4.58 | 3.16 | 5.38 | 4.51 | 8.05 | 6.13 |
| | CH505w030.36D8gp120 | 0.00 | 0.00 | 0.00 | 0.00 | 0.00 | 4.72 | 4.80 | 12.14 | 9.03 | 6.39 | 5.80 | 7.27 | 6.69 | 9.08 | 7.83 |
| | CH505.w30.12D8gp140 | 0.00 | 0.00 | 0.00 | 0.21 | 0.29 | 7.20 | 7.32 | 7.62 | 5.72 | 6.22 | 3.88 | 7.28 | 7.05 | 10.66 | 8.20 |
| | CH505w030.20D8gp120/293F | 0.00 | 0.00 | 0.00 | 0.00 | 0.00 | 1.16 | 1.19 | 8.59 | 2.84 | 4.89 | 4.62 | 6.26 | 5.65 | 9.48 | 7.49 |
| | CH505w030.27D8gp120/293F | 0.00 | 0.00 | 0.00 | 0.00 | 0.00 | 7.13 | 7.07 | 12.75 | 8.96 | 6.52 | 5.98 | 7.90 | 7.31 | 9.12 | 8.17 |
| | CH505w030.10D8gp120 | 0.18 | 1.26 | 3.24 | 5.06 | 5.77 | 12.02 | 12.32 | 12.48 | 7.56 | 9.03 | 7.79 | 10.98 | 10.10 | 12.50 | 10.34 |
| | CH505w030.13D8gp120/293F | 0.25 | 1.96 | 4.72 | 6.48 | 7.39 | 13.37 | 13.60 | 13.30 | 9.19 | 10.03 | 8.65 | 11.44 | 10.47 | 12.89 | 11.29 |
| | CH505w030.25D8gp120 | 0.00 | 0.00 | 0.36 | 0.49 | 0.36 | 11.46 | 11.68 | 14.73 | 9.99 | 8.75 | 8.78 | 9.93 | 9.08 | 12.50 | 10.33 |
| | CH505w030.11D8gp120 | 0.00 | 0.00 | 0.73 | 0.48 | 0.49 | 10.21 | 10.14 | 13.59 | 10.92 | 7.02 | 6.82 | 9.12 | 8.40 | 10.92 | 9.48 |
| | CH505w030.18D8gp120 | 0.00 | 0.00 | 0.00 | 0.00 | 0.00 | 4.27 | 4.50 | 10.44 | 8.76 | 8.59 | 8.13 | 9.42 | 9.92 | 13.05 | 10.91 |
| | CH505w030.5D8gp120 | 0.00 | 0.00 | 0.00 | 0.00 | 0.00 | 10.12 | 10.26 | 14.05 | 8.91 | 7.40 | 6.70 | 8.09 | 7.75 | 11.43 | 9.44 |
| | CH505w030.23D8gp120 | 0.00 | 0.00 | 0.00 | 0.00 | 0.00 | 10.43 | 10.47 | 13.87 | 9.53 | 7.75 | 7.83 | 8.86 | 8.42 | 11.08 | 9.58 |
| | CH505w030.9D8gp120 | 0.00 | 0.00 | 0.00 | 0.00 | 0.00 | 8.32 | 8.51 | 13.64 | 9.74 | 7.41 | 7.11 | 8.59 | 7.79 | 10.23 | 8.94 |
| | CH505w030.15D8gp120 | 0.00 | 0.00 | 0.00 | 0.00 | 0.00 | 3.92 | 3.78 | 10.84 | 8.12 | 6.91 | 7.84 | 8.37 | 8.04 | 10.06 | 9.67 |
| | CH505w030.28D8gp120 | 0.00 | 1.59 | 3.52 | 6.34 | 6.47 | 12.33 | 12.50 | 12.61 | 7.51 | 9.64 | 7.73 | 11.07 | 10.07 | 12.78 | 10.68 |
| | CH505w030.17D8gp120 | 0.00 | 0.00 | 0.00 | 0.00 | 0.00 | 6.69 | 7.21 | 13.59 | 6.10 | 6.57 | 4.11 | 7.00 | 5.79 | 9.92 | 6.99 |
| | CH505.w30.12D8gp120 | 0.00 | 0.36 | 0.98 | 1.22 | 1.91 | 11.70 | 11.64 | 12.02 | 7.29 | 9.35 | 7.58 | 11.64 | 10.62 | 13.25 | 11.62 |
| | CH505w030.21D8gp120 | 0.00 | 0.00 | 0.00 | 0.00 | 0.00 | 0.00 | 0.00 | 0.00 | 3.17 | 9.50 | 11.00 | 11.46 | 11.78 | 12.25 | 11.30 |
| | CH505w030.19D8gp120/293F | 0.00 | 0.00 | 0.00 | 0.00 | 0.00 | 0.00 | 0.00 | 0.00 | 0.26 | 9.46 | 6.38 | 8.24 | 8.23 | 12.85 | 8.88 |
| Week 53 | CH505w053.16D8gp120 | 0.00 | 0.00 | 0.00 | 0.00 | 0.22 | 2.00 | 2.10 | 7.55 | 5.12 | 8.03 | 7.76 | 9.26 | 8.79 | 11.62 | 9.94 |
| | CH505w053.25D8gp120 | 0.00 | 0.00 | 0.00 | 0.00 | 0.00 | 0.85 | 1.17 | 8.55 | 7.97 | 8.50 | 8.67 | 10.23 | 10.00 | 11.64 | 10.61 |
| | CH505w053.3D8gp120 | 0.00 | 0.00 | 0.00 | 0.00 | 0.00 | 1.04 | 1.49 | 9.17 | 6.13 | 7.92 | 8.31 | 9.45 | 9.21 | 11.21 | 10.41 |
| | CH505w053.13D8gp120/293F | 0.00 | 0.00 | 0.00 | 0.00 | 0.00 | 0.79 | 1.05 | 8.34 | 7.14 | 8.28 | 9.20 | 10.47 | 9.93 | 11.22 | 9.99 |
| | CH505w053.31D8gp120/293F | 0.00 | 0.00 | 0.00 | 0.00 | 0.00 | 0.00 | 0.00 | 1.13 | 5.80 | 11.26 | 13.01 | 13.34 | 13.36 | 13.63 | 13.73 |
| | CH505.w53.19gp D8gp120 | 0.00 | 0.00 | 0.00 | 0.00 | 0.00 | 0.00 | 0.00 | 0.42 | 3.36 | 11.78 | 13.22 | 12.61 | 13.56 | 13.49 | 13.82 |
| | CH505w053.6D8gp120 | 0.00 | 0.00 | 0.00 | 0.00 | 0.00 | 0.00 | 0.00 | 0.00 | 1.27 | 9.90 | 11.17 | 11.95 | 11.37 | 12.66 | 12.05 |
| | CH505w053.29D8gp120 | 0.00 | 0.00 | 0.00 | 0.00 | 0.00 | 0.46 | 0.82 | 7.64 | 2.42 | 7.56 | 7.72 | 9.16 | 8.79 | 10.17 | 9.80 |

*FIG. 47 cont.*

| | Envelope ID | CH105 | CH106 | CH243 | CH244 | CH245 | CH247 | CH248 |
|---|---|---|---|---|---|---|---|---|
| | | | | | CH103 Lineage | | | |
| Week 30 | CH505w030.6D8gp120/293F | 6.47 | 6.56 | 8.07 | 7.95 | 9.25 | 10.28 | 8.88 |
| | CH505w030.36D8gp120 | 7.46 | 8.47 | 10.01 | 9.61 | 12.14 | 11.98 | 11.14 |
| | CH505.w30.12D8gp140 | 7.63 | 8.13 | 10.29 | 9.96 | 9.48 | 11.85 | 9.71 |
| | CH505w030.20D8gp120/293F | 7.10 | 7.25 | 9.03 | 10.06 | 9.90 | 11.61 | 9.97 |
| | CH505w030.27D8gp120/293F | 7.88 | 8.17 | 10.10 | 9.49 | 11.87 | 11.61 | 10.96 |
| | CH505w030.10D8gp120 | 9.26 | 11.14 | 12.62 | 12.40 | 12.77 | 13.78 | 12.69 |
| | CH505w030.13D8gp120/293F | 10.46 | 11.88 | 13.79 | 13.74 | 13.97 | 14.50 | 13.48 |
| | CH505w030.25D8gp120 | 9.96 | 10.19 | 12.12 | 11.82 | 13.44 | 12.58 | 12.82 |
| | CH505w030.11D8gp120 | 8.97 | 9.41 | 11.56 | 11.41 | 13.73 | 12.68 | 11.85 |
| | CH505w030.18D8gp120 | 11.14 | 10.54 | 13.24 | 13.55 | 14.17 | 13.07 | 12.96 |
| | CH505w030.5D8gp120 | 8.98 | 9.41 | 11.45 | 11.09 | 13.15 | 12.93 | 12.40 |
| | CH505w030.23D8gp120 | 9.18 | 9.98 | 11.69 | 11.44 | 12.97 | 12.36 | 12.26 |
| | CH505w030.9D8gp120 | 8.67 | 9.61 | 11.06 | 8.65 | 13.08 | 12.77 | 11.97 |
| | CH505w030.15D8gp120 | 9.27 | 9.33 | 11.17 | 10.60 | 12.57 | 11.18 | 11.98 |
| | CH505w030.28D8gp120 | 9.13 | 11.71 | 12.65 | 12.46 | 12.42 | 13.77 | 12.74 |
| | CH505w030.17D8gp120 | 6.73 | 8.20 | 9.93 | 9.56 | 12.83 | 13.03 | 11.50 |
| | CH505.w30.12D8gp120 | 10.68 | 11.76 | 13.89 | 13.68 | 13.80 | 13.89 | 13.22 |
| | CH505w030.21D8gp120 | 10.55 | 10.91 | 12.86 | 12.95 | 12.50 | 11.55 | 13.33 |
| | CH505w030.19D8gp120/293F | 9.46 | 7.39 | 12.61 | 13.20 | 11.64 | 12.72 | 13.55 |
| Week 53 | CH505w053.16D8gp120 | 9.00 | 9.78 | 11.64 | 11.51 | 13.45 | 12.38 | 12.94 |
| | CH505w053.25D8gp120 | 10.00 | 10.88 | 11.76 | 11.82 | 13.14 | 12.17 | 12.61 |
| | CH505w053.3D8gp120 | 9.41 | 10.09 | 11.74 | 11.52 | 13.30 | 11.93 | 12.78 |
| | CH505w053.13D8gp120/293F | 9.37 | 10.17 | 11.45 | 11.80 | 12.34 | 11.53 | 12.19 |
| | CH505w053.31D8gp120/293F | 13.52 | 13.35 | 14.44 | 15.25 | 15.04 | 14.15 | 15.19 |
| | CH505.w53.19gp D8gp120 | 13.75 | 13.24 | 14.43 | 15.75 | 15.37 | 14.20 | 14.82 |
| | CH505w053.6D8gp120 | 11.74 | 10.93 | 13.06 | 14.13 | 13.65 | 13.02 | 13.46 |
| | CH505w053.29D8gp120 | 8.51 | 9.70 | 10.73 | 10.38 | 11.51 | 11.14 | 11.51 |

*FIG. 47 cont.*

| | Envelope ID | UCA | IA8 | IA7 | IA6 | IA4 | CH187 | CH188 | CH186 | CH200 | 1AH92U | IA3 | IA2 | IA1 | CH103 | CH104 |
|---|---|---|---|---|---|---|---|---|---|---|---|---|---|---|---|---|
| Week 78 | CH0505.w78.env5.D11gp120/293F | 0.00 | 0.00 | 0.00 | 0.00 | 0.00 | 0.00 | 0.00 | 4.95 | 2.91 | 4.33 | 3.39 | 6.57 | 5.64 | 10.24 | 7.67 |
| | CH505w078.33D8gp120/293F | 0.00 | 0.00 | 0.00 | 0.00 | 0.00 | 0.00 | 0.00 | 0.00 | 0.56 | 8.07 | 7.10 | 8.97 | 8.24 | 11.08 | 8.97 |
| | CH505w078.1D8gp120/293F | 0.00 | 0.00 | 0.00 | 0.00 | 0.00 | 0.00 | 0.00 | 0.00 | 0.00 | 7.70 | 6.06 | 7.73 | 7.53 | 11.03 | 8.34 |
| | CH505w078.9D8gp120 | 0.00 | 0.00 | 0.00 | 0.00 | 0.00 | 0.00 | 0.00 | 1.86 | 2.27 | 6.11 | 5.78 | 7.18 | 6.29 | 8.93 | 6.85 |
| | CH505w078.6D8gp120 | 0.00 | 0.00 | 0.00 | 0.00 | 0.00 | 0.00 | 0.00 | 0.00 | 0.13 | 3.43 | 1.04 | 4.57 | 3.00 | 9.94 | 4.50 |
| | CH505w078.33D8gp120 | 0.00 | 0.00 | 0.00 | 0.00 | 0.00 | 1.07 | 1.22 | 0.00 | 0.57 | 3.76 | 1.94 | 4.70 | 4.41 | 7.69 | 4.22 |
| | CH505w078.15D8gp120/293F | 0.00 | 0.00 | 0.68 | 0.99 | 1.32 | 5.54 | 5.65 | 6.19 | 1.86 | 9.25 | 10.66 | 11.49 | 10.91 | 10.70 | 10.83 |
| | CH505w078.10D8gp120 | 0.00 | 0.00 | 0.00 | 0.00 | 0.00 | 5.29 | 5.80 | 9.55 | 1.45 | 6.53 | 4.40 | 6.56 | 6.63 | 11.13 | 8.09 |
| | CH505w078.17D8gp120 | 0.00 | 0.00 | 0.00 | 0.00 | 0.00 | 0.00 | 0.00 | 12.35 | 0.09 | 8.31 | 8.95 | 9.91 | 8.99 | 11.32 | 9.98 |
| | CH505w078.7D8gp120/293F | 0.00 | 0.00 | 0.00 | 0.00 | 0.00 | 0.00 | 0.00 | 0.00 | 0.00 | 8.36 | 8.26 | 9.19 | 8.94 | 11.38 | 9.49 |
| | CH0505.w78.env4.D11gp120/293i | 0.00 | 0.00 | 0.00 | 0.00 | 0.00 | 0.00 | 0.00 | 0.00 | 0.00 | 8.98 | 9.29 | 10.21 | 9.80 | 11.72 | 10.08 |
| | CH505w078.25D8gp120 | 0.00 | 0.00 | 0.00 | 0.00 | 0.00 | 0.00 | 0.00 | 0.00 | 0.16 | 3.59 | 1.37 | 3.19 | 2.40 | 8.75 | 3.47 |
| Week 100 | CH505w100.C7D8gp120/293F | 0.00 | 0.00 | 0.00 | 0.00 | 0.00 | 0.00 | 0.00 | 0.00 | 0.00 | 0.10 | 6.85 | 9.14 | 8.86 | 4.78 | 9.20 |
| | CH505w100.A13D8gp120 | 0.00 | 0.00 | 0.00 | 0.00 | 0.00 | 0.00 | 0.00 | 0.00 | 0.10 | 10.66 | 10.95 | 12.47 | 12.56 | 12.89 | 12.94 |
| | CH505w100.B6D8gp120 | 0.00 | 0.00 | 0.00 | 0.00 | 0.00 | 0.00 | 0.00 | 0.00 | 0.00 | 1.84 | 9.81 | 12.11 | 12.21 | 7.07 | 11.02 |
| | CH505_w100.B7D8gp120/293F | 0.00 | 0.00 | 0.00 | 0.00 | 0.00 | 0.00 | 0.00 | 0.00 | 0.00 | 2.43 | 10.56 | 12.37 | 11.90 | 7.77 | 11.62 |
| | CH505_w100V115b7.D7gp120/293F | 0.00 | 0.00 | 0.00 | 0.00 | 0.00 | 0.00 | 0.00 | 0.00 | 0.00 | 2.62 | 11.34 | 12.92 | 12.87 | 8.66 | 13.49 |
| | CH505_w100.A10D8gp120 | 0.00 | 0.00 | 0.00 | 0.00 | 0.00 | 7.23 | 7.93 | 12.41 | 3.02 | 8.52 | 8.67 | 10.45 | 9.89 | 11.73 | 10.08 |
| | 505_w100.A4.D8.gp120/293F | 0.00 | 0.00 | 0.00 | 0.00 | 0.00 | 5.35 | 5.76 | 11.31 | 2.85 | 7.32 | 7.39 | 8.84 | 8.72 | 11.29 | 9.55 |
| | CH505_w100V115A10.D7gp120 | 0.00 | 0.00 | 0.00 | 0.00 | 0.00 | 8.00 | 8.66 | 13.44 | 4.09 | 8.31 | 7.16 | 9.58 | 8.82 | 12.54 | 10.20 |
| | CH505w100.A12D8gp120 | 0.00 | 0.00 | 0.00 | 0.00 | 0.00 | 0.00 | 0.00 | 0.00 | 0.00 | 0.12 | 7.40 | 9.42 | 8.56 | 4.70 | 10.41 |
| | CH505w100.A3D8gp120/293F | 0.00 | 0.00 | 0.00 | 0.00 | 0.00 | 0.00 | 0.00 | 0.00 | 0.00 | 8.21 | 6.37 | 9.34 | 8.54 | 11.40 | 9.97 |
| | CH505w100.A6D8gp120 | 0.00 | 0.00 | 0.00 | 0.00 | 0.00 | 0.00 | 0.00 | 0.00 | 0.00 | 9.78 | 9.48 | 11.38 | 11.00 | 12.14 | 11.60 |
| | CH505w100.B4D8gp120 | 0.00 | 0.00 | 0.00 | 0.00 | 0.00 | 0.00 | 0.00 | 0.00 | 0.00 | 7.83 | 12.89 | 13.42 | 13.74 | 9.73 | 13.07 |
| | CH505_w100V115A13.D7gp120/293F | 0.00 | 0.00 | 0.00 | 0.00 | 0.00 | 0.00 | 0.00 | 0.00 | 0.00 | 0.20 | 8.26 | 9.84 | 8.86 | 6.13 | 10.83 |
| | CH505_w100V115A6.D11gp120 | 0.00 | 0.00 | 0.00 | 0.00 | 0.00 | 0.00 | 0.00 | 0.00 | 0.00 | 10.38 | 11.20 | 12.60 | 12.20 | 12.62 | 13.47 |
| | CH505_w100V115B4.D11gp120 | 0.00 | 0.00 | 0.00 | 0.00 | 0.00 | 0.00 | 0.00 | 0.00 | 0.00 | 8.18 | 12.68 | 13.42 | 13.50 | 12.52 | 14.02 |
| | CH505w100.B2D8gp120/293F | 0.00 | 0.00 | 0.00 | 0.00 | 0.00 | 0.00 | 0.00 | 0.00 | 0.00 | 0.10 | 4.11 | 7.49 | 7.33 | 3.22 | 6.13 |

*FIG. 47 cont.*

| | Envelope ID | CH103 Lineage | | | | | | |
|---|---|---|---|---|---|---|---|---|
| | | CH105 | CH106 | CH243 | CH244 | CH245 | CH247 | CH248 |
| Week 78 | CH505.w78.env5.D11gp120/293F | 6.61 | 7.89 | 10.04 | 11.29 | 11.15 | 12.47 | 10.90 |
| | CH505w078.33D8gp120/293F | 8.86 | 9.48 | 10.77 | 11.46 | 12.22 | 11.66 | 12.08 |
| | CH505w078.1D8gp120/293F | 7.48 | 7.29 | 10.55 | 11.24 | 8.36 | 11.02 | 10.38 |
| | CH505w078.9D8gp120 | 6.59 | 8.34 | 8.96 | 9.22 | 11.09 | 10.34 | 10.60 |
| | CH505w078.6D8gp120 | 3.80 | 6.72 | 8.99 | 9.77 | 10.16 | 10.78 | 9.68 |
| | CH505w078.38D8gp120 | 3.98 | 5.25 | 6.04 | 6.32 | 7.60 | 9.77 | 7.02 |
| | CH505w078.15D8gp120/293F | 10.08 | 10.95 | 12.13 | 11.86 | 11.70 | 11.62 | 11.57 |
| | CH505w078.10D8gp120 | 7.61 | 7.84 | 10.95 | 10.91 | 12.38 | 12.76 | 11.44 |
| | CH505w078.17D8gp120 | 9.53 | 8.72 | 11.65 | 12.18 | 11.57 | 11.40 | 11.67 |
| | CH505w078.7D8gp120/293F | 9.41 | 8.71 | 11.51 | 12.05 | 10.76 | 11.12 | 11.07 |
| | CH0505.w78.env4.D11gp120/293i | 9.53 | 9.25 | 12.00 | 12.40 | 11.73 | 11.11 | 11.99 |
| | CH505w078.25D8gp120 | 3.33 | 4.64 | 6.47 | 6.68 | 10.41 | 10.10 | 9.71 |
| Week 100 | CH505w100.C7D8gp120/293F | 8.96 | 9.30 | 11.30 | 11.78 | 12.06 | 7.94 | 10.76 |
| | CH505w100.A13D8gp120 | 11.40 | 11.99 | 13.90 | 13.85 | 14.42 | 12.88 | 14.01 |
| | CH505w100.B6D8gp120 | 11.04 | 11.77 | 13.62 | 13.91 | 14.47 | 12.58 | 13.82 |
| | CH505w100.B7D8gp120/293F | 11.58 | 11.53 | 13.14 | 13.62 | 14.04 | 12.28 | 13.27 |
| | CH505_w100V115b7.D7gp120/293F | 12.44 | 12.16 | 14.32 | 14.61 | 15.30 | 13.25 | 14.93 |
| | CH505w100.A10D8gp120 | 9.06 | 10.37 | 12.10 | 11.83 | 12.99 | 12.69 | 12.43 |
| | 505_w100.A4.D8.gp120/293F | 8.51 | 9.43 | 11.03 | 10.97 | 12.50 | 12.61 | 12.19 |
| | CH505_w100V115A10.D7gp120 | 9.20 | 10.79 | 12.90 | 12.73 | 13.65 | 13.70 | 12.79 |
| | CH505w100.A12D8gp120 | 9.56 | 9.65 | 12.26 | 12.81 | 12.90 | 9.01 | 13.17 |
| | CH505w100.A3D8gp120/293F | 7.21 | 8.59 | 11.91 | 11.99 | 10.84 | 11.19 | 11.45 |
| | CH505w100.A6D8gp120 | 10.12 | 11.11 | 12.23 | 12.53 | 12.74 | 11.93 | 12.39 |
| | CH505w100.B4D8gp120 | 11.91 | 12.55 | 12.48 | 13.29 | 13.35 | 12.56 | 13.00 |
| | CH505_w100V115A13.D7gp120/293F | 10.55 | 10.12 | 12.60 | 13.35 | 13.34 | 9.78 | 13.74 |
| | CH505_w100V115A6.D11gp120 | 12.24 | 11.93 | 13.62 | 14.17 | 14.54 | 13.15 | 14.09 |
| | CH505_w100V115B4.D11gp120 | 13.55 | 12.87 | 13.75 | 14.61 | 14.78 | 13.54 | 14.28 |
| | CH505w100.B2D8gp120/293F | 7.51 | 7.80 | 11.29 | 11.41 | 11.60 | 8.61 | 11.13 |

| | Envelope ID | UCA | IA8 | IA7 | IA6 | IA4 | CH187 | CH188 | CH186 | CH200 | 1AH92U | IA3 | A2 | IA1 | CH103 | CH104 |
|---|---|---|---|---|---|---|---|---|---|---|---|---|---|---|---|---|
| Week 136 | CH505w136.B18D8gp120 | 0.00 | 0.00 | 0.00 | 0.00 | 0.00 | 0.00 | 0.00 | 0.00 | 0.00 | 8.70 | 13.82 | 14.27 | 14.36 | 11.79 | 14.25 |
| | CH505w136.B2D8gp120/293F | 0.00 | 0.00 | 0.00 | 0.00 | 0.00 | 0.00 | 0.00 | 0.00 | 0.00 | 7.65 | 12.60 | 13.07 | 13.25 | 10.80 | 13.20 |
| | CH505_w137V201B12.D11gp120 | 0.00 | 0.00 | 0.00 | 0.00 | 0.00 | 0.00 | 0.00 | 0.00 | 0.00 | 11.40 | 11.13 | 12.81 | 12.50 | 12.90 | 12.17 |
| | CH505w136.B3D8gp120/293F | 0.00 | 0.00 | 0.00 | 0.00 | 0.00 | 0.00 | 0.00 | 0.00 | 0.22 | 5.00 | 12.05 | 13.06 | 13.10 | 9.93 | 13.10 |
| | CH505w136.B5D8gp120 | 0.00 | 0.00 | 0.00 | 0.00 | 0.00 | 0.00 | 0.00 | 0.00 | 0.00 | 0.13 | 8.59 | 9.94 | 9.46 | 4.33 | 10.59 |
| | CH505w136.B8D8gp120 | 0.00 | 0.00 | 0.00 | 0.00 | 0.00 | 0.00 | 0.00 | 0.00 | 0.00 | 11.49 | 11.80 | 13.23 | 12.94 | 11.90 | 11.73 |
| | CH505w136.B36D8gp120 | 0.00 | 0.00 | 0.00 | 0.00 | 0.00 | 0.00 | 0.00 | 0.00 | 0.00 | 12.04 | 12.76 | 13.63 | 13.76 | 13.75 | 13.84 |
| | CH505w136.B20D8gp120 | 0.00 | 0.00 | 0.00 | 0.00 | 0.00 | 0.00 | 0.00 | 0.00 | 0.00 | 11.08 | 11.21 | 12.70 | 12.40 | 12.43 | 11.66 |
| | CH505_w137V209C12.D11gp120 | 0.00 | 0.00 | 0.00 | 0.00 | 0.00 | 0.00 | 0.00 | 0.00 | 0.00 | 3.81 | 11.62 | 12.61 | 12.47 | 8.72 | 12.70 |
| | CH505w136.B27D8gp120 | 0.00 | 0.00 | 0.00 | 0.00 | 0.00 | 0.00 | 0.00 | 0.00 | 0.10 | 10.57 | 9.89 | 11.91 | 11.24 | 12.60 | 11.51 |
| | CH505w136.B29D8gp120 | 0.00 | 0.00 | 0.00 | 0.00 | 0.00 | 0.00 | 0.00 | 0.00 | 0.00 | 11.03 | 10.90 | 12.52 | 12.25 | 12.73 | 11.37 |
| | CH505w136.B4D8gp120 | 0.00 | 0.00 | 0.00 | 0.00 | 0.00 | 0.00 | 0.00 | 0.00 | 0.00 | 10.87 | 10.56 | 12.17 | 11.76 | 13.38 | 12.17 |
| | CH505w136.B12D8gp120 | 0.00 | 0.00 | 0.00 | 0.00 | 0.00 | 0.00 | 0.00 | 0.00 | 0.00 | 11.18 | 10.85 | 12.40 | 12.24 | 12.70 | 10.66 |
| | CH505w136.B10D8gp120 | 0.00 | 0.00 | 0.00 | 0.00 | 0.00 | 0.00 | 0.00 | 0.00 | 0.00 | 8.89 | 7.55 | 9.69 | 9.19 | 11.48 | 8.94 |
| Week 160 | CH505w160.T4D8gp120/293F | 0.00 | 0.00 | 0.00 | 0.00 | 0.00 | 0.00 | 0.00 | 0.00 | 0.00 | 4.84 | 12.55 | 13.44 | 13.55 | 9.03 | 12.85 |
| | CH505w160.C2D8gp120 | 0.00 | 0.00 | 0.00 | 0.00 | 0.00 | 0.00 | 0.00 | 0.00 | 0.00 | 9.64 | 9.07 | 10.09 | 9.62 | 12.16 | 9.24 |
| | CH505w160.C4D8gp120 | 0.00 | 0.00 | 0.00 | 0.00 | 0.00 | 0.00 | 0.00 | 0.00 | 0.00 | 7.65 | 3.88 | 6.15 | 5.26 | 12.19 | 7.23 |
| | CH505w160.C12D8gp120 | 0.00 | 0.00 | 0.00 | 0.00 | 0.00 | 0.00 | 0.00 | 0.00 | 0.00 | 3.05 | 12.02 | 12.90 | 12.91 | 7.76 | 11.33 |
| | CH505w160.C14D8gp120 | 0.00 | 0.00 | 0.00 | 0.00 | 0.00 | 0.00 | 0.00 | 0.00 | 0.00 | 7.86 | 5.43 | 7.05 | 5.84 | 12.15 | 6.83 |
| | CH505w160.A1D8gp120 | 0.00 | 0.00 | 0.00 | 0.00 | 0.00 | 0.00 | 0.00 | 0.00 | 0.00 | 7.68 | 5.85 | 7.58 | 6.35 | 10.71 | 7.31 |
| | CH505w160.C11D8gp120 | 0.00 | 0.00 | 0.00 | 0.00 | 0.00 | 0.00 | 0.00 | 0.00 | 0.00 | 8.93 | 6.73 | 8.53 | 7.70 | 11.89 | 7.44 |
| | CH505w160.D1D8gp120 | 0.00 | 0.00 | 0.00 | 0.00 | 0.00 | 0.00 | 0.00 | 0.00 | 0.00 | 8.20 | 5.15 | 7.34 | 6.39 | 11.50 | 5.71 |
| | CH505w160.D5D8gp120/293F | 0.00 | 0.00 | 0.00 | 0.00 | 0.00 | 0.00 | 0.00 | 0.00 | 0.00 | 7.32 | 3.03 | 4.99 | 3.78 | 10.95 | 4.51 |
| | CH505w160.T2D8gp120 | 0.00 | 0.00 | 0.00 | 0.00 | 0.00 | 0.00 | 0.00 | 0.00 | 0.00 | 7.56 | 3.82 | 5.64 | 4.68 | 11.15 | 5.41 |

CH103 Lineage

| | Envelope ID | CH103 Lineage | | | | | | |
|---|---|---|---|---|---|---|---|---|
| | | CH105 | CH106 | CH243 | CH244 | CH245 | CH247 | CH248 |
| Week 136 | CH505w136.B18D8gp120 | 13.69 | 13.35 | 14.26 | 14.83 | 15.42 | 13.40 | 14.27 |
| | CH505w136.B2D8gp120/293F | 12.38 | 12.74 | 13.48 | 13.40 | 13.98 | 12.27 | 13.40 |
| | CH505_w137V201B12.D11gp120 | 10.96 | 12.53 | 13.17 | 13.91 | 14.34 | 13.53 | 13.41 |
| | CH505w136.B3D8gp120/293F | 12.00 | 12.57 | 13.71 | 14.11 | 14.30 | 13.17 | 13.97 |
| | CH505w136.B5D8gp120 | 10.55 | 10.90 | 13.19 | 14.39 | 14.35 | 13.33 | 14.55 |
| | CH505w136.B8D8gp120 | 9.86 | 11.71 | 10.95 | 12.28 | 12.32 | 11.97 | 12.29 |
| | CH505w136.B36D8gp120 | 12.82 | 13.09 | 14.06 | 14.72 | 15.30 | 14.43 | 14.37 |
| | CH505w136.B20D8gp120 | 10.66 | 12.09 | 13.02 | 13.10 | 13.50 | 12.53 | 12.92 |
| | CH505_w137V209C12.D11gp120 | 12.67 | 12.21 | 13.97 | 14.45 | 14.78 | 13.49 | 14.68 |
| | CH505w136.B27D8gp120 | 10.38 | 11.20 | 12.79 | 12.85 | 13.13 | 12.22 | 12.89 |
| | CH505w136.B29D8gp120 | 10.21 | 12.02 | 12.42 | 12.96 | 13.58 | 12.71 | 12.32 |
| | CH505w136.B4D8gp120 | 10.74 | 11.81 | 13.44 | 13.98 | 14.40 | 13.51 | 13.38 |
| | CH505w136.B12D8gp120 | 9.67 | 11.90 | 12.75 | 13.29 | 13.34 | 12.90 | 12.94 |
| | CH505w136.B10D8gp120 | 8.52 | 8.97 | 11.74 | 11.91 | 11.75 | 11.40 | 11.46 |
| Week 160 | CH505w160.T4D8gp120/293F | 12.21 | 12.33 | 13.39 | 13.89 | 14.23 | 12.29 | 13.52 |
| | CH505w160.C2D8gp120 | 8.61 | 9.29 | 11.24 | 11.88 | 10.53 | 11.47 | 11.09 |
| | CH505w160.C4D8gp120 | 6.55 | 6.80 | 10.61 | 12.06 | 9.83 | 11.17 | 10.48 |
| | CH505w160.C12D8gp120 | 11.14 | 12.17 | 12.09 | 12.61 | 12.05 | 11.82 | 12.89 |
| | CH505w160.C14D8gp120 | 6.58 | 6.94 | 11.03 | 12.24 | 10.05 | 11.80 | 10.29 |
| | CH505w160.A1D8gp120 | 6.66 | 7.60 | 9.67 | 9.63 | 8.96 | 9.31 | 8.62 |
| | CH505w160.C11D8gp120 | 7.70 | 8.15 | 10.91 | 11.50 | 10.40 | 11.36 | 10.67 |
| | CH505w160.D1D8gp120 | 6.03 | 7.06 | 9.51 | 10.81 | 8.34 | 10.47 | 8.75 |
| | CH505w160.D5D8gp120/293F | 4.58 | 5.64 | 8.57 | 10.05 | 7.32 | 10.29 | 7.84 |
| | CH505w160.T2D8gp120 | 4.94 | 6.16 | 9.14 | 10.83 | 7.85 | 10.31 | 8.34 |

*FIG. 47 cont.*

| | Envelope ID | UCA | IA8 | IA7 | IA6 | IA4 | CH187 | CH188 | CH186 | CH200 | IA9H92U | IA3 | IA2 | IA1 | CH103 | CH104 |
|---|---|---|---|---|---|---|---|---|---|---|---|---|---|---|---|---|
| | | | | | | | CH103 Lineage | | | | | | | | | |
| CH505 TF Mutants Loop D | CH505.M5D8gp120293F | 0.00 | 0.57 | 2.33 | 3.30 | 3.76 | 9.44 | 9.01 | 12.22 | 8.90 | 6.12 | 6.88 | 7.79 | 7.04 | 9.84 | 9.02 |
| | CH505.M10D8gp120 | 1.35 | 4.68 | 8.82 | 9.18 | 9.78 | 12.67 | 12.64 | 13.93 | 10.46 | 11.08 | 11.37 | 11.75 | 11.08 | 13.25 | 11.68 |
| | CH505.M6D8gp120/293F | 5.23 | 7.05 | 10.46 | 10.70 | 10.89 | 12.67 | 12.60 | 13.82 | 9.64 | 11.89 | 11.87 | 12.07 | 11.79 | 13.09 | 11.58 |
| | CH505.M11D8gp120/293F | 2.62 | 6.22 | 10.13 | 10.04 | 10.46 | 12.61 | 13.02 | 13.63 | 10.52 | 11.82 | 11.92 | 12.67 | 12.19 | 13.38 | 12.03 |
| | CH505.M19D8gp120 | 1.74 | 5.03 | 8.41 | 8.38 | 9.53 | 13.55 | 13.78 | 13.53 | 10.31 | 9.99 | 9.79 | 11.71 | 11.30 | 13.29 | 11.26 |
| | CH505.M8D8gp120 | 0.00 | 0.79 | 3.65 | 4.92 | 5.40 | 11.41 | 11.30 | 12.29 | 9.12 | 9.00 | 8.85 | 9.97 | 9.49 | 11.52 | 10.11 |
| | CH505.M20D8gp120/293F | 0.00 | 0.68 | 3.59 | 5.21 | 5.58 | 11.86 | 12.04 | 13.27 | 10.75 | 9.66 | 9.92 | 10.78 | 10.38 | 12.21 | 10.85 |
| | CH505.M21D8gp120/293F | 0.00 | 0.66 | 3.45 | 5.12 | 5.51 | 10.82 | 11.04 | 11.47 | 10.24 | 10.07 | 10.94 | 11.59 | 11.22 | 11.40 | 11.23 |
| | CH505.M9D8gp120/293F | 0.12 | 1.33 | 4.88 | 5.73 | 6.33 | 11.65 | 11.70 | 13.46 | 8.96 | 9.77 | 9.52 | 10.35 | 9.85 | 11.60 | 10.84 |
| | CH505.M7D8gp120/293F | 0.44 | 2.23 | 4.38 | 5.34 | 6.39 | 11.26 | 11.15 | 12.94 | 7.36 | 9.06 | 7.73 | 9.31 | 8.70 | 11.06 | 9.73 |

*FIG. 47 cont.*

| | Envelope ID | CH105 | CH106 | CH243 | CH244 | CH245 | CH247 | CH248 |
|---|---|---|---|---|---|---|---|---|
| CH505 TF | CH505.M5D8gp120293F | 8.63 | 8.37 | 10.41 | 10.38 | 10.74 | 11.47 | 10.98 |
| Mutants Loop D | CH505.M10D8gp120 | 11.30 | 11.81 | 13.61 | 13.40 | 13.74 | 13.09 | 13.77 |
| | CH505.M6D8gp120/293F | 11.05 | 12.60 | 13.65 | 13.24 | 13.62 | 13.57 | 13.64 |
| | CH505.M11D8gp120/293F | 11.72 | 12.77 | 13.97 | 13.66 | 13.76 | 13.67 | 13.64 |
| | CH505.M19D8gp120 | 10.92 | 12.18 | 13.79 | 13.72 | 14.06 | 13.82 | 13.21 |
| | CH505.M8D8gp120 | 9.33 | 10.19 | 11.50 | 11.57 | 11.51 | 12.61 | 12.32 |
| | CH505.M20D8gp120/293F | 10.57 | 10.69 | 12.82 | 12.66 | 12.57 | 13.39 | 13.20 |
| | CH505.M21D8gp120/293F | 11.19 | 11.46 | 13.41 | 13.05 | 12.66 | 13.31 | 13.78 |
| | CH505.M9D8gp120/293F | 10.58 | 10.98 | 13.04 | 12.95 | 13.07 | 12.54 | 13.01 |
| | CH505.M7D8gp120/293F | 10.17 | 10.99 | 12.85 | 12.35 | 12.37 | 12.49 | 12.42 |

*FIG. 47 cont.*

| Region | R# | DH511 | DH511 mutation |
|---|---|---|---|
| CDRH3 | 92 | C | |
| | 93 | T | |
| | 94 | A | |
| | 95 | D | |
| | 96 | L | W |
| | 97 | G | W,F |
| | 98 | E | W |
| | 99 | P | W |
| | 100 | V | F,L |
| | 100a | V | W |
| | 100b | S | W |
| | 100c | R | W |
| | 100d | F | W |
| | 100e | F | W |
| | 100f | E | W |
| | 100g | W | |
| | 100h | G | W |
| | 100i | S | W |
| | 100j | Y | W |
| | 100k | Y | |
| | 100k | Y | W |
| | 100l | Y | |
| | 100m | M | |
| | 101 | D | |
| | 102 | L | |
| | 103 | W | |
| | 104 | G | |

Figure 48A

| Region | R# | DH512 | DH512 mutation |
|---|---|---|---|
| CDRH3 | 92 | C | |
| | 93 | T | |
| | 94 | M | |
| | 95 | D | |
| | 96 | E | W |
| | 97 | G | W,F |
| | 98 | T | W |
| | 99 | P | W |
| | 100 | V | F,L |
| | 100a | T | W |
| | 100b | R | W |
| | 100c | F | W |
| | 100d | L | W,F |
| | 100e | E | W |
| | 100f | W | |
| | 100g | G | W |
| | 100h | Y | W |
| | 100i | F | W |
| | 100j | Y | |
| | 100k | Y | W |
| | 100l | Y | |
| | 100m | M | |
| | 101 | A | |
| | 102 | V | |
| | 103 | W | |
| | 104 | G | |

Figure 48B

Mutations outside of CDRH3

| Region | R# | DH511 | DH511 mutation | Region | R# | DH512 | DH512 mutation |
|---|---|---|---|---|---|---|---|
| CDRH1 | 26 | G | W | CDRH1 | 26 | G | W |
| | 27 | F | | | 27 | F | |
| | 28 | T | W | | 28 | F | W |
| | 29 | F | | | 29 | F | |
| | 30 | S | | | 30 | D | |
| | 31 | N | W | | 31 | N | W |
| | 32 | T | | | 32 | S | |
| | 33 | W | | | 33 | W | |

| Region | R# | DH511 | DH511 mutation | Region | R# | DH512 | DH512 mutation |
|---|---|---|---|---|---|---|---|
| CDRH2 | 51 | I | | CDRH2 | 51 | I | |
| | 52 | S | W | | 52 | R | W |
| | 52a | R | | | 52a | R | |
| | 52b | N | W | | 52b | L | W |
| | 52c | K | W | | 52c | K | W |
| | 53 | D | W | | 53 | D | W |
| | 54 | G | | | 54 | G | |
| | 55 | A | | | 55 | A | |
| | 56 | K | | | 56 | T | |
| | 57 | T | | | 57 | G | |

| Region | R# | DH511 | DH511 mutation | Region | R# | DH512 | DH512 mutation |
|---|---|---|---|---|---|---|---|
| FR3 | 72 | D | | FR3 | 72 | D | |
| | 73 | D | W | | 73 | D | W |
| | 74 | S | W | | 74 | S | W |
| | 75 | R | W | | 75 | R | W |

Figure 48C

DH512 Nucleotide Sequence (SEQ ID NO: 195)

CAGGTGCAGCTGGTACAGTCTGGGGGAGGTCTGGTGAAGCCGGGGGGGTCCCTCACACTCTCCTGTTC
AGCCTCTGGATTCTTTTTCGATAATTCATGGATGGGGTGGGTCCGTCAGGCGCCAGGGAAGGGACTGG
AGTGGGTTGGCCGCATTAGAAGGCTCAAAGACGGTGCGACAGGAGAATATGGTGCAGCCGTGAAGGAC
AGATTCACCATTTCAAGAGATGACAGTAGAAATATGCTGTACCTGCACATGAGGACCCTGAAAACCGA
GGACTCAGGCACTTATTATTGTACCATGGATGAGGGGACCCCAGTAACACGCTTCTTAGAATGGGGCT
ACTTCTATTATTATATGGCCGTTTGGGGCAGAGGGACCACGGTCATCGTCTCTTCA

DH512 Translated (Amino Acid) Sequence (SEQ ID NO: 196)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWGYFYYYMAVWGRGTTVIVSS

Amino Acid Sequences of DH512 Heavy Chain Mutants

>DH512_E96W (SEQ ID NO: 197)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDWGTPVTRFLEWGYFYYYMAVWGRGTTVIVSS

>DH512_G97W (SEQ ID NO: 198)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEWTPVTRFLEWGYFYYYMAVWGRGTTVIVSS

>DH512_T98W (SEQ ID NO: 199)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGWPVTRFLEWGYFYYYMAVWGRGTTVIVSS

>DH512_P99W (SEQ ID NO: 200)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTWVTRFLEWGYFYYYMAVWGRGTTVIVSS

>DH512_V100F (SEQ ID NO: 201)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPFTRFLEWGYFYYYMAVWGRGTTVIVSS

>DH512_V100I (SEQ ID NO: 202)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPITRFLEWGYFYYYMAVWGRGTTVIVSS

>DH512_T100aW (SEQ ID NO: 203)
QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVWRFLEWGYFYYYMAVWGRGTTVIVSS

Figure 48D

>DH512_R100bW (SEQ ID NO: 204)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTWFLEWGYFYYYMAVWGRGTTVIVSS

>DH512_F100cW (SEQ ID NO: 205)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRWLEWGYFYYYMAVWGRGTTVIVSS

>DH512_L100dW (SEQ ID NO: 206)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFWEWGYFYYYMAVWGRGTTVIVSS

>DH512_L100dF (SEQ ID NO: 207)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFFEWGYFYYYMAVWGRGTTVIVSS

>DH512_E100eW (SEQ ID NO: 208)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLWWGYFYYYMAVWGRGTTVIVSS

>DH512_G100gW (SEQ ID NO: 209)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWWYFYYYMAVWGRGTTVIVSS

>DH512_Y100hW (SEQ ID NO: 210)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWGWFYYYMAVWGRGTTVIVSS

>DH512_F100iW (SEQ ID NO: 211)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWGYWYYMAVWGRGTTVIVSS

>DH512_Y100kW (SEQ ID NO: 212)

QVQLVQSGGGLVKPGGSLTLSCSASGFFFDNSWMGWVRQAPGKGLEWVGRIRRLKDGATGEYGAAVKD
RFTISRDDSRNMLYLHMRTLKTEDSGTYYCTMDEGTPVTRFLEWGYFYWYMAVWGRGTTVIVSS

Figure 48D cont.

SEQUENCE LISTING

```
<160> NUMBER OF SEQ ID NOS: 302

<210> SEQ ID NO 1
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tggtgcagtc tggggctcaa atgaagaacc ctggggcctc agtgaaggtc      60
tcctgcgcgc cttctggata taccttcacc gactttttaca tacattggtt gcgccaggcc    120
cctggccagg ggcttcagtg gatgggatgg atgaaccctc agactggtcg cacaaacact    180
gcacgaaact ttcaggggag ggtcaccatg accagggaca cgtccatcgg cacagcctac    240
atggagttga aagcctgac atctgacgac acggccatat attactgtac gacagggga     300 tggatcagtc tttactatga tagtagttat taccccaact ttgaccactg gggtcaggga    360
accctgctca ccgtctcctc ag                                             382

<210> SEQ ID NO 2
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
accagtctgc tgactcagcc tgcctccgtg tctgggtctc ctggacagtc gatcaccatc      60
tcctgcactg gaaccaagta tgatgttggg agtcatgacc ttgtctcctg gtaccaacag    120
```

```
tacccaggca aagtccccaa atacatgatt tatgaagtca ataaacggcc ctcaggagtt    180
tctaatcgct tctctggctc caaatctggc aacacggcct ccctgacaat ctctgggctc    240
cgggctgagg acgaggctga ctattattgc tgttcatttg agggagtgc caccgtggtc     300 tgcggcggcg ggaccaaggt gaccgtccta g                                   331
```

```
<210> SEQ ID NO 3
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Leu Arg Gln Ala Pro Gly Gln Gly Leu Gln Trp Met
        35                  40                  45

Gly Trp Met Asn Pro Gln Thr Gly Arg Thr Asn Thr Ala Arg Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Ile Tyr Tyr Cys
                85                  90                  95

Thr Thr Gly Gly Trp Ile Ser Leu Tyr Tyr Asp Ser Ser Tyr Tyr Pro
            100                 105                 110

Asn Phe Asp His Trp Gly Gln Gly Thr Leu Leu Thr Val Ser Ser
        115                 120                 125

```
<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

Thr Ser Leu Leu Thr Gln Pro Ala Ser Val Ser Gly Ser Pro Gly Gln
1               5                   10                  15

Ser Ile Thr Ile Ser Cys Thr Gly Thr Lys Tyr Asp Val Gly Ser His
            20                  25                  30

Asp Leu Val Ser Trp Tyr Gln Gln Tyr Pro Gly Lys Val Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Cys Ser Phe Gly Gly Ser
                85                  90                  95

Ala Thr Val Val Cys Gly Gly Gly Thr Lys Val Thr Val Leu
            100                 105                 110

```
<210> SEQ ID NO 5
<211> LENGTH: 382
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 5

```
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccctc acagtggtgg cacaaactat    180
gcacagaagt tcagggcag ggtcaccatg accagggaca cgtccatcag cacagcctac    240
atggagctga gcaggctgag atctgacgac acggccgtgt attactgtgc gagaggggr    300 tggatcrgtc tttactatga tagtagtggt taccctaact ttgactactg gggccaggga   360
accctggtca ccgtctcctc ag                                             382
```

<210> SEQ ID NO 6
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
caggtgcagc tggtgcagtc tggggctgag rtgaagaagc ctggggcctc agtgaaggtc    60
tcctgcaagg cttctggata caccttcacc gactactata tacactgggt gcgacaggcc   120
cctggacaag gcttgagtg gatgggatgg atcaaccctc acastggtcg cacaaactmt    180
gcacagaagt tcagggcag ggtcaccatg accagggaca cgtccatcag cacagcctac    240
atggagctga gcagvctgag atctgacgac acggccgtgt attactgtgc gagaggggr    300 tggatcrgtc tttactatga tagtagtggt taccctaact ttgactactg gggccaggga   360
accctggtca ccgtctcctc ag                                             382
```

<210> SEQ ID NO 7
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
caggtgcagc tggtgcagtc tggggctgag dtgaagaagc ctggggcctc agtgaaggtc    60
tcctgcaagg cttctggata caccttcacc gactactata tacactgggt gcgacaggcc   120
cctggacaag gcttgagtg gatggcatgg atcaaccctc ccastggtcg cacaarctmt    180
gcacggaagt tcagggcag ggtcaccatg accagggaca cgtccatcag cacrgcctac    240
atggaactga gaagmctgag atctgacgac acggccgtct attactgtgc gagagggga    300 tggatcrgtc tttacgttga ttatagtggt taccctaact ttgactcctg gggccaggga   360
accctggtca ccgtctcctc ag                                             382
```

<210> SEQ ID NO 8
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
gaggttcagc tggtggagtc tgggcctgag ttgaaggagc ctggggcctc agtgaaagtc    60
tcctgcaagg cttctggata caccttcacc gactactaca tacactgggt gcgacaggcc   120
cctggacaag gtcttgagtg gatggcatgg atcaaccctg ccactggtcg ctctagcttt   180
gcccgggggt ttcagggcag ggtcaccatg accaggaaaa cgtccgtcag cacggcctat   240
atggaactga aagactgag atctgacgac acggccgtct attactgtgc gaaagcggga   300
tacatcgccc tttacgttga ctatagtggt taccctaact ttaattcctg gggccaggga   360
accctggtca ccgtctcctc ag                                            382
```

<210> SEQ ID NO 9
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
caggtgcagc tggtgcagtc tggggctgaa ctgaagaagc ctggggcctc agtgaaggtc    60
tcctgcaagg cttctggata caccctcagc gactactatg tacactggct gcgacaggcc   120
cctggacagg ggcttgagtg ggtggcttgg atcaaccctg ccagtggtcg cacaatctct   180
ccacggaagt ttcagggcag ggtcacgatg actacggaca cgtccatgaa tgttgcctac   240
atggaactga gaggcttgag atctgacgac acggccgtct atttctgtgc gagaggggga   300
tggatcagtc tctacgttga ttacagttat taccctaact ttgactcgtg gggccaggga   360
accctggtct ccgtctcttc ag                                            382
```

<210> SEQ ID NO 10
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
caggtgcagc tggtgcagtc tggggctgag atgaagaagc ctggggcctc agtgaaggtc    60
tcctgcaagg cttctggata caccttcacc gactactata tacactgggt gcgacaggcc   120
cctggacaag ggcttgagtg gatgggatgg atcaaccctg acactggtcg cacaaactmt   180
gcacagaagt ttcagggcag ggtcaccatg accaggaca cgtccatcag cacagcctac   240
atggagctga gcagvctgac atctgacgac acggccgtgt attactgtgc gacaggrggr   300
tggatcrgtc tttactatga tagtagtggt taccctaact ttgactactg gggccaggga   360
accctggtca ccgtctcctc ag                                            382
```

<210> SEQ ID NO 11
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
caggtgcagc tggtgcagtc tggggctgaa atgaagaacc ctggggcctc agtgaaggtc    60
```

```
tcctgcgcgs cttctggata taccttcacc gacttctaca tacactgggt gcgacaggcc    120
cctggacaag ggcttsagtg gatgggatgg atgaacccta agactggtcg cacaaacamt    180
gcacaaaact ttcagggcag ggtcaccatg accagggaca cgtccatcgg cacagcctac    240
atggagytga gvagcctgac atctgacgac acggccgtvt attactgtgc gacaggggr    300 tggatcagtc tttactatga tagtagttat taccctaact ttgaccactg gggtcaggga    360
accctggtca ccgtctcctc ag                                              382
```

<210> SEQ ID NO 12
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
caggtgcagc tggtgcagtc tggggctcaa atgaagaacc ctggggcctc agtgaaggtc     60
tcctgcgcgc cttctggata taccttcacc gactttttaca tacattggtt gcgccaggcc    120
cctggccagg gcttcagtg gatgggatgg atgaaccctc agactggtcg cacaaacact     180
gcacgaaact ttcaggggag ggtcaccatg accagggaca cgtccatcgg cacagcctac    240
atggagttga gaagcctgac atctgacgac acggccatat attactgtac gacagggga    300 tggatcagtc tttactatga tagtagttat taccccaact ttgaccactg gggtcaggga    360
accctgctca ccgtctcctc ag                                              382
```

<210> SEQ ID NO 13
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
caggtgcagc tggtgcagtc tggggctgaa atgaagaacc ctggggcctc agtgaaagtc     60
tcctgcgcgs cttctggata taccttcacc gacttctaca tacactgggt gcgactggcc    120
cctggacaag ggcttsagtg gatgggatgg atgaacccta agactggtcg cacaaataat    180
gcacaaaact ttcagggcag ggtcaccatg accagggaca cgtccatcgg cacagcctac    240
atggagytga ggagcctgac atctgacgac acggccgtct attactgtgt gacaggggr    300 tggatcagtc httattatga tagtagttat taccctaact ttgaccactg gggtcaggga    360
accctggtca ccgtctcctc ag                                              382
```

<210> SEQ ID NO 14
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
caggtgcagc tggtgcagtc tggggctgaa gtgaagaacc ctggggcctc agtgaaagtc     60
tcctgcgcgc cttctggata taccttcact gacttctaca tacactgggt gcgactggcc    120
cctggacaag ggcttgagtg gctggggtgg atgaacccta agactggtcg cacaaatcaa    180
```

```
ggacaaaact tcagggcag ggtcaccatg accagggaca cgtccatcgg cacagcctac    240
atggagttga ggagcctcac atctgacgac acggccgtct attactgtgt gacaggggcc    300
tggatcagtg attattatga tagtagttat tatcctaact ttgaccactg gggtcaggga    360
accctggtca ccgtctcctc ag                                             382
```

<210> SEQ ID NO 15
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
gaggtgcagc tggtgcagtc tggggctgaa atgaagaacc ctggggcctc agtgaaagtc    60
tcctgcgcgg cttctggata tggtttcacc gacttctaca tacactgggt gcgactggcc    120
cctggacacg gctccagtg atgggatgg atgaacccta agactggtcg cacaaataat      180
gcacaagatt ttcagggcag ggtcaccctg accagggaca cgtccatcgg cacagcctac    240
atggagctga ggaggctgac atctgacgac acggccgtct attactgtgt gacaggggggg  300 tggatcagtc cttattatga tagtagttat taccctaatt ttgaccactg gggtcaggga    360
accctgatca ccgtctcctc ag                                             382
```

<210> SEQ ID NO 16
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
caggtgcagc tggtgcagtc tggggctgag atgaagaagc ctggggcctc agtgagggtc    60
tcctgcaagg cttctggata caccttcacc gactactata tacactgggt gcgacaggcc    120
cctggacaag gcctgagtg atgggatgg atcaacccta gcactggtcg cacaaactct      180
ccacagaagt ttcagggcag ggtcaccatg accagggaca cgtccatcag cacagcctac    240
atggacctga acagactgac gtctgacgac acggccatgt attactgtac gaccgggggg    300
tggatcggtc tttactctga tactagtggt taccctaact ttgactactg gggccaggga    360
accctggtca ccgtctcctc ag                                             382
```

<210> SEQ ID NO 17
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 17

Gln Val Gln Leu Val Gln Ser Gly Ala Glu Val Lys Lys Pro Gly Ala

```
1               5                   10                  15
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Xaa Trp Ile Xaa Leu Tyr Tyr Asp Ser Ser Gly Tyr Pro
                100                 105                 110

Asn Phe Asp Tyr Trp Gly Gln Gly Thr Leu Val Thr Val Ser Ser
            115                 120                 125
```

<210> SEQ ID NO 18
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 18

```
Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
            35                  40                  45

Gly Trp Ile Asn Pro Asn Xaa Gly Arg Thr Asn Xaa Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Xaa Leu Arg Ser Asp Asp Thr Ala Val Tyr Tyr Cys
                85                  90                  95

Ala Arg Gly Xaa Trp Ile Xaa Leu Tyr Tyr Asp Ser Ser Gly Tyr Pro
                100                 105                 110
```

Asn Phe Asp Tyr Trp Gly Gln Gly Thr Leu Val Thr Val Ser Ser
            115                 120                 125

<210> SEQ ID NO 19
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (59)..(60)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 19

Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Ala Trp Ile Asn Pro Thr Xaa Gly Arg Thr Xaa Xaa Ala Arg Lys Phe
    50                  55                  60

Gln Gly Arg Val Thr Met Thr Arg Asp Thr Ser Ile Ser Xaa Ala Tyr
65                  70                  75                  80

Met Glu Leu Arg Xaa Leu Arg Ser Asp Asp Thr Ala Val Tyr Tyr Cys
                85                  90                  95

Ala Arg Gly Gly Trp Ile Xaa Leu Tyr Val Asp Tyr Ser Gly Tyr Pro
            100                 105                 110

Asn Phe Asp Ser Trp Gly Gln Gly Thr Leu Val Thr Val Ser Ser
            115                 120                 125

<210> SEQ ID NO 20
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Pro Glu Leu Lys Glu Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
            35                  40                  45

Ala Trp Ile Asn Pro Thr Thr Gly Arg Ser Ser Phe Ala Arg Gly Phe
 50                  55                  60

Gln Gly Arg Val Thr Met Thr Arg Glu Thr Ser Val Ser Thr Ala Tyr
65                  70                  75                  80

Met Glu Leu Arg Arg Leu Arg Ser Asp Asp Thr Ala Val Tyr Tyr Cys
                85                  90                  95

Ala Lys Ala Gly Tyr Ile Ala Leu Tyr Val Asp Tyr Ser Gly Tyr Pro
                100                 105                 110

Asn Phe Asn Ser Trp Gly Gln Gly Thr Leu Val Thr Val Ser Ser
                115                 120                 125

<210> SEQ ID NO 21
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Leu Ser Asp Tyr
                20                  25                  30

Tyr Val His Trp Leu Arg Gln Ala Pro Gly Gln Gly Leu Glu Trp Val
            35                  40                  45

Ala Trp Ile Asn Pro Thr Ser Gly Arg Thr Ile Ser Pro Arg Lys Phe
 50                  55                  60

Gln Gly Arg Val Thr Met Thr Thr Asp Thr Ser Met Asn Val Ala Tyr
65                  70                  75                  80

Met Glu Leu Arg Gly Leu Arg Ser Asp Asp Thr Ala Val Tyr Phe Cys
                85                  90                  95

Ala Arg Gly Gly Trp Ile Ser Leu Tyr Val Asp Tyr Ser Tyr Tyr Pro
                100                 105                 110

Asn Phe Asp Ser Trp Gly Gln Gly Thr Leu Val Ser Val Ser Ser
                115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 22

Gln Val Gln Leu Val Gln Ser Gly Ala Glu Met Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Asn Pro Asn Thr Gly Arg Thr Asn Xaa Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Xaa Leu Thr Ser Asp Asp Thr Ala Val Tyr Tyr Cys
                85                  90                  95

Ala Thr Gly Xaa Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
            115                 120                 125

<210> SEQ ID NO 23
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (83)..(84)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (100)..(100)
<223> OTHER INFORMATION: Any amino acid

<400> SEQUENCE: 23

Gln Val Gln Leu Val Gln Ser Gly Ala Glu Met Lys Asn Pro Gly Ala
1               5                   10                  15

Ser Val Lys Val Ser Cys Ala Xaa Ser Gly Tyr Thr Phe Thr Asp Phe
                20                  25                  30

Tyr Ile His Trp Val Arg Gln Ala Pro Gly Gln Gly Leu Xaa Trp Met
            35                  40                  45

Gly Trp Met Asn Pro Lys Thr Gly Arg Thr Asn Xaa Ala Gln Asn Phe
50                  55                  60

Gln Gly Arg Val Thr Met Thr Arg Asp Thr Ser Ile Gly Thr Ala Tyr
65                  70                  75                  80

Met Glu Xaa Xaa Ser Leu Thr Ser Asp Asp Thr Ala Xaa Tyr Tyr Cys
                85                  90                  95

Ala Thr Gly Xaa Trp Ile Ser Leu Tyr Tyr Asp Ser Ser Tyr Tyr Pro

```
                    100                 105                 110
Asn Phe Asp His Trp Gly Gln Gly Thr Leu Val Thr Val Ser Ser
            115                 120                 125

<210> SEQ ID NO 24
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Leu Arg Gln Ala Pro Gly Gln Gly Leu Gln Trp Met
        35                  40                  45

Gly Trp Met Asn Pro Gln Thr Gly Arg Thr Asn Thr Ala Arg Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Ile Tyr Tyr Cys
                85                  90                  95

Thr Thr Gly Gly Trp Ile Ser Leu Tyr Tyr Asp Ser Ser Tyr Tyr Pro
            100                 105                 110

Asn Phe Asp His Trp Gly Gln Gly Thr Leu Leu Thr Val Ser Ser
        115                 120                 125

<210> SEQ ID NO 25
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (104)..(104)
<223> OTHER INFORMATION: Any amino acid

<400> SEQUENCE: 25

Gln Val Gln Leu Val Gln Ser Gly Ala Glu Met Lys Asn Pro Gly Ala
1               5                   10                  15

Ser Val Lys Val Ser Cys Ala Xaa Ser Gly Tyr Thr Phe Thr Asp Phe
            20                  25                  30

Tyr Ile His Trp Val Arg Leu Ala Pro Gly Gln Gly Leu Xaa Trp Met
        35                  40                  45
```

Gly Trp Met Asn Pro Lys Thr Gly Arg Thr Asn Asn Ala Gln Asn Phe
            50                  55                  60

Gln Gly Arg Val Thr Met Thr Arg Asp Thr Ser Ile Gly Thr Ala Tyr
 65                  70                  75                  80

Met Glu Xaa Arg Ser Leu Thr Ser Asp Asp Thr Ala Val Tyr Tyr Cys
                85                  90                  95

Val Thr Gly Xaa Trp Ile Ser Xaa Tyr Tyr Asp Ser Ser Tyr Tyr Pro
            100                 105                 110

Asn Phe Asp His Trp Gly Gln Gly Thr Leu Val Thr Val Ser Ser
            115                 120                 125

<210> SEQ ID NO 26
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Asn Pro Gly Ala
 1               5                   10                  15

Ser Val Lys Val Ser Cys Ala Pro Ser Gly Tyr Thr Phe Thr Asp Phe
                20                  25                  30

Tyr Ile His Trp Val Arg Leu Ala Pro Gly Gln Gly Leu Glu Trp Leu
            35                  40                  45

Gly Trp Met Asn Pro Lys Thr Gly Arg Thr Asn Gln Gly Gln Asn Phe
            50                  55                  60

Gln Gly Arg Val Thr Met Thr Arg Asp Thr Ser Ile Gly Thr Ala Tyr
 65                  70                  75                  80

Met Glu Leu Arg Ser Leu Thr Ser Asp Asp Thr Ala Val Tyr Tyr Cys
                85                  90                  95

Val Thr Gly Ala Trp Ile Ser Asp Tyr Tyr Asp Ser Ser Tyr Tyr Pro
            100                 105                 110

Asn Phe Asp His Trp Gly Gln Gly Thr Leu Val Thr Val Ser Ser
            115                 120                 125

<210> SEQ ID NO 27
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Gln Ser Gly Ala Glu Met Lys Asn Pro Gly Ala
 1               5                   10                  15

Ser Val Lys Val Ser Cys Ala Ala Ser Gly Tyr Gly Phe Thr Asp Phe
                20                  25                  30

Tyr Ile His Trp Val Arg Leu Ala Pro Gly His Gly Leu Gln Trp Met
            35                  40                  45

Gly Trp Met Asn Pro Lys Thr Gly Arg Thr Asn Asn Ala Gln Asp Phe
            50                  55                  60

Gln Gly Arg Val Thr Leu Thr Arg Asp Thr Ser Ile Gly Thr Ala Tyr
 65                  70                  75                  80

Met Glu Leu Arg Arg Leu Thr Ser Asp Asp Thr Ala Val Tyr Tyr Cys
                85                  90                  95

Val Thr Gly Gly Trp Ile Ser Pro Tyr Tyr Asp Ser Ser Tyr Tyr Pro
            100                 105                 110

Asn Phe Asp His Trp Gly Gln Gly Thr Leu Ile Thr Val Ser Ser
            115                 120                 125

<210> SEQ ID NO 28
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Gln Ser Gly Ala Glu Met Lys Lys Pro Gly Ala
1               5                   10                  15

Ser Val Arg Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Met
        35                  40                  45

Gly Trp Ile Asn Pro Ser Thr Gly Arg Thr Asn Ser Pro Gln Lys Phe
    50                  55                  60

Gln Gly Arg Val Thr Met Thr Arg Asp Thr Ser Ile Ser Thr Ala Tyr
65                  70                  75                  80

Met Asp Leu Asn Arg Leu Thr Ser Asp Thr Ala Met Tyr Tyr Cys
                85                  90                  95

Thr Thr Gly Gly Trp Ile Gly Leu Tyr Ser Asp Thr Ser Gly Tyr Pro
            100                 105                 110

Asn Phe Asp Tyr Trp Gly Gln Gly Thr Leu Val Thr Val Ser Ser
            115                 120                 125

<210> SEQ ID NO 29
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
cagtctgccc tgactcagcc tgcctccgtg tctgggtctc ctggacagtc gatcaccatc      60
tcctgcactg gaaccagcag tgatgttggg agttataacc ttgtctcctg gtaccaacag     120
cacccaggca aagcccccaa actcatgatt tatgaggtca gtaagcggcc ctcaggggtt     180
tctaatcgct tctctggctc caagtctggc aacacggcct ccctgacaat ctctgggctc     240
caggctgagg acgaggctga ttattactgc tgctcatatg caggtagtag cactgtawta     300
ttcggcggag ggaccaagct gaccgtccta g                                    331

<210> SEQ ID NO 30
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
cagtctgccc tgactcagcc tgcctccgtg tctgggtctc ctggacagtc gatcaccatc      60
tcctgcactg gaaccagcwr tgatgttggg agttataacc ttgtctcctg gtaccaacag     120

```
cacccaggca agcccccaa actcatgatt tatgaggtca rtaagcggcc ctcagggggtt    180 tctaatcgct tctctggctc caagtctggc aacacggcct ccctgacaat ctctgggctc    240
caggctgagg acgaggctga ttattactgy tgctcatatg caggtagtag cactgtawta    300
ttcggcggag ggaccaagct gaccgtccta g                                   331
```

<210> SEQ ID NO 31
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
cagtctgccc tgactcagcc tgcctccgtg tctgggtctc ctggacagtc gatcaccatc    60
tcctgcactg gaaccagcwr tgatgttggg agttataacc ttgtctcctg gtaccaacag   120
cacccaggca agcccccaa actcatgatt tatgaggtca rtaagtggcc ctcagggggtt    180 tctaatcgct tctctggctc caagtctggc aacacggcct ccctgacaat ctctgggctc    240
caggctgagg acgaggctva ttattactgt tgctcatatg caggtagtag cactgtaata    300
ttcggcggag ggaccaagct gaccgtccta g                                   331
```

<210> SEQ ID NO 32
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
cagtctgccc tgactcagcc tgcctccgtg tctgggtctc ctggccagtc gatcaccatc    60
tcctgcactg gaaccagcta tgatgttggg agttataatc ttgtctcctg gtaccaacag   120
cacccaggca agcccccaa actcattatt tatgaggtca gtcagtggcc ctcagggggtt    180 tctaagcgct tctctggctc caagtctggc aacacggcct ccctgacaat ctctgggctc    240
caggctgagg acgaggctca ttattactgt tgctcatatg caggcagtag cactgtaata    300
ttcggcggag ggacctcgct gaccgtccta g                                   331
```

<210> SEQ ID NO 33
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
cagcctgtgc tgactcagcc tgcctccgtg tctgggtctc ctggacagtc gatcaccatc    60
tcctgcactg gaagcagcag tgatgttggg agttataacc ttgtgtcctg gtaccagcag   120
cacccaggca agcccccaa actgatgatt tatgaggtca ataagtgggc ctcagggggtt    180 tctgatcgct tcgctggctc caagtctggc aacacggcct ccctgacaat ctctagactc    240
caggctgagg acgaggctaa ttactttttgt tcctcatcta caaatagtgc cactgtcata    300
ttcggcggag ggaccaagct gaccgtccta g                                   331
```

<210> SEQ ID NO 34
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
cagtctgccc tgactcagcc tgcctccgtg tctgggtctc ctggacagtc gatcaccatc      60
tcctgcactg gaaccagtta tgatgttggg agttataacc ttgtctcctg gtaccaacag     120
cacccaggca aagcccccaa atacatgatt tatgaggtca ataagcggcc ctcagggggtt    180
tctaatcgct tctctggctc caagtctggc aacacggcct ccctgacaat ctctgggctc     240
caggctgagg acgaggctga ttattactgy tgctcatatg caggtagtag cactgtadtw     300
ttcggcggag ggaccaagct gaccgtccta g                                    331
```

<210> SEQ ID NO 35
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
cagtctgysc tgactcagcc tgcctccgtg tctgggtctc ctggacagtc gatcaccatc      60
tcctgcactg gaaccagtta tgatgttggg agttatgacc ttgtctcctg gtaccaacag     120
cacccaggca aagcccccaa atacatgatt tatgaagtca ataagcggcc ctcaggagtt     180
tctaatcgct tctctggctc caaatctggc aacacggcct ccctgacaat ctctgggctc     240
caggctgagg acgaggctga ctattattgc tgctcatttg gaggtagtgc cactgtrgtc     300
tgcggcggag ggaccaaggt gaccgtccta g                                    331
```

<210> SEQ ID NO 36
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
accagtctgc tgactcagcc tgcctccgtg tctgggtctc ctggacagtc gatcaccatc      60
tcctgcactg gaaccaagta tgatgttggg agtcatgacc ttgtctcctg gtaccaacag     120
tacccaggca aagtccccaa atacatgatt tatgaagtca ataaacggcc ctcaggagtt     180
tctaatcgct tctctggctc caaatctggc aacacggcct ccctgacaat ctctgggctc     240
cgggctgagg acgaggctga ctattattgc tgttcatttg gagggagtgc caccgtggtc     300
tgcggcggcg gaccaaggt gaccgtccta g                                     331
```

<210> SEQ ID NO 37
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
cagtctgysc tgactcagcc tgcctccgtg tctgggtctc ctggacagtc gatcaccatc      60
tcctgcactg gaaccagtta tgatgttggg aagtttgacc ttgtctcctg gtaccaacag     120
cacccaggca aagcccccaa atacatgatt tatgaagtca ataagtggcc ctcaggagtt     180
tctcatcgct tctctggctc caaatctggc aacacggcct ccctgacaat ctctgggctc     240
caggctgagg acgaggctga ctattattgc tgctcattcg aggtagtgc cactgtrgtc      300 tgcggcggag ggaccaaggt gaccgtccta g                                    331

<210> SEQ ID NO 38
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
ctgcctgtgc tgactcagcc tgcctccgtg tctgggtctc ctgggcagtc gatcaccatc      60
tcctgcactg ggaccattta tgatgttggg aagtttgacc ttgtctcctg gtaccagcac     120
cacccaggca aagcccccaa atatttgatt tatgaagtca aaaagtggcc ctcaggagtt     180
tctcatcgct tctctggctc caaatctggc aacacggcct ccctgacaat ctctgggctc     240
caggttgagg acgaggctga ctattattgc tgctcattcg aggtagtgc cgctgtggtc      300 tgcggcggag ggaccaaggt gaccgtccta g                                    331

<210> SEQ ID NO 39
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
cagtctgccc tgactcagcc tgcctccgtg tctgggtctc ctggacagtc gatcaccatc      60
tcctgcactg gaaccagtta tgatgttgcg aagtttgacc ttgtctcctg gttccaacag     120
cacccaggca aagcccccaa atacatgatt tatgaagtca ataagtggcc ctcaggagtt     180
tctcatcgct tctctggttc caaatctggc aacacggcct ccctgacaat ctctgggctc     240
caggctgagg acgaggctga ctattattgc tgctcattcg aggtagtgc cactgtagtc      300 tgcggcggag ggaccaaggt gaccgtccta g                                    331

<210> SEQ ID NO 40
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
cagtctgccc tgactcagcc tgcctccgtg tctgggtctc ctggacagtc gatcaccatc      60
tcctgcactg gaaccaatta tgatgttggg agttataacc ttgtctcctg gtatcaacag     120
cacccaggca aagtccccaa atacataatt tatgaggtca ataagcggcc ctcagggstt     180
tctaatcgct tctctggctc caagtctggc aacacggcct ccctgacaat ctctgggctc     240
caggctgagg acgaggccac ttattactgt tgttcatatg caggtagtag cattatattc     300
```
ttcggcggtg ggaccaagct gaccgtcata g                                    331

<210> SEQ ID NO 41
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Any amino acid

<400> SEQUENCE: 41

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Val Xaa
            100

<210> SEQ ID NO 42
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (100)..(100)
<223> OTHER INFORMATION: Any amino acid

<400> SEQUENCE: 42

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Xaa Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Xaa Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

```
Gln Ala Glu Asp Glu Ala Asp Tyr Tyr Xaa Cys Ser Tyr Ala Gly Ser
                85                  90                  95

Ser Thr Val Xaa
            100

<210> SEQ ID NO 43
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (87)..(87)
<223> OTHER INFORMATION: Any amino acid

<400> SEQUENCE: 43

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Xaa Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Val Xaa Lys Trp Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Xaa Tyr Tyr Cys Ser Tyr Ala Gly Ser
                85                  90                  95

Ser Thr Val Ile
            100

<210> SEQ ID NO 44
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
                20                  25                  30

Asn Leu Val Ser Trp Tyr Gln Gln His Pro Gly Lys Ala Pro Lys Leu
            35                  40                  45

Ile Ile Tyr Glu Val Ser Gln Trp Pro Ser Gly Val Ser Lys Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala His Tyr Tyr Cys Ser Tyr Ala Gly Ser
                85                  90                  95
```

Ser Thr Val Ile
            100

<210> SEQ ID NO 45
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Pro Val Leu Thr Gln Pro Ala Ser Val Ser Gly Ser Pro Gly Gln
1               5                   10                  15

Ser Ile Thr Ile Ser Cys Thr Gly Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Asn Lys Trp Ala Ser Gly Val Ser Asp Arg Phe
    50                  55                  60

Ala Gly Ser Lys Ser Gly Asn Thr Ala Ser Leu Thr Ile Ser Arg Leu
65                  70                  75                  80

Gln Ala Glu Asp Glu Ala Asn Tyr Phe Cys Ser Ser Ser Thr Asn Ser
                85                  90                  95

Ala Thr Val Ile
            100

<210> SEQ ID NO 46
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (100)..(100)
<223> OTHER INFORMATION: Any amino acid

<400> SEQUENCE: 46

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asn Leu Val Ser Trp Tyr Gln Gln His Pro Gly Lys Ala Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Xaa Cys Ser Tyr Ala Gly Ser
                85                  90                  95

Ser Thr Val Xaa
            100

<210> SEQ ID NO 47
<211> LENGTH: 100

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (99)..(99)
<223> OTHER INFORMATION: Any amino acid

<400> SEQUENCE: 47

Gln Ser Xaa Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asp Leu Val Ser Trp Tyr Gln Gln His Pro Gly Lys Ala Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Gly Gly Ser
                85                  90                  95

Ala Thr Xaa Val
            100

<210> SEQ ID NO 48
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Thr Ser Leu Leu Thr Gln Pro Ala Ser Val Ser Gly Ser Pro Gly Gln
1               5                   10                  15

Ser Ile Thr Ile Ser Cys Thr Gly Thr Lys Tyr Asp Val Gly Ser His
            20                  25                  30

Asp Leu Val Ser Trp Tyr Gln Gln Tyr Pro Gly Lys Val Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Cys Ser Phe Gly Gly Ser
                85                  90                  95

Ala Thr Val Val
            100

<210> SEQ ID NO 49
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

<222> LOCATION: (3)..(3)
<223> OTHER INFORMATION: Any amino acid
<220> FEATURE:
<221> NAME/KEY: MOD_RES
<222> LOCATION: (99)..(99)
<223> OTHER INFORMATION: Any amino acid

<400> SEQUENCE: 49

Gln Ser Xaa Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Lys Phe
            20                  25                  30

Asp Leu Val Ser Trp Tyr Gln Gln His Pro Gly Lys Ala Pro Lys Tyr
        35                  40                  45

Met Ile Tyr Glu Val Asn Lys Trp Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Gly Gly Ser
                85                  90                  95

Ala Thr Xaa Val
            100

<210> SEQ ID NO 50
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Leu Pro Val Leu Thr Gln Pro Ala Ser Val Ser Gly Ser Pro Gly Gln
1               5                   10                  15

Ser Ile Thr Ile Ser Cys Thr Gly Thr Ile Tyr Asp Val Gly Lys Phe
            20                  25                  30

Asp Leu Val Ser Trp Tyr Gln His His Pro Gly Lys Ala Pro Lys Tyr
        35                  40                  45

Leu Ile Tyr Glu Val Lys Lys Trp Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Val Glu Asp Glu Ala Asp Tyr Tyr Cys Cys Ser Phe Gly Gly Ser
                85                  90                  95

Ala Ala Val Val
            100

<210> SEQ ID NO 51
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Ala Lys Phe
            20                  25                  30

Asp Leu Val Ser Trp Phe Gln Gln His Pro Gly Lys Ala Pro Lys Tyr
            35                  40                  45

Met Ile Tyr Glu Val Asn Lys Trp Pro Ser Gly Val Ser His Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Phe Gly Gly Ser
                 85                  90                  95

Ala Thr Val Val
            100

<210> SEQ ID NO 52
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ser Ala Leu Thr Gln Pro Ala Ser Val Ser Gly Ser Pro Gly Gln
1               5                   10                  15

Ser Ile Thr Ile Ser Cys Thr Gly Thr Asn Tyr Asp Val Gly Ser Tyr
                20                  25                  30

Asn Leu Val Ser Trp Tyr Gln Gln His Pro Gly Lys Val Pro Lys Tyr
            35                  40                  45

Ile Ile Tyr Glu Val Asn Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Thr Tyr Tyr Cys Cys Ser Tyr Ala Gly Ser
                 85                  90                  95

Ser Ile Ile Phe
            100

<210> SEQ ID NO 53
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gaggttcagc tggtggagtc tggggggaggc ttggtgaagc cggggggtc tcttagactc      60 cccggtgcag cctctggttt cactttcacc aacacgtgga tgagttgggt ccgtcaggcg     120
ccagggaagg gactggagtg ggtcggtcgg attagccgga acaaagatgg cgcgaaaaca     180
gagtacgccg cacccgtgag aggcagattc accatctcaa gagatgactc cagagacaca     240
ttgtatctgc agatgaccag cctgaaaata gaggattcag ccggtatttt tgcaccgca      300 gatcttgggg agcccgtggt gtcacgatcc atttttgagt ggggggtctta ttattattat     360 atggacctct ggggcaaggg gaccacggtc accgtctctt ca                         402

<210> SEQ ID NO 54
<211> LENGTH: 328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

| gacatccagt tgacccagtc tccatctccc ctgtctgcgt ctgtgggaga cacagtcact | 60 |
| atcacttgtc gggccagcca gaagattagc gactatttga actggtacca acagaagccg | 120 |
| gggagagccc ccaaaatact catttacgct gcgtccaagt tggggagtgg cgtcccatca | 180 |
| aggttcagtg gcagtggata tggcagagat ttcactctca ccatcaccgg tctgcagcct | 240 |
| gaagattttg caacctatta ttgtcaggag gcttacagtt ctactcccac gttaactttt | 300 |
| ggccagggga ccaggctgga tctcaaac | 328 |

<210> SEQ ID NO 55
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

| caggtgcagc tggtacagtc tgggggaggt ctggtgaagc cggggggtc cctcacactc | 60 |
| tcctgttcag cctctggatt cttttttcgat aattcatgga tggggtgggt ccgtcaggcg | 120 |
| ccagggaagg gactggagtg ggttggccgc attagaaggc tcaaagacgg tgcgacagga | 180 |
| gaatatggtg cagccgtgaa ggacagattc accatttcaa gagatgacag tagaaatatg | 240 |
| ctgtacctgc acatgaggac cctgaaaacc gaggactcag gcacttatta ttgtaccatg | 300 |
| gatgagggga ccccagtaac acgcttctta gaatggggct acttctatta ttatatggcc | 360 |
| gtttggggca gagggaccac ggtcatcgtc tcttca | 396 |

<210> SEQ ID NO 56
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

| gacatcgtga tgacccagtc tccgtcctcc gtgtctgcat ctgtgggaga cagagtcacc | 60 |
| atcacttgcc gggcaagtca gaatattaga gactatttaa attggtatca acataaaccc | 120 |
| gggggatccc ctagactcct aatttatgct gcgtcaactt tgcaaactgg ggtcccgtcc | 180 |
| agattcagcg gcagtggatc tgggaacctt ttcactctca ccattaccaa tctgcaacct | 240 |
| gaagattttg caacttatta ttgtcaagag aattataata ctatccctc gctcagcttt | 300 |
| ggtcagggga ccaaggtgga catcaggc | 328 |

<210> SEQ ID NO 57
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

| gaggttcagc tggtggagtc tgggggaggc ttggtgaagc cggggggtc tcttagactc | 60 |
| tcctgtgtag cctctggctt cactttcagc aacacgtgga tgagttgggt ccgtcaggcg | 120 |

```
ccagggaagg gactggagtg ggtcggtcgg attagccgga acaaagatgg cgcgaaaaca    180
gagtacgccg cacccgtgag aggcagattc accatctcaa gagatgactc cagagacaca    240
ttgtatctgc agatgagcag cctgaaaata gaggattcag gccggtattt ttgcaccgca    300
gatcttgggg aggccgttgt gtcacgattt tttgagtggg ggtcctatta ttactacatg    360
gacttctggg gcaaggggac cacggtcacc gtctcttca                           399

<210> SEQ ID NO 58
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gacattcaga tgacccaatc tccatctccc ctgtctgcgt ctgtgggaga cacagtcact     60
atcacttgcc gggccagcca gaagattagc gactatttga actggtacca acagaggccg    120
gggagagccc ccaagatcct catttacgct gcgtccaagt tggcaagcga cgtcccatca    180
agatttagtg gcagtggata tggcagagat ttcactctca ccataaccgg tctgcagcct    240
gaagattttg caacctatta ttgtcaggag gcttacagtt ctaccccac gttaactttt     300 ggccaggga ccaggctgga tctcaaac                                        328

<210> SEQ ID NO 59
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gaggtgcagc tggtggagtc tgggggcggc ttgataaagc cgggacagtc actcacacta     60
ttctgtgtgg gctttggatt caacttcgct aacgactgga tgggctgggt ccgccaggct    120
ccagggaagg gactggaatg ggttgggcgt ataaggagac tgaaagatgg tgcgaaagct    180
gaatatggat cttccgtgaa gggtagattc accatctcaa gggatgattc caaaaacacc    240
ctatacttgc acatgagcag cctcaaggtc gaagacacag ccgtctacta ttgcacccga    300 gacgagggg ccccagttac ccggtttctg gagtggggct cctattacta ctacatggcc    360
gtctggggca aagggaccac ggtcaccgtc tcttca                              396

<210> SEQ ID NO 60
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gacatccagt tgacccagtc tccagcctct ctgtctgcat ctgtaggaga cacagtgact     60
atcacttgcc gggcaagtca gagtataaaa gattacataa attggtatca acacaaatcc    120
gggagcgccc ctagactcct gatttatgct gcgtcaacct acaaagtgg aatctcgtca     180 aggttcactg gcagtgggtc tgggacacag ttcactctca ccattaacag tctgcaacct    240
gaagattttg cgacttatta ttgtcaagag gcttataaca ccaaccccac actctccttt    300
```
ggtcagggga ccagggtgga caagaagc           328

<210> SEQ ID NO 61
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gaggttcagc tggtggagtc tgggggcggc ttggtgaagc cgggacagtc actcacactt    60
tcctgtgtgg gctttggatt caatttcgct aacgactgga tgggctgggt ccgccaggct   120
ccagggaagg gactggaatg ggttggtcga ataaggagac taaaagacgg tgcgacaaca   180
gaatattctt catccgtgaa ggggagattc agtgtctcaa gagatgattc aaggaacaca   240
gtatacttac acatgagtag cctcaaagtc caggacattg gcgtctatta ttgtactcga   300
gacgaggggg ccccggttac tcgatttctg gagtggggct cctattacta ctatatggcc   360
gtctggggca gagggaccac ggtcaccgtc tcttca                             396

<210> SEQ ID NO 62
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
gacatccaga tgacccagtc tccaacctct ctgtctgcat ctgtaggaga cacagttgct    60
atcacttgcc gggcaagtca gagtgttaaa gattatgtga attggtatca acacaaatcc   120
gggagcgccc ctcgactcct gatttatgct gcctcagtct tacatactgg agtctcgtca   180
aggttcactg gcagtgggtc tgggacacag ttcactctca ccattagcag tctacaacct   240
gaagattttg ctacttatta ttgtcaagag gcttataaca cctatcccac actctccttt   300
ggtcagggga ccagggtgga caggaaac                                      328

<210> SEQ ID NO 63
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gaggttcagc tggtggagtc tggggggaggc ttggtgaagc cggggggggtc tcttagactc    60 tcctgtgtag cctctggctt cactttcagc aacacgtgga tgagttgggt ccgtcaggcg   120
ccagggaagg gactggagtg ggtcggtcgg attagccgga acaaagatgg cgcgaaaaca   180
gactacgccg cacccgtgag aggcagattc accatctcca gagatgactc cagagacaca   240
ttgtatctgc agatgagcag cctgaaaata gaggattcag ccggtatttt ttgcaccgca   300
gatcttgggg aggccgtggt gtcacgattt tttgagtggg ggtcctatta ttactacatg   360
gacttctggg gcaaggggac cacggtcacc gtctcttca                          399

<210> SEQ ID NO 64
<211> LENGTH: 328
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 64

```
gatattgtga tgacccagtc tccacctccc ctgtctgcgt ctgtgggaga cacagtcact    60
atcacttgcc gggccagcca aagattagc gactatttga actggtacca acagaggccg   120
gggagagccc ccaaaatact catttacgct gcgtccaagt tgggaagcga cgtcccatca   180
aggttcagtg gcagtggata tggcagagat ttcactctca ccatcaccgg tctgcagcct   240
gaagattttg caacctatta ttgtcaggag gcttacagtt ctactcccac gttaagtttt   300
ggccagggga ccaggctgga tctcaaac                                      328
```

<210> SEQ ID NO 65
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
gaaaggcagg tggtggaata tggggggaggc ttggtgaagc cggggggggtc tcttagactc    60 tcttgtttac cgtttgcctt tgggttcagg gcccccctgga ggagttctgt ccgtcacgcg   120
cctgggggcg gagcggagtg ggtcggtcgg attagccgga acaaagatgg cgcgaaaaca   180
gagtacgccg cacccgtgag aggcagattc accatctcaa gagatgactc cagagacaca   240
ttgtatctgc agatgaccag cctgaaaata gaggattcag gccggtattt tgcaccgca   300 gatcttgggg agcccgtggt gtcacgattt tttgagtggg ggtcttatta ttattatatg   360
gacctctggg gcaaggggac cacggtcacc gtctcttca                          399
```

<210> SEQ ID NO 66
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
tcttctgagc tgactcagga ccccactgtg tctgtggcct tgggccagac agtcaagatc    60
agatgccaag gagccagcct cagagactgt tatgcgacct ggtaccggca gaagccagga   120
caggccccaa cacttctcat ttatgatata aataagaggc cctcaggtat cccagaccga   180
ttctctgcct cctactcagg gagcacttct tccttgacca ttattggggc tcagccggaa   240
gatgaggctg actattttg tgcttcgcgg gacaggagtg gtgaccgtct ggcgtcttc    300 ggcggtggga ccaaactgac cgtcctg                                       327
```

<210> SEQ ID NO 67
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
cagctgcagg agtcgggtcc cagactggtg aggccttcgg agaccctgtc cctcacctgc    60
```

```
actgtatctg gctctggtgt ctccgtcagt cgtgggagtt attattgggg ctggatacgc    120
cagtccccag aaaagggact cgaatggatt ggaagtgtct attccactac tagtggaaaa    180
acctactaca acccgtccct caagagtcga gtcaccttttt cgaaggacac gtcccagaac    240
gccttctccc tgactctgac gtctattacc gccgcggaca cggccgtcta ttactgtgca    300
agacaatttg gcttcatggg gggcttttttg gagtggtatc cgcactattt tgacttctgg    360
ggcccgggaa tccaggtcgt cgtgtcttct                                     390
```

<210> SEQ ID NO 68
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
gacattgtga tgacccagtc tccatcctac ctgtctacat ctgtcggtga cagcatcacc     60
atcacttgcc gggcaagtca gagtattaaa acatatgtaa attggtatca acaaagacca    120
gggagagccc ctaaactcct catctattct tcatccactt gcaacctgg ggtcccgtca     180 agattcagcg ccagtggatc tgggacagat ttcgttctct ccatcaccaa tttgcagtct    240
gaagattttg caacttacta ctgtcaacag acctactaca cccctctac ttttggccag     300 gggaccacac tggacatcaa g                                              321
```

<210> SEQ ID NO 69
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
caggtgcagc tggtacagtc tggggctgag gtgaagaagc ctgggtcctc ggtcaaggtc     60
tcctgcaagg cctctggagg ctccttctac acctatacta tcaactgggt gcgacaggcc    120
cctggacaag gcttgagtg gatgggcagg gtcaccacta tgtttggtgt aacactttac     180
gcacagaaat tccagggcag agtcacactt accgcgaca aatccacgag cacagcctac     240
atggaactga gcagtctaag atctgaggac acggccgtct attattgtgc gacagatggg    300
cctgacaatt tttggagtgg cttgtctcat gctttcgatc tctggggcca ggggacaatg    360
gtcaccgtct cttca                                                     375
```

<210> SEQ ID NO 70
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
cagtctgccc tgactcagcc tgcctccgtg gctgggtctc ctggacagtc gatcaccatc     60
tcctgcactg gaaccagcag tgacattggt gattctaagt atgtctcctg gtaccaacag    120
ttcccaggca aagcccccaa agtcatgatt tatgaggtca gttatcggcc ctcaggagtc    180
tctagccgct tctctggctc caagtctggc aacacggcct ccctgaccat ctctggactc    240
```

```
cagactgagg acgaggctga ttattattgc atggcatata caggcacctt cactgctatt    300
ttcggcggag ggaccaagct gaccgtcctg                                     330
```

<210> SEQ ID NO 71
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
caggtgcagc tggtgcagtc tggggctgag gtgaggaagg ctgggtcgtc ggtgaaggtc    60
tcctgcaagg cttctggagg caccttcacc agctatggct tcagctggat acggcaggcc    120
cctggccaag ggcttgagtg gatgggaaac gtcatccctg tctttggttc aacaaactac    180
gcacagaaat ttcagggcag agtcagtatt accgcggacg aagccacggg cacagtccac    240
atggacctca ccagcctgac atctgacgac acggccgttt attactgtgt gaggtcgagt    300
agagaactgc caacgtcaat ggaacggtgg ttcgaccct ggggccaggg aacccaggtc    360
attgtctcct cg                                                        372
```

<210> SEQ ID NO 72
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
gacatccaga tgacccagtc tccatcctcc ctgtctgcat ctgtgggaga cagcgtcacc    60
attacttgcc gggcaagtca gagcattaac acctatttaa attggtatca gcagaaacca    120
gggaaggccc ctaaactcct gatctattct gcatccaatt tacacaatgg ggtcccatcg    180
aggttcagtg gcagtggatc tgggacatct ttcactctca ccatcaacaa tctacaacct    240
gaagattttg caacttacta ctgtcaacag agttacagtg ccccttacac ttttggccag    300
gggaccaagt cagacaccaa a                                              321
```

<210> SEQ ID NO 73
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Glu Val Gln Leu Val Glu Ser Gly Gly Gly Leu Val Lys Pro Gly Gly
1               5                   10                  15

Ser Leu Arg Leu Pro Gly Ala Ala Ser Gly Phe Thr Phe Thr Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80
```

```
Leu Tyr Leu Gln Met Thr Ser Leu Lys Ile Glu Asp Ser Gly Arg Tyr
                85                  90                  95

Phe Cys Thr Ala Asp Leu Gly Glu Pro Val Val Ser Arg Ser Ile Phe
            100                 105                 110

Glu Trp Gly Ser Tyr Tyr Tyr Met Asp Leu Trp Gly Lys Gly Thr
        115                 120                 125

Thr Val Thr Val Ser Ser
    130
```

<210> SEQ ID NO 74
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Asp Ile Gln Leu Thr Gln Ser Pro Ser Leu Ser Ala Ser Val Gly
1               5                   10                  15

Asp Thr Val Thr Ile Thr Cys Arg Ala Ser Gln Lys Ile Ser Asp Tyr
                20                  25                  30

Leu Asn Trp Tyr Gln Gln Lys Pro Gly Arg Ala Pro Lys Ile Leu Ile
            35                  40                  45

Tyr Ala Ala Ser Lys Leu Gly Ser Gly Val Pro Ser Arg Phe Ser Gly
50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105
```

<210> SEQ ID NO 75
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Asp Asn Ser
                20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Thr Gly Glu Tyr Gly Ala
50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
            115                 120                 125
```

Ile Val Ser Ser
    130

<210> SEQ ID NO 76
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Ser Pro Ser Val Ser Ala Ser Val Gly
1               5                   10                  15

Asp Arg Val Thr Ile Thr Cys Arg Ala Ser Gln Asn Ile Arg Asp Tyr
            20                  25                  30

Leu Asn Trp Tyr Gln His Lys Pro Gly Gly Ser Pro Arg Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Asn Leu Phe Thr Leu Thr Ile Thr Asn Leu Gln Pro
65                  70                  75                  80

Glu Asp Phe Ala Thr Tyr Tyr Cys Gln Glu Asn Tyr Asn Thr Ile Pro
                85                  90                  95

Ser Leu Ser Phe Gly Gln Gly Thr Lys Val Asp Ile Arg
            100                 105

<210> SEQ ID NO 77
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
        115                 120                 125

Val Thr Val Ser Ser
    130

<210> SEQ ID NO 78
<211> LENGTH: 111
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 78

Val Lys Asp Ile Gln Met Thr Gln Ser Pro Ser Pro Leu Ser Ala Ser
1               5                   10                  15

Val Gly Asp Thr Val Thr Ile Thr Cys Arg Ala Ser Gln Lys Ile Ser
            20                  25                  30

Asp Tyr Leu Asn Trp Tyr Gln Gln Arg Pro Gly Arg Ala Pro Lys Ile
        35                  40                  45

Leu Ile Tyr Ala Ala Ser Lys Leu Ala Ser Asp Val Pro Ser Arg Phe
50                  55                  60

Ser Gly Ser Gly Tyr Gly Arg Asp Phe Thr Leu Thr Ile Thr Gly Leu
65                  70                  75                  80

Gln Pro Glu Asp Phe Ala Thr Tyr Tyr Cys Gln Glu Ala Tyr Ser Ser
                85                  90                  95

Thr Pro Thr Leu Thr Phe Gly Gln Gly Thr Arg Leu Asp Leu Lys
            100                 105                 110

<210> SEQ ID NO 79
<211> LENGTH: 132
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 79

Glu Val Gln Leu Val Glu Ser Gly Gly Gly Leu Ile Lys Pro Gly Gln
1               5                   10                  15

Ser Leu Thr Leu Phe Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
50                  55                  60

Ser Val Lys Gly Arg Phe Thr Ile Ser Arg Asp Asp Ser Lys Asn Thr
65                  70                  75                  80

Leu Tyr Leu His Met Ser Ser Leu Lys Val Glu Asp Thr Ala Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Met Ala Val Trp Gly Lys Gly Thr Thr Val
        115                 120                 125

Thr Val Ser Ser
    130

<210> SEQ ID NO 80
<211> LENGTH: 109
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 80

Asp Ile Gln Leu Thr Gln Ser Pro Ala Ser Leu Ser Ala Ser Val Gly
1               5                   10                  15

Asp Thr Val Thr Ile Thr Cys Arg Ala Ser Gln Ser Ile Lys Asp Tyr

```
                 20                  25                  30

Ile Asn Trp Tyr Gln His Lys Ser Gly Ser Ala Pro Arg Leu Leu Ile
             35                  40                  45

Tyr Ala Ala Ser Thr Leu Gln Ser Gly Ile Ser Ser Arg Phe Thr Gly
         50                  55                  60

Ser Gly Ser Gly Thr Gln Phe Thr Leu Thr Ile Asn Ser Leu Gln Pro
 65                  70                  75                  80

Glu Asp Phe Ala Thr Tyr Tyr Cys Gln Glu Ala Tyr Asn Thr Asn Pro
                 85                  90                  95

Thr Leu Ser Phe Gly Gln Gly Thr Arg Val Asp Lys Lys
                100                 105

<210> SEQ ID NO 81
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Gly Gly Leu Val Lys Pro Gly Gln
 1               5                  10                  15

Ser Leu Thr Leu Ser Cys Val Gly Phe Gly Phe Asn Phe Ala Asn Asp
                 20                  25                  30

Trp Met Gly Trp Val Arg Gln Ala Pro Gly Lys Gly Leu Glu Trp Val
             35                  40                  45

Gly Arg Ile Arg Arg Leu Lys Asp Gly Ala Thr Thr Glu Tyr Ser Ser
         50                  55                  60

Ser Val Lys Gly Arg Phe Ser Val Ser Arg Asp Asp Ser Arg Asn Thr
 65                  70                  75                  80

Val Tyr Leu His Met Ser Ser Leu Lys Val Gln Asp Ile Gly Val Tyr
                 85                  90                  95

Tyr Cys Thr Arg Asp Glu Gly Ala Pro Val Thr Arg Phe Leu Glu Trp
                100                 105                 110

Gly Ser Tyr Tyr Tyr Met Ala Val Trp Gly Arg Gly Thr Thr Val
            115                 120                 125

Thr Val Ser Ser
        130

<210> SEQ ID NO 82
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Thr Ser Leu Ser Ala Ser Val Gly
 1               5                  10                  15

Asp Thr Val Ala Ile Thr Cys Arg Ala Ser Gln Ser Val Lys Asp Tyr
                 20                  25                  30

Val Asn Trp Tyr Gln His Lys Ser Gly Ser Ala Pro Arg Leu Leu Ile
             35                  40                  45

Tyr Ala Ala Ser Val Leu His Thr Gly Val Ser Ser Arg Phe Thr Gly
         50                  55                  60

Ser Gly Ser Gly Thr Gln Phe Thr Leu Thr Ile Ser Ser Leu Gln Pro
```

```
                65                  70                  75                  80
Glu Asp Phe Ala Thr Tyr Tyr Cys Gln Glu Ala Tyr Asn Thr Tyr Pro
                    85                  90                  95

Thr Leu Ser Phe Gly Gln Gly Thr Arg Val Asp Arg Lys
                100                 105

<210> SEQ ID NO 83
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
                20                  25                  30

Trp Met Ser Trp Val Arg Gln Ala Pro Gly Lys Gly Leu Glu Trp Val
            35                  40                  45

Gly Arg Ile Ser Arg Asn Lys Asp Gly Ala Lys Thr Asp Tyr Ala Ala
        50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
                100                 105                 110

Trp Gly Ser Tyr Tyr Tyr Tyr Met Asp Phe Trp Gly Lys Gly Thr Thr
            115                 120                 125

Val Thr Val Ser Ser
        130

<210> SEQ ID NO 84
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Val Met Thr Gln Ser Pro Pro Leu Ser Ala Ser Val Gly
1               5                   10                  15

Asp Thr Val Thr Ile Thr Cys Arg Ala Ser Gln Lys Ile Ser Asp Tyr
                20                  25                  30

Leu Asn Trp Tyr Gln Gln Arg Pro Gly Arg Ala Pro Lys Ile Leu Ile
            35                  40                  45

Tyr Ala Ala Ser Lys Leu Gly Ser Asp Val Pro Ser Arg Phe Ser Gly
        50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Ser Phe Gly Gln Gly Thr Arg Leu Asp Leu Lys
                100                 105
```

<210> SEQ ID NO 85
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Glu Arg Gln Val Val Glu Tyr Gly Gly Gly Leu Val Lys Pro Gly Gly
1               5                   10                  15

Ser Leu Arg Leu Ser Cys Leu Pro Phe Ala Phe Gly Phe Arg Ala Pro
                20                  25                  30

Trp Arg Ser Ser Val Arg His Ala Pro Gly Gly Gly Ala Glu Trp Val
            35                  40                  45

Gly Arg Ile Ser Arg Asn Lys Asp Gly Ala Lys Thr Glu Tyr Ala Ala
        50                  55                  60

Pro Val Arg Gly Arg Phe Thr Ile Ser Arg Asp Asp Ser Arg Asp Thr
65                  70                  75                  80

Leu Tyr Leu Gln Met Thr Ser Leu Lys Ile Glu Asp Ser Gly Arg Tyr
                85                  90                  95

Phe Cys Thr Ala Asp Leu Gly Glu Pro Val Val Ser Arg Phe Phe Glu
                100                 105                 110

Trp Gly Ser Tyr Tyr Tyr Tyr Met Asp Leu Trp Gly Lys Gly Thr Thr
            115                 120                 125

Val Thr Val Ser Ser
        130
```

<210> SEQ ID NO 86
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Ser Ser Glu Leu Thr Gln Asp Pro Thr Val Ser Val Ala Leu Gly Gln
1               5                   10                  15

Thr Val Lys Ile Arg Cys Gln Gly Ala Ser Leu Arg Asp Cys Tyr Ala
                20                  25                  30

Thr Trp Tyr Arg Gln Lys Pro Gly Gln Ala Pro Thr Leu Leu Ile Tyr
            35                  40                  45

Asp Ile Asn Lys Arg Pro Ser Gly Ile Pro Asp Arg Phe Ser Ala Ser
        50                  55                  60

Tyr Ser Gly Ser Thr Ser Ser Leu Thr Ile Ile Gly Ala Gln Pro Glu
65                  70                  75                  80

Asp Glu Ala Asp Tyr Phe Cys Ala Ser Arg Asp Arg Ser Gly Asp Arg
                85                  90                  95

Leu Gly Val Phe Gly Gly Gly Thr Lys Leu Thr Val Leu
            100                 105
```

<210> SEQ ID NO 87
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Leu Gln Glu Ser Gly Pro Arg Leu Val Arg Pro Ser Glu Thr Leu
1               5                   10                  15

Ser Leu Thr Cys Thr Val Ser Gly Val Ser Val Ser Arg Gly
            20                  25                  30

Ser Tyr Tyr Trp Gly Trp Ile Arg Gln Ser Pro Glu Lys Gly Leu Glu
            35                  40                  45

Trp Ile Gly Ser Val Tyr Ser Thr Thr Ser Gly Lys Thr Tyr Tyr Asn
50                  55                  60

Pro Ser Leu Lys Ser Arg Val Thr Phe Ser Lys Asp Thr Ser Gln Asn
65                  70                  75                  80

Ala Phe Ser Leu Thr Leu Thr Ser Ile Thr Ala Ala Asp Thr Ala Val
            85                  90                  95

Tyr Tyr Cys Ala Arg Gln Phe Gly Phe Met Gly Gly Phe Leu Glu Trp
            100                 105                 110

Tyr Pro His Tyr Phe Asp Phe Trp Gly Pro Gly Ile Gln Val Val Val
            115                 120                 125

Ser Ser
    130

<210> SEQ ID NO 88
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Tyr Thr Tyr
            20                  25                  30

Thr Ile Asn Trp Val Arg Gln Ala Pro Gly Gln Gly Leu Glu Trp Met
            35                  40                  45

Gly Arg Val Thr Thr Met Phe Gly Val Thr Leu Tyr Ala Gln Lys Phe
50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Thr Asp Gly Pro Asp Asn Phe Trp Ser Gly Leu Ser His Ala Phe
            100                 105                 110

Asp Leu Trp Gly Gln Gly Thr Met Val Thr Val Ser Ser
            115                 120                 125

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Val Met Thr Gln Ser Pro Ser Tyr Leu Ser Thr Ser Val Gly
1               5                   10                  15

Asp Ser Ile Thr Ile Thr Cys Arg Ala Ser Gln Ser Ile Lys Thr Tyr
            20                  25                  30

```
Val Asn Trp Tyr Gln Gln Arg Pro Gly Arg Ala Pro Lys Leu Leu Ile
        35                  40                  45

Tyr Ser Ser Ser Thr Leu Gln Pro Gly Val Pro Ser Arg Phe Ser Ala
 50                  55                  60

Ser Gly Ser Gly Thr Asp Phe Val Leu Ser Ile Thr Asn Leu Gln Ser
65                  70                  75                  80

Glu Asp Phe Ala Thr Tyr Tyr Cys Gln Gln Thr Tyr Tyr Thr Pro Ser
                85                  90                  95

Thr Phe Gly Gln Gly Thr Thr Leu Asp Ile Lys
                100                 105

<210> SEQ ID NO 90
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Tyr Thr Tyr
            20                  25                  30

Thr Ile Asn Trp Val Arg Gln Ala Pro Gly Gln Gly Leu Glu Trp Met
        35                  40                  45

Gly Arg Val Thr Thr Met Phe Gly Val Thr Leu Tyr Ala Gln Lys Phe
 50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Pro Asp Asn Phe Trp Ser Gly Leu Ser His Ala Phe
                100                 105                 110

Asp Leu Trp Gly Gln Gly Thr Met Val Thr Val Ser Ser
            115                 120                 125

<210> SEQ ID NO 91
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Ser Ala Leu Thr Gln Pro Ala Ser Val Ala Gly Ser Pro Gly Gln
1               5                   10                  15

Ser Ile Thr Ile Ser Cys Thr Gly Thr Ser Ser Asp Ile Gly Asp Ser
            20                  25                  30

Lys Tyr Val Ser Trp Tyr Gln Gln Phe Pro Gly Lys Ala Pro Lys Val
        35                  40                  45

Met Ile Tyr Glu Val Ser Tyr Arg Pro Ser Gly Val Ser Ser Arg Phe
 50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Met Ala Thr Gly Thr
                85                  90                  95
```

Phe Thr Ala Ile Phe Gly Gly Gly Thr Lys Leu Thr Val Leu
            100                 105                 110

<210> SEQ ID NO 92
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Val Gln Ser Gly Ala Glu Val Arg Lys Ala Gly Ser
1               5                   10                  15

Ser Val Lys Val Ser Cys Lys Ala Ser Gly Gly Thr Phe Thr Ser Tyr
            20                  25                  30

Gly Phe Ser Trp Ile Arg Gln Ala Pro Gly Gln Gly Leu Glu Trp Met
        35                  40                  45

Gly Asn Val Ile Pro Val Phe Gly Ser Thr Asn Tyr Ala Gln Lys Phe
    50                  55                  60

Gln Gly Arg Val Ser Ile Thr Ala Asp Glu Ala Thr Gly Thr Val His
65                  70                  75                  80

Met Asp Leu Thr Ser Leu Thr Ser Asp Thr Ala Val Tyr Tyr Cys
                85                  90                  95

Val Arg Ser Ser Arg Glu Leu Pro Thr Ser Met Glu Arg Trp Phe Asp
            100                 105                 110

Pro Trp Gly Gln Gly Thr Gln Val Ile Val Ser Ser
        115                 120

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Ser Ile Asn Thr Tyr
            20                  25                  30

Leu Asn Trp Tyr Gln Gln Lys Pro Gly Lys Ala Pro Lys Leu Leu Ile
        35                  40                  45

Tyr Ser Ala Ser Asn Leu His Asn Gly Val Pro Ser Arg Phe Ser Gly
    50                  55                  60

Ser Gly Ser Gly Thr Ser Phe Thr Leu Thr Ile Asn Asn Leu Gln Pro
65                  70                  75                  80

Glu Asp Phe Ala Thr Tyr Tyr Cys Gln Gln Ser Tyr Ser Ala Pro Tyr
                85                  90                  95

Thr Phe Gly Gln Gly Thr Lys Ser Asp Thr Lys
            100                 105

<210> SEQ ID NO 94
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Lys Pro Gly Gly
1               5                   10                  15

Ser Leu Arg Leu Pro Gly Ala Ala Ser Gly Phe Thr Phe Thr Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
50                  55                  60

Pro Val Arg Gly Arg Phe Thr Ile Ser Arg Asp Asp Ser Arg Asp Thr
65                  70                  75                  80

Leu Tyr Leu Gln Met Thr Ser Leu Lys Ile Glu Asp Ser Gly Arg Tyr
                85                  90                  95

Phe Cys Thr Ala Asp Leu Gly Glu Pro Val Ser Arg Ser Ile Phe
            100                 105                 110

Glu Trp Gly Ser Tyr Tyr Tyr Met Asp Leu Trp Gly Lys Gly Thr
        115                 120                 125

Thr Val Thr Val Ser Ser
    130

<210> SEQ ID NO 95
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Met Ala Val Trp Gly Arg Gly Thr Thr Val
        115                 120                 125

Ile Val Ser Ser
    130

<210> SEQ ID NO 96
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
                115                 120                 125

Val Thr Val Ser Ser
    130

<210> SEQ ID NO 97
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Val Glu Ser Gly Gly Gly Leu Ile Lys Pro Gly Gln
1               5                   10                  15

Ser Leu Thr Leu Phe Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Lys Ala Glu Tyr Gly Ser
    50                  55                  60

Ser Val Lys Gly Arg Phe Thr Ile Ser Arg Asp Asp Ser Lys Asn Thr
65                  70                  75                  80

Leu Tyr Leu His Met Ser Ser Leu Lys Val Glu Asp Thr Ala Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Lys Gly Thr Thr Val
                115                 120                 125

Thr Val Ser Ser
    130

<210> SEQ ID NO 98
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Val Glu Ser Gly Gly Gly Leu Val Lys Pro Gly Gln
1               5                   10                  15

```
Ser Leu Thr Leu Ser Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Thr Glu Tyr Ser Ser
 50                  55                  60

Ser Val Lys Gly Arg Phe Ser Val Ser Arg Asp Asp Ser Arg Asn Thr
65                  70                  75                  80

Val Tyr Leu His Met Ser Ser Leu Lys Val Gln Asp Ile Gly Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Met Ala Val Trp Gly Arg Gly Thr Thr Val
            115                 120                 125

Thr Val Ser Ser
        130
```

```
<210> SEQ ID NO 99
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Asp Tyr Ala Ala
 50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Met Asp Phe Trp Gly Lys Gly Thr Thr
            115                 120                 125

Val Thr Val Ser Ser
130
```

```
<210> SEQ ID NO 100
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Leu Thr Gln Ser Pro Ser Pro Leu Ser Ala Ser Val Gly
1               5                   10                  15

Asp Thr Val Thr Ile Thr Cys Arg Ala Ser Gln Lys Ile Ser Asp Tyr
            20                  25                  30
```

Leu Asn Trp Tyr Gln Gln Lys Pro Gly Arg Ala Pro Lys Ile Leu Ile
            35                  40                  45

Tyr Ala Ala Ser Lys Leu Gly Ser Gly Val Pro Ser Arg Phe Ser Gly
 50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105

<210> SEQ ID NO 101
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Val Met Thr Gln Ser Pro Ser Ser Val Ser Ala Ser Val Gly
1               5                   10                  15

Asp Arg Val Thr Ile Thr Cys Arg Ala Ser Gln Asn Ile Arg Asp Tyr
            20                  25                  30

Leu Asn Trp Tyr Gln His Lys Pro Gly Ser Pro Arg Leu Leu Ile
            35                  40                  45

Tyr Ala Ala Ser Thr Leu Gln Thr Gly Val Pro Ser Arg Phe Ser Gly
 50                  55                  60

Ser Gly Ser Gly Asn Leu Phe Thr Leu Thr Ile Thr Asn Leu Gln Pro
65                  70                  75                  80

Glu Asp Phe Ala Thr Tyr Tyr Cys Gln Glu Asn Tyr Asn Thr Ile Pro
                85                  90                  95

Ser Leu Ser Phe Gly Gln Gly Thr Lys Val Asp Ile Arg
            100                 105

<210> SEQ ID NO 102
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Gln Met Thr Gln Ser Pro Ser Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Arg Pro Gly Arg Ala Pro Lys Ile Leu Ile
            35                  40                  45

Tyr Ala Ala Ser Lys Leu Ala Ser Asp Val Pro Ser Arg Phe Ser Gly
 50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105

```
<210> SEQ ID NO 103
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Leu Thr Gln Ser Pro Ala Ser Leu Ser Ala Ser Val Gly
1               5                   10                  15

Asp Thr Val Thr Ile Thr Cys Arg Ala Ser Gln Ser Ile Lys Asp Tyr
            20                  25                  30

Ile Asn Trp Tyr Gln His Lys Ser Gly Ser Ala Pro Arg Leu Leu Ile
        35                  40                  45

Tyr Ala Ala Ser Thr Leu Gln Ser Gly Ile Ser Ser Arg Phe Thr Gly
    50                  55                  60

Ser Gly Ser Gly Thr Gln Phe Thr Leu Thr Ile Asn Ser Leu Gln Pro
65                  70                  75                  80

Glu Asp Phe Ala Thr Tyr Tyr Cys Gln Glu Ala Tyr Asn Thr Asn Pro
                85                  90                  95

Thr Leu Ser Phe Gly Gln Gly Thr Arg Val Asp Lys Lys
            100                 105

<210> SEQ ID NO 104
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Thr Ser Leu Ser Ala Ser Val Gly
1               5                   10                  15

Asp Thr Val Ala Ile Thr Cys Arg Ala Ser Gln Ser Val Lys Asp Tyr
            20                  25                  30

Val Asn Trp Tyr Gln His Lys Ser Gly Ser Ala Pro Arg Leu Leu Ile
        35                  40                  45

Tyr Ala Ala Ser Val Leu His Thr Gly Val Ser Ser Arg Phe Thr Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln Glu Ala Tyr Asn Thr Tyr Pro
                85                  90                  95

Thr Leu Ser Phe Gly Gln Gly Thr Arg Val Asp Arg Lys
            100                 105

<210> SEQ ID NO 105
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asp Ile Val Met Thr Gln Ser Pro Pro Leu Ser Ala Ser Val Gly
1               5                   10                  15

Asp Thr Val Thr Ile Thr Cys Arg Ala Ser Gln Lys Ile Ser Asp Tyr
```

```
                 20                  25                  30

Leu Asn Trp Tyr Gln Gln Arg Pro Gly Arg Ala Pro Lys Ile Leu Ile
             35                  40                  45

Tyr Ala Ala Ser Lys Leu Gly Ser Asp Val Pro Ser Arg Phe Ser Gly
         50                  55                  60

Ser Gly Tyr Gly Arg Asp Phe Thr Leu Thr Ile Thr Gly Leu Gln Pro
 65                  70                  75                  80

Glu Asp Phe Ala Thr Tyr Tyr Cys Gln Glu Ala Tyr Ser Ser Thr Pro
                 85                  90                  95

Thr Leu Ser Phe Gly Gln Gly Thr Arg Leu Asp Leu Lys
            100                 105

<210> SEQ ID NO 106
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Gln Leu Val Glu Ser Gly Gly Gly Leu Val Lys Pro Gly Gly
 1               5                  10                  15

Ser Leu Arg Leu Pro Gly Ala Ala Ser Gly Phe Thr Phe Thr Asn Thr
             20                  25                  30

Trp Met Ser Trp Val Arg Gln Ala Pro Gly Lys Gly Leu Glu Trp Val
         35                  40                  45

Gly Arg Ile Ser Arg Asn Lys Asp Gly Ala Lys Thr Glu Tyr Ala Ala
     50                  55                  60

Pro Val Arg Gly Arg Phe Thr Ile Ser Arg Asp Asp Ser Arg Asp Thr
 65                  70                  75                  80

Leu Tyr Leu Gln Met Thr Ser Leu Lys Ile Glu Asp Ser Gly Arg Tyr
                 85                  90                  95

Phe Cys Thr Ala Asp Leu Gly Glu Pro Val Val Ser Arg Ser Ile Phe
            100                 105                 110

Glu Trp Gly Ser Tyr Tyr Tyr Met Asp Leu Trp Gly Lys Gly Thr
        115                 120                 125

Thr Val Thr Val Ser Ser
        130

<210> SEQ ID NO 107
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Gln Ser Gly Gly Gly Leu Val Lys Pro Gly Gly
 1               5                  10                  15

Ser Leu Thr Leu Ser Cys Ser Ala Ser Gly Phe Phe Phe Asp Asn Ser
             20                  25                  30

Trp Met Gly Trp Val Arg Gln Ala Pro Gly Lys Gly Leu Glu Trp Val
         35                  40                  45

Gly Arg Ile Arg Arg Leu Lys Asp Gly Ala Thr Gly Glu Tyr Gly Ala
     50                  55                  60

Ala Val Lys Asp Arg Phe Thr Ile Ser Arg Asp Asp Ser Arg Asn Met
```

```
            65                  70                  75                  80
Leu Tyr Leu His Met Arg Thr Leu Lys Thr Glu Asp Ser Gly Thr Tyr
                    85                  90                  95
Tyr Cys Thr Met Asp Glu Gly Thr Pro Val Thr Arg Phe Leu Glu Trp
                    100                 105                 110
Gly Tyr Phe Tyr Tyr Met Ala Val Trp Gly Arg Gly Thr Thr Val
                    115                 120                 125
Ile Val Ser Ser
        130

<210> SEQ ID NO 108
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Gln Leu Val Glu Ser Gly Gly Gly Leu Val Lys Pro Gly Gly
1               5                   10                  15
Ser Leu Arg Leu Ser Cys Val Ala Ser Gly Phe Thr Phe Ser Asn Thr
                20                  25                  30
Trp Met Ser Trp Val Arg Gln Ala Pro Gly Lys Gly Leu Glu Trp Val
            35                  40                  45
Gly Arg Ile Ser Arg Asn Lys Asp Gly Ala Lys Thr Glu Tyr Ala Ala
        50                  55                  60
Pro Val Arg Gly Arg Phe Thr Ile Ser Arg Asp Ser Arg Asp Thr
65                  70                  75                  80
Leu Tyr Leu Gln Met Ser Ser Leu Lys Ile Glu Asp Ser Gly Arg Tyr
                85                  90                  95
Phe Cys Thr Ala Asp Leu Gly Glu Ala Val Val Ser Arg Phe Phe Glu
                100                 105                 110
Trp Gly Ser Tyr Tyr Tyr Tyr Met Asp Phe Trp Gly Lys Gly Thr Thr
            115                 120                 125
Val Thr Val Ser Ser
        130

<210> SEQ ID NO 109
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Glu Ser Gly Gly Gly Leu Ile Lys Pro Gly Gln
1               5                   10                  15
Ser Leu Thr Leu Phe Cys Val Gly Phe Gly Phe Asn Phe Ala Asn Asp
                20                  25                  30
Trp Met Gly Trp Val Arg Gln Ala Pro Gly Lys Gly Leu Glu Trp Val
            35                  40                  45
Gly Arg Ile Arg Arg Leu Lys Asp Gly Ala Lys Ala Glu Tyr Gly Ser
        50                  55                  60
Ser Val Lys Gly Arg Phe Thr Ile Ser Arg Asp Asp Ser Lys Asn Thr
65                  70                  75                  80
Leu Tyr Leu His Met Ser Ser Leu Lys Val Glu Asp Thr Ala Val Tyr
```

```
            85                  90                  95
Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Lys Gly Thr Thr Val
        115                 120                 125

Thr Val Ser Ser
    130

<210> SEQ ID NO 110
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Val Glu Ser Gly Gly Gly Leu Val Lys Pro Gly Gln
1               5                   10                  15

Ser Leu Thr Leu Ser Cys Val Gly Phe Gly Phe Asn Phe Ala Asn Asp
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Thr Glu Tyr Ser Ser
    50                  55                  60

Ser Val Lys Gly Arg Phe Ser Val Ser Arg Asp Asp Ser Arg Asn Thr
65                  70                  75                  80

Val Tyr Leu His Met Ser Ser Leu Lys Val Gln Asp Ile Gly Val Tyr
                85                  90                  95

Tyr Cys Thr Arg Asp Glu Gly Ala Pro Val Thr Arg Phe Leu Glu Trp
            100                 105                 110

Gly Ser Tyr Tyr Tyr Tyr Met Ala Val Trp Gly Arg Gly Thr Thr Val
        115                 120                 125

Thr Val Ser Ser
    130

<210> SEQ ID NO 111
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Asp Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
```

```
                100             105                 110
Trp Gly Ser Tyr Tyr Tyr Tyr Met Asp Phe Trp Gly Lys Gly Thr Thr
            115                 120                 125

Val Thr Val Ser Ser
    130

<210> SEQ ID NO 112
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125

Val Ser Ser
    130

<210> SEQ ID NO 113
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Gln Ser Gly Ala Glu Val Lys Arg Pro Gly Ser
1               5                   10                  15

Ser Val Thr Val Ser Cys Lys Ala Ser Gly Gly Ser Phe Ser Thr Tyr
            20                  25                  30

Ala Leu Ser Trp Val Arg Gln Ala Pro Gly Arg Gly Leu Glu Trp Met
        35                  40                  45

Gly Gly Val Ile Pro Leu Leu Thr Ile Thr Asn Tyr Ala Pro Arg Phe
    50                  55                  60

Gln Gly Arg Ile Thr Ile Thr Ala Asp Arg Ser Thr Ser Thr Ala Tyr
65                  70                  75                  80

Leu Glu Leu Asn Ser Leu Arg Pro Glu Asp Thr Ala Val Tyr Tyr Cys
                85                  90                  95

Ala Arg Glu Gly Thr Thr Gly Trp Gly Trp Leu Gly Lys Pro Ile Gly
            100                 105                 110

Ala Phe Ala His Trp Gly Gln Gly Thr Leu Val Thr Val Ser Ser
```

```
                    115                 120                 125

<210> SEQ ID NO 114
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Arg Ile Thr Leu Lys Glu Ser Gly Pro Pro Leu Val Lys Pro Thr Gln
1               5                   10                  15

Thr Leu Thr Leu Thr Cys Ser Phe Ser Gly Phe Ser Leu Ser Asp Phe
            20                  25                  30

Gly Val Gly Val Gly Trp Ile Arg Gln Pro Pro Gly Lys Ala Leu Glu
        35                  40                  45

Trp Leu Ala Ile Ile Tyr Ser Asp Asp Lys Arg Tyr Ser Pro Ser
    50                  55                  60

Leu Asn Thr Arg Leu Thr Ile Thr Lys Asp Thr Ser Lys Asn Gln Val
65              70                  75                  80

Val Leu Val Met Thr Arg Val Ser Pro Val Asp Thr Ala Thr Tyr Phe
                85                  90                  95

Cys Ala His Arg Arg Gly Pro Thr Thr Leu Phe Gly Val Pro Ile Ala
            100                 105                 110

Arg Gly Pro Val Asn Ala Met Asp Val Trp Gly Gln Gly Ile Thr Val
        115                 120                 125

Thr Ile Ser Ser
    130

<210> SEQ ID NO 115
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Asp Ile Gln Leu Thr Gln Ser Pro Ser Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Lys Pro Gly Arg Ala Pro Lys Ile Leu Ile
        35                  40                  45

Tyr Ala Ala Ser Lys Leu Gly Ser Gly Val Pro Ser Arg Phe Ser Gly
    50                  55                  60

Ser Gly Tyr Gly Arg Asp Phe Thr Leu Thr Ile Thr Gly Leu Gln Pro
65              70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105

<210> SEQ ID NO 116
<211> LENGTH: 109
<212> TYPE: PRT
<213> ORGANISM: Artificial Sequence
<220> FEATURE:
<223> OTHER INFORMATION: Description of Artificial Sequence: Synthetic
```

-continued

```
      polypeptide

<400> SEQUENCE: 116

Asp Ile Val Met Thr Gln Ser Pro Ser Ser Val Ser Ala Ser Val Gly
1               5                   10                  15

Asp Arg Val Thr Ile Thr Cys Arg Ala Ser Gln Asn Ile Arg Asp Tyr
            20                  25                  30

Leu Asn Trp Tyr Gln His Lys Pro Gly Gly Ser Pro Arg Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Asn Leu Phe Thr Leu Thr Ile Thr Asn Leu Gln Pro
65                  70                  75                  80

Glu Asp Phe Ala Thr Tyr Tyr Cys Gln Glu Asn Tyr Asn Thr Ile Pro
                85                  90                  95

Ser Leu Ser Phe Gly Gln Gly Thr Lys Val Asp Ile Arg
            100                 105

<210> SEQ ID NO 117
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asp Ile Gln Met Thr Gln Ser Pro Ser Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Arg Pro Gly Arg Ala Pro Lys Ile Leu Ile
        35                  40                  45

Tyr Ala Ala Ser Lys Leu Ala Ser Asp Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105

<210> SEQ ID NO 118
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Leu Thr Gln Ser Pro Ala Ser Leu Ser Ala Ser Val Gly
1               5                   10                  15

Asp Thr Val Thr Ile Thr Cys Arg Ala Ser Gln Ser Ile Lys Asp Tyr
            20                  25                  30

Ile Asn Trp Tyr Gln His Lys Ser Gly Ser Ala Pro Arg Leu Leu Ile
        35                  40                  45

Tyr Ala Ala Ser Thr Leu Gln Ser Gly Ile Ser Ser Arg Phe Thr Gly
    50                  55                  60
```

Ser Gly Ser Gly Thr Gln Phe Thr Leu Thr Ile Asn Ser Leu Gln Pro
65                  70                  75                  80

Glu Asp Phe Ala Thr Tyr Tyr Cys Gln Glu Ala Tyr Asn Thr Asn Pro
                85                  90                  95

Thr Leu Ser Phe Gly Gln Gly Thr Arg Val Asp Lys Lys
            100                 105

<210> SEQ ID NO 119
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Gln Met Thr Gln Ser Pro Thr Ser Leu Ser Ala Ser Val Gly
1               5                   10                  15

Asp Thr Val Ala Ile Thr Cys Arg Ala Ser Gln Ser Val Lys Asp Tyr
            20                  25                  30

Val Asn Trp Tyr Gln His Lys Ser Gly Ser Ala Pro Arg Leu Leu Ile
        35                  40                  45

Tyr Ala Ala Ser Val Leu His Thr Gly Val Ser Ser Arg Phe Thr Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln Glu Ala Tyr Asn Thr Tyr Pro
                85                  90                  95

Thr Leu Ser Phe Gly Gln Gly Thr Arg Val Asp Arg Lys
            100                 105

<210> SEQ ID NO 120
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Ile Val Met Thr Gln Ser Pro Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Arg Pro Gly Arg Ala Pro Lys Ile Leu Ile
        35                  40                  45

Tyr Ala Ala Ser Lys Leu Gly Ser Asp Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Ser Phe Gly Gln Gly Thr Arg Leu Asp Leu Lys
            100                 105

<210> SEQ ID NO 121
<211> LENGTH: 108
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 121

Glu Ile Val Leu Thr Gln Ser Pro Gly Thr Gln Ser Leu Ser Pro Gly
1               5                   10                  15

Glu Arg Ala Thr Leu Ser Cys Arg Ala Ser Gln Ser Val Gly Asn Asn
            20                  25                  30

Lys Leu Ala Trp Tyr Gln Gln Arg Pro Gly Gln Ala Pro Arg Leu Leu
        35                  40                  45

Ile Tyr Gly Ala Ser Ser Arg Pro Ser Gly Val Ala Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Gln Ser Leu
                85                  90                  95

Ser Thr Phe Gly Gln Gly Thr Lys Val Glu Val Lys
            100                 105

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Leu Gln Leu Thr Gln Ser Pro Ser Ser Leu Ser Ala Ser Val Gly
1               5                   10                  15

Asp Arg Ile Thr Ile Thr Cys Arg Ala Ser Gln Gly Val Thr Ser Ala
            20                  25                  30

Leu Ala Trp Tyr Arg Gln Lys Pro Gly Ser Pro Pro Gln Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Thr Leu Arg Pro
65                  70                  75                  80

Glu Asp Phe Ala Thr Tyr Tyr Cys Gln Gln Leu His Phe Tyr Pro His
                85                  90                  95

Thr Phe Gly Gly Gly Thr Arg Val Asp Val Arg
            100                 105

<210> SEQ ID NO 123
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Ile Leu Leu Phe Tyr
        35                  40                  45
```

```
Gly Lys Asn Asn Arg Pro Ser Gly Val Pro Asp Arg Phe Ser Gly Ser
    50                  55                  60
Ala Ser Gly Asn Arg Ala Ser Leu Thr Ile Ser Gly Ala Gln Ala Glu
 65                  70                  75                  80
Asp Asp Ala Glu Tyr Tyr Cys Ser Ser Arg Asp Lys Ser Gly Ser Arg
                 85                  90                  95
Leu Ser Val Phe Gly Gly Gly Thr Lys Leu Thr Val Leu
            100                 105
```

<210> SEQ ID NO 124
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Gln Val Arg Leu Ala Gln Tyr Gly Gly Val Lys Arg Leu Gly Ala
 1               5                  10                  15
Thr Met Thr Leu Ser Cys Val Ala Ser Gly Tyr Thr Phe Asn Asp Tyr
                20                  25                  30
Tyr Ile His Trp Val Arg Gln Ala Pro Gly Gln Gly Phe Glu Leu Leu
                35                  40                  45
Gly Tyr Ile Asp Pro Ala Asn Gly Arg Pro Tyr Ala Gly Ala Leu
    50                  55                  60
Arg Glu Arg Leu Ser Phe Tyr Arg Asp Lys Ser Met Glu Thr Leu Tyr
 65                  70                  75                  80
Met Asp Leu Arg Ser Leu Arg Tyr Asp Thr Ala Met Tyr Tyr Cys
                 85                 90                   95
Val Arg Asn Val Gly Thr Ala Gly Ser Leu Leu His Tyr Asp His Trp
                100                 105                 110
Gly Ser Gly Ser Pro Val Ile Val Ser Ser
            115                 120
```

<210> SEQ ID NO 125
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Glu Ile Val Leu Thr Gln Ser Pro Ala Thr Leu Ser Ala Ser Pro Gly
 1               5                  10                  15
Glu Arg Val Thr Leu Thr Cys Arg Ala Ser Arg Ser Val Arg Asn Asn
                20                  25                  30
Val Ala Trp Tyr Gln His Lys Gly Gly Gln Ser Pro Arg Leu Leu Ile
                35                  40                  45
Tyr Asp Ala Ser Thr Arg Ala Ala Gly Val Pro Ala Arg Phe Ser Gly
    50                  55                  60
Ser Ala Ser Gly Thr Glu Phe Thr Leu Ala Ile Ser Asn Leu Glu Ser
 65                  70                  75                  80
Glu Asp Phe Thr Val Tyr Phe Cys Leu Gln Tyr Asn Asn Trp Trp Thr
                 85                 90                   95
Phe Gly Gln Gly Thr Arg Val Asp Ile Lys
            100                 105
```

<210> SEQ ID NO 126
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

```
caggtccgac tagcccaata tggtggtggg gtgaagaggc tagggggccac aatgacccct      60
tcctgcgtgg catctggata caccttcaac gactactaca tacattgggt gcggcaggcc     120
cctggacaag gctttgagtt gttgggatac atcgaccccg ctaatggtcg cccagactac     180
gcagggcgt tgagggagag actctccttc tacaggggaca agtccatgga gacgctgtac     240
atggacctga ggagcctaag atatgacgac acggccatgt attattgtgt tagaaatgtg     300
gggaccgctg gcagcttgct gcattatgac cactgggggct cgggaagccc ggtcatcgtc     360
tcctcc                                                                366
```

<210> SEQ ID NO 127
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

```
gaaattgtgt tgacgcagtc tccagccacc ctgtccgcgt ctccagggga aagagtcacc      60
ctaacttgca gggccagtcg gagtgtccga aacaacgtgg cctggtatca gcacaagggt     120
ggccagagtc ccaggctcct catttatgat gcgtccacga gggccgctgg tgtcccagcc     180
aggttcagcg gcagtgcatc tgggacagag ttcactctcg ccatcagcaa cttggagtct     240
gaagatttta cagtctactt ctgtctgcag tataataact ggtggacctt cggccaaggg     300
accagggtgg acatcaaa                                                   318
```

<210> SEQ ID NO 128
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Val Gly Thr Glu Gly Ser Leu Leu His Phe Asp Tyr Trp
            100                 105                 110
```

Gly Gln Gly Thr Leu Val Thr Val Ser Ser
        115                 120

<210> SEQ ID NO 129
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Val Gln Leu Val Gln Ser Gly Thr Glu Val Arg Lys Pro Gly Ala
1               5                   10                  15

Ser Val Thr Ile Ser Cys Lys Ala Ser Gly Tyr Thr Phe Asn Asn Phe
            20                  25                  30

Tyr Val His Trp Val Arg Gln Ala Pro Gly Gln Gly Leu Glu Cys Met
        35                  40                  45

Gly Trp Ile Asp Pro Ser Val Gly Arg Ile Ser Tyr Gly Gln Lys Phe
    50                  55                  60

Gln Gly Arg Val Thr Met Thr Arg Asp Arg Ser Thr Ser Thr Val Tyr
65                  70                  75                  80

Met Gly Leu Ser Ser Leu Arg Ser Glu Asp Thr Ala Met Tyr Tyr Cys
                85                  90                  95

Val Arg Asp Val Gly Thr Glu Gly Ser Leu Leu His Phe Asp His Trp
            100                 105                 110

Gly Gln Gly Thr Leu Val Ile Val Ser Ala
        115                 120

<210> SEQ ID NO 130
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Val Gln Ser Gly Ala Glu Val Lys Lys Pro Gly Ala
1               5                   10                  15

Ser Val Thr Val Ser Cys Gln Ala Ser Gly Tyr Thr Phe Thr Asn Tyr
            20                  25                  30

Tyr Val His Trp Val Arg Gln Ala Pro Gly Gln Gly Leu Gln Leu Met
        35                  40                  45

Gly Trp Ile Asp Pro Ser Trp Gly Arg Thr Asn Tyr Ala Gln Asn Phe
    50                  55                  60

Gln Gly Arg Ile Thr Met Thr Arg Asp Thr Ser Thr Ser Thr Val Tyr
65                  70                  75                  80

Met Glu Met Arg Ser Leu Arg Ser Glu Asp Thr Ala Val Tyr Tyr Cys
                85                  90                  95

Ala Arg Asn Val Ala Thr Glu Gly Ser Leu Leu His Tyr Asp Tyr Trp
            100                 105                 110

Gly Gln Gly Thr Leu Val Thr Val Ser Ala
        115                 120

<210> SEQ ID NO 131
<211> LENGTH: 122
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 131

Gln Val Gln Leu Val Gln Ser Gly Ala Glu Val Arg Lys Pro Gly Ala
1               5                   10                  15

Ser Val Thr Val Ser Cys Lys Ala Ser Gly Tyr Thr Phe Asn Asn Phe
                20                  25                  30

Tyr Val His Trp Val Arg Gln Ala Pro Gly Gln Gly Leu Glu Cys Met
            35                  40                  45

Gly Trp Ile Asp Pro Ser Val Gly Arg Ile Asn Tyr Ala Gln Lys Phe
    50                  55                  60

Gln Gly Arg Val Thr Met Thr Arg Asp Arg Ser Thr Ser Thr Val Tyr
65                  70                  75                  80

Met Gly Leu Ser Ser Leu Arg Ser Glu Asp Thr Ala Ile Tyr Tyr Cys
                85                  90                  95

Val Arg Asp Val Gly Thr Glu Gly Ser Leu Leu His Phe Asp His Trp
                100                 105                 110

Gly Gln Gly Thr Leu Val Ile Val Ser Ala
        115                 120

<210> SEQ ID NO 132
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
                20                  25                  30

Tyr Ile His Trp Val Arg Gln Ala Pro Gly Gln Arg Leu Glu Leu Met
            35                  40                  45

Gly Met Ile Asp Pro Ser Arg Gly Arg Thr Asp Tyr Ala Gln Lys Phe
    50                  55                  60

Gln Gly Arg Val Thr Met Ser Arg Asp Thr Ser Thr Ser Thr Leu Tyr
65                  70                  75                  80

Met Glu Leu Arg Ser Leu Arg Pro Asp Asp Thr Ala Leu Tyr Tyr Cys
                85                  90                  95

Val Arg Asn Val Gly Thr Glu Gly Ser Leu Leu His Tyr Asp Tyr Trp
                100                 105                 110

Gly Gln Gly Thr Leu Val Thr Val Ser Ser
        115                 120

<210> SEQ ID NO 133
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Gln Ser Gly Ala Ala Val Lys Lys Pro Gly Ala
1               5                   10                  15
```

```
Ser Val Arg Val Ser Cys Lys Ala Ser Gly Tyr Thr Phe Thr Ser Ser
            20                  25                  30

His Ile His Trp Val Arg Gln Ala Pro Gly Gln Gly Pro Glu Trp Met
        35                  40                  45

Gly Met Ile Asp Pro Ser Val Gly Arg Pro Thr Thr Ala Gly Lys Phe
    50                  55                  60

Gln Gly Arg Val Thr Met Thr Arg Asp Arg Tyr Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Ser Val Glu Thr Thr Gly Ser Leu Leu Tyr Phe Asp Tyr Trp
            100                 105                 110

Gly Gln Gly Thr Leu Ile Thr Val Ser Ser
        115                 120

<210> SEQ ID NO 134
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
            20                  25                  30

Tyr Ile His Trp Val Arg Gln Ala Pro Gly Gln Gly Leu Glu Leu Met
        35                  40                  45

Gly Trp Ile Asn Pro Arg Gly Gly Arg Thr Asp Tyr Ser Tyr Arg Phe
    50                  55                  60

Glu Asp Arg Val Ser Met Tyr Arg Asp Thr Ser Met Ser Ile Val Tyr
65                  70                  75                  80

Met Asp Leu Arg Asn Leu Lys Ser Ala Asp Thr Ala Val Tyr Tyr Cys
                85                  90                  95

Val Arg Asn Val Gly Thr Ser Gly Ser Leu Leu His Tyr Asp Phe Trp
            100                 105                 110

Gly Gln Gly Ser Leu Val Thr Val Ser Ser
        115                 120

<210> SEQ ID NO 135
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Arg Leu Leu Gln Tyr Gly Gly Gly Val Lys Arg Pro Gly Ala
1               5                   10                  15

Ser Met Thr Ile Ser Cys Val Ala Ser Gly Tyr Asn Phe Asn Asp Tyr
            20                  25                  30

Tyr Ile His Trp Val Arg Gln Ala Pro Gly Gln Gly Leu Glu Leu Met
        35                  40                  45

Gly Trp Ile Asp Pro Ser Gly Gly Arg Thr Asp Tyr Ala Gly Ala Phe
    50                  55                  60
```

```
Gly Asp Arg Val Ser Met Tyr Arg Asp Lys Ser Met Asn Thr Leu Tyr
65                  70                  75                  80

Met Asp Leu Arg Ser Leu Arg Ser Gly Asp Thr Ala Met Tyr Tyr Cys
                85                  90                  95

Val Arg Asn Val Gly Thr Ala Gly Ser Leu Leu His Tyr Asp His Trp
            100                 105                 110

Gly Leu Gly Val Met Val Thr Val Ser Ser
        115                 120
```

<210> SEQ ID NO 136
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Gln Val Gln Leu Val Gln Ser Gly Ala Thr Val Lys Lys Pro Arg Ala
1               5                   10                  15

Ser Val Thr Leu Ser Cys Arg Thr Ser Gly Tyr Asn Phe Ile Asp Tyr
            20                  25                  30

Phe Ile His Trp Val Arg Arg Ala Pro Gly Gln Arg Leu Glu Val Met
        35                  40                  45

Gly Tyr Ile Asp Pro Ser Arg Gly Arg Pro Tyr Ala Pro Asn Phe
    50                  55                  60

Arg Asp Arg Val Ser Leu Tyr Arg Asp Thr Ser Met Ser Ile Val Tyr
65                  70                  75                  80

Leu Asp Leu Arg Asp Leu Thr Pro Asp Thr Ala Ile Tyr Tyr Cys
                85                  90                  95

Val Arg Ser Glu Gly Thr Glu Gly Thr Val Leu His Tyr Asp His Trp
            100                 105                 110

Gly Pro Gly Thr Arg Val Thr Val Ser Pro
        115                 120
```

<210> SEQ ID NO 137
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Gln Val Gln Leu Val Gln Ser Gly Gly Gly Val Lys Arg Pro Gly Ser
1               5                   10                  15

Thr Thr Thr Ile Ser Cys Val Ala Ser Gly Tyr Ser Phe Asn Asp Tyr
            20                  25                  30

Tyr Ile His Trp Val Arg Gln Ala Pro Gly Gln Gly Leu Glu Val Leu
        35                  40                  45

Gly Phe Ile Asp Pro Ser Asn Gly Arg Thr Asn Tyr Ala Gly Ala Phe
    50                  55                  60

Gly Asp Arg Phe Ser Met Tyr Arg Asp Lys Ser Met Glu Thr Leu Tyr
65                  70                  75                  80

Met Asp Leu Arg Asn Leu Arg Ser Asp Thr Ala Met Tyr Tyr Cys
                85                  90                  95

Val Arg Asn Val Gly Thr Ala Gly Ser Leu Leu His Tyr Asp His Trp
            100                 105                 110
```

```
Gly Thr Gly Ser Lys Ile Ile Val Ser Ser
            115                 120
```

<210> SEQ ID NO 138
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Gln Val Gln Leu Val Gln Ser Gly Gly Thr Val Lys Ser Pro Gly Thr
1               5                   10                  15

Ser Val Thr Leu Ser Cys Lys Thr Ser Gly Tyr Asn Phe Ile Asp Tyr
            20                  25                  30

Tyr Ile His Trp Val Arg Arg Ala Pro Gly Gln Arg Pro Glu Leu Met
        35                  40                  45

Gly Tyr Ile Asp Pro Ser His Gly Arg Pro Asp Tyr Glu Gly Lys Phe
    50                  55                  60

Arg Asp Arg Ile Ser Leu Tyr Arg Asp Thr Ser Thr Ser Val Val Tyr
65                  70                  75                  80

Met Asp Val Arg Gly Leu Arg Leu Asp Thr Ala Leu Tyr Tyr Cys
                85                  90                  95

Val Arg Gly Gly Gly Val Glu Val Ser Ser Asn His Tyr Asp His Trp
            100                 105                 110

Gly Pro Gly Thr Met Val Phe Val Ser Pro
            115                 120
```

<210> SEQ ID NO 139
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Gln Val Arg Leu Ala Gln Tyr Gly Gly Val Lys Arg Leu Gly Ala
1               5                   10                  15

Thr Met Thr Leu Ser Cys Val Ala Ser Gly Tyr Thr Phe Asn Asp Tyr
            20                  25                  30

Tyr Ile His Trp Val Arg Gln Ala Pro Gly Gln Gly Phe Glu Leu Leu
        35                  40                  45

Gly Tyr Ile Asp Pro Ala Asn Gly Arg Pro Asp Tyr Ala Gly Ala Leu
    50                  55                  60

Arg Glu Arg Leu Ser Phe Tyr Arg Asp Lys Ser Met Glu Thr Leu Tyr
65                  70                  75                  80

Met Asp Leu Arg Ser Leu Arg Tyr Asp Thr Ala Met Tyr Tyr Cys
                85                  90                  95

Val Arg Asn Val Gly Thr Ala Gly Ser Leu Leu His Tyr Asp His Trp
            100                 105                 110

Gly Ser Gly Ser Pro Val Ile Val Ser Ser
            115                 120
```

<210> SEQ ID NO 140
<211> LENGTH: 106
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 140

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
            100                 105

<210> SEQ ID NO 141
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Val Arg Asn Asn
            20                  25                  30

Leu Ala Trp Tyr Arg Gln Lys Arg Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Met Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
            100                 105

<210> SEQ ID NO 142
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Ser Asn
            20                  25                  30

Leu Ala Trp Tyr Gln Gln Lys Arg Gly Gln Ala Pro Arg Leu Leu Ile
        35                  40                  45

Tyr Ser Ala Ser Thr Arg Ala Thr Gly Ile Pro Ala Arg Phe Ser Gly

```
                   50                  55                  60
Ser Gly Ser Gly Thr Glu Phe Thr Leu Thr Ile Ser Ser Val Gln Ser
 65                  70                  75                  80

Glu Asp Phe Ala Val Tyr Tyr Cys Leu Gln Tyr Asn Asn Trp Trp Thr
                 85                  90                  95

Phe Gly Gln Gly Thr Lys Val Glu Ile Lys
                100                 105
```

<210> SEQ ID NO 143
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

```
Glu Ile Val Leu Thr Gln Ser Pro Ala Thr Leu Ser Val Ser Pro Gly
  1               5                  10                  15

Glu Arg Ala Thr Leu Ser Cys Arg Ala Ser Gln Ser Val Arg Ser Asn
                 20                  25                  30

Ile Ala Trp Tyr Gln Gln Lys Pro Gly Gln Ala Pro Arg Leu Leu Ile
             35                  40                  45

His Gly Ala Ser Thr Arg Ala Thr Gly Ile Pro Gly Arg Phe Ser Gly
         50                  55                  60

Ser Gly Ser Gly Pro Glu Phe Thr Leu Ala Ile Ser Ser Val Gln Ser
 65                  70                  75                  80

Glu Asp Phe Ala Val Tyr Tyr Cys Gln Gln Tyr Asn Asp Trp Trp Thr
                 85                  90                  95

Phe Gly Gln Gly Thr Lys Val Glu Ile Lys
                100                 105
```

<210> SEQ ID NO 144
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

```
Glu Ile Val Leu Thr Gln Ser Pro Ala Thr Leu Ser Val Ser Pro Gly
  1               5                  10                  15

Glu Arg Ala Thr Leu Ser Cys Arg Ala Ser Gln Ser Val Arg Ser Asn
                 20                  25                  30

Leu Ala Trp Tyr Gln Gln Arg Pro Gly Gln Ala Pro Arg Leu Leu Ile
             35                  40                  45

Tyr Gly Thr Ser Thr Arg Ala Thr Gly Val Pro Ala Arg Phe Ser Gly
         50                  55                  60

Arg Gly Ser Gly Thr Glu Phe Thr Leu Ala Ile Ser Ser Met Gln Ser
 65                  70                  75                  80

Glu Asp Phe Ala Val Tyr Leu Cys Leu Gln Tyr Asn Asn Trp Trp Thr
                 85                  90                  95

Phe Gly Gln Gly Thr Lys Val Glu Ile Lys
                100                 105
```

<210> SEQ ID NO 145
<211> LENGTH: 106
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 145

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Ser Asn
            20                  25                  30

Val Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ala Ser Met Gln Ser
65                  70                  75                  80

Glu Asp Phe Ala Val Tyr Tyr Cys Leu Gln Tyr Asp Asp Trp Trp Thr
                85                  90                  95

Phe Gly Gln Gly Thr Lys Val Glu Ile Lys
            100                 105

<210> SEQ ID NO 146
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Ile Val Leu Thr Gln Ser Pro Ala Thr Leu Ser Ala Ser Pro Gly
1               5                   10                  15

Glu Arg Val Thr Leu Thr Cys Arg Ala Ser Arg Gly Val Arg Asn Asn
            20                  25                  30

Val Ala Trp Tyr Gln His Asn Val Gly Gln Ser Pro Arg Leu Leu Ile
        35                  40                  45

Tyr Asp Ala Ser Thr Arg Ala Pro Gly Ile Pro Ala Arg Phe Ser Gly
    50                  55                  60

Ser Ala Ser Gly Thr Glu Phe Thr Leu Ala Ile Ser Ser Ile Gln Ser
65                  70                  75                  80

Glu Asp Phe Thr Leu Tyr Tyr Cys His Gln Tyr Asn Asn Trp Trp Thr
                85                  90                  95

Phe Gly Gln Gly Thr Arg Val Asp Ile Asn
            100                 105

<210> SEQ ID NO 147
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Ile Val Leu Thr Gln Ser Pro Ala Thr Leu Ser Ala Ser Pro Gly
1               5                   10                  15

Glu Arg Val Thr Leu Thr Cys Arg Ala Ser Arg Ser Val Arg Asn Asn
            20                  25                  30

Val Ala Trp Tyr Gln His Lys Gly Gly Gln Ser Pro Arg Leu Leu Ile
        35                  40                  45
```

Tyr Asp Ala Ser Thr Arg Ala Ala Gly Val Pro Ala Arg Phe Ser Gly
            50                  55                  60

Ser Ala Ser Gly Thr Glu Phe Thr Leu Ala Ile Ser Asn Leu Glu Ser
 65                  70                  75                  80

Glu Asp Phe Thr Val Tyr Phe Cys Leu Gln Tyr Asn Asn Trp Trp Thr
                 85                  90                  95

Phe Gly Gln Gly Thr Arg Val Asp Ile Lys
            100                 105

<210> SEQ ID NO 148
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Ile Val Leu Thr Gln Ser Pro Asp Thr Leu Ser Ala Ser Pro Gly
 1               5                  10                  15

Glu Arg Val Thr Leu Ser Cys Arg Ala Ser Gln Ser Val Gly Thr Lys
             20                  25                  30

Val Ala Trp Tyr Arg His Val Arg Gly Gln Pro Pro Arg Leu Leu Ile
         35                  40                  45

Tyr Gly Ala Ser Thr Arg Ala Ala Gly Ile Pro Ala Arg Phe Ser Gly
     50                  55                  60

Gly Gly Ser Gly Thr Asn Phe Thr Leu Ile Ile Asn Asn Phe Gln Ser
 65                  70                  75                  80

Glu Asp Phe Ala Glu Tyr Leu Cys Gln Gln Tyr Lys Ser Trp Trp Thr
                 85                  90                  95

Phe Gly Gln Gly Thr Lys Val Asp Asn Lys
            100                 105

<210> SEQ ID NO 149
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Thr Thr Leu Thr Gln Ser Pro Asp Thr Leu Ser Ala Ser Pro Gly
 1               5                  10                  15

Glu Arg Val Thr Leu Ser Cys Arg Ala Ala Gln Ser Val Gly Ser Gln
             20                  25                  30

Val Ala Trp Phe Arg His Ile Arg Gly Gln Pro Pro Arg Leu Leu Ile
         35                  40                  45

Ser Gly Ala Ser Thr Arg Ala Ala Gly Val Pro Ala Arg Phe Ser Gly
     50                  55                  60

Ser Gly Ser Gly Thr Asp Phe Thr Leu Thr Ile Ser Gly Met Gln Ser
 65                  70                  75                  80

Glu Asp Phe Ala Glu Tyr Phe Cys Gln Gln Tyr His Met Trp Trp Thr
                 85                  90                  95

Phe Gly Gln Gly Thr Arg Val Asp Lys Asn
            100                 105

<210> SEQ ID NO 150

<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Val Gly Thr Glu Gly Ser Leu Leu His Phe Asp Tyr Trp
            100                 105                 110

Gly Gln Gly Thr Leu Val Thr Val Ser Ser
        115                 120

<210> SEQ ID NO 151
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
            20                  25                  30

Tyr Ile His Trp Val Arg Gln Ala Pro Gly Gln Arg Leu Glu Leu Met
        35                  40                  45

Gly Met Ile Asp Pro Ser Arg Gly Arg Thr Asp Tyr Ala Gln Lys Phe
    50                  55                  60

Gln Gly Arg Val Thr Met Ser Arg Asp Thr Ser Thr Ser Thr Leu Tyr
65                  70                  75                  80

Met Glu Leu Arg Ser Leu Arg Pro Asp Asp Thr Ala Leu Tyr Tyr Cys
                85                  90                  95

Val Arg Asn Val Gly Thr Glu Gly Ser Leu Leu His Tyr Asp Tyr Trp
            100                 105                 110

Gly Gln Gly Thr Leu Val Thr Val Ser Ser
        115                 120

<210> SEQ ID NO 152
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Val Gln Ser Gly Ala Glu Val Lys Lys Pro Gly Ala
1               5                   10                  15

Ser Val Thr Val Ser Cys Gln Ala Ser Gly Tyr Thr Phe Thr Asn Tyr
            20                  25                  30

Tyr Val His Trp Val Arg Gln Ala Pro Gly Gln Gly Leu Gln Leu Met
            35                  40                  45

Gly Trp Ile Asp Pro Ser Trp Gly Arg Thr Asn Tyr Ala Gln Asn Phe
50                  55                  60

Gln Gly Arg Ile Thr Met Thr Arg Asp Thr Ser Thr Ser Thr Val Tyr
65                  70                  75                  80

Met Glu Met Arg Ser Leu Arg Ser Glu Asp Thr Ala Val Tyr Tyr Cys
                85                  90                  95

Ala Arg Asn Val Ala Thr Glu Gly Ser Leu Leu His Tyr Asp Tyr Trp
            100                 105                 110

Gly Gln Gly Thr Leu Val Thr Val Ser Ala
            115                 120

<210> SEQ ID NO 153
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Arg Leu Leu Gln Tyr Gly Gly Gly Val Lys Arg Pro Gly Ala
1               5                   10                  15

Ser Met Thr Ile Ser Cys Val Ala Ser Gly Tyr Asn Phe Asn Asp Tyr
            20                  25                  30

Tyr Ile His Trp Val Arg Gln Ala Pro Gly Gln Gly Leu Glu Leu Met
            35                  40                  45

Gly Trp Ile Asp Pro Ser Gly Gly Arg Thr Asp Tyr Ala Gly Ala Phe
50                  55                  60

Gly Asp Arg Val Ser Met Tyr Arg Asp Lys Ser Met Asn Thr Leu Tyr
65                  70                  75                  80

Met Asp Leu Arg Ser Leu Arg Ser Gly Asp Thr Ala Met Tyr Tyr Cys
                85                  90                  95

Val Arg Asn Val Gly Thr Ala Gly Ser Leu Leu His Tyr Asp His Trp
            100                 105                 110

Gly Leu Gly Val Met Val Thr Val Ser Ser
            115                 120

<210> SEQ ID NO 154
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Val Arg Leu Ala Gln Tyr Gly Gly Gly Val Lys Arg Leu Gly Ala
1               5                   10                  15

Thr Met Thr Leu Ser Cys Val Ala Ser Gly Tyr Thr Phe Asn Asp Tyr
            20                  25                  30

Tyr Ile His Trp Val Arg Gln Ala Pro Gly Gln Gly Phe Glu Leu Leu
            35                  40                  45

```
Gly Tyr Ile Asp Pro Ala Asn Gly Arg Pro Asp Tyr Ala Gly Ala Leu
        50                  55                  60

Arg Glu Arg Leu Ser Phe Tyr Arg Asp Lys Ser Met Glu Thr Leu Tyr
 65                  70                  75                  80

Met Asp Leu Arg Ser Leu Arg Tyr Asp Thr Ala Met Tyr Tyr Cys
                 85                  90                  95

Val Arg Asn Val Gly Thr Ala Gly Ser Leu Leu His Tyr Asp His Trp
                100                 105                 110

Gly Ser Gly Ser Pro Val Ile Val Ser Ser
            115                 120

<210> SEQ ID NO 155
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Trp Thr
                 85                  90                  95

Phe Gly Gln Gly Thr Lys Val Glu Ile Lys
            100                 105

<210> SEQ ID NO 156
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Ile Val Leu Thr Gln Ser Pro Ala Thr Leu Ser Val Ser Pro Gly
 1               5                  10                  15

Glu Arg Val Thr Leu Ser Cys Arg Ala Ser Gln Ser Val Arg Asn Asn
                 20                  25                  30

Leu Ala Trp Tyr Arg Gln Lys Arg Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Met Gln Ser
 65                  70                  75                  80

Glu Asp Phe Ala Val Tyr Tyr Cys Gln Gln Tyr Asn Asn Trp Trp Thr
                 85                  90                  95

Phe Gly Gln Gly Thr Lys Val Glu Ile Lys
            100                 105
```

<210> SEQ ID NO 157
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Arg Pro Gly Gln Ala Pro Arg Leu Leu Ile
        35                  40                  45

Tyr Gly Thr Ser Thr Arg Ala Thr Gly Val Pro Ala Arg Phe Ser Gly
    50                  55                  60

Arg Gly Ser Gly Thr Glu Phe Thr Leu Ala Ile Ser Ser Met Gln Ser
65                  70                  75                  80

Glu Asp Phe Ala Val Tyr Leu Cys Leu Gln Tyr Asn Asn Trp Trp Thr
                85                  90                  95

Phe Gly Gln Gly Thr Lys Val Glu Ile Lys
            100                 105

<210> SEQ ID NO 158
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Ile Val Leu Thr Gln Ser Pro Ala Thr Leu Ser Ala Ser Pro Gly
1               5                   10                  15

Glu Arg Val Thr Leu Thr Cys Arg Ala Ser Arg Ser Val Arg Asn Asn
            20                  25                  30

Val Ala Trp Tyr Gln His Lys Gly Gly Gln Ser Pro Arg Leu Leu Ile
        35                  40                  45

Tyr Asp Ala Ser Thr Arg Ala Ala Gly Val Pro Ala Arg Phe Ser Gly
    50                  55                  60

Ser Ala Ser Gly Thr Glu Phe Thr Leu Ala Ile Ser Asn Leu Glu Ser
65                  70                  75                  80

Glu Asp Phe Thr Val Tyr Phe Cys Leu Gln Tyr Asn Asn Trp Trp Thr
                85                  90                  95

Phe Gly Gln Gly Thr Arg Val Asp Ile Lys
            100                 105

<210> SEQ ID NO 159
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gln Val Gln Leu Val Gln Ser Gly Ala Ala Val Lys Lys Pro Gly Ala
1               5                   10                  15

Ser Val Arg Val Ser Cys Lys Ala Ser Gly Tyr Thr Phe Thr Ser Ser

```
                20                  25                  30
His Ile His Trp Val Arg Gln Ala Pro Gly Gln Ala Leu Glu Trp Leu
            35                  40                  45

Gly Met Ile Asp Pro Arg Phe Gly Arg Pro Thr Arg Pro Gln Lys Phe
        50                  55                  60

Gln Gly Arg Val Thr Leu Thr Arg Asp Thr Tyr Thr Thr Thr Val Tyr
65                  70                  75                  80

Met Ser Leu Ser Ser Leu Thr Pro Glu Asp Thr Ala Val Tyr Tyr Cys
                85                  90                  95

Ala Arg Ser Val Glu Thr Ser Glu Ser Tyr Leu His Phe Asp Tyr Trp
            100                 105                 110

Gly Gln Gly Thr Leu Val Thr Val Ser Ser
        115                 120

<210> SEQ ID NO 160
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
            20                  25                  30

Tyr Ile His Trp Val Arg Gln Ala Pro Gly Gln Gly Leu Glu Leu Met
            35                  40                  45

Gly Trp Ile Asn Pro Arg Gly Gly Arg Thr Asp Tyr Ser Tyr Arg Phe
        50                  55                  60

Glu Asp Arg Val Ser Met Tyr Arg Asp Thr Ser Met Ser Ile Val Tyr
65                  70                  75                  80

Met Asp Leu Arg Asn Leu Lys Ser Ala Asp Thr Ala Val Tyr Tyr Cys
                85                  90                  95

Val Arg Asn Val Gly Thr Ser Gly Ser Leu Leu His Tyr Asp Phe Trp
            100                 105                 110

Gly Gln Gly Ser Leu Val Thr Val Ser Ser
        115                 120

<210> SEQ ID NO 161
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Val Gln Ser Gly Ala Ala Val Lys Lys Pro Gly Ala
1               5                   10                  15

Ser Val Arg Val Ser Cys Lys Ala Ser Gly Tyr Thr Phe Thr Ser Ser
            20                  25                  30

His Ile His Trp Val Arg Gln Ala Pro Gly Gln Gly Pro Glu Trp Met
            35                  40                  45

Gly Met Val Asp Pro Arg Phe Gly Arg Pro Thr Tyr Ala Gln Lys Phe
        50                  55                  60

Gln Gly Arg Val Ala Met Thr Arg Asp Ile Tyr Thr Ser Thr Val Tyr
```

```
                65                  70                  75                  80
Met Asp Leu Arg Ser Leu Lys Ser Glu Asp Thr Ala Ile Tyr Phe Cys
                    85                  90                  95

Val Arg Asn Ala Glu Thr Glu Gly Ser Leu Leu His Ile Glu Tyr Trp
                100                 105                 110

Gly Gln Gly Thr Arg Val Thr Val Ser Ser
            115                 120

<210> SEQ ID NO 162
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Arg Leu Leu Gln Tyr Gly Gly Gly Val Lys Arg Pro Gly Ala
1               5                   10                  15

Ser Met Thr Ile Ser Cys Val Ala Ser Gly Tyr Asn Phe Asn Asp Tyr
                20                  25                  30

Tyr Ile His Trp Val Arg Gln Ala Pro Gly Gln Gly Leu Glu Leu Met
            35                  40                  45

Gly Trp Ile Asp Pro Ser Gly Gly Arg Thr Asp Tyr Ala Gly Ala Phe
        50                  55                  60

Gly Asp Arg Val Ser Met Tyr Arg Asp Lys Ser Met Asn Thr Leu Tyr
65                  70                  75                  80

Met Asp Leu Arg Ser Leu Arg Ser Gly Asp Thr Ala Met Tyr Tyr Cys
                    85                  90                  95

Val Arg Asn Val Gly Thr Ala Gly Ser Leu Leu His Tyr Asp His Trp
                100                 105                 110

Gly Leu Gly Val Met Val Thr Val Ser Ser
            115                 120

<210> SEQ ID NO 163
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Val Arg Asn Asn
                20                  25                  30

Leu Ala Trp Tyr Arg Gln Lys Arg Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Met Gln Ser
65                  70                  75                  80

Glu Asp Phe Ala Val Tyr Tyr Cys Gln Gln Tyr Asn Asn Trp Trp Thr
                    85                  90                  95

Phe Gly Gln Gly Thr Lys Val Glu Ile Lys
                100                 105
```

<210> SEQ ID NO 164
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Ile Ala Trp Tyr Gln Gln Lys Pro Gly Gln Ala Pro Arg Leu Leu Ile
        35                  40                  45

His Gly Ala Ser Thr Arg Ala Thr Gly Ile Pro Gly Arg Phe Ser Gly
    50                  55                  60

Ser Gly Ser Gly Pro Glu Phe Thr Leu Ala Ile Ser Ser Val Gln Ser
65                  70                  75                  80

Glu Asp Phe Ala Val Tyr Tyr Cys Gln Gln Tyr Asn Asp Trp Trp Thr
                85                  90                  95

Phe Gly Gln Gly Thr Lys Val Glu Ile Lys
            100                 105

<210> SEQ ID NO 165
<211> LENGTH: 367
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 165
caggtgcagc tggtgcagtc tggggctgcg gtgaagaagc ctggggcctc agtgagggtt      60
tcctgcaagg catctggata caccttcacc agttctcata tccactgggt gcgacaggcc     120
cctggacaag cacttgagtg gttgggaatg atcgaccctc gttttggtag gccaacccgc     180
cctcagaagt tccagggcag agtcaccctg accagagaca cgtacacgac tacagtgtac     240
atgtcactga gcagcctgac acctgaagac acggccgttt actactgtgc gagaagcgtg     300
gaaacgagtg agagctatct ccactttgac tactggggcc agggaaccct ggtcaccgtc     360
tcctcag                                                               367

<210> SEQ ID NO 166
<211> LENGTH: 367
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166
caggtgcagc tggtgcagtc tggggctgcg gtgaagaggc ctggggcctc agtgacgatt      60
tcctgcaggg catctggata caccttcacc acctactata tacactgggt gcgacaggcc     120
cctggacaag gacttgagtt gatgggatgg atcaaccctc gtggcggtcg cacagactac     180
tcttacagat ttgaggacag agtcagtatg tacagggaca cgtccatgag tatagtctac     240
atggacttga ggaacctgaa atctgcggac acggccgtct actattgtgt gagaaatgtg     300
ggaaccagtg ggagcttgct ccactatgac ttctgggggcc agggaagcct ggtcaccgtc     360

<210> SEQ ID NO 167
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167

```
caggtgcagc tggtgcagtc tggggctgcg gtgaagaagc ctggggcctc agtgagggtt      60
tcctgcaagg catctggata caccttcacc agttctcata tccactgggt gcgacaggcc     120
cctggacaag gccctgagtg gatgggcatg gtcgaccccc gttttggtcg cccaacctac     180
gcacagaagt tcagggcag gtcgccatg accaggaca tttacacgag cacagtctac        240
atggacttga ggagcctaaa atctgaggac acggccatct atttctgtgt gagaaatgcg     300
gaaacggagg gcagcttact ccacattgag tactggggcc agggaacccg ggtcaccgtc     360
tcctcag                                                               367
```

<210> SEQ ID NO 168
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168

```
caggtgcgac tactacaata tggggtgga gtgaagaggc ctggggcctc aatgacgatt       60
tcctgcgtgg cgtctggata caacttcaac gactactata tacactgggt gcgacaggcc     120
cctggacaag gcctcgaatt gatgggatgg atcgaccctta gtggtggtcg cacagattac    180
gcaggggcgt ttggggacag agtgtccatg tacagggaca gtccatgaa cacactctac      240
atggacctga ggagcctgag atctggcgac acggccatgt attattgtgt tagaaatgtg     300
ggaacggctg gcagcttgct ccactatgac cactgggcc tgggagttat ggtcaccgtc     360
tcctcag                                                               367
```

<210> SEQ ID NO 169
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169

```
gaaattgtgt tgacgcagtc tccagccacc ctgtctgtat ctccagggga aagagtcacc      60
ctctcctgca gggccagtca gagtgttaga aacaacttag cctggtaccg gcagaaacgt     120
ggccaggctc ccagactcct catctatggt gcatccacca gggccactgg tatcccagcc     180
aggttcagtg gcagtgggtc tgggacagag ttcactctta ccatcagcag catgcagtct     240
gaagattttg cagtttatta ctgtcagcag tataataact ggtggacgtt cggccaaggg     300
accaaggtgg aaatcaaac                                                  319
```

<210> SEQ ID NO 170
<211> LENGTH: 319
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 170
gaaattgtgt tgacgcagtc tccagccacc ctgtctgtgt ctccagggga aagagccacc    60
ctctcctgca gggccagtca gagtgttaga agcaacatag cctggtacca acaaaaacct   120
ggccaggctc ccaggctcct catccatggt gcatccacca gggccacagg tatcccaggc   180
aggttcagtg gcagtgggtc tgggccagag ttcactctcg ccatcagcag cgtgcagtct   240
gaagattttg cagtttatta ctgtcagcag tataatgact ggtggacgtt cggccaaggg   300
accaaggtgg aaatcaaac                                                319

<210> SEQ ID NO 171
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171
```

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
            20                  25                  30

Tyr Ile His Trp Val Arg Gln Ala Pro Gly Gln Arg Leu Glu Leu Met
        35                  40                  45

Gly Met Ile Asp Pro Ser Arg Gly Arg Thr Asp Tyr Ala Gln Lys Phe
    50                  55                  60

Gln Gly Arg Val Thr Met Ser Arg Asp Thr Ser Thr Ser Thr Leu Tyr
65                  70                  75                  80

Met Glu Leu Arg Ser Leu Arg Pro Asp Asp Thr Ala Leu Tyr Tyr Cys
                85                  90                  95

Val Arg Asn Val Gly Thr Glu Gly Ser Leu Leu His Tyr Asp Tyr Trp
            100                 105                 110

Gly Gln Gly Thr Leu Val Thr Val Ser Ser
        115                 120

```
<210> SEQ ID NO 172
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172
```

Gln Val Arg Leu Leu Gln Tyr Gly Gly Gly Val Lys Arg Pro Gly Ala
1               5                   10                  15

Ser Met Thr Ile Ser Cys Val Ala Ser Gly Tyr Asn Phe Asn Asp Tyr
            20                  25                  30

Tyr Ile His Trp Val Arg Gln Ala Pro Gly Gln Gly Leu Glu Leu Met
        35                  40                  45

Gly Trp Ile Asp Pro Ser Gly Gly Arg Thr Asp Tyr Ala Gly Ala Phe
    50                  55                  60

Gly Asp Arg Val Ser Met Tyr Arg Asp Lys Ser Met Asn Thr Leu Tyr
65                  70                  75                  80

```
Met Asp Leu Arg Ser Leu Arg Ser Gly Asp Thr Ala Met Tyr Tyr Cys
            85                  90                  95

Val Arg Asn Val Gly Thr Ala Gly Ser Leu Leu His Tyr Asp His Trp
            100                 105                 110

Gly Leu Gly Val Met Val Thr Val Ser Ser
            115                 120

<210> SEQ ID NO 173
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Val Arg Leu Ala Gln Tyr Gly Gly Gly Val Lys Arg Leu Gly Ala
1               5                   10                  15

Thr Met Thr Leu Ser Cys Val Ala Ser Gly Tyr Thr Phe Asn Asp Tyr
            20                  25                  30

Tyr Ile His Trp Val Arg Gln Ala Pro Gly Gln Gly Phe Glu Leu Leu
            35                  40                  45

Gly Tyr Ile Asp Pro Ala Asn Gly Arg Pro Asp Tyr Ala Gly Ala Leu
            50                  55                  60

Arg Glu Arg Leu Ser Phe Tyr Arg Asp Lys Ser Met Glu Thr Leu Tyr
65                  70                  75                  80

Met Asp Leu Arg Ser Leu Arg Tyr Asp Thr Ala Met Tyr Tyr Cys
            85                  90                  95

Val Arg Asn Val Gly Thr Ala Gly Ser Leu Leu His Tyr Asp His Trp
            100                 105                 110

Gly Ser Gly Ser Pro Val Ile Val Ser Ser
            115                 120

<210> SEQ ID NO 174
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Leu Val Gln Ser Gly Gly Gly Val Lys Arg Pro Gly Ser
1               5                   10                  15

Thr Thr Thr Ile Ser Cys Val Ala Ser Gly Tyr Ser Phe Asn Asp Tyr
            20                  25                  30

Tyr Ile His Trp Val Arg Gln Ala Pro Gly Gln Gly Leu Glu Val Leu
            35                  40                  45

Gly Phe Ile Asp Pro Ser Asn Gly Arg Thr Asn Tyr Ala Gly Ala Phe
            50                  55                  60

Gly Asp Arg Phe Ser Met Tyr Arg Asp Lys Ser Met Glu Thr Leu Tyr
65                  70                  75                  80

Met Asp Leu Arg Asn Leu Arg Ser Asp Thr Ala Met Tyr Tyr Cys
            85                  90                  95

Val Arg Asn Val Gly Thr Ala Gly Ser Leu Leu His Tyr Asp His Trp
            100                 105                 110

Gly Thr Gly Ser Lys Ile Ile Val Ser Ser
            115                 120
```

<210> SEQ ID NO 175
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Val Gln Ser Gly Ala Thr Val Lys Lys Pro Arg Ala
1               5                   10                  15

Ser Val Thr Leu Ser Cys Arg Thr Ser Gly Tyr Asn Phe Ile Asp Tyr
            20                  25                  30

Phe Ile His Trp Val Arg Arg Ala Pro Gly Gln Arg Leu Glu Val Met
        35                  40                  45

Gly Tyr Ile Asp Pro Ser Arg Gly Arg Pro Asp Tyr Ala Pro Asn Phe
    50                  55                  60

Arg Asp Arg Val Ser Leu Tyr Arg Asp Thr Ser Met Ser Ile Val Tyr
65                  70                  75                  80

Leu Asp Leu Arg Asp Leu Thr Pro Asp Thr Ala Ile Tyr Tyr Cys
                85                  90                  95

Val Arg Ser Glu Gly Thr Glu Gly Thr Val Leu His Tyr Asp His Trp
            100                 105                 110

Gly Pro Gly Thr Arg Val Thr Val Ser Pro
        115                 120

<210> SEQ ID NO 176
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Val Gln Leu Val Gln Ser Gly Gly Thr Val Lys Ser Pro Gly Thr
1               5                   10                  15

Ser Val Thr Leu Ser Cys Lys Thr Ser Gly Tyr Asn Phe Ile Asp Tyr
            20                  25                  30

Tyr Ile His Trp Val Arg Arg Ala Pro Gly Gln Arg Pro Glu Leu Met
        35                  40                  45

Gly Tyr Ile Asp Pro Ser His Gly Arg Pro Asp Tyr Glu Gly Lys Phe
    50                  55                  60

Arg Asp Arg Ile Ser Leu Tyr Arg Asp Thr Ser Thr Ser Val Val Tyr
65                  70                  75                  80

Met Asp Val Arg Gly Leu Arg Leu Asp Asp Thr Ala Leu Tyr Tyr Cys
                85                  90                  95

Val Arg Gly Gly Gly Val Glu Val Ser Ser Asn His Tyr Asp His Trp
            100                 105                 110

Gly Pro Gly Thr Met Val Phe Val Ser Pro
        115                 120

<210> SEQ ID NO 177
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
            20                  25                  30

Tyr Ile His Trp Val Arg Gln Ala Pro Gly Gln Gly Leu Glu Leu Met
        35                  40                  45

Gly Trp Ile Asn Pro Arg Gly Gly Arg Thr Asp Tyr Ser Tyr Arg Phe
    50                  55                  60

Glu Asp Arg Val Ser Met Tyr Arg Asp Thr Ser Met Ser Ile Val Tyr
65                  70                  75                  80

Met Asp Leu Arg Asn Leu Lys Ser Ala Asp Thr Ala Val Tyr Tyr Cys
                85                  90                  95

Val Arg Asn Val Gly Thr Ser Gly Ser Leu Leu His Tyr Asp Phe Trp
                100                 105                 110

Gly Gln Gly Ser Leu Val Thr Val Ser Ser
            115                 120

<210> SEQ ID NO 178
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
caggtgcagc tggtgcagtc tggggctcaa atgaagaacc ctggggcctc agtgaaggtc      60
tcctgcgcgc cttctggata taccttcacc gacttttaca tacattggtt gcgccaggcc     120
cctggccagg ggcttcagtg gatgggatgg atgaaccctc agactggtcg cacaaacact     180
gcacgaaact ttcaggggag ggtcaccatg accaggdaca cgtccatcgg cacagcctac     240
atggagttga agcctgaca tctgacgac acggccatat attactgtac gacaggggga      300
tggatcagtc tttactatga tagtagttat taccccaact ttgaccactg gggtcaggga     360
accctgctca ccgtctcctc ag                                              382

<210> SEQ ID NO 179
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Leu Arg Gln Ala Pro Gly Gln Gly Leu Gln Trp Met
        35                  40                  45

Gly Trp Met Asn Pro Gln Thr Gly Arg Thr Asn Thr Ala Arg Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Ile Tyr Tyr Cys

```
                85                  90                  95
Thr Thr Gly Gly Trp Ile Ser Leu Tyr Tyr Asp Ser Tyr Tyr Pro
            100                 105                 110

Asn Phe Asp His Trp Gly Gln Gly Thr Leu Leu Thr Val Ser Ser
        115                 120                 125
```

<210> SEQ ID NO 180
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180

```
cagtctgccc tgactcagcc tgcctccgtg tctgggtctc ctggacagtc gatcaccatc    60
tcctgcactg gaaccaagta tgatgttggg agtcatgacc ttgtctcctg gtaccaacag   120
tacccaggca aagtccccaa atacatgatt tatgaagtca ataaacggcc ctcaggagtt   180
tctaatcgct tctctggctc caaatctggc aacacggcct ccctgacaat ctctgggctc   240
cgggctgagg acgaggctga ctattattgc tgttcatttg agggagtgca caccgtggtc   300
tgcggcggcg ggaccaaggt gaccgtccta g                                  331
```

<210> SEQ ID NO 181
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

```
Gln Ser Ala Leu Thr Gln Pro Ala Ser Val Ser Gly Ser Pro Gly Gln
1               5                   10                  15

Ser Ile Thr Ile Ser Cys Thr Gly Thr Lys Tyr Asp Val Gly Ser His
            20                  25                  30

Asp Leu Val Ser Trp Tyr Gln Gln Tyr Pro Gly Lys Val Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Cys Ser Phe Glu Gly Ser
                85                  90                  95

Ala Thr Val Val Cys Gly Gly Gly Thr Lys Val Thr Val Leu
            100                 105                 110
```

<210> SEQ ID NO 182
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182

```
gacatccaga tgacccagtc tccgtctttc ctgtacggct ctgtaggcga tagagtcacc    60
atcacttgcc gggcaagtca gaatattaag gactatttaa attggtatca gcagagacca   120
gggagagccc ctagactcct gatctatgct gcatccaatt tgcaaagtgg ggtcccgtca   180
```
aggttcagtg gcagtggata tgggacagac tttactctca tcatcagcag tctgcaacct  240
gaggactttg cgacttattt ctgtcaagag agttatagtt ctacgcccac acacattttt  300
ggcctgggga ccaaattgga gaagaaac  328

<210> SEQ ID NO 183
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Any amino acid

<400> SEQUENCE: 183

Asp Ile Gln Met Thr Gln Ser Pro Ser Phe Leu Tyr Gly Ser Val Gly
1               5                   10                  15

Asp Arg Val Thr Ile Thr Cys Arg Ala Ser Gln Asn Ile Lys Asp Tyr
            20                  25                  30

Leu Asn Trp Tyr Gln Gln Arg Pro Gly Arg Ala Pro Arg Leu Leu Ile
        35                  40                  45

Tyr Ala Ala Ser Asn Leu Gln Ser Gly Val Pro Ser Arg Phe Ser Gly
    50                  55                  60

Ser Gly Tyr Gly Thr Asp Phe Thr Leu Ile Ile Ser Ser Leu Gln Pro
65                  70                  75                  80

Glu Asp Phe Ala Thr Tyr Phe Cys Gln Glu Ser Tyr Ser Ser Thr Pro
                85                  90                  95

Thr His Ile Phe Gly Leu Gly Thr Lys Leu Glu Lys Lys Xaa
            100                 105                 110

<210> SEQ ID NO 184
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
cgtggcgtct ggatacaact tcaccgacta ctatatac  38

<210> SEQ ID NO 185
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cgtctggata caacttcaac acctactata tacactgggt gc  42

<210> SEQ ID NO 186
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
ggtcgcacag attacgcaca ggcgtttggg ga                                    32

<210> SEQ ID NO 187
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
gattacgcag gggcgtttca ggacagagtg tcca                                  34

<210> SEQ ID NO 188
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gttagaaatg tgggaacgga gggcagcttg ctccactatg                            40

<210> SEQ ID NO 189
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ggtcgcacag attacgcaca ggcgtttcag gacagagtgt cca                        43

<210> SEQ ID NO 190
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ggatcgaccc tagggtggt cgcacag                                           27

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
gtggtcgcac agattactca ggggcgtttg                                       30

<210> SEQ ID NO 192
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
ggggaagacc gatgggccct tggtgg                                              26

<210> SEQ ID NO 193
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
ccatctcatc cctgcgtgtc tccgactcag aagcagtggt atcaacgcag agt             53

<210> SEQ ID NO 194
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
cctatcccct gtgtgccttg gcagtctcag ggggaagacc gatgggccct tggtgg         56

<210> SEQ ID NO 195
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
caggtgcagc tggtacagtc tgggggaggt ctggtgaagc cggggggtc cctcacactc       60
tcctgttcag cctctggatt cttttttcgat aattcatgga tgggtgggt ccgtcaggcg    120
ccagggaagg gactggagtg ggttggccgc attagaaggc tcaaagacgg tgcgacagga   180
gaatatggtg cagccgtgaa ggacagattc accatttcaa gagatgacag tagaaatatg   240
ctgtacctgc acatgaggac cctgaaaacc gaggactcag gcacttatta ttgtaccatg   300
gatgagggga ccccagtaac acgcttctta gaatggggct acttctatta ttatatggcc   360
gtttggggca gagggaccac ggtcatcgtc tcttca                             396

<210> SEQ ID NO 196
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

```
Leu Tyr Leu His Met Arg Thr Leu Lys Thr Glu Asp Ser Gly Thr Tyr
            85                  90                  95

Tyr Cys Thr Met Asp Glu Gly Thr Pro Val Thr Arg Phe Leu Glu Trp
        100                 105                 110

Gly Tyr Phe Tyr Tyr Tyr Met Ala Val Trp Gly Arg Gly Thr Thr Val
            115                 120                 125

Ile Val Ser Ser
    130

<210> SEQ ID NO 197
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
            85                  90                  95

Tyr Cys Thr Met Asp Trp Gly Thr Pro Val Thr Arg Phe Leu Glu Trp
        100                 105                 110

Gly Tyr Phe Tyr Tyr Tyr Met Ala Val Trp Gly Arg Gly Thr Thr Val
            115                 120                 125

Ile Val Ser Ser
    130

<210> SEQ ID NO 198
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
            85                  90                  95
```

```
Tyr Cys Thr Met Asp Glu Trp Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
        130

<210> SEQ ID NO 199
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Trp Pro Val Thr Arg Phe Leu Glu Trp
            100                 105                 110

Gly Tyr Phe Tyr Tyr Met Ala Val Trp Gly Arg Gly Thr Thr Val
        115                 120                 125

Ile Val Ser Ser
        130

<210> SEQ ID NO 200
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Trp Val Thr Arg Phe Leu Glu Trp
            100                 105                 110
```

```
Gly Tyr Phe Tyr Tyr Tyr Met Ala Val Trp Gly Arg Gly Thr Thr Val
            115                 120                 125

Ile Val Ser Ser
        130

<210> SEQ ID NO 201
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Phe Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
        130

<210> SEQ ID NO 202
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Ile Thr Arg Phe Leu Glu Trp
            100                 105                 110

Gly Tyr Phe Tyr Tyr Tyr Met Ala Val Trp Gly Arg Gly Thr Thr Val
        115                 120                 125
```

```
Ile Val Ser Ser
    130

<210> SEQ ID NO 203
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Trp Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 204
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Trp Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 205
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Trp Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 206
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Trp Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 207
<211> LENGTH: 132

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Phe Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 208
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Trp Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 209
<211> LENGTH: 132
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 209

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Trp Tyr Phe Tyr Tyr Tyr Met Ala Val Trp Gly Arg Gly Thr Thr Val
        115                 120                 125

Ile Val Ser Ser
    130

<210> SEQ ID NO 210
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Trp Phe Tyr Tyr Tyr Met Ala Val Trp Gly Arg Gly Thr Thr Val
        115                 120                 125

Ile Val Ser Ser
    130

<210> SEQ ID NO 211
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 211

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Trp Tyr Tyr Tyr Met Ala Val Trp Gly Arg Gly Thr Thr Val
        115                 120                 125

Ile Val Ser Ser
    130

<210> SEQ ID NO 212
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Trp Tyr Met Ala Val Trp Gly Arg Gly Thr Thr Val
        115                 120                 125

Ile Val Ser Ser
    130

<210> SEQ ID NO 213
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gln Val Gln Leu Val Gln Ser Gly Gly Gly Leu Val Lys Pro Gly Gly
```

```
            1               5                  10                  15
Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Thr Gly Glu Tyr Gly Ala
        50                  55                  60

Ala Val Lys Asp Arg Phe Thr Ile Ser Arg Asp Asp Ser Arg Asn Met
 65                  70                  75                  80

Leu Tyr Leu His Met Arg Thr Leu Lys Thr Glu Asp Ser Gly Thr Tyr
                    85                  90                  95

Tyr Cys Thr Met Asp Glu Gly Thr Pro Val Thr Arg Phe Leu Glu Trp
                    100                 105                 110

Gly Tyr Phe Tyr Tyr Met Ala Val Trp Gly Arg Gly Thr Thr Val
            115                 120                 125

Ile Val Ser Ser
        130
```

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

```
Gly Gly Gly Gly Ser Gly Gly Gly Ser Gly Gly Gly Gly Ser
1               5                   10                  15
```

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

```
Cys Val Arg Asn Val Gly Thr Ala Gly Ser Leu Leu His Tyr Asp His
1               5                   10                  15

Trp
```

<210> SEQ ID NO 216
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

```
Gln Val Gln Leu Ile Gln Ser Gly Pro Gln Phe Lys Thr Pro Gly Ala
1               5                   10                  15

Ser Val Thr Val Ser Cys Lys Ala Ser Gly Tyr Ile Phe Thr Asp Tyr
            20                  25                  30

Leu Ile His Trp Val Arg Leu Val Pro Gly Lys Gly Leu Glu Trp Leu
            35                  40                  45

Gly Arg Ile Asn Thr Asn Ala Gly Leu Met Tyr Leu Ser His Lys Phe
        50                  55                  60
```

Glu Gly Arg Leu Ile Leu Arg Arg Val Val Asp Trp Arg Thr Pro Ser
65                  70                  75                  80

Leu Gly Thr Val Asn Met Glu Leu Arg Asn Val Arg Ser Asp Asp Ser
                85                  90                  95

Ala Ile Tyr Phe Cys Gly Arg Val Val Asp Gly Phe Asn Ala Ala Gly
            100                 105                 110

Pro Leu Glu Phe Trp Gly Gln Gly Ser Pro Val Ile Val Ser Ser
        115                 120                 125

<210> SEQ ID NO 217
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gln Val Arg Leu Met Gln Ser Gly Pro Gln Leu Lys Thr Pro Gly Ala
1               5                   10                  15

Ser Val Thr Val Ser Cys Lys Ala Ser Gly Tyr Ile Phe Thr Asp Tyr
                20                  25                  30

Leu Ile His Trp Val Arg Leu Val Pro Gly Lys Gly Leu Glu Trp Leu
            35                  40                  45

Gly Arg Ile Asn Thr Asn Gly Gly Leu Met Tyr Leu Ser Tyr Lys Phe
        50                  55                  60

Glu Gly Arg Leu Ile Leu Arg Arg Asp Val Asp Trp Arg Thr Pro Ser
65                  70                  75                  80

Leu Gly Thr Val Tyr Met Glu Leu Lys Asn Leu Arg Ser Asp Asp Ser
                85                  90                  95

Ala Ile Tyr Phe Cys Gly Arg Val Val Asp Gly Phe Asn Ala Ala Gly
            100                 105                 110

Pro Leu Glu Phe Trp Gly Gln Gly Ser Pro Val Ile Val Ser Ser
        115                 120                 125

<210> SEQ ID NO 218
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Gln Val Gln Leu Ile Gln Ser Gly Pro Gln Leu Lys Thr Pro Gly Ala
1               5                   10                  15

Ser Val Thr Val Ser Cys Lys Ala Ser Gly Tyr Val Phe Ala Asp Tyr
                20                  25                  30

Leu Ile His Trp Val Arg Leu Val Pro Gly Lys Gly Leu Glu Trp Leu
            35                  40                  45

Gly Arg Ile Asn Thr Asn Ala Gly Leu Met Tyr Leu Ser His Lys Phe
        50                  55                  60

Glu Gly Arg Leu Ile Leu Arg Arg Asp Arg Asp Trp Arg Thr Pro Ser
65                  70                  75                  80

Leu Gly Thr Leu Tyr Met Glu Leu Arg Asn Leu Lys Ser Asp Asp Ser
                85                  90                  95

Ala Ile Tyr Phe Cys Gly Arg Val Val Asp Gly Phe Asn Ala Ala Gly
            100                 105                 110

Pro Leu Glu Phe Trp Gly Gln Gly Ser Pro Val Ile Val Ser Ser
            115                 120                 125

<210> SEQ ID NO 219
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gln Val Arg Leu Met Gln Ser Gly Thr Glu Phe Lys Thr Pro Gly Ala
1               5                   10                  15

Ser Val Lys Val Ser Cys Lys Thr Ser Gly Tyr Ile Phe Ser Asp Tyr
            20                  25                  30

Leu Ile His Trp Val Arg Leu Val Pro Gly Lys Gly Leu Glu Trp Leu
        35                  40                  45

Gly Arg Ile Asn Thr Asn Ala Gly Leu Met Tyr Leu Ser Pro Arg Phe
    50                  55                  60

Glu Gly Arg Val Ile Leu Arg Arg Glu Ser Ser Phe Arg Thr Pro Ser
65                  70                  75                  80

Leu Gly Thr Val Tyr Met Glu Leu Arg Asn Leu Lys Phe Asp Asp Ser
                85                  90                  95

Ala Val Tyr Phe Cys Gly Arg Val Val Asp Gly Phe Asn Ala Ala Gly
            100                 105                 110

Pro Leu Glu Phe Trp Gly Gln Gly Ser Leu Val Ile Val Ser Ser
            115                 120                 125

<210> SEQ ID NO 220
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Val Val Met Thr Gln Ser Pro Ala Thr Leu Ser Leu Ser Pro Gly
1               5                   10                  15

Glu Thr Ala Ala Val Ser Cys Arg Ala Ser Gln Tyr Val Asp Arg Ser
            20                  25                  30

Ile Ser Trp Tyr Gln Leu Lys Thr Gly Arg Ala Pro Arg Leu Leu Val
        35                  40                  45

Tyr Ala Ala Ser Ser Arg Ser Ile Gly Val Pro Asp Arg Phe Ser Gly
    50                  55                  60

Ser Gly Ser Gly Arg Asp Phe Thr Leu Thr Ile Arg Gly Val Gln Ser
65                  70                  75                  80

Asp Asp Phe Ala Leu Tyr Tyr Cys Gln Gln Asp Tyr Tyr Trp Pro Val
                85                  90                  95

Thr Phe Gly Gln Gly Thr Arg Leu Asp Met Lys
            100                 105

<210> SEQ ID NO 221
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Val Val Met Thr Gln Ser Pro Val Thr Leu Ser Val Ser Pro Gly
1               5                   10                  15

Glu Thr Ala Ala Val Ser Cys Arg Ala Ser Gln Tyr Val Asp Arg Ser
            20                  25                  30

Ile Ser Trp Tyr Gln Leu Lys Thr Gly Arg Ala Pro Arg Leu Leu Val
        35                  40                  45

Tyr Ala Ala Ser Ser Arg Ser Ile Gly Val Pro Asp Arg Phe Ser Gly
    50                  55                  60

Ser Gly Ser Gly Arg Asp Phe Thr Leu Thr Ile Arg Gly Val Gln Ser
65                  70                  75                  80

Asp Asp Phe Ala Val Tyr Tyr Cys Gln Gln Asp Tyr Tyr Trp Pro Val
                85                  90                  95

Thr Phe Gly Gln Gly Thr Arg Leu Asp Met Lys
            100                 105

<210> SEQ ID NO 222
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gln Val Leu Met Thr Gln Ser Pro Ala Thr Leu Ser Val Ser Pro Gly
1               5                   10                  15

Glu Thr Ala Ala Val Ser Cys Arg Ala Ser Gln Tyr Val Asp Arg Ser
            20                  25                  30

Ile Ser Trp Tyr Gln Val Lys Ser Gly Arg Ala Pro Arg Leu Leu Val
        35                  40                  45

Tyr Ala Ala Ser Ser Arg Ser Ile Gly Val Pro Asp Arg Phe Ser Gly
    50                  55                  60

Ser Gly Ser Gly Thr Asp Phe Thr Leu Thr Ile Arg Gly Val Gln Ser
65                  70                  75                  80

Asp Asp Phe Ala Leu Tyr Tyr Cys Gln Gln Asp Tyr Gly Trp Pro Val
                85                  90                  95

Thr Phe Gly Gln Gly Thr Arg Leu Asp Met Lys
            100                 105

<210> SEQ ID NO 223
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Glu Val Val Met Thr Gln Ser Pro Ala Thr Leu Ser Val Ser Pro Gly
1               5                   10                  15

Glu Glu Ala Ala Leu Ser Cys Gly Ala Ser Asp Tyr Ile Asp Arg Ser
            20                  25                  30

Val Ser Trp Tyr Gln Leu Lys Pro Gly Arg Ala Pro Arg Leu Leu Val
        35                  40                  45

Tyr Ala Ala Ser Ser Arg Ser Ile Gly Ile Pro Asp Arg Phe Ser Gly
    50                  55                  60

Ser Gly Ser Gly Thr Ala Phe Thr Leu Thr Ile Arg Gly Val Gln Ser

```
                65                  70                  75                  80
Asp Asp Phe Ala Leu Tyr Tyr Cys Gln Gln Asp Lys Tyr Trp Pro Val
                    85                  90                  95

Thr Phe Gly Gln Gly Thr Arg Leu Asp Met Lys
                100                 105

<210> SEQ ID NO 224
<211> LENGTH: 96
<212> TYPE: PRT
<213> ORGANISM: Homo sapiens

<400> SEQUENCE: 224

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

<210> SEQ ID NO 225
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Val Gln Leu Val Gln Ser Gly Ala Glu Val Lys Lys Pro Gly Ala
1               5                   10                  15

Ser Val Thr Val Ser Cys Gln Ala Ser Gly Tyr Thr Phe Thr Asn Tyr
                20                  25                  30

Tyr Val His Trp Val Arg Gln Ala Pro Gly Gln Gly Leu Gln Leu Met
            35                  40                  45

Gly Trp Ile Asp Pro Ser Trp Gly Arg Thr Asn Tyr Ala Gln Asn Phe
        50                  55                  60

Gln Gly Arg Ile Thr Met Thr Arg Asp Thr Ser Thr Ser Thr Val Tyr
65                  70                  75                  80

Met Glu Met Arg Ser Leu Arg Ser Glu Asp Thr Ala Val Tyr Tyr Cys
                85                  90                  95

<210> SEQ ID NO 226
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Arg Leu Leu Gln Tyr Gly Gly Gly Val Lys Arg Pro Gly Ala
1               5                   10                  15

Ser Met Thr Ile Ser Cys Val Ala Ser Gly Tyr Asn Phe Asn Asp Tyr
                20                  25                  30
```

Tyr Ile His Trp Val Arg Gln Ala Pro Gly Gln Gly Leu Glu Leu Met
            35                  40                  45

Gly Trp Ile Asp Pro Ser Gly Arg Thr Asp Tyr Ala Gly Ala Phe
    50                  55                  60

Gly Asp Arg Val Ser Met Tyr Arg Asp Lys Ser Met Asn Thr Leu Tyr
65                  70                  75                  80

Met Asp Leu Arg Ser Leu Arg Ser Gly Asp Thr Ala Met Tyr Tyr Cys
                85                  90                  95

<210> SEQ ID NO 227
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gln Val Arg Leu Ala Gln Tyr Gly Gly Gly Val Lys Arg Leu Gly Ala
1               5                   10                  15

Thr Met Thr Leu Ser Cys Val Ala Ser Gly Tyr Thr Phe Asn Asp Tyr
                20                  25                  30

Tyr Ile His Trp Val Arg Gln Ala Pro Gly Gln Gly Phe Glu Leu Leu
            35                  40                  45

Gly Tyr Ile Asp Pro Ala Asn Gly Arg Pro Asp Tyr Ala Gly Ala Leu
    50                  55                  60

Arg Glu Arg Leu Ser Phe Tyr Arg Asp Lys Ser Met Glu Thr Leu Tyr
65                  70                  75                  80

Met Asp Leu Arg Ser Leu Arg Tyr Asp Asp Thr Ala Met Tyr Tyr Cys
                85                  90                  95

<210> SEQ ID NO 228
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gln Val Gln Leu Glu Gln Ser Gly Thr Ala Val Arg Lys Pro Gly Ala
1               5                   10                  15

Ser Val Thr Leu Ser Cys Gln Ala Ser Gly Tyr Asn Phe Val Lys Tyr
                20                  25                  30

Ile Ile His Trp Val Arg Gln Lys Pro Gly Leu Gly Phe Glu Trp Val
            35                  40                  45

Gly Met Ile Asp Pro Tyr Arg Gly Arg Pro Trp Ser Ala His Lys Phe
    50                  55                  60

Gln Gly Arg Leu Ser Leu Ser Arg Asp Thr Ser Met Glu Ile Leu Tyr
65                  70                  75                  80

Met Thr Leu Thr Ser Leu Lys Ser Asp Asp Thr Ala Thr Tyr Phe Cys
                85                  90                  95

<210> SEQ ID NO 229
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gln Gly Gln Leu Val Gln Ser Gly Gly Leu Lys Lys Pro Gly Thr
1               5                   10                  15

Ser Val Thr Ile Ser Cys Leu Ala Ser Glu Tyr Thr Phe Asn Glu Phe
                20                  25                  30

Val Ile His Trp Ile Arg Gln Ala Pro Gly Gln Gly Pro Leu Trp Leu
            35                  40                  45

Gly Leu Ile Lys Arg Ser Gly Arg Leu Met Thr Ala Tyr Asn Phe Gln
    50                  55                  60

Asp Arg Leu Ser Leu Arg Arg Asp Arg Ser Thr Gly Thr Val Phe Met
65                  70                  75                  80

Glu Leu Arg Gly Leu Arg Pro Asp Asp Thr Ala Val Tyr Tyr Cys
                85                  90                  95

<210> SEQ ID NO 230
<211> LENGTH: 96
<212> TYPE: PRT
<213> ORGANISM: Homo sapiens

<400> SEQUENCE: 230

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

<210> SEQ ID NO 231
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
                20                  25                  30

Thr Leu Asn Trp Ile Arg Leu Ala Pro Gly Lys Arg Pro Glu Trp Met
            35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

<210> SEQ ID NO 232
<211> LENGTH: 105

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

Tyr Trp Val Asn Pro Ala Pro Glu His Phe Ile His Phe Leu Arg Gln
            35                  40                  45

Ala Pro Gly Gln Gln Leu Glu Trp Leu Ala Trp Met Asn Pro Thr Asn
50                  55                  60

Gly Ala Val Asn Tyr Ala Trp Tyr Leu Asn Gly Arg Val Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys
                100                 105

<210> SEQ ID NO 233
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
            35                  40                  45

Ile Gly Trp Val Lys Thr Val Thr Gly Ala Val Asn Phe Gly Ser Pro
50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys

<210> SEQ ID NO 234
<211> LENGTH: 98
<212> TYPE: PRT
<213> ORGANISM: Homo sapiens

<400> SEQUENCE: 234

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
50                  55                  60
```

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 235
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Trp Val Arg Gln Ala Pro Gly Gln Gly Leu Glu Trp Met Gly Met Ile
1               5                  10                  15

Asn Pro Ser Gly Gly Ser Thr Ser Tyr Ala Gln Lys Phe Gln Gly Arg
            20                  25                  30

Val Thr Met Thr Arg Asp Thr Ser Thr Ser Thr Val Tyr Met Tyr Leu
        35                  40                  45

Ser Ser Leu Arg Ser Glu Asp Thr Ala Val Tyr Tyr Cys Val Arg
    50                  55                  60

<210> SEQ ID NO 236
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Trp Val Arg Gln Ala Pro Gly Gln Gly Leu Glu Trp Met Gly Met Ile
1               5                  10                  15

Asn Pro Ser Gly Gly Arg Thr Ser Tyr Pro Tyr Lys Phe Gln Gly Arg
            20                  25                  30

Val Thr Met Thr Arg Asp Thr Ser Thr Ser Thr Val Tyr Met Glu Val
        35                  40                  45

Ser Ser Leu Arg Ser Glu Asp Thr Ala Val Tyr Tyr Cys Val Arg
    50                  55                  60

<210> SEQ ID NO 237
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Trp Val Arg Gln Ala Pro Gly Gln Gly Leu Glu Trp Met Gly Met Ile
1               5                  10                  15

Asp Pro Ser Gly Gly Arg Thr Ser Tyr Ala Gln Lys Phe Gln Gly Arg
            20                  25                  30

Val Thr Met Thr Arg Asp Thr Ser Thr Ser Thr Val Tyr Met Glu Leu
        35                  40                  45

Ser Ser Leu Arg Ser Glu Asp Thr Ala Val His Tyr Cys Ala Arg
    50                  55                  60
```

```
<210> SEQ ID NO 238
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Trp Val Arg Gln Ala Pro Gly Gln Gly Leu Glu Trp Met Gly Met Ile
1               5                   10                  15

Asp Pro Ser Val Gly Arg Thr Thr Tyr Ala Glu Lys Phe Gln Gly Arg
            20                  25                  30

Val Thr Met Thr Arg Asp Thr Ser Thr Ser Thr Val Tyr Met Asp Leu
        35                  40                  45

Ser Ser Leu Arg Ser Glu His Thr Ala Val Tyr Tyr Cys Ala Arg
    50                  55                  60

<210> SEQ ID NO 239
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Trp Val Arg Gln Ala Pro Gly Gln Gly Leu Glu Trp Met Gly Met Ile
1               5                   10                  15

Asp Pro Ser Val Gly Arg Thr Thr Tyr Ala Glu Lys Phe Gln Gly Arg
            20                  25                  30

Val Thr Met Thr Arg Asp Thr Ser Thr Ser Thr Val Tyr Met Asp Leu
        35                  40                  45

Ser Ser Leu Arg Ser Glu Asp Thr Ala Val Tyr Tyr Cys Ala Arg
    50                  55                  60

<210> SEQ ID NO 240
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Trp Val Arg Gln Ala Pro Gly Gln Gly Leu Glu Trp Met Gly Met Ile
1               5                   10                  15

Asp Pro Ser Val Gly Arg Thr Thr Tyr Ala Glu Lys Phe Gln Gly Arg
            20                  25                  30

Val Thr Met Thr Arg Asp Thr Ser Thr Ser Thr Val Tyr Met Asp Leu
        35                  40                  45

Ser Ser Leu Arg Ser Glu Asp Thr Ala Val Tyr Tyr Cys Ala Arg
    50                  55                  60

<210> SEQ ID NO 241
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241
```

-continued

Trp Val Arg Gln Ala Pro Gly Gln Gly Leu Glu Trp Met Gly Met Ile
1               5                   10                  15

Asn Pro Arg Gly Gly Ser Thr Thr Tyr Ala Gln Arg Phe Gln Gly Arg
            20                  25                  30

Val Thr Met Thr Arg Asp Thr Ser Thr Ser Ile Val Tyr Met Glu Leu
        35                  40                  45

Ser Arg Leu Arg Ser Glu Asp Thr Ala Val Tyr Tyr Cys Val Arg
    50                  55                  60

<210> SEQ ID NO 242
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Trp Val Arg Gln Ala Pro Gly Gln Gly Leu Glu Trp Met Gly Met Ile
1               5                   10                  15

Asn Pro Ser Gly Gly Arg Thr Ser Ser Pro Tyr Lys Phe Gln Gly Arg
            20                  25                  30

Leu Thr Met Thr Arg Asp Thr Ser Thr Ser Thr Val Tyr Met Asp Leu
        35                  40                  45

Ser Ser Leu Arg Pro Asp Thr Ala Val Tyr Tyr Cys Val Arg
    50                  55                  60

<210> SEQ ID NO 243
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Trp Val Arg Gln Ala Pro Gly Gln Gly Leu Glu Trp Met Gly Met Val
1               5                   10                  15

Asn Pro Ser Gly Gly Arg Thr Ser Tyr Pro His Lys Phe Gln Gly Arg
            20                  25                  30

Val Thr Met Thr Arg Asp Thr Ser Thr Ser Thr Val Tyr Met Gly Leu
        35                  40                  45

Ser Ser Leu Arg Ser Glu Asp Thr Ala Val Tyr Tyr Cys Ala Arg
    50                  55                  60

<210> SEQ ID NO 244
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Trp Val Arg Gln Ala Pro Gly Ala Gly Leu Glu Trp Met Gly Met Ile
1               5                   10                  15

Asn Pro Ser Gly Gly Arg Thr Thr Tyr Pro Gln Lys Phe Gln Gly Arg
            20                  25                  30

Val Thr Met Thr Arg Asp Thr Ser Thr Ser Thr Val His Met Lys Leu
        35                  40                  45

Ser Ser Leu Arg Ser Gln Asp Thr Ala Val Tyr Tyr Cys Ala Arg
    50                  55                  60

<210> SEQ ID NO 245
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Trp Val Arg Gln Ala Pro Gly Ala Gly Leu Glu Trp Met Gly Met Ile
1               5                   10                  15

Asn Pro Ser Gly Gly Arg Thr Thr Tyr Pro Gln Lys Phe Gln Gly Arg
            20                  25                  30

Val Thr Met Thr Arg Asp Thr Ser Thr Ser Val Tyr Met Lys Leu
        35                  40                  45

Ser Ser Leu Arg Ser Gln Asp Thr Ala Val Tyr Tyr Cys Ala Arg
    50                  55                  60

<210> SEQ ID NO 246
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Trp Val Arg Gln Ala Pro Gly Ala Gly Leu Glu Trp Met Gly Met Ile
1               5                   10                  15

Asn Pro Ser Gly Gly Arg Thr Thr Tyr Pro Gln Lys Phe Gln Gly Arg
            20                  25                  30

Val Thr Met Thr Arg Asp Thr Ser Thr Ser Val Tyr Met Lys Leu
        35                  40                  45

Ser Ser Leu Arg Ser Gln Asp Thr Ala Val Tyr Tyr Cys Ala Arg
    50                  55                  60

<210> SEQ ID NO 247
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Trp Val Arg Gln Ala Pro Gly Gln Gly Leu Glu Trp Met Gly Met Ile
1               5                   10                  15

Asp Pro Ser Gly Gly Arg Thr Ser Tyr Ala Pro Lys Phe Gln Gly Arg
            20                  25                  30

Leu Thr Met Thr Arg Asp Thr Ser Thr Asp Thr Leu Tyr Met Gln Leu
        35                  40                  45

Asn Ser Leu Arg Ser Glu Asp Thr Ala Val Tyr Tyr Cys Ala Arg
    50                  55                  60

<210> SEQ ID NO 248
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Trp Val Arg Gln Ala Pro Gly Gln Gly Leu Glu Trp Met Gly Met Ile
1               5                   10                  15

Asp Pro Ser Tyr Gly Arg Thr Ser Tyr Ala Gln Lys Phe Gln Gly Arg
            20                  25                  30

Val Thr Met Thr Arg Asp Thr Ser Thr Ser Val Tyr Met Glu Leu
        35                  40                  45

Ser Ser Leu Arg Ser Glu Asp Thr Ala Val Phe Tyr Cys Ala Arg
    50                  55                  60

<210> SEQ ID NO 249
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Trp Val Arg Gln Ala Pro Gly Gln Gly Leu Glu Trp Met Gly Met Ile
1               5                   10                  15

Asp Pro Ser Tyr Gly Arg Thr Ser Tyr Ala Gln Lys Phe Gln Gly Arg
            20                  25                  30

Val Thr Met Thr Arg Asp Thr Ser Thr Ser Val Tyr Met Glu Leu
        35                  40                  45

Ser Ser Leu Arg Ser Glu Asp Thr Ala Val Phe Tyr Cys Ala Arg
    50                  55                  60

<210> SEQ ID NO 250
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Trp Val Arg Gln Ala Pro Gly Gln Gly Leu Glu Trp Met Gly Met Ile
1               5                   10                  15

Asp Pro Ser Val Gly Arg Thr Thr Tyr Ala Glu Lys Phe Gln Gly Arg
            20                  25                  30

Val Thr Met Thr Arg Asp Thr Ser Thr Ser Val Tyr Met Asp Leu
        35                  40                  45

Ser Ser Leu Arg Ser Glu Asp Thr Ala Val Tyr Tyr Cys Ala Arg
    50                  55                  60

<210> SEQ ID NO 251
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Trp Val Arg Gln Ala Pro Gly Gln Gly Leu Glu Trp Met Gly Met Leu
1               5                   10                  15

Asp Pro Ser Gly Gly Arg Thr Ser Tyr Pro Gln Lys Phe Gln Gly Arg
            20                  25                  30

Val Thr Met Thr Arg Asp Thr Ser Thr Ser Val Tyr Met Tyr Leu

```
                35                  40                  45
Ser Ser Leu Arg Ser Glu Asp Thr Ala Val Tyr Tyr Cys Val Arg
     50                  55                  60

<210> SEQ ID NO 252
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Trp Val Arg Gln Ala Pro Gly Gln Arg Leu Glu Trp Met Gly Leu Ile
1               5                   10                  15

Asn Pro Ser Gly Gly Arg Thr Ser Tyr Pro His Gln Phe Gln Gly Arg
            20                  25                  30

Val Thr Met Thr Arg Asp Thr Ser Thr Ser Val Tyr Met Tyr Leu
        35                  40                  45

Ser Ser Leu Arg Ala Glu Asp Thr Ala Val Tyr Tyr Cys Val Arg
     50                  55                  60

<210> SEQ ID NO 253
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Trp Val Arg Gln Ala Pro Gly Gln Gly Leu Glu Trp Met Gly Met Leu
1               5                   10                  15

Asp Pro Ser Gly Gly Arg Thr Ser His Pro His Lys Phe Gln Gly Arg
            20                  25                  30

Val Thr Leu Thr Arg Asp Thr Ser Thr Ser Val Tyr Met Tyr Leu
        35                  40                  45

Ser Ser Leu Arg Ser Glu Asp Thr Ala Val Tyr Tyr Cys Val Arg
     50                  55                  60

<210> SEQ ID NO 254
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Trp Val Arg Gln Ala Pro Gly Gln Gly Leu Glu Trp Met Gly Met Ile
1               5                   10                  15

Asn Pro Ser Gly Gly Arg Thr Ser Pro Tyr Lys Phe Gln Gly Arg
            20                  25                  30

Leu Thr Met Thr Arg Asp Thr Ser Thr Ser Val Tyr Met Asp Leu
        35                  40                  45

Ser Ser Leu Arg Pro Asp Asp Thr Ala Val Tyr Tyr Cys Val Arg
     50                  55                  60

<210> SEQ ID NO 255
<211> LENGTH: 63
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 255

Trp Val Arg Gln Ala Pro Gly Gln Gly Leu Glu Trp Met Gly Met Ile
1               5                   10                  15

Asp Pro Ser Gly Gly Arg Pro Ser Tyr Ala Gln Lys Phe Gln Gly Arg
            20                  25                  30

Val Ser Met Thr Arg Asp Thr Ser Thr Val Tyr Met Glu Leu
        35                  40                  45

Ser Ser Leu Arg Ser Glu Asp Thr Ala Leu Tyr Tyr Cys Val Arg
    50                  55                  60

<210> SEQ ID NO 256
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Trp Val Arg Gln Ala Pro Gly Gln Gly Leu Glu Trp Met Gly Met Ile
1               5                   10                  15

Asp Pro Ser Gly Gly Arg Thr Ser Tyr Ala Pro Lys Phe Gln Gly Arg
            20                  25                  30

Leu Thr Met Thr Arg Asp Thr Ser Thr Asp Thr Leu Tyr Met Gln Leu
        35                  40                  45

Asn Ser Leu Arg Ser Glu Asp Thr Ala Val Tyr Tyr Cys Ala Arg
    50                  55                  60

<210> SEQ ID NO 257
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Trp Val Arg Gln Ala Pro Gly Gln Gly Leu Lys Trp Val Gly Met Leu
1               5                   10                  15

Asp Pro Ser Gly Gly Arg Thr Thr Leu Ala His Thr Phe Gln Gly Arg
            20                  25                  30

Val Thr Met Thr Arg Asp Thr Ser Thr Val Tyr Met Glu Leu
        35                  40                  45

Asn Ser Leu Arg Ser Glu Asp Thr Ala Val Tyr Tyr Cys Ala Arg
    50                  55                  60

<210> SEQ ID NO 258
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Pro Gly Gln Gly Leu Lys Trp Val Gly Met Leu Asp Pro Ser Gly Gly
1               5                   10                  15

Arg Thr Thr Leu Ala His Thr Phe Gln Gly Arg Val Thr Met Thr Arg
```

```
                    20                  25                  30

Asp Thr Ser Thr Ser Thr Val Tyr Met Glu Leu Asn Ser Leu Arg Ser
            35                  40                  45

Glu Asp Thr Ala Val Tyr Tyr Cys Ala Arg
        50                  55

<210> SEQ ID NO 259
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Trp Val Arg Gln Ala Pro Gly Gln Gly Leu Lys Trp Val Gly Met Leu
1               5                   10                  15

Asp Pro Ser Gly Gly Arg Thr Thr Leu Ala His Thr Phe Gln Gly Arg
            20                  25                  30

Val Thr Met Thr Arg Asp Thr Ser Thr Val Tyr Met Glu Leu
        35                  40                  45

Asn Ser Leu Arg Ser Glu Asp Thr Ala Val Tyr Tyr Cys Ala Arg
    50                  55                  60

<210> SEQ ID NO 260
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Trp Val Arg Gln Ala Pro Gly Gln Gly Leu Glu Trp Val Gly Met Ile
1               5                   10                  15

Asp Pro Ser Val Gly Arg Thr Thr Leu Pro His Lys Phe Gln Gly Arg
            20                  25                  30

Val Thr Met Thr Arg Asp Thr Ser Thr Ser Thr Val Tyr Met Lys Leu
        35                  40                  45

Ser Thr Leu Arg Ser Glu Asp Thr Ala Val Tyr Phe Cys Ala Arg
    50                  55                  60

<210> SEQ ID NO 261
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Val Arg Gln Ala Pro Gly Gln Arg Leu Glu Leu Met Gly Met Ile Asp
1               5                   10                  15

Pro Ser Arg Gly Arg Thr Asp Tyr Ala Gln Lys Phe Gln Gly Arg Val
            20                  25                  30

Thr Met Ser Arg Asp Thr Ser Thr Ser Thr Leu Tyr Met Glu Leu Arg
        35                  40                  45

Ser Leu Arg Pro Asp Asp Thr Ala Leu Tyr Tyr Cys Val Arg
    50                  55                  60

<210> SEQ ID NO 262
```

```
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Trp Val Arg Gln Ala Pro Gly Gln Gly Leu Asp Ser Met Gly Trp Ile
1               5                   10                  15

Asp Pro Ser Val Gly Arg Thr Ser Tyr Ser Tyr Lys Phe Arg Asp Arg
            20                  25                  30

Ile Ser Met Phe Arg Asp Thr Ser Thr Asn Thr Val Tyr Met Glu Leu
        35                  40                  45

Arg Ser Leu Arg Ser Asp Asp Thr Ala Val Tyr Tyr Cys Val Arg
    50                  55                  60

<210> SEQ ID NO 263
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Trp Val Arg Gln Ala Pro Gly Gln Arg Leu Glu Trp Met Gly Met Ile
1               5                   10                  15

Asp Pro Ser Val Gly Arg Pro Thr Val Ala Gly Asn Phe Gln Gly Arg
            20                  25                  30

Val Thr Leu Thr Arg Asp Arg Ser Thr Asp Thr Val Tyr Met Asp Leu
        35                  40                  45

Ser Ser Leu Arg Ser Glu Asp Thr Ala Val Tyr Tyr Cys Ala Arg
    50                  55                  60

<210> SEQ ID NO 264
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Trp Val Arg Gln Ala Pro Gly Gln Gly Leu Glu Trp Met Gly Met Ile
1               5                   10                  15

Asp Pro Ser Val Gly Arg Pro Thr Arg Ala Gly Lys Phe Gln Gly Arg
            20                  25                  30

Val Thr Met Thr Arg Asp Arg Ser Thr Ser Thr Val Tyr Met Asp Leu
        35                  40                  45

Ser Ser Leu Arg Ser Glu Asp Thr Ala Met Tyr Tyr Cys Ala Arg
    50                  55                  60

<210> SEQ ID NO 265
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Trp Val Arg Gln Ala Pro Gly Gln Gly Leu Glu Trp Met Gly Met Ile
```

```
1               5                   10                  15
Asp Pro Ser Val Gly Arg Pro Thr Arg Ala Gly Lys Phe Gln Gly Arg
            20                  25                  30

Val Thr Met Thr Arg Asp Arg Ser Thr Ser Val Tyr Met Asp Leu
        35                  40                  45

Ser Ser Leu Lys Ser Glu Asp Thr Ala Val Tyr Tyr Cys Ala Arg
    50                  55                  60
```

<210> SEQ ID NO 266
<211> LENGTH: 63
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 266

```
Trp Val Arg Gln Ala Pro Gly Gln Gly Pro Glu Trp Met Gly Met Ile
1               5                   10                  15

Asp Pro Ser Phe Gly Arg Pro Thr Arg Pro Gly Arg Phe Gln Asp Arg
            20                  25                  30

Val Thr Leu Thr Arg Asp Lys Ser Thr Ser Val Tyr Met Asp Leu
        35                  40                  45

Ser Ser Leu Arg Pro Glu Asp Thr Ala Val Tyr Tyr Cys Ala Arg
    50                  55                  60
```

<210> SEQ ID NO 267
<211> LENGTH: 63
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 267

```
Trp Val Arg Gln Ala Pro Gly Gln Arg Leu Glu Trp Met Gly Met Ile
1               5                   10                  15

Asp Pro Ser Val Gly Arg Pro Ser Arg Pro Tyr Lys Phe Gln Asp Arg
            20                  25                  30

Val Thr Met Thr Arg Asp Arg Phe Thr Asn Thr Val Tyr Met Asp Leu
        35                  40                  45

Ser Ser Leu Arg Ser Glu Asp Thr Ala Val Tyr Tyr Cys Ala Arg
    50                  55                  60
```

<210> SEQ ID NO 268
<211> LENGTH: 63
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 268

```
Trp Val Arg Gln Ala Pro Gly Gln Gly Phe Glu Cys Met Gly Met Leu
1               5                   10                  15

Asp Pro Ser Gly Gly Arg Thr Asp Tyr Ser His Lys Phe Gln Gly Arg
            20                  25                  30

Val Thr Met Thr Arg Asp Thr Ser Thr Ser Val Tyr Met Ser Leu
        35                  40                  45

Arg Ser Leu Lys Ser Glu Asp Thr Ala Val Tyr Tyr Cys Val Arg
    50                  55                  60
```

<210> SEQ ID NO 269
<211> LENGTH: 63
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 269

Trp Val Arg Gln Ala Pro Gly Gln Gly Phe Glu Cys Met Gly Met Leu
1               5                   10                  15

Asp Pro Ser Gly Gly Arg Thr Asp Tyr Ser His Lys Phe Gln Gly Arg
            20                  25                  30

Val Thr Met Thr Arg Asp Thr Ser Thr Ser Thr Val Tyr Met Ser Leu
        35                  40                  45

Arg Ser Leu Lys Ser Glu Asp Thr Ala Val Tyr Tyr Cys Val Arg
    50                  55                  60

<210> SEQ ID NO 270
<211> LENGTH: 63
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 270

Trp Val Arg Gln Ala Pro Gly Gln Gly Phe Glu Cys Met Gly Met Leu
1               5                   10                  15

Asp Pro Ser Gly Gly Arg Thr Asp Tyr Ser His Lys Phe Gln Gly Arg
            20                  25                  30

Val Thr Met Thr Arg Asp Thr Ser Thr Ser Thr Val Tyr Met Ser Leu
        35                  40                  45

Arg Ser Leu Lys Ser Glu Asp Thr Ala Val Tyr Tyr Cys Val Arg
    50                  55                  60

<210> SEQ ID NO 271
<211> LENGTH: 98
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 271

Gln Val Gln Leu Val Gln Ser Gly Ala Glu Val Lys Lys Pro Gly Ala
1               5                   10                  15

Ser Val Thr Val Ser Cys Gln Ala Ser Gly Tyr Thr Phe Thr Asn Tyr
            20                  25                  30

Tyr Val His Trp Val Arg Gln Ala Pro Gly Gln Gly Leu Gln Leu Met
        35                  40                  45

Gly Trp Ile Asp Pro Ser Trp Gly Arg Thr Asn Tyr Ala Gln Asn Phe
    50                  55                  60

Gln Gly Arg Ile Thr Met Thr Arg Asp Thr Ser Thr Ser Thr Val Tyr
65                  70                  75                  80

Met Glu Met Arg Ser Leu Arg Ser Glu Asp Thr Ala Val Tyr Tyr Cys
                85                  90                  95

Ala Arg

<210> SEQ ID NO 272
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 272

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
            20                  25                  30

Tyr Ile His Trp Val Arg Gln Ala Pro Gly Gln Arg Leu Glu Leu Met
        35                  40                  45

Gly Met Ile Asp Pro Ser Arg Gly Arg Thr Asp Tyr Ala Gln Lys Phe
    50                  55                  60

Gln Gly Arg Val Thr Met Ser Arg Asp Thr Ser Thr Ser Thr Leu Tyr
65                  70                  75                  80

Met Glu Leu Arg Ser Leu Arg Pro Asp Asp Thr Ala Leu Tyr Tyr Cys
                85                  90                  95

Val Arg

<210> SEQ ID NO 273
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 273

Gln Val Gln Leu Val Gln Ser Gly Ala Glu Val Arg Lys Pro Gly Ala
1               5                   10                  15

Ser Val Thr Val Ser Cys Lys Ala Ser Gly Tyr Thr Phe Asn Asn Phe
            20                  25                  30

Tyr Val His Trp Val Arg Gln Ala Pro Gly Gln Gly Leu Glu Cys Met
        35                  40                  45

Gly Trp Ile Asp Pro Ser Val Gly Arg Ile Asn Tyr Ala Gln Lys Phe
    50                  55                  60

Gln Gly Arg Val Thr Met Thr Arg Asp Arg Ser Thr Ser Thr Val Tyr
65                  70                  75                  80

Met Gly Leu Ser Ser Leu Arg Ser Glu Asp Thr Ala Ile Tyr Tyr Cys
                85                  90                  95

Val Arg Asp Val Gly Thr Glu Gly Ser Leu Leu His Phe Asp His Trp
                100                 105                 110

Gly Gln Gly Thr Leu Val Ile Val Ser Ala
        115                 120

<210> SEQ ID NO 274
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 274

Gln Val Gln Leu Val Gln Ser Gly Thr Glu Val Arg Lys Pro Gly Ala
1               5                   10                  15

-continued

Ser Val Thr Ile Ser Cys Lys Ala Ser Gly Tyr Thr Phe Asn Asn Phe
            20                  25                  30

Tyr Val His Trp Val Arg Gln Ala Pro Gly Gln Gly Leu Glu Cys Met
        35                  40                  45

Gly Trp Ile Asp Pro Ser Val Gly Arg Ile Ser Tyr Gly Gln Lys Phe
    50                  55                  60

Gln Gly Arg Val Thr Met Thr Arg Asp Arg Ser Thr Ser Thr Val Tyr
65                  70                  75                  80

Met Gly Leu Ser Ser Leu Arg Ser Glu Asp Thr Ala Met Tyr Tyr Cys
                85                  90                  95

Val Arg Asp Val Gly Thr Glu Gly Ser Leu Leu His Phe Asp His Trp
            100                 105                 110

Gly Gln Gly Thr Leu Val Ile Val Ser Ala
        115                 120

<210> SEQ ID NO 275
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Gln Val Gln Leu Val Gln Ser Gly Ala Ala Val Lys Lys Pro Gly Ala
1               5                   10                  15

Ser Val Arg Val Ser Cys Lys Ala Ser Gly Tyr Thr Phe Thr Ser Ser
            20                  25                  30

His Ile His Trp Val Arg Gln Ala Pro Gly Gln Gly Pro Glu Trp Met
        35                  40                  45

Gly Met Ile Asp Pro Ser Val Gly Arg Pro Thr Thr Ala Gly Lys Phe
    50                  55                  60

Gln Gly Arg Val Thr Met Thr Arg Asp Arg Tyr Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Ser Val Glu Thr Thr Gly Ser Leu Leu Tyr Phe Asp Tyr Trp
            100                 105                 110

Gly Gln Gly Thr Leu Ile Thr Val Ser Ser
        115                 120

<210> SEQ ID NO 276
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Trp Val Arg Gln Ala Pro Gly Gln Gly Leu Glu Leu Met Gly Trp Ile
1               5                   10                  15

Asp Pro Ser Val Gly Arg Ile Asn Tyr Gly Gln Lys Phe Glu Gly Arg
            20                  25                  30

Val Thr Met Thr Arg Asp Arg Ser Thr Ser Thr Val Tyr Met Gly Leu
        35                  40                  45

Ser Ser Leu Lys Ser Glu Asp Thr Ala Val Tyr Tyr Cys Val Arg
    50                  55                  60

<210> SEQ ID NO 277
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Trp Val Arg Gln Ala Pro Gly Gln Gly Leu Glu Leu Met Gly Trp Ile
1               5                   10                  15

Asp Pro Ser Val Gly Arg Ile Asn Tyr Gly Gln Lys Phe Gln Gly Arg
                20                  25                  30

Val Thr Met Thr Arg Asp Arg Ser Thr Ser Thr Val Tyr Met Gly Leu
            35                  40                  45

Ser Ser Leu Arg Ser Glu Asp Thr Ala Ile Tyr Tyr Cys Val Arg
        50                  55                  60

<210> SEQ ID NO 278
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Trp Val Arg Gln Ala Pro Gly Gln Gly Leu Glu Leu Met Gly Trp Ile
1               5                   10                  15

Asp Pro Ser Val Gly Arg Ile Asn Tyr Gly Gln Lys Phe Gln Gly Arg
                20                  25                  30

Val Thr Met Thr Arg Asp Arg Ser Thr Ser Thr Val Tyr Met Gly Leu
            35                  40                  45

Ser Ser Leu Arg Ser Glu Asp Thr Ala Ile Tyr Tyr Cys Val Arg
        50                  55                  60

<210> SEQ ID NO 279
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Trp Val Arg Gln Ala Pro Gly Gln Arg Leu Glu Leu Met Gly Trp Ile
1               5                   10                  15

Asp Pro Tyr Arg Gly Arg Thr Asp Tyr Ala Gln Lys Phe Gln Asp Arg
                20                  25                  30

Val Ser Met Tyr Arg Asp Thr Ser Thr Asn Thr Leu Tyr Met Asp Leu
            35                  40                  45

Arg Ser Leu Arg Pro Asp Asp Thr Ala Leu Tyr Tyr Cys Val Arg
        50                  55                  60

<210> SEQ ID NO 280
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Trp Val Arg Gln Ala Pro Gly Gln Gly Leu Glu Leu Met Gly Trp Ile
1               5                   10                  15

Asp Pro Ser Gly Gly Arg Thr Asp Tyr Ser Gln Ala Phe Gln Gly Arg
            20                  25                  30

Ile Ser Met Phe Arg Asp Thr Thr Ser Thr Val Tyr Met Glu Leu
        35                  40                  45

Arg Ser Leu Arg Ser Gly Asp Thr Ala Met Tyr Tyr Cys Val Arg
    50                  55                  60

<210> SEQ ID NO 281
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Gln Val Gln Leu Val Gln Ser Gly Ala Ala Val Lys Lys Pro Gly Ala
1               5                   10                  15

Ser Val Arg Val Ser Cys Lys Ala Ser Gly Tyr Thr Phe Thr Ser Ser
            20                  25                  30

His Ile His Trp Val Arg Gln Ala Pro Gly Gln Ala Leu Glu Trp Leu
        35                  40                  45

Gly Met Ile Asp Pro Arg Phe Gly Arg Pro Thr Arg Pro Gln Lys Phe
    50                  55                  60

Gln Gly Arg Val Thr Leu Thr Arg Asp Thr Tyr Thr Thr Thr Val Tyr
65                  70                  75                  80

Met Ser Leu Ser Ser Leu Thr Pro Glu Asp Thr Ala Val Tyr Tyr Cys
                85                  90                  95

Ala Arg

<210> SEQ ID NO 282
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
            20                  25                  30

Tyr Ile His Trp Val Arg Gln Ala Pro Gly Gln Gly Leu Glu Leu Met
        35                  40                  45

Gly Trp Ile Asn Pro Arg Gly Gly Arg Thr Asp Tyr Ser Tyr Arg Phe
    50                  55                  60

Glu Asp Arg Val Ser Met Tyr Arg Asp Thr Ser Met Ser Ile Val Tyr
65                  70                  75                  80

Met Asp Leu Arg Asn Leu Lys Ser Ala Asp Thr Ala Val Tyr Tyr Cys
                85                  90                  95

Val Arg

<210> SEQ ID NO 283
<211> LENGTH: 98
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 283

Gln Val Gln Leu Val Gln Ser Gly Ala Ala Val Lys Lys Pro Gly Ala
1               5                   10                  15

Ser Val Arg Val Ser Cys Lys Ala Ser Gly Tyr Thr Phe Thr Ser Ser
            20                  25                  30

His Ile His Trp Val Arg Gln Ala Pro Gly Gln Gly Pro Glu Trp Met
        35                  40                  45

Gly Met Val Asp Pro Arg Phe Gly Arg Pro Thr Tyr Ala Gln Lys Phe
    50                  55                  60

Gln Gly Arg Val Ala Met Thr Arg Asp Ile Tyr Thr Ser Thr Val Tyr
65                  70                  75                  80

Met Asp Leu Arg Ser Leu Lys Ser Glu Asp Thr Ala Ile Tyr Phe Cys
                85                  90                  95

Val Arg

<210> SEQ ID NO 284
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Gln Val Arg Leu Leu Gln Tyr Gly Gly Gly Val Lys Arg Pro Gly Ala
1               5                   10                  15

Ser Met Thr Ile Ser Cys Val Ala Ser Gly Tyr Asn Phe Asn Asp Tyr
            20                  25                  30

Tyr Ile His Trp Val Arg Gln Ala Pro Gly Gln Gly Leu Glu Leu Met
        35                  40                  45

Gly Trp Ile Asp Pro Ser Gly Gly Arg Thr Asp Tyr Ala Gly Ala Phe
    50                  55                  60

Gly Asp Arg Val Ser Met Tyr Arg Asp Lys Ser Met Asn Thr Leu Tyr
65                  70                  75                  80

Met Asp Leu Arg Ser Leu Arg Ser Gly Asp Thr Ala Met Tyr Tyr Cys
                85                  90                  95

Val Arg

<210> SEQ ID NO 285
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Gln Val Gln Leu Val Gln Ser Gly Ala Thr Val Lys Lys Pro Arg Ala
1               5                   10                  15

Ser Val Thr Leu Ser Cys Arg Thr Ser Gly Tyr Asn Phe Ile Asp Tyr
            20                  25                  30

Phe Ile His Trp Val Arg Arg Ala Pro Gly Gln Arg Leu Glu Val Met
        35                  40                  45

Gly Tyr Ile Asp Pro Ser Arg Gly Arg Pro Asp Tyr Ala Pro Asn Phe

```
                    50                  55                  60
Arg Asp Arg Val Ser Leu Tyr Arg Asp Thr Ser Met Ser Ile Val Tyr
 65                  70                  75                  80

Leu Asp Leu Arg Asp Leu Thr Pro Asp Thr Ala Ile Tyr Tyr Cys
                 85                  90                  95

Val Arg

<210> SEQ ID NO 286
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Gln Val Gln Leu Val Gln Ser Gly Gly Thr Val Lys Ser Pro Gly Thr
 1               5                  10                  15

Ser Val Thr Leu Ser Cys Lys Thr Ser Gly Tyr Asn Phe Ile Asp Tyr
                 20                  25                  30

Tyr Ile His Trp Val Arg Arg Ala Pro Gly Gln Arg Pro Glu Leu Met
             35                  40                  45

Gly Tyr Ile Asp Pro Ser His Gly Arg Pro Tyr Glu Gly Lys Phe
         50                  55                  60

Arg Asp Arg Ile Ser Leu Tyr Arg Asp Thr Ser Thr Ser Val Val Tyr
 65                  70                  75                  80

Met Asp Val Arg Gly Leu Arg Leu Asp Asp Thr Ala Leu Tyr Tyr Cys
                 85                  90                  95

Val Arg

<210> SEQ ID NO 287
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Gln Val Arg Leu Ala Gln Tyr Gly Gly Val Lys Arg Leu Gly Ala
 1               5                  10                  15

Thr Met Thr Leu Ser Cys Val Ala Ser Gly Tyr Thr Phe Asn Asp Tyr
                 20                  25                  30

Tyr Ile His Trp Val Arg Gln Ala Pro Gly Gln Gly Phe Glu Leu Leu
             35                  40                  45

Gly Tyr Ile Asp Pro Ala Asn Gly Arg Pro Tyr Ala Gly Ala Leu
         50                  55                  60

Arg Glu Arg Leu Ser Phe Tyr Arg Asp Lys Ser Met Glu Thr Leu Tyr
 65                  70                  75                  80

Met Asp Leu Arg Ser Leu Arg Tyr Asp Asp Thr Ala Met Tyr Tyr Cys
                 85                  90                  95

Val Arg

<210> SEQ ID NO 288
<211> LENGTH: 98
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 288

Gln Val Gln Leu Val Gln Ser Gly Gly Gly Val Lys Arg Pro Gly Ser
1               5                   10                  15

Thr Thr Thr Ile Ser Cys Val Ala Ser Gly Tyr Ser Phe Asn Asp Tyr
                20                  25                  30

Tyr Ile His Trp Val Arg Gln Ala Pro Gly Gln Gly Leu Glu Val Leu
            35                  40                  45

Gly Phe Ile Asp Pro Ser Asn Gly Arg Thr Asn Tyr Ala Gly Ala Phe
        50                  55                  60

Gly Asp Arg Phe Ser Met Tyr Arg Asp Lys Ser Met Glu Thr Leu Tyr
65                  70                  75                  80

Met Asp Leu Arg Asn Leu Arg Ser Asp Asp Thr Ala Met Tyr Tyr Cys
                85                  90                  95

Val Arg

<210> SEQ ID NO 289
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Gln Val Gln Leu Glu Gln Ser Gly Thr Ala Val Arg Lys Pro Gly Ala
1               5                   10                  15

Ser Val Thr Leu Ser Cys Gln Ala Ser Gly Tyr Asn Phe Val Lys Tyr
                20                  25                  30

Ile Ile His Trp Val Arg Gln Lys Pro Gly Leu Gly Phe Glu Trp Val
            35                  40                  45

Gly Met Ile Asp Pro Tyr Arg Gly Arg Pro Trp Ser Ala His Lys Phe
        50                  55                  60

Gln Gly Arg Leu Ser Leu Ser Arg Asp Thr Ser Met Glu Ile Leu Tyr
65                  70                  75                  80

Met Thr Leu Thr Ser Leu Lys Ser Asp Asp Thr Ala Thr Tyr Phe Cys
                85                  90                  95

Ala Arg

<210> SEQ ID NO 290
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Gln Gly Gln Leu Val Gln Ser Gly Gly Gly Leu Lys Lys Pro Gly Thr
1               5                   10                  15

Ser Val Thr Ile Ser Cys Leu Ala Ser Glu Tyr Thr Phe Asn Glu Phe
                20                  25                  30

Val Ile His Trp Ile Arg Gln Ala Pro Gly Gln Gly Pro Leu Trp Leu
            35                  40                  45

Gly Leu Ile Lys Arg Ser Gly Arg Leu Met Thr Ala Tyr Asn Phe Gln
        50                  55                  60

Asp Arg Leu Ser Leu Arg Arg Asp Arg Ser Thr Gly Thr Val Phe Met

-continued

```
                65                  70                  75                  80
Glu Leu Arg Gly Leu Arg Pro Asp Asp Thr Ala Val Tyr Tyr Cys Ala
                85                  90                  95
Arg

<210> SEQ ID NO 291
<211> LENGTH: 98
<212> TYPE: PRT
<213> ORGANISM: Homo sapiens

<400> SEQUENCE: 291

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 292
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
                20                  25                  30

Thr Leu Asn Trp Ile Arg Leu Ala Pro Gly Lys Arg Pro Glu Trp Met
            35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg

<210> SEQ ID NO 293
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gln Val Gln Leu Val Gln Ser Gly Ala Ala Val Arg Lys Pro Gly Ala
1               5                   10                  15
```

Ser Val Thr Val Ser Cys Lys Phe Ala Glu Asp Asp Tyr Ser Pro
            20                  25                  30

Tyr Trp Val Asn Pro Ala Pro Glu His Phe Ile His Phe Leu Arg Gln
        35                  40                  45

Ala Pro Gly Gln Gln Leu Glu Trp Leu Ala Trp Met Asn Pro Thr Asn
 50                  55                  60

Gly Ala Val Asn Tyr Ala Trp Tyr Leu Asn Gly Arg Val Thr Ala Thr
 65                  70                  75                  80

Arg Asp Arg Ser Met Thr Thr Ala Phe Leu Glu Val Lys Ser Leu Arg
            85                  90                  95

Ser Asp Asp Thr Ala Val Tyr Tyr Cys Ala Arg
            100                 105

<210> SEQ ID NO 294
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gln Val Gln Leu Val Gln Ser Gly Ser Gly Val Lys Lys Pro Gly Ala
 1               5                  10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
 50                  55                  60

Asp Phe Arg Gln Arg Val Ser Leu Thr Arg Asp Arg Asp Leu Phe Thr
 65                  70                  75                  80

Ala His Met Asp Ile Arg Gly Leu Thr Gln Gly Asp Thr Ala Thr Tyr
            85                  90                  95

Phe Cys Ala Arg
            100

<210> SEQ ID NO 295
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Cys Thr Ala Asp Leu Gly Glu Pro Val Val Ser Arg Phe Phe Glu Trp
 1               5                  10                  15

Gly Ser Tyr Tyr Tyr Tyr Met Asp Leu Trp Gly
            20                  25

<210> SEQ ID NO 296
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

```
Cys Thr Met Asp Glu Gly Thr Pro Val Thr Arg Phe Leu Glu Trp Gly
1               5                   10                  15

Tyr Phe Tyr Tyr Tyr Met Ala Val Trp Gly
            20                  25

<210> SEQ ID NO 297
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Phe Thr Phe Ser Asn Thr Trp
1               5

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Phe Phe Phe Asp Asn Ser Trp
1               5

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ile Ser Arg Asn Lys Asp Gly Ala Lys Thr
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ile Arg Arg Leu Lys Asp Gly Ala Thr Gly
1               5                   10

<210> SEQ ID NO 301
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asp Asp Ser Arg
1

<210> SEQ ID NO 302
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Asp Asp Ser Arg
1
```

HIV-1 NEUTRALIZING ANTIBODIES AND USES THEREOF (CD4BS ANTIBODIES)

This is a U.S. National Stage application under 35 U.S.C. § 371 of International Patent Application No. PCT/US2016/023355, filed, Mar. 21, 2016, which claims the benefit of and priority to U.S. Ser. No. 62/135,309 filed Mar. 19, 2015, U.S. Ser. No. 62/260,100 filed Nov. 25, 2015, U.S. Ser. No. 62/191,095 filed Jul. 10, 2015, U.S. Ser. No. 62/222,115 filed Sep. 22, 2015, and U.S. Ser. No. 62/301,993 filed Mar. 1, 2016, the contents of each of which are hereby incorporated by reference in their entireties.

GOVERNMENT SUPPORT

This invention was made with government support under Center for HIV/AIDS Vaccine Immunology-Immunogen Design grant UM1-AI100645 from the NIH, NIAID, Division of AIDS. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosure of these publications in their entireties are hereby incorporated by reference into this application in order to more fully describe the state of the art as known to those skilled therein as of the date of the invention described herein.

SEQUENCE LISTING

The instant application contains a Sequence Listing which has been filed electronically in ASCII format and is hereby incorporated by reference in its entirety. Said ASCII copy, created on Oct. 11, 2018, is named 1234300_279US1_SL.txt and is 282,897 bytes in size.

FIELD OF THE INVENTION

The invention relates to the identification of monoclonal HIV-1 neutralizing antibodies, such as, but not limited to, antibodies that bind to the CD4 binding site (CD4bs) of HIV-1 gp120, their recombinant expression and purification and uses.

BACKGROUND

It is well documented that essentially all HIV-1 infected individuals develop antibodies capable of binding HIV-1 envelope, but that only a small subset of these antibodies are neutralizing and capable of blocking viral entry in target cells. See e.g. Doria-Rose N. "HIV Neutralizing Antibodies: Clinical Correlates and Implications for Vaccines" The Journal of Infectious Diseases (2010) Volume 201, Issue 7, Pp. 981-983. Over the time of an infection, some individuals develop neutralizing antibodies, and with some of these neutralizing antibodies having activity against diverse primary HIV-1 isolates. A number of broad neutralizing monoclonal antibodies (mAbs) have been identified from HIV-1 infected individuals and these define specific regions on the virus envelope, e.g. CD4 binding site, V3 loop, membrane proximal region (MPER) of gp41, that are vulnerable to neutralizing Abs.

Broadly neutralizing HIV-1 antibodies have been isolated only from natural HIV-1 infection. See e.g. Mascola and Haynes, Immunological Reviews (2013) Vol. 254: 225-244. Some examples of broadly neutralizing antibodies (bnAbs) targeting CD4 binding site or V3 loop are VRC01, CH103, CH31, CH98, 8ANC131, PGT121, PGT128. Unfortunately, so far none of these antibodies have been developed for HIV prevention or treatment. Thus, the need exists for monoclonal broadly neutralizing antibodies that can be developed and used for prevention and treatment for an infectious agent, such as HIV.

SUMMARY OF THE INVENTION

In certain aspects the invention provides an antibody or fragment thereof with the binding specificity of CD4 binding site antibody DH491 or CH493, or CH558, or CH557.

In certain aspects, the invention provides a recombinant antibody or fragment thereof comprising: a variable heavy chain (VH) amino acid sequence, or fragment thereof, selected from the group of VH amino acid sequences of an antibody CH490, CH491, CH492, CH493, CH555, CH556 and CH557 and a variable light chain (VL) amino acid sequence or fragment thereof, selected from the group of VL amino acid sequences of an antibody CH490, CH491, CH492, CH493, CH555, CH556 and CH557, wherein the recombinant antibody or fragment thereof binds to the CD4 binding site of the HIV-1 envelope. In certain aspects the antibodies bind to the CD4 binding site on the HIV-1 envelope and are neutralizing.

In certain embodiments, the antibody or fragment thereof is fully human and recombinantly produced. In certain embodiments, some of the VH and VL chains are identified from human subject who have been naturally infected with HIV-1. In certain embodiments the antibody is not naturally occurring. In certain embodiments the antibody comprises naturally occurring pair of VH and VL chains. In certain embodiments the antibody comprises naturally occurring pair of VH and VL chains wherein the Fc portion of the antibody is not the natural isotype or portion of the naturally occurring pair of VH and VL chains. In certain embodiments the antibody is computationally designed, for example based on some naturally identified VH and VL sequences. In certain embodiments the antibody is computationally designed, e.g. UCA, Intermediates in the antibody lineages. In certain embodiments the antibody comprises a non-naturally occurring pairing of VH and VL chains, wherein the VH or VL individually could be identified from a subject. In some embodiments, the antibody comprises VH chain or HCDRs of a VH chain of one clonal member, and VL or LCDRs of another clonal member, i.e., a non-naturally occurring antibody comprising sequences derived from natural pairs. In certain embodiments the antibody comprises naturally occurring VH and VL chains modified by substituting one or more amino acids.

In certain embodiments, the antibody or fragment thereof comprises a VH chain that is 90%, 91%, 92%, 93%, 94%, 95%, 96%, 97%, 98%, 99% or 100% identical to the VH chain of antibody CH557, or any of the other lineage members. In certain embodiments, the antibody or fragment thereof comprises a VL chain that is 90%, 91%, 92%, 93%, 94%, 95%, 96%, 97%, 98%, 99% or 100% identical to the VL chain of antibody CH557, or any of the other lineage members.

In certain embodiments, the antibody or fragment thereof comprises a VH chain that is 90%, 91%, 92%, 93%, 94%, 95%, 96%, 97%, 98%, 99% or 100% identical to the VH chain of antibody DH542, or any of the other lineage members. In certain embodiments, the antibody or fragment thereof comprises a VL chain that is 90%, 91%, 92%, 93%, 94%, 95%, 96%, 97%, 98%, 99% or 100% identical to the VL chain of antibody DH542, or any of the other lineage members.

In certain embodiments, the antibody or fragment thereof comprises a VH chain that is 90%, 91%, 92%, 93%, 94%, 95%, 96%, 97%, 98%, 99% or 100% identical to the VH chain of antibody DH511, DH512, DH513, DH514, DH515, DH516, DH517, DH518, DH536, DH537, CH491 or CH493 and further comprises a VL chain that is 90%, 91%, 92%, 93%, 94%, 95%, 96%, 97%, 98%, 99% or 100% identical to the VL chain of antibody DH511, DH512, DH513, DH514, DH515, DH516, DH517, DH518, DH536, DH537, CH491 or CH493.

In certain embodiments, the antibody or fragment thereof comprises a VH which comprises the HCDR1, HCDR2, and HCDR3 of antibody CH557. In certain embodiments, the antibody or fragment thereof comprises a VL which comprises the LCDR1, LCDR2, and LCDR3 of antibody CH557.

In certain embodiments, the antibody or fragment thereof comprises a VH which comprises the HCDR3 of CH557 and further comprises a VL which comprises the LCDR3 of CH557.

In certain embodiments, the antibody or fragment thereof comprises a VH which comprises the HCDR1, HCDR2, and HCDR3 of antibody DH542. In certain embodiments, the antibody or fragment thereof comprises a VL which comprises the LCDR1, LCDR2, and LCDR3 of antibody DH542.

In certain embodiments, the antibody or fragment thereof comprises a VH which comprises the HCDR1, HCDR2, and HCDR3 of antibody CH557 and further comprises the complementary VL which comprises the LCDR1, LCDR2, LCDR3 of antibody CH557.

In certain embodiments, the antibody or fragment thereof comprises VH and VL of antibody CH557.

In certain embodiments, the antibody or fragment thereof comprises a VH which comprises the HCDR1, HCDR2, and HCDR3 of antibody DH542 and further comprises the complementary VL which comprises the LCDR1, LCDR2, LCDR3 of antibody DH542. In certain embodiments, the antibody or fragment thereof comprises VH and VL of antibody DH542.

In certain embodiments, the antibody is DH542. In certain embodiments, the antibody is CH557.

In certain embodiments, the invention provides a recombinant antibody or fragment thereof with the binding specificity of CD4 binding site antibody DH491 or CH493, or CH558, or CH557 comprising an engineered constant domain. In some embodiments, the recombinant antibody or fragment thereof is capable of neutralizing an HIV-1 Env pseudovirus with an IC50 of less than 50 µg/mL in an in vitro assay.

In certain aspects, the invention provides a pharmaceutical composition comprising anyone of the antibodies of the invention or fragments thereof or any combination thereof.

In certain aspects, the invention provides a pharmaceutical composition comprising anyone of the antibodies of the invention, or a combination thereof.

In certain embodiments, the composition comprises an antibody or a fragment thereof which is recombinantly produced in CHO cells.

In certain aspects, the invention provides a pharmaceutical composition comprising a vector comprising a nucleic acid encoding anyone of inventive antibodies or fragments. In certain embodiments, the nucleic acids are optimized for expression in human host cells. In other embodiments, the nucleic acids are optimized for recombinant expression in a suitable host cell. In certain embodiments, the vector is suitable for gene delivery and expression. Non-limiting examples of such vectors include adenoviral vectors (Ads), adeno associated virus based vectors (AAVs), or a combination thereof. In certain aspects, the invention provides isolated cells comprising vectors and/or nucleic acids for expression of the inventive antibodies and fragments thereof. In certain aspects, the invention provides compositions of cells comprising vectors and/or nucleic acids for expression of the inventive antibodies and fragments thereof.

In certain embodiments, the compositions further comprise an additional antibody or fragment thereof. In certain embodiments, the compositions further comprise an antibody or a fragment thereof comprising CDR1, 2, and/or 3 of the VH and VL chains, or the VH and VL chains of antibody DH540. In certain embodiments, the compositions further comprise an antibody or a fragment thereof comprising CDR1, 2, and/or 3 of the VH and VL chains, or the VH and VL chains of antibody DH512.

In certain embodiments, the compositions further comprise an antibody or a fragment thereof comprising VH and VL chain of antibody DH429 or DH270IA1.

In certain embodiments, the antibody or antigen binding fragment can include an Fc domain that has been modified compared to a native Fc domain. In non-limiting embodiments, the Fc domain can be modified by amino acid substitution to increase binding to the neonatal Fc receptor and therefore the half-life of the antibody when administered to a subject.

In certain embodiments, the invention provides antibodies or fragments comprising a CDR(s) of the VH and/or VL chains, or VH and/or VL chains of the inventive antibodies, as the HIV-1 binding arm(s) of a bispecific molecules, e.g. but not limited to DARTS, diabodies, toxin labeled HIV-1 binding molecules.

In certain aspects the invention provides methods to treat or prevent HIV-1 infection in a subject comprising administering to the subject a pharmaceutical composition comprising any one of the inventive antibodies or fragments thereof in a therapeutically effective amount. The methods of the invention contemplate combination therapeutic methods, including but not limited to administering combinations of various antibodies or fragments thereof.

In certain embodiments of the methods, the pharmaceutical compositions are administered in a therapeutically effective dose and regimen.

BRIEF DESCRIPTION OF THE DRAWINGS

To conform to the requirements for PCT patent applications, many of the figures presented herein are black and white representations of images originally created in color.

FIG. 1 shows DH542 sequences (CDRs are bolded and underlined) (SEQ ID NOs: 1-4).

FIG. 2 shows the amino acids sequences of VH and VL chains of antibodies of the DH270 lineage, and nucleic acid sequences encoding these amino acids. CDRs are highlighted in each antibody. DH270IA1 as listed in FIG. 3 is the same antibody referred to as I1 in the sequence of FIG. 2. The figure shows SEQ ID NOs: 5-16 (Heavy chain nucleotide sequences in order of appearance from UCA-DH270H), SEQ ID NOs: 17-28 (Heavy chain amino acid sequences in order of appearance from UCA-DH270H), SEQ ID NOs: 29-40 (Light chain nucleotide sequences in order of appearance from UCA-DH270H), SEQ ID NOs: 41-52 (Light chain amino acid sequences in order of appearance from UCA-DH270H).

FIG. 3 shows Neutralizing Breadth and Potency of various HIV-1 BnAbs that are candidates for being combined with the inventive antibodies or other antibodies for a potent mixture of bnAbs. DH270IA1 is I1 in the DH270 lineage.

FIG. 4 shows Neutralizing Breadth and Potency of some candidate bnAbs for single or combination use.

FIG. 5 shows comparison of some of the bnAbs of the invention with other bnAbs in the same class. % breadth refers to number of tested HIV-1 strains.

FIG. 6 shows nucleic acid sequences of antibodies DH511-518, DH537 and 538 (SEQ ID NOs: 53-72).

FIG. 7 shows amino acid sequences of antibodies DH511-518, DH537 and 538 (SEQ ID NOs: 73-93).

FIGS. 8A and 8B show Alignment of VH (8A) and VL (8B) Sequences of BnAb DH511 Clonal Lineage. Bolded is the sequence of CDR1, underlined is the sequence of CDR2 and italicized is the sequence of CDR3 of the DH511 VH chain and DH511 VL chain. The CDRs of the VH and VL sequences of the other antibodies DH512, DH513, DH514, DH515, and DH516 can be readily determined based on the sequence alignment. FIG. 8A shows SEQ ID NOs: 94-99 (in order of appearance from DH511-DH516). FIG. 8B shows SEQ ID NOs: 100-105 (in order of appearance from DH511-DH516).

FIGS. 9A and 9B show Alignment of VH (FIG. 9A) and VL (FIG. 9B) sequences of MPER BnAbs. Bolded is the sequence of CDR1, italicized is the sequence of CDR2 and underlined is the sequence of CDR3 of VH or VL of the listed MPER antibodies. FIG. 9A shows SEQ ID NOs: 106-114 (in order of appearance from DH511-2F5). FIG. 9B shows SEQ ID NOs: 115-123 (in order of appearance from DH511-2F5).

FIG. 10 shows neutralization by antibodies CH555, CH556, CH557, CH558, CH560, CH561, CH562, DH210 and DH211 identified from subject CH505 measured in TZM-bl cells. Pseudoviruses were produced by transfection in 293T cells. Values are the antibody concentration (m/ml) at which relative luminescence units (RLUs) were reduced 50% compared to virus control wells (no test sample). Values in bold are considered positive for neutralizing antibody activity. CH557 IC50 neutralization summary: mean IC50=3.66 µg/ml; geometric mean IC50=0.66 µg/ml; median=0.62 µg/ml.

FIG. 11 shows CH557 gene information (SEQ ID NO: 215).

FIG. 12 shows sequences of CH557 (SEQ ID NOs: 124-127). CDRs are bolded and underlined.

FIG. 13 shows a sequence alignment of the CD540-VRC40 antibodies, listing the heavy and light chain variable region sequences, kabat and IMGT CDR and framework regions, and kabat numbering (heavy chain sequences disclosed as SEQ ID NOS 216-219, respectively, in order of appearance, and light chain sequences disclosed as SEQ ID NOS 220-223, respectively, in order of appearance). The heavy and light chain variable region sequences of the CH540-VRC40.01, CH540-VRC40.02, CH540-VRC40.03, CH540-VRC40.04 are shown.

FIG. 14 shows gene information for antibodies in the CH235 lineage.

FIGS. 15A and 15B show amino acid alignment of CH235 lineage antibody heavy chain (FIG. 15A) and light chain (FIG. 15B). Antibodies are listed in ascending order of somatic mutations and compared to the inferred unmutated common ancestor previously published (Gao, Bonsignori, Liao et al. Cell 2014). FIG. 15A shows SEQ ID NOs: 128-139 (in order of appearance from UCA-CH557). FIG. 15B shows SEQ ID NOs: 140-149 (in order of appearance from UCA-CH556).

FIG. 16 shows alignment of CH557 heavy chain amino acid sequence compared to CH235 lineage antibodies with increasing levels of somatic mutations and neutralization breadth. Contact sites with gp120 identified from CH235/gp120 co-crystal structure are indicated with asterisks. Amino acid mutations within the contact sites are bolded and underlined. FIG. 16 shows SEQ ID NOs: 150-154 (in order of appearance from UCA-CH557).

FIG. 17 shows alignment of CH557 light chain amino acid sequence compared to CH235 lineage antibodies with increasing levels of somatic mutations and neutralization breadth. FIG. 17 shows SEQ ID NOs: 155-158 (in order of appearance from UCA-CH557).

FIG. 18 shows amino acid sequences of VH and VL chains of antibodies CH490, CH491, CH492 and CH493 (CH235_129w66=CH490; CH235_68w100=CH491; CH235_115w100=CH492; CH235_75w152=CH493) (SEQ ID NOs: 159-164).

FIG. 19 shows nucleic acid sequences of VH and VL chains of antibodies CH490, CH491, CH492 and CH493 (CH235_129w66=CH490; CH235_68w100=CH491; CH235_115w100=CH492; CH235_75w152=CH493) (SEQ ID NOs: 165-170).

FIG. 22 shows a summary of neutralization data of CH490, CH491, CH492 and CH493 antibodies for various HIV-1 strains in TZMbl assay. Intermediate antibodies are described in Gao, Bonsignori, Liao et al. Cell 158, 481-491, Jul. 31, 2014.

FIG. 23 shows a summary of neutralization data for antibodies CH235, CH490, CH491, and CH493. The viruses are CH505 TF (autologous virus) in which either point or multiple single mutations were introduced in the loop D region. The loop D mutations are described in Gao et al Cell 158, 481-491, Jul. 31, 2014 (incorporated by reference). These mutations reflect mutations in the loop D region that naturally occurred in the autologous virus of this subject over time. They were artificially introduced into the CH505 TF to study their effect in absence of other mutations in other parts of the autologous virus that also occurred during virus evolution. These mutations were induced by CH235 lineage antibodies identified early during the course of infection. These data show that the more mutated antibody CH493 which came from a later time point and that is broadly neutralizing also acquired the ability of recognizing virus escape mutants that escaped earlier antibodies from the same lineage, before they acquired substantial breadth.

FIG. 24 shows a summary of neutralization (TZMbl assay) data of CH505 D loop mutants by various antibodies. The summary shows that CH493 neutralizes all Loop D CH505 mutants.

FIG. 25 shows results of HEp-2 cell IF staining for CH557.

FIG. 27A shows summary results of neutralization data of CH557, CH235, VRC01, VRC07-523-LS, N6, 3BNC117, 8ANC131, CH103, F105, and DH522 against a panel of HIV-1 isolates in the Luc/TZM-bl neutralization assay. Values represent IC50 in µg/ml.

FIG. 27B shows the mean IC50 and percent of isolates neutralized at different IC50 values.

FIG. 28A shows summary results of neutralization data of CH557, CH235, VRC01, VRC07-523-LS, N6, 3BNC117, 8ANC131, CH103, F105, and DH522 against a panel of HIV-1 isolates in the Luc/TZM-bl neutralization assay. Values represent IC80 in µg/ml.

FIG. 28B shows the mean IC80 and percent of isolates neutralized at different IC80<50 ug/ml values.

FIGS. 30A-30E show structures of CH235-Lineage Members in Complex with HIV-1 Env. (A) Co-crystal structures of the antigen-binding fragments (Fabs) of CH235-lineage members with core gp120. Structures are shown in ribbon diagram, with gp120 in gray and residues altered by SHM in stick representation colored by time-of-appearance. (B) Negative stain EM of Fabs of CH235-lineage members and trimeric HIV-1 Env from BG505 (top row) and B41 (bottom row). Structures in surface representation, with Env portions colored gray and Fabs by time-of-appearance. (C) Epitope displayed on the gp120 surface and colored by antibody time-of-appearance, with the vulnerable portion of the CD4bs highlighted in yellow and select regions labeled. (D) Targeting precision of CD4bs-directed antibodies vs neutralization breadth. (E) $V_H$-gene SHM of CD4bs-directed antibodies vs neutralization breadth. See also FIGS. 37A-G, and 42.

FIGS. 32A-32D show binding Kinetics of CH103 and CH235 Lineage Antibodies. Binding association ($k_a$) and dissociation ($k_d$) rates of the CH103 (A-B, squares) and CH235 (C-D, circles) lineage mAbs to CH505.TF gp120 Env were measured with SPR and used to calculate the dissociation rate constants ($K_d$). $K_d$s are shown in A and C, $k_a$ (solid lines, plotted on the left y-axis) and $k_d$ (dashed lines, plotted on the right y-axis) are shown in B and D. See also FIGS. 44A-B.

FIGS. 33A-33C show CH235 Lineage Antibodies Neutralization of Autologous Virus and CH505.TF Loop D Mutants. (A) Heatmap analysis of neutralization of 76 pseudoviruses (row) by 16 CH235 lineage mAbs (column). Coloration is by $IC_{50}$. This analysis extends previous observations on early CH235 lineage antibodies (Gao et al., 2014) by including late mAbs CH235.7, CH235.8, CH235.10, CH235.11, CH235.12 and CH235.13 and by adding pseudoviruses isolated from wk 136 to 323 post-transmission. (B) CH505 TF and loop D mutants M5, M6, M10, M19, M11, M7, M8, M9, M20 and M21 neutralization by CH236 mAb, late mAbs CH235.7, CH235.9 CH235.10, CH235.11, CH235.12, CH235.13 (left panel) and CH235.9 mAb mutants (right panel). Neutralization is expressed as $IC_{50}$ µg/ml. CH505 TF sequence mutations are shown on the right. (C) The CDR H1 N30 (sticks, dark red) in CH235.9, which interacts with the β20-β21 loop in the bridging sheet of gp120 (cyan), is over 19 Å away from the N280S mutation site in loop D (orange). See also FIGS. 39A-B, 45, and 46.

FIGS. 35A-35D show CH235 Antibody Lineage Auto- and Polyreactivity. (A) CH235 lineage antibody binding to ANA measured in ELISA. LogAUC was calculated from duplicate samples. Results representative of duplicate experiments. (B) Binding to cardiolipin was determined using Quanta Lite ACA IgG III ELISA Assay. (C) Hep2 cell IF staining. Size bars=50 µm. (D) Measurement of polyreactivity against 9,400 human antigens using ProtoArray 5 microchip: CH235 lineage mAbs binding (x-axis) was compared to non-polyreactive control mAb 151K (y-axis). Polyreactivity is defined as 1 log stronger binding than 151k mAb to more than 90% of the test proteins. High affinity binding was measured as a >2 log increase in binding (dotted line) (Liu et al., 2015).

(A) Alignment of NGS sequences (SEQ ID NOS 234 and 234-294, respectively, in order of appearance) and antibodies identified from 17 time points from 6 to 323 weeks post-transmission and comparison of mutation patterns to other IGHV1-46 (1B2530 and 8ANC131) and IGHV1-2 (VRC01, VRC-CH31 and VRC-PG04) derived broadly neutralizing antibodies. Antibodies identified from single B cells are shown in bold. The positions mutated in CH235 were color coded based on the time points at which these mutations were firstly observed in the NGS reads. Mutated positions not seen in the NGS data are colored based on the time of isolation of CH235 (41 weeks). IGHV1-46*01 is used as reference for IGHV1-46 derived antibodies and IGHV1-2*02 is used as reference for the three VRC01-class antibodies. (B) The neutralization fingerprints for three antibodies from the CH235 lineage were compared to the fingerprints for other VH1-46 class antibodies and non-VH1-46 class CD4-binding-site antibodies; coloring same as in FIG. 31A-C. Antibodies targeting other sites of vulnerability on HIV-1 Env are shown as control (black).

FIGS. 37A-37G show CH235 Lineage Versus Other CD4-Binding Site Antibodies and Negative-stain EM Reconstructions of gp140 SOSIP Trimers with CH235-lineage Fabs, Related to FIG. 30A-E. (A) CD4-mimicry by CH235. Recognition of gp120 by the N-terminal domain of the CD4 receptor (far left) is compared to VH genes from CH235 and prototypic antibodies VRC01 (from VH1-2) and 8ANC131 (from VH1-46). (B) Conserved molecular interactions between antibody CH235, receptor CD4 and antibody VRC01. Top row shows intermolecular antiparallel strand interactions and bottom row Asp368 electrostatic interaction. (C) Binding orientation of VH-gene derived antibodies relative to CD4. (D) Negative-stain EM 3D models with BG505 SOSIP.664. (left) Top and side views of CH235.12 in complex with BG505 SOSIP (purple) aligned to the EM volume of VRC01 in complex with BG505 (gold mesh; EMD-6252). (middle) Top and side views of the CH235.12-BG505 complex (purple mesh) aligned to the EM volume of CH103 in complex with BG505 SOSIP (gray; EMD-6250). (right) Top and side views of the CH103-BG505 complex (gray mesh) aligned to the EM reconstruction of BG505 SOSIP in complex with soluble CD4 and 17b Fab (blue; EMDB ID 5723). (E) Negative-stain EM of gp140 SOSIP trimers with CH235-lineage Fabs. (F) Top and side views of 3D reconstructions of each complex. (G) Fourier shell correlation curves for each dataset with a resolution estimate using an FSC cutoff of 0.5.

Figure 31A:
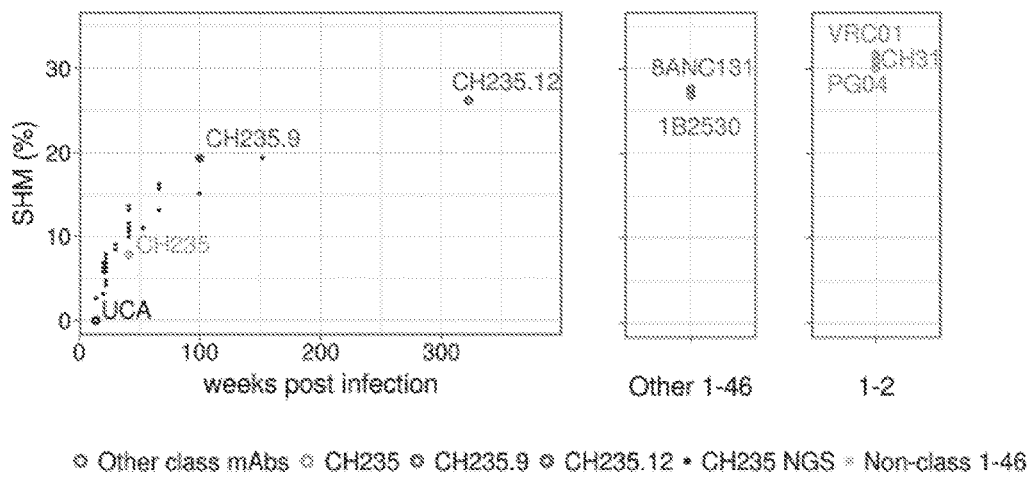
FIGS. 31A-C show sequence Evolution of CH235 Lineage: SHM, Timing, and Conformity of CH235-Lineage Development from UCA to Antibody with 90% Breadth. (A) Heavy chain SHM over time for the CH235 lineage (left panel). SHM levels of other $V_H$1-46-derived CD4bs mAbs and selected $V_H$1-2-derived VRC01-class mAbs are shown (middle and right panels, respectively); the time since infection is unknown for these mAbs. (B) Maturation conformity vs overall heavy chain SHM. Positional conformity (top row) is defined as the number of aa positions differing from the germline sequence in both the conforming and reference sequences, divided by the total number of aa changes in the conforming antibody. Identity conformity (bottom row) is defined as the number of such positions which are additionally mutated to the same residue, divided by the total number of mutations in the conforming antibody. Conformity to 1B2530 (left) and to 8ANC131 (right) is shown for both position and identity. (C) $V_H$-gene mutability accounts for the majority of positional conformity of CH235 lineage. The mutability of the $V_H$-gene for $V_H$1-46 (top; SEQ ID NOS 224-229, respectively, in order of appearance) and $V_H$1-2 (bottom; SEQ ID NOS 230-233, respectively, in order of appearance) is shown. Sequence logos are shown at each position; the height of each logo corresponds to the percent of mutated reads. Green bars are shown for SHM in antibody CH235, which are altered in over a quarter of $V_H$1-46-derived antibodies. See also FIGS. 38A-E, and 43A-C.
Figure 31B:
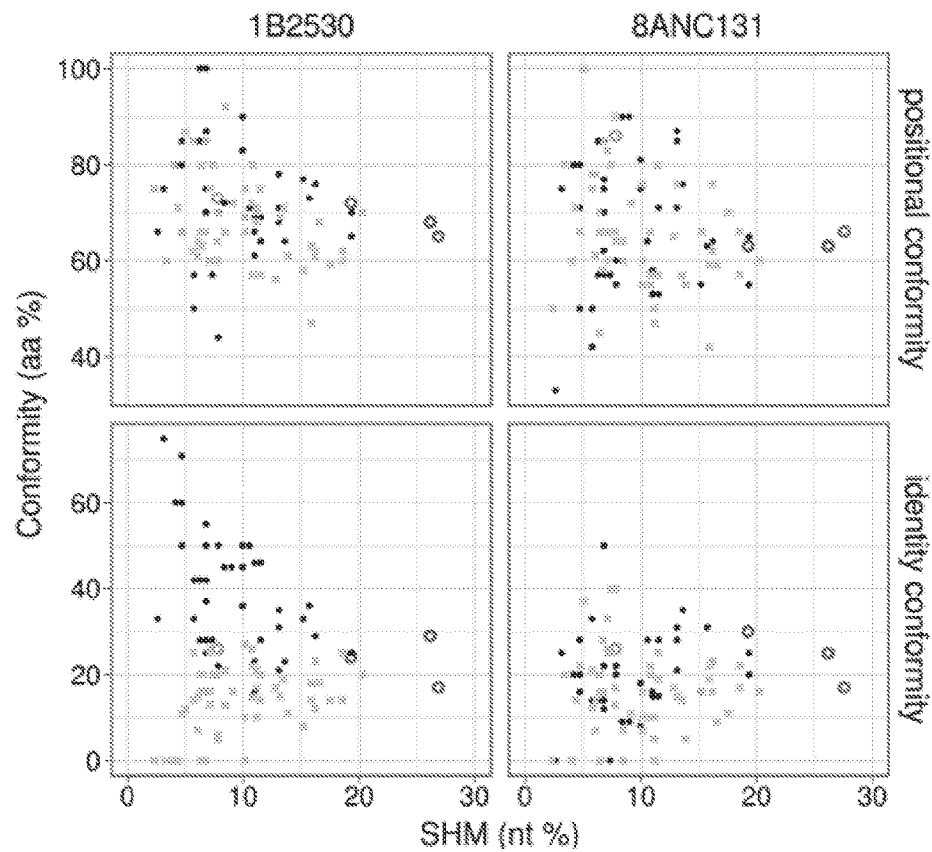
Figure 31C:
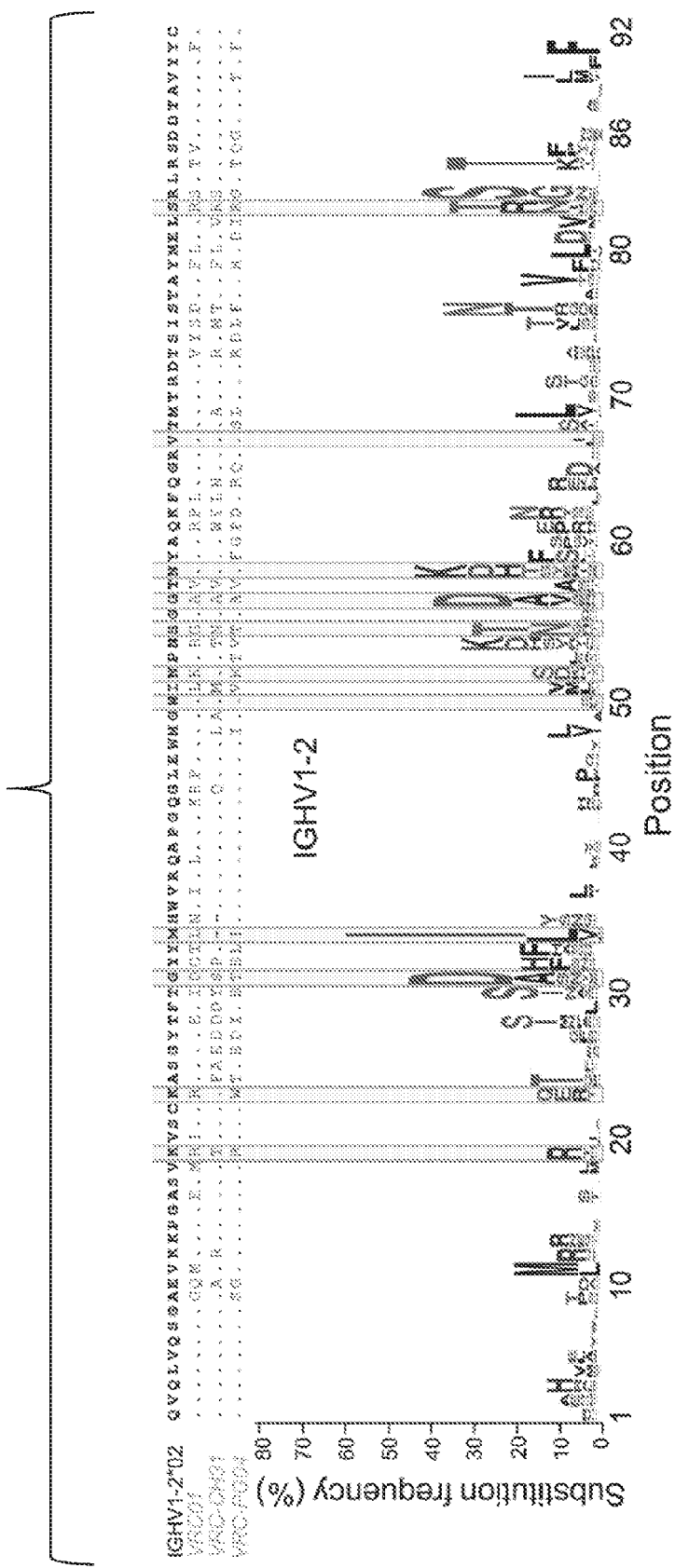

FIGS. 38A-38E show Sequence Similarity Between VH1-2 and VH1-46 Broadly Neutralizing Antibodies and Mutability of Germline Genes, Related to FIG. 31A-C. (A) Amino acid alignment of 8ANC131 (SEQ ID NO: 290) and CH235 (SEQ ID NO: 271) to the IGHV1-46 germline gene (SEQ ID NO: 234) showing the definition of conformity. (B) Probability distribution of the number of sharing mutation positions for each pair of antibodies. (C) Probability distribution of the number of identical mutations for each pair of antibodies. (D) SHM frequency is shown versus VH-gene position for VH1-46, VH1-2 and three others. Sequences were aligned to VH1-46 and positions not aligned to VH1-46 (indels) were removed. (E) Dendrogram showing sequence segregation of VH1-2 and VH1-46 derived broadly neutralizing antibodies, despite similarity of VH1-2 and VH1-46 germline genes shown with underline.

Figure 33A:
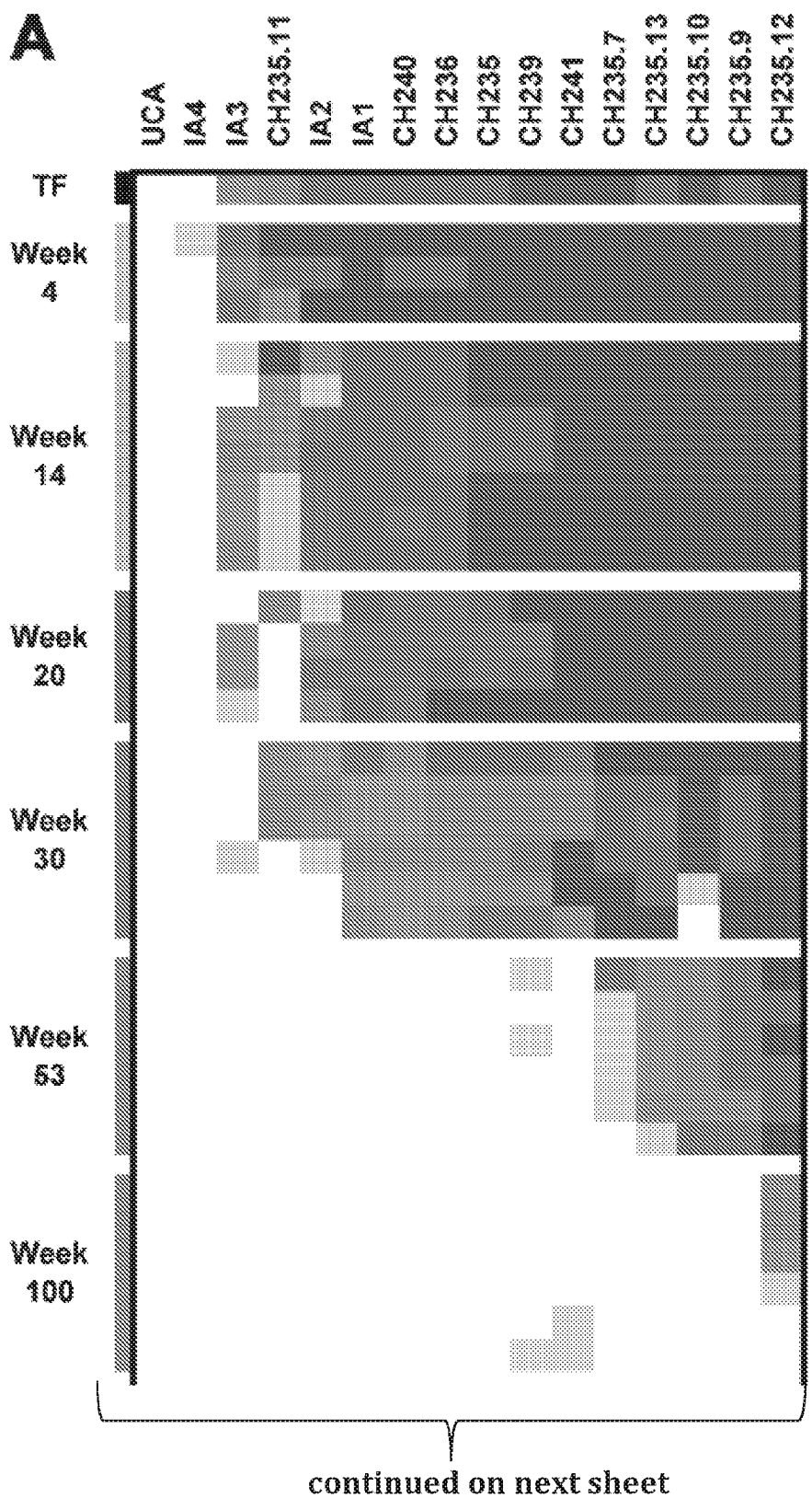
Figure 33A:
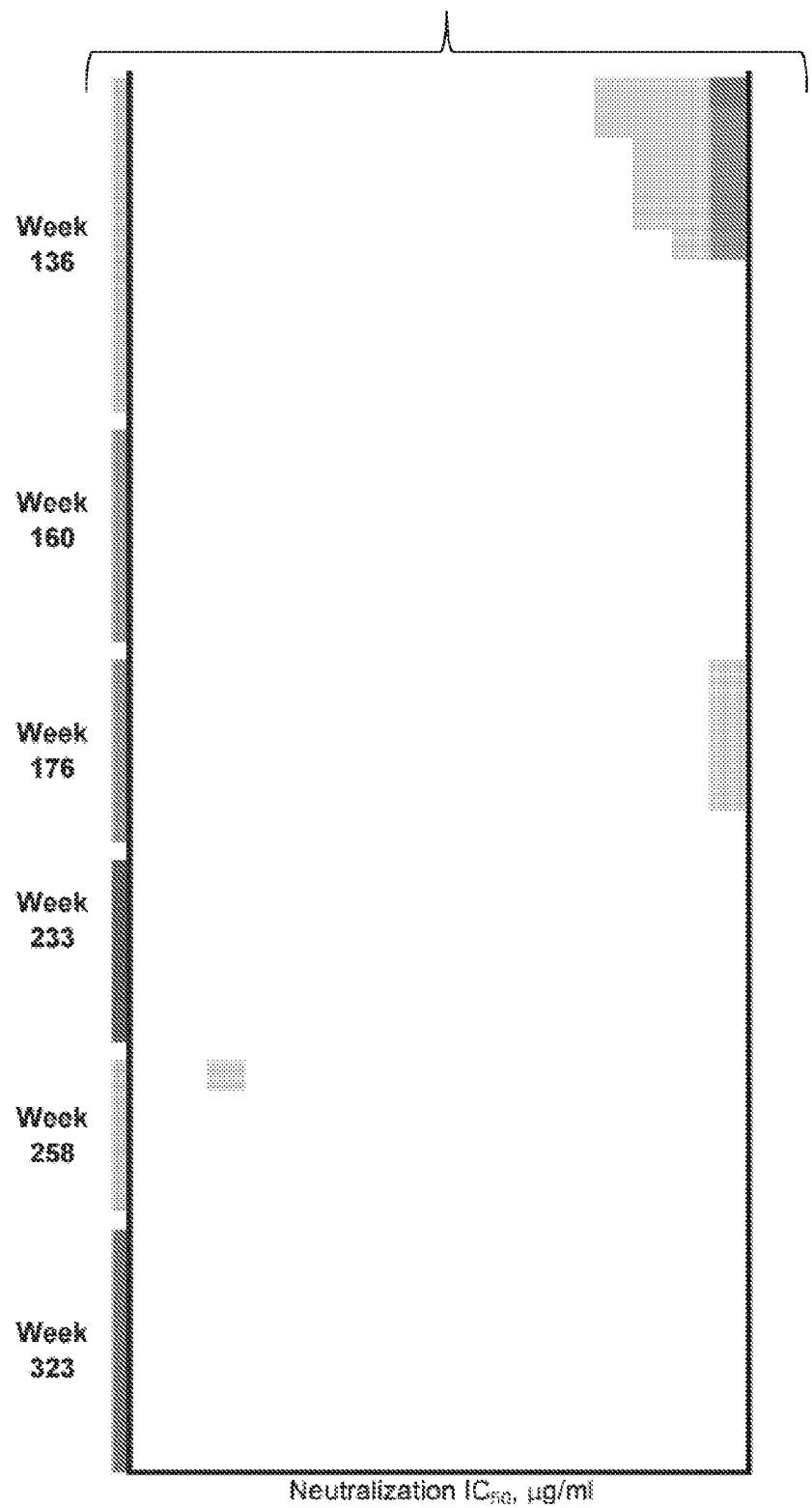
Figure 33B:
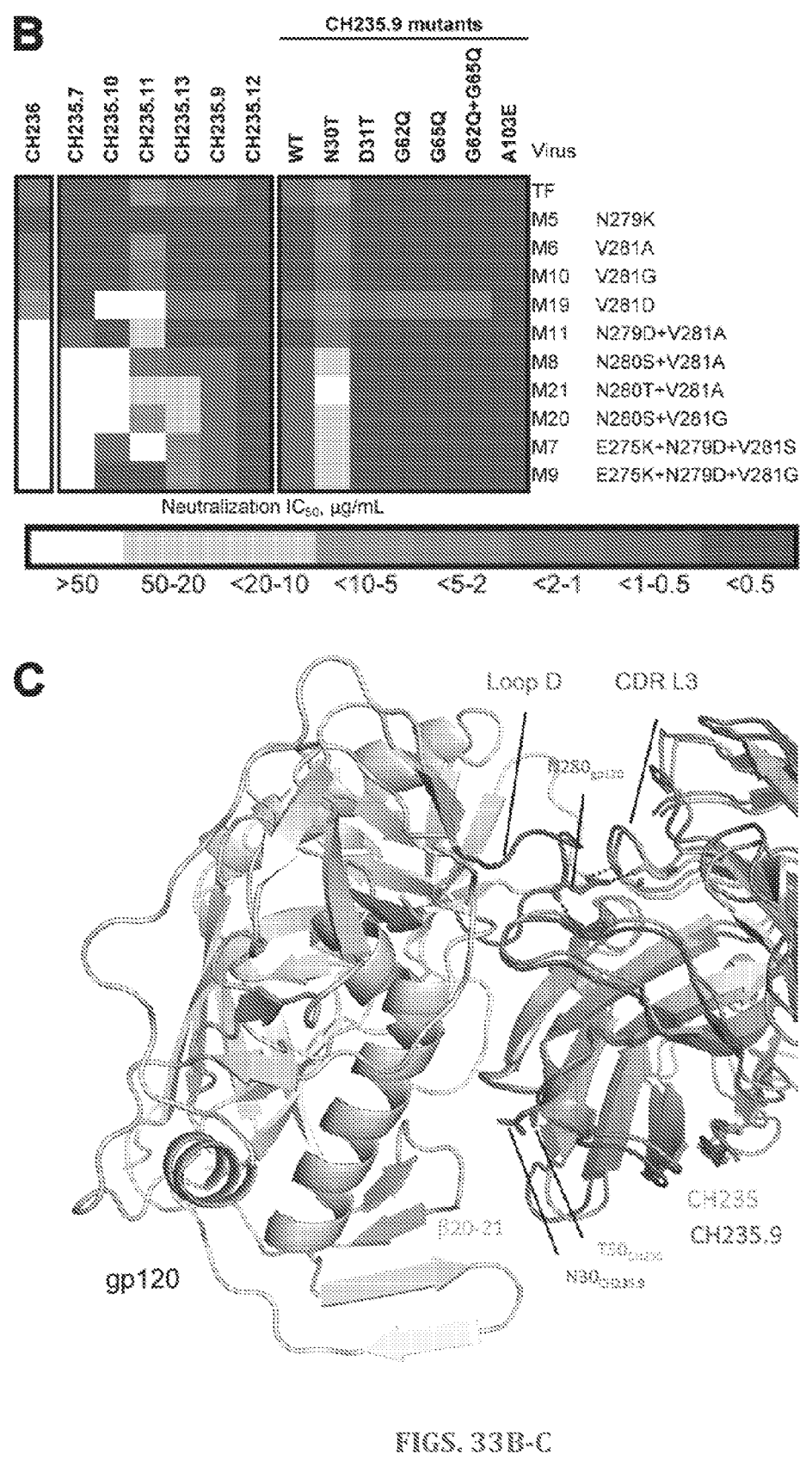
Figure 39A:
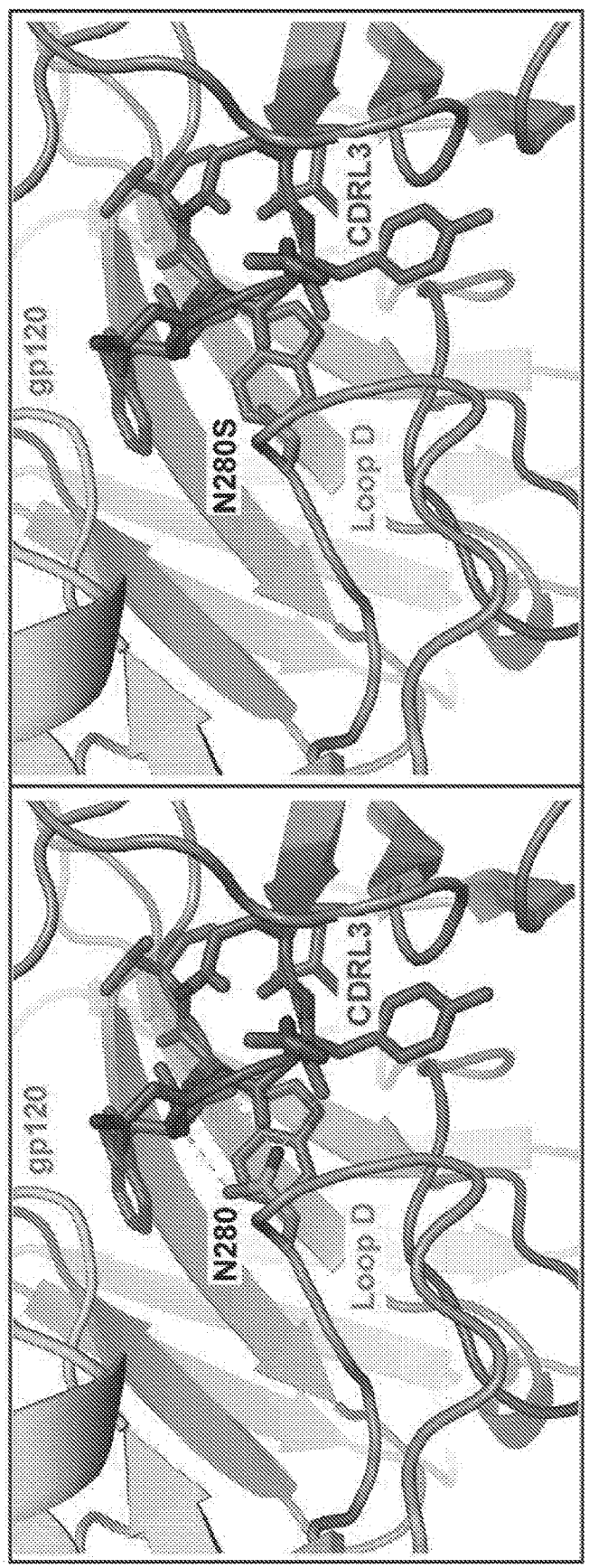

FIGS. 39A-39B show Generation of CH235.9 Mutants to Evaluate the Effect of Mutations in the V-heavy Chain on the Ability of CH235.9 to Neutralize loop D Mutant CH505 Autologous Viruses, Related to FIG. 33A-C. (A) The interaction between CH235 CDR L3 (purple) and N280 in the HIV-1 gp120 Env loop D (orange) from the crystal structure of the CH235-gp120 complex (left panel). Asparagine in position 280 in gp120 forms three hydrogen bonds (yellow dotted lines) with residues in the CDR L3 (left panel). Structural modeling predicted these hydrogen bonds to be disrupted in the N280S (right panel) and N280T (not shown) mutations which occur in autologous CH505 escape mutants. (B) Alignment of CH235.7 and CH235.9 through CH235.13 VH amino acid sequences to CH236 VH (SEQ ID NOs: 171-177 (in order of appearance from CH236-CH235.7)). CH235.9 aa mutations expressed as recombinant IgG and tested for neutralization of CH505 TF loop D mutants are shown in red. Asterisks indicate points of contact with gp120 derived from the CH235 crystal structure in complex with gp120 Env.

Figure 34A:
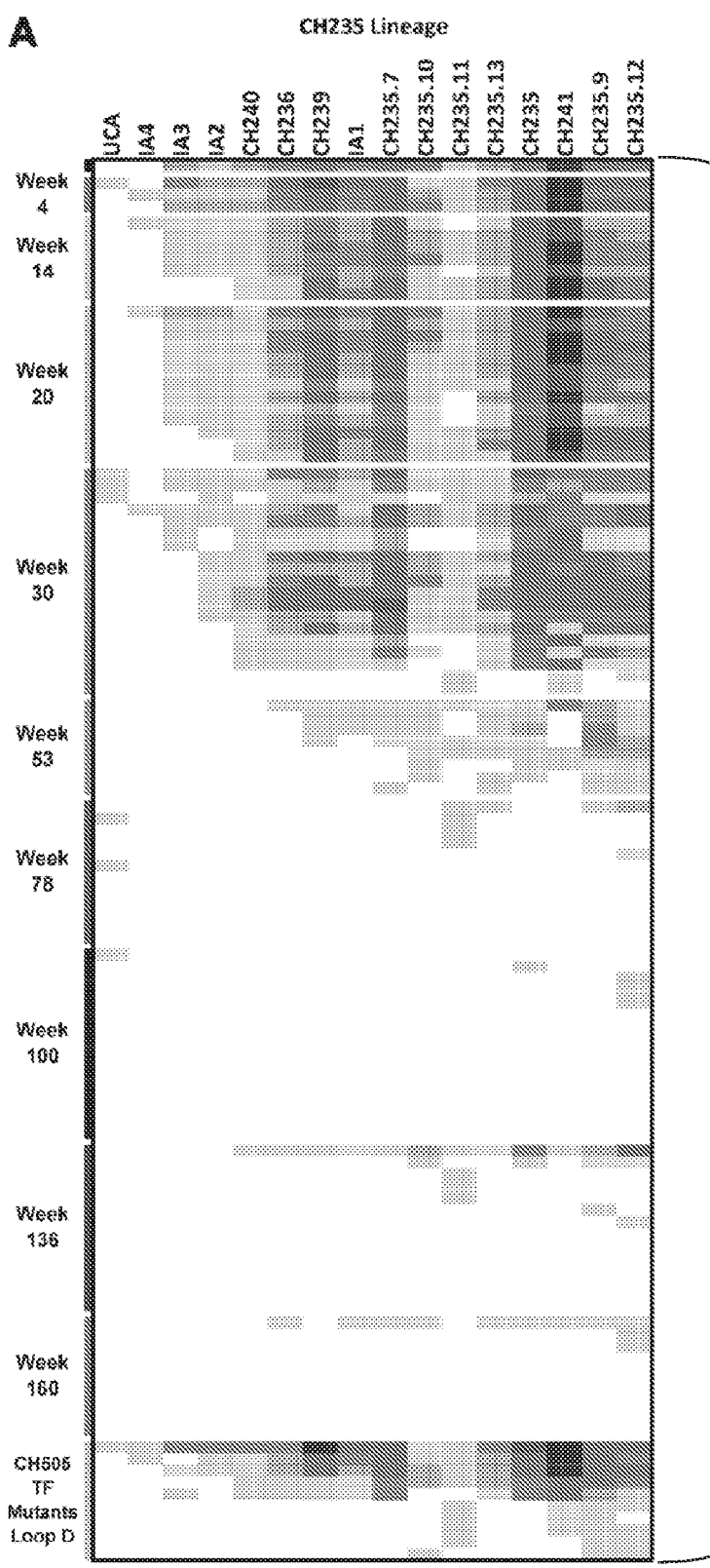
FIGS. 34A-34B show binding of CH235 and CH103 Lineage mAbs to Autologous CH505. (A) and CH235 UCA Binding to Heterologous HIV-1 Env Glycoproteins (B). (A) Heatmap analysis of UCA, intermediate (IA) and mature CH235 and CH103 lineage mAbs binding to 113 CH505 autologous Env isolated from time of infection (TF) to 160 wks post-infection and to the CH505.TF mutants (Gao et al., Cell 2014). Mabs were tested in ELISA at concentrations ranging from 100 µg/ml to 0.6 ng/ml. Binding is expressed as a LogAUC. (B) Affinity of CH235 UCA, CH235 wild-type and select SHM variants to a panel of 15 heterologous gp120 Envs. See also FIGS. 40A-40B and 43.
Figure 34A:
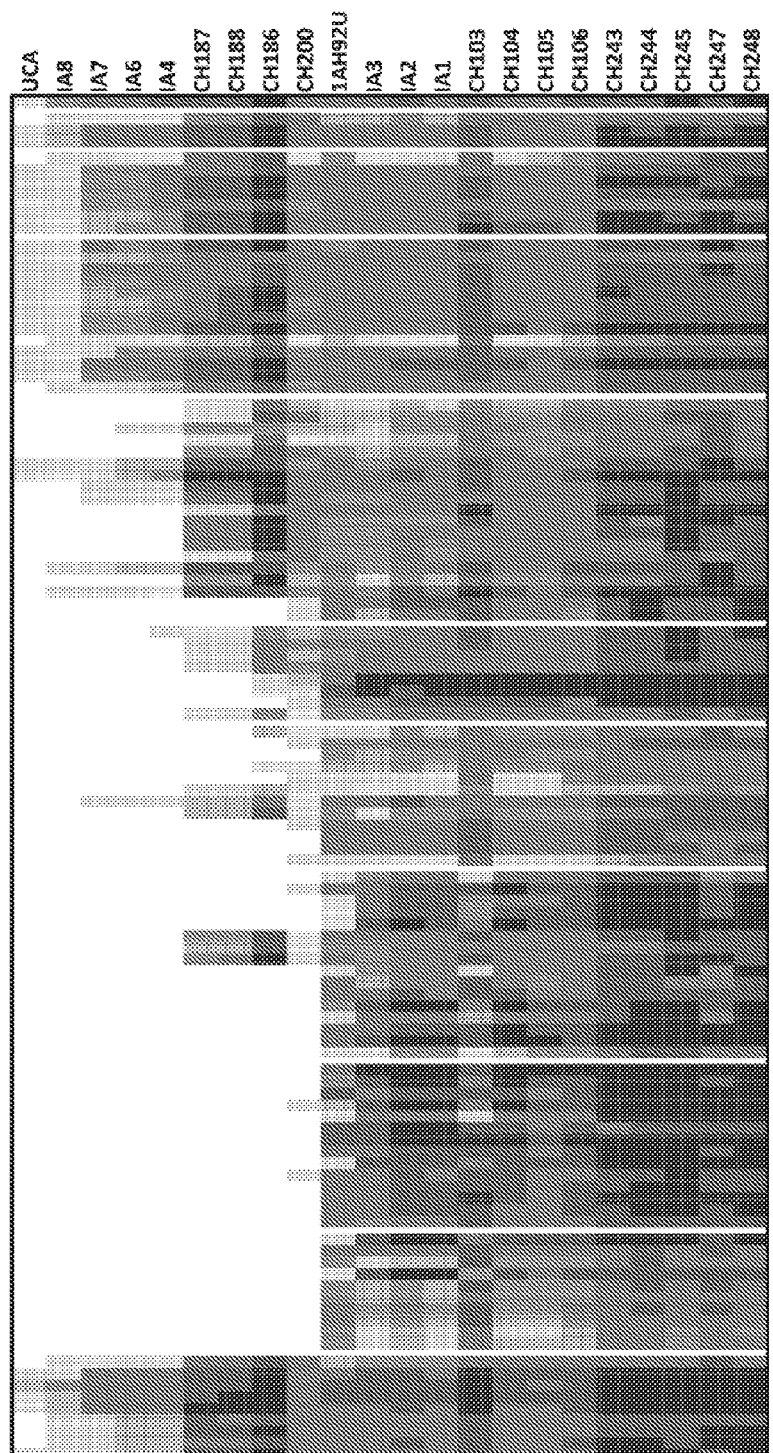
Figure 34B:
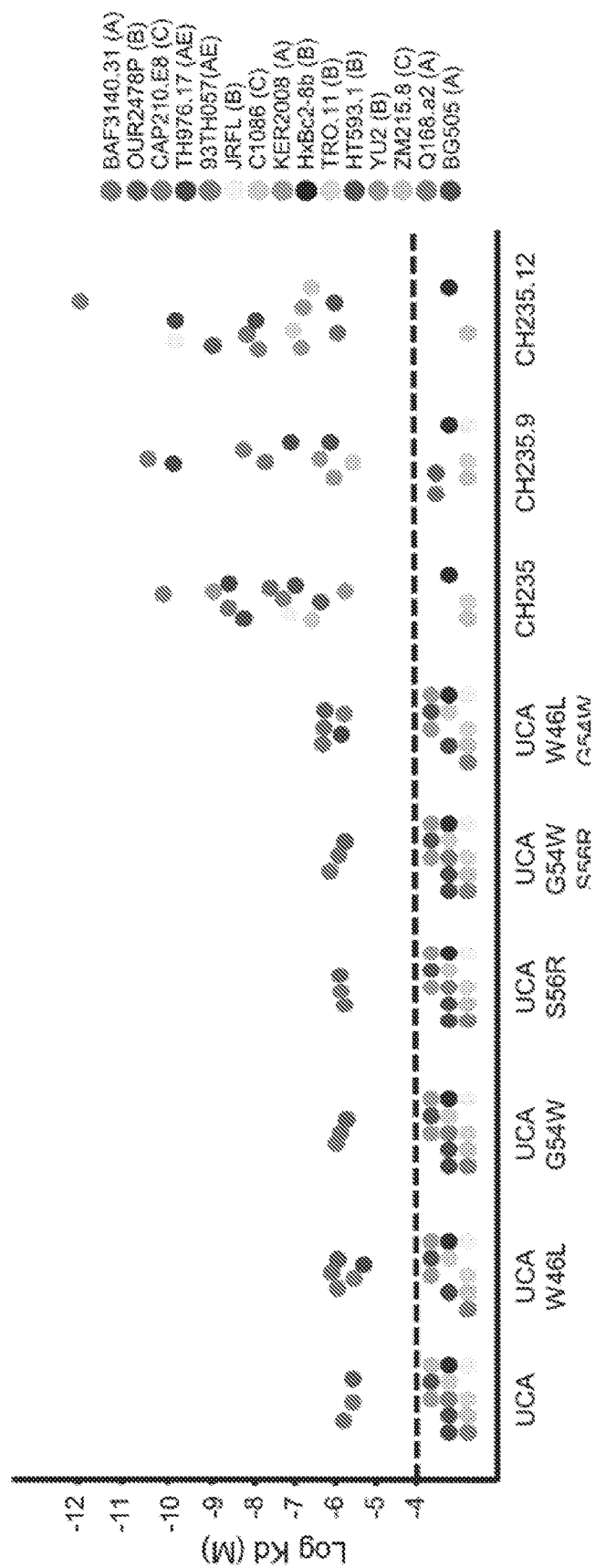
Figure 40A:
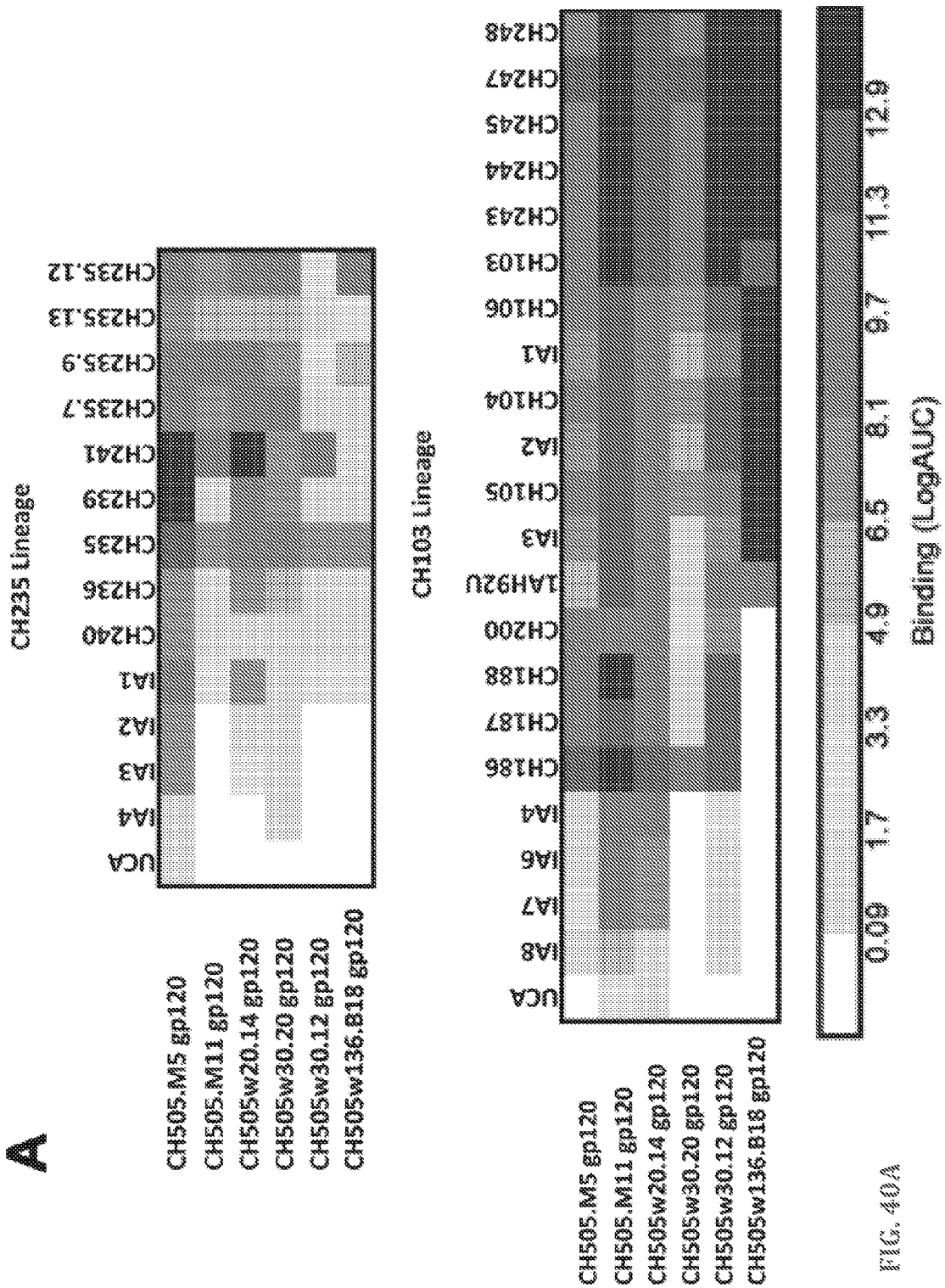
Figure 40B:
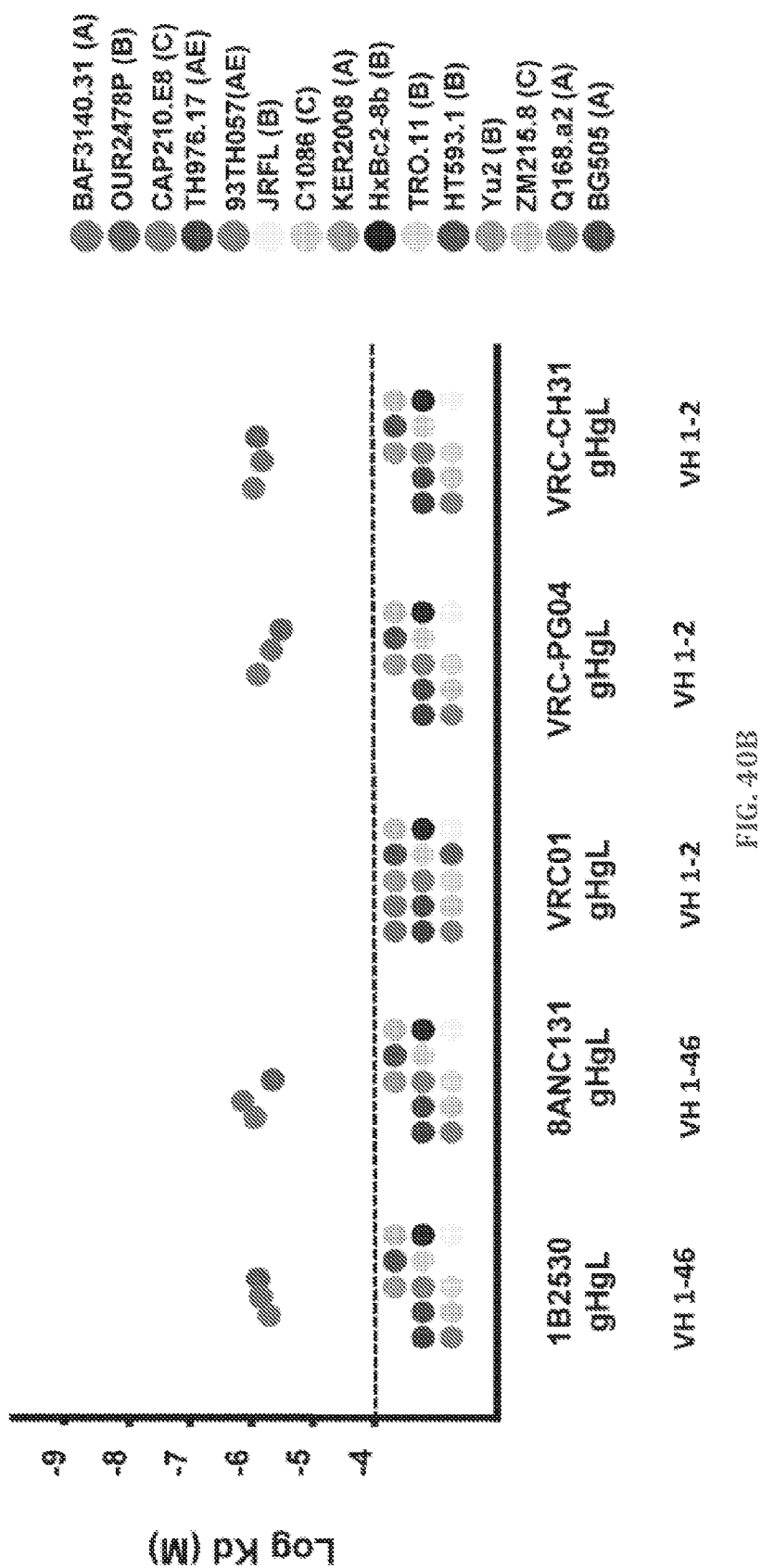

FIGS. 40A-40B show CH505 gp120 Env Quasi-species Selected as Optimized Immunogens to Induce Both CH235 and CH103-like bnAbs, Related to FIG. 34A-B. (A) Heatmap of the binding data of selected CH235 and CH103 lineage members to the CH505 Env glycoproteins selected to be used as immunogens. Individual Env clone names and weeks of isolation are shown on the left. (B) Affinity of gHgL of 1B2530, 8ANC131, VRC01, VRC-PG04 and VRC-CH31 to a panel of 15 heterologous gp120 envelope glycoproteins.

FIG. 40C shows a Table with characteristics of the V(D)J rearrangements of key CH235 lineage antibodies. Related to FIG. 29.

Figure 41:
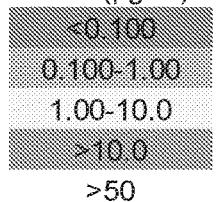

FIG. 41 shows a Table with a summary of the Breadth and Potency of Antibody Neutralization Against 199 HIV-1 Env-Pseudoviruses. Related to FIG. 29.

FIG. 42 shows a Table with crystallographic Data Collection and Refinement Statistics. Related to FIGS. 30A-30E.

FIGS. 43A-43C show Sequence Similarity Between VH1-2 and VH1-46 Broadly Neutralizing Antibodies and Mutability of Germline Genes. Related to FIGS. 31A-31C. (A) The probability of a conforming VH1-46 antibody with x $V_H$ mutations, having c common mutation positions with a reference antibody were estimated based on 100,000 simulated events, with the likelihood of each residue being mutated based on uniform distribution (position) ($P_{uniform}$), or the mutation frequency at each residue position derived from the VH1-46 antibodies ($P_{VH1-46}$). (B) The probability of a conforming VH1-46 antibody with x $V_H$ mutations, having i identical mutations with a reference antibody were estimated based on 100,000 simulated events, with the likelihood of each residue being mutated based on uniform distribution (position and mutation type) ($P_{uniform}$), or the mutation frequency at each residue position derived from the VH1-46 antibodies ($P_{VH1-46}$). (C) Pearson correlation coefficients of positional somatic mutation frequency between VH1-46, VH1-2 and three others.

FIGS. 44A-44B show CH235 Lineage and CH106 Monoclonal Antibodies Cross-Blocking. Related to FIG. 32. (A) CH235 lineage antibodies blocking of sCD4 and CH106 binding to CH505 TF gp120 and B.63521 gp120 Envs. Results expressed as IC50 ug/ml. nb=no blocking. (B) Monoclonal antibody CH106 blocking of CH235 lineage antibodies to CH505 TF gp120. Results expressed as IC50 ug/ml. nb=no blocking.

FIG. 45 shows CH235 lineage autologous neutralization. Related to FIG. 33A-C.

FIG. 46 shows CH235 lineage antibodies and CH235.9 mutants neutralization of CH505 TF loop D mutant viruses. Related to FIG. 33A-C.

FIG. 47 shows binding of antibodies in the CH235 and CH103 lineages to CH505 autologous Env glycoproteins, Related to FIG. 34A-B.

FIGS. 48A-48D show non-limiting examples of mutations in the VH chain of DH511 and DH512, and non-limiting examples of sequences including mutations in DH512 VH chain. FIG. 48A shows positions in the VHCDR3 chain of DH511 (SEQ ID NO: 295) which could be mutated. Amino acid positions refer to Kabat numbering. Most mutations are to changes to W, but F, L or possibly other substitutions can also be tried. FIG. 48B shows positions in the VHCDR3 chain of DH512 (SEQ ID NO: 296) which could be mutated. Amino acid positions refer to Kabat numbering for the DH512VH chain: QVQLVQSGGGLVK-PGGSLTLSCSASGFFFDNSWMGWVRQAPGK-GLEWVGRIRRLKDGAT GEY-GAAVKDRFTISRDDSRNMLYLHMRTLKTEDSGTYYC TMDEGTPVTRFLEWGYFYYY MAVWGRGTTVIVSS (SEQ ID NO: 213). Most mutations are to changes to W, but F, L or possibly other substitutions can also be tried. For both DH511 and DH512 position V100 can be changed to I. Position L100d can be changed to F. For both DH511 and DH512 combination mutations in the DH512 or DH511 VHCDR3 could include VH_L100dF together with T100aW; VH_L100dW together with T100aW. FIG. 48C shows positions outside of VHCDR3 which could be mutated (SEQ ID NOS 297-302, respectively, in order of appearance). Most mutations are to changes to W, F, L or possibly other substitutions can also be tried. FIG. 48D shows amino acid sequences (SEQ ID NOs: 195-212) of some of the DH512 mutants from FIG. 48B.

DETAILED DESCRIPTION

Broadly neutralizing and potent HIV-1 envelope glycoprotein (Env) antibodies are now being developed for both prevention of HIV-1 (Rudicell R S et al. J. Virol 88: 12669, -82, 2014) and for treatment of HIV-1 infected individuals (Barouch D H, et al. Nature 503: 224-8, 2013; Shingai M et al. Nature 503: 277-80, 2013). Thus, human recombinant antibodies either alone or in combinations have great prophylactic and therapeutic potential for the prevention and treatment of HIV-1 infection. Moreover, antibodies that bind with high affinity to Env may be useful in eliminating the latent pool of HIV-1-infected CD4 T cells and curing HIV-1 infection, when either used to sensitize HIV-1 expressing target cells with bispecific bnAbs for NK or CD8 T cell killing or when bnAbs are conjugated with toxins or radionucleotides.

In certain aspects the invention provides fully human antibodies and fragments that specifically bind to and potently neutralize various isolates of HIV-1. In some embodiments, the antibodies bind to HIV-1 env V3 glycan. In some embodiments, the antibodies of the invention bind to HIV-1 gp120 Env CD4 binding site.

In certain aspects the invention provides pharmaceutical compositions including these human antibodies and a pharmaceutically acceptable carrier. In certain aspects the invention provides antibodies for passive immunization against HIV/AIDS. Nucleic acids encoding these antibodies, expression cassettes and vectors including these nucleic acids, and isolated cells that express the nucleic acids which encode the antibodies of the invention are also provided.

In some embodiments, the invention provides antibodies which are clonal variants. In some embodiments, clonal variants are sequences that differ by one or more nucleotides or amino acids, and have a V region with shared mutations compared to the germline, identical VHDJH or VJH gene usage, identical or similar HCDR3 length, and the same VL and JL usage. The germline sequence (unmutated common ancestor "UCA") is intended to be the sequence coding for the antibody/immunoglobulin (or of any fragment thereof) deprived of mutations, for example somatic mutations. Antibodies in a clone that are designated as UCA and/or I (for "Intermediate") are typically not identified from a biological sample, but are derived computationally based on VH and/or VL sequences identified from subjects infected with HIV-1.

Compositions including the human antibodies of the invention, including V3 glycan and CD4 binding site antibodies, can be used for any purpose including but not limited to research, diagnostic and therapeutic purposes. In non-limiting embodiments, the human monoclonal antibodies disclosed herein can be used to detect HIV-1 in a biological sample or interfere with the HIV-1 activity, for example to diagnose or treat a subject having an HIV-1 infection and/or AIDS. For example, the antibodies can be used to determine HIV-1 titer in a subject. The antibodies disclosed herein also can be used to study the biology of the human immunodeficiency virus. The antibodies of the invention can be used for therapeutic purposes for treatment or prevention of HIV-1 infection, alone or in combination with other therapeutic modalities, including ART and/or combination with other HIV-1 targeting antibodies, neutralizing antibodies and/or ADCC inducing antibodies.

Figure 26A:
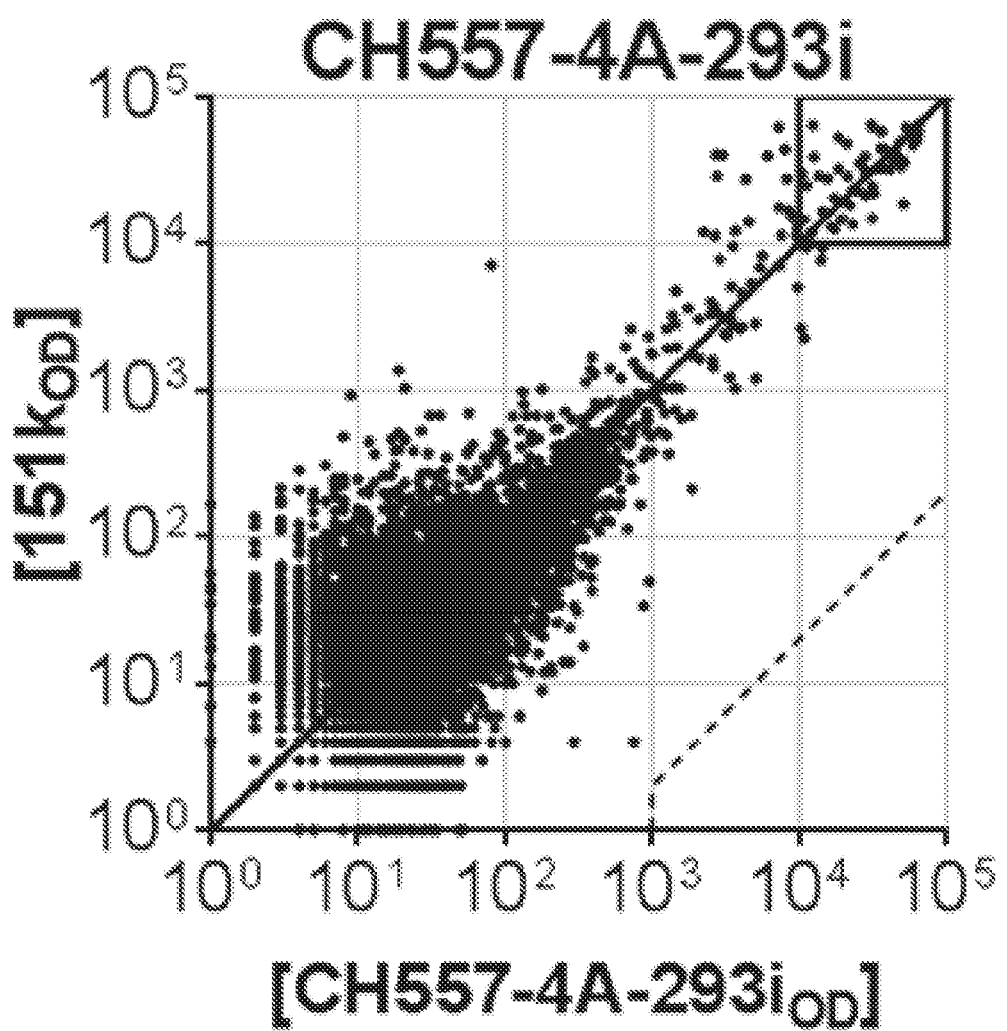
FIGS. 26A and 26B shows summary of data from CH557 microarray polyreactivity.
Figure 26B:
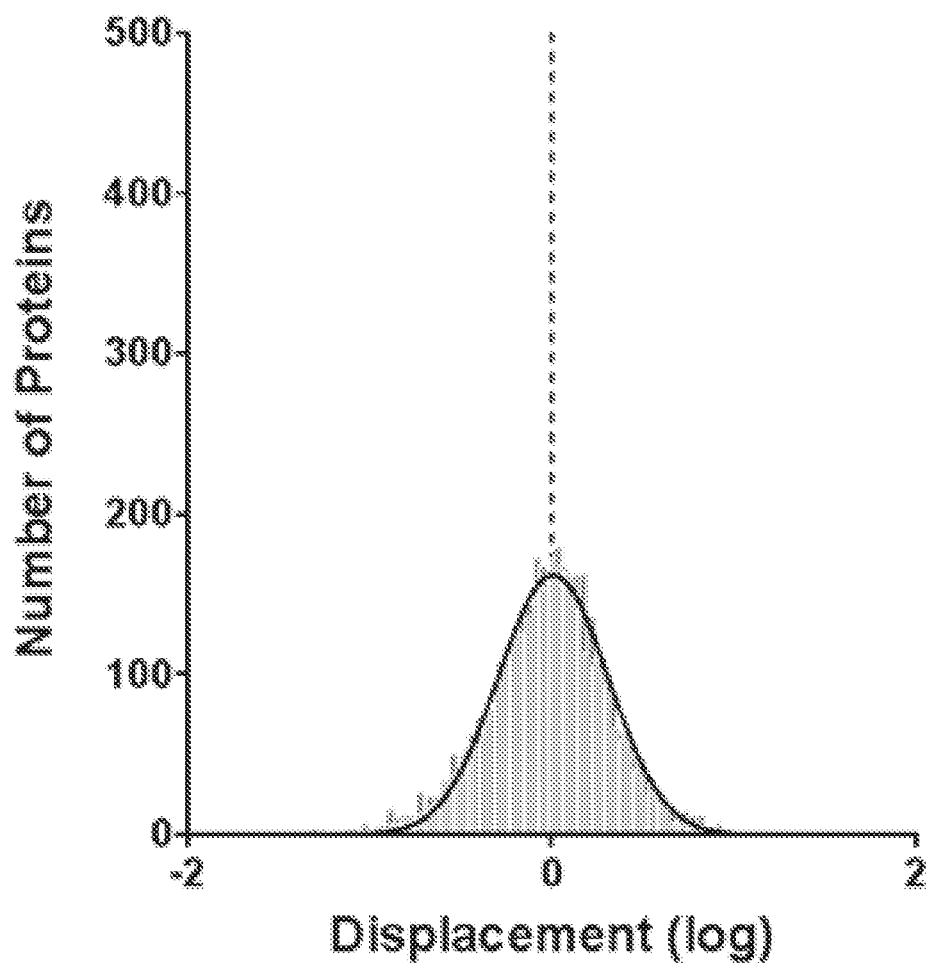

In some embodiments, the antibodies of the invention are expected not to exhibit self-reactivity—they do not bind or bind very weakly to self-antigens, such as human protein. For example, the antibodies of clone DH511 are not self-reactive although their UCA and some IAs are polyreactive. For use as preventive or therapeutic agents, what matters is whether the mature antibody will be polyreactive or not, and for example DH542 is not. DH270IA1 does not show self-reactivity, while DH491 and DH493 antibodies are polyreactive to varying degrees. Broadly neutralizing antibody CH557 displays exceptional neutralization breadth and high potency (FIG. 10) and it is not autoreactive nor polyreactive as determined by lack of binding to known human antigens associated with autoimmune disorders), negativity in Hep-2 cells IF staining (FIG. 25) and lack of binding to an array of 9,400 human antigens (FIGS. 26A and B), including UBE3A and STUB-1 proteins, known to be bound by previously described broadly neutralizing antibodies targeting the CD4bs of gp120 Env (Liu et al J Virol 2014, Bonsignori et al JCI 2014).

The neutralization breadth of the inventive antibodies is demonstrated by the diversity of viruses which are neutralized in the TZMbl Env pseudovirus inhibition assay. In certain embodiments, the neutralization breadth and/or binding of the antibodies of the invention can be maintained in the presence of tolerate changes to the epitope. Comparing the sequences of the neutralized viruses, versus viruses that are not neutralized, a skilled artisan can readily determine the % virus changes, including changes in the epitope, which can be tolerated while neutralization and/or binding is maintained.

Comparing the sequences of the antibodies and their neutralization properties, a skilled artisan can readily determine sequence identity, compare sequence length and determine the % sequence identity and/or changes, including % sequence identity and/or changes in the VH and VL sequences, including % sequence identity and/or changes in the CDRs, as well as the specific positions and types of substitutions which can be tolerated while neutralization potency and breadth is maintained.

Various algorithms for sequence alignment are known in the art. The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. U.S.A. 85:2444, 1988. Altschul et al., Nature Genet. 6:119, 1994, presents a detailed consideration of sequence alignment methods and homology calculations.

The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a VL or a VH of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80% identical to the VH and VL amino acid sequences of the antibodies described herein and still maintain the neutralization breadth, biding and/or potency. In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80% identical to the CDR1, 2, and/or 3 of VH and CDR1, 2, and/or 3 VL amino acid sequences of the antibodies described herein and still maintain the neutralization breadth, biding and/or potency.

In certain embodiments, the invention provides antibodies which can tolerate a larger percent variation in the sequences outside of the VH and/VL sequences of the antibodies. In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65% identical, wherein the identity is outside of the VH or VL regions, or the CDRs of the VH or VL chains of the antibodies described herein.

Antibodies of the invention are expected to have the same binding specificity, for example as intact immunoglobulins and antigen binding variants or fragments e.g. as a number of well characterized fragments produced by digestion with various peptidases. For instance and without limitation, Fabs, Fvs, scFvs are fragments which are expected to have the same binding specificities as intact antibodies. Binding specificity can be determined by any suitable assay in the art, for example but not limited competition binding assays, epitope mapping, etc. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. Provided are also genetically engineered forms such as chimeric antibodies and heteroconjugate antibodies such as bispecific antibodies. See also, Pierce Catalog and Handbook, 1994-1995 (Pierce Chemical Co., Rockford, Ill.); Kuby, Immunology, 3.sup.rd Ed., W.H. Freeman & Co., New York, 1997.

In certain embodiments the invention provides antibody fragments, which have the binding specificity and/or properties of the inventive antibodies. Non-limiting examples include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab').sub.2, the fragment of the antibody obtained by treating whole antibody with the enzyme pepsin without subsequent reduction; (4) F(ab').sub.2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. In certain embodiments, the antibody fragments can be produces recombinantly.

In certain embodiments, VH refers to the variable region of an immunoglobulin heavy chain, including but not limited to that of an antibody fragment, such as Fv, scFv, dsFv or Fab. In certain embodiments, VL refers to the variable region of an immunoglobulin light chain, including but not limited to that of an Fv, scFv, dsFv or Fab.

Any of the nucleic acids encoding any of the antibodies, or fragment thereof can be expressed in a recombinantly engineered cell such as bacteria, plant, yeast, insect and mammalian cells. The nucleic acid sequences include any sequence necessary for expression, including but not limited to a promoter, a leader sequence. These antibodies can be expressed as individual VH and/or VL chain, or can be expressed as a fusion protein. In certain embodiments, the antibodies can be expressed by viral vector mediated delivery of genes encoding the antibodies of the invention (See e.g. Yang et al. Viruses 2014, 6, 428-447).

To create a single chain antibody, (scFv) the VH- and VL-encoding DNA fragments are operatively linked to another fragment encoding a flexible linker, e.g., encoding the amino acid sequence $(Gly_4\text{-}Ser)_3$ (SEQ ID NO: 214), such that the VH and VL sequences can be expressed as a contiguous single-chain protein, with the VH and VL domains joined by the flexible linker (see, e.g., Bird et al., Science 242:423-426, 1988; Huston et al., Proc. Natl. Acad. Sci. USA 85:5879-5883, 1988; McCafferty et al., Nature 348:552-554, 1990). Optionally, a cleavage site can be included in a linker, such as a furin cleavage site.

In some embodiments, a single chain antibody may be monovalent, if only a single VH and VL are used, bivalent, if two VH and VL are used, or polyvalent, if more than two VH and VL are used. Bispecific or polyvalent antibodies may be generated that bind specifically to different epitopes within the envelope. Bispecific or polyvalent antibodies may be generated that bind specifically to different epitopes within the envelope, and/or to another molecule.

There are numerous expression systems available for expression of proteins including *E. coli*, other bacterial hosts, yeast, and various higher eukaryotic cells such as the COS, CHO, HeLa and myeloma cell lines.

The antibodies described herein, or fragments thereof, may be recombinantly produced in prokaryotic or eukaryotic expression systems. These systems are well described in the art. In general, protein therapeutics are produced from mammalian cells. The most widely used host mammalian cells are Chinese hamster ovary (CHO) cells and mouse myeloma cells, including NSO and Sp2/0 cells. Two derivatives of the CHO cell line, CHO-K1 and CHO pro-3, gave rise to the two most commonly used cell lines in large scale production, DUKX-X11 and DG44. (See, e.g., Kim, J., et al., "CHO cells in biotechnology for production of recombinant proteins: current state and further potential," *Appl. Microbiol. Biotechnol.*, 2012, 93:917-30, which is hereby incorporated-by-reference.) Other mammalian cell lines for recombinant antibody expression include, but are not limited to, COS, HeLa, HEK293T, U205, A549, HT1080, CAD, P19, NIH 3T3, L929, N2a, HEK 293, MCF-7, Y79, SO-Rb50, HepG2, J558L, and BHK. If the aim is large-scale production, the most currently used cells for this application are CHO cells. Guidelines to cell engineering for mAbs production were also reported. (Costa et al., "Guidelines to cell engineering for monoclonal antibody production," *Eur J Pharm Biopharm*, 2010, 74:127-38, which is hereby incorporated-by-reference.) Using heterologous promoters, enhancers and amplifiable genetic markers, the yields of antibody and antibody fragments can be increased. Thus, in certain embodiments, the invention provides an antibody, or antibody fragment, that is recombinantly produced from a mammalian cell-line, including a CHO cell-line. In certain embodiments, the invention provides a composition comprising an antibody, or antibody fragment, wherein the antibody or antibody fragment was recombinantly produced in a mammalian cell-line, and wherein the antibody or antibody fragment is present in the composition at a concentration of at least 1, 10, 100, 1000 micrograms/mL, or at a concentration of at least 1, 2, 3, 4, 5, 6, 7, 8, 9, 10, 20, 50, or 100 milligrams/mL.

Furthermore, large-scale production of therapeutic-grade antibodies are much different than those for laboratory scale. There are extreme purity requirements for therapeutic-grade. Large-scale production of therapeutic-grade antibodies requires multiples steps, including product recovery for cell-culture harvest (removal of cells and cell debris), one or more chromatography steps for antibody purification, and formulation (often by tangential filtration). Because mammalian cell culture and purification steps can introduce antibody variants that are unique to the recombinant production process (i.e., antibody aggregates, N- and C-terminal variants, acidic variants, basic variants, different glycosylation profiles), there are recognized approaches in the art for analyzing and controlling these variants. (See, Fahrner, et al., Industrial purification of pharmaceutical antibodies: Development, operation, and validation of chromatography processes, *Biotech. Gen. Eng. Rev.*, 2001, 18:301-327, which is hereby incorporated-by-reference.) In certain embodiments of the invention, the antibody composition comprises less than 1, 2, 3, 4, 5, 10, 15, 20, 25, 30, 35, 50, or 100 nanograms of host cell protein (i.e., proteins from the cell-line used to recombinantly produce the antibody)). In other embodiments, the antibody composition comprises less than 1, 2, 3, 4, 5, 6, 7, 8, 9, 10, 15, 20, or 25 ng of protein A per milligram of antibody or antibody fragment (i.e., protein A is a standard approach for purifying antibodies from recombinant cell culture, but steps should be done to limit the amount of protein A in the composition, as it may be immunogenic). (See, e.g., U.S. Pat. No. 7,458,704, Reduced protein A leaching during protein A affinity chromatography; which is hereby incorporated-by-reference.)

In certain embodiments, the invention provides monoclonal antibodies. In certain embodiments the monoclonal antibodies are produced by a clone of B-lymphocytes. In certain embodiments the monoclonal antibody is a recombinant and is produced by a host cell into which the light and heavy chain genes of a single antibody have been transfected. Any suitable cell could be used for transfection and expression of the antibodies of the invention. Suitable cell lines include without limitation 293T cells or CHO cells.

Monoclonal antibodies are produced by any suitable method known to those of skill in the art. In some embodiments, monoclonal antibodies are produced by immortalizing B-cell expressing an antibody. Methods for immortalizing B-cells are known in the art, for example but not limited to using EBV transformation, treatment with various stimulants, and/or apoptotic inhibitors (Bonsignori et al. J. Virol. 85: 9998-10009, 2011). In some embodiments, monoclonal antibodies are produced by making hybrid antibody-forming cells from a fusion of myeloma cells with immune spleen cells to make hybridomas. In some embodiments monoclonal antibodies are identified from a subject, for example but not limited as described in Example 1 (Liao H X et al. J Virol Methods. 2009 June; 158(1-2):171-9). The amino acid and nucleic acid sequences of such identified monoclonal antibodies can be determined.

The antibodies of the invention can be of any isotype. In certain embodiments, the antibodies of the invention can be used as IgG1, IgG2, IgG3, IgG4, whole IgG1 or IgG3s, whole monomeric IgAs, dimeric IgAs, secretory IgAs, IgMs as monomeric, pentameric or other polymer forms of IgM. The class of an antibody comprising the VH and VL chains described herein can be specifically switched to a different class of antibody by methods known in the art.

In some embodiments, the nucleic acid encoding the VH and VL can encode an Fc domain (immunoadhesin). The Fc domain can be an IgA, IgM or IgG Fc domain. The Fc domain can be an optimized Fc domain, as described in U.S. Published Patent Application No. 20100093979, incorporated herein by reference. In one example, the immunoadhesin is an IgG1 Fc. In one example, the immunoadhesin is an IgG3 Fc.

In certain embodiments the antibodies comprise amino acid alterations, or combinations thereof, for example in the Fc region outside of epitope binding, which alterations can improve their properties. Various Fc modifications are known in the art. Amino acid numbering is according to the EU Index in Kabat. In some embodiments, the invention contemplates antibodies comprising mutations that affect neonatal Fc receptor (FcRn) binding, antibody half-life, and localization and persistence of antibodies at mucosal sites. See e.g. Ko S Y et al., Nature 514: 642-45, 2014, at FIG. 1a and citations therein; Kuo, T. and Averson, V., mAbs 3(5): 422-430, 2011, at Table 1, US Pub 20110081347 (an aspartic acid at Kabat residue 288 and/or a lysine at Kabat residue 435), US Pub 20150152183 for various Fc region mutation, incorporated by reference in their entirety. In certain embodiments, the antibodies comprise AAAA substitution in and around the Fc region of the antibody that has been reported to enhance ADCC via NK cells (AAA mutations) containing the Fc region aa of S298A as well as E333A and K334A (Shields R I et al JBC, 276: 6591-6604, 2001) and the $4^{th}$ A (N434A) is to enhance FcR neonatal mediated transport of the IgG to mucosal sites (Shields R I et al. ibid). Other antibody mutations have been reported to improve antibody half-life or function or both and can be incorporated in sequences of the antibodies. These include the DLE set of mutations (Romain G, et al. Blood 124: 3241, 2014), the LS mutations M428L/N434S, alone or in a combination with other Fc region mutations, (Ko S Y et al. Nature 514: 642-45, 2014, at FIG. 1a and citations therein; Zlevsky et al., Nature Biotechnology, 28(2): 157-159, 2010; US Pub 20150152183); the YTE Fc mutations (Robbie G et al Antimicrobial Agents and Chemotherapy 12: 6147-53, 2013) as well as other engineered mutations to the antibody such as QL mutations, IHH mutations (Ko S Y et al. Nature 514: 642-45, 2014, at FIG. 1a and relevant citations; See also Rudicell R et al. J. Virol 88: 12669-82, 201). In some embodiments, modifications, such as but not limited to antibody fucosylation, may affect interaction with Fc receptors (See e.g. Moldt, et al. JVI 86(11): 66189-6196, 2012). In some embodiments, the antibodies can comprise modifications, for example but not limited to glycosylation, which reduce or eliminate polyreactivity of an antibody. See e.g. Chuang, et al. Protein Science 24: 1019-1030, 2015. In some embodiments the antibodies can comprise modifications in the Fc domain such that the Fc domain exhibits, as compared to an unmodified Fc domain enhanced antibody dependent cell mediated cytotoxicity (ADCC); increased binding to Fc.gamma.RIIA or to Fc.gamma.RIIIA; decreased binding to Fc.gamma RIM; or increased binding to Fc.gamma.RIIB See e.g. US Pub 20140328836.

In certain embodiments, antibodies of the invention including but not limited to antibodies comprising a CDR(s) of VH and/or VL chains, or antibody fragments of the inventive antibodies can be used as the HIV-1 binding arm(s) of a bispecific molecule, e.g. DARTS, diabodies, toxin labeled HIV-1 binding molecules.

In accordance with the methods of the present invention, either the intact antibody or a fragment thereof can be used. Either single chain Fv, bispecific antibody for T cell engagement, or chimeric antigen receptors can be used (Chow et al, Adv. Exp. Biol. Med. 746:121-41 (2012)). That is, in non-limiting embodiments, intact antibody, a Fab fragment, a diabody, or a bispecific whole antibody can be used to inhibit HIV-1 infection in a subject (e.g., a human). A bispecific F(ab)$_2$ can also be used with one arm a targeting molecule like CD3 to deliver it to T cells and the other arm the arm of the native antibody (Chow et al, Adv. Exp. Biol. Med. 746:121-41 (2012)). Toxins that can be bound to the antibodies or antibody fragments described herein include unbound antibody, radioisotopes, biological toxins, boronated dendrimers, and immunoliposomes (Chow et al, Adv. Exp. Biol. Med. 746:121-41 (2012)). Toxins (e.g., radionucleotides or other radioactive species) can be conjugated to the antibody or antibody fragment using methods well known in the art (Chow et al, Adv. Exp. Biol. Med. 746: 121-41 (2012)). The invention also includes variants of the antibodies (and fragments) disclosed herein, including variants that retain the ability to bind to recombinant Env protein, the ability to bind to the surface of virus-infected cells and/or ADCC-mediating properties of the antibodies specifically disclosed, and methods of using same to, for example, reduce HIV-1 infection risk. Combinations of the antibodies, or fragments thereof, disclosed herein can also be used in the methods of the invention.

Antibodies of the invention and fragments thereof can be produced recombinantly using nucleic acids comprising nucleotide sequences encoding VH and VL sequences selected from those shown in the figures and examples.

In certain embodiments the invention provides intact/whole antibodies. In certain embodiments the invention provides antigen binding fragments thereof. Typically, fragments compete with the intact antibody from which they were derived for specific binding to the target including separate heavy chains, light chains Fab, Fab', F(ab').sub.2, F(ab)c, diabodies, Dabs, nanobodies, and Fv. Fragments can be produced by recombinant DNA techniques, or by enzymatic or chemical separation of intact immunoglobulins.

In certain embodiments the invention provides a bispecific antibody. A bispecific or bifunctional/dual targeting antibody is an artificial hybrid antibody having two different heavy/light chain pairs and two different binding sites (see, e.g., Romain Rouet & Daniel Christ "Bispecific antibodies with native chain structure" Nature Biotechnology 32, 136-137 (2014); Garber "Bispecific antibodies rise again" Nature Reviews Drug Discovery 13, 799-801 (2014), FIG. 1a; Byrne et al. "A tale of two specificities: bispecific antibodies for therapeutic and diagnostic applications" Trends in Biotechnology, Volume 31, Issue 11, November 2013, Pages 621-632 Songsivilai and Lachmann, Clin. Exp. Immunol., 79:315-321 (1990); Kostelny et al., J. Immunol. 148:1547-53 (1992) (and references therein)). In certain embodiments the bispecific antibody is a whole antibody of any isotype. In other embodiments it is a bispecific fragment, for example but not limited to F(ab)$_2$ fragment. In some embodiments, the bispecific antibodies do not include Fc portion, which makes these diabodies relatively small in size and easy to penetrate tissues.

In certain embodiments, the bispecific antibodies could include Fc region. Fc bearing diabodies, for example but not limited to Fc bearing DARTs are heavier, and could bind neonatal Fc receptor, increasing their circulating half-life. See Garber "Bispecific antibodies rise again" Nature Reviews Drug Discovery 13, 799-801 (2014), FIG. 1a; See US Pub 20130295121, incorporated by reference in their entirety. In certain embodiments, the invention encompasses diabody molecules comprising an Fc domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In some embodiments, the Fc domain (or portion thereof) is derived from IgG. In some embodiments, the IgG isotype is IgG1, IgG2, IgG3 or IgG4 or an allotype thereof. In some embodiments, the diabody molecule comprises an Fc domain, which Fc domain comprises a CH2 domain and CH3 domain independently selected from any immunoglobulin isotype (i.e. an Fc domain comprising the CH2 domain derived from IgG and the CH3 domain derived from IgE, or the CH2 domain derived from IgG1 and the CH3 domain derived from IgG2, etc.). In some embodiments, the Fc domain may be engineered into a polypeptide chain comprising the diabody molecule of the invention in any position relative to other domains or portions of the polypeptide chain (e.g., the Fc domain, or portion thereof, may be c-terminal to both the VL and VH domains of the polypeptide of the chain; may be n-terminal to both the VL and VH domains; or may be N-terminal to one domain and c-terminal to another (i.e., between two domains of the polypeptide chain)).

The present invention also encompasses molecules comprising a hinge domain. The hinge domain be derived from any immunoglobulin isotype or allotype including IgA, IgD, IgG, IgE and IgM. In preferred embodiments, the hinge domain is derived from IgG, wherein the IgG isotype is IgG1, IgG2, IgG3 or IgG4, or an allotype thereof. The hinge domain may be engineered into a polypeptide chain comprising the diabody molecule together with an Fc domain such that the diabody molecule comprises a hinge-Fc domain. In certain embodiments, the hinge and Fc domain are independently selected from any immunoglobulin isotype known in the art or exemplified herein. In other embodiments the hinge and Fc domain are separated by at least one other domain of the polypeptide chain, e.g., the VL domain. The hinge domain, or optionally the hinge-Fc domain, may be engineered in to a polypeptide of the invention in any position relative to other domains or portions of the polypeptide chain. In certain embodiments, a polypeptide chain of the invention comprises a hinge domain, which hinge domain is at the C-terminus of the polypeptide chain, wherein the polypeptide chain does not comprise an Fc domain. In yet other embodiments, a polypeptide chain of the invention comprises a hinge-Fc domain, which hinge-Fc domain is at the C-terminus of the polypeptide chain. In further embodiments, a polypeptide chain of the invention comprises a hinge-Fc domain, which hinge-Fc domain is at the N-terminus of the polypeptide chain.

In some embodiments, the invention encompasses multimers of polypeptide chains, each of which polypeptide chains comprise a VH and VL domain, comprising CDRs as described herein. In certain embodiments, the VL and VH domains comprising each polypeptide chain have the same specificity, and the multimer molecule is bivalent and monospecific. In other embodiments, the VL and VH domains comprising each polypeptide chain have differing specificity and the multimer is bivalent and bispecific. In some embodiments, the polypeptide chains in multimers further comprise an Fc domain. Dimerization of the Fc domains leads to formation of a diabody molecule that exhibits immunoglobulin-like functionality, i.e., Fc mediated function (e.g., Fc-Fc.gamma.R interaction, complement binding, etc.).

In yet other embodiments, diabody molecules of the invention encompass tetramers of polypeptide chains, each of which polypeptide chain comprises a VH and VL domain. In certain embodiments, two polypeptide chains of the tetramer further comprise an Fc domain. The tetramer is therefore comprised of two 'heavier' polypeptide chains, each comprising a VL, VH and Fc domain, and two 'lighter' polypeptide chains, comprising a VL and VH domain. Interaction of a heavier and lighter chain into a bivalent monomer coupled with dimerization of the monomers via the Fc domains of the heavier chains will lead to formation of a tetravalent immunoglobulin-like molecule (exemplified in Example 6.2 and Example 6.3). In certain aspects the monomers are the same, and the tetravalent diabody molecule is monospecific or bispecific. In other aspects the monomers are different, and the tetra valent molecule is bispecific or tetraspecific.

Formation of a tetraspecific diabody molecule as described supra requires the interaction of four differing polypeptide chains. Such interactions are difficult to achieve with efficiency within a single cell recombinant production system, due to the many variants of potential chain mispairings. One solution to increase the probability of mispairings, is to engineer "knobs-into-holes" type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a 'knob', e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the diabody molecule, and further, engineered into any portion of the polypeptides chains of the pair. Methods of protein engineering to favor heterodimerization over homodimerization are well known in the art, in particular with respect to the engineering of immunoglobulin-like molecules, and are encompassed herein (see e.g., Ridgway et al. (1996) "Knobs-Into-Holes' Engineering Of Antibody CH3 Domains For Heavy Chain Heterodimerization," Protein Engr. 9:617-621, Atwell et al. (1997) "Stable Heterodimers From Remodeling The Domain Interface Of A Homodimer Using A Phage Display Library," J. Mol. Biol. 270: 26-35, and Xie et al. (2005) "A New Format Of Bispecific Antibody: Highly Efficient Heterodimerization, Expression And Tumor Cell Lysis," J. Immunol. Methods 296:95-101; each of which is hereby incorporated herein by reference in its entirety).

The invention also encompasses diabody molecules comprising variant Fc or variant hinge-Fc domains (or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain variants identified as altering effector function are known in the art. For example International Application WO04/063351, U.S. Patent Application Publications 2005/0037000 and 2005/0064514.

The bispecific diabodies of the invention can simultaneously bind two separate and distinct epitopes. In certain embodiments the epitopes are from the same antigen. In other embodiments, the epitopes are from different antigens. In preferred embodiments, at least one epitope binding site is specific for a determinant expressed on an immune effector cell (e.g. CD3, CD16, CD32, CD64, etc.) which are expressed on T lymphocytes, natural killer (NK) cells or other mononuclear cells. In one embodiment, the diabody molecule binds to the effector cell determinant and also activates the effector cell. In this regard, diabody molecules of the invention may exhibit Ig-like functionality independent of whether they further comprise an Fc domain (e.g., as assayed in any effector function assay known in the art or exemplified herein (e.g., ADCC assay).

Non-limiting examples of bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include but are not limited to BiTE (Micromet), DART (MacroGenics) (e.g, U.S. Pat. No. 8,795,667; No. 2014-0099318; 2013-0295121; 2010-0174053 and 2009-0060910; European Patent Publication No. EP 2714079; EP 2601216; EP 2376109; EP 2158221 and PCT Publications No. WO 2015/026894; WO 2015/026892; WO 2015/021089; WO 2014/159940; WO 2012/162068; WO 2012/018687; WO 2010/080538), the content of each of these publications in herein incorporated by reference in its entirety), Fcab and Mab2 (F-star), Fc-engineered IgG1 (Xencor) or DuoBody (based on Fab arm exchange, Genmab).

In certain embodiments, the bispecific antibody comprises an HIV envelope binding fragment, for example but not limited to an HIV envelope binding fragment from any of the antibodies described herein. In other embodiments, the bispecific antibody further comprises a second antigen-interaction-site/fragment. In other embodiments, the bispecific antibody further comprises at least one effector domain.

In certain embodiments the bispecific antibodies engage cells for Antibody-Dependent Cell-mediated Cytotoxicity (ADCC). In certain embodiments the bispecific antibodies engage natural killer cells, neutrophil polymorphonuclear leukocytes, monocytes and macrophages. In certain embodiments the bispecific antibodies are T-cell engagers. In certain embodiments, the bispecific antibody comprises an HIV envelope binding fragment and CD3 binding fragment. Various CD3 antibodies are known in the art. See for example U.S. Pat. No. 8,784,821. In certain embodiments, the bispecific antibody comprises an HIV envelope binding fragment and CD16 binding fragment.

In certain embodiments the invention provides antibodies with dual targeting specificity. In certain aspects the invention provides bi-specific molecules that are capable of localizing an immune effector cell to an HIV-1 envelope expressing cell, so as facilitate the killing of the HIV-1 envelope expressing cell. In this regard, bispecific antibodies bind with one "arm" to a surface antigen on target cells, and with the second "arm" to an activating, invariant component of the T cell receptor (TCR) complex. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e. the immunological synapse is mimicked. Particularly desirable are bispecific antibodies that do not require lymphocyte preconditioning or co-stimulation in order to elicit efficient lysis of target cells.

Several bispecific antibody formats have been developed and their suitability for T cell mediated immunotherapy investigated. Out of these, the so-called BiTE (bispecific T cell engager) molecules have been very well characterized and already shown some promise in the clinic (reviewed in Nagorsen and Bauerle, Exp Cell Res 317, 1255-1260 (2011)). BiTEs are tandem scFv molecules wherein two scFv molecules are fused by a flexible linker. Further bispecific formats being evaluated for T cell engagement include diabodies (Holliger et al., Prot Eng 9, 299-305 (1996)) and derivatives thereof, such as tandem diabodies (Kipriyanov et al., J Mol Biol 293, 41-66 (1999)). DART (dual affinity retargeting) molecules are based on the diabody format that separates cognate variable domains of heavy and light chains of the two antigen binding specificities on two separate polypeptide chains but feature a C-terminal disulfide bridge for additional stabilization (Moore et al., Blood 117, 4542-51 (2011)). The invention also contemplates Fc-bearing DARTs. The so-called triomabs, which are whole hybrid mouse/rat IgG molecules and also currently being evaluated in clinical trials, represent a larger sized format (reviewed in Seimetz et al., Cancer Treat Rev 36, 458-467 (2010)).

The invention also contemplates bispecific molecules with enhanced pharmacokinetic properties. In some embodiments, such molecules are expected to have increased serum half-life. In some embodiments, these are Fc-bearing DARTs (see supra).

In certain embodiments, such bispecific molecules comprise one portion which targets HIV-1 envelope and a second portion which binds a second target. In certain embodiments, the first portion comprises VH and VL sequences, or CDRs from the antibodies described herein. In certain embodiments, the second target could be, for example but not limited to an effector cell. In certain embodiments the second portion is a T-cell engager. In certain embodiments, the second portion comprises a sequence/paratope which targets CD3, CD16, or another suitable target. In certain embodiments, the second portion is an antigen-binding region derived from a CD3 antibody, optionally a known CD3 antibody. In certain embodiments, the anti-CD antibody induce T cell-mediated killing. In certain embodiments, the bispecific antibodies are whole antibodies. In other embodiments, the dual targeting antibodies consist essentially of Fab fragments. In other embodiments, the dual targeting antibodies comprise a heavy chain constant region (CH1. In certain embodiments, the bispecific antibody does not comprise Fc region. In certain embodiments, the bispecific antibodies have improved effector function. In certain embodiments, the bispecific antibodies have improved cell killing activity. Various methods and platforms for design of bispecific antibodies are known in the art. See for example US Pub. 20140206846, US Pub. 20140170149, US Pub. 20090060910, US Pub 20130295121, US Pub. 20140099318, US Pub. 20140088295 which contents are herein incorporated by reference in their entirety.

In certain embodiments the invention provides human, humanized and/or chimeric antibodies.

Pharmaceutical Compositions

In certain aspects the invention provides a pharmaceutical composition comprising an antibody of the invention wherein the composition is used for therapeutic purposes such as but not limited to prophylaxis, treatments, prevention, and/or cure. In certain aspects the invention provides a pharmaceutical composition comprising an antibody of the invention in combination with any other suitable antibody. In certain embodiments, the pharmaceutical compositions comprise nucleic acids which encode the antibodies of the invention. In certain embodiments, these nucleic acids can be expressed by any suitable vector for expression of antibodies. Non-limiting examples include attenuated viral hosts or vectors or bacterial vectors, recombinant vaccinia virus, adenovirus, adeno-associated virus (AAV), herpes virus, retrovirus, cytomegalovirus or other viral vectors can be used to express the antibody.

Various methods to make pharmaceutical compositions are known in the art and are contemplated by the invention. In some embodiments, the compositions include excipient suitable for a biologic molecule such as the antibodies of the invention. In some embodiments, the antibodies could be produced in specific cell lines and conditions so as to control glycosylation of the antibody. In some embodiments, the antibody framework for example, could comprise specific modification so as to increase stability of the antibody.

In certain aspects, the invention provides that the antibodies, and fragments thereof, described herein can be formulated as a composition (e.g., a pharmaceutical composition). Suitable compositions can comprise an inventive antibody (or antibody fragment) dissolved or dispersed in a pharmaceutically acceptable carrier (e.g., an aqueous medium). The compositions can be sterile and can be in an injectable form (e.g. but not limited to a form suitable for intravenous injection, intramascular injection). The antibodies (and fragments thereof) can also be formulated as a composition appropriate for topical administration to the skin or mucosa. Such compositions can take the form of liquids, ointments, creams, gels and pastes. The antibodies (and fragments thereof) can also be formulated as a composition appropriate for intranasal administration. The antibodies (and fragments thereof) can be formulated so as to be administered as a post-coital douche or with a condom. Standard formulation techniques can be used in preparing suitable compositions.

The antibody (and fragments thereof), described herein have utility, for example, in settings including but not limited to the following:

i) in the setting of anticipated known exposure to HIV-1 infection, the antibodies described herein (or fragments thereof) and be administered prophylactically (e.g., IV, topically or intranasally) as a microbiocide, ii) in the setting of known or suspected exposure, such as occurs in the setting of rape victims, or commercial sex workers, or in any homosexual or heterosexual transmission without condom protection, the antibodies described herein (or fragments thereof) can be administered as post-exposure prophylaxis, e.g., IV or topically, and iii) in the setting of Acute HIV infection (AHI), the antibodies described herein (or fragments thereof) can be administered as a treatment for AHI to control the initial viral load or for the elimination of virus-infected CD4 T cells.

In accordance with the invention, the antibodies (or antibody fragments) described herein can be administered prior to contact of the subject or the subject's immune system/cells with HIV-1 or within about 48 hours of such contact. Administration within this time frame can maximize inhibition of infection of vulnerable cells of the subject with HIV-1.

In addition, various forms of the antibodies described herein can be administered to chronically or acutely infected HIV patients and used to kill remaining virus infected cells by virtue of these antibodies binding to the surface of virus infected cells and being able to deliver a toxin to these reservoir cells.

Suitable dose ranges can depend on the antibody (or fragment) and on the nature of the formulation and route of administration. Optimum doses can be determined by one skilled in the art without undue experimentation. For example but not limited, doses of antibodies in the range of 0.1-50 mg/kg, 1-50 mg/kg, 1-10 mg/kg, 1, 1.25, 1.5, 2, 2.5, 3, 3.5, 4, 4.5, 5, 5.5, 6, 6.5, 7, 7.5, 8, 8.5, 9, 9.5 or 10 mg/kg of unlabeled or labeled antibody (with toxins or radioactive moieties) can be used. If antibody fragments, with or without toxins are used or antibodies are used that can be targeted to specific CD4 infected T cells, then less antibody can be used (e.g., from 5 mg/kg to 0.01 mg/kg). In other embodiments, the antibodies of the invention can be administered at a suitable fixed dose, regardless of body size or weight. See Bai et al. Clinical Pharmacokinetics February 2012, Volume 51, Issue 2, pp 119-135.

In certain aspects the invention provides use of the antibodies of the invention, including bispecific antibodies, in methods of treating and preventing HIV-1 infection in an individual, comprising administering to the individual a therapeutically effective amount of a composition comprising the antibodies of the invention in a pharmaceutically acceptable form. In certain embodiment, the methods include a composition which includes more than one HIV-1 targeting antibody. In certain embodiments, the HIV-1 targeting antibodies in such combination bind different epitopes on the HIV-1 envelope. In certain embodiments, such combinations of bispecific antibodies targeting more than one HIV-1 epitope provide increased killing of HIV-1 infected cells. In other embodiments, such combinations of bispecific antibodies targeting more than one HIV-1 epitope provide increased breadth in recognition of different HIV-1 subtypes.

In certain embodiments, the composition comprising the antibodies of the invention alone or in any combination can be administered via IM, subcutaneous, or IV delivery, or could be deposited at mucosal sites, such as the oral cavity to prevent maternal to child transmission, the rectal space or the vagina as a microbicide. In certain embodiments, the antibodies can be administered locally in the rectum, vagina, or in the oral cavity, and can be formulated as a microbiocide (Hladik F et al ELIFE Elife. 2015 Feb. 3; 4. doi: 10.7554/eLife.04525; Multipurpose prevention technologies for reproductive and sexual health. Stone A. Reprod Health Matters. 2014 November; 22(44):213-7. doi: 10.1016/S0968-8080(14)44801-8). In other embodiments, antibodies can be formulated such that the therapeutic antibody or combination thereof is impregnated on a vaginal ring (Chen Y et al. Drug Des. Devel. Ther 8: 1801-15, 2014; Malcolm R K et al BJOG 121 Suppl 5: 62-9, 2014). Antibodies can be administered alone or with anti-retroviral drugs for a combination microbicide (Hladik F et al ELIFE Elife. 2015 Feb. 3; 4. doi: 10.7554/eLife.04525).

Alternatively they can be administered in complex with a form of HIV Env, optimally gp120, but also an Env trimer, to enhance Env immunogenicity. In certain embodiments, the antibodies can be delivered by viral vector mediated delivery of genes encoding the antibodies of the invention (See e.g. Yang et al. Viruses 2014, 6, 428-447). In certain embodiments, the antibodies can be administered in viral vector, for example but not limited to adenoassociated viral vector, for expression in muscle and plasma.

In certain embodiments, antibodies with different binding specificities are combined for use in pharmaceutical compositions and therapeutic methods. For example: CD4 binding site antibodies are combined with V3 antibodies, MPER antibodies and so forth. FIGS. 2, 3, and 4 show a selection of potent HIV-1 neutralizing antibodies which can be used in pharmaceutical compositions, and therapeutic methods. Non-limiting examples of selections of combinations of certain antibodies include: DH542, DH542_L4, DH542_QSA, DH429 and DH512 (or any of the DH512 variants); DH512 and CH31 (See US Publication 20140205607); DH512 (or any of the DH512 variants) and DH540 (See Example 9, and this antibody will be described elsewhere); DH542, DH542_4, DH542_QSA, DH429, DH512 and DH540; DH542, DH542_L4, DH542_QSA, DH429 and CH557; CH557 and DH512 (or any of the DH512 variants). These combinations are expected to give a greater overall potency and breadth. A polyclonal mixture of Abs is expected reduce or eliminate viral escape. It is readily understood by skilled artisans that in some embodiments a combination therapy envisions a composition which combines various antibodies. In other embodiments a combination therapy is provided wherein antibodies are administered as individual compositions, for example at different times, by different means, or at administered at different locations. In other embodiments, a combination therapy is provides wherein a therapeutic antibody or antibodies is combined with other therapeutic means, for example antiretroviral drug cocktails, or drugs which activate latently infected HIV-1 cells.

In some embodiments, the disclosed antibodies or antigen binding fragments thereof are used to determine whether HIV-1 envelope(s) is a suitable antigen for inclusion in a vaccine composition. For example the antibodies can be used to determine whether an antigen in a vaccine composition including gp120 assumes a conformation including an epitope bound by the inventive antibodies or fragments thereof. This can be readily determined by a method which includes contacting a sample containing the vaccine, such as a gp120 antigen, with a disclosed antibody or antigen binding fragment under conditions sufficient for formation of an immune complex, and detecting the immune complex, to detect an HIV-1 antigen including an epitope of an inventive antibody in the sample. In one example, the detection of the immune complex in the sample indicates that vaccine component, such as a HIV-1 Env antigen assumes a conformation capable of binding the antibody or antigen binding fragment.

The following examples are provided to illustrate particular features of certain embodiments, but the scope of the claims should not be limited to those features exemplified.

EXAMPLES

Example 1: Isolating Antibodies from Natural HIV-1 Infected Individuals

Methods to identify and isolate antigen specific reactive antibodies were carried out essentially as described in Liao H X et al. J. Virol. Methods 158: 171-9, 2009. Specific hooks are designed to identify antibodies which bind to specific HIV-1 envelope targets/antigens. Using such hooks, with fluorophore labeled streptavidin in two colors, cells are sorted by flow cytometry, into single wells, and the diagonally (that reacted with both colors hooks) reactive memory B cells are picked. B cells enriched from PBMC are sorted, and plated at limiting dilution (as single cell per well). Optionally, these cultures are grown and supernatants are functionally characterized.

PCR on these cells is carried out according to the protocol in Liao H X et al. J. Virol. Methods 158: 171-9, 2009. PCR amplifications are carried out to amplify rearranged VH and VL fragment pairs from the diagonally sorted memory B cells (Liao et al JVM). Overlapping PCR is used to construct full length Ig heavy and Ig light linear genes comprising the rearranged VH and VL fragment pairs. RT-PCR and PCR reactions is carried out essentially as described in Liao H X et al. J. Virol. Methods 158: 171-9, 2009, see for example FIG. 1, Section 3.3. Sequence analysis of the VH and VL genes was carried out to determine the VH and VL gene usage, CDR lengths, the % mutation of HCDR3 and LCDR3. Based on this sequence analysis, one to two pairs of linear VH and VL genes are selected and made in linear cassettes (essentially as described in Liao H X et al. J. Virol. Methods 158: 171-9, 2009, see for example FIG. 1, Section 3.3) to produce recombinant monoclonal antibodies by transient transfection, e.g. in 293T cells.

Recombinant antibodies are grown and supernatants and/ or purified antibodies are functionally characterized.

Pairs of VH and VL genes as selected above can also be used to produce plasmids for stable expression of recombinant antibodies. In certain embodiments, the plasmids or linear constructs for recombinant antibody expression also comprise AAAA substitution in and around the Fc region of the antibody that has been reported to enhance ADCC via NK cells (AAA mutations) containing the Fc region aa of S298A as well as E333A and K334A (Shields R I et al JBC, 276: 6591-6604, 2001) and the $4^{th}$ A (N434A) is to enhance FcR neonatal mediated transport of the IgG to mucosal sites (Shields R I et al. ibid).

The antibodies of the invention were selected based on a combination of criteria including sequence analyses, and functional analyses including but not limited as neutralization breadth, and potency.

In certain embodiments, the antibodies of the invention comprise naturally rearranged VH and VL fragment pairs, wherein the rest of the Ig gene is not naturally occurring with the identified rearranged VH and VL fragments. In certain embodiments, the antibodies of the invention are recombinantly produced.

Example 2: TZM-bl Cells Pseudo-viruses Neutralization Assay

TZMbl neutralization assay is a standard way to evaluate antibody breadth and potency. See Montefiori, D. Methods Mol Biol. 2009; 485:395-405; HIV-1 Env-pseudoviruses infection of TZM-bl cells. Exemplary pseudovirus neutralization assays and panels of HIV-1 pseudovirus are described for example, in Li et al., J Virol 79, 10108-10125, 2005, Seaman et al, J. Virol., 84:1439-1452, 2010; Sarzotti-Kelsoe et al., J. Immunol. Methods, 409:131-46, 2014; and WO2011/038290, each of which is incorporated by reference herein. Various HIV-1 isolates, both Tier 1 and Tier 2 viruses can be included in this assay.

The TZMbl assay was conducted to determine neutralization potency and breadth of the various antibodies of the invention on different HIV-1 pseudoviruses.

FIG. 27A shows summary results of neutralization data of CH557, CH235, VRC01, VRC07-523-LS, N6, 3BNC117, 8ANC131, CH103, F105, and DH522 against a panel of HIV-1 isolates in the Luc/TZM-bl neutralization assay. Values represent IC50 in µg/ml.

FIG. 27B shows the mean IC50 and percent of isolates neutralized at different IC50 values. FIG. 28A shows summary results of neutralization data of CH557, CH235, VRC01, VRC07-523-LS, N6, 3BNC117, 8ANC131, CH103, F105, and DH522 against a panel of HIV-1 isolates in the Luc/TZM-bl neutralization assay. Values represent IC80 in ug/ml.

FIG. 28B shows the mean IC80 and percent of isolates neutralized at different IC80<50 ug/ml values.

Example 3: Epitope Mapping of Antibodies

Binding and/or neutralization assays using various envelop antigens can be used to determine the envelop epitope recognized by these antibodies.

Example 4: Kd Determination

Kd measurements of antibody binding to HIV-1 envelope, e.g. gp120 or any other suitable peptide, will be determined by Surface Plasmon Resonance measurements, for example using Biacore, or any other suitable technology which permits detection of interaction between two molecules in a quantitative way.

Various assays and experiments can be designed to analyze prevention, treatment and/or cure.

Example 5: Assay for Self-reactivity

Table 3 below summarizes some of the known types of disease associated antibodies.

| Autoantibody | Disease Association (s) |
|---|---|
| SSA | SLE, Sjogrens Syndrome (SS) |
| SSB | Sjogrens Syndrome |
| Sm (Smith antigen) | SLE |
| RNP (ribonucleoprotein) | Mixed connective tissue disease (MCTD) |
| Scl-70 | Scleroderma |
| Jo-1 | Myositis |
| Centromere B | Scleroderma CREST variant (calcinosis), Raynaud's, esophogeal dysmotility, sclerodactyly and talangiectasia |
| Histones | Drug induced SLE |

Various assays for self-reactivity of human antibodies are known in the art. AtheNA Multi-Lyte ANA Plus Test System is one such assay. This is luminex-based assay, which is also used to screen patient sera. In our experiments the criteria for positivity is as follows: an antibody is positive for autoreactivity if reactive at 25 µg/ml.

TABLE 4

Summary of immunoflourescent (IF) staining of Hep2 cells data for antibodies DH270IA1, CH491, CH493. DH270IA1 does not show self-reactivity. CH491 and CH493 show some self-reactivity in this assay.

| Antibody ID | Concentration | Score | Staining Pattern |
|---|---|---|---|
| DH270_IA1/293i | [50 ug/mL} | — | |
| DH270_IA1/293i | [25 ug/mL} | — | |
| CH491_4A/293i | [50 ug/mL} | 2+ | nuclear diffuse, cytoplasmic |
| CH491_4A/293i | [25 ug/mL} | 1+ | nuclear diffuse, cytoplasmic |
| CH493_4A/293i | [50 ug/mL} | 2+ | cytoplasmic |
| CH493_4A/293i | [25 ug/mL} | 1+ | cytoplasmic |

TABLE 5

Summary of Athena data for DH270IA1, CH491, CH493. DH270IA1 does not show self-reactivity. CH491 and CH493 show some self-reactivity in this assay.

| Lot | Antibody ID | | SSA | SSB | Sm | RNP | Scl 70 | Jo 1 | dsDNA | Cent B | Histone |
|---|---|---|---|---|---|---|---|---|---|---|---|
| 294HC | DH270_IA1/293i | 50 | 5 | 6 | 5 | 2 | 4 | 5 | 32 | 10 | 9 |
| | | 25 | 3 | 6 | 5 | 2 | 1 | 3 | 18 | 5 | 4 |
| | | 12.5 | 3 | 6 | 5 | 3 | 2 | 6 | 11 | 3 | 4 |
| | | 6.25 | 5 | 1 | 3 | 2 | 2 | 5 | 6 | 2 | 2 |
| 21RKK | CH491_4A | 50 | 68 | 144 | 6 | 43 | 16 | 169 | 47 | 54 | 59 |
| | | 25 | 44 | 95 | 4 | 30 | 9 | 118 | 39 | 45 | 44 |
| | | 12.5 | 28 | 60 | 3 | 24 | 7 | 79 | 29 | 34 | 34 |
| | | 6.25 | 21 | 42 | 4 | 18 | 4 | 56 | 11 | 26 | 26 |
| 23RKK | CH493_4A | 50 | 155 | 70 | 37 | 69 | 36 | 198 | 0 | 94 | 166 |
| | | 25 | 100 | 38 | 53 | 55 | 34 | 167 | 0 | 129 | 202 |
| | | 12.5 | 54 | 22 | 42 | 49 | 26 | 102 | 0 | 165 | 200 |
| | | 6.25 | 22 | 15 | 46 | 32 | 17 | 54 | 0 | 177 | 174 |

Development of auto and polyreactivity during antibody maturation toward neutralization breadth is a critical aspect that may limit the ability of generating bnAbs during natural infection and upon vaccination. We have previously reported that, in subject CH505, the CD4bs CH103 bnAb lineage is polyreactive and, similarly to CD4 mimic VRC01-class bnAbs, bound to human ubiquitin ligase E3A (UBE3A) with avidity correlated with neutralization (Liao et al Nature 2013; Liu et al J Virol 2015). Since CH557 is a potent and extremely broad CD4 mimic CD4bs bnAb, we compared the auto- and polyreactivity profiles of CH557 with those of early precursors of the CH235 antibody lineage (UCA, IA4, IA3, IA2, IA1, CH235, CH236, CH239, CH240 and CH241). In line with previous observations, reactivity against autoantigens developed among early CH235 lineage members with maturation. However, bnAb CH557 itself became exquisitely HIV-1 specific: it does not react with cardiolipin or other antigens associated with autoimmune disorders, it is negative in Hep-2 IF staining (FIG. 25), or any of 9,400 human antigens, including UBE3A (FIG.

26A-B). Albeit reactivity against other human antigens cannot be formally ruled out, these data demonstrate that bnAb CH557 lost the auto and polyreactivity developed by its precursors, and demonstrates that decoupling neutralization breadth of CD4 mimic CDbs bnAbs from auto- and polyreactivity is an achievable goal.

TABLE 6

Summary of Athena assay results for CH557. Results are expressed as relative luminescence units. Readings <100 are considered negative, results between 100 and 120 are considered "indeterminate" and results >120 are considered positive. CH557 is negative for all the antigens tested at all antibody concentrations ranging from 6.25 ug/ml to 50 ug/ml.

| Antibody | ug/ml | SSA | SSB | Sm | RNP | Scl 70 | Jo 1 | dsDNA | Cent B | Histone |
|---|---|---|---|---|---|---|---|---|---|---|
| 4 e 10 | 50 | 49 | 263 | 5 | 4 | 1 | 190 | 2 | 3 | 16 |
|  | 25 | 33 | 227 | 2 | 3 | 1 | 160 | 2 | 3 | 10 |
|  | 12.5 | 21 | 199 | 3 | 3 | 0 | 131 | 3 | 1 | 7 |
|  | 6.25 | 17 | 178 | 3 | 3 | 1 | 113 | 0 | 2 | 6 |
| synagis | 50 | 5 | 6 | 11 | 10 | 3 | 5 | 25 | 9 | 11 |
|  | 25 | 3 | 7 | 3 | 4 | 2 | 2 | 11 | 4 | 5 |
|  | 12.5 | 2 | 5 | 7 | 3 | 3 | 6 | 7 | 2 | 3 |
|  | 6.25 | 2 | 5 | 2 | 3 | 2 | 1 | 0 | 2 | 3 |
| CH557_4A/293i | 50 | 6 | 15 | 8 | 10 | 6 | 10 | 29 | 46 | 16 |
|  | 25 | 4 | 12 | 6 | 6 | 4 | 2 | 18 | 25 | 8 |
|  | 12.5 | 3 | 9 | 6 | 3 | 3 | 5 | 10 | 16 | 6 |
|  | 6.25 | 4 | 5 | 4 | 4 | 3 | 5 | 9 | 11 | 4 |

TABLE 7

Summary of Athena assay results for various other antibodies of the CH235 lineage. Results are expressed as relative luminescence units. Readings <100 are considered negative, results between 100 and 120 are considered "indeterminate" and results >120 are considered positive. CH236, CH239, CH235 IA1 and IA2 are positive for multiple antigens.

| Antibody ID |  | SSA | SSB | Sm | RNP | Scl 70 | Jo 1 | dsDNA | Cent B | Histone |
|---|---|---|---|---|---|---|---|---|---|---|
| synagis | 50 | 13 | 9 | 6 | 2 | 1 | 4 | 3 | 3 | 0 |
|  | 25 | 11 | 4 | 4 | 0 | 2 | 4 | 0 | 2 | 2 |
| 4E10 IgG1 | 50 | 99 | 207 | 55 | 28 | 5 | 227 | 14 | 14 | 32 |
|  | 25 | 81 | 189 | 46 | 20 | 4 | 206 | 14 | 9 | 24 |
| CH235_4A | 50 | 12 | 7 | 16 | 11 | 8 | 7 | 25 | 11 | 14 |
|  | 25 | 13 | 5 | 7 | 5 | 4 | 4 | 13 | 6 | 7 |
|  | 12.5 | 13 | 5 | 8 | 6 | 2 | 3 | 0 | 5 | 5 |
|  | 6.25 | 12 | 6 | 5 | 3 | 2 | 2 | 3 | 3 | 5 |
| CH236_4A/293i | 50 | 177 | 207 | 128 | 65 | 57 | 145 | 2 | 84 | 138 |
|  | 25 | 224 | 175 | 165 | 69 | 62 | 72 | 42 | 129 | 193 |
|  | 12.5 | 185 | 63 | 258 | 78 | 50 | 19 | 179 | 233 | 234 |
|  | 6.25 | 44 | 15 | 184 | 40 | 31 | 7 | 228 | 208 | 154 |
| CH239_4A/293i | 50 | 289 | 10 | 250 | 93 | kriss | 15 | 38 | 173 | 228 |
|  | 25 | 306 | 8 | 237 | 96 | 51 | 11 | 61 | 199 | 253 |
|  | 12.5 | 277 | 6 | 277 | 85 | 48 | 8 | 108 | 216 | 263 |
|  | 6.25 | 178 | 5 | 285 | 78 | 49 | 8 | 181 | 260 | 266 |
| CH240_4A/293i | 50 | 16 | 17 | 33 | 17 | 6 | 13 | 75 | 37 | 42 |
|  | 25 | 16 | 11 | 22 | 11 | 6 | 11 | 50 | 24 | 27 |
|  | 12.5 | 14 | 5 | 13 | 8 | 4 | 7 | 37 | 15 | 18 |
|  | 6.25 | 12 | 5 | 9 | 6 | 3 | 5 | 14 | 8 | 9 |
| CH241 | 50 | 23 | 10 | 12 | 8 | 5 | 8 | 23 | 21 | 30 |
|  | 25 | 15 | 6 | 11 | 6 | 4 | 5 | 18 | 14 | 20 |
|  | 12.5 | 14 | 8 | 7 | 5 | 3 | 6 | 2 | 8 | 13 |
|  | 6.25 | 15 | 4 | 4 | 3 | 1 | 2 | 6 | 6 | 9 |
| CH235UA/293i | 50 | 11 | 3 | 8 | 5 | 3 | 3 | 7 | 5 | 7 |
|  | 25 | 9 | 3 | 6 | 4 | 3 | 5 | 0 | 3 | 3 |
|  | 12.5 | 9 | 4 | 6 | 3 | 3 | 5 | 4 | 3 | 4 |
|  | 6.25 | 10 | 5 | 5 | 2 | 3 | 3 | 3 | 2 | 2 |
| CH235VH_UCAtk_v2_4A/293i | 50 | 14 | 10 | 13 | 11 | 5 | 6 | 22 | 28 | 17 |
|  | 25 | 11 | 6 | 10 | 6 | 3 | 4 | 13 | 18 | 11 |
|  | 12.5 | 10 | 7 | 9 | 7 | 4 | 6 | 9 | 10 | 7 |
|  | 6.25 | 10 | 5 | 7 | 6 | 3 | 3 | 4 | 7 | 5 |
| CH235VH_I1_v2_4A/293i | 50 | 149 | 217 | 104 | 80 | 57 | 176 | 12 | 80 | 100 |
|  | 25 | 150 | 197 | 110 | 67 | 52 | 171 | 19 | 80 | 99 |
|  | 12.5 | 151 | 167 | 77 | 56 | 40 | 152 | 58 | 81 | 100 |
|  | 6.25 | 175 | 117 | 77 | 46 | 31 | 129 | 61 | 87 | 118 |
| CH235VH_I2_v2_4A/293i | 50 | 73 | 69 | 259 | 101 | 69 | 55 | 444 | 256 | 371 |
|  | 25 | 43 | 36 | 256 | 93 | 49 | 26 | 496 | 228 | 302 |
|  | 12.5 | 34 | 31 | 279 | 85 | 44 | 20 | 617 | 225 | 287 |
|  | 6.25 | 18 | 15 | 204 | 66 | 28 | 12 | 599 | 183 | 207 |
| CH235VH_I3_v2_4A/293i | 50 | 14 | 10 | 18 | 10 | 5 | 6 | 35 | 37 | 17 |
|  | 25 | 10 | 9 | 13 | 7 | 4 | 8 | 33 | 27 | 12 |
|  | 12.5 | 12 | 6 | 12 | 5 | 3 | 3 | 23 | 15 | 7 |
|  | 6.25 | 12 | 3 | 7 | 4 | 2 | 2 | 15 | 9 | 5 |

TABLE 7-continued

Summary of Athena assay results for various other antibodies of the CH235 lineage. Results are expressed as relative luminescence units. Readings <100 are considered negative, results between 100 and 120 are considered "indeterminate" and results >120 are considered positive. CH236, CH239, CH235 IA1 and IA2 are positive for multiple antigens.

| Antibody ID | | SSA | SSB | Sm | RNP | Scl 70 | Jo 1 | dsDNA | Cent B | Histone |
|---|---|---|---|---|---|---|---|---|---|---|
| CH235VH_I4_v2_4A/293i | 50 | 12 | 6 | 12 | 9 | 4 | 5 | 15 | 14 | 13 |
| | 25 | 12 | 4 | 12 | 5 | 2 | 2 | 7 | 10 | 9 |
| | 12.5 | 11 | 3 | 6 | 4 | 2 | 3 | 11 | 5 | 6 |
| | 6.25 | 11 | 5 | 6 | 3 | 2 | 4 | 4 | 5 | 4 |
| Cat-CH106 | 50 | 12 | 3 | 5 | 2 | 3 | 3 | 6 | 2 | 2 |
| | 25 | 8 | 3 | 1 | 3 | 2 | 2 | 3 | 2 | 3 |
| | 12.5 | 11 | 5 | 4 | 2 | 3 | 3 | 5 | 2 | 2 |
| | 6.25 | 10 | 6 | 5 | 1 | 2 | 4 | 7 | 1 | 2 |

TABLE 8

Summary of ELISA cardiolipin assay results for CH557 and various other antibodies. Antibodies were tested at concentrations ranging from 100 ug/ml to 12.5 ug/ml. Results are expressed as optical density at wavelength of 450 nm (OD450). OD450 < 0.2 are negative. Synagis is used as negative control and 4E10 is used as positive control. CH557 did not bind to cardiolipin.

| Antibody | lot | ug/ml | 100 | 50 | 25 | 12.5 |
|---|---|---|---|---|---|---|
| 4 e 10 | | 11.94 | 2.0997 | 2.346 | 1.9027 | 1.6277 |
| synagis | | 1.05 | 0.0424 | 0.0474 | 0.0408 | 0.0408 |
| Ab901754RhK/PEI | ZRJ070 | 3.86 | 0.0382 | 0.0859 | 0.0299 | 0.0394 |
| Ab901754RhKMut58_9 | ZRJ93 | 2.8 | 0.6665 | 0.428 | 0.2898 | 0.1681 |
| AbTr900114147Rh/293i | 226JAH | 7.44 | 0.4615 | 0.2596 | 0.1778 | 0.1018 |
| DH522 | 64RKK | 6.67 | 0.1206 | 0.079 | 0.0613 | 0.0491 |
| DH522UCA_Rh/293i | 362HC | 13.19 | 0.6156 | 0.415 | 0.2179 | 0.1302 |
| DH522_v2Rh/293i | 363HC | 6.93 | 0.3497 | 0.1652 | 0.1081 | 0.0828 |
| DH522I1.2Rh/293i | 372HC | 13.99 | 0.5506 | 0.2738 | 0.183 | 0.1073 |
| CH557_4A/293i | 70RKK | 11.94 | 0.0942 | 0.0761 | 0.0591 | 0.0475 |
| DH542-293i | 014RM | 2.51 | 0.062 | 0.0503 | 0.0525 | 0.0511 |

TABLE 9

Summary of binding of listed antibodies to cardiolipin in ELISA. Antibodies were tested at concentrations ranging from 100 ug/ml to 12.5 ug/ml. Results are expressed as optical density at wavelength of 450 nm (OD450). OD450 < 0.2 are negative. Synagis is used as negative control and 4E10 is used as positive control. The majority of CH235 lineage antibodies, with the exception of CH235_IA3, IA4, CH235 and CH240 (the former has borderline binding), bound to cardiolipin.

| | | 100 | 33.33333 | 11.11111 | 3.703704 | 1.234568 | 0.411523 | 0.137174 | 0.045725 |
|---|---|---|---|---|---|---|---|---|---|
| | synagis | 0.0391 | 0.0375 | 0.0359 | 0.0378 | | | | |
| | 4E10 IgG1 | 2.3179 | 2.2324 | 2.1165 | 1.941 | | | | |
| 105SJA | CH235_4A | 0.1198 | 0.0555 | 0.0423 | 0.0411 | 0.0413 | 0.0377 | 0.0378 | 0.0387 |
| 121SMI | CH236_4A/293i | 0.5104 | 0.1936 | 0.0849 | 0.0524 | 0.0423 | 0.0382 | 0.0425 | 0.0385 |
| 98JAH | CH239_4A/293i | 0.5001 | 0.2554 | 0.1078 | 0.0612 | 0.0476 | 0.0424 | 0.0386 | 0.0405 |
| 96GEH | CH240_4A/293i | 0.194 | 0.0893 | 0.0543 | 0.0434 | 0.0399 | 0.0408 | 0.0444 | 0.0421 |
| 108SJA | CH241 | 0.248 | 0.1061 | 0.0617 | 0.0491 | 0.0405 | 0.0437 | 0.0409 | 0.0384 |
| 132SMI | CH235UA/293i | 0.2337 | 0.1074 | 0.0738 | 0.0504 | 0.0436 | 0.0417 | 0.0395 | 0.0391 |
| 137SMI | DH235VH_UCAtk_v2_4A/293i | 0.5112 | 0.253 | 0.1353 | 0.0658 | 0.0486 | 0.0428 | 0.0415 | 0.0427 |
| 121JAH | DH235VH_I1_v2_4A/293i | 0.5321 | 0.2638 | 0.0955 | 0.0637 | 0.0473 | 0.0409 | 0.0414 | 0.041 |
| 138SMI | DH235VH_I2_v2_4A/293i | 0.9691 | 0.4951 | 0.1929 | 0.0894 | 0.0603 | 0.0488 | 0.0582 | 0.0442 |
| 119JAH | DH235VH_I3_v2_4A/293i | 0.1317 | 0.0743 | 0.0518 | 0.046 | 0.0439 | 0.0412 | 0.0429 | 0.0426 |
| | synagis | 0.0405 | 0.0453 | 0.0414 | 0.0414 | | | | |
| | 4E10 IgG1 | 2.249 | 2.2353 | 2.105 | 1.9205 | | | | |
| 120JAH | DH235VH_I4_v2_4A/293i | 0.1076 | 0.0609 | 0.0475 | 0.0416 | 0.0439 | 0.0399 | 0.0366 | 0.0403 |
| | Cat-CH106 | 0.0437 | 0.0443 | 0.0413 | 0.04 | 0.043 | 0.0404 | 0.0399 | 0.0407 |

Example 6: Antibodies from CH235 Lineage

DH493 (Also Referred as CH493) and DH491 (Also Referred as CH491)

Figure 15A:
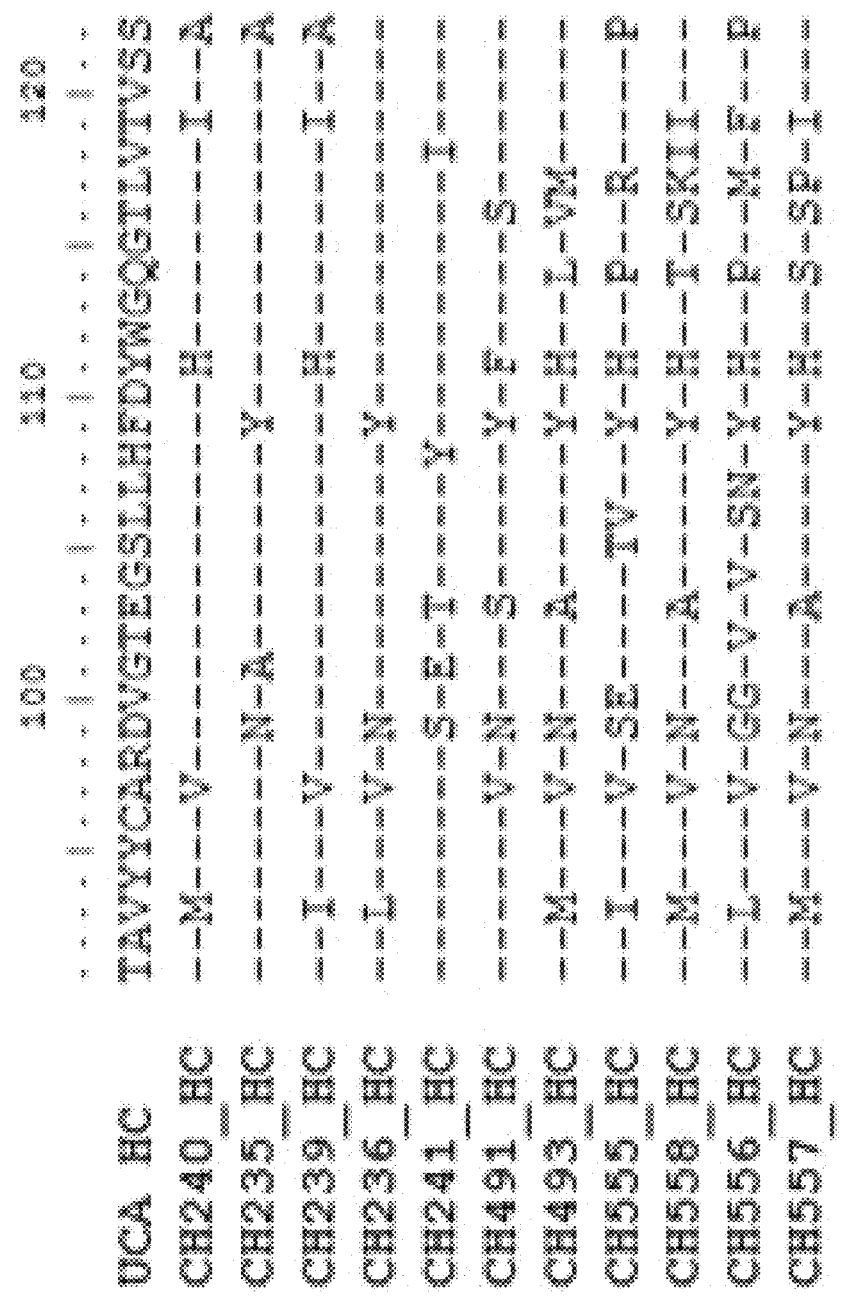
Figure 20:
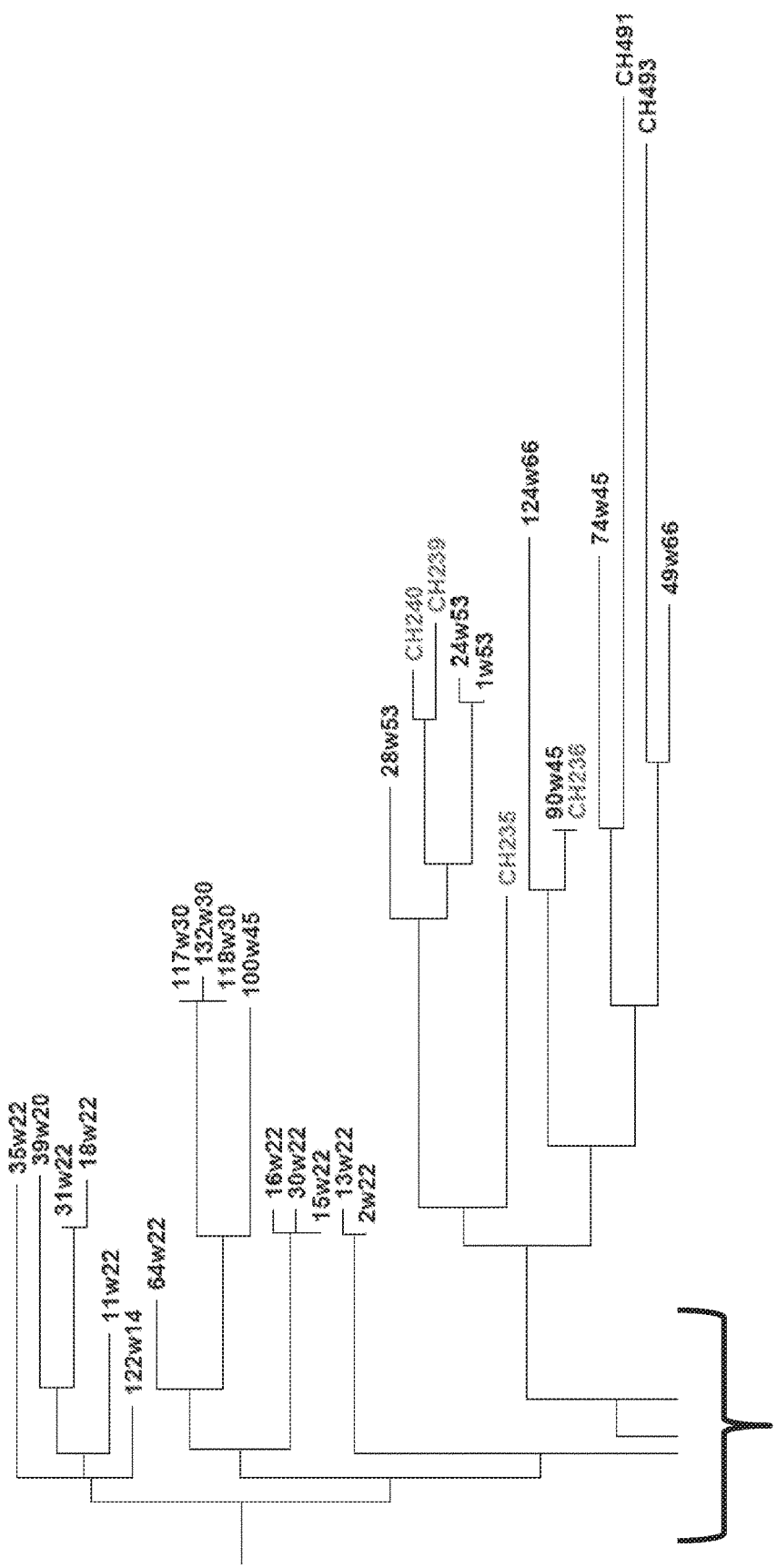
FIG. 20 shows phylogenetic tree of the heavy chains of antibodies CH490, CH491, CH492 and CH493 (see table in FIG. 19). See also Example 6: CH240, CH239, CH235, CH236, CH241 VH chains were identified from cultured memory B cells. The rest of the VH chains were retrieved with deep sequencing.
Figure 20:
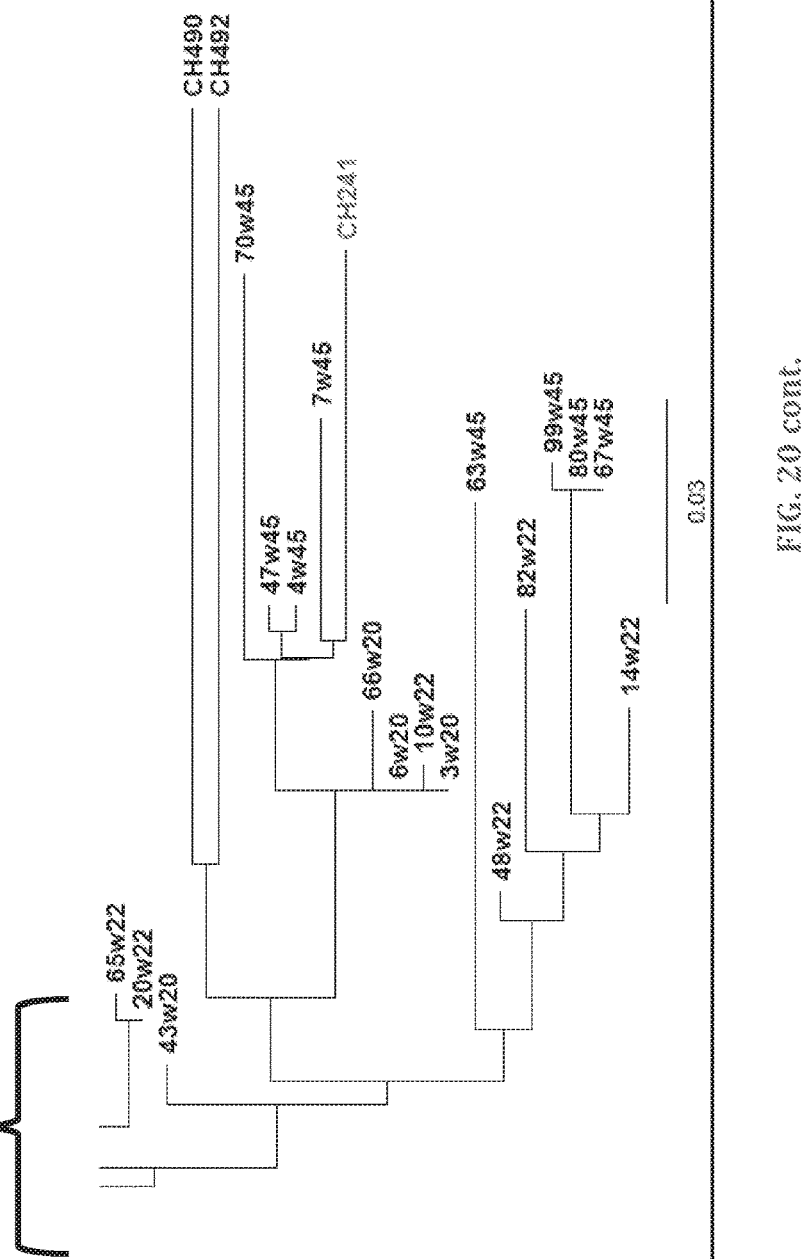

This example describes the design and making of non-naturally occurring CD4bs broad neutralizing HIV-1 antibodies Monoclonal antibody CH493 was designed as follows: the heavy chain VDJ rearrangement was derived from genomic DNA deep sequencing performed on memory B cells isolated from PBMCs of the 703-01-050-5 subject (CHAVI001 protocol) obtained 152 weeks post-infection. Other V-heavy chain VDJ rearrangement sequences were retrieved with this technology from multiple time points. FIG. 20 shows the heavy chain phylogenetic tree including all the sequences retrieved with deep sequencing (in black: all except for CH240, CH239, CH235, CH236, CH241). V-light chains were not identified.

FIG. 20 shows the heavy chain phylogenetic tree including all the sequences retrieved from RNA of cultured memory B cells isolated from PBMCs obtained 41 weeks post-infection (in red: CH240, CH239, CH235, CH236, CH241). V-light chains of these antibodies from cultures were also identified.

Four recombinant non-naturally occurring antibodies were produced using V-heavy VDJ rearrangements identified from deep sequencing and they are called CH490, CH491, CH492 and CH493. These V-heavy sequences were chosen because they are the most mutated.

The V-heavy chains were paired with the V-light chains of the antibodies identified from memory B cell cultures that are closest in the phylogenetic tree shown above. Therefore, CH491 and CH493 heavy chains were paired with CH236 light chain, while CH490 and CH492 heavy chains were paired with the CH241 light chain, CH235 antibodies from week 41 are characterized by their inability to bind and neutralize CH505.TF envelope mutants with specific point mutations in the D loop (Gao, Bonsignori, Liao et al. Cell 158, 481-491, Jul. 31, 2014, see also U.S. Provisional Application No. 62/027,427 filed Jul. 22, 2014, and U.S. Provisional Application No. 61/972,531 filed Mar. 31, 2014).

Figure 21:
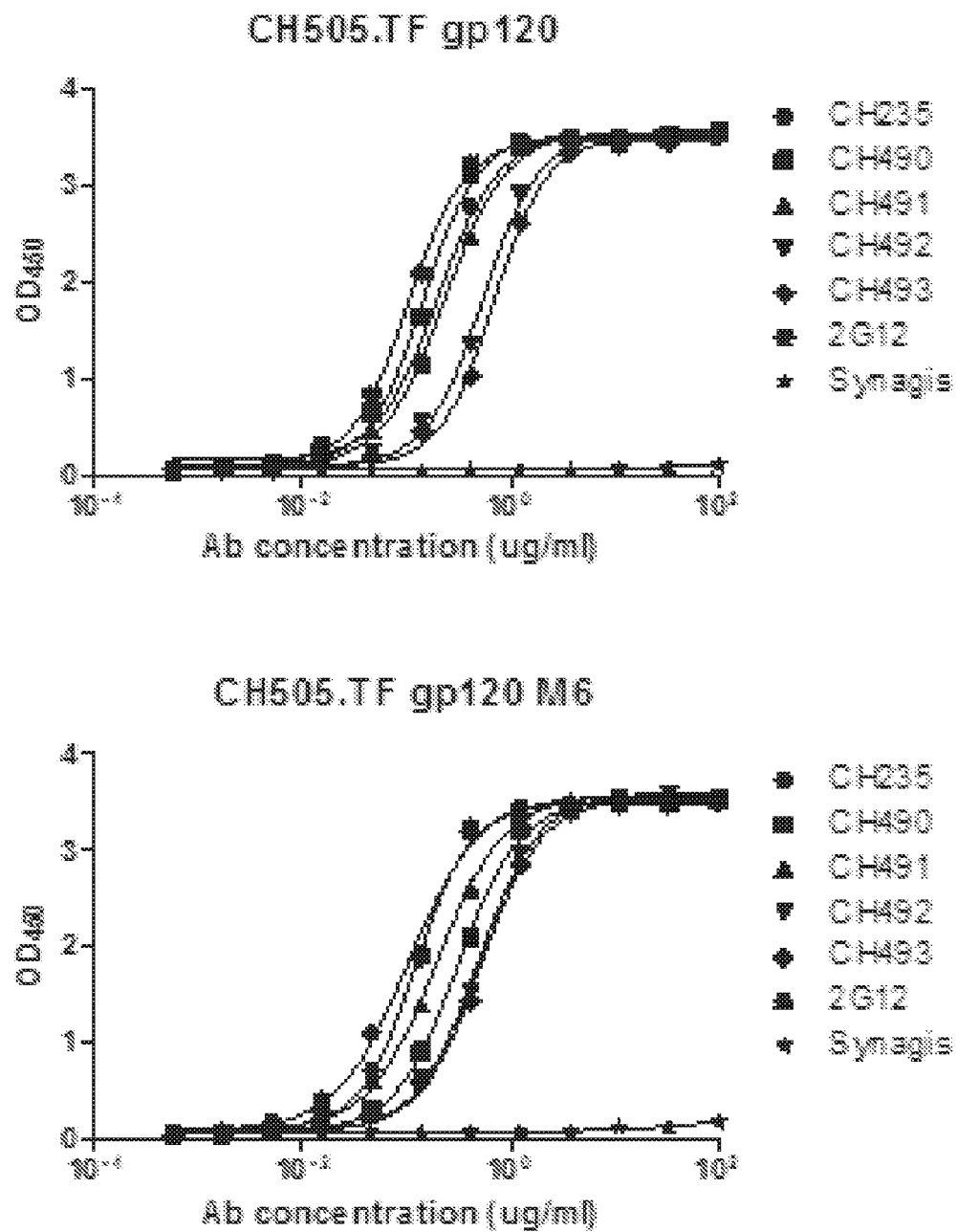
FIG. 21 shows ELISA binding of CH490, CH491, CH492 and CH493 antibodies to various antigens as listed in the figure.
Figure 21:
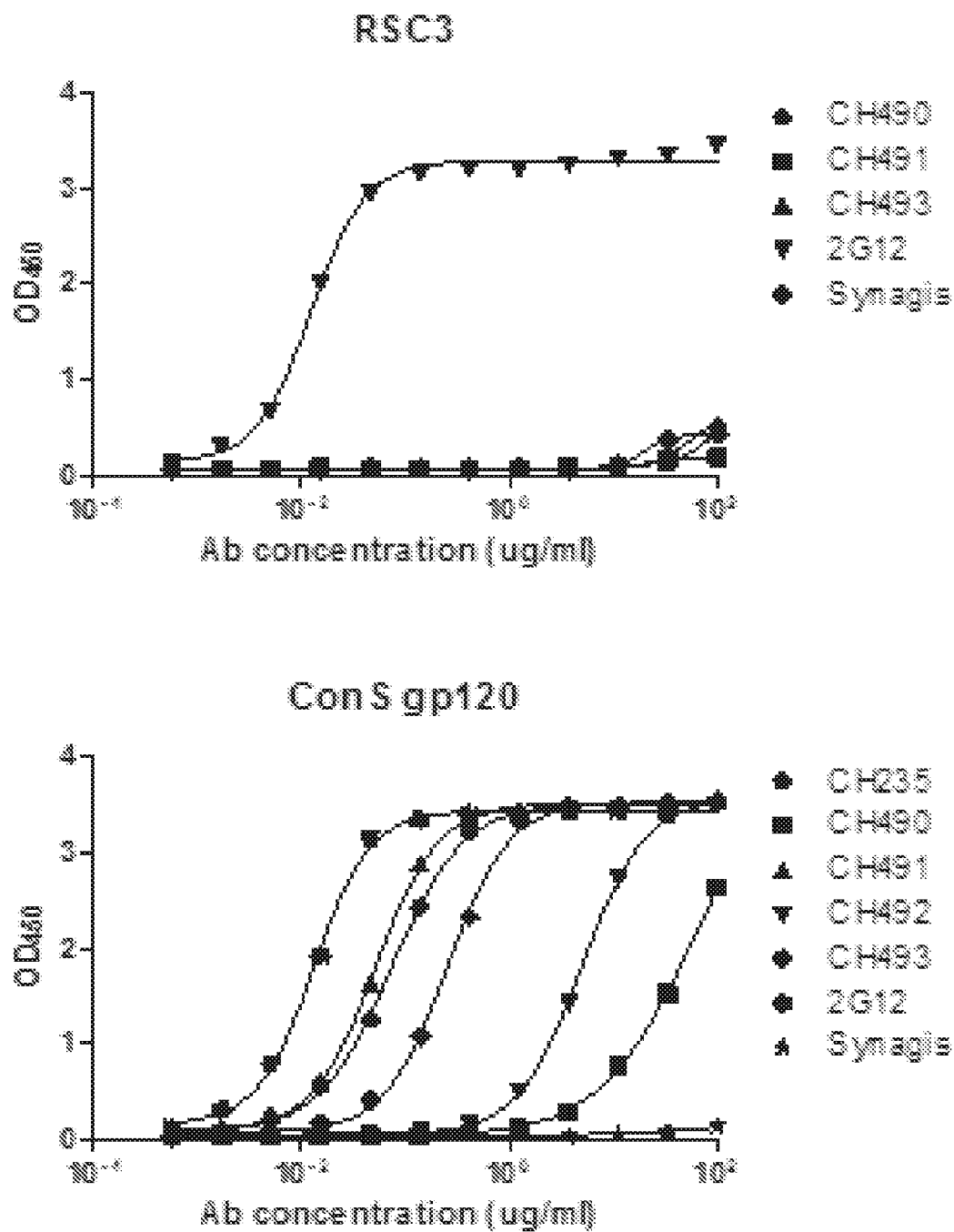
Figure 21:
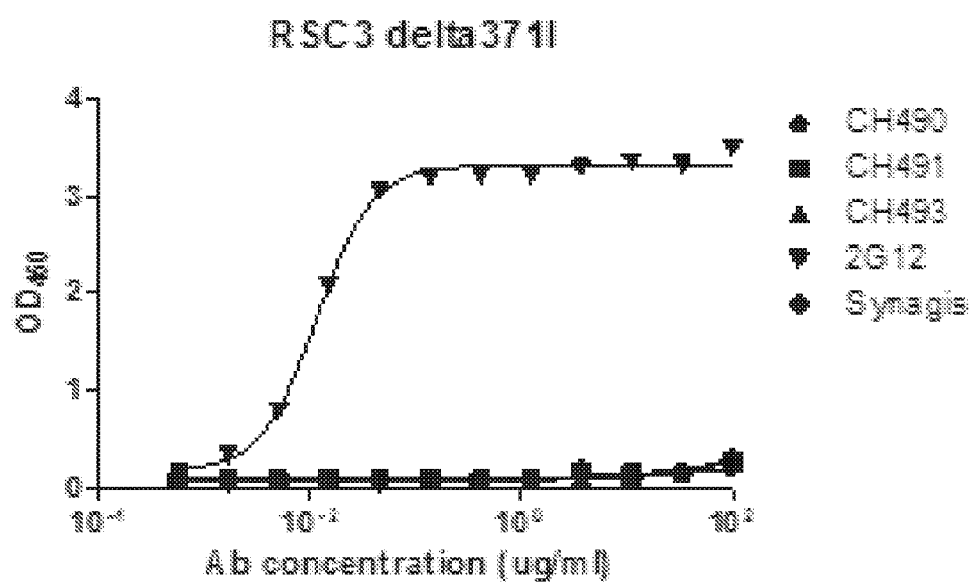

FIG. 21 shows that CH493 restores almost completely the ability to bind the mutants not recognized by the early members of the lineage, indicating that this antibody is not constrained by the amino acid makeup of the D loop as tightly as the naturally occurring CH235 early lineage antibodies. CH493 still retained differential binding to the CH505.TF gp120 delta 371I mutant. Binding dependence to I371 is a hallmark of neutralizing CD4bs antibodies.

Most notably, CH493 neutralized 20 of 24 tier-2 HIV-1 viruses (83%) in a multiclade virus panel optimized to represent diversity among globally circulating viruses. Naturally occurring antibodies in the same lineage neutralized only 25% of the viruses in the same panel and other engineered antibodies neutralized max 46% (FIG. 22).

CH235, CH236, CH239, CH240 and CH241 are all Abs with natural pairs VH and VL from week 41 of infection of CH505 individual. CH241 is the most mutated at ~11%. CH490, CH491, CH492 and CH493 are antibodies which comprise VH chains identified by deep sequencing and are near 20% mutated. These VH chains were paired with VL chains from the closest natural pair antibodies. So in the natural tree, CH241 is the most mutated from week 41 and it hit 38% of isolates.

For Abs CH491 and CH493, the VH chains were complemented with the VL of CH236. For antibodies CH490 and CH492 that were complemented with the VL of CH241. CH491 neutralized 46% of isolates and CH493 neutralized 83%.

In summary these antibodies were designed to include heavy chains form 454 sequencing and the heavy chains were paired with VL from observed antibodies:

CH490 and CH492 VH from 454 were paired with CH241 VL.

CH491 and CH493 VH from 454 were paired with CH236 VL. Pairing was done with the observed VL that was closer to the 454 sequence in the phylogenetic tree.

VH chains source: CH490 is from week 66; CH491 and CH492 are from week 100; CH493 is from week 152. The heavy chains were selected because were the most mutated ones.

Example 7: Antibodies from CH235 Lineage

Antibodies CH555, CH556, CH557 and CH558

CH505 transmitted/founder (CH505.TF) gp120 Env-specific memory B cells were isolated from 20 million PBMCs using fluorescent-activated single cell sorting (FACS) collected from chronically HIV-1 infected African CHAVI subject 703-01-050-5 264 and 323 weeks post-infection (10 million PBMCs/timepoint). Viable memory B cells were defined as AquaVital Dye neg, CD16neg, CD14neg, CD3neg, CD19pos, IgDneg cells. Sorted cells were cultured overnight in RPMI+10% FCS supplemented with 2.5 ug/mL ODN2006, 2.5 ug/mL CHK2-inhibitor, 50 ng/mL rHu IL-21 and 1:1 EBV-containing supernatants in a 96-well plates well containing 5000 CD40L-expressing MS40L feeder cells. Cells were then plated at limiting dilution in 96-well plates containing feeder cells, 2.5 ug/mL ODN2006, 2.5 ug/mL CHK2-inhibitor and 50 ng/mL rHu IL-21, and cultured for 14 days, with medium refresh at days 3, 7 and 10. Culture supernatants were collected at day 14 and tested for neutralization of CH505.TF virus and binding to CH505.TF gp120, CH505.TF gp120 delta371I, RSC3 protein, RSC3 protein delta371I and CH505.TF mutant envelopes M6, M8 and M20 (described in Gao, Bonsignori, Liao et al. Cell 2014. Jul. 31; 158(3):481-91). From selected positive cultures, recombinant monoclonal antibodies were produced as previously described (Bonsignori et al. J Virol. 2011. October; 85(19):9998-10009). Monoclonal antibodies CH557 was identified from a culture that neutralized 91% infectivity of CH505.TF virus, differentially bound to CH505.TF gp120 Env and CH505.TF gp120 delta371I Env, bound to M6, weakly bound to M8 but did not bind to M20 CH505.TF mutant gp120s. CH557 was identified from memory B cells collected 323 weeks post-infection. CH557 is a member of the previously described CH235 clonal lineage (Gao, Bonsignori, Liao et al. Cell 2014. Jul. 31; 158(3):481-91). From the same experiment we also identified monoclonal antibodies CH555, CH556 and CH558—all members of the CH235 clonal lineage. All monoclonal antibodies but CH555, which was identified from memory B cells collected 236 weeks post-infection, are from week 323 post-infection.

Example 8: Maturation Pathway from Germline to Broad HIV-1 Neutralizer of a CD4-Mimic Antibody See Bonsignori et al. Cell 165, 1-15, Apr. 7, 2016, published on-line Mar. 3, 2016, the contents of which are hereby incorporated by reference in its entirety. Antibodies with ontogenies from $V_H1$-2 or $V_H1$-46—germline genes dominate the broadly neutralizing response against the CD4-binding site (CD4bs) on HIV-1. Here we define with longitudinal sampling from time-of-infection the development of a $V_H1$-46-derived antibody lineage that matured to neutralize 90% of HIV-1 isolates. Structures of lineage antibodies CH235 (week 41 from time-of-infection, 18% breadth), CH235.9 (week 152, 77%) and CH235.12 (week 323, 90%) demonstrated the maturing epitope to focus on the conformationally invariant portion of the CD4bs. Similarities between CH235 lineage and five unrelated CD4bs lineages in epitope focusing, length-of-time to develop breadth, and extraordinary levels of somatic hypermutation suggested commonalities in maturation among all CD4bs antibodies. Fortunately, the required CH235-lineage hypermutation appeared substantially guided by the intrinsic mutability of the $V_H1$-46 gene, which closely resembled $V_H1$-2. The CH235-lineage findings were integrated with a second broadly neutralizing lineage and HIV-1 co-evolution to suggest a vaccination strategy for inducing both lineages.

Introduction

Understanding the pathways and mechanisms of broadly neutralizing antibody (bnAb) induction is a critical goal of HIV-1 vaccine development (Bonsignori et al., 2012; Haynes, 2015; Haynes and Bradley, 2015; Haynes et al., 2012; Mascola and Haynes, 2013). In chronic HIV-1 infections, breadth of plasma neutralization follows a uniform distribution and broad neutralization arises in ~50% of individuals after 5 years or more of infection (Hraber et al., 2014). The delayed appearance of bnAbs suggests roadblocks to their development, and one vaccine approach is to decipher these roadblocks and devise strategies to overcome them. It is possible that—because of the high diversity of antibodies resulting from recombination and somatic hypermutation (SHM)—different bnAb lineages may have different developmental pathways and roadblocks. However, for the CD4-binding site (CD4bs), a population-level analysis on 14 donors indicated only two general types of CD4bs bnAbs: $V_H$-gene restricted and CDR H3-dominated (Zhou et al., 2015).

The $V_H$-gene restricted classes arise from two highly similar $V_H$-genes: $V_H$1-2 and $V_H$1-46 (Scheid et al., 2011; Wu et al., 2011). $V_H$1-2*02 and $V_H$1-46*01 share 93.4% (269/288) nucleotide sequence identity. Both classes give rise to antibodies that recognize the CD4bs via $V_H$ structural mimicry of the immunoglobulin-like N-terminal domain of CD4 (Zhou et al., 2010; Zhou et al., 2015). For the $V_H$1-2 gene-derived antibodies, analysis of their ontogeny suggests two roadblocks based on: (i) a requirement for high levels of SHM (Klein et al., 2013; Scheid et al., 2009; Scheid et al., 2011; Wu et al., 2010), and (ii) weak binding of the inferred unmutated common ancestor (UCA) to gp120 (Jardine et al., 2013; McGuire et al., 2013; Scheid et al., 2011; Wu et al., 2011; Zhou et al., 2010; Zhou et al., 2015), although a definitive analysis from time-of-infection had not yet provided detail. In addition, several of the CD4bs bnAbs are autoreactive with ubiquitinase enzymes (Bonsignori et al., 2014; Liao et al., 2013; Liu et al., 2015).

Structure-based design of UCA-interacting immunogens has recently demonstrated a means to overcome this second roadblock, with priming of $V_H$1-2 bnAb lineages in knock-in mice (Dosenovic et al., 2015; Jardine et al., 2015). However, the maturation of primed $V_H$1-2 CD4bs B cell lineages to broad neutralization as well as the mechanism for the development of breadth remain unresolved.

For the $V_H$1-46-derived antibodies, far less is known. Two chronically HIV-infected individuals, RU1 and RU8, have developed $V_H$1-46-derived bnAbs, 1B2530 and 8ANC131 (Scheid et al., 2011). An African individual (donor CH505) was recently described who, over time, developed a CD4bs bnAb lineage (the CH103 lineage) that recognized the CD4 supersite through a CDR H3-dominated mode of interaction (Liao et al., 2013). Analysis of the co-evolution between virus and CH103 lineage demonstrated a second B cell lineage (the CH235 lineage) that cooperated by selection of escape mutants from the CH235 lineage that drove the CH103 bnAb lineage (Gao et al., 2014). Described herein is the finding that the CH235 lineage itself progressed to bnAb over 5 years of affinity maturation. Described herein are sequences of the CH235 lineage that were identified through longitudinal samples of 17 time points spanning weeks (wks) 6-323 post infection, assessment of the neutralization breadth of sequential lineage members on a panel of ~200 diverse isolates, and determination of Env-complexed crystal and EM structures for lineage members. The conformity (i.e. the level of shared mutation positions and identical sequence mutations) of CH235 lineage development is analyzed relative to other $V_H$ gene-specific bnAb lineages in other donors, as well as the co-evolution of virus and CH235 lineage. Despite an early near-optimal binding orientation, the CH235 lineage required over 20% SHM to reach 90% neutralization breadth. The results described herein provide insight into the difficulties in focusing recognition to the conserved site of HIV-1 vulnerability, and suggest that CD4bs-directed antibodies, whether $V_H$-gene restricted or CDR H3-dominated, face similar obstacles in development. For $V_H$1-46- and $V_H$1-2-derived CD4-mimic antibodies, the unique genetic mutability inherent in each of these two $V_H$-germline genes helps to direct maturation, potentially providing an explanation for the prevalence of effective CD4bs antibodies derived from these two germline genes.

Results

Sequencing of B Cell Antibody Gene Rearrangements in Longitudinal Samples.

Figure 29A:
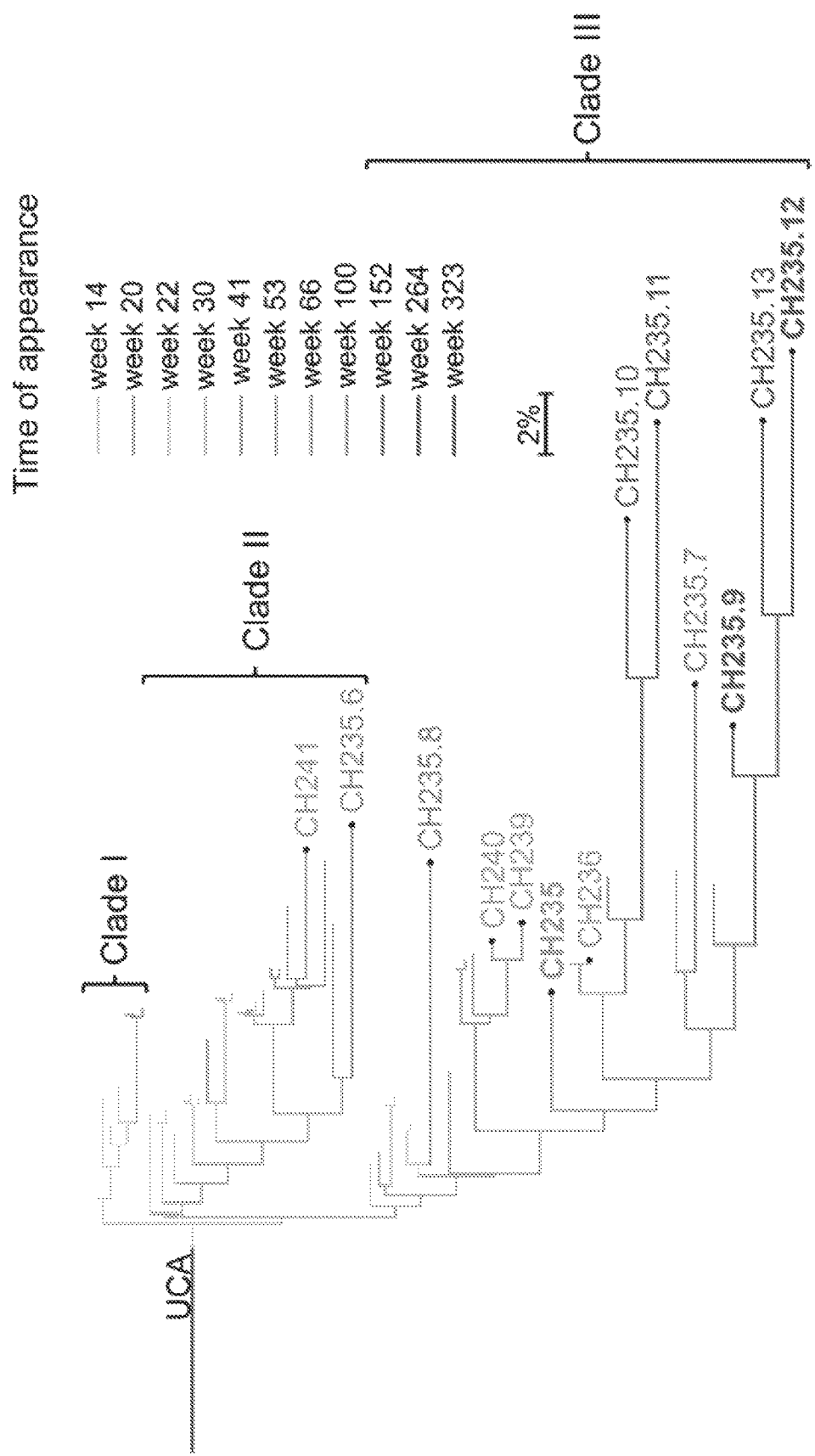
FIGS. 29A-29B show CH235 Lineage, with Time of Appearance and Neutralization by Select Members. (A) Phylogram of CH235 lineage. Phylogenetic tree is colored by first time (wk post-infection) from which sequences were obtained. Key members of the CH235 lineage are labeled. CH235.6, CH235.7, CH235.8 and CH235.9 $V_H$ were complemented with full heavy chain gene regions and paired with the $V_L$ from the closest natural antibody. (B) Neutralization dendrograms display single mAb neutralization of a genetically diverse panel of 199 HIV-1 isolates. Coloration is by $IC_{50}$. See also FIGS. 36A-B, 40C, and 41.
Figure 36A:
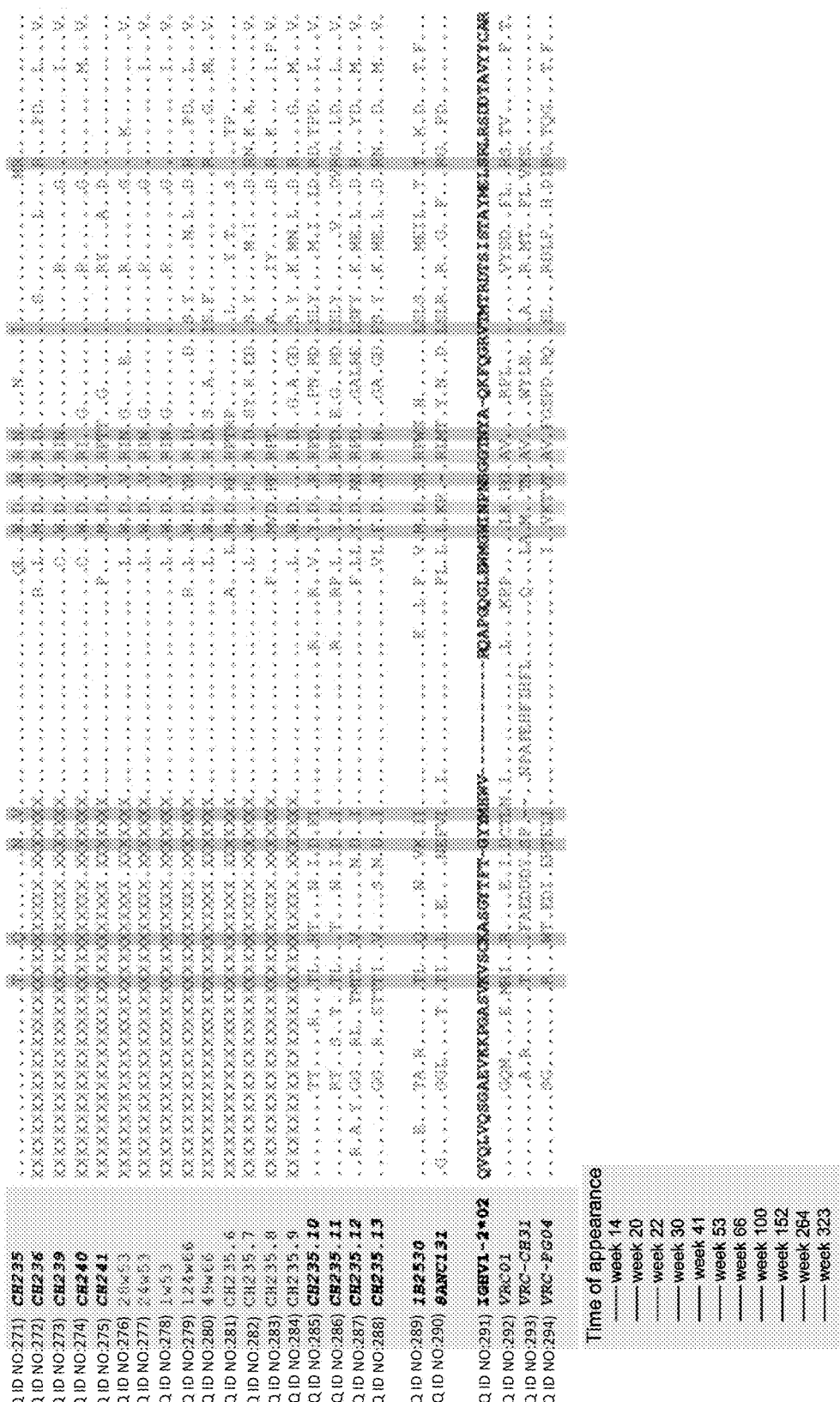
FIGS. 36A-36B show CH235 Lineage: Sequences and Neutralization Fingerprint Dendrogram, Related to FIG. 29.

To understand the maturation of the cooperating CH235 lineage in donor CH505, we sought to identify sequences of lineage members at 17 time points, spanning wks 6 to 323 from time of infection. First it was asked when we could detect members of the CH235 lineage. Next-generation sequencing (NGS) of antibody heavy chain gene rearrangements amplified from genomic DNA template of blood mononuclear cells from wk 6 to 152 (15 time points) identified a total of 479,028 unique, non-duplicated V-heavy sequences. The first V-heavy sequences belonging to the CH235 B cell lineage were found at wk 14, and additional CH235 lineage members were found at all subsequent time points. Only unique sequences in the CH235 lineage were further investigated and they were assigned to the earliest time-point (time-of-appearance) in which they were identified. Four V-heavy sequences were paired with the closest $V_L$ from identified antibodies and produced as recombinant monoclonal antibodies (mAbs) (CH235.6 through CH235.9). From cultured memory B cells collected 41 wks post-transmission we had previously identified five members of the CH235 lineage (CH235, CH236, CH239, CH240 and CH241) (Gao et al., 2014) and we have now identified four additional members with natural $V_H$ and $V_L$ pairing from cultured memory B cells collected at wks 264 and 323 post-transmission: CH235.10 through CH235.13 (FIG. 29A, FIG. 36A and FIG. 40C). CH235 lineage antibodies represented 0.018% of the total memory B cell repertoire and 0.5% of the CH505 TF gp120-specific memory B cell population.

The CH235 lineage could be separated into three clades (clade I, II and III). Clade I showed a number of early lineage members, but no additional clade I sequences were observed after wk 30; clade II showed further development and included members CH241 (wk 41) and CH235.6 (wk 66), but no additional sequences were observed after wk 66; clade III developed through wk 323 and included antibodies CH235 (wk 41), CH235.9 (wk 152), and CH235.12 (wk 323) (FIG. 29A).

CH235 Lineage HIV-1 Neutralization.

Figure 29B:
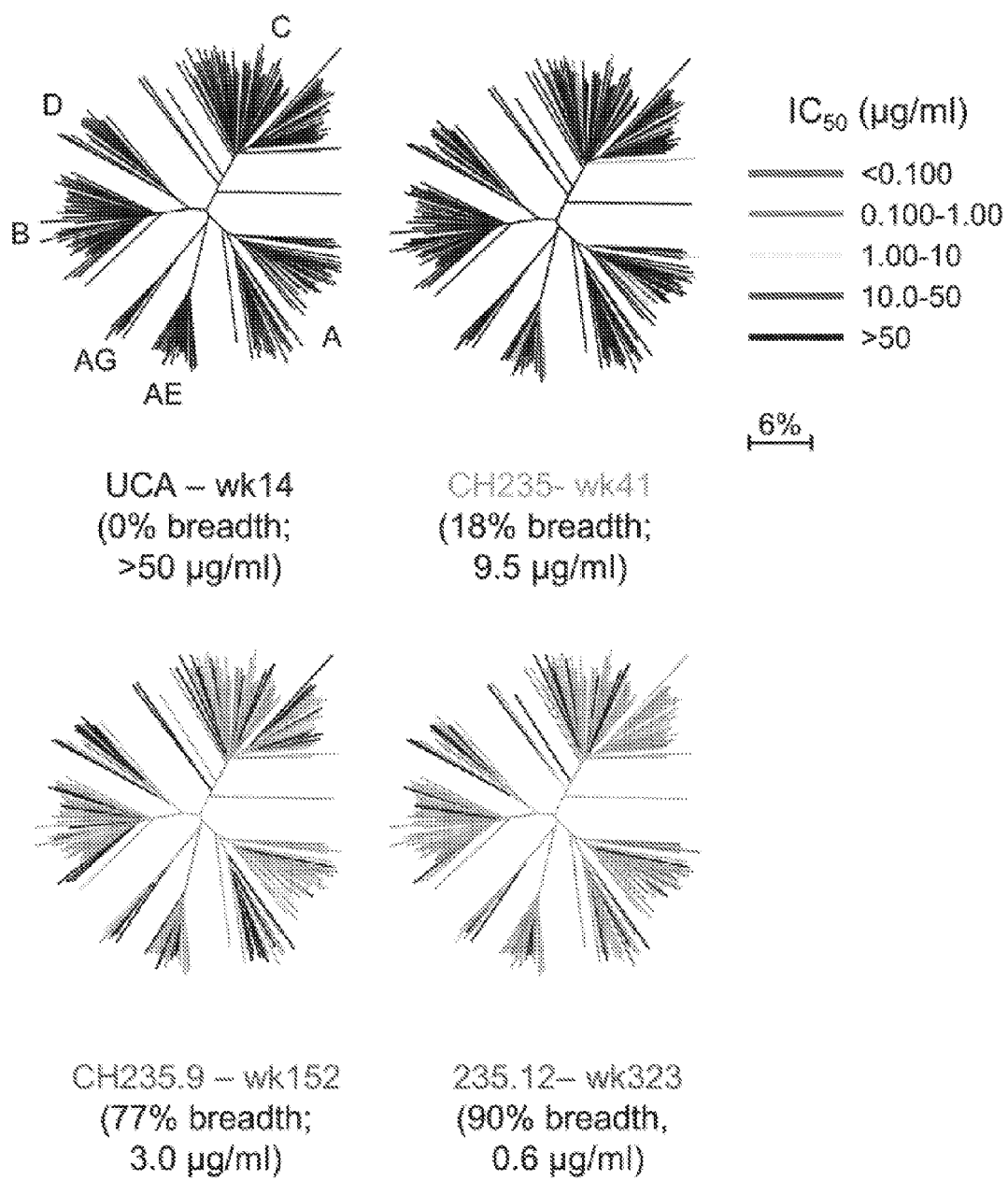

To characterize the development of neutralization breadth in the CH235 lineage, antibodies in clade III were assessed for their ability to neutralize diverse HIV-1 isolates in a 199-isolate panel (FIG. 29B and FIG. 41). No isolates were neutralized by the unmutated common ancestor (UCA), whereas 18% of the viruses were neutralized by CH235 at wk 41. By wk 152, CH235.9 neutralized 77% of viruses, although with a relatively weak potency of 3 µg/ml. By wk 323, however, CH235.12 was able to neutralize 90% of viruses, and the neutralization 50% inhibitory concentration ($IC_{50}$) potency increased by 5-fold to 0.6 μg/ml.

Figure 36B:
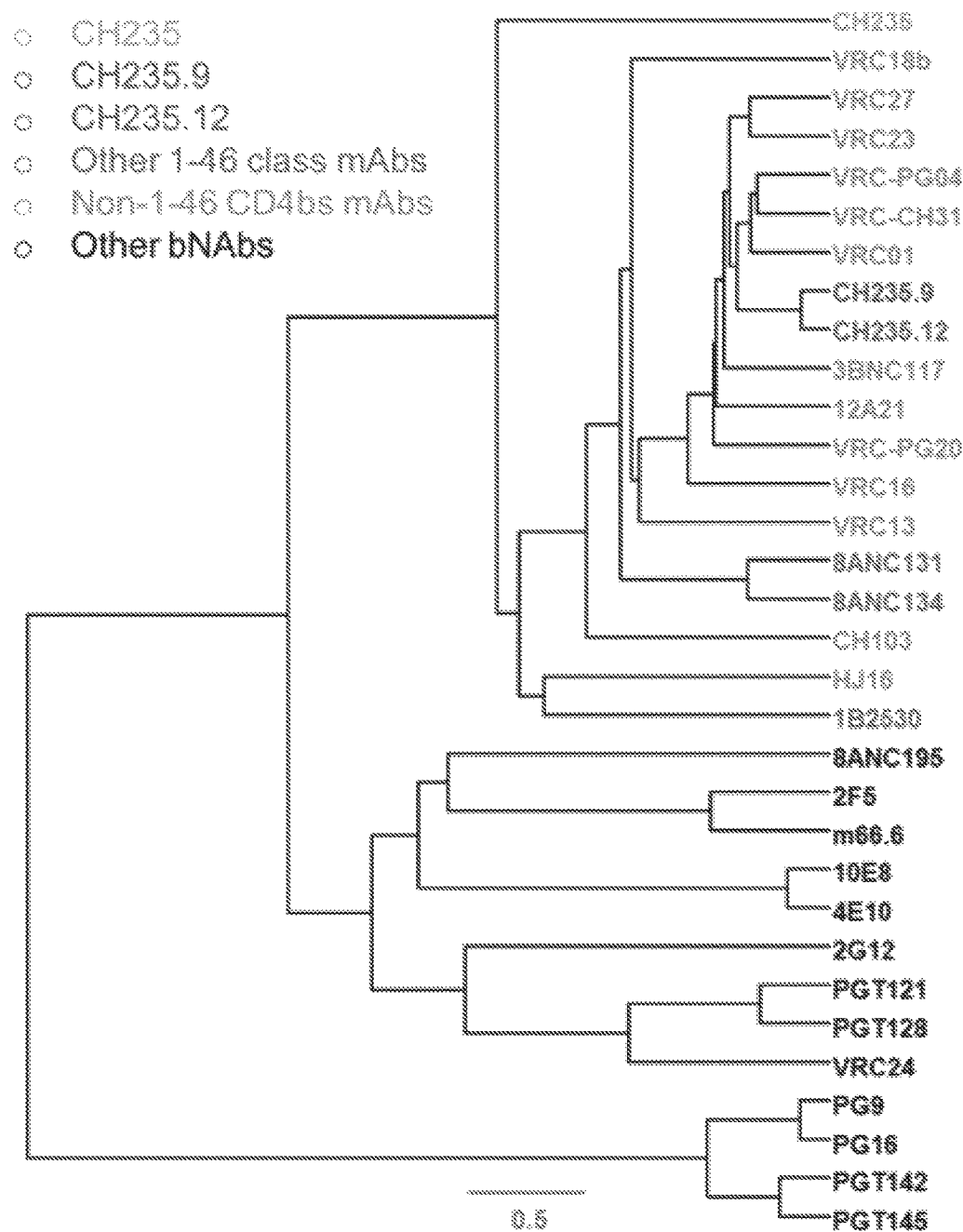
Figure 37B:
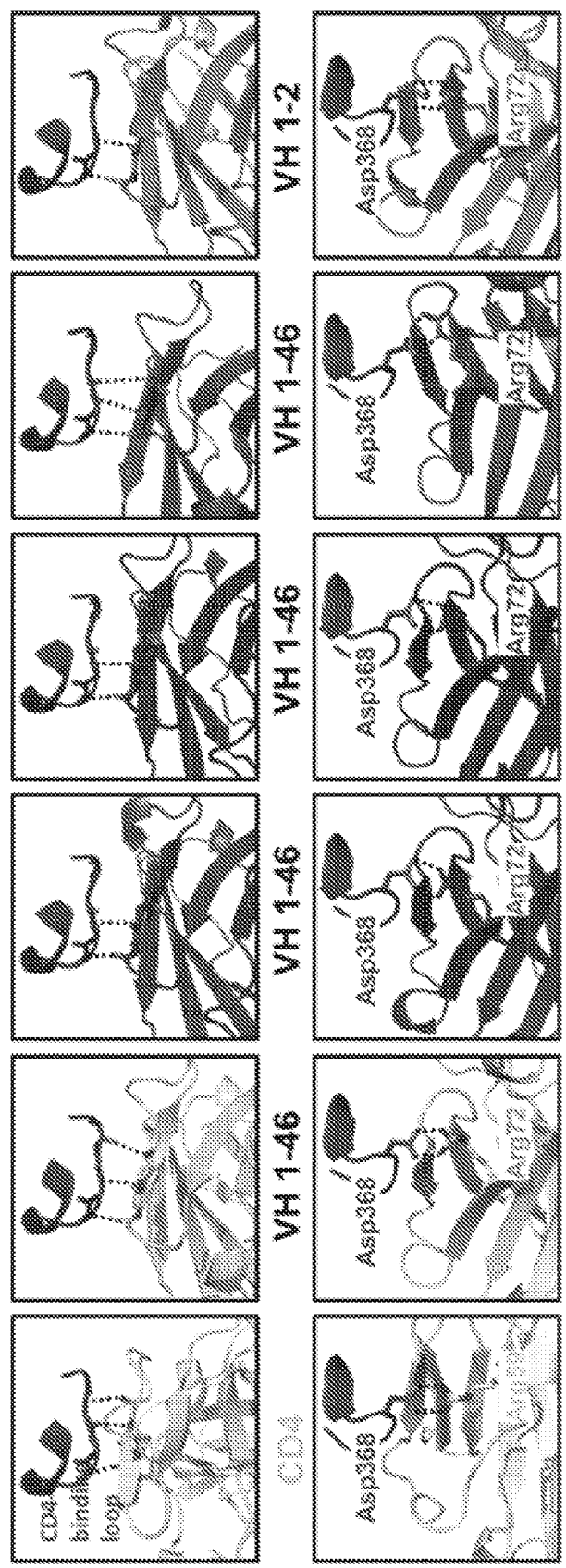
Figure 37D:
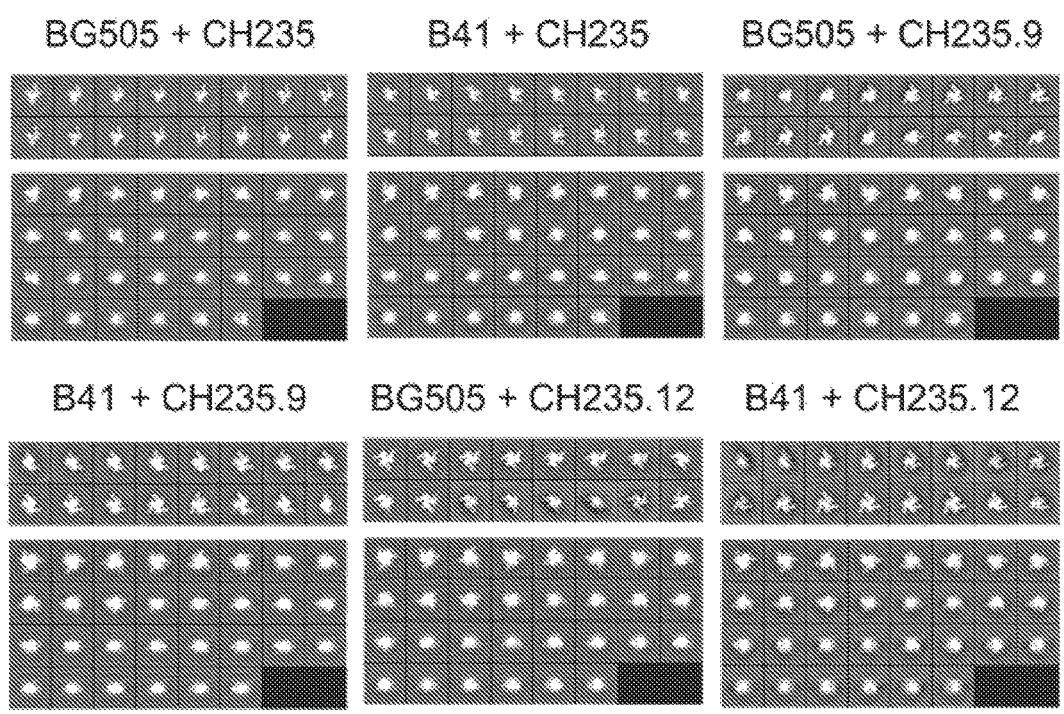
Figure 37E:
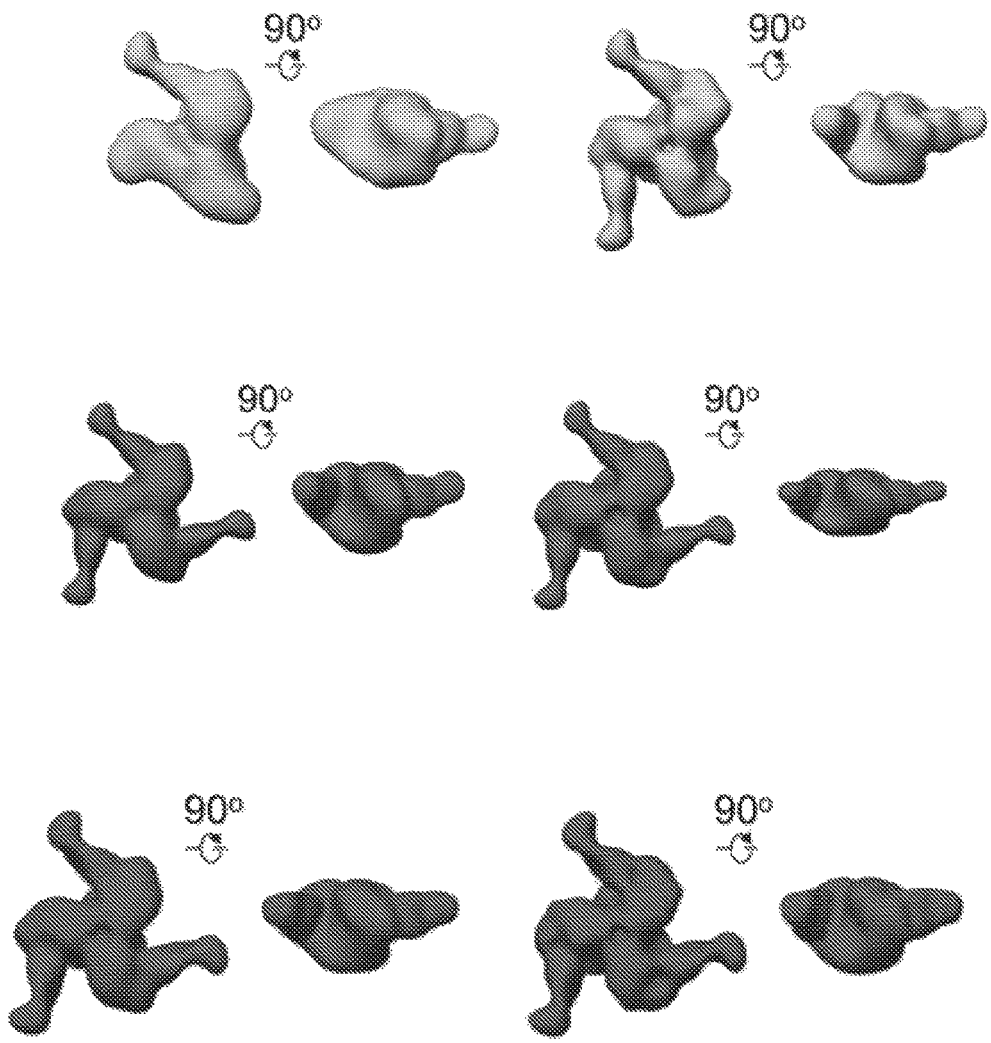
Figure 37F:
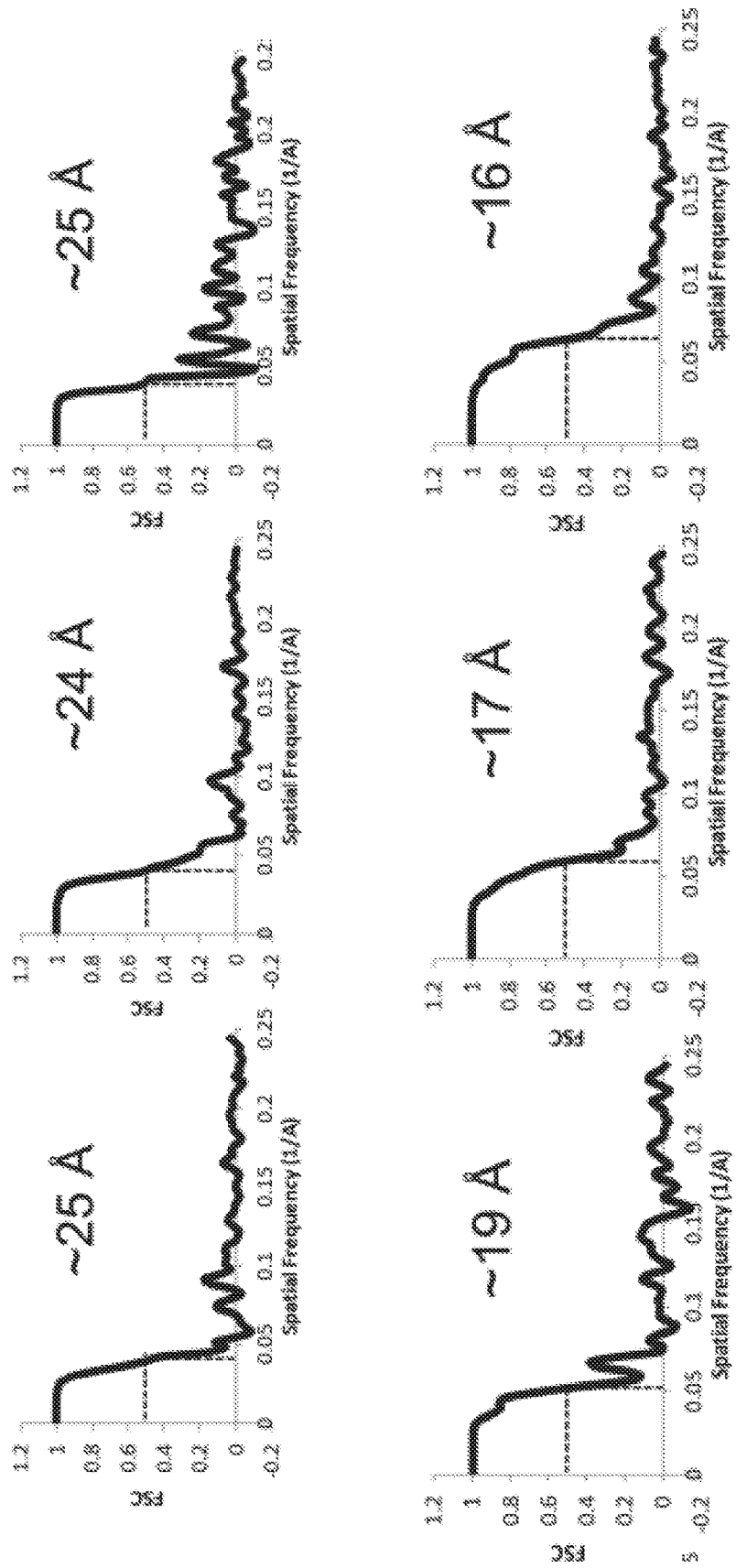

Next the heterologous neutralization pattern of these antibodies were analyzed to understand their development of broad neutralization (FIG. 36B) (Georgiev et al., 2013). CH235 lineage members and previously identified HIV-1 bnAbs were clustered based on heterologous neutralization activity. CH235 neutralization activity was more similar to CD4bs bnAbs than to bnAbs with other epitope specificities. While the CH235 neutralization profile was the most divergent from other CD4bs bnAbs, CH235.9 and CH235.12 were much more similar to other CD4bs bnAbs and each other. Interestingly, despite $V_H$1-46 usage, the CH235.9 and CH235.12 neutralizing profile was more similar to that of $V_H$1-2-derived antibodies, such as VRC01, than $V_H$1-46-derived antibodies, such as 8ANC131 (FIG. 36B).

Crystal Structures of CH235-lineage Members with HIV-1 gp120.

To provide structural insight into the recognition and maturation of the CH235 lineage, the antigen-binding fragments (Fabs) of antibodies CH235 (wk 41 from time of infection, 18% breadth), CH235.9 (wk 152, 77%) and CH235.12 (wk 323, 90%), were prepared and co-crystallized, solved and refined these in complex with the gp120 core of HIV-1 isolate strain (93TH057) (FIG. 30, FIG. 42). We mapped the location of residues altered during SHM and observed changes throughout the variable domain (FIG. 30A).

Comparison of the orientation of the $V_H$ of CH235 in Env binding with that of CD4, VRC01 and 8ANC131 (Scheid et al., 2011) showed that the CH235 $V_H$ domain mimicked CD4 in Env binding and was highly similar to the $V_H$ orientation and structure of the VRC01 and 8ANC131 $V_H$ chains: in particular, the $V_H$1-46 of CH235 preserved key contacts mediated by the CDR H2 loop for the CD4 binding loop and for the gp120 D368 (FIG. 37A,B).

Analysis of the angle of recognition for the CH235 lineage indicated little change during maturation, with CH235, CH235.9 and CH235.12 all clustering within the larger VRC01-class of antibodies. Interestingly, other $V_H$1-46 antibodies clustered differently, with antibody 1B2530 from HIV-1-positive donor RU1 at a highly similar angle and 1.5 Å translated, and antibodies 8ANC131 and 8ANC134 from HIV-1-positive donor RU8 occupying a cluster about 55 degrees and 3.5 Å translated related to the CD4 (FIG. 37C).

These results suggest that the gp120-antibody orientation was determined early in bnAb lineage ontogeny, with further maturation maintaining the same general orientation. Overall, the structures of CH235 lineage members with HIV-1 gp120 Env revealed CD4 mimicry. While the $V_H$ gene usage classifies the CH235 lineage within the $V_H$1-46-derived 8ANC131 bnAb class, it is both functionally and structurally closer to the VRC01 class (Zhou et al., 2015).

Negative Stain EM of CH235-lineage Members with Trimeric HIV-1 Env.

To visualize the recognition of the CH235 lineage in the context of the HIV-1 Env trimer, negative stain EM was used to determine 3D-reconstructions of Fabs CH235, CH235.9 and CH235.12 bound to trimeric BG505 and B41 HIV-1 Env glycoproteins (FIG. 30B)(Pugach et al., 2015; Sanders et al., 2013). Notably, the stoichiometry increased with antibody maturation, with CH235 (8% $V_H$ mutation) binding with a stoichiometry of 1:1 (BG505; FIG. 30B, top, FIG. 37D-F) or 2:1 (B41; FIG. 30B, bottom, FIG. 37D-F) Fabs per trimer and CH235.9 and CH235.12 (19% and 25% $V_H$ mutation, respectively) binding with a 3:1 Fab to trimer ratio (FIG. 30B). Next the orientation and stoichiometry of CH235.12 Fab was compared with that of CH103, a CDR H3-dependent CD4bs bnAb identified from the same subject (Liao et al., 2013). EM analysis of either CH235.12 or CH103 Fab in complex with BG505 SOSIP.664 revealed structural differences between the CDR H3-dominated CH103 class bnAb and the 8ANC131-class CH235.12 bnAb and, in accordance with crystallographic results, the angle of approach of CH235 was similar to that of VRC01 and other CD4 mimicking bnAbs (FIG. 37G).

Despite the CD4 mimicry by CH235, the trimer remained in a closed conformation when the CH235 lineage members were bound. However, the EM-derived model of CH103 in complex with BG505 revealed that CH103 either bound to or induced a more open version of the trimer. This conformation represents an intermediate state between the closed, compact trimer in complex with CH235 or VRC01, and the CD4-induced open model in complex with soluble CD4 or 17b Fab (FIG. 37G). Similar to more mature CH235 lineage bnAb Fabs, bnAb CH103 bound to BG505 with a stoichiometry of 3 Fabs per trimer. (FIG. 37G).

Maturation Focuses CH235 Lineage Recognition to a Conserved Site of CD4 Vulnerability.

To gain insight into the structural consequences of maturation, the epitope of CH235 lineage members was mapped relative to the conformationally invariant CD4 supersite of vulnerability (Zhou et al., 2015). When the CH235 footprint was mapped on gp120, we observed portions of the CH235-binding surface on gp120 to be outside of the CD4 supersite of vulnerability (FIG. 30C, left). This surface was reduced in CH235.9 and CH235.12 structures, especially on variable loop V5. Recognition by the CH235.12 antibody concentrated almost entirely on the CD4 supersite of vulnerability, with little interactions with the inner domain or variable loop V5; there was, however, a large remaining interaction with the conserved loop D region (FIG. 30C, middle and right).

Figure 30D:
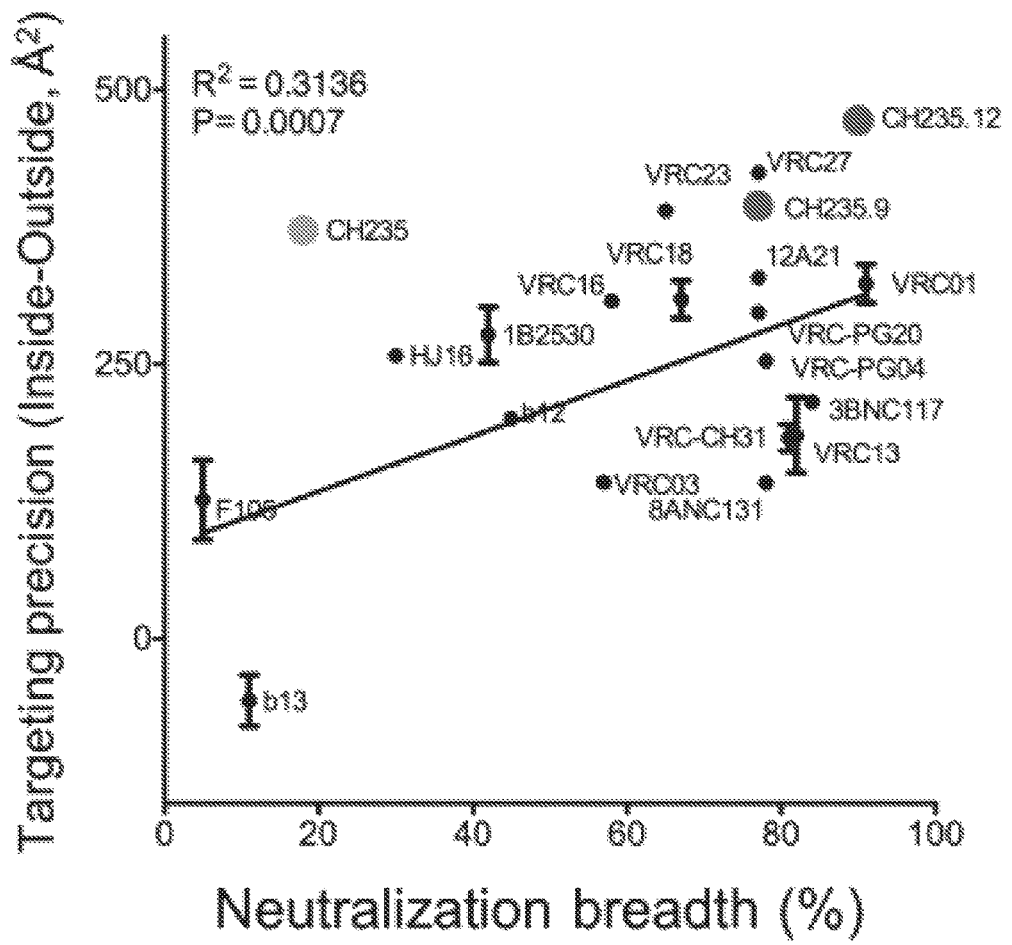
Figure 30E:
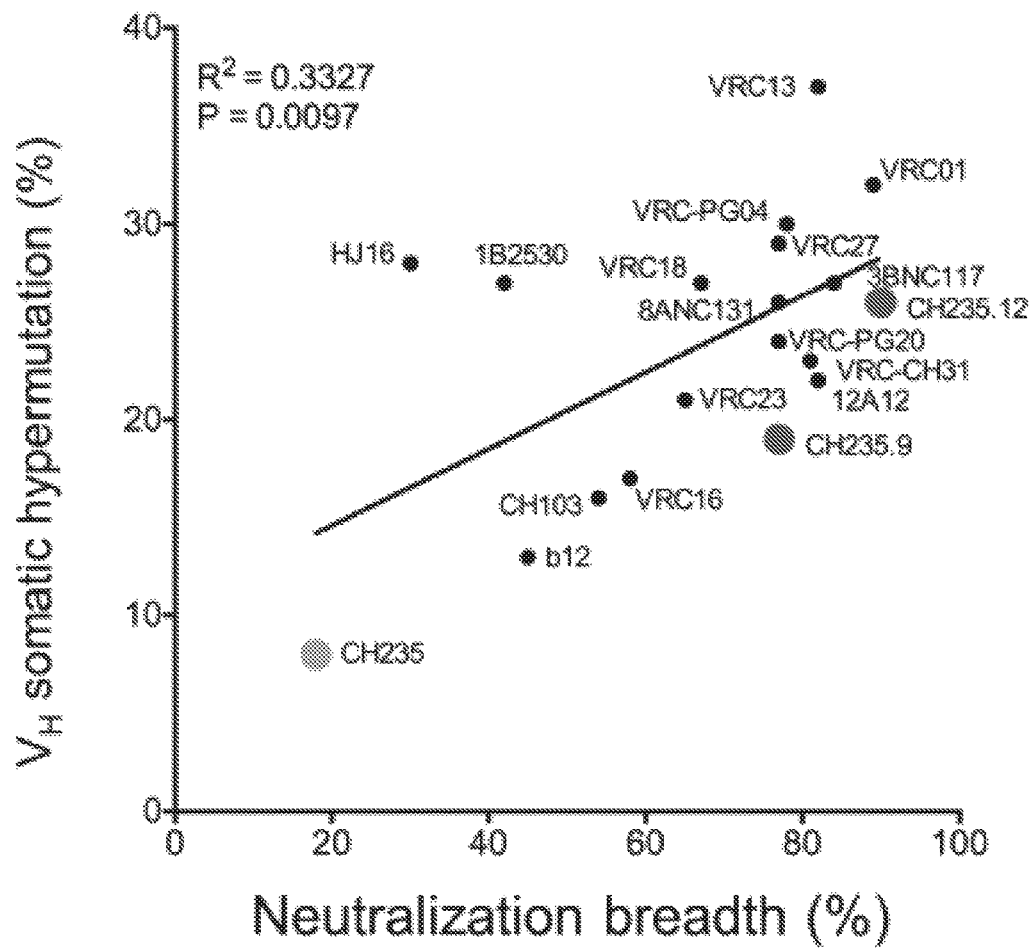

To quantify targeting precision, the buried surface between antibodies and gp120 co-crystal complexes was computed, for the region overlapping the CD4 supersite of vulnerability minus the region outside the vulnerable site. Overall targeting precision correlated with neutralization breadth (P=0.0007) (FIG. 30D). The CH235-lineage antibodies all showed good targeting precision. The correlation of SHM versus neutralization breadth was also analyzed (P=0.0097) (FIG. 30E): While the CH235 lineage generally trended towards lower SHM relative to neutralization breadth, all CD4bs bnAbs appeared to require a high degree of SHM, independent of whether the antibody derived from a specific $V_H$-gene or used a CDR H3-dominated mode of recognition.

Overall, the results suggest that maturation requires a high degree of SHM to focus recognition onto the CD4 supersite of vulnerability and that this high degree of SHM is a general requirement of all CD4bs bnAb lineages, even those that begin with highly favorable orientations such as CH235.

Conformity of Sequence Evolution of CH235 Lineage.

The mutation levels of CH235-lineage antibodies identified 41 wks post infection from memory B cell cultures was markedly lower (range 7-11%) than that of all previously reported $V_H$1-46 and $V_H$1-2 CD4bs bnAbs (>25%) (Scheid et al., 2011; Sui et al., 2010; Wu et al., 2010; Zhou et al., 2015) (FIG. 40C). The mutation levels of CH235-lineage antibodies identified up to 264 wks post infection increased to ~20%, but were still lower than those of most other bnAbs until 323 wks post infection (CH235.12:26% mutations) (FIG. 31A).

Figure 38A:
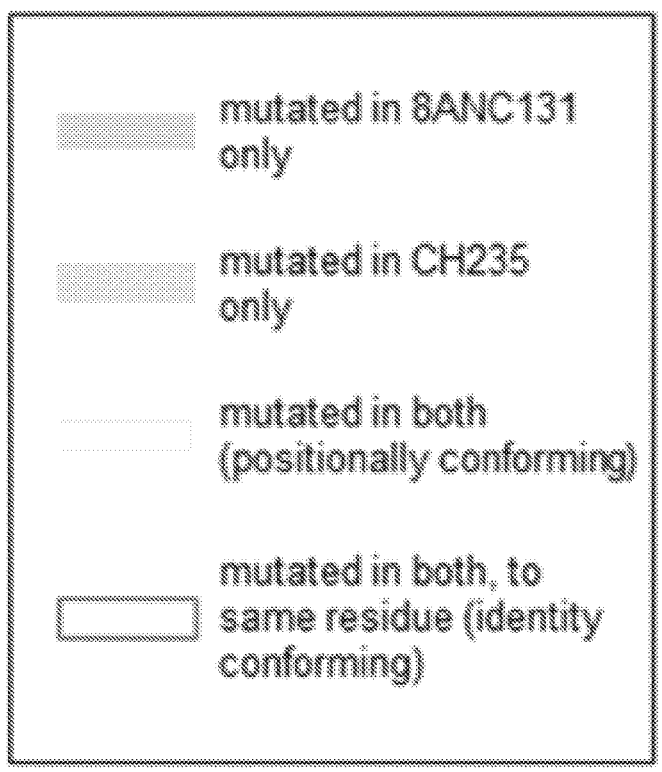

To quantify the conformity of CH235-lineage antibodies to the two $V_H$1-46-derived bnAbs (1B2530 from donor RU1 and 8ANC131 from donor RU8) (Scheid et al., 2011; Zhou et al., 2015), we analyzed the similarity of shared mutation positions (positional conformity) and shared identical mutations (identity conformity) of the $V_H$ genes (FIG. 31B, FIG. 38A). As a comparison, the positional conformity and identity conformity of non-HIV-1 targeting antibodies identified from 3 HIV-1 negative donors relative to template antibodies 1B2530 and 8ANC131 were also calculated. Positional conformity in SHM was spread over a large range (50-90%), and there did not seem to be much discrimination between $V_H$1-46 in antibodies that effectively neutralized HIV-1 and those that did not (FIG. 31B, top panels). Identity conformity in SHM was also spread over a large range (0-75%) (FIG. 31B, bottom panels), and while little discrimination was observed between $V_H$1-46 in antibodies that effectively neutralized HIV-1 and those that did not for antibody 8ANC131, there was discrimination among CD4bs antibodies when 1B2530 was used as a reference (FIG. 31B, bottom left panel). The differences in CH235-lineage identify conformity to 1B2530 or to 8ANC131 may reflect the greater similarity of the recognition orientation of CH235-lineage members with 1B2530 (FIG. 37C) and suggested that slight differences in recognition orientation can substantially alter factors associated with identity conformity.

Figure 38B:
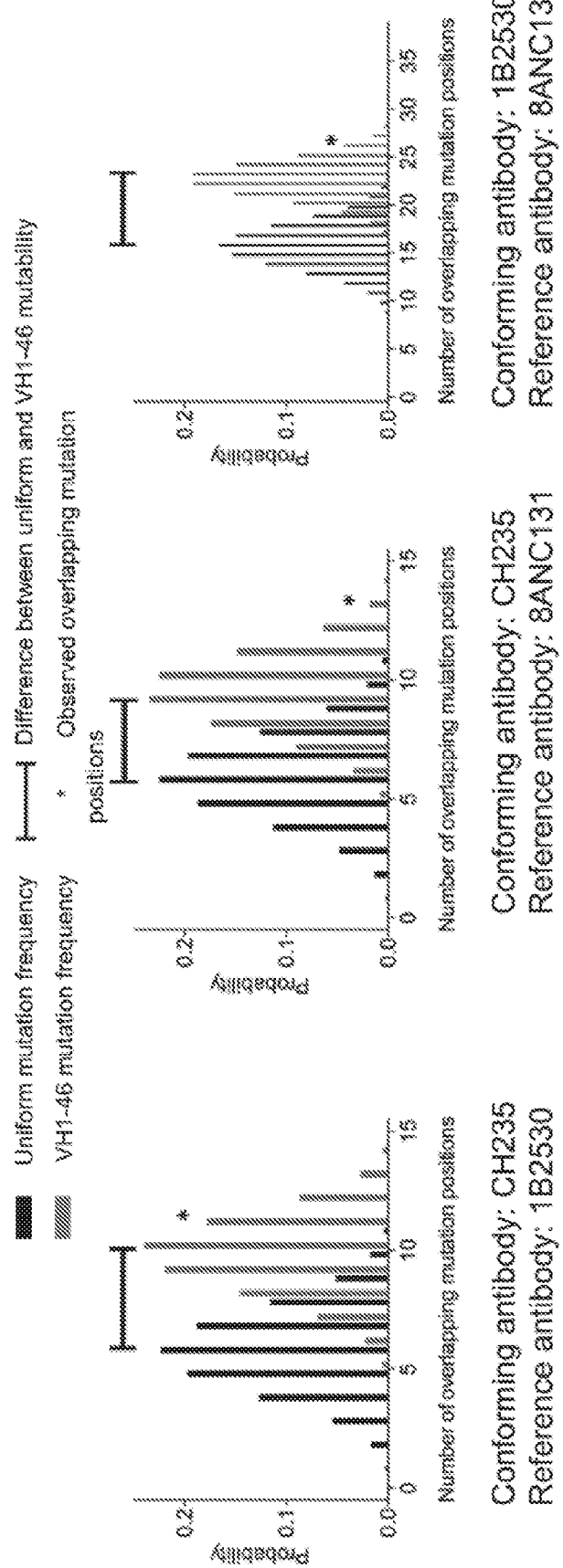
Figure 38C:
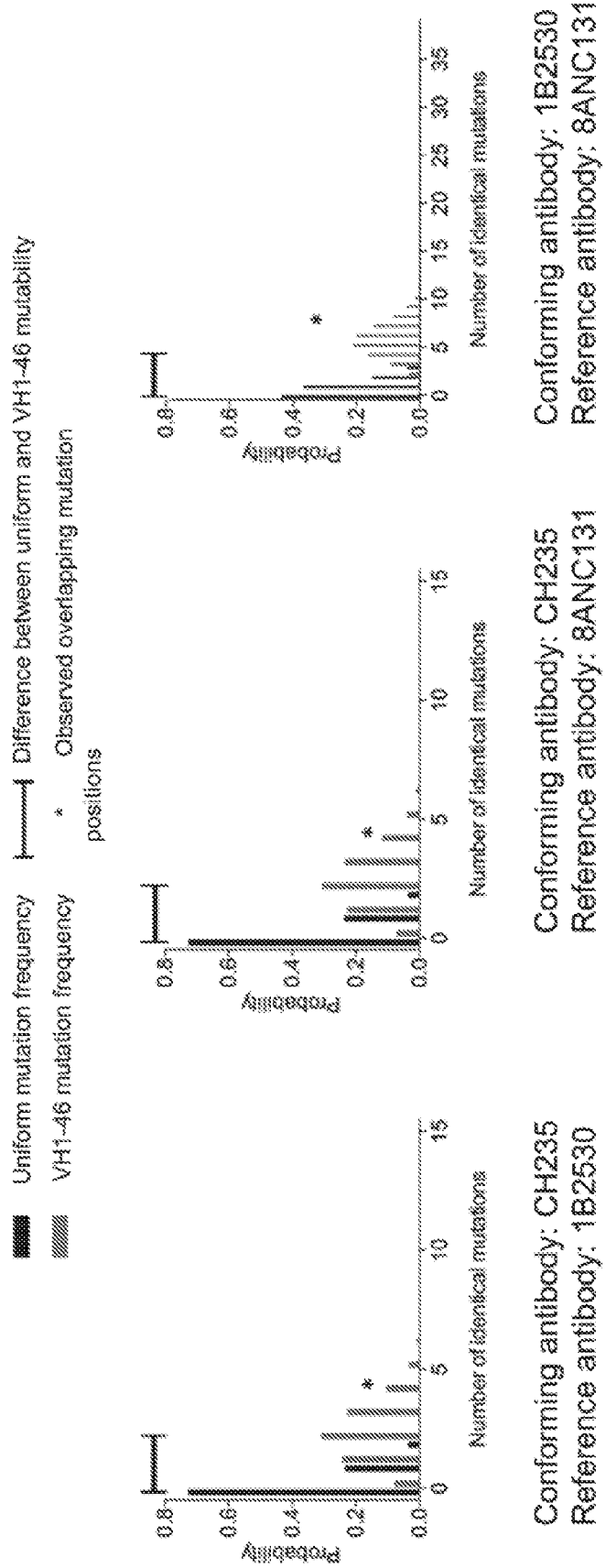

Overall, these results indicated SHM in response to HIV-1 infection to proceed in a manner that depended less on functional selection and more on intrinsic properties of the $V_H$1-46-gene, especially related to the position of residues that undergo SHM. To investigate further the contribution of the $V_H$1-46 gene, we analyzed SHM observed in $V_H$1-46 gene transcripts from three uninfected individuals (FIG. 31C, top); notably, all 11 positions mutated in CH235, 1B2530 and 8ANC131 were also mutated among non-HIV-1 neutralizing antibodies with high frequency (≥20%). Moreover, the residue substitutions in CH235 were frequently found in the top three most commonly observed substitutions for that position in the $V_H$1-46 gene. To quantify the impact of gene mutability, we compared the difference in probability distributions of positional and identity conformity for sequences simulated with and without taking into account the intrinsic $V_H$1-46 gene mutability. The simulations showed that both positional and identity conformity shifted to a higher level of similarity when considering gene mutability (FIGS. 38B and 38C). Notably, a substantial shift in probability was observed for the positional conformity of CH235 (FIG. 38B, FIG. 43A). Similar shifts in identity conformity were also observed for CH235 (FIG. 38C, FIG. 43B). Thus, the intrinsic susceptibility at specific sites of the $V_H$1-46 germline gene to mutation as well as to the frequency of specific mutations that existed at each of these sites appeared to be a dominant factor in the SHM alteration of the CH235 lineage. These results are in line with our previous finding that selection and mutability synergized during affinity maturation of an influenza HA-reactive clone from a non-HIV-1 infected person to hemagglutinin (HA) (Kepler et al., 2014): hence, the dominant role of intrinsic susceptibility at specific sites may be a more general biological phenomenon in dictating the course of SHM.

Because $V_H$1-2 is genetically the most closely related germline gene to $V_H$1-46, we also examined the mutability of the $V_H$1-2 gene (FIG. 31C, bottom). Consistent with $V_H$1-46 antibodies, the mutated positions among $V_H$1-2 derived bnAbs also showed high frequency of mutation among non-HIV-1 targeting $V_H$1-2 antibodies, suggesting that gene mutability contributes to $V_H$1-2 derived HIV-1 antibody evolution. Notably, the average mutability of the $V_H$1-2 gene at positions where the CH235 antibody showed SHM was generally high: 9 of 15 positions mutated in CH235 antibody were also mutated in more than 15% of $V_H$1-2-derived NGS reads. In 10 of these 15 positions, the mature $V_H$1-2-derived bnAbs (VRC01, VRC-CH31 and VRC-PG04) also showed changes. When we analyzed mutability of other $V_H$ genes used by CD4bs bnAbs ($V_H$1-69, $V_H$3-23, $V_H$3-30, and $V_H$4-59) (Zhou et al., 2015) (FIG. 38D), we observed gene mutability patterns different from that of $V_H$1-46 while, in contrast, the mutability patterns of $V_H$1-2 and $V_H$1-46 were more similar (FIG. 43C). Despite the similarity between $V_H$1-2 and $V_H$1-46, we did observe that antibody sequences from CD4bs bnAbs of each gene segregated phylogenetically (FIG. 31E), indicating differences in maturation pathway between bnAbs evolving from these two germline genes.

These data suggested that for both $V_H$1-2 and $V_H$1-46 germline genes-derived bnAbs, somatic mutations that lead to neutralization breadth appeared to be primarily determined by the intrinsic mutability of $V_H$1-46 and $V_H$1-2 germline genes. The differences in the intrinsic mutabilities of these $V_H$ genes may contribute to the high occurrence of CD4bs bnAbs that originate from either $V_H$1-2 or $V_H$1-46 (Zhou et al., 2015).

Interaction between CH235 and CH103 bnAb Lineages.

While gene mutability plays a role in determining the position where SHM occurs, binding between antibody and HIV-1 Env likely also plays a role in selecting or fixing a mutation. A hallmark of cooperating B cell lineages is that they interact at the same site as the bnAb lineage that is being driven (Gao et al., 2014).

To determine a mechanism whereby the initial interaction of the early CH235 and CH103 lineage members bind to the same or similar epitope and result in CH235 selection of escape mutants that stimulated the CH103 bnAb lineage (Gao et al., 2014), cross-competition between early CH235 lineage antibodies and the CH103 lineage antibody CH106 in ELISA was evaluated, as an example of early CH103 lineage development, and measured their association rate constant with surface plasmon resonance (SPR). Since both the CH235 and CH103 lineages bound to the loop D gp120 region, we asked if the early CH235 lineage antibodies could block the binding of the CH103 lineage mature antibody CH106, or block the binding of soluble (s)CD4 to CH505 TF gp120 Env. CH241 was the only antibody in the CH235 lineage that strongly blocked CH106 bnAb and sCD4 binding to CH505 gp120 ($IC_{50}$=2.6 and 1.5 µg/ml, respectively) (FIG. 44A).

To confirm early dominance of the binding of CH103 lineage compared to the CH235 lineage to CH505 TF Env, the blocking assay was reversed and asked if bnAb CH106 could block the binding of biotinylated CH235, CH236, CH239, CH240 or CH241. CH106 strongly blocked the binding of all the CH235 mature antibodies with IC50s ranging from 2.3 µg/ml (for CH240) to 14.3 µg/ml (for CH241) (FIG. 44B). These data suggested that the earliest maturation intermediates of the CH235 lineage antibodies could not outcompete CH106 bnAb for binding to CH505 TF gp120 Env.

Affinity maturation in germinal centers is subjected to kinetic selection and involves improvement in dissociation rate constant ($K_d$) that is often driven by an improvement in the kinetic association rate ($k_a$), which is a key variable in conferring a binding advantage for the cognate epitope to an antibody over other competing antibodies (Foote and Milstein, 1991; Kepler et al., 2014). The $k_a$ and dissociation kinetic rate ($k_d$) of the CH505 TF gp120 Env binding by CH235 and CH103 was measured with SPR to identify differences that might explain the relative inability of the CH235 lineage to block the binding of the CH103 lineage bnAbs to autologous CH505 TF Env and found that the two lineages followed two distinct trajectories and modalities to increase their overall affinity.

The UCA of the CH103 lineage bound to CH505 TF Env with a $K_d$ of 227 nM which increased one order of magnitude throughout affinity maturation (FIG. 32A). The CH103 UCA displayed a fast association rate ($k_a=37\times10^3$ $M^{-1}s^{-1}$) which was maintained across the intermediate and mature mAbs ($k_a=11.9-37.3\times10^3$ $M^{-1}s^{-1}$), suggesting that maintaining the fast association rate was important for survival and maturation of the CH103 lineage (FIG. 32B). In contrast, the CH235 lineage mAb $K_d$ increased four orders of magnitude during affinity maturation (from 30.6 mM of IA4—the earliest intermediate mAb in the CH235 lineage for which kinetic rates could be measured—to 0.7 nM of CH241) (FIG. 32C). Such increase was predominantly facilitated by slower dissociation rates ($k_d$) observed in later intermediates and mature mAbs, which decreased from $88.1\times10^{-3}$ $s^{-1}$ of IA4 to $0.33\times10^{-3}$ $s^{-1}$ of CH241 (FIG. 32D). Conversely, CH235 lineage mAbs bound to CH505 TF gp120 Env with $k_a$ that started off an order of magnitude slower than CH103 UCA and its earlier intermediates (IA4 $k_a=2.9\times10^3$ $M^{-1}s^{-1}$) and only modestly improved—primarily between IA1 and CH235 mAbs—with the majority of the early CH235 mAbs having slower $k_a$ than CH103 mAbs (FIG. 32D).

Thus, the relative inability of wk 41 CH235 lineage antibodies to block early mature CH103 lineage mAbs could be explained by the observed differences in their association rates, and these data provide an explanation of how the CH235 antibody lineage exerted its cooperating function in driving autologous virus toward better neutralization by the CH103 antibody lineage without impeding concurrent development of the CH103 antibody lineage itself.

Late CH235 Lineage Broadly Neutralizing Antibodies Neutralize Autologous Loop D Escape Viruses Selected by Early CH235 Lineage Members.

It has previously been demonstrated that the CH235 lineage selected escape viruses with mutations in the loop D region of gp120 Env that rendered loop D mutant viruses more sensitive to the CH103 bnAb lineage and that autologous virus escaped from early CH235 lineage antibodies by wk 30 after infection (Gao et al., 2014). Described herein is the isolation of autologous viruses through wk 323 and the determination of the neutralization capacity of the late CH235 lineage bnAbs. Viruses partially sensitive to the later members of the CH235 lineage (particularly bnAbs CH235.9 and CH235.12) were found as late as wk 176 (FIG. 33A, FIG. 45). These viruses still contained the loop D mutations that were selected by virus escape from early antibody members of the CH235 lineage (Gao et al., 2014). Hence, the ability of the late CH235 lineage bnAbs to neutralize the panel of CH505 TF loop D mutants was tested (Gao et al., 2014). Remarkably, CH235.9, CH235.12 and CH235.13 bnAbs acquired the ability to neutralize all loop D mutants that were resistant to the early members of the CH235 lineage (FIG. 33B and FIG. 46). In particular, CH235.9, CH235.12 and CH235.13 neutralized CH505 TF gp120 M8, M20 and M21 (not neutralized by early lineage member CH236), which differed from CH505 TF gp120 M6 and M10 (neutralized by CH236) by a single mutation at position 280 (N280S for M8 and M20, and N280T for M21) (FIG. 33B).

In the gp120-complexed structure, the side chains of N280 forms three hydrogen bonds with two residues in the CDR L3 and these hydrogen bonds are predicted to be disrupted by the N280S and N280T mutations (FIG. 39A). Since the CH235.9 antibody had the $V_L$ of CH236, the direct implication was that mutations in the heavy chain were responsible for the ability of CH235.9 to neutralize loop D mutant viruses. Interestingly, CH235.7, which did not neutralize autologous viruses beyond wk 53, also had the $V_L$ of CH236 but, in contrast to CH235.9, failed to neutralize CH236-resistant loop D mutants M7, M8, M9, M20 and M21.

Therefore, we reverted the 5 amino acids (aa) in CH235.9 $V_H$ at gp120 contact positions that were different from those present in CH236 $V_H$ but not shared with CH235.7 $V_H$: N30T and D31T in CDR H1, G62Q and G65Q in FR H3 and A103E in CDR H3 (FIG. 39B). Five of the six CH235.9 mutants retained the ability to potently neutralize all the CH505 TF loop D mutant viruses. In contrast, the N30T mutation in CDR H1 reverted CH235.9 to the CH236 phenotype (CH236 has a threonine in position 30): M21 neutralization was abrogated, M20, M7 and M9 were near completely abrogated (CH235.9 N30T $IC_{50}>44$ µg/ml) and M8 $IC_{50}$ increased 37-fold (CH235.9 $IC_{50}=0.66$ µg/ml vs CH235.9 N30T $IC_{50}=24.31$ µg/ml) (FIG. 46).

Thus, acquisition of extraordinary breadth in the CH235 bnAb lineage was associated with accumulation of somatic mutations in CDR H1 that enabled late CH235 lineage antibodies to neutralize autologous loop D mutant viruses that were escape mutants from early CH235 antibodies. CH235.9 bnAb residue N30 contacts R429 in the β20-β21 loop of the C4 region of gp120 Env, which is on the opposite face of the CD4bs from loop D (FIG. 33C). In addition, CH505 TF has a glutamic acid in position 429 that is in close enough proximity to N30 to form a hydrogen bond.

These findings indicate a mechanism for acquiring the ability to neutralize loop D mutants via a compensatory mutation in the CH235 $V_HDJ_H$ which strengthens the binding to the gp120 C4 region by introducing hydrogen bonds that correct the loss of neutralization due to disruption of the hydrogen bonds between loop D and the CH235 mAb light chain.

CH235 and CH103 Lineage Antibody Binding to C11505 gp120 Env.

The CH235 lineage antibodies were tested for binding to 113 recombinant CH505 gp120 Env isolated from time of transmission to wk 160 post-transmission, including CH505 TF loop D mutant Envs (FIG. 34A and FIG. 47). Of note, CH235.9 and CH235.12 bound to 4/22 and 8/22 Envs isolated from wk 136 and 160 post-transmission, respectively, including Envs from viruses that were also neutralized. Env binding to the initial members of the CH103 lineage has previously been reported (Hraber et al., 2015), and described herein is the same Env binding analysis of the CH103 lineage with 10 additional matured bnAb members of the CH103 lineage (FIG. 34A and FIG. 47). We have used these data to select CH505 gp120 Env quasi-species that bound to mature and precursor bnAbs of both lineages, defining a series of CH505 Env immunogens now optimized and predicted to induce both bnAb lineages (FIG. 40A).

It has previously been reported that CH235 UCA weakly reacted with CH505 TF gp120 at ~10 µM as determined by SPR (Gao et al., 2014). Here we show stronger binding of the CH235 UCA to 8/113 autologous CH505 gp120 Envs measured in ELISA (FIG. 34A and FIG. 47). Moreover, in a panel of 15 heterologous Envs from multiple clades, CH235 UCA bound to 3/15 Envs and the introduction of only 3 mutations (W47L, G54W and S56R), which were selected based on the increase in surface area of interaction (G54W and S56R) or the reduction in clash score (W47L), increased this recognition (to 5/15 Envs), of which the dominant effect appeared to be reduction in clash (FIG. 34B and FIG. 40B).

Autoreactivity in the CH235 B Cell Lineage.

Figure 35B:
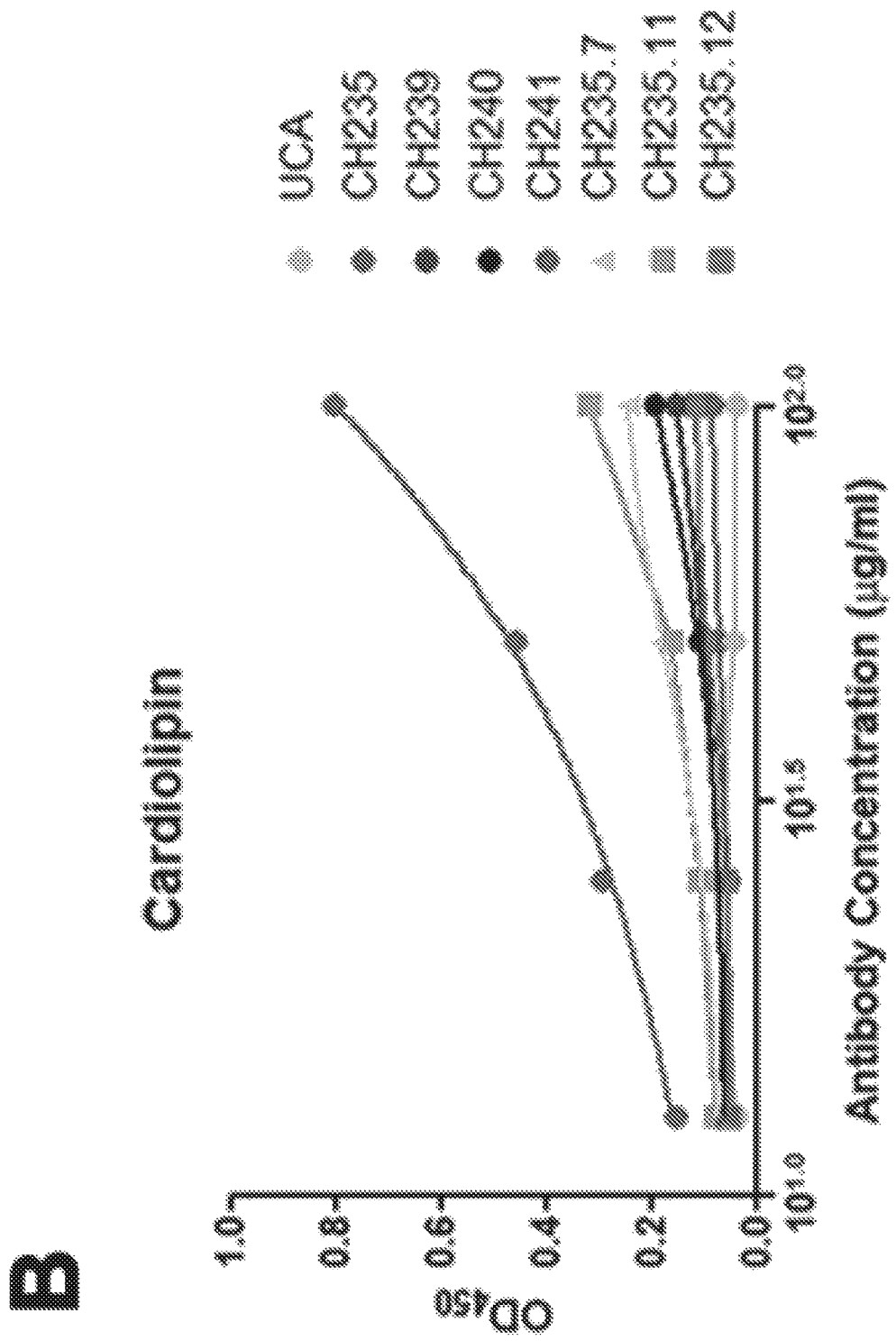

Development of auto- and polyreactivity during antibody maturation toward neutralization breadth is a critical aspect that may limit the ability of generating bnAbs during natural infection and upon vaccination (Bonsignori et al., 2014; Haynes et al., 2005; Haynes et al., 2012; Haynes and Verkoczy, 2014; Liu et al., 2015; Verkoczy et al., 2013; Verkoczy et al., 2010; Verkoczy et al., 2011). It has previously been reported that in HIV-1-infected individual CH505, the CD4bs CH103 bnAb lineage was polyreactive and, similar to VRC01-class bnAbs, bound to human ubiquitin ligase E3A (UBE3A) with avidity correlated with neutralization (Liao et al., 2013; Liu et al., 2015). In addition, most of the mutations introduced in VRC07—a somatic variant of VRC01—that enhanced neutralizing activity also resulted in increased autoreactivity (Rudicell et al., 2014). Since CH235.12 is a potent and extremely broad CD4-mimic CD4bs bnAb, we compared the auto- and polyreactivity profile of CH235.12 with other members of the CH235 lineage. Most CH235 lineage antibodies displayed reactivity against DNA and sporadic reactivity with Scl70 (CH235.7) (FIG. 35A). CH241 bound to cardiolipin (FIG. 35B). In Hep-2 IF staining CH236, CH235.7 and CH235.9 were all cytoplasmic positive (FIG. 35C). Conversely, CH235.12, despite being highly mutated and broadly neutralizing, did not display autoreactivity in any of these assays (FIG. 35A-C) Of particular note, CH235 lineage antibodies, including CH235.12, did not react with UBE3A (FIG. 35D).

These data identify CH235.12 as an antibody that has developed neutralization breadth without being itself auto- and polyreactive, while less mutated precursor antibodies (CH235 is in the same clade of CH235.12) did develop autoreactivity. Therefore, in vivo decoupling of neutralization breadth of CD4 mimic CD4bs bnAbs from auto- and polyreactivity can occur, even for bnAb lineages that have developed autoreactivity during the course of their maturation and, therefore, inducing such bnAbs from such lineages through vaccination, though difficult, is an achievable goal.

Discussion

Here we have traced the ontogeny of the CH235 $V_H1-46$ 8ANC131 class of CD4bs bnAbs from acute infection to chronic infection and defined both the structural and functional pathways of bnAb lineage induction. That the CH235 bnAb lineage that selected virus escape mutants that drove the CH103 CD4bs CDR H3-dependent bnAb lineage is itself an 8ANC131-class bnAb lineage and co-evolved with the CH103 bnAb is a remarkable demonstration of a bnAb-to-virus-to bnAb interaction in the same HIV-1 infected individual. In addition, the similarity of $V_H1-46$ 8ANC131-like and $V_H1-2$ VRC01 family CD4 supersite bnAbs demonstrates dramatic convergence of antibody structures to recognize the CD4 supersite. The CH235 lineage required over 20% SHM in heavy chain variable domain to achieve 90% breadth. Fortunately, a substantial portion of the $V_H$-gene SHM was guided by the intrinsic mutability of the $V_H1-46$ germline gene. Moreover, the CH235 lineage Ab that became broadly neutralizing acquired the ability to neutralize loop D mutants selected by early Ab lineage members (Gao et al., 2014) with a mechanism involving a compensatory mutation (T30N) in CDR H1, which allowed the formation of H-bonds with the HIV-1 gp120 C4 region, thus correcting the original loss of binding.

The driving forces of the CH235 lineage were the natural transmitted/founder and M5 Envs. In addition, despite near-complete autologous virus escape from CH235 lineage antibodies by wk 100, viruses arose later during the course of infection, which were sensitive to the more mature CH235 bnAb members and likely contributed to antigen drive. It is interesting to note that many of these late viruses were less sensitive to CH103 CDR H3 binder bnAbs prompting the hypothesis that the CH103 lineage may have the capacity for cooperation with the CH235 lineage after 5-6 years of co-development. Finally, the CH235.12 antibody that evolved late in CH235 development is an extraordinary broad and potent non-autoreactive antibody and is a candidate for preventive and therapeutic uses.

In summary, the acquisition of neutralization breadth in the CH235 VRC01-like $V_H1-46$ CD4 mimic bnAb occurred with the sequence of transmitted/founder and early mutant-initiated antigen drive, selection of Env loop D mutants that cooperated with the CH103 bnAb lineage to drive it to bnAb breadth, followed by acquisition of the ability of the CH235 lineage itself to neutralize autologous loop D mutants coincident with potent neutralization of a broad array of heterologous HIV-1 isolates. Mapping these events points to a strategy for the simultaneous induction of both CDR H3 and VRC01-class CD4bs bnAbs, whereby sequential immunizations with transmitted founder Env followed by loop D mutant Envs comprise a rational immunization strategy.

Experimental Procedures

Donor and Sample Information. Donor and sample information was previously reported (Liao et al., 2013) and is summarized in Supplemental Experimental Procedures. Memory B cell cultures were performed on PBMCs collected at 264 and 323 wks post-transmission. All work related to human subjects was in compliance with Institutional Review Board protocols approved by the Duke University Health System Institutional Review Board.

Preparation of Libraries for 454 DNA Pyrosequencing. 454 DNA pyrosequencing was performed on genomic DNA template isolated with Qiagen kits from PBMCs collected at 6, 7, 8, 9, 14, 20, 22, 30, 41, 53, 66, 92, 100, 144 and 152 wks post-transmission as described in (Boyd et al., 2009) and in Supplemental Experimental Procedures. Only unique V-heavy rearrangements were included in the analysis to generate the phylogeny; in the case of duplicated sequences, the earliest occurrence was included in the analysis.

Phylogenetic Analysis. For clonal phylogenetics, the UCA was inferred using Cloanalyst (Kepler, 2013), which simultaneously estimates the UCA and the phylogenetic tree relating the observed sequences to each other and to the UCA. Internally, Cloanalyst uses dnaml from the PHYLIP suite of phylogenetic software (Felsenstein, 2005). The CH235 antibody lineage clonogram was displayed using the ete2 Python package.

Isolation of CH235 Lineage Antibodies from Donor CH505. Fluorescence-activated cell sorting of antigen-specific IgG+ B cells from PBMC and the amplification and cloning of immunoglobulin genes were performed as described in (Bonsignori et al., 2011). CH505.TF gp120 Env-positive memory B cells were cultured as described in Supplemental Experimental Procedures.

Neutralization Assays. Neutralization of donor CH235 mAbs were measured using single-round-of-infection HIV-1 Env pseudoviruses and TZM-bl target cells as described in Supplemental Experimental Procedures.

Neutralization Signature. Antibody neutralization signatures were computed and compared as described in Supplemental Experimental Procedures.

Monoclonal Antibody and Antigen-Binding Fragment (Fab) Production. Ig genes of mAbs were amplified from RNA and expression plasmids for heavy and kappa chains were constructed. Expression and purification of recombinant IgG mAbs and preparation of Fab fragments are described in Supplemental Experimental Procedures.

Crystallization, X-Ray Data Collection, Structure Determination, and Refinement of Donor CH235 Antibodies in Complex with HIV-1 gp120. Purification, crystallization of antibody-gp120 complexes, data collection, structure solution, refinement and analysis are described in Supplemental Experimental Procedures. Diffraction data were integrated and scaled with the HKL2000 suite (Otwinowski and Minor, 1997).

Electron Microscopy Data Collection and Processing. BG505 SOSIP.664 and B41 SOSIP.664 gp140 trimers and donor CH235-derived Fab complex negative-stain electron microscopy images, analysis and visualization are described in the Supplemental Experimental Procedures.

Focused Maturation and Conformity Analysis. Focused maturation and mAb conformity analysis are described in the Supplemental Experimental Procedures.

Surface Plasmon Resonance Affinity and Kinetics Measurements. MAb binding to autologous CH505 gp140 was measured using a BIAcore 3000 or BIAcore T200 instrument (GE Healthcare) as described in (Alam et al., 2007; Alam et al., 2009; Liao et al., 2013) and in Supplemental Experimental Procedures.

Direct-Binding ELISA. Direct-binding ELISAs were performed as described in Supplemental Experimental Procedures.

MAb CH235.9 Amino Acid Reversion. Site-directed mutagenesis of the CH235.9 mAb genes was performed using the Quikchange lightning multi-site-directed mutagenesis kit (Agilent) following manufacturer's protocol. Primers are listed in Supplemental Experimental Procedures.

Structural Modeling. Loop D mutations were structurally modeled using PyMOL with sidechains placed in the most frequently observed rotamer that did not result in steric clashing with neighboring residues. Hydrogen bonds were calculated using HBPLUS software (McDonald and Thornton, 1994).

Recombinant HIV-1 Proteins. HIV-1 genes of autologous CH505 Env were determined from samples collected from 4 to 323 wks post-infection by single genome amplification (Keele et al., 2008) and produced as described in (Liao et al., 2013).

Protein Array. MAbs were screened for binding on protein microarrays (ProtoArray) (PAH0525101; Invitrogen) pre-coated with 9,400 human proteins in duplicate and screened following manufacturer's instructions and as described in (Liu et al., 2015; Yang et al., 2013).

HEp-2 Cell Staining. Indirect immunofluorescence binding of mAbs or plasma to HEp-2 cells (Zeuss Scientific) was performed as previously described (Bonsignori et al., 2014; Haynes et al., 2005).

Supplemental Experimental Procedures

Donor and Sample Information.

The CH505 donor, from which the CH103 and the CH235 antibody lineages were identified, is an African male enrolled in the CHAVI001 acute HIV-1 infection cohort (Tomaras et al., 2008) and followed for over 6 years. During this time viral load ranged from 14,460 to 847,279 copies/ml (median=173,667 copies/ml), and CD4 counts ranged from 69 to 431 cells/mm$^3$ (median=294 cells/mm$^3$).

The time of infection was estimated by analyzing the sequence diversity in the first available sample using the Poisson Fitter tool (Giorgi et al., 2010) as described in (Liao et al., Nature 2013). Results were consistent with a single founder virus establishing the infection and with the earliest isolated virus sequences being taken 4 weeks post-transmission.

Flow Cytometry, Memory B Cell Cultures and mAb Isolation.

The HIV-1 CH505.TF gp120 envelope glycoprotein was produced and used in flow cytometry on PBMC collected from donor CH505 at week 264 and 323 post-transmission using a two-color technique as described (Gray et al., 2011).

CH505.TF gp120 Env-positive memory B cells were cultured as described (Bonsignori et al., 2011) with the following modifications: non-irradiated MS40L cells were used as feeder cells at a concentration of 3,000 cells/well and were added to wells in which memory B cells were sorted in bulk; 50 ng/ml of recombinant human (rHu) IL-21 (200-21; Peprotech, Rocky Hill, N.J.) were added to the complete medium; memory B cells were distributed by limiting dilution at a calculated concentration of 2 cells/well; culture medium was refreshed every 5 days.

Cell culture supernatants were screened for neutralization of autologous CH505.TF virus using the tzm-bl neutralization assay (Bonsignori et al., 2011; Montefiori, 2005) and for binding to CH505.TF gp120 Env, CH505.TF Δ371I gp120 Env mutant, HIV-1 Env resurface core protein 3 (RSC3) and RSC3 Δ371I (Wu et al., 2010).

MAbs CH235.10 through CH235.13 were identified from cultures that displayed differential binding of CH505.TF and CH505 TF Δ371I gp120 Env, did not bind to RSC3 (Gao et al., 2014) and neutralized 13 to 99% CH505.TF infectivity.

CH235 lineage antibody frequency over total memory B cells was calculated by dividing the number of CH235 lineage antibodies identified at week 41 (n=5; Gao et al., 2014) for the number of memory B cells analyzed (n=27, 950). CH235 lineage antibody frequency over CH505.TF gp120 Env-specific memory B cells was calculated by dividing the number of CH235 lineage antibodies identified at weeks 264 and 323 (n=4) for the number of CH505.Env gp120-specific memory B cells analyzed (n=794).

454 Pyrosequencing of CH235 Lineage Heavy Chains.

Antibody heavy chain gene rearrangements were PCR amplified from 6 independent 100 ng genomic DNA aliquots to generate 6 barcoded libraries per sample. Multiplexed primers complementary to the IGHV FR1 or FR2 framework regions, and an IGHJ-primer were modified from the BIOMED-2 consortium primers (Boyd et al., 2009; van Dongen et al., 2003). 10-nucleotide 'barcode' sequences in the primer sets encoded sample identity and replicate library identity. AmpliTaq Gold (Roche) enzyme was used for PCR following the manufacturer's instructions, with a thermocycler program: 94° C. 5 min; 35 cycles of (94° C. 30 sec, 60° C. 45 sec, 72° C. 90 sec); and final extension at 72° C. for 10 min. Following quantitation, PCR products from each replicate library were pooled in equimolar amounts, then the pooled library was run on a 1.5% agarose gel and gel extracted (Qiagen). High-throughput sequencing was performed on the 454 (Roche) platform using Titanium chemistry.

Antibody Production.

Immunoglobulin genes of mAbs CH235.10 through CH235.13 were amplified from RNA from isolated cells, expression cassettes made, and mAbs expressed as described (Gao et al. 2014). The $V_H$ genes of mAbs CH235.6 through CH235.9 were retrieved from sequences obtained through genomic DNA 454 sequencing, which were restored to full length and complemented with the $V_L$ of the phylogenetically closest identified antibody in the CH235 lineage (i.e. CH241 for CH235.6 and CH235.8, and CH236 for CH235.7 and CH235.9). We have previously described the isolation of mAbs CH235, CH236, CH239, CH240 and CH241 and the inference of unmutated common ancestor (UCA) and intermediate antibodies IA1 through IA4 (Gao et al., 2014; Kepler, 2013).

Heavy chain plasmids were co-transfected with appropriate light chain plasmids at an equal ratio in Expi 293 cells using either 293Fectin or ExpiFectamine 293 transfection reagents (Thermo Fisher Scientific) according to the manufacturer's protocols. Cultures were supplemented with AbBooster antibody expression enhancer media (ABI Scientific) at 10% of the final culture volume 24 h after transfection. Cultures were then incubated at 33° C. for 5 more days, and supernatants were harvested and passed over a protein A affinity column. Following PBS wash and low pH elution, the pH of eluate was neutralized with 1M Tris pH 8.5 and samples were dialyzed against PBS. Antibodies were then aliquoted and stored at −80° C. prior to use. Alternatively, for ExpiFectamine transfections we used the enhancer provided with the kit, transfected cultures were incubated at 37° C. 8% $CO_2$ for 2-6 days, harvested, concentrated and incubated overnight with Protein A beads at 4° C. on a rotating shaker before loading the bead mixture in columns for purification; following PBS/NaCl wash, eluate was neutralized with trizma hydrochloride and antibody concentration was determined by Nanodrop. Purified antibodies were tested in SDS-Page Coomassie and western blots, and stored at 4° C.

Direct-binding ELISA.

Direct-binding ELISAs were performed as described previously (Bonsignori et al., 2011) with the following modifications: plates were blocked for 1 h at room temperature (RT) or overnight at 4° C. (both procedures were previously validated); primary purified antibodies were tested at a starting concentrations of 100 µg/ml, serially three-fold diluted and incubated for 1 h at RT; HRP-conjugated human IgG antibody was added at optimized concentration of 1:30,000 in assay diluent for 1 hour and developed using TMB substrate; plates were read at 450 nm in a SpectraMax 384 PLUS reader (Molecular Devices, Sunnyvale, Calif.); results are reported as logarithm area under the curve (LogAUC) unless otherwise noted.

For cell culture supernatant screening of RSC3 and RSC3 Δ371I HIV-1 Env core proteins reactivity, plates were coated with streptavidin (2 µg/ml); blocked plates were stored at −20° C. until used; 10 µl/well of biotinylated avi-tagged RSC3 and RSC3 Δ371I were added at 2 µg/ml for 30 minutes at RT and culture supernatants were added at 1:3 dilution in assay diluent; plates were developed for 10 min using SureBlue Reserve TMB (53-00-03; KPL, Gaithersburg, Md.) equilibrated at RT.

Competition ELISAs were performed using 10 µl of primary purified monoclonal antibody, starting at 100 µg/ml and diluted in a two-fold concentration, incubated for 1 h at RT; for CD4 binding site blocking assays, 10 µl of a saturating concentration soluble CD4 (Progenics Pharm Inc.) was added following antibody incubation step. Ten µl of biotinylated target Mab was added at the EC50 determined by a direct binding of biotinylated-Mab for one hour at RT. After background subtractions, percent inhibition was calculated as follows: 100−(sera triplicate mean/no inhibition control mean)*100.

Autoimmune purified antigens histones (whole), Jo-1, RNP/Sm, Scl-70, Sm, SSA (Ro), SSB (all from ImmunoVision) and centromere B (Prospec) were coated at optimal concentrations determined by lot-specific checkerboard with positive controls. All plasma antibody positive controls were purchased from ImmunoVision; lot-specific optimal ranges for standard curves were determined. All antibodies were tested using the same lots for each antigen and positive controls with the protocol described above. For DNA ELISA, plates were coated with 2 µg/ml poly-lysine (Sigma-Aldrich) for 2 h at RT, washed 3× with PBS and blocked with PBS/2% BSA/0.05% Tween-20 for 2 h at RT. After 3× wash, DNA (LS002195, Worthington) in saline sodium citrate buffer was added for 1 h, washed and antibodies were incubated for 1 h. Secondary antibody was diluted in PBS/0.05% Tween-20. Plates were developed for 30 min. Human recombinant monoclonal antibody Ab008391 (courteously provided by David Easterhoff, Duke Human Vaccine Institute) was used as positive control. For all autoantigen ELISAs, palivizumab was used as negative control. For each antibody, LogAUC was calculated and data are presented semi-quantitatively: no binding=$logAUC_{Ab} \leq 2\times$ negative control $logAUC_{neg\ ctrl}$; to quantify antibody binding we divided ($logAUC_{pos\ ctrl} - 2 \times logAUC_{neg\ ctrl}$) in tertiles and expressed test antibody binding as weak (+), intermediate (++) or strong (+++) if $logAUC_{Ab}$ was in the first, second or higher tertile, respectively.

Anti-cardiolipin ELISA was performed using the QUANTA Lite ACA IgG III kit (708625; INOVA Diagnostics) following manufacturer's protocol.

Assessment of Virus Neutralization Using a Large Panel and Calculation of Neutralization Dendrograms.

Neutralizing antibody assays in TZM-bl cells were performed as described previously (Montefiori, 2005). Neutralization breadth of CH235 UCA, CH235, CH235.9 and CH235.12 neutralization breadth was assessed using the 384-well plate declination of the assay using an updated panel of 199 geographically and genetically diverse Env-pseudoviruses representing the major circulating genetic subtypes and recombinant forms as described (Seaman et al., 2010; Wu et al., 2010). The data were calculated as a reduction in luminescence units compared with control wells, and reported as $IC_{50}$ in µg/ml (Montefiori, 2005).

Dendrograms were calculated using the neighbor-joining method, showing the protein sequence distance from the HIV-1 Env gp160 sequences of 190 HIV-1 primary isolates. The clades of HIV-1, including circulating recombinant forms (CRFs) are indicated.

Antibody Neutralization Fingerprinting Analysis.

Neutralization fingerprints were computed and compared for CH235, CH235.9 and CH235.12 from the CH235 lineage, other CD4-binding-site antibodies, and antibodies targeting other sites of vulnerability on HIV-1 Env. The fingerprints were computed over a common panel of 165 HIV-1 strains with neutralization data for all antibodies, and a hierarchical clustering procedure was applied for building the tree, as described in (Georgiev et al., 2013). Briefly, for each antibody, the neutralization data for the common set of 165 HIV-1 strains formed that antibody's neutralization fingerprint. The Spearman correlation coefficients for all pairs of antibody neutralization fingerprints were then computed, transforming the antibody-virus neutralization matrix into an antibody-antibody correlation matrix. This correlation matrix was then input into a hierarchical clustering procedure as a way to visualize the similarities between the neutralization fingerprints for the different antibodies. The distances in the resulting tree are thus a function of the differences between fingerprints.

VH1-46 and VH1-2 Antibody Dendrogram Calculation.

Phylogenic trees for multiple antibodies derived from VH1-46 and VH1-2 heavy chain variable genes were calculated using the neighbor-joining method. The sequences are aligned by Clustal Omega, calculated using ClustalW2. Dendrograms were drawn in Figtree.

Production and Purification of HIV-1 Env Protein Complexed to Antigen-binding Fragments.

HIV-1 gp120 protein from clade AE 93TH057 and antibodies of CH235, CH235.9 and CH235.12 were produced and purified as described previously (Zhou et al., 2010). Fab fragments of antibodies were prepared by digesting purified IgG with Lys-C at 37° C. for 2-4 h. The digestion reaction was quenched by the addition of cOmplete protease inhibitors (Roche). The digested antibodies were passed over Protein A agarose to remove the Fc fragment. The Fab was further purified over a Superdex 200 gel filtration column and concentrated aliquots were stored at −80° C.

X-ray Crystallography.

The gp120-antibody complexes were formed by mixing deglycosylated gp120 with the antibody Fab in a 1:1.5 molar ratio. The complexes were purified by size exclusion chromatography (Hiload 26/60 Superdex S200 prep grade; GE Healthcare) with buffer containing 0.35 M NaCl, 2.5 mM Tris (pH 7.0), and 0.02% $NaN_3$. Fractions with gp120-antibody complexes were concentrated to ~10 mg/ml and used for crystallization experiments. All gp120-Fab complexes were screened against 576 crystallization conditions using a Cartesian Honeybee crystallization robot. Initial crystals were grown by the vapor diffusion method in sitting drops at 20° C. by mixing 0.2 µl of protein complex with 0.2 µl of reservoir solution. Crystals were manually reproduced in hanging drops by mixing 0.50 µl protein complex solution with 0.5 µl reservoir solution.

The 93TH057 $core_e$ gp120-CH235 complex was crystallized with a reservoir solution of 25% (w/v) of PEG2000, 0.2 M of $Li_2SO_4$, 0.1 M of Tris-HCl pH 8.5 and 5% (v/v) of isopropanol and was flash frozen in liquid nitrogen in mother liquor supplemented with 15% of 2R,3R-butanediol as a cryoprotectant. The 93TH057 $core_e$ gp120-CH235.9 complex was crystallized with a reservoir solution of 9% (w/v) of PEG8000, 19% (w/v) of PEG400, 0.1 M HEPES pH 7.5 and was flash frozen in mother liquor supplemented with an additional 15% PEG 400 as a cryoprotectant. The 93TH057 $core_e$ gp120-CH235.12 complex was crystallized with a reservoir solution of 10% PEG 8000, 20% PEG 400 and 100 mM HEPES, pH7.5 and was flash frozen in mother liquor supplemented with an additional 15-20% PEG 400 as a cryoprotectant.

Data for all crystals were collected at a wavelength of 1.00 Å at SER-CAT beamlines ID-22 and BM-22 (Advanced Photon Source, Argonne National Laboratory). All diffraction data were processed with the HKL2000 suite, structures were solved by molecular replacement using PHASER, and iterative model building and refinement were performed in COOT and PHENIX, respectively. For 93TH057$core_e$ complexes with CH235.9 and CH235.12, molecular replacement solutions were obtained using EAF31403.1-CH235 complex as a search model.

Throughout the refinement processes, a cross validation ($R_{free}$) test set consisting of 5% of the data was used and hydrogen atoms were included in the refinement model. Structure validations were performed periodically during the model building/refinement process with MolProbity. The 93TH057 $core_e$-CH235 structure was refined to a final $R_{free}$ value of 22.9% with 96% residues in the favored region of the Ramachandran plot, and 0.1% outliers. The 93TH057 $core_e$-CH235.9 structure was refined to a final $R_{free}$ value of 22% with 97.1% residues in the favored region of the Ramachandran plot, and 0% outliers. The 93TH057 $core_e$-CH235.12 structure was refined to a final $R_{free}$ value of 23% with 97.0% residues in the favored region of the Ramachandran plot, and 0.1% outliers. All figures containing representations of the protein crystal structures were made with PyMOL. Gp120 and antibody interactions were analyzed with the PISA server.

Surface Plasmon Resonance Affinity and Kinetics Measurements.

For kinetic measurement, each antibody was captured on an anti-human IgFc immobilized sensor surface (200-500RU) and gp120 proteins at varying concentrations were injected to monitor association and dissociation phases. Buffer reference and non-specific binding to a control antibody (palivizumab) captured surface were used to derive specific binding signals. Kinetic rate constants and dissociation constant (Kd) were derived from global curve fitting analysis using a Langmuir 1:1 interaction model using the BIAevaluation 4.1 software (GE Healthcare).

Electron Microscopy Data Collection and Processing.

BG505 SOSIP.664 and B41 SOSIP.664 gp140 trimers were expressed in HEK293F cells and purified by 2G12-affinity and gel filtration chromatography as described elsewhere (Pugach et al., 2015; Sanders et al., 2013). Trimers were incubated with a 10 molar excess of Fab (CH235, CH235.9, or CH235.12) overnight at room temperature and the complexes were diluted to ~0.03 mg/mL prior to application onto a carbon-coated 400 Cu mesh grid that had been glow discharged at 20 mA for 30 s. The grids were stained with 2% (w/v) uranyl formate for 60 seconds. Samples were imaged using a FEI Tecnai T12 electron microscope operating at 120 keV, with an electron dose of ~25 $e^-/Å^2$ and a magnification of 52,000× that resulted in a pixel size of 2.05 Å at the specimen plane. Images were acquired with Leginon (Suloway et al., 2005) using a Tietz TemCam-F416 CMOS camera with a nominal defocus range of 1000-1500 nm. Automated particle picking, stack creation, and initial 2D classification was performed in the Appion software suite (Lander et al., 2009). Noise and junk particles were discarded and the remaining stack was subjected to 3D classification using Relion (Scheres, 2012) with an EM volume created from the x-ray structure of ligand-free BG505 SOSIP.664 (PDB: 4zmj) low pass filtered to 60 Å as the reference model. While both CH235.9 and CH235.12 bound to either B41 or BG505 at predominantly full stoichiometry (3 Fabs per trimer), CH235 bound to either trimer at sub-stoichiometric ratios (1 Fab per BG505 trimer and 2 Fabs per B41 trimer). The 3D classes representing the predominant stoichiometry for each complex were used as the initial models (low pass filtered to 40 Å) for further refinement using Relion, with C3 symmetry imposed for complexes with CH235.9 or CH235.12. The total number of particles used in refinement and final resolution of the map using a Fourier shell correlation of 0.5 are as follows: BG505 in complex with CH235—3,467 particles (~25 Å); B41 in complex with CH235—4,248 particles (~24 Å); BG505 in complex with CH235.9—2,567 particles (25 Å); B41 in complex with CH235.9—8,061 particles (19 Å); BG505 in complex with CH235.12—15,565 particles (17 Å); B41 in complex with CH235.12—17,023 particles (16 Å).

To create figures of each Fab in complex with a representative trimer, the 3D reconstructions for each complex were fit into an EM volume created from the x-ray structure of unliganded BG505 SOSIP.664 (PDB: 4ZMJ) low pass filtered to 30 Å in UCSF Chimera (Pettersen et al., 2004) and using the "segment map" option to isolate the density of the Fab components alone. Two-dimensional back projections of the final 3D models were generated using EMAN (Tang et al., 2007).

Epitope Visualization.

The HIV-1 gp120 epitopes targeted by donor CH235 antibodies were visualized using PyMOL (Schrodinger, 2010). In this graphic program, we used 5.5-Å distance for selection of epitope atom sets which were virtually identical to those defined by protein interface analysis program PISA.

Monoclonal Antibody CH235.9 Amino Acid Reversion.

Primers were designed with the online Agilent Quikchange primer designer tool (www.thermofisher.com) and were as follows (SEQ ID NOs: 184-191, in order of appearance):

CH235.9$_{N30T}$:
CGTGGCGTCTGGATACAACTTCACCGACTACTATATAC;

CH235.9$_{D31T}$:
CGTCTGGATACAACTTCAACACCTACTATATACACTGGGTGC;

CH235.9$_{G62Q}$:
GGTCGCACAGATTACGCACAGGCGTTTGGGGA;

CH235.9$_{G65Q}$:
GATTACGCAGGGGCGTTTCAGGACAGAGTGTCCA;

CH235.9$_{A103E}$:
GTTAGAAATGTGGGAACGGAGGGCAGCTTGCTCCACTATG;

CH235.9$_{G62Q/G65Q}$:
GGTCGCACAGATTACGCACAGGCGTTTCAGGACAGAGTGTCCA;

CH235.9$_{S54R}$:
GGATCGACCCTAGGGGTGGTCGCACAG;

CH235.9$_{A61S}$:
GTGGTCGCACAGATTACTCAGGGGCGTTTG.

Presence of mutations in plasmid products was confirmed by single-colony sequencing.

Structural Bioinformatics.

Average buried surface area (BSA) on gp120 was calculated for residues with BSA>1 Å$^2$ for the gp120-antibody complexes, and the corresponding antibody neutralization potencies were averaged for each of those residues based on data from neutralization assays. Spearman correlation between BSA on gp120 and antibody potencies was calculated for BSA cutoffs=0 to 85 Å$^2$ and potency log IC$_{50}$ cutoffs=0.60 to 1.62 µg/ml.

Sample Preparation for 5' RACE Method and 454 Pyrosequencing.

Human PBMCs (6×10$^7$) were obtained from three HIV-1 and hepatitis C negative individuals (LP32647, LP08248 and LP23810). A 5'RACE approach was developed to amplify immunoglobulin genes based on previously described methods (Venturi et al., 2011). Briefly, the PBMCs were pelleted at 1200 rpm for 8 min. mRNA was then extracted and eluted in 50 µl elution buffer using µMACS mRNA isolation kit (Miltenyi Biotec) according to manufacturer's instructions. To synthesize cDNA, 10 µl mRNA was mixed with 1 µl 5'CDS Oligo dT primers (12 µM) and incubated at 70° C. for 1 min and then −20° C. for 1 min. Then 1 µl SMARTER Oligo Primer (12 µM) (Clontech), 4 µl 5×RT buffer, 1 µl DTT 20 (20 mM), 1 µl dNTP (10 mM), 1 µl RNAse out and 1 µl SuperScript II reverse transcriptase (Invitrogen) were added to the reaction. After 2 hours incubation at 42° C., the cDNA products were purified using Nucleospin II kit (Macherey-Nagel) and eluted in 50 µl water. 454 pyrosequencing was performed as described previously (Wu et al., 2011). The first PCR amplification was performed with a common 5' primer II A (Clontech) and an Ig gene specific 3' primer (5'GGGGAAGAC-CGATGGGCCCTTGGTGG3') (SEQ ID NO: 192) using KAPA HIFI qPCR kit (Kapa Biosystems). The PCR products were purified with 2% Size Select Clonewell E-gel (Invitrogen) and Agencourt AMPure XP beads (Beckman Coulter). The second PCR amplification was performed with primers with 454 sequencing adapters (454-RACE-F: 5'CCATCTCATCCCTGCGTGTCTCCGACTCA-GAAGCAGTGGTATCAACGCAGAGT3' (SEQ ID NO: 193); 454-IgG-R: 5'CCTATCCCCTGTGTGCCTTGGCA-GTCTCAGGGGGAAGACCGATGGGCCCTTGGTGG3' (SEQ ID NO: 194)). The PCR products were again purified with 2% Size Select Clonewell E-gel and Agencourt AMPure XP beads.

Germline V Gene Specific Substitution Profile.

The raw reads from three healthy donors shorter than 300 nucleotides or longer than 600 nucleotides in length were not analyzed. Germline V gene was then assigned to each read using an in-house bioinformatics pipeline (Wu et al., 2015). We removed reads containing stop codons. Functional reads were then clustered using Usearch at 97% sequence identity, and one unique sequence was selected from each cluster to derive a curated dataset. To further reduce reads containing sequencing errors in the curated dataset, unique sequences having only one read in the clustering step were excluded. Finally, the curated dataset of the three donors were pooled for substitution frequency analyses.

Reads from the curated dataset that were assigned to germline V genes of interest were extracted, and were aligned using MUSCLE (Edgar, 2004). The amino acid substitution frequency or mutability of a V gene position was calculated by counting how many reads contain amino acids that are different from the germline V gene, and normalized by the total number of reads. We further calculated the frequency of the 19 types of amino acid substitutions at a position, which was used to generate positional substitution logo. The similarity of positional substitution frequency profiles between V genes of interest was measured by Pearson correlation coefficient.

Conformity Analysis.

The positional conformity of a conforming antibody sequence A to a reference sequence B is defined as the number of mutated positions shared by both sequences divided by the total number of mutations in the conforming sequence. Thus:

$$c_p(A; B) = \frac{|M_A \cap M_B|}{|M_A|}$$

where $M_i$ represents the set of amino acid positions in sequence i which are mutated from the germline V residue. Insertions and missing data are ignored, but deletions relative to the germline V are counted as mutations. For 8ANC131 and CH235 (FIG. 38A):
$M_{8ANC131}$={2, 9, 10, 11, 16, 19, 20, 23, 26, 30, 31, 32, 33, 34, 37, 45, 46, 48, 50, 52, 53, 55, 57, 58, 59, 60, 62, 63, 66, 68, 69, 70, 71, 74, 77, 80, 84, 85, 88, 89}

$M_{CH235}$={19, 23, 31, 34, 46, 47, 50, 52, 55, 57, 59, 63, 68, 83, 84}

$M_{8ANC131} \cap M_{CH235}$={19, 23, 31, 34, 46, 50, 52, 55, 57, 59, 63, 68, 84}

$c_p$(8ANC131, CH235)=13/15=86.7%

Identity conformity was defined the number of positionally conforming sites in conforming antibody A which were also mutated to the same residue as in the reference antibody B. Thus:

$$c_i(A;B) = \frac{\sum_{x \in \{M_A \cap M_B\}} \delta_{A_x B_x}}{|M_A|}$$

where δ is the Kronecker delta function and $A_x$ is the identity of the residue at position x of sequence A. For 8ANC131 and CH235 (FIG. 38B): $c_i$(8ANC131, CH235)=4/15=26.7%

Targeting Precision of CD4bs-directed Antibodies.

The targeting precision of the CD4bs-directed antibodies was defined as the buried surface area inside of the CD4 binding site minus the buried surface area outside of the CD4 binding site. The buried surface area of each antigen residue was determined by NACCESS. The buried surface area from the following residue numbers were considered inside of the CD4 binding site: 257, 279, 280, 281, 282, 283, 365, 366, 367, 368, 370, 371, 455, 456, 457, 458, 459, 460, 469, 472, 473, 474, 475, 476, and 477 (Zhou et al., 2007). The buried surface areas from the rest of the residues were considered outside of the CD4 binding site. Somatic hypermutation was defined using nucleotide sequences and P values were calculated based on linear regression.

Antibody Binding Orientation Calculation.

To calculate the relative rotation angles and translation to gp120-bound CD4 for gp120-bound CD4-binding site antibodies, all antibody-gp120 complexes to be analyzed were first superposed over the outer domain of gp120 (residue ranges: 252-392, 412-422, 437-476) with gp120 in its CD4 complex (PDB ID: 2NXY). The calculations of rotation angles and translation were then carried out with the gp120-aligned structures. For comparison of position of heavy chain variable domain relative to gp120-bound CD4, the frame work regions (residues 46-52, 56-59, 66-71 and 76-82) were superimposed to regions of CD4 domain 1 (residues 34-40, 43-46, 54-59, 65-71). The superposition procedures were performed with the Superpose Molecules module in CCP4 (Collaborative Computational Project, 1994). The Chi angle and distance between centroids in the Superpose output was taken as the rotation angle and translation distance between CD4 and a CD4-binding site antibody.

Supplemental References

Collaborative Computational Project (1994). The CCP4 suite: programs for protein crystallography. Acta Crystallogr., Sect D: Biol. Crystallogr. 50, 760-763.

Edgar, R. C. (2004). MUSCLE: multiple sequence alignment with high accuracy and high throughput. Nucleic Acids Res. 32, 1792-1797.

Giorgi, E. E., Funkhouser, B., Athreya, G., Perelson, A. S., Korber, B. T., Bhattacharya, T. (2010). Estimating time since infection in early homogeneous HIV-1 samples using a poisson model. BMC Bioinformatics 11, 532.

Gray, E. S., Moody, M. A., Wibmer, C. K., Chen, X., Marshall, D., Amos, J., Moore, P. L., Foulger, A., Yu, J. S., Lambson, B., et al. (2011). Isolation of a monoclonal antibody that targets the alpha-2 helix of gp120 and represents the initial autologous neutralizing-antibody response in an HIV-1 subtype C-infected individual. J. Virol. 85, 7719-7729.

Lander, G. C., Stagg, S. M., Voss, N. R., Cheng, A., Fellmann, D., Pulokas, J., Yoshioka, C., Irving, C., Mulder, A., Lau, P. W., et al. (2009). Appion: an integrated, database-driven pipeline to facilitate EM image processing. J. Struct. Biol. 166, 95-102.

Montefiori, D. C. (2005). Evaluating neutralizing antibodies against HIV, SIV, and SHIV in luciferase reporter gene assays. Current protocols in immunology/edited by John E Coligan [et al] Chapter 12, Unit 12 11.

Pettersen, E. F., Goddard, T. D., Huang, C. C., Couch, G. S., Greenblatt, D. M., Meng, E. C., and Ferrin, T. E. (2004). UCSF Chimera—a visualization system for exploratory research and analysis. J. Comput. Chem. 25, 1605-1612.

Scheres, S. H. (2012). A Bayesian view on cryo-EM structure determination. J. Mol. Biol. 415, 406-418.

Seaman, M. S., Janes, H., Hawkins, N., Grandpre, L. E., Devoy, C., Giri, A., Coffey, R. T., Harris, L., Wood, B., Daniels, M. G., et al. (2010). Tiered categorization of a diverse panel of HIV-1 Env pseudoviruses for assessment of neutralizing antibodies. J. Virol. 84, 1439-1452.

Schrodinger, LLC (2010). The PyMOL Molecular Graphics System, Version 1.3r1.

Subway, C., Pulokas, J., Fellmann, D., Cheng, A., Guerra, F., Quispe, J., Stagg, S., Potter, C. S., and Carragher, B. (2005). Automated molecular microscopy: the new Leginon system. J. Struct. Biol. 151, 41-60.

Tang, G., Peng, L., Baldwin, P. R., Mann, D. S., Jiang, W., Rees, I., and Ludtke, S. J. (2007). EMAN2: an extensible image processing suite for electron microscopy. J. Struct. Biol. 157, 38-46.

Tomaras, G. D., Yates, N. L., Liu, P., Qin, L., Fouda, G. G., Chavez, L. L., Decamp, A. C., Parks, R. J., Ashley, V. C., Lucas, J. T., et al. (2008). Initial B-cell responses to transmitted human immunodeficiency virus type 1: virion-binding immunoglobulin M (IgM) and IgG antibodies followed by plasma anti-gp41 antibodies with ineffective control of initial viremia. J. Virol. 82, 12449-12463 van Dongen, J. J., Langerak, A. W., Bruggemann, M., Evans, P. A., Hummel, M., Lavender, F. L., Delabesse, E., Davi, F., Schuuring, E., Garcia-Sanz, R., et al. (2003). Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia 17, 2257-2317.

Venturi, V., Quigley, M. F., Greenaway, H. Y., Ng, P. C., Ende, Z. S., McIntosh, T., Asher, T. E., Almeida, J. R., Levy, S., Price, D. A., et al. (2011). A mechanism for TCR sharing between T cell subsets and individuals revealed by pyrosequencing. J Immunol. 186, 4285-4294.

Wu, X., Yang, Z. Y., Li, Y., Hogerkorp, C. M., Schief, W. R., Seaman, M. S., Zhou, T., Schmidt, S. D., Wu, L., Xu, L., et al. (2010). Rational design of envelope identifies broadly neutralizing human monoclonal antibodies to HIV-1. Science 329, 856-861.

Wu, X., Zhang, Z., Schramm, C. A., Joyce, M. G., Kwon, Y. D., Zhou, T., Sheng, Z., Zhang, B., O'Dell, S., McKee, K., et al. (2015). Maturation and Diversity of the VRC01-Antibody Lineage over 15 Years of Chronic HIV-1 Infection. Cell 161, 470-485.

Zhou, T., Xu, L., Dey, B., Hessell, A. J., Van Ryk, D., Xiang, S. H., Yang, X., Zhang, M. Y., Zwick, M. B., Arthos, J., et al. (2007). Structural definition of a conserved neutralization epitope on HIV-1 gp120. Nature 445, 732-737.

Accession Numbers

Coordinates and structure factors for CH235, CH235.9 and CH235.12 in complex with HIV-1 gp120 have been deposited with the Protein Data Bank (PDB ID 5F9W, 5F90 and 5F96). Next-generation sequencing data have been deposited with the NCBI Sequence Reads Archive (SRP067168). Antibody heavy and light chains have been deposited with GenBank (KU570032-KU570053).

Antibodies Names Correlation

Various antibodies names are used throughout the application. Antibodies names correlation is as follows: CH490=CH235.6; CH491=CH235.7; CH492=CH235.8; CH493=CH235.9; CH555=CH235.10; CH556=CH235.11; CH557=CH235.12.

References For Example 8

Alam, S. M., McAdams, M., Boren, D., Rak, M., Scearce, R. M., Gao, F., Camacho, Z. T., Gewirth, D., Kelsoe, G., Chen, P., et al. (2007). The role of antibody polyspecificity and lipid reactivity in binding of broadly neutralizing anti-HIV-1 envelope human monoclonal antibodies 2F5 and 4E10 to glycoprotein 41 membrane proximal envelope epitopes. J. Immunol. 178, 4424-4435.

Alam, S. M., Morelli, M., Dennison, S. M., Liao, H. X., Zhang, R., Xia, S. M., Rits-Volloch, S., Sun, L., Harrison, S. C., Haynes, B. F., et al. (2009). Role of HIV membrane in neutralization by two broadly neutralizing antibodies. Proc. Natl. Acad. Sci. U.S.A 106, 20234-20239.

Bonsignori, M., Alam, S. M., Liao, H. X., Verkoczy, L., Tomaras, G. D., Haynes, B. F., and Moody, M. A. (2012). HIV-1 antibodies from infection and vaccination: insights for guiding vaccine design. Trends Microbiol. 20, 532-539.

Bonsignori, M., Hwang, K. K., Chen, X., Tsao, C. Y., Morris, L., Gray, E., Marshall, D. J., Crump, J. A., Kapiga, S. H., Sam, N. E., et al. (2011). Analysis of a clonal lineage of HIV-1 envelope V2/V3 conformational epitope-specific broadly neutralizing antibodies and their inferred unmutated common ancestors. J. Virol. 85, 9998-10009.

Bonsignori, M., Wiehe, K., Grimm, S. K., Lynch, R., Yang, G., Kozink, D. M., Perrin, F., Cooper, A. J., Hwang, K. K., Chen, X., et al. (2014). An autoreactive antibody from an SLE/HIV-1 individual broadly neutralizes HIV-1. J. Clin. Invest. 124, 1835-1843.

Boyd, S. D., Marshall, E. L., Merker, J. D., Maniar, J. M., Zhang, L. N., Sahaf, B., Jones, C. D., Simen, B. B., Hanczaruk, B., Nguyen, K. D., et al. (2009). Measurement and Clinical Monitoring of Human Lymphocyte Clonality by Massively Parallel V-D-J Pyrosequencing. Sci. Transl. Med. 1.

Dosenovic, P., von Boehmer, L., Escolano, A., Jardine, J., Freund, N. T., Gitlin, A. D., McGuire, A. T., Kulp, D. W., Oliveira, T., Scharf, L., et al. (2015). Immunization for HIV-1 Broadly Neutralizing Antibodies in Human Ig Knockin Mice. Cell 161, 1505-1515.

Felsenstein, J. (2005). PHYLIP (Phylogeny Inference Package), 3.6a3 edn (Seattle, Wash.: distributed by the author: Department of Genome Sciences, University of Washington).

Foote, J., and Milstein, C. (1991). Kinetic maturation of an immune response. Nature 352, 530-532.

Gao, F., Bonsignori, M., Liao, H. X., Kumar, A., Xia, S. M., Lu, X., Cai, F., Hwang, K. K., Song, H., Zhou, T., et al. (2014). Cooperation of B cell lineages in induction of HIV-1-broadly neutralizing antibodies. Cell 158, 481-491.

Georgiev, I. S., Doria-Rose, N. A., Zhou, T. Q., Do Kwon, Y., Staupe, R. P., Moquin, S., Chuang, G. Y., Louder, M. K., Schmidt, S. D., Altae-Tran, H. R., et al. (2013). Delineating Antibody Recognition in Polyclonal Sera from Patterns of HIV-1 Isolate Neutralization. Science 340, 751-756.

Haynes, B. F. (2015). New approaches to HIV vaccine development. Curr. Opin. Immunol. 35, 39-47.

Haynes, B. F., and Bradley, T. (2015). Broadly Neutralizing Antibodies and the Development of Vaccines. JAMA 313, 2419-2420.

Haynes, B. F., Fleming, J., St Clair, E. W., Katinger, H., Stiegler, G., Kunert, R., Robinson, J., Scearce, R. M., Plonk, K., Staats, H. F., et al. (2005). Cardiolipin polyspecific autoreactivity in two broadly neutralizing HIV-1 antibodies. Science 308, 1906-1908.

Haynes, B. F., Kelsoe, G., Harrison, S. C., and Kepler, T. B. (2012). B-cell-lineage immunogen design in vaccine development with HIV-1 as a case study. Nat. Biotechnol. 30, 423-433.

Haynes, B. F., and Verkoczy, L. (2014). AIDS/HIV. Host controls of HIV neutralizing antibodies. Science 344, 588-589.

Hraber, P., Korber, B., Wagh, K., Giorgi, E. E., Bhattacharya, T., Gnanakaran, S., Lapedes, A. S., Learn, G. H., Kreider, E. F., Li, Y., et al. (2015). Longitudinal Antigenic Sequences and Sites from Intra-Host Evolution (LASSIE) Identifies Immune-Selected HIV Variants. Viruses 7, 5443-5475.

Hraber, P., Seaman, M. S., Bailer, R. T., Mascola, J. R., Montefiori, D. C., and Korber, B. T. (2014). Prevalence of broadly neutralizing antibody responses during chronic HIV-1 infection. AIDS 28, 163-169.

Jardine, J., Julien, J. P., Menis, S., Ota, T., Kalyuzhniy, O., McGuire, A., Sok, D., Huang, P. S., MacPherson, S., Jones, M., et al. (2013). Rational HIV immunogen design to target specific germline B cell receptors. Science 340, 711-716.

Jardine, J. G., Ota, T., Sok, D., Pauthner, M., Kulp, D. W., Kalyuzhniy, O., Skog, P. D., Thinnes, T. C., Bhullar, D., Briney, B., et al. (2015). HIV-1 VACCINES. Priming a broadly neutralizing antibody response to HIV-1 using a germline-targeting immunogen. Science 349, 156-161.

Keele, B. F., Giorgi, E. E., Salazar-Gonzalez, J. F., Decker, J. M., Pham, K. T., Salazar, M. G., Sun, C., Grayson, T., Wang, S., Li, H., et al. (2008). Identification and characterization of transmitted and early founder virus envelopes in primary HIV-1 infection. Proc. Natl. Acad. Sci. U.S.A. 105, 7552-7557.

Kepler, T. B. (2013). Reconstructing a B-cell clonal lineage. I. Statistical inference of unobserved ancestors. F1000Res 2, 103.

Kepler, T. B., Munshaw, S., Wiehe, K., Zhang, R., Yu, J. S., Woods, C. W., Denny, T. N., Tomaras, G. D., Alam, S. M., Moody, M. A., et al. (2014). Reconstructing a B-Cell Clonal Lineage. II. Mutation, Selection, and Affinity Maturation. Front. Immunol. 5, 170.

Klein, F., Diskin, R., Scheid, J. F., Gaebler, C., Mouquet, H., Georgiev, I. S., Pancera, M., Zhou, T., Incesu, R. B., Fu, B. Z., et al. (2013). Somatic mutations of the immunoglobulin framework are generally required for broad and potent HIV-1 neutralization. Cell 153, 126-138.

Liao, H. X., Lynch, R., Zhou, T., Gao, F., Alam, S. M., Boyd, S. D., Fire, A. Z., Roskin, K. M., Schramm, C. A., Zhang, Z., et al. (2013). Co-evolution of a broadly neutralizing HIV-1 antibody and founder virus. Nature 496, 469-476.

Liu, M., Yang, G., Wiehe, K., Nicely, N. I., Vandergrift, N. A., Rountree, W., Bonsignori, M., Alam, S. M., Gao, J., Haynes, B. F., et al. (2015). Polyreactivity and autoreactivity among HIV-1 antibodies. J. Virol. 89, 784-798.

Mascola, J. R., and Haynes, B. F. (2013). HIV-1 neutralizing antibodies: understanding nature's pathways. Immunol. Rev. 254, 225-244.

McDonald, I. K., and Thornton, J. M. (1994). Satisfying hydrogen bonding potential in proteins. J. Mol. Biol. 238, 777-793.

McGuire, A. T., Hoot, S., Dreyer, A. M., Lippy, A., Stuart, A., Cohen, K. W., Jardine, J., Menis, S., Scheid, J. F., West, A. P., et al. (2013). Engineering HIV envelope protein to activate germline B cell receptors of broadly neutralizing anti-CD4 binding site antibodies. J. Exp. Med. 210, 655-663.

Otwinowski, Z., and Minor, W. (1997). Processing of X-ray diffraction data collected in oscillation mode. Method Enzymol. 276, 307-326.

Pugach, P., Ozorowski, G., Cupo, A., Ringe, R., Yasmeen, A., de Val, N., Derking, R., Kim, H. J., Korzun, J., Golabek, M., et al. (2015). A native-like SOSIP.664 trimer based on an HIV-1 subtype B env gene. J. Virol. 89, 3380-3395.

Rudicell, R. S., Do Kwon, Y., Ko, S. Y., Pegu, A., Louder, M. K., Georgiev, I. S., Wu, X. L., Zhu, J., Boyington, J. C., Chen, X. J., et al. (2014). Enhanced Potency of a Broadly Neutralizing HIV-1 Antibody In Vitro Improves Protection against Lentiviral Infection In Vivo. J. Virol. 88, 12669-12682.

Sanders, R. W., Derking, R., Cupo, A., Julien, J. P., Yasmeen, A., de Val, N., Kim, H. J., Blattner, C., de la Pena, A. T., Korzun, J., et al. (2013). A next-generation cleaved, soluble HIV-1 Env trimer, BG505 SOSIP.664 gp140, expresses multiple epitopes for broadly neutralizing but not non-neutralizing antibodies. PLoS Pathog. 9, e1003618.

Scheid, J. F., Mouquet, H., Feldhahn, N., Seaman, M. S., Velinzon, K., Pietzsch, J., Ott, R. G., Anthony, R. M., Zebroski, H., Hurley, A., et al. (2009). Broad diversity of neutralizing antibodies isolated from memory B cells in HIV-infected individuals. Nature 458, 636-640.

Scheid, J. F., Mouquet, H., Ueberheide, B., Diskin, R., Klein, F., Oliveira, T. Y., Pietzsch, J., Fenyo, D., Abadir, A., Velinzon, K., et al. (2011). Sequence and structural convergence of broad and potent HIV antibodies that mimic CD4 binding. Science 333, 1633-1637.

Sui, Z. W., Chen, Q. J., Wu, R., Zhang, H. B., Zheng, M., Wang, H. Z., and Chen, Z. (2010). Cross-protection against influenza virus infection by intranasal administration of M2-based vaccine with chitosan as an adjuvant. Arch. Virol. 155, 535-544.

Verkoczy, L., Chen, Y., Zhang, J., Bouton-Verville, H., Newman, A., Lockwood, B., Scearce, R. M., Montefiori, D. C., Dennison, S. M., Xia, S. M., et al. (2013). Induction of HIV-1 broad neutralizing antibodies in 2F5 knock-in mice: selection against membrane proximal external region-associated autoreactivity limits T-dependent responses. J. Immunol. 191, 2538-2550.

Verkoczy, L., Diaz, M., Holl, T. M., Ouyang, Y. B., Bouton-Verville, H., Alam, S. M., Liao, H. X., Kelsoe, G., and Haynes, B. F. (2010). Autoreactivity in an HIV-1 broadly reactive neutralizing antibody variable region heavy chain induces immunologic tolerance. Proc. Natl. Acad. Sci. U.S.A 107, 181-186.

Verkoczy, L., Kelsoe, G., Moody, M. A., and Haynes, B. F. (2011). Role of immune mechanisms in induction of HIV-1 broadly neutralizing antibodies. Curr. Opin. Immunol. 23, 383-390.

Wu, X., Yang, Z. Y., Li, Y., Hogerkorp, C. M., Schief, W. R., Seaman, M. S., Zhou, T., Schmidt, S. D., Wu, L., Xu, L., et al. (2010). Rational design of envelope identifies broadly neutralizing human monoclonal antibodies to HIV-1. Science 329, 856-861.

Wu, X., Zhou, T., Zhu, J., Zhang, B., Georgiev, I., Wang, C., Chen, X., Longo, N. S., Louder, M., McKee, K., et al. (2011). Focused evolution of HIV-1 neutralizing antibodies revealed by structures and deep sequencing. Science 333, 1593-1602.

Yang, G., Holl, T. M., Liu, Y., Li, Y., Lu, X., Nicely, N. I., Kepler, T. B., Alam, S. M., Liao, H. X., Cain, D. W., et al. (2013). Identification of autoantigens recognized by the 2F5 and 4E10 broadly neutralizing HIV-1 antibodies. J. Exp. Med. 210, 241-256.

Zhou, T., Georgiev, I., Wu, X., Yang, Z. Y., Dai, K., Finzi, A., Kwon, Y. D., Scheid, J. F., Shi, W., Xu, L., et al. (2010). Structural basis for broad and potent neutralization of HIV-1 by antibody VRC01. Science 329, 811-817.

Zhou, T., Lynch, R. M., Chen, L., Acharya, P., Wu, X., Doria-Rose, N. A., Joyce, M. G., Lingwood, D., Soto, C., Bailer, R. T., et al. (2015). Structural Repertoire of HIV-1-Neutralizing Antibodies Targeting the CD4 Supersite in 14 Donors. Cell 161, 1280-1292.

Example 9: DH540 Antibody is Described Elsewhere

DH540 sequences are described in FIG. 13 and the antibody is described in detail in U.S. Ser. No. 62/170,558, filed Jun. 3, 2015.

Example 10: DH542 Antibodies

The nucleotide and amino acid sequences of the VH and VL of DH542 QSA are shown below. DH542 QSA antibody has the VH of DH542 and the VL called DH542-QSA

```
>DH542_HC_nt
                                           (SEQ ID NO: 178)
CAGGTGCAGCTGGTGCAGTCTGGGGCTCAAATGAAGAACCCTGGGGCCTC

AGTGAAGGTCTCCTGCGCGCCTTCTGGATATACCTTCACCGACTTTTACA

TACATTGGTTGCGCCAGGCCCCTGGCCAGGGGCTTCAGTGGATGGGATGG

ATGAACCCTCAGACTGGTCGCACAAACACTGCACGAAACTTTCAGGGGAG

GGTCACCATGACCAGGGACACGTCCATCGGCACAGCCTACATGGAGTTGA

GAAGCCTGACATCTGACGACACGGCCATATATTACTGTACGACAGGGGGA

TGGATCAGTCTTTACTATGATAGTAGTTATTACCCCAACTTTGACCACTG

GGGTCAGGGAACCCTGCTCACCGTCTCCTCAG

>DH542_HC_aa
                                           (SEQ ID NO: 179)
QVQLVQSGAQMKNPGASVKVSCAPSGYTFTDFYIHWLRQAPGQGLQWMGW

MNPQTGRTNTARNFQGRVTMTRDTSIGTAYMELRSLTSDDTAIYYCTTGG

WISLYYDSSYYPNFDHWGQGTLLTVSS

>DH542_LC_nt_corrected (DH542_QSA)
                                           (SEQ ID NO: 180)
CAGTCTGCCCTGACTCAGCCTGCCTCCGTGTCTGGGTCTCCTGGACAGTC

GATCACCATCTCCTGCACTGGAACCAAGTATGATGTTGGGAGTCATGACC

TTGTCTCCTGGTACCAACAGTACCCAGGCAAAGTCCCCAAATACATGATT

TATGAAGTCAATAAACGGCCCTCAGGAGTTTCTAATCGCTTCTCTGGCTC
```

```
CAAATCTGGCAACACGGCCTCCCTGACAATCTCTGGGCTCCGGGCTGAGG

ACGAGGCTGACTATTATTGCTGTTCATTTGGAGGGAGTGCCACCGTGGTC

TGCGGCGGCGGGACCAAGGTGACCGTCCTGa

>DH542_LC_aa_corrected (DH542_QSA)
                                        (SEQ ID NO: 181)
QSALTQPASVSGSPGQSITISCTGTKYDVGSHDLVSWYQQYPGKVPKYMI

YEVNKRPSGVSNRFSGSKSGNTASLTISGLRAEDEADYYCCSFGGSATVV

CGGGTKVTVL
```

DH542-L4 is an antibody that has a VH of DH542 and VL of DH429 (FIG. 2).

Example 11: MPER Antibodies

DH512 K3 is a combination of VH DH512 and VL called DH511_2AVK

```
>DH511_2AVK Kappa Chain Nucleotide Sequence
                                        (SEQ ID NO: 182)
GACATCCAGATGACCCAGTCTCCGTCTTTCCTGTACGGCTCTGTAGGCGA

TAGAGTCACCATCACTTGCCGGGCAAGTCAGAATATTAAGGACTATTTAA

ATTGGTATCAGCAGAGACCAGGGAGAGCCCCTAGACTCCTGATCTATGCT

GCATCCAATTTGCAAAGTGGGGTCCCGTCAAGGTTCAGTGGCAGTGGATA

TGGGACAGACTTTACTCTCATCATCAGCAGTCTGCAACCTGAGGACTTTG

CGACTTATTTCTGTCAAGAGAGTTATAGTTCTACGCCCACACACATTTTT

GGCCTGGGGACCAAATTGGAGAAGAAAC

>DH511_2AVK Kappa Chain Amino Acid Sequence
                                        (SEQ ID NO: 183)
DIQMTQSPSFLYGSVGDRVTITCRASQNIKDYLNWYQQRPGRAPLLIYAA

SNLQSGVPSRFSGSGYGTDFTLIISSLQPEDFATYFCQESYSSTPTHIFG

LGTKLEKKX
```

There are also MPER antibodies which have a mutated VH from DH512 (See FIG. 48).

Other Assays

Epitope mapping of antibodies: Binding and/or neutralization assays using various envelope antigens can be used to determine the epitope recognized by these antibodies.

The stability and properties of the antibodies, for example as formulated in a composition for treatment will be tested.

Animal studies (PK and PD studies) could be conducted to determine the distribution and half life of the antibodies.

Various assays and experiments can be designed to analyze prevention, treatment and/or cure.

The antibodies will be expressed in a CHO line, e.g. CHO-DG44 cell line for preparation of pharmaceutical compositions. These CHO-expressed antibodies will be analyzed in various suitable assays.

What is claimed is:

1. An anti-HIV-1 envelope recombinant monoclonal antibody or antigen-binding fragment thereof wherein the antibody or antigen-binding fragment thereof comprises a VH chain that is 90%, 91%, 92%, 93%, 94%, 95%, 96%, 97%, 98%, 99% or 100% identical to the VH chain of antibody CH557 (SEQ ID NO: 124) and comprises a VL chain that is 90%, 91%, 92%, 93%, 94%, 95%, 96%, 97%, 98%, 99% or 100% identical to the VL chain of antibody CH557 (SEQ ID NO: 125).

2. An anti-HIV-1 envelope recombinant monoclonal antibody or antigen-binding fragment thereof wherein the antibody or antigen-binding fragment thereof comprises the VH chain of antibody CH557 (SEQ ID NO: 124) and the VL chain of antibody CH557 (SEQ ID NO: 125).

3. The anti-HIV-1 envelope recombinant monoclonal antibody or antigen-binding fragment thereof of claim 1 wherein the antibody or fragment thereof comprises a modified Fc portion.

4. The anti-HIV-1 envelope recombinant monoclonal antibody or antigen-binding fragment thereof of claim 1 wherein the antibody or antigen-binding fragment thereof is bispecific.

5. A pharmaceutical composition comprising any one of the antibodies or antigen-binding fragments thereof of claim 1.

6. A composition comprising a vector comprising a nucleic acid encoding the anti-HIV-1 envelope antibody or antigen-binding fragment thereof of claim 1.

7. The composition of claim 6, wherein the vector is suitable for gene delivery and expression.

8. A method to treat HIV-1 infection in a subject comprising administering to the subject a composition comprising an anti-HIV-1 envelope recombinant monoclonal antibody or antigen-binding fragment thereof wherein the antibody or antigen-binding fragment thereof comprises a VH chain that is 90%, 91%, 92%, 93%, 94%, 95%, 96%, 97%, 98%, 99% or 100% identical to the VH chain of antibody CH557 (SEQ ID NO: 124) and comprises a VL chain that is 90%, 91%, 92%, 93%, 94%, 95%, 96%, 97%, 98%, 99% or 100% identical to the VL chain of antibody CH557 (SEQ ID NO: 125) in a therapeutically effective amount.

9. The method of claim 8 further comprising administering an additional HIV-1 broad neutralizing antibody.

10. The method of claim 8, wherein the antibody or antigen-binding fragment thereof is administered as a nucleic acid.

11. The method of claim 8, wherein the antibody or antigen-binding fragment thereof comprises a modified Fc portion.

12. The antibody or antigen-binding fragment thereof of claim 2 wherein the antibody or antigen-binding fragment thereof comprises a modified Fc portion.

13. The antibody or antigen-binding fragment thereof of claim 2 wherein the antibody or antigen-binding fragment thereof is bispecific.

14. A pharmaceutical composition comprising any one of the antibodies or antigen-binding fragments thereof of claim 2.

15. A pharmaceutical composition comprising any one of the antibodies or antigen-binding fragments thereof of claim 12.

16. A pharmaceutical composition comprising any one of the antibodies or antigen-binding fragments thereof of claim 13.

17. A pharmaceutical composition comprising any one of the antibodies or antigen-binding fragments thereof of claim 3.

18. A pharmaceutical composition comprising any one of the antibodies or antigen-binding fragments thereof of claim 4.

19. A composition comprising a vector comprising a nucleic acid encoding the antibody or antigen-binding fragment thereof of any one of claim 2.

20. The composition of claim 19, wherein the vector is suitable for gene delivery and expression.

21. An anti-HIV-1 envelope recombinant monoclonal antibody or antigen-binding fragment thereof wherein the antibody or antigen-binding fragment thereof comprises a heavy chain variable region comprising a heavy chain complementarity determining region (HCDR)1, a HCDR2, and a HCDR3 comprising amino acids 26-33, 51-58, and 96-112 of SEQ ID NO: 124, respectively; and a light chain variable region comprising a light chain complementarity determining region (LCDR)1, a LCDR2, and a LCDR3, comprising amino acids 27-32, 50-52 and 88-97 of SEQ ID NO: 125, respectively.

22. The anti-HIV-1 envelope recombinant monoclonal antibody or antigen-binding fragment thereof of claim 21 wherein the antibody or fragment thereof comprises a modified Fc portion.

23. The anti-HIV-1 envelope recombinant monoclonal antibody or antigen-binding fragment thereof of claim 21 wherein the antibody or antigen-binding fragment thereof is bispecific.

24. A pharmaceutical composition comprising any one of the antibodies or antigen-binding fragments thereof of claim 21.

25. A composition comprising a vector comprising a nucleic acid encoding the anti-HIV-1 envelope antibody or antigen-binding fragment thereof of claim 21.

26. The composition of claim 25, wherein the vector is suitable for gene delivery and expression.

27. A method to treat HIV-1 infection in a subject comprising administering to the subject in a therapeutically effective amount a composition comprising an anti-HIV-1 envelope recombinant monoclonal antibody or antigen-binding fragment thereof wherein the antibody or antigen-binding fragment thereof comprises a heavy chain variable region comprising a heavy chain complementarity determining region (HCDR)1, a HCDR2, and a HCDR3 comprising amino acids 26-33, 51-58, and 96-112 of SEQ ID NO: 124, respectively; and a light chain variable region comprising a light chain complementarity determining region (LCDR)1, a LCDR2, and a LCDR3, comprising amino acids 27-32, 50-52 and 88-97 of SEQ ID NO: 125, respectively.

28. The method of claim 27 further comprising administering an additional HIV-1 broad neutralizing antibody.

29. The method of claim 27, wherein the antibody or antigen-binding fragment thereof is administered as a nucleic acid.

30. The method of claim 27, wherein the antibody or antigen-binding fragment thereof comprises a modified Fc portion.

31. An anti-HIV-1 envelope recombinant monoclonal antibody or antigen-binding fragment thereof wherein the antibody or antigen-binding fragment thereof comprises a VH chain that is 90%, 91%, 92%, 93%, 94%, 95%, 96%, 97%, 98%, 99% or 100% identical to the VH chain of antibody CH557 (SEQ ID NO: 124) and comprises a VL chain that is 90%, 91%, 92%, 93%, 94%, 95%, 96%, 97%, 98%, 99% or 100% identical to the VL chain of antibody CH557 (SEQ ID NO: 125) produced by a process comprising transfecting a mammalian host cell with one or more vectors comprising a nucleic acid encoding the anti-HIV-1 envelope antibody or antigen-binding fragment thereof and culturing the transfected mammalian host cells.

32. The anti-HIV-1 envelope recombinant monoclonal antibody or antigen-binding fragment thereof of claim 31, wherein the antibody or antigen-binding fragment thereof comprises the VH chain of antibody CH557 (SEQ ID NO: 124) and the VL chain of antibody CH557 (SEQ ID NO: 125).

33. The anti-HIV-1 envelope recombinant monoclonal antibody or antigen-binding fragment thereof of claim 31, wherein the antibody or fragment thereof comprises a modified Fc portion.

34. The anti-HIV-1 envelope recombinant monoclonal antibody or antigen-binding fragment thereof of claim 31, wherein the antibody or antigen-binding fragment thereof is bispecific.

35. A pharmaceutical composition comprising any one of the antibodies or antigen-binding fragments thereof of claim 31.

36. An anti-HIV-1 envelope recombinant monoclonal antibody or antigen-binding fragment thereof wherein the antibody or antigen-binding fragment thereof comprises a heavy chain variable region comprising a heavy chain complementarity determining region (HCDR)1, a HCDR2, and a HCDR3 comprising amino acids 26-33, 51-58, and 96-112 of SEQ ID NO: 124, respectively; and a light chain variable region comprising a light chain complementarity determining region (LCDR)1, a LCDR2, and a LCDR3, comprising amino acids 27-32, 50-52 and 88-97 of SEQ ID NO: 125, respectively produced by a process comprising transfecting a mammalian host cell with one or more vectors comprising a nucleic acid encoding the anti-HIV-1 envelope antibody or antigen-binding fragment thereof and culturing the transfected mammalian host cells.

37. The anti-HIV-1 envelope recombinant monoclonal antibody or antigen-binding fragment thereof of claim 36, wherein the antibody or fragment thereof comprises a modified Fc portion.

38. The anti-HIV-1 envelope recombinant monoclonal antibody or antigen-binding fragment thereof of claim 36, wherein the antibody or antigen-binding fragment thereof is bispecific.

39. A pharmaceutical composition comprising any one of the antibodies or antigen-binding fragments thereof of claim 36.

* * * * *